(12) United States Patent
Hornberger et al.

(10) Patent No.: US 8,378,104 B2
(45) Date of Patent: Feb. 19, 2013

(54) 7-AMINOFUROPYRIDINE DERIVATIVES

(75) Inventors: Keith R. Hornberger, Mount Sinai, NY (US); Dan M. Berger, New City, NY (US); Xin Chen, Commack, NY (US); Andrew P. Crew, N. Babylon, NY (US); Hanqing Dong, Syosset, NY (US); Andrew Kleinberg, East Meadow, NY (US); An-Hu Li, Commack, NY (US); Lifu Ma, Melville, NY (US); Mark J. Mulvihill, Melville, NY (US); Bijoy Panicker, Holbrook, NY (US); Kam W. Siu, Farmingdale, NY (US); Arno G. Steinig, East Northport, NY (US); James G. Tarrant, Lindenhurst, NY (US); Jing Wang, Syosset, NY (US); Qinghua Weng, Hicksville, NY (US); Rajaram Sangem, Port Jefferson Station, NY (US); Ramesh C. Gupta, Port Jefferson Station, NY (US)

(73) Assignee: OSI Pharmaceuticals, LLC, Farmingdale, NY (US)

( * ) Notice: Subject to any disclaimer, the term of this patent is extended or adjusted under 35 U.S.C. 154(b) by 85 days.

(21) Appl. No.: 13/025,281

(22) Filed: Feb. 11, 2011

(65) Prior Publication Data

US 2012/0046267 A1 Feb. 23, 2012

Related U.S. Application Data

(60) Provisional application No. 61/414,667, filed on Nov. 17, 2010, provisional application No. 61/303,399, filed on Feb. 11, 2010.

(51) Int. Cl.
*C07D 471/02* (2006.01)
(52) U.S. Cl. .................................................. 546/115
(58) Field of Classification Search .................. 546/115
See application file for complete search history.

(56) References Cited

U.S. PATENT DOCUMENTS

| | | |
|---|---|---|
| 2003/0004344 A1 | 1/2003 | Lam |
| 2004/0097485 A1 | 5/2004 | Burkitt |
| 2006/0074102 A1 | 4/2006 | Cusack |
| 2007/0178573 A1 | 8/2007 | Cheetham |
| 2009/0012079 A1 | 1/2009 | Lewthwaite |
| 2009/0124604 A1 | 5/2009 | Nash |

FOREIGN PATENT DOCUMENTS

WO 2009/099982 A1 8/2009

OTHER PUBLICATIONS

International Search Report and the Written Opinion of the International Searching Authority in PCT/US2011/024449, Jun. 28, 2011.
Barkett M. and Gilmore T. D. Oncogene (1999) 18, pp. 6910-6924.
Davis R.J. Trends in Biochem Sci. (1994) 19, pp. 470-473.
Erdogan M. et al. Cancer Res. (2008); 68: (15) pp. 6224-6231.
Ikushima H., et al. Nature Reviews Cancer (2010) 10, pp. 415-424.
Irie T. et al. FEBS Lett(2000) 467, pp. 160-164.
Ishitani T. et al. Nature (1999) vol. 399, pp. 798-802.
Kishimoto K. et al. J. Biol. Chem. (2000) vol. 275, No. 10, pp. 7359-7364.
Lee J. et al. J. Leukocyte Biology (2000) vol. 68 ,pp. 909-915.
Meneghini M.D. et al. Nature (1999) vol. 399, pp. 793-797.
Mizukami J. et al. Mol. Cell. Biol. (2002) vol. 22, No. 4, pp. 992-1000.
Moriguchi T. et al. J. Biol. Chem. (1996) vol. 271, No. 23, pp. 13675-13679.
Neil J. et al. Cancer Res. (2008); 68: pp. 1462-1470.
Ninomiya-Tsuji J. et al. Nature (1999) vol. 398 pp. 252-256.
Nierkens S. et al. J. Immunol. (2002); 168; pp. 3747-3754.
Ninomiya-Tsuji J. et al. J. Biol. Chem (2003) vol. 278, No. 20, pp. 18485-18490.
Ono K. et al. J. Biol. Chem. (2001) vol. 276, No. 26, pp. 24396-24400.
Safina A. et al. Oncogene (2007) 26, pp. 2407-2422.
Safina A. et al. Oncogene (2008) 27 (9) pp. 1198-1207.
Sakurai H. et al. J. Biol. Chem (1999) vol. 274, No. 15 pp. 10641-10648.
Sakurai H. et al. FEBS Letters (2000) 474 pp. 141-145.
Shibuya H. et al. The EMBO Journal (1998), vol. 17 pp. 1019-1028.
Shibuya H. et al. Science (1996), vol. 272 pp. 1179-1182.
Shih S-C. et al. PNAS (2003), vol. 100, No. 26 pp. 15859-15864.
Su B. & Karin M. Curr. Opin. Immunol (1996) 8 pp. 402-411.
Takaesu G. et al. J. Mol. Biol. (2003) 326 pp. 105-115.
Treisman R. Curr. Opin. Cell Biol. (1996) 8 pp. 205-215.
Vidal S. et al. Genes Dev. (2001) 15 pp. 1900-1912.
Wang W. et al. J. Biol.Chem. (1997) vol. 272, No. 36, pp. 22771-22775.
Yamaguchi K. et al. Science (1995), vol. 270 pp. 2008-2011.
Zhang D. et al. Nature Med. (2000), vol. 6, No. 5 pp. 556-563.

*Primary Examiner* — Nizal Chandrakumar

(57) ABSTRACT

Compounds of Formula 1, as shown below and defined herein:

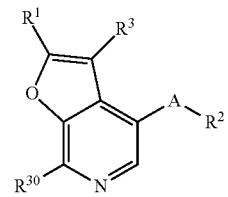

pharmaceutically acceptable salts thereof, synthesis, intermediates, formulations, and methods of disease treatment therewith, including treatment of cancers, such as tumors driven at least in part by TAK1 or for which an appropriate TAK1 inhibitor is effective. This Abstract is not limiting of the invention.

24 Claims, No Drawings

7-AMINOFUROPYRIDINE DERIVATIVES

This application claims the benefits of prior U.S. Appl. Nos. 61/414,667 (Nov. 17, 2010) and 61/303,399 (Feb. 11, 2010), the contents of which are incorporated herein in their entireties by this reference.

FIELD AND BACKGROUND

The present invention pertains at least in part to cancer treatment, cancers mediated at least in part by TAK1 and/or other targets, certain chemical compounds, and methods of treating tumors and cancers with the compounds. The present invention also pertains to treating inflammatory and allergic disorders.

In general, protein kinases mediate intracellular signaling by effecting a phosphoryl transfer from a nucleoside triphosphate to a protein acceptor that is involved in a signaling pathway. These phosphorylation events act as molecular on/off switches that can modulate or regulate the target protein biological function. These phosphorylation events are ultimately triggered in response to a variety of extracellular and other stimuli. Examples of such stimuli include environmental and chemical stress signals (e.g., osmotic shock, heat shock, ultraviolet radiation, bacterial endotoxin, and $H_2O_2$), cytokines (e.g., interleukin-1 (IL-1) and tumor necrosis factor $\alpha$ (TNF-$\alpha$)), and growth factors (e.g., granulocyte macrophage-colony-stimulating factor (GM-CSF), and fibroblast growth factor (FGF). An extracellular stimulus may affect one or more cellular responses related to cell growth, migration, differentiation, secretion of hormones, activation of transcription factors, muscle contraction, glucose metabolism, control of protein synthesis, and regulation of the cell cycle.

Among medically important serine/threonine kinases is the family of mitogen-activated protein kinases (MAPKs), which have been shown to function in a wide variety of biological processes (Davis D. J. *Trends in Biochem Sci.* 19 470-473 (1994); Su B. & Karin M *Curr. Opin. Immunol* 8 402-411 (1996); Treisman R. *Curr. Opin. Cell Biol.* 8 205-215 (1996)). MAPKs are activated by phosphorylation on specific tyrosine and threonine residues by MAPK kinases (MAPKKs), which are in turn activated by phosphorylation on serine and serine/threonine residues by MAPKK kinases (MAPKKKs). The MAPKKK family comprises several members including MEKK1, MEKK3, NIK and ASK1 and Raf. Different mechanisms are involved in the activation of MAPKKKs in response to a variety of extracellular stimuli including cytokines, growth factors and environmental stresses.

Transforming growth factor-$\beta$ (TGF-$\beta$)-activated kinase 1 (TAK1) is a member of the mitogen-activated protein kinase kinase kinase (MAPKKK) family and has been shown to play critical roles in signaling pathways stimulated by transforming growth factor-$\beta$, interleukin-1 (IL-1), tumor necrosis factor-$\alpha$ (TNF-$\alpha$), lipopolysaccharide, receptor activator of NF-$\kappa$B ligand where it regulates osteoclast differentiation and activation, and IL-8 (Yamaguchi K et al. *Science* 270 2008-11 (1995); Ninomiya-Tsuji J et al. *Nature* 398 252-256 (1999); Sakurai H. et al. *J. Biol. Chem.* 274 10641-10648 (1999); He T. et al. *FEBS Lett.* 467 160-164 (2000); Lee J. et al. *J. Leukoc Biol.* 68 909-915 (2000); Mizukami J et al. *Mol. Cell. Biol.* 22 992-1000 (2002); Wald D. et al. *J. Immunol.* 31 3747-3754 (2002)). TAK1 regulates both the c-Jun N-terminal kinase (JNK) and p38 MAPK cascades in which it phosphorylates MAPK kinases MKK4 and MKK3/6, respectively (Wang W. et al. *J. Biol. Chem.* 272 22771-22775 (1997); Moriguchi T. et al. *J. Biol. Chem.* 271 13675-13679 (1996)). NF-kB factors regulate expression of a variety of genes involved in apoptosis, cell cycle, transformation, immune response, and cell adhesion (Barkett M and Gilmore T D. *Oncogene*, 18, 6910-6924 (1999). TAK1 regulates the I$\kappa$B kinase (IKK) signaling pathways, leading to the activation of transcription factors AP-1 and NF-$\kappa$B (Ninomiya-Tsuji J et al. *Nature* 398 252-256 (1999); Sakurai H. et al. *J. Biol. Chem.* 274 10641-10648 (1999); Takaesu G. et al. *J. Mol. Biol.* 326 110-115 (2003)). In early embryos of the amphibian *Xenopus*, TAK1 also participates in mesoderm induction and patterning mediated by bone morphogenetic protein (BMP), which is another transforming growth factor $\beta$ family ligand (Shibuya H. et al. *EMBO J.* 17 1019-1028 (1998)). In addition, TAK1 is a negative regulator of the Wnt signaling pathway, in which TAK1 down-regulates transcription regulation mediated by a complex of $\beta$-catenin and T-cell factor/lymphoid enhancer factor (Meneghini M. D. et al. *Nature* 399 793-797 (1999); Ishitani T. et al. *Nature* 399 798-802 (1999)). The role of TAK1 in TNF-$\alpha$ and IL-1$\beta$-induced signaling events is evident from TAK1 RNAi experiments in mammalian cells (Takaesu G. et al. *J. Mol. Biol.* 326 105-115 (2003)) in which IL-1 and TNF-$\alpha$ induced NF-$\kappa$B and MAPK activation were both inhibited. Over-expression of kinase dead TAK1 inhibits IL-1 and TNK-induced activation of both JNK/p38 and NF-kB (Ninomiya-Tsuji J et al. *Nature* 398 252-256 (1999); Sakurai H. et al. *J. Biol. Chem.* 274 10641-10648 (1999)). TAK1–/– mouse embryonic fibroblasts have diminished IL-1-induced signaling and are embryonic lethal (E11.5) (S. Akira, personal communication). In adult mouse, TAK1 is activated in the myocardium after pressure overload. Expression of constitutively-active TAK1 in myocardium induced myocardial hypertrophy and heart failure in transgenic mice (Zhang D. et al. *Nature Med.* 6 556-563 (2000)).

TAK1 is activated by the TAK1 binding protein (TAB1) (Shibuya H et al. *Science* 272 1179-1182 (1996)) via an association with the N-terminal kinase domain of TAK1. It has been reported that the C-terminal 68 amino acids of TAB1 is sufficient for the association and activation of TAK1 (Shibuya H et al. *Science* 272 1179-1182 (1996)). However, more recent work indicates that the minimum TAB1 segment required includes only residues 480-495 (Ono K. et al. *J. Biol. Chem.* 276 24396-24400 (2001); Sakurai H. et al. *FEBS Lett* 474 141-145 (2000)). Deletion mutants of TAB1 show that the aromatic Phe484 residue is critical for TAK1 binding (Ono K. et al. *J. Biol. Chem.* 276 24396-24400 (2001)). Autophosphorylation of threonine/serine residues in the kinase activation loop are necessary for TAB1-induced TAK1 activation (Sakurai H. et al. *FEBS Lett* 474 141-145 (2000); Kishimoto K. et al. *J. Biol. Chem.* 275 7359-7364 (2000)), Ser192 appears as the most likely candidate since a Ser192Ala mutation shows no kinase activity (Kishimoto K. et al. *J. Biol. Chem.* 275 7359-7364 (2000)).

Since TAK1 is a key molecule in the pro-inflammatory NF-$\kappa$B signaling pathway a TAK1 inhibitor would be effective in diseases associated with inflammation and tissue destruction such as rheumatoid arthritis and inflammatory bowel disease (Crohn's), as well as in cellular processes such as stress responses, apoptosis, proliferation and differentiation. Various pro-inflammatory cytokines and endotoxins trigger the kinase activity of endogenous TAK1 (Ninomiya-Tsuji J et al. *Nature* 398 252-256 (1999); Irie T et al. *FEBS Lett.* 467 160-164 (2000); Sakurai H. et al. *J. Biol. Chem.* 274 10641-10648 (1999)) and the *Drosophila* homolog of TAK1 was recently identified as an essential molecule for host defense signaling in *Drosophila* (Vidal S. et al. *Genes Dev.* 15 1900-1912 (1999)). A naturally occurring inhibitor of TAK1, 5Z-7-oxozeaenol, has been identified with an $IC_{50}$ value of 8 nM. 5Z-7-oxozeaenol has been shown to be selective for TAK1 within the MAPKKK family and relieves inflammation in a picryl chloride-induced ear swelling mouse model (Ninomiya-Tsuji J. et al. *J. Biol. Chem.* 278 18485 (2003)).

A potential mechanism of TAK1 mediated survival is driven by the ability of TAK1 to phosphorylate IKK and MKKs ultimately leading to the activation of both NF-kB and AP-1, transcription factors that play a role in cell survival.

Others have reported that the TAB1:TAK1:IKKβ:NF-κB signaling axis forms aberrantly in breast cancer cells, and consequently, enables oncogenic signaling by TGF-β (Neil J et al. *Cancer Res.* 68 1462 (2008)).

Others have reported that TGF-β signaling contributes to tumor angiogenesis and invasion via a mechanism involving matrix metalloproteinase 9 (MMP9) (Safina A et al. *Oncogene* 26 p2407 (2007)), and that TAK1 is required for TGFb1-mediated regulation of matrix metalloproteinase-9 and metastasis (Safina A et al. *Oncogene* 2008; 27(9):1198-12072008). Others have reported that TGF-β signaling can induce an epithelial-to-mesenchymal transition (EMT) and contributes to tumor invasion and progression (Ikushima H et al. *Nature Reviews Cancer* 10 p415 (2010)) and that TAK1 is required for this process (Neil J et al. *Cancer Res.* 68 1462 (2008)). Thus, TAK1 has been suggested as providing an opportunity for selective inhibition of pro-oncogenic function of TGF-β.

Others have proposed that the signaling pathways by which MDP-NOD2 and LPS-TLR4 induce the production of IL-1β and TNFα converge at the level of TAK1.

Accordingly, there has been an interest in finding selective inhibitors of TAK1 that are effective as therapeutic agents. A challenge has been to find protein kinase inhibitors that act in a selective manner, targeting only TAK1. Since there are numerous protein kinases that are involved in a variety of cellular responses, non-selective inhibitors may lead to unwanted side effects. In this regard, the three-dimensional structure of the kinase would assist in the rational design of inhibitors. The determination of the amino acid residues in TAK1 binding pockets and the determination of the shape of those binding pockets would allow one to design selective inhibitors that bind favorably to this class of enzymes. The determination of the amino acid residues in TAK1 binding pockets and the determination of the shape of those binding pockets would also allow one to determine the binding of compounds to the binding pockets and to, e.g., design inhibitors that can bind to TAK1.

Others have reported that TAK1 plays a key role in proinflammatory signaling by activating JNK, p38, and NF-κB, suggesting that TAK1 inhibition may be effective in preventing inflammation and tissue destruction promoted by proinflammatory cytokines. Ninomiya-Tsuji et al., *J. Bio. Chem.*, 278, 20, pp. 18485-90 (2003). Inhibitors of p38 have also been proposed for treating inflammatory and allergic disorders. US2009/0124604; US2009/0012079.

The following published documents are also noted: Erdogan M et al. *Cancer Res.* 68 p6224 (2008); Shih S-C et al. *PNAS* 100 p15859 (2003); US2006/0074102; US2004/0097485; US2003/0004344.

There is a need for effective therapies for use in proliferative disease, including treatments for primary cancers, prevention of metastatic disease, and targeted therapies, including tyrosine kinase inhibitors, such as TAK1 inhibitors, including selective inhibitors, and for potent, orally bioavailable, and efficacious inhibitors.

SUMMARY

In some aspects, the present invention provides compounds of Formula 1, and pharmaceutically acceptable salt thereof, as shown below and defined herein:

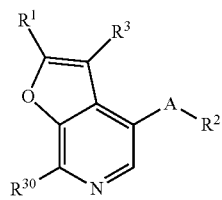

wherein:
A is optionally substituted 5-membered heterocyclic; $R^1$ is optionally substituted $_{5-6}$cyclic that is optionally substituted by $R^4$ or fused to $R^4$ at two atoms; $R^2$ is an optional substituent; $R^3$ is H, $C_{1-6}$aliphatic (including alkynes, including —CCH) CN, or halogen; in some embodiments, $R^3$ can be —$SO_2R^{31}$ or —$C(O)NR^{31}R^{32}$ or —$SO_2R^{12}$ or —$C(O)NR^{12}R^{13}$; $R^4$ is optionally substituted $_{5-10}$cyclic; and $R^{30}$ is —$NR^{31}R^{32}$ or —$NR^{12}R^{13}$, or wherein $R^{31}$ and $R^{32}$ are independently H or $C_{1-3}$aliphatic, and $R^{12}$ and $R^{13}$ are defined below.

In some aspects thereof, the compound or salt has the Formula 2:

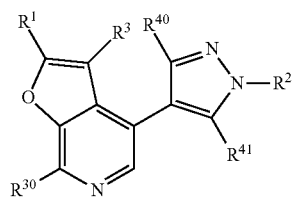

wherein: $R^2$ is H or an optional substituent; and each $R^{40}$ and $R^{41}$ is independently H, —CN, $C_{1-3}$aliphatic, —$OC_{1-3}$aliphatic, or —C(O)O—($C_{1-3}$aliphatic). In some further embodiments thereof, $R^{40}$ and $R^{41}$ can be independently —$C(O)NR^{31}R^{32}$ or —$C(O)NR^{12}R^{13}$.

The invention includes the compounds and any pharmaceutically acceptable salts thereof.

In some aspects, compounds of the invention are inhibitors of kinases, including TAK1.

In some aspects, the invention includes treating proliferative disease, particularly cancers, including cancers and inflammation disorders mediated or driven at least in part by TAK1 or for which an appropriate TAK1 inhibitor is effective, alone or in combination regimens with other agents.

The invention includes the compounds and salts thereof, and their physical forms, preparation of the compounds, useful intermediates, and pharmaceutical compositions and formulations thereof.

DETAILED DESCRIPTION

Compounds

In some aspects, a subgenus (1) of Formula 1 or 2 is provided wherein: $R^1$ is $_{9-10}$heterocyclic or substituted $_{9-10}$heterocyclic.

In some aspects, a subgenus (2) of Formula 1 or 2 or of subgenus 1 is provided wherein: $R^2$ is $_{4-9}$cyclic or substituted $_{4-9}$cyclic or $R^2$ is $_{4-7}$cyclic or substituted $_{4-7}$cyclic.

In some aspects, a subgenus (3) of Formula 1 or 2 or of subgenus 2 is provided wherein: $R^1$ is optionally substituted $_{5-6}$heteroaryl or phenyl and $R^1$ is fused to $R^4$ at two atoms; and $R^4$ is optionally substituted $_{5-6}$heterocyclic.

In some aspects, a subgenus (4) of Formula 1 or 2 or of any of subgenera 1-3 is provided wherein: each $R^{40}$ and $R^{41}$ is independently H, methyl, or methoxy.

In some aspects, a subgenus (5) of Formula 1 or 2 or of any of subgenera 1-4 is provided wherein: $R^{31}$ and $R^{32}$ are independently H or $C_{1-2}$aliphatic.

In some aspects, a subgenus (6) of Formula 1 or 2 or of any of subgenera 1-5 is provided wherein: $R^3$ is H or methyl or Cl.

In some aspects, a subgenus (7) of Formula 1 or 2 or of any of subgenera 1-6 is provided wherein: $R^3$ is H or Cl.

In some aspects, a subgenus (8) of Formula 1 or 2 or of any of subgenera 1-7 is provided wherein:

$R^1$ and $R^4$ are independently unsubstituted or substituted by one or more G1 groups;

each G1 is independently selected from —$PR^{12}R^{13}$, —$P(OR^{12})(OR^{13})$, —$PR^{12}(OR^{13})$, —$P(O)R^{12}R^{13}$, —$P(O)(OR^{12})(OR^{13})$, —$P(O)R^{12}(OR^{13})$, —$BR^{12}R^{13}$, —$B(OR^{12})(OR^{13})$, —$SF_5$, —$NHS(O)(R^{12})$=$NR^{13}$, or —$C_{1-6}$aliphatic-$S(O)(R^{12})$=$NR^{13}$;

or selected from halo, —CN, —$CF_3$, —$OCF_3$, —$NO_2$, $C_{1-12}$aliphatic, $_{3-12}$heterocyclic$C_{0-12}$aliphatic, $C_{4-12}$-carbocyclic$C_{0-12}$aliphatic;

or selected from —$OR^{12}$, —$S(O)_mR^{12}$, —$NR^{12}R^{13}$, —$SO_2NR^{12}R^{13}$, —$C(O)R^b$, —$C(O)NR^{12}R^{13}$, —$C(O)C(O)NR^{12}R^{13}$, —$C(O)OR^{12}$, —$C(O)C(O)OR^{12}$, —$OC(O)R^b$, —$NR^{12}C(O)R^b$, —$NR^{12}S(O)_2R^{13}$, —$(CR^{14}R^{15})_nC(O)R^b$, —$(CR^{14}R^{15})_nC(O)OR^{12}$, —$(CR^{14}R^{15})_nC(O)NR^{12}R^{13}$, —$(CR^{14}R^{15})_nS(O)_2NR^{12}R^{13}$, —$(CR^{14}R^{15})_nNR^{12}R^{13}$, —$(CR^{14}R^{15})_nOR^{12}$, —$(CR^{14}R^{15})_nS(O)_mR^{12}$, —$NR^{16}C(O)NR^{12}R^{13}$, —$NR^{16}S(O)_2NR^{12}R^{13}$ or —$NR^{16}S(O)NR^{12}R^{13}$;

each G1 is optionally substituted with 1 or 2 independent E1 substituents;

each E1 is independently selected from halo, —CN, —OH, —$NH_2$, —$NO_2$, oxo, —$CF_3$, —$OCF_3$, —$CO_2H$, —$S(O)_mH$, —$OC_{1-12}$aliphatic, $C_{1-12}$aliphatic, $_{3-12}$heterocyclic$C_{0-12}$aliphatic, $C_{4-12}$carbocyclic$C_{0-12}$aliphatic;

or selected from aryl$C_{3-12}$cycloalkyl, heteroaryl$C_{3-12}$cycloalkyl, $C_{3-12}$heterocycloalkyl$C_{3-12}$cycloalkyl, $C_{3-12}$cycloalkyl$C_{3-12}$cycloalkyl, $C_{1-12}$aliphatic$C_{3-12}$heterocycloalkyl, $C_{3-12}$heterocycloalkyl$C_{3-12}$heterocycloalkyl, aryl$C_{3-12}$heterocycloalkyl or heteroaryl $C_{3-12}$heterocycloalkyl, any of which is optionally substituted with one or more independent halo, —CN, —OH, —$NH_2$, $C_{1-10}$aliphatic which may be partially or fully halogenated, or —$OC_{1-10}$aliphatic which may be partially or fully halogenated;

each $R^{12}$, $R^{13}$, $R^{14}$, $R^{15}$, $R^{16}$, and $R^b$ is independently selected from H, $C_{1-12}$aliphatic, $_{3-12}$heterocyclic$C_{0-12}$aliphatic, $C_{4-12}$carbocyclic$C_{0-12}$aliphatic, aryl$C_{3-12}$cycloalkyl, heteroaryl$C_{3-12}$cycloalkyl, $C_{3-12}$heterocycloalkyl$C_{3-12}$cycloalkyl, $C_{3-12}$cycloalkyl$C_{3-12}$cycloalkyl, $C_{1-12}$alkyl$C_{3-12}$heterocycloalkyl, $C_{3-12}$heterocycloalkyl$C_{3-12}$heterocycloalkyl, aryl$C_{3-12}$heterocycloalkyl, or heteroaryl$C_{3-12}$heterocycloalkyl substituents;

each $R^{12}$ and $R^{13}$ pair, or $R^{14}$ and $R^{15}$ pair, respectively, is optionally taken together with the nitrogen atom to which they are attached to form a 3-12 membered saturated or unsaturated ring which optionally includes one or more heteroatoms selected from O, N, or $S(O)_m$;

wherein any H atom of $R^1$ or $R^4$ can be deuterium;
each m is independently 0-2; and
each n is independently 0-6.

In some aspects, a subgenus (9) of subgenus 8 is provided wherein: each G1 is independently selected from oxo, $C_{1-3}$aliphatic, amino, carboxyl, amido, $_{5-6}$cyclic, or hydroxy, any of which is optionally substituted, or selected from nitro or halogen.

In some aspects, a subgenus (10) of any of subgenera 8-9 is provided wherein: $R^1$ is $_{5-6}$heteroaryl or phenyl, either of which is optionally fused to $_{5-6}$cyclic and optionally substituted by one or more G1 groups.

In some aspects, a subgenus (11) of Formula 1 or 2 or of any of subgenera 2 or 4-7 is provided wherein: $R^1$ is $_{9-10}$heteroaryl. In some aspects thereof, $R^1$ can be substituted by one or more of oxo, halo, hydroxy, nitro, cyano, $C_{1-3}$aliphatic, or —$OC_{1-3}$aliphatic.

In some aspects, a subgenus (12) of Formula 1 or 2 or of any of subgenera 1-11 is provided wherein:

$R^2$ is $_{4-9}$cyclic (or $_{4-6}$cyclic) that is optionally substituted by one or more Q1 groups;

each Q1 is independently selected from —$PR^{17}R^{18}$, —$P(OR^{17})(OR^{18})$, —$PR^{17}(OR^{18})$, —$P(O)R^{17}R^{18}$, —$P(O)(OR^{17})(OR^{18})$, —$P(O)R^{17}(OR^{18})$, —$BR^{17}R^{18}$, —$B(OR^{17})(OR^{18})$, —$SF_5$, —$NHS(O)(R^{17})$=$NR^{18}$, or —$C_{1-6}$aliphatic-$S(O)(R^{17})$=$NR^{18}$;

or selected from halogen, —CN, —$CF_3$, —$OCF_3$, —$NO_2$, $C_{1-12}$aliphatic, $_{3-12}$heterocyclic$C_{0-12}$aliphatic, $C_{4-12}$-carbocyclic$C_{0-12}$aliphatic;

or selected from —$OR^{17}$, —$S(O)_mR^{17}$, —$NR^{17}R^{18}$, —$SO_2NR^{17}R^{18}$, —$C(O)R^c$, —$C(O)NR^{17}R^{18}$, —$C(O)C(O)NR^{17}R^{18}$, —$C(O)OR^{17}$, —$C(O)C(O)OR^{17}$, —$OC(O)R^c$, —$NR^{17}C(O)R^c$, —$NR^{17}S(O)_2R^{18}$, —$(CR^{19}R^{20})_nC(O)R^c$, —$(CR^{19}R^{20})_nNR^{17}R^{18}$, —$(CR^{19}R^{20})_nOR^{17}$, —$(CR^{19}R^{20})_nC(O)NR^{17}R^{18}$, —$(CR^{19}R^{20})_nS(O)_2NR^{17}R^{18}$, —$(CR^{19}R^{20})_nNR^{17}R^{18}$, —$(CR^{19}R^{20})_nOR^{17}$, —$(CR^{19}R^{20})_nS(O)_mR^{17}$, —$NR^{21}C(O)NR^{17}R^{18}$, —$NR^{21}S(O)_2NR^{17}R^{18}$ or —$NR^{21}S(O)NR^{17}R^{18}$;

wherein each Q1 is optionally substituted with 1-2 independent F1 substituents;

each F1 is independently selected from halogen, —CN, —OH, —$NH_2$, —$NO_2$, oxo, —$CF_3$, —$OCF_3$, —$CO_2H$, —$S(O)_mH$, —$OC_{1-12}$aliphatic, $C_{1-12}$aliphatic, $_{3-12}$heterocyclic$C_{0-12}$aliphatic, $C_{4-12}$-carbocyclic$C_{0-12}$aliphatic;

or from aryl$C_{3-12}$cycloalkyl, heteroaryl$C_{3-12}$cycloalkyl, $C_{3-12}$heterocycloalkyl $C_{3-12}$cycloalkyl, $C_{3-12}$cycloalkyl $C_{3-12}$cycloalkyl, $C_{1-12}$aliphatic$C_{3-12}$heterocycloalkyl, $C_{3-12}$heterocycloalkyl$C_{3-12}$heterocycloalkyl, aryl$C_{3-12}$heterocycloalkyl or heteroaryl $C_{3-12}$heterocycloalkyl, any of which is optionally substituted with one or more independent halo, —CN, —OH, —$NH_2$, $C_{1-10}$aliphatic which may be partially or fully halogenated, or —$OC_{1-10}$ aliphatic which may be partially or fully halogenated;

each $R^{17}$-$R^{21}$ and $R^c$ is independently selected from H, $C_{1-12}$aliphatic, $_{3-12}$heterocyclic$C_{0-12}$aliphatic, $C_{4-12}$carbocyclic$C_{0-12}$aliphatic, aryl$C_{3-12}$cycloalkyl, heteroaryl$C_{3-12}$cycloalkyl, $C_{3-12}$heterocycloalkyl$C_{3-12}$cycloalkyl, $C_{3-12}$cycloalkyl$C_{3-12}$cycloalkyl, $C_{1-12}$alkyl$C_{3-12}$heterocycloalkyl, $C_{3-12}$heterocycloalkyl$C_{3-12}$heterocycloalkyl, aryl$C_{3-12}$heterocycloalkyl, or heteroaryl $C_{3-12}$heterocycloalkyl substituents;

each $R^{17}$ and $R^{18}$ pair, or $R^{19}$ and $R^{20}$ pair, respectively, is optionally taken together with the nitrogen atom to which they are attached to form a 3-12 membered saturated or unsaturated ring, wherein said ring optionally includes one or more heteroatoms selected from O, N, or $S(O)_m$;

wherein any H atom of $R^2$ can be deuterium;
each m is independently 0-2; and
each n is independently 0-6.

In some aspects, a subgenus (13) of Formula 1 or 2 or of any of subgenera 1-11 is provided wherein:

$R^2$ is $_{5-6}$heterocyclic that is optionally substituted by 1-2 Q1 groups;

each Q1 is independently selected from halo, —CN, —NO$_2$, oxo, —CF$_3$, —OCF$_3$, C$_{1-12}$aliphatic, —(CR$^{19}$R$^{20}$)$_n$C(O)R$^c$, —(CR$^{19}$R$^{20}$)$_n$C(O)OR$^{17}$, —(CR$^{19}$R$^{20}$)$_n$C(O)NR$^{17}$R$^{18}$, —C(O)C(O)NR$^{17}$R$^{18}$, —(CR$^{19}$R$^{20}$)$_n$S(O)$_2$NR$^{17}$R$^{18}$, —(CR$^{19}$R$^{20}$)$_n$NR$^{17}$R$^{18}$, —(CR$^{19}$R$^{20}$)$_n$OR$^{17}$, —(CR$^{19}$R$^{20}$)$_n$S(O)$_m$R$^{17}$, —NR$^{21}$C(O)NR$^{17}$R$^{18}$, —NR$^{21}$S(O)$_2$NR$^{17}$R$^{18}$ or —NR$^{21}$S(O)NR$^{17}$R$^{18}$;

each $R^{17}$-$R^{21}$ and $R^c$ is independently selected from H, C$_{1-12}$aliphatic, arylC$_{0-12}$aliphatic, heteroarylC$_{0-12}$aliphatic, C$_{3-12}$cycloalkylC$_{0-12}$aliphatic, C$_{3-12}$heterocycloalkylC$_{0-12}$aliphatic, arylC$_{3-12}$cycloalkyl, heteroarylC$_{3-12}$cycloalkyl, C$_{3-12}$heterocycloalkylC$_{3-12}$cycloalkyl, C$_{3-12}$cycloalkylC$_{3-12}$cycloalkyl, C$_{1-12}$alkylC$_{3-12}$heterocycloalkyl, C$_{3-12}$heterocycloalkylC$_{3-12}$heterocycloalkyl, arylC$_{3-12}$heterocycloalkyl, or heteroarylC$_{3-12}$heterocycloalkyl substituents;

each m is independently 0-2; and each n is independently 0-6.

In some aspects, a subgenus (14) of any of subgenera 12-13 is provided wherein: $R^2$ is a six membered saturated or partially unsaturated ring containing 0-2 heteroatoms and substituted by 1-2 Q1 groups.

In some aspects, a subgenus (15) of Formula 1 or 2 or of any of subgenera 1-11 is provided having the formula:

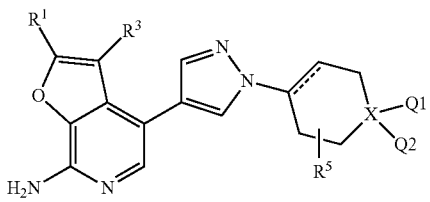

wherein the dashed line indicates a single or double bond;

$R^3$ is H or Cl;

$R^5$ can be at any open position and is selected from C$_{0-6}$aliphatic optionally substituted by —N(C$_{0-6}$aliphatic)(C$_{0-6}$aliphatic), —S(O)$_{0-2}$—C$_{0-6}$aliphatic, or —OC$_{0-6}$aliphatic;

X is >O and Q1 and Q2 are absent, or

X is >C, Q1 is H or C$_{1-6}$aliphatic optionally substituted by one or more halogen atoms, and Q2 is OH or —OC$_{1-6}$aliphatic optionally substituted by one or more halogen atoms;

X is >N, Q1 is absent, and Q2 is selected from H, C$_{1-6}$aliphatic, R$^8$O—C$_{2-6}$aliphatic, R$^8$R$^9$N—C$_{2-6}$aliphatic, R$^8$S(O)$_{0-2}$—C$_{2-6}$aliphatic, —C(O)R$^a$, R$^8$O—C$_{0-6}$aliphaticC(O)—, R$^8$R$^9$N—C$_{0-6}$aliphaticC(O)—, R$^8$S(O)$_{0-2}$C$_{0-6}$aliphaticC(O)—, —CO$_2$R$^8$, —C(O)NR$^8$R$^9$, —S(O)$_{0-2}$R$^8$, —SO$_2$NR$^8$R$^9$, —C(S)OR$^8$, C$_{3-6}$cycloalkylC$_{0-6}$aliphatic, C$_{3-6}$cycloalkenylC$_{1-6}$aliphatic, C$_{3-6}$heterocycloalkylC$_{0-6}$aliphatic, arylC$_{0-6}$aliphatic, heteroarylC$_{0-6}$aliphatic, C$_{1-6}$aliphaticC$_{3-6}$cycloalkyl, C$_{3-6}$cycloalkylC$_{3-6}$cycloalkyl, C$_{3-6}$cycloalkenylC$_{3-6}$cycloalkyl, C$_{3-6}$heterocycloalkylC$_{3-6}$cycloalkyl, arylC$_{3-6}$cycloalkyl, heteroarylC$_{3-6}$cycloalkyl, C$_{1-6}$aliphaticC$_{3-6}$heterocycloalkyl, C$_{3-6}$cycloalkylC$_{3-6}$heterocycloalkyl, C$_{3-6}$cycloalkenylC$_{3-6}$heterocycloalkyl, C$_{3-6}$heterocycloalkylC$_{3-6}$heterocycloalkyl, arylC$_{3-6}$heterocycloalkyl, or heteroarylC$_{3-6}$heterocycloalkyl, any of which is optionally substituted by one or more halogen atoms; and each $R^a$, $R^8$, and $R^9$ is independently selected from H or C$_{1-6}$aliphatic optionally substituted by one or more C$_{0-3}$alkoxy or halogen.

In some aspects, a subgenus (16) of subgenus 15 is provided wherein:

X is >N;

Q1 is selected from H, —(CR$^8$R$^9$)$_n$C(O)R$^a$—OR$^{10}$, —(CR$^8$R$^9$)$_n$C(O)R$^{10}$, —(CR$^8$R$^9$)$_n$C(O)OR$^{10}$, —(CR$^8$R$^9$)$_n$C(O)NR$^{10}$R$^{11}$, —(CR$^8$R$^9$)$_n$S(O)$_{0-2}$NR$^{10}$R$^{11}$, —(CR$^8$R$^9$)$_n$NR$^{10}$R$^{11}$, —(CR$^8$R$^9$)$_n$OR$^{10}$, —(CR$^8$R$^9$)$_n$S(O)$_{0-2}$R$^{10}$, C$_{1-6}$aliphatic, or C$_{1-6}$aliphatic-OC$_{0-6}$aliphatic, wherein any of the foregoing can be singly or multiply halogen substituted;

each $R^a$ and $R^8$-$R^{11}$ is independently selected from H or C$_{1-6}$aliphatic optionally substituted by one or more C$_{0-3}$alkoxy or halogen;

each n is independently 0-6; and each $R^8$ and $R^9$ pair is optionally taken together to form a 3-6 membered saturated or unsaturated ring, wherein said ring optionally includes one or more heteroatoms selected from O, N, or S(O)$_{0-2}$.

In some aspects, a subgenus (17) of subgenus 16 is provided wherein: Q1 is H, C$_{1-6}$aliphatic, —C(O)R$^a$, wherein any of the foregoing can be singly or multiply halogen substituted.

In some aspects, a subgenus (18) of subgenus 15 is provided wherein: X is >C; Q1 is H or C$_{1-3}$aliphatic; and Q2 is OH.

In some aspects, a subgenus (19) of subgenus 15 is provided having the formula:

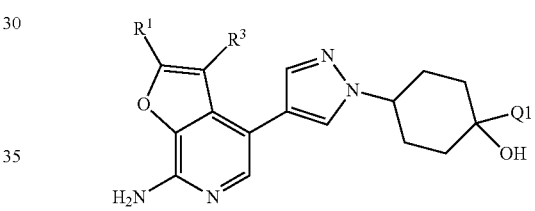

wherein Q1 is H or C$_{1-3}$aliphatic.

In some aspects, a subgenus (20) of Formula 1 is provided, having the formula:

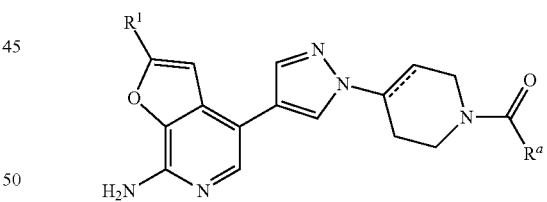

wherein:

$R^1$ is optionally substituted $_{9-10}$unsaturated heterocyclic; and $R^a$ is H or C$_{1-6}$aliphatic optionally substituted by one or more C$_{0-3}$alkoxy or halogen. In some aspects, a subgenus (21) of subgenus 20 is provided wherein R1 is $_{9-10}$unsaturated heterocyclic optionally substituted by 1-2 independent oxo, halogen, or C$_{1-3}$aliphatic groups.

In some aspects, a subgenus (22) of subgenus 20 is provided wherein R1 is optionally substituted $_{9-10}$heteroaryl.

In some aspects, a subgenus (23) of subgenus 20 is provided wherein R1 is $_{9-10}$heteroaryl.

In some aspects, a subgenus (24) of Formula 1 is provided wherein: $R^1$ is phenyl optionally substituted by 1-2 independent —NO$_2$, —OH, or —CN.

In some aspects, a subgenus (25) of Formula 1 or 2 or of any of subgenera 1-24 is provided wherein:

$R^1$ is selected from azaindolyl, quinolinyl, isoquinolinyl, isoindolinonyl, indazolyl, benzothiophenyl, thienopyridinyl, benzothiazoyl, benzoisothiazoyl, benzothiadiazoyl, or indolyl. In some aspects thereof, $R^1$ is optionally substituted by one or more —$NH_2$, —$CONH_2$, —COOR, —CN, halogen, or lower alkyl.

In some aspects, a subgenus (26) of Formula 1 or 2 or of any of subgenera 1-25 is provided wherein: the compound exhibits inhibition of TAK1 in a biochemical assay with an $IC_{50}$ of about 100 nM or less.

Each variable definition above includes any subset thereof and the compounds of Formula I include any combination of such variables or variable subsets.

In some aspects, the invention includes any of the compound examples herein and pharmaceutically acceptable salts thereof.

The invention includes the compounds and salts thereof, and their physical forms, preparation of the compounds, useful intermediates, and pharmaceutical compositions and formulations thereof.

The compounds of the invention and term "compound" in the claims include any pharmaceutically acceptable salts or solvates, and any amorphous or crystal forms, or tautomers, whether or not specifically recited in context.

The invention includes the isomers of the compounds. Compounds may have one or more asymmetric carbon atoms can exist as two or more stereoisomers. Where a compound of the invention contains an alkenyl or alkenylene group, geometric cis/trans (or Z/E) isomers are possible. Where the compound contains, for example, a keto or oxime group or an aromatic moiety, tautomeric isomerism ('tautomerism') can occur. A single compound may exhibit more than one type of isomerism.

The present invention includes any stereoisomers, even if not specifically shown, individually as well as mixtures, geometric isomers, and pharmaceutically acceptable salts thereof. Where a compound or stereocenter is described or shown without definitive stereochemistry, it is to be taken to embrace all possible individual isomers, configurations, and mixtures thereof. Thus, a material sample containing a mixture of stereoisomers would be embraced by a recitation of either of the stereoisomers or a recitation without definitive stereochemistry. Also contemplated are any cis/trans isomers or tautomers of the compounds described.

Included within the scope of the invention are all stereoisomers, geometric isomers and tautomeric forms of the inventive compounds, including compounds exhibiting more than one type of isomerism, and mixtures of one or more thereof.

When a tautomer of the compound of Formula (I) exists, the compound of formula (I) of the present invention includes any possible tautomers and pharmaceutically acceptable salts thereof, and mixtures thereof, except where specifically stated otherwise.

The compounds of the invention are not limited to those containing all of their atoms in their natural isotopic abundance. The present invention includes compounds wherein one or more hydrogen, carbon or other atoms are replaced by different isotopes thereof. Such compounds can be useful as research and diagnostic tools in metabolism pharmacokinetic studies and in binding assays. A recitation of a compound or an atom within a compound includes isotopologs, i.e., species wherein an atom or compound varies only with respect to isotopic enrichment and/or in the position of isotopic enrichment. For nonlimiting example, in some cases it may be desirable to enrich one or more hydrogen atoms with deuterium (D) or to enrich carbon with $^{13}C$. Other examples of isotopes suitable for inclusion in the compounds of the invention include isotopes of hydrogen, chlorine, fluorine, iodine, nitrogen, oxygen, phosphorus, and sulfur. Certain isotopically-labeled compounds of the invention may be useful in drug and/or substrate tissue distribution studies. Substitution with heavier isotopes such as deuterium may afford certain therapeutic advantages resulting from greater metabolic stability, for example, increased in vivo half-life or reduced dosage requirements, and hence may be preferred in some circumstances. Thus, substitution with deuterium, for example may be preferred at sites of known or suspected metabolism. Substitution with positron emitting isotopes may be useful in Positron Emission Topography (PET) studies for examining substrate receptor occupancy.

Further, the compounds may be amorphous or may exist or be prepared in various crystal forms or polymorphs, including solvates and hydrates. The invention includes any such forms provided herein, at any purity level. A recitation of a compound per se means the compound regardless of any unspecified stereochemistry, physical form and whether or not associated with solvent or water.

The compounds of the invention may exist in both unsolvated and solvated forms. The term 'solvate' is used herein to describe a molecular complex comprising the compound of the invention and one or more pharmaceutically acceptable solvent molecules, for example, ethanol. The term 'hydrate' is employed when the solvent is water. Pharmaceutically acceptable solvates in accordance with the invention include hydrates and solvates wherein the solvent of crystallization may be isotopically substituted, e.g., $D_2O$, $d_6$-acetone, $d_6$-DMSO.

Also included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionized, partially ionized, or non-ionized.

The invention includes prodrugs of compounds of the invention which may, when administered to a patient, be converted into the inventive compounds, for example, by hydrolytic cleavage. Prodrugs in accordance with the invention can, for example, be produced by replacing appropriate functionalities present in the inventive compounds with certain moieties known to those skilled in the art as 'pro-moieties' as known in the art. Particularly favored derivatives and prodrugs of the invention are those that increase the bioavailability of the compounds when such compounds are administered to a patient, enhance delivery of the parent compound to a given biological compartment, increase solubility to allow administration by injection, alter metabolism or alter rate of excretion.

A pharmaceutically acceptable salt of the inventive compounds can be readily prepared by mixing together solutions of the compound and the desired acid or base, as appropriate. The salt may precipitate from solution and be collected by filtration or may be recovered by evaporation of the solvent. The degree of ionization in the salt may vary from completely ionized to almost non-ionized.

Compounds that are basic are capable of forming a wide variety of salts with various inorganic and organic acids. The acids that can be used to prepare pharmaceutically acceptable acid addition salts of such basic compounds are those that form acceptable acid addition salts. When the compound of the present invention is basic, its corresponding salt can be conveniently prepared from pharmaceutically acceptable non-toxic acids, including inorganic and organic acids. Such acids include, for example, acetic, benzenesulfonic, benzoic, camphorsulfonic, citric, ethanesulfonic, formic, fumaric, gluconic, glutamic, hydrobromic, hydrochloric, isethionic, lactic, maleic, malic, mandelic, methanesulfonic, mucic, nitric, pamoic, pantothenic, phosphoric, succinic, sulfuric, tartaric, p-toluenesulfonic acid and the like. Other salts are aspartate, besylate, bicarbonate/carbonate, bisulphate/sulfate, borate, camsylate, edisylate, gluceptate, glucuronate, hexafluorophosphate, hibenzate, hydrobromide/bromide, hydroiodide/iodide, malonate, methylsulfate, naphthylate, 2-napsylate, nicotinate, orotate, oxalate, palmitate, phosphate/hydrogen, phosphate/dihydrogen, phosphate, saccharate, stearate, tartrate, tosylate, and trifluoroacetate.

When the compound of the present invention is acidic, its corresponding salt can be conveniently prepared from pharmaceutically acceptable bases, including inorganic bases and organic bases. Salts derived from such inorganic bases include aluminum, ammonium, calcium, copper (ic and ous), ferric, ferrous, lithium, magnesium, manganese (ic and ous), potassium, sodium, zinc and the like salts. Salts derived from pharmaceutically acceptable organic bases include salts of primary, secondary, and tertiary amines, as well as cyclic amines and substituted amines such as naturally occurring and synthesized substituted amines. Other pharmaceutically acceptable organic bases from which salts can be formed include ion exchange resins such as, for example, arginine, betaine, caffeine, choline, N',N'-dibenzylethylenediamine, diethylamine, 2-diethylaminoethanol, 2-dimethylaminoethanol, ethanolamine, ethylenediamine, N-ethylmorpholine, N-ethylpiperidine, glucamine, glucosamine, histidine, hydrabamine, isopropylamine, lysine, methylglucamine, morpholine, piperazine, piperidine, polyamine resins, procaine, purines, theobromine, triethylamine, trimethylamine, tripropylamine, tromethamine and the like. Other examples include benzathine, diolamine, glycine, meglumine, and olamine.

Preparation

The invention includes the intermediates, examples, and synthetic methods described herein.

Compounds of the invention may be prepared by the general methods described below in conjunction with the adaptable specific methods of the examples, together with synthetic methods and knowledge known in the art. When a general or exemplary synthetic procedure is referred to, one skilled in the art can readily determine appropriate reagents, if not indicated, extrapolating from the general or exemplary procedures.

In the descriptions below, the substituents in the schemes are defined as above, unless otherwise indicated or modified by the accompanying description. Representation of an unsubstituted position in structures shown or referred to in the general procedures is for convenience and does not preclude substitution as described elsewhere herein. For specific groups that can be present, either as R groups in the general procedures or as optional substituents not shown, refer to the descriptions in the remainder of this document, including the claims, summary and detailed description.

During any of the following synthetic sequences it may be necessary and/or desirable to protect sensitive or reactive groups on any of the molecules concerned. This can be achieved by means of conventional protecting groups, such as those described in T. W. Greene, Protective Groups in Organic Chemistry, John Wiley & Sons, 1981; T. W. Greene and P. G. M. Wuts, Protective Groups in Organic Chemistry, John Wiley & Sons, 1991, and T. W. Greene and P. G. M. Wuts, Protective Groups in Organic Chemistry, John Wiley & Sons, 1999, which are hereby incorporated by reference. Isolation and purification of the products can be accomplished by standard procedures, which are known to a chemist of ordinary skill.

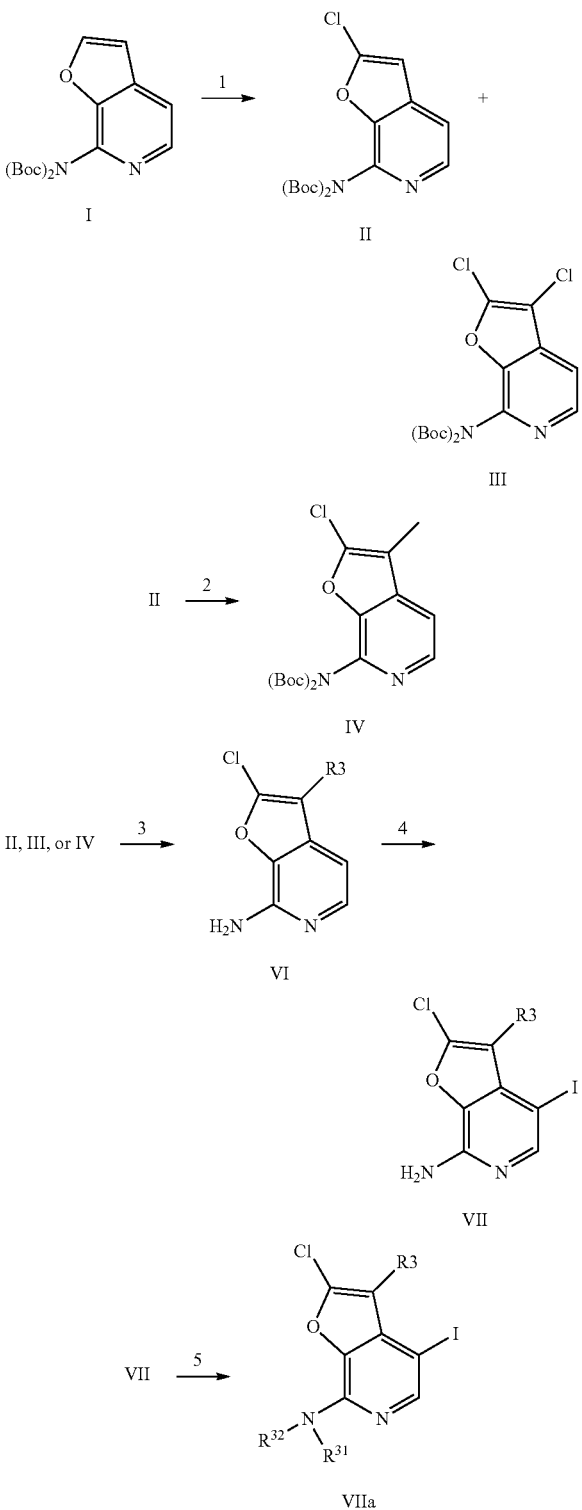

Scheme 1

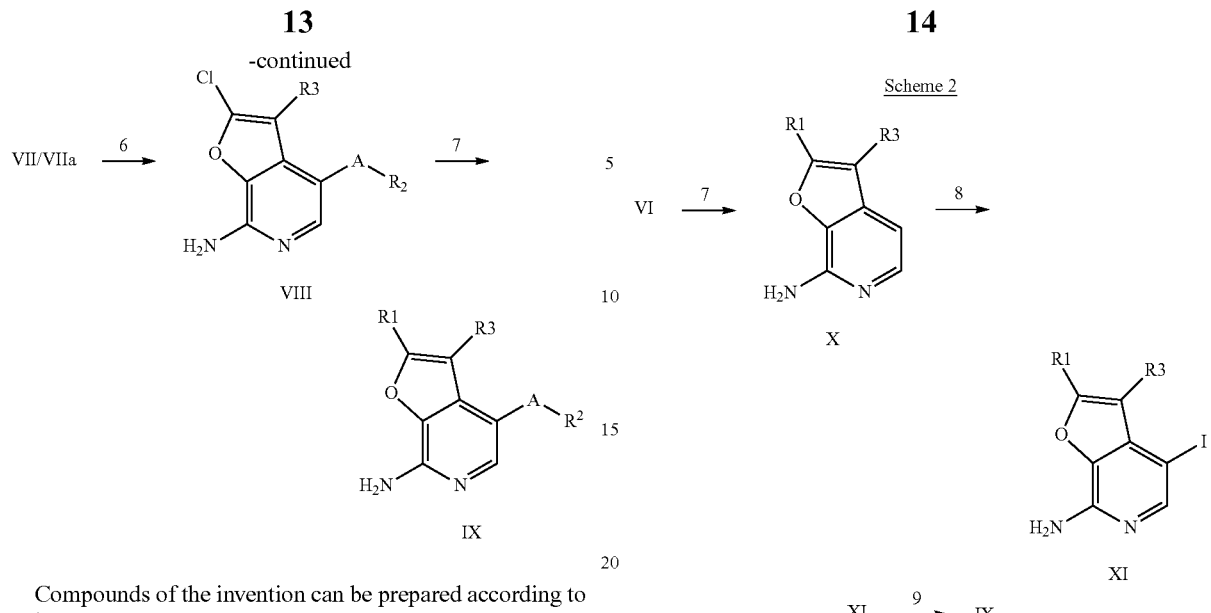

Compounds of the invention can be prepared according to Scheme 1.

Compound I can be obtained according to the preparations herein. Compound I can be chlorinated as in Step 1 to attain II and III with a chlorinating agent such as $Cl_3CCCl_3$ in the presence of a strong base such as LDA. For example, to a stirring cooled solution of the starting material (e.g., THF, −50 to −78° C.) can be added at least one eq. of LDA (e.g., about 2M). After stirring for about 1 h, the $Cl_3CCCl_3$ (e.g., about 4 eq.) can be added. The reaction can be quenched with water or aqueous HCl (e.g., 4 N) at rt, followed by an appropriate work-up and purification.

Compounds IV can be obtained from II as in Step 2 by treatment with an alkylating agent such as MeI and a strong base such as LDA. For example, to a stirring cooled solution of the starting material (e.g., THF, −50 to −78° C.) can be added at least one eq. of about LDA (e.g., about 2 M). After stirring for about 1 h, the MeI (e.g., about 1.5 eq.) can be added. The reaction can be quenched with water at rt, followed by an appropriate work-up and purification.

Compounds VI can be prepared by deprotecting II, III, or IV, as in Step 3, by standard methods, such as by treating a cooled solution of the starting material with slowly added 4N HCl, followed by heating, and appropriate work-up and purification.

Compounds VII can be prepared, as in Step 4, such as by appropriate treatment (e.g., at rt) with an iodinating agent such as NIS (e.g., about 1 eq) in a solvent such as acetonitrile, followed by appropriate work-up and purification.

At this or other stage in preparation, an amine such as VII can be alkylated as in Step 5 such as with an appropriate alkyl halide such as methyl or ethyl iodide in the presence of strong base such as NaH.

Compounds VIII can be prepared, as in Step 6, such as under appropriate coupling conditions to install a desired heterocycle-containing group, wherein A-R² can be that of Formula 1 or a precursor thereto. The skilled artisan may consider, e.g., palladium-catalyzed Suzuki or Stille couplings, wherein about 1 eq. of the desired coupling reagent is used in conjunction with a suitable palladium catalyst and a base, followed by appropriate work-up and purification.

Compounds IX can be prepared, as in Step 7, also by employing generally known coupling conditions. Compounds IX can be further derivatized to attain additional compounds of the invention.

Compounds IX can alternatively be prepared from Compounds VI, according to Scheme 2.

Compounds X can be prepared, as in Step 7, by appropriate coupling conditions, as described above for Compound VIII.

Compounds XI can be prepared, as in Step 8, by halogenating, such as with NIS using methods such as described above for Compound VII.

Compounds IX can be prepared, as in Step 9, by appropriate coupling conditions, as described above for Compounds VIII. Compounds IX can be further derivatized to attain additional compounds of the invention.

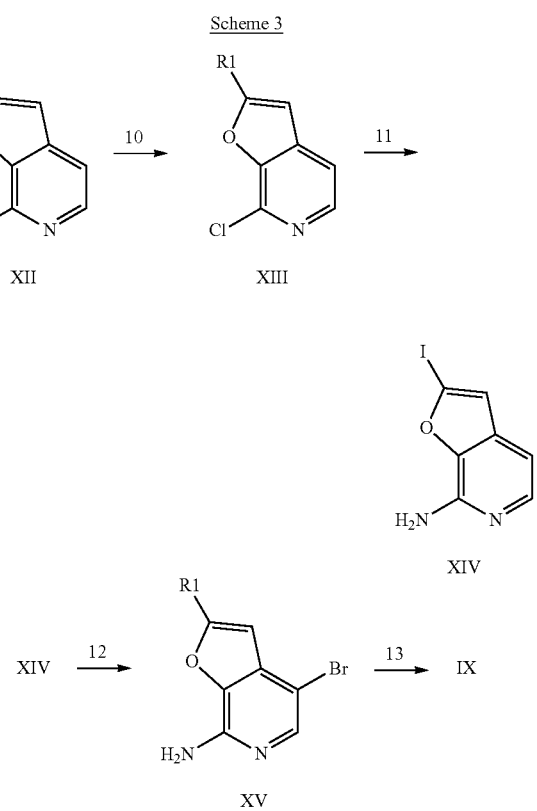

Compound XII can be prepared as described elsewhere herein. Compounds IX wherein R³ is H can be prepared from XII according to Scheme 3.

Compounds XIII can be prepared from XII, as in Step 10, under appropriate coupling conditions, such as described above for VIII.

Compounds XIV can then be obtained, as in Step 11, under amination conditions, for example, by treating XIII with excess hydrazine under reflux as first step, followed by Raney nickel at reflux, and appropriate work-up and purification.

Compounds XV can be obtained, as in Step 12, by brominating XIV with a brominating agent such as NBS (e.g., about 1 eq.) under appropriate conditions.

Compound IX wherein R³ is H, can be obtained from XV under appropriate coupling conditions, such as described above for VIII.

Compound I can be borylated as in Step 14 to attain XVI by appropriate treatment (e.g. at −78° C.) with a strong base such as LDA and a borylating agent such as trimethyl borate, followed by hydrolysis e.g. with aqueous HCl at rt.

Compound I may alternatively be stannylated as in Step 15 by appropriate treatment (e.g. at −78° C.) with a strong base such as LDA and a stannylating agent such as trimethyltin chloride.

Compounds XVIII can be prepared, as in Step 16, under appropriate coupling conditions as described above for Compounds IX in Scheme 1.

Compounds XIV can be prepared, as in Step 17, by deprotecting Compounds XVIII by standard methods, as described above for Compounds VI. As noted above, the amine can be derivatized, e.g., alkylated.

Compounds XIX can be prepared, as in Step 18, by appropriate treatment with an iodinating agent, as described above for Compounds VII.

Compounds IX can be prepared, as in Step 19, under appropriate coupling conditions as described above for Compounds VIII. Compound IX can be further derivatized to attain additional compounds of the invention.

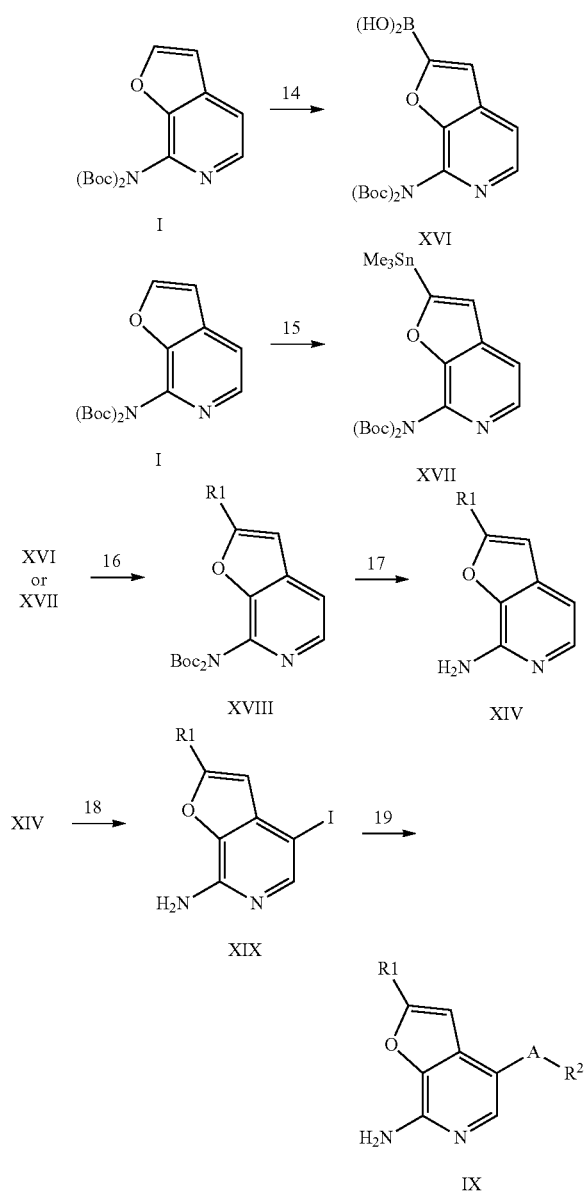

Scheme 4

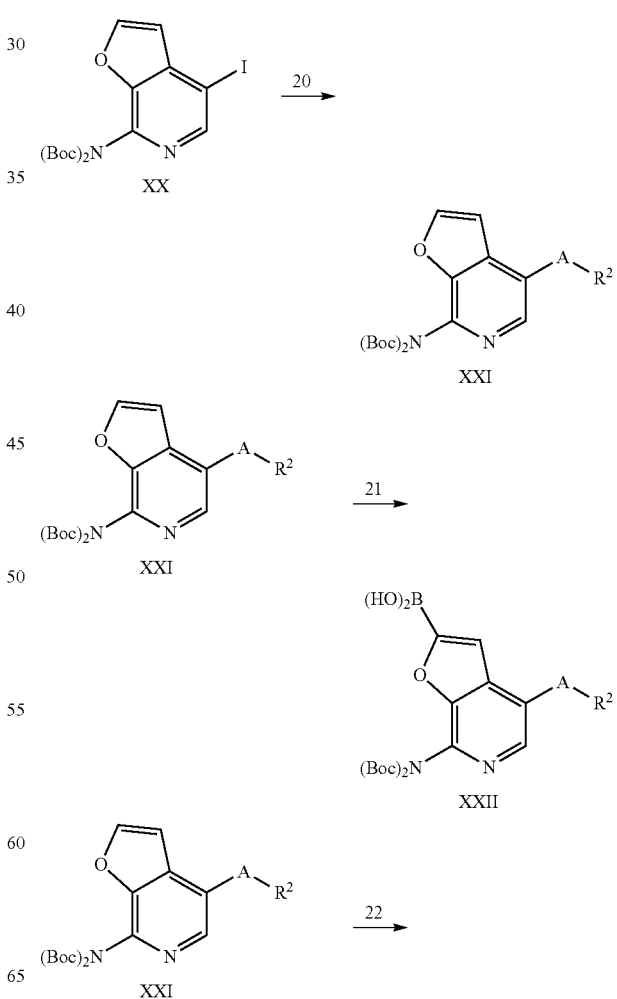

Scheme 5

Compounds IX can alternatively be prepared from Compound I, according to Scheme 4.

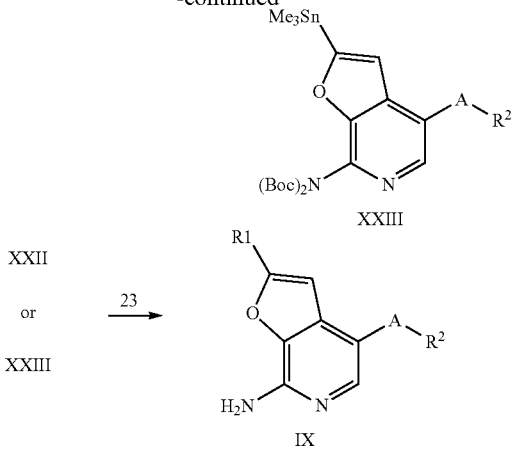

Compounds IX can alternatively be prepared from Compound XX, according to Scheme 5.

Compounds XXI can be prepared, as in Step 20, under appropriate coupling conditions as described above for Compounds VIII in Scheme 1. Compound XXI can be borylated as in Step 21 to attain XXII by appropriate treatment (e.g. at −78° C.) with a strong base such as LDA and a borylating agent such as trimethyl borate, followed by hydrolysis, e.g., with water or aqueous HCl at rt.

Compounds XXI may alternatively be stannylated as in Step 15 to attain XXIII by appropriate treatment (e.g. at −78° C.) with a strong base such as LDA and a stannylating agent such as trimethyltin chloride.

Compounds IX can be prepared, as in Step 23, under appropriate coupling conditions as described above for Compounds VIII, and then by deprotecting by standard methods, as described above for Compounds VI. Compounds IX can be further derivatized to attain additional compounds of the invention.

As will be apparent to the skilled artisan, the synthetic route/sequence can be modified as desired for the preparation of any desired compound. The functional groups present in $R^1$, $R^2$, $R^3$, etc., may be further modified to modified according to the skill in the art such as Comprehensive Organic Transformations, by R. C. Larock.

Preparations

Unless otherwise noted, all materials/reagents were obtained from commercial suppliers and used without further purification. Reactions were monitored by thin layer chromatography (TLC) on silica gel 60 $F_{254}$ (0.2 mm) precoated aluminum foil or glass-backed and visualized using UV light. Flash chromatography (alternatively called "ISCO chromatography") was performed using an ISCO CombiFlash Rf 4× Organic Purification System or equivalent with RediSep normal-phase silica gel cartridges. Preparative TLC was performed on Whatman LK6F Silica Gel 60 Å size 20×20 cm plates with a thickness of 1000 μm or equivalent. Hydromatrix (=diatomaceous earth) was purchased from Varian.

$^1$H NMR (300 or 400 MHz) and $^{13}$C NMR (100.6 MHz) spectra were recorded on Bruker or Varian spectrometers at RT with TMS or the residual solvent peak as the internal standard. The line positions or multiples are given in (δ) and the coupling constants (J) are given as absolute values in Hertz (Hz). The multiplicities in $^1$H NMR spectra are abbreviated as follows: s (singlet), d (doublet), t (triplet), q (quartet), quint (quintet), m (multiplet), $m_c$ (centered multiplet), br or broad (broadened), AA'BB'. The signal multiplicities in $^{13}$C NMR spectra were determined using the DEPT135 experiment and are abbreviated as follows: +(CH or $CH_3$), —($CH_2$), $C_{quart}$ (C).

Preparative HPLC purifications ("MDP") were performed on a Waters® Mass-Directed Purification System equipped with 2525 Binary Gradient Module, 2767 Sample Manager, a Column Fluidics Organizer (CFO), 2996 Photodiode Array Detector, a 515 pump for column regeneration, a reagent manager for the makeup flow, a 515 pump for at-column-dilution, ZQ™ single-quadrupole Mass Detector equipped with a Z-spray electrospray interface, controlled by MassLynx™ Version 4.1 with FractionLynx™ software. All purification work was completed using a parallel dual-column Luna C18(2) 21×150 mm, 5 μm LC/MS system and ARW (accelerated retention window). The mobile phases were water (0.1% TFA) and acetonitrile (0.1% TFA); all reagents used were of HPLC grade. The flow rate was 30 mL/min. After the columns, a 1:1000 LC packings flow splitter allowed transfer of a small portion of the eluent into the UV detector and, subsequently, a 10% portion into the ZQ MS. The electrospray source was set at 3.0 kV capillary voltage, 30 V cone voltage, 110° C. source temperature, 350° C. desolvation temperature, 600 L/h desolvation gas flow, and 60 L/h cone gas flow. For the analyzer, the multiplier was set at 550 for preparative tune method.

Analytical LC-MS data was collected on ZQ3, TOF, or HPLC instruments with a mobile phase of Acetonitrile (A) and 0.01% Formic Acid in HPLC grade water (B).

ZQ3 is an Agilent 1100 HPLC equipped with an ESA CAD secondary detector and Waters Micromass ZQ2000 for ionization. The system uses the following conditions for either 5 or 4 min run time.

5 minute run: Xterra MS C18 column, 5 μm, 4.6×50 mm. The flow rate is 1.3 mL/min, the run time is 5 min, and the gradient profiles are 0.00 min 5% A, 3.00 min 90% A, 3.50 min 90% A, 4.00 min 5% A, 5.00 min 5% A for polar__5 min; and 0.00 min 25% A, 3.00 min 99% A, 3.50 min 99% A, 4.00 min 25% A, 5.00 min 25% A for nonpolar__5 min. The flow rate is 1.0 mL/min, the run time is 5 min, and the gradient profiles are 0.00 min 1% A, 0.3 min 1% A, 3.00 min 90% A, 3.50 min 90% A, 4.00 min 1% A, 5.00 min 1% A for vvpolar__5 min. The Waters Micromass ZQ2000 instrument utilized electrospray ionization in positive (ES+) or negative (ES−) mode. The Waters Micromass ZQ2000 instrument can also utilize atmospheric pressure chemical ionization in positive (AP+) or negative (AP−) mode.

4 minute run: XTerra MS C18 column, 3.5 μm, 4.6×50 mm. The flow rate is 1.0 mL/min, the run time is 4 min, and the gradient profiles are 0.00 min 5% A, 2.00 min 90% A, 2.50 min 90% A, 3.00 min 5% A, 4.00 min 5% A for polar__4 min; and 0.00 min 25% A, 2.00 min 99% A, 2.50 min 99% A, 3.00 min 25% A, 4.00 min 25% A for nonpolar__4 min.

TOF is a Waters HPLC-LCT Premier system consisting of an ACQUITY HPLC equipped with an ACQUITY Sample Manager and LCT Premier XE MS for ionization. It uses an ACQUITY HPLC BEH® C18 2.1×50 mm, 1.7 μm column with a mobile phase of Acetonitrile (A) and 0.01% formic acid in water (B). The flow rate is 0.6 mL/min, run time is 3 min, and the gradient profile is 0.00 min 5% A, 0.2 min 5% A, 1.50 min 90% A, 2 min 90% A, 2.2 min 5% A, 5 min 5% A for polar__3 min; and 0.00 min 25% A, 0.2 min 25% A, 1.50 min 99% A, 2 min 99% A, 2.2 min 25% A, 3 min 25% A for nonpolar__3 min. The LCT Premier XE MS utilized electrospray ionization in positive (ES+) or negative (ES−), as well positive (AP+) or negative (AP−) in W mode.

HPLC is an ACQUITY sample manager attached to an ACQUITY SQ detector. ACQUITY UPLC® BEH C18 1.7

μm 2.1×50 mm or 2.1×100 mm column was heated to 60° C. with detection at 254 nm and electrospray ionization in positive mode was used. The table below lists the mobile phase gradient (solvent A: 0.1% formic acid in water; solvent B: 0.1% formic acid in acetonitrile) and flow rate for the analytical HPLC program.

| Analytical Method: Purity_2 min (column: 2.1 × 50 mm) | | | |
|---|---|---|---|
| Time (min) | A % | B % | Flow Rate (mL/min) |
| 0.00 | 95.0 | 5.0 | 1.00 |
| 1.50 | 1.0 | 99.0 | 1.00 |
| 1.80 | 1.0 | 99.0 | 1.00 |
| 2.00 | 95.0 | 5.0 | 1.00 |

| Analytical Method: Analytical_2 min (column: 2.1 × 100 mm) | | | |
|---|---|---|---|
| Time (min) | A % | B % | Flow Rate (mL/min) |
| 0.00 | 85.0 | 15.0 | 0.80 |
| 1.50 | 1.0 | 99.0 | 0.80 |
| 1.80 | 1.0 | 99.0 | 0.80 |
| 2.00 | 85.0 | 15.0 | 0.80 |

Unless otherwise noted, all HPLC retention times are reported using the ZQ3 polar_5 min gradient method.

All melting points were determined with a MeI-Temp II apparatus and are uncorrected. Elemental analyses were obtained by Atlantic Microlab, Inc., Norcross, Ga.

INTERMEDIATES

Intermediate 1:
2-chloro-4-iodofuro[2,3-c]pyridin-7-amine

Step A: 3-(furan-3-yl)prop-2-enoyl azide

In an oven-dried three-necked flask were placed a mixture of 3-(furan-3-yl)prop-2-enoic acid (20.0 g, 145 mmol) and dry triethylamine (17.2 g, 171 mmol) in acetone (200 mL, dried over anhydrous MgSO$_4$). The mixture was cooled to 0 to 2° C. To the cold mixture, isobutyl chloroformate (25.2 mL, 193 mmol) was added at 0° C. The mixture was stirred at 0 to 2° C. for 30 min, then a solution of sodium azide (14.0 g, 215 mmol) in water (60 mL) was added slowly at 0° C. The reaction mixture was stirred for 1 h at the same temperature. It was quenched with an ice-water (500 mL) and the title azide was extracted with toluene (4×100 mL), dried over an anhydrous sodium sulfate and filtered. The filtrate containing the crude title compound was used as such for the next reaction.

Step B: furo[2,3-c]pyridin-7(6H)-one

In an oven-dried three-necked flask were placed tributylamine (35.99 g, 194.2 mmol) and diphenylmethane (160 mL). The mixture was stirred at 180-185° C. for 10 min. To the stirred mixture, was added the solution of 3-(furan-3-yl)prop-2-enoyl azide in toluene (~24 g, 147.2 mmol) drop-wise using a dropping funnel. During this process toluene was removed by using a Dean-Stark assembly. The heating at 180-185° C. was continued for ~1.5 h. Diphenylmethane was distilled from the reaction mixture using a high vacuum pump. To the residue, hexane (4×100 mL) was added, and the mixture was triturated with a spatula then decanted. Subsequently it was triturated with a mixture of hexane (60 mL) and diisopropyl ether (20 mL). The dark brown crystals that were obtained were filtered and dried to give 14.0 g (69%) of the title compound. $^1$H NMR (300 MHz, CD$_3$OD) δ 6.69 (d, J=6.9 Hz, 1H), 6.84 (d, J=1.8 Hz, 1H), 7.20 (d, J=6.9 Hz, 1H), 7.78 (d, J=1.8 Hz, 1H).

Step C: 7-chlorofuro[2,3-c]pyridine

The mixture of furo[2,3-c]pyridin-7(6H)-one (12.0 g, 87.6 mmol) and phosphorous oxychloride (21.3 g, 139 mmol) was placed in an oven-dried two-necked flask, then was heated to reflux for 3-4 h under a nitrogen atmosphere. The reaction mixture was cooled to RT, then poured into ice-cold water (250 mL). After it was basified with 10% aq. NaOH solution, the mixture was extracted with diethyl ether (3×100 mL), dried over anhydrous potassium carbonate, filtered and concentrated to give 10.0 g (75%) of the title compound as brown crystals. $^1$H NMR (300 MHz, CDCl$_3$): δ 6.87 (d, J=1.8 Hz, 1H), 7.50 (d, J=6.0 Hz, 1H), 7.82 (d, J=1.8 Hz, 1H), 8.20 (d, J=6.0 Hz, 1H).

Step D: N-methoxyfuro[2,3-c]pyridin-7-amine

A three-necked flask was charged with 7-chloro-furo[2,3-c]pyridine (40 g, 0.26 mol) and n-butanol (300 mL) and heated at 125° C. Methoxyamine hydrochloride (54 g, 0.65 mol) was added as a solid and then additional methoxyamine hydrochloride (54 g, 0.65 mol) dissolved in water (50 mL) was added slowly. The resulting mixture was heated at reflux overnight. After cooling to RT, the reaction mixture was concentrated in vacuo. The remaining aqueous solution was basified to pH ~8.5 with saturated NaHCO$_3$ and extracted several times with DCM. The combined DCM extracts were washed with saturated NaHCO$_3$ and brine. This solution was concentrated in vacuo leaving a dark brown syrup which was used without further purification.

Step E: furo[2,3-c]pyridin-7-amine

N-methoxyfuro[2,3-c]pyridin-7-amine (43.0 g, 0.26 mol) in DCM (200 mL) was cooled in a water bath. Zinc dust (36.0 g, 0.64 mol) was added in one portion and stirred for a few min. Acetic acid (18.8 g, 0.31 mol) was added slowly over 5-10 min and stirred for 30 min. The water bath was removed and the mixture was stirred at RT for 16 h. At this point, TLC analysis (5% MeOH in DCM) indicated complete consumption of the starting material. The mixture was diluted with 400 mL of DCM and washed with saturated NaHCO$_3$ until the pH of the wash was about 8.5. The DCM layer was then washed with water (2×100 mL) and then brine. The solution was dried over anhydrous Na$_2$SO$_4$, filtered and concentrated in vacuo. The resulting crude product was purified by flash chromatography (2% MeOH:DCM) to provide 34 g (97%) of the title compound. $^1$H NMR (300 MHz, CDCl$_3$): δ 4.89 (br s, 2H), 6.71 (d, J=1.8 Hz, 1H), 6.94 (d, J=5.4 Hz, 1H), 7.63 (d, J=1.8 Hz, 1H), 7.84 (d, J=5.4 Hz, 1H).

Step F: di-tert-butyl
furo[2,3-c]pyridin-7-ylimidodicarbonate

Furo[2,3-c]pyridin-7-amine (34.0 g, 0.25 mol) in DCM (200 mL) was treated with di-tert butyl dicarbonate (165 g, 0.76 mol) in 100 mL DCM, added over a period of 10-15 min. DMAP (1.5 g) was added and the mixture was stirred at RT overnight. Water was added and the phases were separated. The organic layer was washed with water (100 mL), dried over Na$_2$SO$_4$, filtered and concentrated in vacuo. The residue was purified by flash chromatography (10% EtOAc:hexane) to provide 62 g (73%) of the title compound as a light brown solid. $^1$H NMR (300 MHz, CDCl$_3$): δ 1.38 (s, 18H), 6.84 (d, J=2.10 Hz, 1H), 7.52 (d, J=5.4 Hz, 1H), 7.74 (d, J=2.10 Hz, 1H), 8.29 (d, J=5.4 Hz, 1H).

Step G: di-tert-butyl (2-chlorofuro[2,3-c]pyridin-7-yl)imidodicarbonate and di-tert-butyl (2,3-dichloro-furo[2,3-c]pyridin-7-yl)imidodicarbonate Di-tert-butyl furo[2,3-c]pyridin-7-ylimidodicarbonate (25 g, 75.3 mmol) in dry THF (350 mL) was cooled to between −65° C. and −75° C. and LDA (1.8 M in THF/heptanes/ethylbenzene, 50 mL, 90 mmol) was added via syringe over a period of 10 min. The mixture was stirred for 1.5 h between −65° C. and −75° C. and then treated with hexachloroethane (71.2 g, 0.30 mol) in dry THF (150 mL) added via syringe over a 30 min period. The mixture was allowed to warm to RT over 16 h and was quenched by the addition of water (100 mL) and stirred for 10 min. The reaction was diluted with EtOAc, the phases were separated and the aqueous phase was extracted with EtOAc (2×100 mL). The combined organic extracts were washed with water, dried over Na$_2$SO$_4$, filtered and concentrated in vacuo. The crude product thus obtained was purified by flash chromatography using triethylamine coated silica gel eluting (EtOAc:hexane mixtures) to provide 18 g (65%) of di-tert-butyl (2-chlorofuro[2,3-c]pyridin-7-yl)imidodicarbonate and 5 g (18%) of di-tert-butyl (2,3-dichlorofuro[2,3-c]pyridin-7-yl)imidodicarbonate.

di-tert-butyl (2-chlorofuro[2,3-c]pyridin-7-yl)imidodicarbonate: $^1$H NMR (CDCl$_3$, 300 MHz): δ 1.41 (s, 18H), 6.66 (s, 1H), 7.41 (d, J=5.10 Hz, 1H), 8.29 (d, J=5.1 Hz, 1H).

di-tert-butyl (2,3-dichlorofuro[2,3-c]pyridin-7-yl)imidodicarbonate: $^1$H NMR (CDCl$_3$, 300 MHz): δ 1.20 (s, 18H), 7.26 (d, J=5.4 Hz, 1H), 8.20 (d, J=5.1 Hz, 1H).

Step H: 2-chlorofuro[2,3-c]pyridin-7-amine

Di-tert-butyl (2-chlorofuro[2,3-c]pyridin-7-yl)imidodicarbonate (18.0 g, 49.1 mmol) in DCM (100 mL) was cooled in an ice bath and treated with 4 N HCl in 1,4-dioxane (75 mL, 300 mmol) added slowly over several minutes. The reaction was removed from the cooling bath and heated at 55° C. for 16 h. The mixture was concentrated in vacuo. The residue was suspended in DCM and treated with saturated NaHCO$_3$ until the pH reached ~8.5. The organic layer was washed with water and brine and then dried over anhydrous Na$_2$SO$_4$. The material was purified by flash chromatography (50% EtOAc:DCM) to provide 8.2 g (100%) of the title compound as a white solid. $^1$H NMR (CDCl$_3$, 400 MHz): δ 4.75 (br s, 2H), 6.54 (s, 1H), 6.85 (d, J=5.3 Hz, 1H), 7.86 (d, J=5.3 Hz, 1H); MS (ESI): 169.12 [M+H]$^+$.

Step I: 2-chloro-4-iodofuro[2,3-c]pyridin-7-amine (Title Compound)

A solution of 2-chlorofuro[2,3-c]pyridin-7-amine (9.0 g, 53.8 mmol) in MeCN (250 mL) was treated with N-iodosuccinimide (18.2 g, 80.8 mmol) added portionwise over a 5-10 min period. The mixture was stirred at RT for 16 h. The reaction was then quenched with 20% aqueous Na$_2$S$_2$O$_3$ and stirred for 10 min. EtOAc (200 mL) was added and the phases separated. The organic phase was washed with 20% aqueous Na$_2$S$_2$O$_3$ (50 mL), then water (2×100 mL) and finally with brine. After drying over Na$_2$SO$_4$, the organic extracts were filtered and concentrated in vacuo. The material was purified using flash chromatography (25% EtOAc:hexane) to afford 12.6 g (80%) of the title compound. $^1$H NMR (300 MHz CDCl$_3$): δ 4.76 (br. s, 2H), 6.49 (s, 1H), 8.05 (s, 1H).

Intermediate 2:
2,3-dichloro-4-iodofuro[2,3-c]pyridin-7-amine

Step A: 2,3-dichlorofuro[2,3-c]pyridin-7-amine

By a procedure analogous to Intermediate 1, Step H, 2.64 g (6.56 mmol) of di-tert-butyl (2,3-dichlorofuro[2,3-c]pyridin-7-yl)imidodicarbonate afforded the title compound in 68% yield upon trituration with hexanes. $^1$H NMR (300 MHz CDCl$_3$): δ 4.82 (br s, 2H), 6.88 (d, J=5.4 Hz, 1H), 7.95 (s, J=5.4 Hz, 1H).

Step B:
2,3-dichloro-4-iodofuro[2,3-c]pyridin-7-amine (Title Compound)

A solution of 2,3-dichlorofuro[2,3-c]pyridin-7-amine (5.7 g, 28.2 mmol) in MeCN (200 mL) was treated with N-iodosuccinimide (9.57 g, 42.3 mmol), added portionwise over 5-10 min. The mixture was heated at 60° C. for 16 h. After cooling to RT, the reaction was quenched with 20% aqueous sodium thiosulfate and stirred for 10 min. EtOAc (200 mL) was added and the phases separated. The organic phase was washed with 20% aqueous sodium thiosulfate (50 mL), then water (2×100 mL) and finally with brine. After drying over Na$_2$SO$_4$, the organic extracts were filtered and concentrated in vacuo. The material was purified using flash chromatography eluting with 2% MeOH in DCM to afford 3.8 g (41%) of the title compound. $^1$H NMR (300 MHz, DMSO-d$_6$): δ 6.75 (br. s, 2H); 8.02 (s, 1H).

Intermediate 3:
2-chloro-4-iodo-3-methylfuro[2,3-c]pyridin-7-amine

Step A: di-tert-butyl (2-chloro-3-methylfuro[2,3-c]pyridin-7-yl)imidodicarbonate Di-tert-butyl (2-chlorofuro[2,3-c]pyridin-7-yl)imidodicarbonate (3.0 g, 8.15 mmol) in dry THF (100 mL) was cooled to −65° C. to −75° C. and LDA (1.8 M in THF/heptanes/ethylbenzene, 6.0 mL, 10.8 mmol), pre-cooled to the same temperature, was added slowly via syringe over a period of 10 min. The mixture was stirred for 1.5 h at −65° C. to −75° C. and then treated with methyl iodide (0.76 mL, 12.2 mmol) in dry THF added slowly via syringe. The mixture was allowed to warm to RT overnight and was quenched by the addition of water (50 mL) and diluted with EtOAc (100 mL). The phases were separated and the organic phase was dried over Na$_2$SO$_4$, and concentrated in vacuo leaving 3.2 g of a brown solid which was used without further purification. $^1$H NMR (400 MHz, CDCl$_3$): δ 8.25 (d, J=5.5 Hz, 1H), 7.39 (d, J=5.5 Hz, 1H), 2.22 (s, 3H), 1.40 (s, 18H).

Step B:
2-chloro-3-methylfuro[2,3-c]pyridin-7-amine

Di-tert-butyl (2-chloro-3-methylfuro[2,3-c]pyridin-7-yl)imidodicarbonate (3.2 g, 8.38 mmol) DCM (25 mL) was cooled in an ice bath and treated with 4 N HCl in 1,4-dioxane (12.5 mL, 50 mmol) added slowly over several minutes. The reaction was removed from the cooling bath and heated at 55° C. for 16 h. The mixture was concentrated in vacuo and the residue was suspended in DCM and treated with saturated NaHCO$_3$ until the pH reached ~8.5. The organic layer was washed with water, then brine and then dried over anhydrous Na$_2$SO$_4$. After concentration in vacuo, the material was purified by flash chromatography (3% MeOH:DCM) to provide 1.0 g (66%) of the title compound. $^1$H NMR (400 MHz, CDCl$_3$) δ 7.87 (d, J=5.4 Hz, 1H), 6.79 (d, J=5.4 Hz, 1H), 4.78 (br s, 2H), 2.16 (s, 3H).

Step C:
2-chloro-4-iodo-3-methylfuro[2,3-c]pyridin-7-amine
(Title Compound)

2-chloro-3-methylfuro[2,3-c]pyridin-7-amine (1.0 g, 5.5 mmol) in MeCN (30 mL) was treated with N-iodosuccinimide (1.70 g, 7.52 mmol), added portionwise over a 5 min period. The mixture was stirred at RT for overnight. The reaction was quenched with 20% aqueous Na$_2$S$_2$O$_3$ and stirred for 10 min. EtOAc (100 mL) was added and the phases separated. The organic phase was washed with 20% aqueous Na$_2$S$_2$O$_3$, then water and finally with brine. After drying over Na$_2$SO$_4$, the organic extracts were filtered and concentrated in vacuo. The material was purified using flash chromatography (30% EtOAc:DCM) to afford 1.15 g (68%) of the title compound. $^1$H NMR (400 MHz, CDCl$_3$) δ 8.07 (s, 1H), 4.73 (br s, 2H), 2.33 (s, 3H).

Intermediate 4: 7-chloro-2-iodofuro[2,3-c]pyridine

7-Chlorofuro[2,3-c]pyridine (7.60 g, 49.7 mmol) was placed in a three-necked flask fitted with a thermometer and nitrogen inlet and then anhydrous tetrahydrofuran (150 mL) was added. The solution was cooled to −78° C. To this cold solution was added gradually 2 M LDA solution (32.3 mL, 64.6 mmol) by syringe and the resulting mixture was stirred for 2 h at −78° C. Then a solution of iodine (15.1 g, 59.5 mmol) in dry THF (100 mL) was added at −78° C. and the resulting mixture was allowed to warm to RT overnight. The reaction was quenched with aqueous sodium thiosulfate (75 mL) and diluted with ethyl acetate (150 mL). The organic layer was separated, and the aqueous layer was extracted with ethyl acetate (2×75 mL). All organic layers were combined, washed with brine, dried over anhydrous Na$_2$SO$_4$, filtered and evaporated to give 13.7 g (99%) of the title compound as a brown solid. $^1$H NMR (300 MHz, CDCl$_3$): δ 7.06 (s, 1H), 7.40 (d, J=6.0 Hz, 1 H), 8.17 (d, J=6.0 Hz, 1H).

Intermediate 5: (2-dihydroxyboronyl-furo[2,3-c]pyridin-7-yl)-carbamic acid di-tert-butyl ester To a cooled (−78° C.) solution of furo[2,3-c]pyridin-7-yl-carbamic acid di-tert-butyl ester (7.0 g, 21 mmol) in dry THF (100 mL) was added 2.0 M LDA (13.0 mL, 26.0 mmol) over 15 min. The reaction mixture was then stirred at −70° C. for 1 h. The mixture was then cooled it to −78° C. and trimethyl borate (3.3 mL, 30 mmol) was added dropwise over 10 min. The reaction mixture was allowed to warm to RT over 4 h. Solvent was removed under reduced pressure keeping the temperature below 40° C. The residue was diluted with ethyl acetate (40 mL) and water (100 mL). The aqueous fraction was washed with ethyl acetate (2×15 mL). The aqueous fraction was then acidified with saturated aqueous ammonium chloride to pH 5 and extracted with ethyl acetate (2×30 mL). The combined organic fractions were washed with water (10 mL) and brine (10 mL), dried over sodium sulfate, and concentrated to afford 3.5 g (44%) of the title compound as a brown solid. $^1$H NMR (300 MHz, DMSO-d$_6$): δ 1.44 (s, 18H), 7.62 (s, 1H), 7.78 (d, J=5.4 Hz, 1H), 8.25 (d, J=5.4 Hz, 1H), 8.90 (s, 2H).

Intermediate 6: (2-trimethylstannanyl-furo[2,3-c]pyridin-7-yl)-carbamic acid di-tert-butyl ester To a cooled (−78° C.) solution of furo[2,3-c]pyridin-7-yl-carbamic acid di-tert-butyl ester (2.0 g, 6.0 mmol) in dry THF (30 mL) was added 1.8 M LDA (4.0 mL, 8.0 mmol) over 15 min. The reaction mixture was then stirred at −70° C. for 1 h, then cooled to −78° C. and 1.0 M trimethyltin chloride in THF (7.5 mL, 7.5 mmol) was added dropwise over 10 min. The reaction mixture was allowed to warm to RT over 6 h. The reaction was cooled to −10° C. and the pH was adjusted to 5 by addition of saturated aqueous ammonium chloride solution. The reaction mixture was extracted with ethyl acetate (2×30 mL). The combined organic fractions were washed with water (10 mL) and brine (10 mL), dried over sodium sulfate, and concentrated to afford 2.2 g (74%) of the title compound as a brown solid. $^1$H NMR (300 MHz, DMSO-d$_6$): δ 0.44 (s, 9H), 1.41 (s, 18H), 6.94 (s, 1H), 7.43 (d, J=5.1 Hz, 1H), 8.21 (d, J=5.4 Hz, 1H).

Intermediates 7 and 8: 2-chloro-4-iodo-N-methylfuro[2,3-c]pyridin-7-amine and 2-chloro-4-iodo-N,N-dimethylfuro[2,3-c]pyridin-7-amine To a cooled (0° C.) suspension of sodium hydride (15 mg, 0.37 mmol) in DMF (200 μL) was added dropwise a solution of 2-chloro-4-iodo-furo[2,3-c]pyridin-7-ylamine (100 mg, 0.340 mmol) in DMF (1 mL). After 5 min, methyl iodide (23 μL, 0.37 mmol) was added and the reaction stirred at room temperature for 2 h. The reaction was then quenched with water (30 mL). The quenched mixture was extracted with dichloromethane (2×10 mL). The combined organic fractions were washed with water (1×10 mL) and brine (1×10 mL), dried over sodium sulfate, filtered, and concentrated. Purification by ISCO chromatography (5 to 25% ethyl acetate:heptane) afforded 18 mg (17%) of 2-chloro-4-iodo-N-methylfuro[2,3-c]pyridin-7-amine and 44 mg (40%) of 2-chloro-4-iodo-N,N-dimethylfuro[2,3-c]pyridin-7-amine as off-white white solids.

2-chloro-4-iodo-N-methylfuro[2,3-c]pyridin-7-amine: $^1$H NMR (400 MHz, CDCl$_3$): δ 8.07 (s, 1 H), 6.48 (s, 1 H), 5.04 (br. s., 1 H), 3.14 (d, J=5.3 Hz, 3 H); MS (ESI): 308.96, 311.01 [M+H]$^+$; HPLC t$_R$=3.48 min (ZQ3, polar_4 min).

2-chloro-4-iodo-N,N-dimethylfuro[2,3-c]pyridin-7-amine: $^1$H NMR (400 MHz, CDCl$_3$): δ 8.08 (s, 1 H), 6.48 (s, 1 H), 3.28 (s, 6 H)

Intermediate 9:
2-chloro-N-ethyl-4-iodofuro[2,3-c]pyridin-7-amine

The title compound was prepared in 45% yield from 2-chloro-4-iodo-furo[2,3-c]pyridin-7-ylamine and iodoethane by a procedure analogous to Intermediate 7. $^1$H NMR (400 MHz, CDCl$_3$): δ 8.08 (s, 1 H), 6.47 (s, 1 H), 4.71 (br. s., 1 H), 3.59 (qd, J=5.6, 7.2 Hz, 2 H), 1.31 (t, J=7.2 Hz, 3 H); MS (ESI): 322.96, 324.96 [M+H]$^+$; HPLC t$_R$=3.75 min (ZQ3: polar_4 min).

Intermediate 10: 4-iodo-2-(isoquinolin-5-yl)furo[2,3-c]pyridin-7-amine

Step A:
2-(isoquinolin-5-yl)furo[2,3-c]pyridin-7-amine

A mixture of 2-chlorofuro[2,3-c]pyridin-7-amine (4.0 g, 23.8 mmol) and 5-isoquinoline boronic acid (4.33 g, 25.0 mmol) in 1,4-dioxane (150 mL) and water (50 mL) was sparged with nitrogen for 15 min and then treated with Pd(PPh$_3$)$_2$Cl$_2$ (250 mg). After sparging with nitrogen for another 5 min, K$_2$CO$_3$ (2.2 g, 59.5 mmol) was added and the mixture heated at reflux overnight. The 1,4-dioxane was removed in vacuo and DCM was added. The phases were separated and the organic phase was washed with water, then brine. The solution was dried over anhydrous Na$_2$SO$_4$, filtered and concentrated in vacuo. The residue was purified by flash chromatography (2% MeOH:DCM) to provide the 5.6 g (90%) of the title compound. $^1$H NMR (300 MHz, CD$_3$OD): δ 6.99 (d, J=5.4 Hz, 1H), 7.27 (s, 1H), 7.73 (d, J=5.4 Hz, 1H); 7.81 (t, J=8.1 Hz, 1H), 8.22 (d, J=8.1 Hz, 1H), 8.29 (dd, J=7.4 Hz, J=1.0 Hz, 1H), 8.44 (d, J=5.4 Hz, 1H), 8.55 (d, J=6.0 Hz, 1H); 9.32 (s, 1 H).

Step B: 4-iodo-2-(isoquinolin-5-yl)furo[2,3-c]pyridin-7-amine (Title Compound)

A suspension of 2-(isoquinolin-5-yl)furo[2,3-c]pyridin-7-amine (5.6 g, 21.5 mmol) in DMF (250 mL) was treated with NIS (8.73 g, 38.6 mmol) added portionwise with stirring over a period of 5 min. The mixture was stirred at RT overnight. The reaction was quenched with aqueous Na$_2$S$_2$O$_3$, diluted with EtOAc (1 L) and the phases separated. The organic layer was concentrated in vacuo. Water was added to the residue resulting in the formation of a solid after stirring overnight. The material was collected by filtration and the filter cake was washed with water and hexane. The material was dried over P$_2$O$_5$ at 50° C. in a high vacuum oven to provide 7.0 g (84%) of the title compound as a brown solid. $^1$H NMR (300 MHz, CDCl$_3$+CD$_3$OD): δ 6.92 (s, 1H), 7.70 (t, J=8.1 Hz, 1H), 7.98 (s, 1H), 8.11 (t, J=7.5 Hz, 2H), 8.20 (d, J=6.0 Hz, 1H), 8.53 (d, J=6.0 Hz, 1H), 9.24 (s, 1H).

Intermediate 11: 2-(1-benzothiophen-7-yl)-4-iodofuro[2,3-c]pyridin-7-amine

Step A: 2-(1-benzothiophen-7-yl)furo[2,3-c]pyridin-7-amine

The title compound was prepared in 76% yield by a procedure analogous to Intermediate 10, Step A. $^1$H NMR (300 MHz, CD$_3$OD): δ ppm 6.99 (d, J=5.7 Hz, 1H), 7.37 (s, 1H), 7.50-7.57 (m, 2H), 7.71 (d, J=5.7 Hz, 2H), 7.96 (dd, J=9.0, J=1.2 Hz, 1H), 8.12 (d, J=6.9 Hz, 1H).

Step B: 2-(1-benzothiophen-7-yl)-4-iodofuro[2,3-c]pyridin-7-amine

The title compound was prepared in 51% yield from 2-(1-benzothiophen-7-yl)furo[2,3-c]pyridin-7-amine by a procedure analogous to Intermediate 10, Step B. $^1$H NMR (300 MHz, DMSO-d$_6$) δ 8.20 (d, J=7.5 Hz, 1H), 8.01 (d, J=7.6 Hz, 1H), 7.95 (d, J=1.5 Hz, 2H), 7.64-7.58 (m, 2H). 7.18 (s, 1H). 6.67 (br s, 2H).

Intermediate 12: 4-iodo-2-phenylfuro[2,3-c]pyridin-7-amine

Step A: 2-phenylfuro[2,3-c]pyridin-7-amine

The title compound was prepared in 94% yield by a procedure analogous to Intermediate 10, Step A. $^1$H NMR (300 MHz, CDCl$_3$): δ ppm 4.85 (br. s, 2H), 6.95 (d, J=5.4 Hz, 1H), 6.96 (s, 1H); 7.40-7.45 (m, 3H), 7.85-7.88 (m, 3H).

Step B: 4-iodo-2-phenylfuro[2,3-c]pyridin-7-amine (Title Compound)

The title compound was prepared in 65% yield from 2-phenylfuro[2,3-c]pyridin-7-amine by a procedure analogous to Intermediate 10, Step B. $^1$H NMR (300 MHz, CDCl$_3$): δ ppm 4.84 (brs, 2H), 6.87 (s, 1H), 7.40-7.55 (m, 3H), 7.85-7.88 (m, 2H), 8.08 (s, 1H).

Intermediate 13: 4-iodo-2-thieno[2,3-c]pyridine-3-vl-furo[2,3-c]pyridine-7-ylamine Step A: 3-(4,4,5,5-tetramethyl-[1,3,2]dioxaborolan-2-yl)-thieno[2,3-c]pyridine A nitrogen degassed mixture of Pd$_2$(dba)$_3$ (0.81 g, 0.96 mmol) and tricyclohexylphosphine (0.99 g, 3.5 mmol) in 1,4-dioxane (250 mL) was stirred for 30 min. To this solution were added 3-bromo-thieno[2,3-c]pyridine (6.3 g, 29 mmol), 4,4,5,5,4',4',5',5'-octamethyl-[2,2']bi[[1,3,2]dioxaborolanyl] (9.7 g, 38 mmol) followed by potassium acetate (4.61 g, 47.1 mmol) and the mixture was heated at 90° C. for 16 h. The reaction mixture was cooled to RT and filtered. Solvent was evaporated from the filtrate and the residue was triturated with diisopropyl ether (50 mL) to afford 6.3 g (82%) of the title compound as a solid. $^1$H NMR (300 MHz, CDCl$_3$): δ 1.38 (s, 12 H), 8.21 (d, J=5.7 Hz, 1H), 8.29 (s, 1H), 8.52 (d, J=5.7 Hz, 1H), 9.17 (s, 1H).

Step B: 2-thieno[2,3-c]pyridin-3-yl-furo[2,3-c]pyridin]-7-ylamine

The title compound was prepared in 79% yield by a procedure analogous to Intermediate 10, Step A. $^1$H NMR (300 MHz, DMSO-d$_6$): δ 6.46 (br. s, 2H), 6.88 (d, J=5.4 Hz, 1H), 7.45 (s, 1H), 7.75 (d, J=5.4 Hz, 1H), 8.54 (d, J=5.4 Hz, 1H), 8.61 (d, J=5.4 Hz 1H), 8.72 (s, 1 H), 9.38 (s, 1H).

Step C: 4-iodo-2-thieno[2,3-c]pyridine-3-yl-furo[2,3-c]pyridine-7-ylamine (Title Compound)

The title compound was prepared in 77% yield from 2-thieno[2,3-c]pyridine-3-yl-furo[2,3-c]pyridin]-7-ylamine by a procedure analogous to Intermediate 10, Step B. $^1$H NMR (300 MHz, CDCl$_3$+CD$_3$OD): δ 6.83 (s, 1H), 7.82 (s, 1H), 8.11 (d, J=5.6 Hz, 1H), 8.26 (s, 1H), 8.44 (d, J=5.8 Hz, 1H), 9.02 (s, 1H).

Intermediate 14: 2-(1,2-benzothiazol-7-yl)-4-iodofuro[2,3-c]pyridin-7-amine

Step A: 3-bromo-2-tert-butylsulfanyl-benzaldehyde

A mixture of 3-bromo-2-fluorobenzaldehyde (5.0 g, 25 mmol), potassium carbonate (4.0 g, 30 mmol) and 2-methyl-2-propanethiol (5.5 mL, 49 mmol) in dry DMF (25 mL) was heated to 110° C. in a sealed tube for 16 h. The reaction mixture was cooled to RT, added to water (100 mL) and extracted with DCM (3×50 mL). The combined organic fractions were washed with water (50 mL), dried, and evaporated to afford 6.7 g (98%) of the crude title compound which was used without further purification. $^1$H NMR (300 MHz, CDCl$_3$): δ 1.31 (s, 9H), 7.26-7.41 (m, 1H), 7.93-7.99 (m, 2H), 10.73 (s, 1H).

Step B: 1-[3-bromo-2-(tert-butylsulfanyl)phenyl]-N-hydroxymethanimine

A mixture of 3-bromo-2-tert-butylsulfanyl-benzaldehyde (6.7 g, 25 mmol) and hydroxylamine hydrochloride (7.9 g, 116 mmol) in 2-propanol (200 mL) and water (40 mL) was heated to 65-70° C. overnight. 2-Propanol was evaporated and water (150 mL) was added to the residue followed by saturated aqueous sodium bicarbonate to bring the pH to ~8.5. The mixture was extracted with DCM (3×80 mL). The combined organic fractions were dried over sodium sulfate, filtered, and concentrated to afford the title compound, which was used immediately without further purification. $^1$H NMR (300 MHz, CD$_3$OD): δ 1.28 (s, 9H), 7.25-7.35 (t, J=7.8 Hz, 1H), 7.79 (d, J=6.6 Hz, 1H), 7.89 (d, J=6.3 Hz, 1H), 8.83 (s, 1H).

Step C: 7-bromo-1,2-benzothiazole

A mixture of crude 1-[3-bromo-2-(tert-butylsulfanyl)phenyl]-N-hydroxymethanimine (7 g) and p-toluenesulfonic acid (730 mg, 3.88 mmol) in n-butanol (100 mL) was heated to reflux for 16 h. n-Butanol was evaporated, water (100 mL) and saturated aqueous sodium bicarbonate (50 mL) were added and the mixture was extracted with DCM (3×80 mL). The combined organic fractions were dried over anhydrous sodium sulfate, filtered and concentrated to afford 900 mg (17%) of the crude title compound as a brown solid. $^1$H NMR (300 MHz, CDCl$_3$): δ 7.26-7.40 (t, J=8.1 Hz, 1H), 7.62 (d, J=6.9 Hz, 1H), 8.02 (d, J=8.4 Hz, 1H), 9.04 (s, 1H).

Step D: 7-(4,4,5,5-tetramethyl-1,3,2-dioxaborolan-2-yl)-1,2-benzothiazole

A solution of trisbenzylideneacetone dipalladium (0) (1.38 g, 1.51 mmol) and tricyclohexylphosphine (1.69 g, 6.0 mmol) in degassed 1,4-dioxane (120 mL) was spared with nitrogen for 10 min. 4,4,5,5,4',4',5',5'-Octamethyl-[2,2']bi[[1,3,2]dioxaborolanyl] (8.3 g, 33 mmol), potassium acetate (3.9 g, 40 mmol) and 7-bromo-1,2-benzothiazole (5.4 g, 25 mmol) were added and the resultant solution was heated to 90-95° C. overnight under nitrogen. The reaction mixture was cooled to RT, filtered, and concentrated. The residue was triturated with hot hexanes (2×) and filtered to afford the title compound. $^1$H NMR (300 MHz, CDCl$_3$): δ 1.40 (s, 12 H), 7.42 (d, J=5.9 Hz, 1H); 8.04 (d, J=5.7 Hz, 1H); 8.21 (d, J=6.9 Hz, 1H); 8.99 (s, 1H).

Step E: 2-(1,2-benzothiazol-7-yl)furo[2,3-c]pyridin-7-amine

The title compound was prepared in 60% yield by a procedure analogous to Intermediate 10, Step A. $^1$H NMR (300 MHz, CDCl$_3$): δ 4.91 (brs, 2H), 7.01 (d, J=5.7 Hz, 1H), 7.17 (s, 1H), 7.60 (t, J=7.2 Hz, 1H), 7.93 (d, J=5.7 Hz, 1H), 8.08-8.15 (m, 2H), 9.02 (s, 1H).

Step F: 2-(1,2-benzothiazol-7-yl)-4-iodofuro[2,3-c]pyridin-7-amine (Title Compound)

The title compound was prepared in 92% yield from 2-(1,2-benzothiazol-7-yl)furo[2,3-c]pyridin-7-amine by a procedure analogous to Intermediate 10, Step B. $^1$H NMR (300 MHz, CDCl$_3$): δ 4.62 (br. s, 2H), 7.13 (s, 1H), 7.73 (t, J=5.7 Hz, 1H), 7.98 (s, 1H), 8.35-8.45 (m, 2H), 9.28 (s, 1H).

Intermediate 15: (2-thieno[2,3-c]pyridin-3-yl-4-trimethylstannanyl-furo[2,3-c]pyridin-7-yl)-bis-carbamic acid tert-butyl ester Step A: (4-iodo-2-thieno[2,3-c]pyridin-3-yl-furo[2,3-c]pyridin-7-yl)-bis-carbamic acid tert-butyl ester To a suspension of 4-iodo-2-thieno[2,3-c]pyridin-3-yl-furo[2,3-c]pyridin-7-ylamine (394 mg, 1.0 mmol) and 4-(dimethylamino)pyridine (244 mg, 2.0 mg) in toluene (5 mL) and DMF (5 mL) was added di-tert-butyl dicarbonate (654 mg, 3.0 mmol). The mixture was heated to 50° C. for 1 h. The mixture was concentrated and then purified by flash chromatography (50% DCM:hexanes) to afford >90% of the title compound, which was used without further purification. MS (ESI): 594.18 [M+H]$^+$; HPLC t$_R$=1.52 min (HPLC: Analytical_2 min)

Step B: (2-thieno[2,3-c]pyridin-3-yl-4-trimethylstannanyl-furo[2,3-c]pyridin-7-yl)-bis-carbamic acid tert-butyl ester (Title Compound)

A stirred solution of (4-iodo-2-thieno[2,3-c]pyridin-3-yl-furo[2,3-c]pyridin-7-yl)-bis-carbamic acid tert-butyl ester (594 mg, 1 mmol), and hexamethylditin (490 mg, 1.5 mmol) in toluene (10 mL) was purged with nitrogen for 5 min, then tetrakis(triphenylphosphine)palladium (0) (116 mg, 0.1 mmol) was added. The mixture was heated to 120° C. overnight. The mixture was concentrated and then purified by flash chromatography to afford 528 mg (89%) of the title compound as an off-white solid. $^1$H NMR (400 MHz, CDCl$_3$): δ 9.28 (s, 1H), 8.67 (s, 1H), 8.33 (d, J=6.1 Hz, 1h), 8.22 (d, J=6.1 Hz, 1H), 7.26 (s, 1H), 7.07 (s, 1H), 1.47 (s, 18H), 0.49 (s, 9H); MS (ESI): 630.57 [M+H]$^+$; HPLC t$_R$=1.50 min (HPLC: Analytical_2 min).

Intermediate 16: cis-1-methyl-4-[4-(4,4,5,5-tetramethyl-1,3,2-dioxaborolan-2-yl)-1H-pyrazol-1-yl]cyclohexanol Step A: 1,4-dioxaspiro[4.5]decan-8-ol A solution of 1,4-dioxaspiro[4.5]decan-8-ol (6 g, 37.3 mmol) in EtOH (50 mL) was cooled to 0° C. and treated with sodium borohydride (2.85 g, 74.5 mmol). The mixture was stirred and allowed to warm to RT over a 3 h period. The solvent was removed in vacuo and the residue partitioned between DCM and water. The combined organic extracts were concentrated in vacuo leaving 5.45 g (92%) of the title compound as a clear oil. $^1$H NMR (400 MHz, DMSO-d$_6$): δ 1.36-1.52 (m, 4H), 1.60-1.71 (m, 4H), 3.55 (br s, 1H), 3.76-3.86 (m, 4H), 4.46 (d, J=4.0 Hz, 1H).

Step B: 1,4-dioxaspiro[4.5]dec-8-yl methanesulfonate

A solution of 1,4-dioxaspiro[4.5]decan-8-ol (1.10 g, 6.81 mmol), triethylamine (1.21 mL, 8.67 mmol) in DCM (25.2 mL) was cooled in an ice/water bath and treated with methanesulfonyl chloride (675 μL, 8.67 mmol) added dropwise under an atmosphere of nitrogen. The mixture was stirred at 25° C. overnight. The mixture was treated with saturated aqueous NaHCO$_3$ (20 mL) and extracted with DCM (2×50 mL). The extracts were washed with brine (50 mL), dried over MgSO$_4$ and concentrated in vacuo leaving a beige oil which was recrystallized from hexanes (22 mL) to give 1.59 g (98%) of the title compound as a white crystalline solid. $^1$H NMR (400 MHz, CDCl$_3$) δ 1.61-1.68 (m, 2H), 1.82-1.90 (m, 2H), 1.94-2.08 (m, 4H), 3.02 (s, 3H), 3.91-4.00 (m, 4H), 4.82-4.88 (m, 1H); MS (ESI): 237.10 [M+H]$^+$; HPLC t$_R$=2.54 min.

Step C: 1-(1,4-dioxaspiro[4.5]dec-8-yl)-4-iodo-1H-pyrazole

A suspension of sodium hydride (72.6 mg, 1.82 mmol) in DMF (1 mL); was cooled in an ice/water bath and treated with a solution of 4-iodopyrazole (242 mg, 1.21 mmol) in DMF (2 mL) added dropwise under an atmosphere of nitrogen in 5 min. After stirring in the cold for another 30 min, a solution of 1,4-dioxaspiro[4.5]dec-8-yl methanesulfonate (321 mg, 1.33 mmol) in DMF (2 mL) was added dropwise at 0° C. The mixture was warmed to RT and was then immersed in 150° C. oil bath and stirred for 2 h. The mixture was treated with water (15 mL), extracted with EtOAc (3×20 mL). The extracts were washed with water (3×15 mL), brine (15 mL), dried over MgSO$_4$. After concentration in vacuo, a brown solid was obtained. It was dissolved in MeOH and after water was added, a solid formed, which was filtered off to give 266 mg (66%) of the title compound as a white crystalline solid. $^1$H NMR (400 MHz, CDCl$_3$): δ 7.50 (s, 1 H), 7.49 (s, 1 H), 4.23 (tt, J=4.2, 11.2 Hz, 1 H), 2.34-2.20 (m, 1 H), 2.21-1.96 (m, 4 H), 1.95-1.81 (m, 2 H), 1.82-1.66 (m, 3 H), 1.33-1.22 (m, 2 H); MS (ESI): 334.96 [M+H]$^+$; HPLC t$_R$=3.26 min.

Step D: 4-(4-iodo-1H-pyrazol-1-yl)cyclohexanone

A mixture of 1-(1,4-dioxa-spiro[4.5]dec-8-yl)-4-iodo-1H-pyrazole (338 mg, 1.00 mmol), pyridinium p-toluenesulfonate (518 mg, 2.00 mmol), acetone (15 mL) and H$_2$O (15 mL) was heated at 60° C. for 2 d. The mixture was extracted with EtOAc (3×30 mL). The combined extracts were washed with water (3×30 mL), brine (30 mL), dried over MgSO$_4$, and concentrated in vacuo leaving 273 mg (89%) of the title compound as a white solid. $^1$H NMR (400 MHz, CDCl$_3$): δ 2.23-2.63 (m, 8 H), 4.57-4.64 (m, 1 H), 7.51 (s, 1 H), 7.54 (s, 1 H). MS (ESI): 291.09 [M+H]$^+$; HPLC t$_R$=2.80 min.

Step E: cis-4-(4-iodo-1H-pyrazol-1-yl)-1-methylcyclohexanol and trans-4-(4-iodo-1H-pyrazol-1-yl)-1-methylcyclohexanol A solution of 4-(4-iodo-1H-pyrazol-1-yl)cyclohexanone (1.21 g, 4.18 mmol) in DCM (50 mL) was cooled to 0° C., and treated with trimethylaluminum (2.0 M in hexane, 6.5 mL, 13 mmol) added dropwise via syringe over 5 min. The reaction mixture was allowed to warm to RT over the course of 1.5 h. The solution was cooled back down to 0° C., after which a saturated solution of sodium potassium tartrate (50 mL) was added and the mixture was stirred for 30 min. The reaction mixture was then extracted with DCM and the combined organic layers were washed with brine, dried over anhydrous Na$_2$SO$_4$, filtered, and concentrated in vacuo. The crude material was purified by flash chromatography (heptane:EtOAc 3:1-1:1-0:1) to provide 403.6 mg (25%) of the cis isomer and 712.8 mg (55%) of the trans isomer.
cis-4-(4-iodo-1H-pyrazol-1-yl)-1-methylcyclohexanol: $^1$H NMR (400 MHz, DMSO-d$_6$): δ 1.13 (s, 3H), 1.37-1.49 (m, 2H), 1.57-1.66 (m, 2H), 1.68-1.77 (m, 2H), 2.05 (qd, J=12.6, 3.5 Hz, 2H), 4.09 (tt, J=12.0, 3.9 Hz, 1H), 4.17 (s, 1H), 7.49 (s, 1H), 7.92 (s, 1H); MS (ESI): 306.95 [M+H]$^+$; HPLC t$_R$=2.89 min.
trans-4-(4-iodo-1H-pyrazol-1-yl)-1-methylcyclohexanol: $^1$H NMR (400 MHz, DMSO-d$_6$): δ 1.17 (s, 3H), 1.45-1.54 (m, 2H), 1.55-1.62 (m, 2H), 1.77_1.96 (m, 4H), 4.17 (tt, J=10.2, 4.5 Hz, 1H), 4.39 (s, 1H), 7.49 (s, 1H), 7.98 (s, 1H); MS (ESI): 306.93 [M+H]$^+$; HPLC t$_R$=2.81 min.

Step F: cis-1-methyl-4-[4-(4,4,5,5-tetramethyl-1,3,2-dioxaborolan-2-yl)-1H-pyrazol-1-yl]cyclohexanol (Title Compound)

To a stirred solution of cis-4-(4-iodo-1H-pyrazol-1-yl)-1-methylcyclohexanol (36.6 mg, 0.120 mmol) in THF (2 mL), cooled to 0° C., isopropylmagnesium chloride (2.0 M in THF, 0.20 mL, 0.40 mmol) was added in parts. The reaction was stirred at 0° C. for 1 h 15 min and then 2-methoxy-4,4,5,5-tetramethyl-1,3,2-dioxaborolane (96.0 mg, 0.608 mmol) in THF (0.5 mL) was added and the reaction was allowed to warm from 0° C. to RT over the course of 2.5 h. After a total reaction time of 4 h, the reaction mixture was cooled back down to 0° C., quenched with saturated aqueous NH$_4$Cl (15 mL), and extracted with EtOAc. The combined organic layers were washed with brine, dried over anhydrous Na$_2$SO$_4$, filtered, and concentrated in vacuo to dryness, giving 34.2 mg (75%) of the title material, as a colorless gummy film. This material was used without further purification. $^1$H NMR (400 MHz, CD$_3$OD): δ 1.25 (s, 3H), 1.31 (s, 12H), 1.60 (td, J=13.7, 3.9 Hz, 2H), 1.75-1.83 (m, 2H), 1.86-1.93 (m, 2H), 2.09-2.22 (m, 2H), 4.16 (tq, J=12.0, 3.9 Hz, 1H), 7.66 (s, 1H), 7.86 (s, 1H); MS (ESI): 306.11 [M+H]$^+$; HPLC t$_R$=2.97 min.

Intermediate 17: trans-1-methyl-4-[4-(4,4,5,5-tetramethyl-1,3,2-dioxaborolan-2-yl)-1H-pyrazol-1-yl]cyclohexanol The trans isomer was prepared from trans-4-(4-iodo-1H-pyrazol-1-yl)-1-methylcyclohexanol in 66% yield by a procedure analogous to Intermediate 16, Step F. $^1$H NMR (400 MHz, CDCl$_3$): δ 1.33 (s, 12H), 1.35 (s, 3H), 1.61-1.71 (m, 2H), 1.82 (ddd, J=13.1, 3.5, 3.3 Hz, 2H), 1.93-2.05 (m, 2H), 2.13-2.22 (m, 2H), 4.28 (tt, J=10.4, 4.2 Hz, 1H), 7.78 (s, 1H), 7.84 (s, 1H); MS (ESI): 306.14 [M+H]$^+$; HPLC t$_R$=2.87 min.

Intermediate 18: 1-(trans-4-{[tert-butyl(dimethyl)silyl]oxy}cyclohexyl)-4-(4,4,5,5-tetramethyl-1,3,2-dioxaborolan-2-yl)-1H-pyrazole Step A: 1-(trans-4-{[tert-butyl(dimethyl)silyl]oxy}cyclohexyl)-4-iodo-1H-pyrazole A mixture of trans-4-(4-iodo-1H-pyrazol-1-yl)-cyclohexanol (1.00 g, 3.42 mmol), tert-butyldimethylsilyl chloride (1.03 g, 6.85 mmol), and DMAP (80 mg, 0.7 mmol), 1H-imidazole (699 mg, 10.3 mmol) in DCM (20 mL) was stirred RT for 20 min. The mixture was diluted with DCM and washed with saturated NaHCO$_3$. The organic layer was dry-loaded onto silica gel. Flash chromatography (3% EtOAc:hexanes) afforded 1.37 g (98%) of the title compound as a clear oil. $^1$H NMR (400 MHz, DMSO-d$_6$): δ 0.05 (s, 6 H), 0.86 (s, 9 H), 1.33-1.47 (m, 2 H), 1.70-1.91 (m, 4 H), 1.96 (d, J=11.9 Hz, 2 H), 3.58-3.75 (m, 1 H), 4.11-4.21 (m, 1 H), 7.49 (s, 1 H), 7.92 (s, 1 H); MS (ESI): 407.05 [M+H]$^+$; HPLC t$_R$=3.22 min.

Step B: 1-(trans-4-{[tert-butyl(dimethyl)silyl]oxy}cyclohexyl)-4-(4,4,5,5-tetramethyl-1,3,2-dioxaborolan-2-yl)-1H-pyrazole (Title Compound)

A stirred solution of 1-(trans-4-{[tert-butyl(dimethyl)silyl]-oxy}cyclohexyl)-4-iodo-1H-pyrazole (1.14 g, 2.80 mmol) in THF (30.0 mL) was cooled to 0° C. and treated with isopropylmagnesium chloride (2.0 M in THF, 2.31 mL, 4.63 mmol), added dropwise under an atmosphere of nitrogen over 5 min. The reaction mixture was stirred at 0° C. for another 1 h, then treated 2-methoxy-4,4,5,5-tetramethyl-1,3,2-dioxaborolane (0.95 mL, 5.6 mmol) and stirred at RT for another hour. The mixture was treated with saturated aqueous NH$_4$Cl (10 mL) and extracted with EtOAc (3×20 mL). The extracts were washed with water (10 mL), brine (15 mL), and dried over Na$_2$SO$_4$. Solvent was removed under reduced pressure to give a residue which was purified by flash chromatography (10% EtOAc:hexane) to provide 1.10 g (96%) of the title compound. MS (ESI): 405.95 [M+H]$^+$; HPLC $t_R$=3.21 min.

Intermediate 19: tert-butyl 4-[4-(4,4,5,5-tetramethyl-1,3,2-dioxaborolan-2-yl)-1H-pyrazol-1-yl]piperidine-1-carboxylate

Step A: tert-butyl 4-[(methylsulfonyl)oxy]piperidine-1-carboxylate

A solution of tert-butyl 4-hydroxypiperidine-1-carboxylate (32.2 g, 0.160 mol) in DCM (400 mL) cooled to 0° C., was treated with triethylamine (26.8 mL, 0.192 mol), methanesulfonyl chloride (13.6 mL, 0.176 mol), and 4-dimethylaminopyridine (0.20 g, 0.0016 mol) at 0° C. under nitrogen atmosphere. The resulting mixture was slowly warmed to RT and stirred overnight. The mixture was washed with saturated aqueous NaHCO$_3$ (3×80 mL), brine (2×80 mL), and dried over anhydrous sodium sulfate. The filtrate was concentrated to provide 44.7 g (100%) of tert-butyl 4-[(methylsulfonyl)oxy]piperidine-1-carboxylate as a white solid. The product was used to next step without further purification. $^1$H NMR (400 MHz, CDCl$_3$): δ 4.89 (tt, J=7.77, 3.85 Hz, 1H), 3.67-3.75 (m, 2H), 3.31 (ddd, J=13.71, 8.27, 3.79 Hz, 2H), 3.04 (s, 3H), 1.93-2.02 (m, 2H), 1.77-1.88 (m, 2H), 1.47 (s, 9H).

Step B: tert-butyl 4-[4-(4,4,5,5-tetramethyl-1,3,2-dioxaborolan-2-yl)-1H-pyrazol-1-yl]piperidine-1-carboxylate (Title Compound)

A mixture of tert-butyl 4-[(methylsulfonyl)oxy]piperidine-1-carboxylate (7.33 g, 26.2 mmol), 4-(4,4,5,5-tetramethyl-1,3,2-dioxaborolan-2-yl)-1H-pyrazole (5.09 g, 26.2 mmol), and Cs$_2$CO$_3$ (12.8 g, 39.3 mmol) in DMF (50 mL) was heated at 100° C. for 24 h. The mixture was cooled to RT and diluted with water (100 mL) and extracted with EtOAc (3×60 mL). The combined organic phases were washed with water (3×50 mL), brine (50 mL), and dried over anhydrous sodium sulfate. The residue was purified by flash chromatography (20 to 40% ethyl acetate:hexanes) to afford 3.84 g (39%) of the title compound as a white solid. $^1$H NMR (400 MHz, CDCl$_3$): δ 7.81 (s, 1H), 7.74 (s, 1H), 4.17-4.35 (m, 3H), 2.89 (m, J=11.12 Hz, 2H), 2.14 (d, J=14.65 Hz, 2H), 1.90 (qd, J=12.25, 4.42 Hz, 3H), 1.48 (s, 9H), 1.33 (s, 12H); MS (ESI): 379.15 [M+H]$^+$; HPLC $t_R$=3.17 min.

Intermediate 20: tert-butyl 3-[4-(4,4,5,5-tetramethyl-1,3,2-dioxaborolan-2-yl)-1H-pyrazol-1-yl]azetidine-1-carboxylate The title compound was prepared in 97% yield by a procedure analogous to Intermediate 19. $^1$H NMR (400 MHz, CDCl$_3$): δ 1.32 (s, 12H), 1.46 (s, 9H), 4.27-4.41 (m, 4H), 5.04-5.11 (m, 1H), 7.84 (d, J=1.6 Hz, 2H); MS (ESI): 349.12 [M+H]$^+$; HPLC $t_R$=3.46 min.

The following Intermediates were prepared by procedures analogous to Intermediate 19.

| Intermediate # | NMR Data | Compound Name | HPLC $t_R$ (min) | MS (ESI) [M + H]$^+$ |
|---|---|---|---|---|
| 21 | $^1$H NMR (400 MHz, CD$_3$OD): δ 7.87-7.98 (m, 1H), 7.66-7.80 (m, 1H), 4.50 (d, J = 5.56 Hz, 1H), 3.39-3.57 (m, 3H), 3.04-3.18 (m, 2H), 2.32 (d, J = 3.79 Hz, 4H), 1.27-1.38 (m, 12H), 1.15-1.23 (m, 6H) | 1-(propan-2-yl)-4-(4,4,5,5-tetramethyl-1,3,2-dioxaborolan-2-yl)-1H-pyrazole | 3.22 | 235.98 |
| 22 | | 1-[(2,2-dimethyl-1,3-dioxolan-4-yl)methyl]-4-(4,4,5,5-tetramethyl-1,3,2-dioxaborolan-2-yl)-1H-pyrazole | 2.61 | 309.17 |
| 23 | | 1-[2-(tetrahydro-2H-pyran-2-yloxy)ethyl]-4-(4,4,5,5-tetramethyl-1,3,2-dioxaborolan-2-yl)-1H-pyrazole | | |
| 24 | $^1$H NMR (400 MHz, CD$_3$OD): δ 7.82 (s, 1H), 7.66 (s, 1H), 5.81 (s, 2H), 5.09 (tt, J = 8.59, 4.42 Hz, 1H), 2.86-3.03 (m, 2H), 2.61-2.75 (m, 2H), 1.31 (s, 12H) | 1-(cyclopent-3-en-1-yl)-4-(4,4,5,5-tetramethyl-1,3,2-dioxaborolan-2-yl)-1H-pyrazole | — | — |
| 25 | $^1$H NMR (400 MHz, CD$_3$OD): δ 7.87 (s, 1H), 7.68 (s, 1H), 4.11-4.25 (m, 1H), 2.08 (dd, J = 12.63, 2.27 Hz, 2H), 1.90 (d, J = 13.64 Hz, 2H), 1.69-1.81 (m, 4H), 1.39-1.54 (m, 2H), 1.25-1.37 (m, 12H) | 1-cyclohexyl-4-(4,4,5,5-tetramethyl-1,3,2-dioxaborolan-2-yl)-1H-pyrazole | — | — |
| 26 | | 1-(tetrahydro-2H-pyran-4-yl)-4-(4,4,5,5-tetramethyl-1,3,2-dioxaborolan-2-yl)-1H-pyrazole | — | — |

Intermediate 27: tert-butyl (3-exo)-3-[4-(4,4,5,5-tetramethyl-1,3,2-dioxaborolan-2-yl)-1H-pyrazol-1-yl]-8-azabicyclo[3.2.1]octane-8-carboxylate

Step A: tert-butyl (3-endo)-3-hydroxy-8-azabicyclo[3.2.1]octane-8-carboxylate To a solution of 8-aza-bicyclo[3.2.1]octan-3-ol hydrochloride salt (16.3 g, 100 mmol) in THF (50 mL) was added aqueous 3 N sodium bicarbonate suspension (50 mL, 150 mmol), followed by di-tert butyl dicarbonate (26.1 g, 120 mmol). The reaction mixture stirred at room temperature for 16 h. The mixture was then cooled to 0° C. and filtered. The organic solvent was evaporated, and the residual material extracted with dichloromethane. The organic fraction was washed with water, dried over sodium sulfate, filtered, and concentrated. Trituration of the residue with hexanes afforded the title compound. $^1$H NMR (300 MHz, CDCl$_3$): δ 4.05-4.18 (m, 3H), 2.1-2.25 (m, 3H), 1.85-2.1 (m, 3H), 1.48-1.78 (m, 3H), 1.46 (s, 9H).

Step B: tert-butyl (3-endo)-3-[(methylsulfonyl)oxy]-8-azabicyclo[3.2.1]octane-8-carboxylate To a solution of tert-butyl (3-endo)-3-hydroxy-8-azabicyclo[3.2.1]octane-8-carboxylate (5 g, 22 mmol) in DCM (30 mL) was added triethylamine (3.6 mL, 26 mmol) and DMAP (20 mg, 0.16 mmol). The reaction mixture was cooled to 0° C. and methanesulfonyl chloride (1.82 mL, 22.4 mmol) was added dropwise. The reaction mixture was stirred at room temperature for 16 h. The reaction mixture was washed with water and the organic layer was dried over sodium sulfate, filtered and concentrated. Trituration of the residue with hexanes afforded the title compound. $^1$H NMR (300 MHz, CDCl$_3$): δ 5.05 (m, 1H), 4.1-4.35 (m, 2H), 3.0 (s, 3H), 1.9-2.4 (m, 8H), 1.45 (s, 9H).

Step C: tert-butyl (3-exo)-3-[4-(4,4,5,5-tetramethyl-1,3,2-dioxaborolan-2-yl)-1H-pyrazol-1-yl]-8-azabicyclo[3.2.1]octane-8-carboxylate (Title Compound)

A solution of 4-(4,4,5,5-tetramethyl-1,3,2-dioxaborolan-2-yl)-1H-pyrazole (1.1 g, 5.7 mmol) in DMF (15 mL) was treated with 60% sodium hydride (326 mg, 8.51 mmol) in portions over a period of 20 min. The reaction mixture was stirred at room temperature for 2 h and tert-butyl (3-endo)-3-[(methylsulfonyl)oxy]-8-azabicyclo[3.2.1]octane-8-carboxylate (2 g, 6.5 mmol) was added and stirred at 65-70° C. for 16 h. The reaction mixture was poured into water and extracted with ethyl acetate. The organic layer was washed with water, dried over sodium sulfate, and concentrated. The residue was triturated with hexanes and isopropyl ether to afford 745 mg (53%) of the title compound. $^1$H NMR (300 MHz, CDCl$_3$): δ 7.76 (s, 1H), 7.27 (s, 1H), 4.69 (m, 1H), 4.32-4.4 (m, 2H), 2.05 (m, 6H), 1.7 (m, 2H), 1.45 (s, 9H), 1.31 (s, 12H).

Intermediate 28: 2-[3-(tert-butyldimethylsilanyloxy)-cyclopentyl]-4-(4,4,5,5-tetramethyl-[1,3,2]dioxaborolan-2-yl)-1H-pyrazole Step A:
3-(tert-butyldimethylsilanyloxy)cyclopentanol To a solution of 1,3-cyclopentanediol (5 g, 49 mmol) and imidazole (5 g, 74 mmol) in DMF (20 mL) added tert-butyldimethylsilyl chloride (5.9 g, 39 mmol). The reaction stirred for 3 h at room temperature and was then poured into water and extracted with diethyl ether. The organic layer was washed with brine, dried over sodium sulfate, filtered, and concentrated. The residue was purified by column chromatography (10% diethyl ether:hexanes) to afford 3.5 g (33%) of the title compound. $^1$H NMR (300 MHz, CDCl$_3$) δ 4.3-4.5 (m, 2H), 1.9-2.15 (m, 2H), 1.65-1.8 (m, 2H), 1.4-1.6 (m, 2H), 1.32-1.41 (m, 1H), 0.86 (s, 9H), 0.05 (s, 6H).

Step B: methanesulfonic acid
3-(tert-butyldimethylsilanyloxy)-cyclopentyl ester

To a solution of 3-(tert-butyldimethylsilanyloxy)cyclopentanol (3.5 g, 16 mmol) in DCM (30 mL) was added triethylamine (2.65 mL, 19.4 mmol) and DMAP (20 mg, 0.16 mmol). The reaction mixture was cooled to 0° C. and methanesulfonyl chloride (1.34 mL, 16.5 mmol) was added dropwise. The reaction mixture was stirred at room temperature for 16 h. The reaction mixture was washed with water and the organic layer was dried over sodium sulfate, filtered, and concentrated. Purification of the residue by column chromatography (20% diethyl ether:hexanes) afforded 2.5 g (53%) of the title compound. $^1$H NMR (300 MHz, CDCl$_3$): δ 5.19-5.3 (m, 1H), 4.4 (m, 1H), 3.0 (s, 3H), 1.8-2.3 (m, 4H), 1.5-1.7 (m, 2H), 0.86 (s, 9H), 0.05 (s, 6H).

Step C: 2-[3-(tert-butyldimethylsilanyloxy)-cyclopentyl]-1'-4-(4,4,5,5-tetramethyl-[1,3,2]dioxaborolan-2-yl)-1H-pyrazole (Title Compound)

A solution of 4-(4,4,5,5-tetramethyl-1,3,2-dioxaborolan-2-yl)-1H-pyrazole (1.5 g, 7.7 mmol) in DMF (15 mL) was treated with 60% sodium hydride (365 mg, 9.29 mmol) in portions over a period of 20 min. The reaction mixture was stirred at room temperature for 2 h and then methanesulfonic acid 3-(tert-butyl-dimethyl-silanyloxy)-cyclopentyl ester (2.5 g, 8.5 mmol) was added and the mixture stirred at 65-70° C. for 16 h. The reaction mixture was poured into water and extracted with ethyl acetate. The organic layer was washed with water, dried over sodium sulfate, and concentrated to afford the crude title compound, which was used without further purification. $^1$H NMR (300 MHz, CDCl$_3$): δ 7.95 (s, 1H), 7.7 (s, 1H), 4.69-4.74 (m, 1H), 4.35-4.32 (m, 1H), 2.39-2.46 (m, 1H), 2.11-2.22 (m, 2H), 1.95-2.01 (m, 1H), 1.71-1.94 (m, 2H), 1.3 (s, 12H), 0.86 (s, 9H), 0.05 (s, 6H).

Intermediate 29: 2-[3-(tert-butyl-dimethyl-silanyloxy)-cyclohexyl]-4-(4,4,5,5-tetramethyl-[1,3,2]dioxaborolan-2-yl)-1H-pyrazole Step A:
3-(tert-butyl-dimethyl-silanyloxy)-cyclohexanol The title compound was prepared in 35% yield from 1,3-cyclohexanediol by a procedure analogous to Intermediate 28, Step A. $^1$H NMR (300 MHz, CDCl$_3$): δ 4.0-4.2 (m, 1H), 3.8-3.95 (m, 1H), 1.3-2.4 (m, 9H), 0.86 (s, 9H), 0.05 (s, 6H).

Step B: methanesulfonic acid
3-(tert-butyl-dimethyl-silanyloxy)-cyclohexyl ester The title compound was prepared in 78% yield from 3-(tert-butyl-dimethyl-silanyloxy)-cyclohexanol by a procedure analogous to Intermediate 28, Step B. $^1$H NMR (300 MHz, CDCl$_3$): δ 4.5-4.68 (m, 1H), 3.5-3.65 (m, 1H), 3.0 (s, 3H), 2.25-2.38 (m, 1H), 2.0-2.1 (m, 1H), 1.8 (m, 2H), 1.15-1.6 (m, 2H), 1.9-2.9 (m, 2H), 0.86 (s, 9H), 0.05 (s, 6H).

Step C: 2-[3-(tert-butyl-dimethyl-silanyloxy)-cyclohexyl]-4-(4,4,5,5-tetramethyl-[1,3,2]dioxaborolan-2-yl)-1H-pyrazole (Title Compound)

The title compound was prepared in 10% yield from methanesulfonic acid 3-(tert-butyl-dimethyl-silanyloxy)-cyclohexyl ester by a procedure analogous to Intermediate 28, Step C. The crude compound was purified by column chromatography (25% ethyl acetate:hexanes and then DCM) to afford the title compound. $^1$H NMR (300 MHz, CDCl$_3$): δ 7.76 (s, 1H), 7.27 (s, 1H), 4.45-4.63 (m, 1H), 4.23 (br. s, 1H), 2.05-2.09 (m, 2H), 1.5-1.9 (m, 6H), 1.45 (s, 9H), 1.31 (s, 12H), 0.05 (s, 6H).

Intermediate 30: 4-[4-(7-amino-2-chloro-furo[2,3-c]pyridin-4-yl)-pyrazol-1-yl]-piperidine-1-carboxylic acid tert-butyl ester A mixture of 2-chloro-4-iodofuro[2,3-c]pyridin-7-amine (7.7 g, 26.2 mmol) and tert-butyl 4-[4-(4,4,5,5-tetramethyl-1,3,2-dioxaborolan-2-yl)-1H-pyrazol-1-yl]piperidine-1-carboxylate (10.52 g, 27.7 mmol) in 1,2-dimethoxyethane (300 mL) and water (100 mL) was sparged with N$_2$ for 15 min, then treated with K$_2$CO$_3$ and Pd(PPh$_3$)$_4$. After sparging again with N$_2$ for 5 min, the mixture was heated at reflux 4-6 h. The 1,2-dimethoxyethane was removed in vacuo, water was added and the mixture extracted with DCM. The combined DCM extracts were dried, filtered and concentrated in vacuo. The residue was purified by flash chromatography using triethylamine-coated silica (2% MeOH:DCM) to afford 10 g (80%) of the title compound. $^1$H NMR (400 MHz, CDCl$_3$): δ 1.44-1.55 (m, 9H) 1.90-2.12 (m, 2H) 2.21 (d, J=10.61 Hz, 2H) 2.84-3.03 (m, 2H) 4.22-4.44 (m, 3H) 5.26 (br s, 2H) 6.77 (s, 1H) 7.65 (s, 1H) 7.73-7.79 (m, 1H) 7.92 (s, 1H).

Intermediate 31: 2,3-dichloro-4-(1-piperidin-4-yl-1H-pyrazol-4-yl)-furo[2,3-c]pyridin-7-ylamine A mixture of 2,3-dichloro-4-iodo-furo[2,3-c]pyridin-7-ylamine (300.0 mg, 0.9121 mmol), 4-[4-(4,4,5,5-tetramethyl-1,3,2-dioxaborolan-2-yl)-pyrazol-1-yl]-piperidine-1-carboxylic acid tert-butyl ester (516 mg, 1.37 mmol) and Pd(PPh$_3$)$_4$ (50 mg, 0.04 mmol) in 1,4-dioxane (20 mL) and H$_2$O (2 mL) was degassed and refilled with argon (3×). The reaction was heated at 100° C. for 20 h using a Biotage Initiator microwave reactor. The reaction was concentrated in vacuo to give a solid which was purified by flash chromatography (30 to 60% EtOAc:hexanes), which afforded the desired intermediate. $^1$H NMR (400 MHz, CDCl$_3$): δ 7.85 (s, 1H), 7.65 (s, 1H), 7.57 (s, 1H), 4.80 (br s, 2H), 4.32 (m, 3H), 2.99 (m, 2H), 2.18 (m, 2H), 1.97 (m, 2H), 1.47 (s, 9H); MS (ESI): 452.00 [M+H]$^+$; HPLC t$_R$=3.14 min.

Intermediate 32: 4-[4-(4,4,5,5-tetramethyl-1,3,2-dioxaborolan-2-yl)-1H-pyrazol-1-yl]piperidine hydrochloride A solution of tert-butyl 4-[4-(4,4,5,5-tetramethyl-1,3,2-dioxaborolan-2-yl)-1H-pyrazol-1-yl]piperidine-1-carboxylate (5.02 g, 13.3 mmol) in 1,4-dioxane (40 mL) was treated with HCl (4.0 M in 1,4-dioxane, 50 mL, 200 mmol) and stirred at 35° C. for 3 h. The reaction mixture was concentrated in vacuo to a white solid, affording 5.01 g (100%) of the title compound. The material was used without additional purification. $^1$H NMR (400 MHz, CDCl$_3$) δ 1.33 (s, 12H), 2.50 (br s, 4H), 3.09-3.41 (m, 2H), 3.57-3.79 (m, 2H), 4.73 (br s, 1H), 7.87 (s, 2H), 9.82 (br s, 2H); MS (ESI): 278.15 [M+H]$^+$; HPLC t$_R$=2.01 min.

Intermediate 33: 1-(propan-2-yl)-4-[4-(4,4,5,5-tetramethyl-1,3,2-dioxaborolan-2-yl)-1H-pyrazol-1-yl]piperidine A solution of 4-[4-(4,4,5,5-tetramethyl-[1,3,2]dioxaborolan-2-yl)-pyrazol-1-yl]-piperidine hydrochloride (500 mg, 1.59 mmol) in DMF (15.0 mL) was charged with (2-bromoethoxy)-tert-butyldimethylsilane (0.376 mL, 1.75 mmol), DIPEA (0.694 mL, 3.99 mmol) and potassium iodide (26 mg, 0.16 mmol) and was heated at 50° C. for 16 h. The DMF was then concentrated in vacuo. The product was purified by flash chromatography (0 to 15% MeOH:EtOAc) to afford the title compound. $^1$H NMR (400 MHz, CD$_3$OD): δ 7.90 (s, 1H), 7.69 (s, 1H), 4.31 (td, J=7.71, 15.41 Hz, 1H), 3.88 (t, J=5.68 Hz, 2H), 3.28 (br s, 2H), 3.00 (s, 3H), 2.86 (s, 3H), 2.76-2.84 (m, 2H), 2.51-2.67 (m, 2H), 2.10-2.19 (m, 4H), 1.31 (s, 12H), 0.91-0.94 (m, 9H); MS (ESI): 436.28 [M+H]$^+$; HPLC t$_R$=1.26 min (TOF polar_3 min).
The following Intermediates were prepared analogously, using procedures similar to Intermediate 33 above.

| Intermediate # | Compound Name | $^1$H NMR data |
|---|---|---|
| 34 | 1-(2-methoxyethyl)-4-[4-(4,4,5,5-tetramethyl-1,3,2-dioxaborolan-2-yl)-1H-pyrazol-1-yl]piperidine | $^1$H NMR (400 MHz, CDCl$_3$): δ 1.32 (s, 12H), 2.06 (td, J = 11.9, 3.7 Hz, 2H), 2.11-2.24 (m, 4H), 2.59-2.64 (m, 2H), 3.07 (d, J = 12.1 Hz, 2H), 3.37 (s, 3H), 3.53 (t, J = 5.6 Hz, 2H), 4.15 (tt, J = 11.4, 4.1 Hz, 1H), 7.74 (s, 1H), 7.79 (s, 1H) |
| 35 | 1-(2-fluoroethyl)-4-[4-(4,4,5,5-tetramethyl-1,3,2-dioxaborolan-2-yl)-1H-pyrazol-1-yl]piperidine | $^1$H NMR (400 MHz, CD$_3$OD): δ 7.91 (s, 1H), 7.69 (s, 1H), 4.67 (m, J = 4.80 Hz, 1H 4.52-4.57 (m, 1H), 4.18-4.30 (m, 1H), 3.13 (d, J = 12.38 Hz, 2H), 2.79-2.84 (m, 1H), 2.71-2.77 (m, 1H), 2.28-2.39 (m, 2H), 2.06-2.15 (m, 4H), 1.33 (s, 12H) |
| 36 | 4-[4-(4,4,5,5-tetramethyl-1,3,2-dioxaborolan-2-yl)-1H-pyrazol-1-yl]-1-(2,2,2-trifluoroethyl)piperidine | $^1$H NMR (400 MHz, CD$_3$OD): δ 7.92 (s, 1H), 7.72 (s, 1H), 4.35-4.47 (m, 1H), 3.40-3.54 (m, 2H), 2.96-3.09 (m, 2H), 2.16-2.35 (m, 4H), 2.03 (s, 2H), 1.33 (s, 12H) |

Intermediate 37: 1-methyl-4-[4-(4,4,5,5-tetramethyl-1,3,2-dioxaborolan-2-yl)-1H-pyrazol-1-yl]piperidine A mixture of 4-[4-(4,4,5,5-tetramethyl-1,3,2-dioxaborolan-2-yl)-1H-pyrazol-1-yl]piperidine (0.500 g, 1.80 mmol) and 37% aqueous formaldehyde solution (0.269 mL, 3.61 mmol) in MeOH (10.0 mL) were combined and stirred at 40° C. for 2 h. Then sodium borohydride (205 mg, 5.41 mmol) was carefully added to the reaction mixture left to stir for 16 h. The reaction was concentrated in vacuo to a solid. The crude product was dissolved in EtOAc and washed with water several times. The organic layer was collected, dried with sodium sulfate, filtered and concentrated in vacuo to a solid to yield the desired product. $^1$H NMR (400 MHz, CD$_3$OD): δ 7.90 (s, 1H), 7.67 (s, 1H), 4.16-4.26 (m, 1H), 3.00 (d, J=12.13 Hz, 2H), 2.34 (s, 3H), 2.25 (td, J=11.75, 3.28 Hz, 2H), 2.03-2.15 (m, 4H), 1.31 (s, 12H).
The following Intermediate was prepared by a procedure analogous to Intermediate 37.

| Int. # | Compound Name | $^1$H NMR data |
|---|---|---|
| 38 | 1-ethyl-4-[4-(4,4,5,5-tetramethyl-1,3,2-dioxaborolan-2-yl)-1H-pyrazol-1-yl]piperidine | $^1$H NMR (400 MHz, CD$_3$OD): δ 1.07-1.22 (m, 3H) 1.25-1.37 (m, 12H) 1.97-2.27 (m, 6H) 2.52 (q, J = 7.16 Hz, 2H) 3.12 (d, J = 12.38 Hz, 2H) 4.15-4.35 (m, 1H) 7.69 (s, 1H) 7.91 (s, 1H). |

Intermediate 39: 1-[2-(methylsulfonyl)ethyl]-4-[4-(4,4,5,5-tetramethyl-1,3,2-dioxaborolan-2-yl)-1H-pyrazol-1-yl]piperidine A solution of 4-[4-(4,4,5,5-tetramethyl-1,3,2-dioxaborolan-2-yl)-1H-pyrazol-1-yl]piperidine (500 mg, 1.80 mmol), (methylsulfonyl)ethene (212 mg, 1.99 mmol), and DIPEA (500 mL, 2.87 mmol) in DMF (6 mL) was stirred at 25° C. for 30 min. The reaction mixture was then concentrated in vacuo to a solid and then purified by flash chromatography (0 to 5% MeOH:EtOAc) to yield 74.5 mg (11%) of the title compound. $^1$H NMR (400 MHz, DMSO-d$_6$): δ 7.98 (s, 1H), 7.59 (s, 1H), 4.17 (tt, J=10.36, 5.05 Hz, 1H), 3.30 (s, 2H), 3.05 (s, 3H), 2.98 (d, J=11.62 Hz, 2H), 2.74 (t, J=6.57 Hz, 2H), 2.13 (td, J=11.37, 3.28 Hz, 2H), 1.88-2.00 (m, 4H), 1.25 (s, 12H).

Intermediate 40: 1-(methylsulfonyl)-4-[4-(4,4,5,5-tetramethyl-1,3,2-dioxaborolan-2-yl)-1H-pyrazol-1-yl]piperidine A suspension of 4-[4-(4,4,5,5-Tetramethyl-[1,3,2]dioxaborolan-2-yl)-pyrazol-1-yl]-piperidine hydrochloride (200 mg, 0.64 mmol) in DCM (4 mL) was cooled to 0° C. and treated with DIPEA (280 μL, 1.6 mmol). Methanesulfonyl chloride (74 μL, 0.96 mmol) was added dropwise slowly and the mixture was stirred at RT for 18 hours. The mixture was concentrated in vacuo, taken up in MeOH and purified by MDP to afford 100 mg (40%) of the title compound. $^1$H NMR (400 MHz, CDCl$_3$): δ 1.34 (s, 12H) 2.05-2.22 (m, 2H) 2.22-2.34 (m, 2H) 2.81-2.90 (m, 4H) 2.90-3.04 (m, 3H) 3.86-4.03 (m, 2H) 4.26-4.43 (m, 1H) 7.77 (s, 1H) 7.81-7.90 (m, 1H).

Intermediate 41: 1-{4-[4-(4,4,5,5-tetramethyl-1,3,2-dioxaborolan-2-yl)-1H-pyrazol-1-yl]piperidin-1-yl}ethanone A solution of 4-[4-(4,4,5,5-tetramethyl-[1,3,2]dioxaborolan-2-yl)-pyrazol-1-yl]-piperidine hydrochloride (3.66 g, 11.7 mmol) in DMF (109.8 mL) was charged with acetyl chloride (0.91 mL, 12.84 mmol) and DIPEA (5.08 mL, 29.17 mmol) at 0° C. and left to warm up to RT in an ice bath overnight. The crude product was concentrated in vacuo to a solid and purified by flash chromatography (0 to 5% MeOH:EtOAc) to afford 3.71 g (99%) of the title compound. $^1$H NMR (400 MHz, DMSO-d$_6$): δ 7.97 (s, 1H), 7.59 (s, 1H), 4.38-4.48 (m, 2H), 3.85-3.94 (m, 1H), 3.13-3.22 (m, 1H), 2.69 (td, J=12.8, 2.7 Hz, 1H), 2.03 (s, 3H), 1.81-2.02 (m, 3H), 1.72 (qd, J=12.1, 4.6 Hz, 1H), 1.24 (s, 12H).

Intermediate 42: cyclopropyl{4-[4-(4,4,5,5-tetramethyl-1,3,2-dioxaborolan-2-yl)-1H-pyrazol-1-yl]piperidin-1-yl}methanone The title compound was prepared by a procedure analogous to Intermediate 41. MS (ESI): 346.22 [M+H]$^+$; HPLC t$_R$=1.29 min (TOF: polar_3 min).

Intermediate 43: 1-{4-[4-(7-amino-2-chlorofuro[2,3-c]pyridin-4-yl)-1H-pyrazol-1-yl]piperidin-1-yl}ethanone A solution of 1-{4-[4-(4,4,5,5-tetramethyl-1,3,2-dioxaborolan-2-yl)-1H-pyrazol-1-yl]piperidin-1-yl}ethanone (422 mg, 1.32 mmol) and 2-chloro-4-iodo-furo[2,3-c]pyridin-7-ylamine (354 mg, 1.20 mmol) in 1,4-dioxane (8.06 mL) and H$_2$O (2 mL) was charged with potassium carbonate (250 mg, 0.0018 mol) and (1,1'-bis(diphenylphosphino)ferrocene) palladium dichloride (9 mg, 0.01 mmol) under an atmosphere of nitrogen. The mixture was heated in a microwave at 100° C. for 40 min. The reaction mixture was dissolved in EtOAc and then washed with brine (2×). The aqueous layer was back-extracted with EtOAc (3×). The combined organic layers were dried over sodium sulfate, filtered, and concentrated in vacuo to a solid. The product was then purified by flash chromatography (0 to 5% 7 N NH$_3$/MeOH:EtOAc) to afford 374 mg (86%) of the title compound. $^1$H NMR (400 MHz, CD$_3$OD): δ 8.05 (s, 1 H), 7.89 (s, 1 H), 7.83 (s, 1 H), 7.05 (s, 1 H), 4.67 (dd, J=13.52, 1.89 Hz, 1 H), 4.50 (tt, J=11.46, 4.20 Hz, 1 H), 4.08 (d, J=13.89 Hz, 1 H), 3.32-3.37 (m, 1 H), 2.79-2.91 (m, 1 H), 1.91-2.24 (m, 7 H). MS (ESI): 362.11 [M+H]$^+$; HPLC t$_R$=0.88 min (TOF: polar_3 min).

The following Intermediates were prepared analogously, using procedures similar to Intermediate 43 above.

| Intermediate # | Compound Name | MS (ESI) [M + H]$^+$ | HPLC t$_R$ (min) |
|---|---|---|---|
| 44 | ethyl [4-(7-amino-2-chlorofuro[2,3-c]pyridin-4-yl)-1H-pyrazol-1-yl]acetate | 323.06 | 0.91 (TOF: polar_3 min) |
| 45 | 2-chloro-4-[1-(propan-2-yl)-1H-pyrazol-4-yl]furo[2,3-c]pyridin-7-amine | 279.08 | 0.87 (TOF: polar_3 min) |
| 46 | 2-chloro-4-{1-[(2,2-dimethyl-1,3-dioxolan-4-yl)methyl]-1H-pyrazol-4-yl}furo[2,3-c]pyridin-7-amine | 351.10 | 0.93 (TOF: polar_3 min) |
| 47 | 2-chloro-4-{1-[2-(tetrahydro-2H-pyran-2-yloxy)ethyl]-1H-pyrazol-4-yl}furo[2,3-c]pyridin-7-amine | 365.12 | 0.99 (TOF: polar_3 min) |
| 48 | tert-butyl 3-[4-(7-amino-2-chlorofuro[2,3-c]pyridin-4-yl)-1H-pyrazol-1-yl]azetidine-1-carboxylate | 392.39 | 1.10 (TOF: polar_3 min) |
| 49 | {4-[4-(7-amino-2-chlorofuro[2,3-c]pyridin-4-yl)-1H-pyrazol-1-yl]piperidin-1-yl}(cyclopropyl)methanone | 386.13 | 0.96 (TOF: polar_3 min) |

Intermediate 50: 4-[1-(trans-4-{[tert-butyl(dimethyl)silyl]oxy}cyclohexyl)-1H-pyrazol-4-yl]-2-chlorofuro[2,3-c]pyridin-7-amine A mixture of 2-chloro-4-iodo-furo[2,3-c]pyridin-7-ylamine (2 g, 7 mmol), [1-(trans-4-{[tert-butyl(dimethyl)silyl]oxy}cyclohexyl)-1H-pyrazol-4-yl]boronic acid (2.75 g, 8.49 mmol), (1,1'bis-(diphenylphosphino)-ferrocene)palladium dichloride (248 mg, 0.340 mmol) and potassium carbonate (2.35 g, 17.0 mmol) in 1,4-dioxane (20 mL) and water (9.5 mL) was heated to 70° C. for 22 h. The mixture was partitioned between ethyl acetate and water and the aqueous phase extracted with DCM. The combined organic extracts were dried over sodium sulfate, filtered, and concentrated. Purification by ISCO chromatography (10% to 50% ethyl acetate:heptane) followed by trituration with ether:heptane afforded 2.0 g (60%) of the title compound as an off-white solid. $^1$H NMR (400 MHz, CDCl$_3$): δ 7.97 (s, 1 H), 7.76-7.69 (m, 1 H), 7.62 (s, 1 H), 6.73 (s, 1 H), 4.73 (s, 2 H), 4.17 (tt, J=3.9, 11.6 Hz, 1 H), 3.73 (tt, J=4.3, 10.5 Hz, 1 H), 2.23 (d, J=12.1 Hz, 2 H), 2.09-1.99 (m, 2 H), 1.91 (dq, J=3.5, 11.9 Hz, 2 H), 1.61-1.48 (m, 2 H), 0.92 (s, 9 H), 0.10 (s, 6 H); MS (ESI): 447.39, 449.35 [M+H]$^+$.

The following Intermediates were prepared analogously, using procedures similar to Intermediate 50 above.

| Intermediate # | NMR Data | Compound Name | MS (ESI) [M + H]+ | HPLC t$_R$ (min) |
|---|---|---|---|---|
| 51 | $^1$H NMR (400 MHz, DMSO-d$_6$): δ 12.98 (br. s., 1H), 8.17 (br. s., 1H), 8.02 (s, 1H), 7.92 (br. s., 1H), 7.33 (s, 1H), 6.48-6.29 (m, 2H) | 2-chloro-4-(1H-pyrazol-4-yl)furo[2,3-c]pyridin-7-amine | 235.06 | 2.08 (ZQ3: polar_4 min) |
| 52 | $^1$H NMR (400 MHz, DMSO-d$_6$): δ 8.14 (s, 1H), 7.99 (s, 1H), 7.85 (s, 1H), 7.30 (s, 1H), 6.42 (s, 2H), 3.87 (s, 3H) | 2-chloro-4-(1-methyl-1H-pyrazol-4-yl)furo[2,3-c]pyridin-7-amine | 249.08, 251.07 | 2.20 (ZQ3: polar_4 min) |
| 53 | $^1$H NMR (400 MHz, CDCl$_3$): δ 7.96 (s, 1H), 7.72 (s, 1H), 7.63 (s, 1H), 6.73 (s, 1H), 4.85 (br. s., 2H), 4.31-4.06 (m, 1H), 2.30-2.12 (m, 2H), 2.02-1.84 (m, 2H), 1.85-1.65 (m, 3H), 1.55-1.38 (m, 2H), 1.35-1.28 (m, 1H) | 2-chloro-4-(1-cyclohexyl-1H-pyrazol-4-yl)furo[2,3-c]pyridin-7-amine | 317.14, 319.13 | 2.66 (ZQ3: polar_4 min) |

Intermediate 54: 1-(4-{4-[2-chloro-7-(methylamino)furo[2,3-c]pyridin-4-yl]-1H-pyrazol-1-yl}piperidin-1-yl)ethanone A mixture of 2-chloro-4-iodo-N-methylfuro[2,3-c]pyridin-7-amine (125 mg, 0.405 mmol), 1-{4-[4-(4,4,5,5-tetramethyl-1,3,2-dioxaborolan-2-yl)-1H-pyrazol-1-yl]piperidin-1-yl}ethanone (142 mg, 0.446 mmol), (1,1'-bis-(diphenylphosphine)-ferrocene)palladium dichloride (29.6 mg, 0.0405 mmol) and potassium carbonate (140 mg, 1.01 mmol) in 1,4-dioxane (1.35 mL) and water (0.58 mL) was heated to 95° C. for 20 h. The mixture was adsorbed directly onto a dry 5 g silica gel cartridge and purified by ISCO chromatography (0 to 10% methanol:ethyl acetate) to afford 150 mg (99%) of the title compound as a tan solid. $^1$H NMR (400 MHz, CD$_3$OD): δ 8.06 (s, 1 H), 7.92 (s, 1 H), 7.82 (s, 1 H), 7.05 (s, 1 H), 4.74-4.60 (m, 1 H), 4.51 (tt, J=4.4, 11.5 Hz, 1 H), 4.14-4.00 (m, 1 H), 3.39-3.34 (m, 1 H), 3.05 (s, 3 H), 2.85 (td, J=3.0, 13.0 Hz, 1 H), 2.28-2.11 (m, 5 H), 2.11-1.89 (m, 2 H); MS (ESI): 374.11, 376.08 [M+H]+; HPLC t$_R$=2.29 min (ZQ3, polar_4 min).

The following Intermediates were prepared by procedures analogous to Intermediate 54:

Intermediate 57: 4-[1-(trans-4-{[tert-butyl(dimethyl)silyl]oxy}cyclohexyl)-1H-pyrazol-4-yl]-2-chloro-N-methylfuro[2,3-c]pyridin-7-amine A mixture of 2-chloro-4-iodo-N-methylfuro[2,3-c]pyridin-7-amine (34.0 mg, 0.110 mmol), 1-[4-(tert-butyldimethylsilanyloxy)-cyclohexyl]-4-(4,4,5,5-tetramethyl-1,3,2-dioxaborolan-2-yl)-1H-pyrazole (55.1 mg, 0.136 mmol), (1,1'-bis-(diphenylphosphino)-ferrocene)palladium dichloride (8.6 mg, 0.012 mmol), and potassium carbonate (41.4 mg, 0.300 mmol) in 1,4-dioxane (2.3 mL) and water (0.9 mL) was irradiated under microwave heating at 85° C. for 30 min. Purification by ISCO chromatography (20 to 50% ethyl acetate:heptane) afforded 42.6 mg (82%) of the title compound as a light brown solid. $^1$H NMR (400 MHz, DMSO-d$_6$): δ 8.15 (s, 1H), 8.07 (s, 1H), 7.84 (s, 1H), 7.36 (s, 1H), 6.88 (q, J=4.55 Hz, 1H), 4.17 (tt, J=3.85, 11.31 Hz, 1H), 3.73 (tt, J=4.01, 10.52 Hz, 1H), 2.91 (d, J=4.55 Hz, 3H), 1.99-2.10 (m, 2H), 1.82-1.97 (m, 4H), 1.38-1.53 (m, 2H), 0.88 (s, 9H), 0.08 (s, 6H); MS (ESI): 461.31, 463.30 [M+H]+; HPLC t$_R$=4.28 min (ZQ3, nonpolar_5 min).

| Intermediate # | NMR Data | Compound Name | MS (ESI) [M + H]+ | HPLC t$_R$ (min) |
|---|---|---|---|---|
| 55 | $^1$H NMR (400 MHz, CD$_3$OD): δ 8.05 (s, 1H), 7.98 (s, 1H), 7.82 (s, 1H), 7.03 (s, 1H), 4.74-4.57 (m, 2H), 4.57-4.37 (m, 2H), 4.17-3.94 (m, 2H), 3.28 (s, 6H), 2.97-2.65 (m, 1H), 2.17 (s, 3H), 2.11-1.84 (m, 2H) | 1-(4-{4-[2-chloro-7-(dimethylamino)furo[2,3-c]pyridin-4-yl]-1H-pyrazol-1-yl}piperidin-1-yl)ethanone | 388.12, 390.11 | 2.55 |
| 56 | $^1$H NMR (400 MHz, CD$_3$OD): δ 8.04 (s, 1H), 7.91 (s, 1H), 7.81 (s, 1H), 7.02 (s, 1H), 4.75-4.58 (m, 1H), 4.57-4.39 (m, 1H), 4.17-3.94 (m, 1H), 3.53 (q, J = 7.3 Hz, 2H), 3.38-3.35 (m, 1H), 2.85 (td, J = 2.8, 12.9 Hz, 1H), 2.27-2.11 (m, 5H), 2.11-1.88 (m, 2H), 1.28 (t, J = 7.2 Hz, 3H) | 1-(4-{4-[2-chloro-7-(ethylamino)furo[2,3-c]pydin-4-yl]-1H-pyrazol-1-yl}piperidin-1-yl)ethanone | 388.22, 390.18 | 2.36 |

Intermediate 58: 4-[1-(trans-4-{[tert-butyl(dimethyl) silyl]oxy}cyclohexyl)-1H-pyrazol-4-yl]-2,3-dichlorofuro[2,3-c]pyridin-7-amine A mixture of 2,3-dichloro-4-iodo-furo[2,3-c]pyridin-7-ylamine (500 mg, 1.52 mmol), [1-(trans-4-{[tert-butyl(dimethyl)silyl]oxy}cyclohexyl)-1H-pyrazol-4-yl]boronic acid (542 mg, 1.67 mmol) (1,1'-bis-(diphenylphosphine)-ferrocene) palladium dichloride (111 mg, 0.152 mmol) and potassium carbonate (525 mg, 3.80 mmol) in 1,4-dioxane (5.06 mL) and water (2.2 mL) was heated to 75° C. for 2 h. The reaction mixture was concentrated, suspended in ethyl acetate (10 mL), filtered through a pad of Celite, and concentrated onto silica gel. Purification by ISCO chromatography (5 to 50% acetone:heptane) afforded 437 mg (51%) of the title compound as a red-brown solid. $^1$H NMR (400 MHz, CDCl$_3$) δ 7.84 (s, 1 H), 7.65 (d, J=0.5 Hz, 1 H), 7.57 (d, J=0.8 Hz, 1 H), 5.03 (br. s., 2 H), 3.99-4.41 (m, 1 H), 3.54-3.86 (m, 1 H), 2.14-2.42 (m, 2 H), 2.03 (dd, J=14.4, 3.5 Hz, 2 H), 1.81-1.96 (m, 2 H), 1.45-1.64 (m, 2 H), 0.91 (s, 9 H), 0.05-0.17 (m, 6 H); MS (APCI): 481.31, 483.37 [M+H]$^+$; HPLC t$_R$=3.99 min (ZQ3: nonpolar_4 min).

Intermediate 59: 7-(4,4,5,5-tetramethyl-1,3,2-dioxaborolan-2-yl)-1,2,3-benzothiadiazole

Step A: 1,2,3-benzothiadiazole

To a mixture of 2-aminobenzenethiol (1.00 g, 7.99 mmol) in water (8 mL) was added aqueous 12 N hydrochloric acid (2 mL, 20 mmol) slowly at rt. Sodium nitrite (827 mg, 12.0 mmol) was then added slowly at rt. THF (4 mL) was added for solubility, and the reaction was stirred at rt for 30 min. The solution was neutralized with saturated aqueous potassium carbonate, and the material was extracted with DCM and saturated aqueous sodium bicarbonate. The organic layer was purified via column chromatography (1% EtOAc:heptane) to afford 850 mg (78%) of the title compound as an orange liquid. $^1$H NMR (400 MHz, CDCl$_3$): δ 7.63-7.73 (m, 2 H), 8.12 (dt, J=8.3, 0.9 Hz, 1 H), 8.66 (dt, J=8.5, 0.9 Hz, 1 H).

Step B: Mixture of nitro-benzo[1,2,3]thiadiazoles

To a cooled (10° C.) solution of 1,2,3-benzothiadiazole (60 g, 441 mmol) in concentrated sulfuric acid (250 mL) was added potassium nitrate (89.1 g, 882 mmol) in portions over 30 min. The reaction mixture was stirred at RT for 16 h. The mixture was poured onto crushed ice (2 kg) with stirring. The solid thus obtained was filtered, washed with water (2.0 L) and dried in air to afford 45.0 g (60%) of a mixture of the title compounds. The crude title compounds thus obtained were used without further purification.

Step C: 7-amino-1,2,3-benzothiadiazole, 5-amino-1,2,3-benzothiadiazole, and 4-amino-1,2,3-benzothiadiazole To a mixture of nitro-benzo[1,2,3]thiadiazoles (35.0 g, 193 mmol) and iron powder (54.1 g, 967 mmol) in ethanol (300 mL) was added concentrated hydrochloric acid (30 mL) and the mixture was heated to reflux for 1 h. The mixture was cooled to RT and the solid was filtered off through Celite. The filtrate was evaporated to a residue which was basified to pH ~8 with aqueous sodium carbonate solution, then extracted with 9:1 DCM:methanol (4×100 mL).

The combined organic fractions were washed with brine (100 mL), dried over sodium sulfate, and concentrated. Purification by column chromatography (10% EtOAc:hexanes) afforded 4.6 g (16%) of 4-amino-1,2,3-benzothiadiazole, 10.0 g (34%) of 7-amino-1,2,3-benzothiadiazole, and 3.0 g (10%) of 5-amino-1,2,3-benzothiadiazole.

4-amino-1,2,3-benzothiadiazole: $^1$H NMR (300 MHz, CDCl$_3$): 5.09 (br. s, 2H), 6.74 (d, J=7.5 Hz, 1H), 7.31 (d, J=8.1 Hz, 1H), 7.42 (t, J=7.5 Hz, 1H)

7-amino-1,2,3-benzothiadiazole: $^1$H NMR (300 MHz, CDCl$_3$): 4.10 (br. s, 2H), 6.90 (dd, J=7.5, 0.6 Hz, 1H), 7.46 (t, J=7.5 Hz, 1H), 8.08 (dd, J=7.5 Hz, 0.6 Hz, 1H).

5-amino-1,2,3-benzothiadiazole: $^1$H NMR (300 MHz, CDCl$_3$): 4.06 (brs, 2H), 7.09 (dd, J=9.0 Hz, 2.5 Hz, 1H), 7.78-7.84 (m, 2H).

Step D: 7-bromo-1,2,3-benzothiadiazole

To a mixture of copper (II) bromide (590.9 mg, 2.646 mmol) and t-butyl nitrite (3.147 mL, 26.46 mmol) in acetonitrile (6 mL) was added a solution of 7-amino-1,2,3-benzothiadiazole (800 mg, 5.29 mmol) in acetonitrile at rt. The mixture was heated to 30° C. for 30 min. Purification of the crude mixture by column chromatography (5 to 10% DCM:heptane) afforded 350 mg (31%) of the title compound as a white solid. $^1$H NMR (400 MHz, CDCl$_3$): δ 7.55 (t, J=8.0 Hz, 1 H), 7.83 (d, J=7.6 Hz, 1 H), 8.60 (d, J=8.3 Hz, 1 H).

Step E: 7-(4,4,5,5-tetramethyl-1,3,2-dioxaborolan-2-yl)-1,2,3-benzothiadiazole (Title Compound)

A mixture of 7-bromo-1,2,3-benzothiadiazole (100.0 mg, 0.4650 mmol), bis(pinacolato)diboron (165 mg, 0.930 mmol), (1,1'bis-(diphenylphosphino)-ferrocene)palladium dichloride (17.0 mg, 0.0464 mmol), and potassium acetate (79.6 mg, 0.811 mmol) in 1,4-dioxane (2 mL) was heated to 95° C. for 16 h. The solution was concentrated in vacuo and purified by column chromatography (2 to 5% EtOAc:heptane) to afford 80 mg (65%) of the title compound as light purple solid. $^1$H NMR (400 MHz, CDCl$_3$): δ 1.41 (s, 12 H), 7.65 (dd, J=8.3, 7.1 Hz, 1 H), 8.12 (dd, J=6.9, 0.9 Hz, 1 H), 8.72 (dd, J=8.3, 1.0 Hz, 1 H).

Intermediate 60: 7-(4,4,5,5-tetramethyl-1,3,2-dioxaborolan-2-yl)-1,3-benzothiazole A mixture of 7-bromobenzothiazole (100.0 mg, 0.4671 mmol), bis(pinacolato)diboron (142 mg, 0.558 mmol), (1,1'-bis-(diphenylphosphino)-ferrocene)palladium dichloride (17.1 mg, 0.0234 mmol), and potassium acetate (80.0 mg, 0.815 mmol) in 1,4-dioxane (4 mL) was heated to 90° C. for 3 h. The solution was concentrated in vacuo and purified by column chromatography (3 to 5% EtOAc:heptane) to afford 100 mg (82%) the title compound as a white solid. $^1$H NMR (400 MHz, CDCl$_3$): δ 1.42 (s, 12 H), 7.56 (dd, J=8.1, 7.1 Hz, 1 H), 7.89-7.97 (m, 1 H), 8.26 (dd, J=8.2, 1.1 Hz, 1 H), 9.08 (s, 1 H); MS (ESI): 262.10 [M+H]$^+$; HPLC t$_R$=1.59 min (TOF: polar_3 min).

Intermediate 61: 7-bromo-5-iodo-benzo[d]isothiazole

Step A: 2-amino-5-bromo-6-fluoro-3-nitro-benzonitrile

To a cooled (0° C.) solution of 6-amino-3-bromo-2-fluoro-benzonitrile (8.0 g, 37 mmol) in acetonitrile (40 mL) under nitrogen was added dropwise a solution of nitronium tetrafluoroborate in acetonitrile. The reaction mixture and stirred for 16 h at RT. The reaction mixture was treated with brine and extracted with ethyl acetate. The organic fraction was washed with water followed by brine and dried over anhydrous sodium sulfate, filtered and concentrated. Purification by column chromatography (10 to 20% ethyl acetate: hexanes) afforded 5.0 g (52%) of the title compound. $^1$H NMR (300 MHz, CDCl$_3$): δ 8.6 (d, J=6.9 Hz, 1H), 6.8-7.1 (br. s, 2H).

Step B: 3-bromo-2-fluoro-5-nitro-benzonitrile

To a cooled (0° C.) solution of 2-amino-5-bromo-6-fluoro-3-nitro-benzonitrile (8.0 g, 30.8 mmol) in tetrahydrofuran (40 mL) was added tert-butyl nitrite (4.6 mL, 37 mmol) dropwise and stirred for 16 h at 50° C. The reaction mixture was treated with water and extracted with ethyl acetate. The organic fraction was washed with water and brine, dried over sodium sulfate, filtered, and concentrated. Purification by column chromatography (2% to 10% ethyl acetate:hexanes) afforded 4.0 g (53%) of the title compound. $^1$H NMR (300 MHz, CDCl$_3$): δ 8.72 (dd, J=3.0, 2.7 Hz, 1H), 8.51 (dd, J=3.0, 2.7 Hz, 1H).

Step C: 3-bromo-2-fluoro-5-nitro-benzaldehyde

A three neck flask, equipped with a thermometer, a nitrogen inlet and a septum containing DCM (50 mL) was charged with 3-bromo-2-fluoro-5-nitro-benzonitrile (3.0 g, 12.24 mmol). The mixture was cooled to 0° C. and then DIBAL-H (1.0 M in toluene, 18.3 mL, 18.3 mmol) was added. The resulting solution was warmed to RT and stirred overnight. The reaction mixture was cooled to 0° C. and quenched with aqueous 1 N hydrochloric acid and stirred for 1 h. The reaction mixture was extracted with dichloromethane, washed with water, dried over sodium sulfate, filtered and concentrated. Purification by column chromatography (10% ethyl acetate:hexanes) afforded 1.5 g (50%) of the title compound. $^1$H NMR (300 MHz, CDCl$_3$): δ 10.4 (s, 1H), 8.65-8.68 (m, 2H).

Step D:
3-bromo-2-tert-butylsulfanyl-5-nitro-benzaldehyde

A mixture of 3-bromo-2-fluoro-5-nitro-benzaldehyde (1.0 g, 4 mmol), potassium carbonate (667 mg, 4.8 mmol) and 2-methyl-2-propanethiol (326 mg, 0.40 mL, 3.6 mmol) in dry DMF (5 mL) was heated at 110° C. in a sealed tube for 16 h. The reaction was cooled to RT, water was added, and the mixture extracted with dichloromethane (2×30 mL). The combined organic fractions were washed with water (3×15 mL), dried over sodium sulfate, filtered and concentrated to afford 1.2 g of the crude title compound, which was used without further purification.

Step E:
3-bromo-2-tert-butylsulfanyl-5-nitro-benzaldehyde oxime

A solution of 3-bromo-2-tert-butylsulfanyl-5-nitro-benzaldehyde (1.2 g, 3.8 mmol) and hydroxylamine hydrochloride (1.2 g, 7.7 mmol) in isopropanol (36 mL) and water (8 mL) was heated to 90° C. for 16 h. The reaction mixture was cooled and concentrated to remove isopropanol. Water was added to the residue, followed by saturated sodium bicarbonate solution until the pH was ~8.0. The residue was extracted with dichloromethane (2×30 mL). The combined organic fractions were dried with sodium sulfate, filtered, and concentrated to afford 1.9 g of the crude title compound which was used without further purification.

Step F: 7-bromo-5-nitro-benzo[d]isothiazole

A mixture of 3-bromo-2-tert-butylsulfanyl-5-nitro-benzaldehyde oxime (1.98 g, 5.97 mmol) and p-toluenesulfonic acid (567 mg, 2.98 mmol) in n-butanol (20 mL) was heated to reflux for 16 h. The reaction mixture was cooled and concentrated. The residue was treated with water followed by saturated sodium bicarbonate solution and then was extracted with dichloromethane (3×20 mL). The combined organic fractions were washed with water, dried over sodium sulfate, filtered and concentrated. Purification by column chromatography (20% ethyl acetate:hexanes) afforded 1.0 g (65%) of the title compound. $^1$H NMR (300 MHz, CDCl$_3$): δ 9.21 (s, 1H), 8.95 (s, 1H), 8.59 (s, 1H).

Step G: 7-bromo-benzo[d]isothiazol-5-ylamine

A mixture of 7-bromo-5-nitro-benzo[d]isothiazole (1.0 g, 3.9 mmol) and iron powder (1.0 g, 19 mmol) in ethanol (40 mL) was heated to reflux with vigorous stirring. An aqueous 0.1 N hydrochloric acid (10 mL, 1 mmol) solution was added and the reaction continued until TLC showed no starting material. The reaction mixture was cooled to RT and filtered. The filtrate was concentrated and aqueous sodium carbonate was added to the residue until it became basic. This mixture was filtered through Celite, washing with ethyl acetate. The organic layer was separated, washed with water, dried over anhydrous sodium sulfate and concentrated to give 500 mg (56%) of the title compound. $^1$H NMR (300 MHz, CDCl$_3$): δ 8.8 (s, 1H), 7.2 (s, 1H), 7.1 (s, 1H), 3.82 (br. s, 2H).

Step H: 7-bromo-5-iodo-benzo[d]isothiazole

To a solution of p-toluenesulfonic acid monohydrate (1.36 g, 7.2 mmol) in acetonitrile (8.5 mL) was added 7-bromo-benzo[d]isothiazol-5-ylamine (400 mg, 1.74 mmol). The resulting suspension was cooled to 10 to 15° C. and a solution of sodium nitrite (331 mg, 4.8 mmol) and potassium iodide (996 mg, 6 mmol) in water (1.5 mL) was added gradually. The reaction mixture was stirred for 10 min and then allowed to come to RT and stirred for 16 h. The reaction mixture was treated with water (5 mL) and aqueous 1.0 N sodium bicarbonate solution (15 mL), and aqueous 2.0 N sodium thiosulfate solution (10 mL). The precipitate was collected by filtration and the purified by column chromatography (25% ethyl acetate:hexanes) to afford 300 mg (50%) of the title compound. $^1$H NMR (300 MHz, CDCl$_3$): δ 8.9 (s, 1H), 8.37 (d, J=1.2 Hz, 1H), 7.91 (d, J=1.5 Hz, 1H).

Intermediate 62:
7-bromo-6-iodo-benzo[d]isothiazole

Step A: (2-fluoro-6-iodo-phenyl)-carbamic acid tert-butyl ester

To a cooled (−78° C.) solution of (2-fluoro-phenyl)-carbamic acid tert-butyl ester (38.0 g, 180 mmol) in THF (700 mL) under nitrogen was added tert-butyllithium (1.7 M, 240 mL, 408 mmol). The mixture was stirred for 1 h at −78° C. and then a solution of iodine (60.8 g, 240 mmol) in THF (150 mL) was added slowly. The reaction mixture was stirred for further 1 h. Saturated aqueous ammonium chloride (100 mL) was added slowly and the mixture was warmed to RT. The layers were separated and the aqueous layer was extracted with ethyl acetate (2×100 mL). The combined organic fractions were washed with brine (200 mL), dried over anhydrous sodium sulfate, and concentrated. The residue was purified by flash chromatography (5% ethyl acetate:hexanes) to afford 39.1 g (65%) of the title compound as a while solid. $^1$H NMR (300 MHz, CDCl$_3$): δ 1.50 (s, 9H), 5.98 (br. s, 1H), 6.92-6.99 (m, 1H), 7.08-7.15 (m, 1H), 7.62 (dt, J=7.8, 1.2 Hz, 1H).

Step B: 2-bromo-1-fluoro-3-iodo-benzene

A solution of (2-fluoro-6-iodo-phenyl)-carbamic acid tert-butyl ester (22.5 g, 67 mmol) in ethanol (100 mL) and 48% aqueous hydrobromic acid (100 mL) was stirred at RT. After 1 h the solvent was removed under reduced pressure and the residue was resuspended in 48% aqueous hydrobromic acid (100 mL). The suspension was heated to 60° C. for 10 min followed by cooling to 0° C. in an ice-water bath. A solution of sodium nitrite (4.9 g, 70 mmol) in water (25 mL) was added dropwise keeping the internal temperature below 5° C. The resulting suspension was stirred for 15 min at 0° C. followed by addition of copper (I) bromide (2.93 g, 20 mmol). The mixture was heated to 80° C. for 1 h and subsequently cooled to RT. The mixture was extracted with dichloromethane (2×250 mL) and the organic layer was washed with brine (150 mL), 10% aqueous sodium hydroxide solution (250 mL), brine (250 mL), dried over anhydrous sodium sulfate, filtered and concentrated. The residue was purified by flash column chromatography (5% ethyl acetate:hexanes) to afford 10.5 g (50%) of the title compound. $^1$H NMR (300 MHz, CDCl$_3$): δ 7.01-7.05 (m, 1H), 7.08-7.12 (m, 1H), 7.67 (d, J=4.8 Hz); $^{13}$C NMR (100 MHz, CDCl$_3$): δ 102.5, 115.9 (d, J=22 Hz), 117.6 (d, J=21 Hz), 129.8 (d, J=14 Hz), 135.4 (d, J=21 Hz), 158.7 (d, J=250 Hz); $^{19}$F NMR (282 MHz, CDCl$_3$): δ–96.3 (m, 1F).

Step C: 3-bromo-2-fluoro-4-iodo-benzaldehyde

To a cooled (−78° C.) solution of 2-bromo-1-fluoro-3-iodo-benzene (10.5 g, 35 mmol) in THF (100 mL) under nitrogen was added LDA (2.0 M, 21 mL, 42 mmol). The mixture was stirred for 1 h at −78° C. and then DMF (4.0 mL, 52 mmol) was added slowly. The reaction mixture was stirred for a further 1 h and then saturated aqueous ammonium chloride (50 mL) was added slowly and the mixture was warmed to RT. The layers were separated and the aqueous layer was extracted with ethyl acetate (2×60 mL). The combined organic fractions were washed with brine (100 mL), dried over anhydrous sodium sulfate, and concentrated. Purification of the residue by flash chromatography (5% ethyl acetate: hexanes) afforded 2.3 g (20%) of the title compound. $^1$H NMR (300 MHz, CDCl$_3$): δ 7.43 (dd, J=9.0, 6.6 Hz, 1H), 7.69 (dd, J=9.0, 1.5 Hz, 1H), 10.08 (d, J=0.9 Hz, 1H); $^{19}$F NMR (282 MHz, CDCl$_3$): δ–109.18 (d, J=7.3 Hz, 1F).

Step D: 3-bromo-2-tert-butylsulfanyl-4-iodo-benzaldehyde

A mixture of 3-bromo-2-fluoro-4-iodo-benzaldehyde (1.3 g, 4.0 mmol), potassium carbonate (0.66 g, 4.7 mmol), and 2-methylpropane-2-thiol (0.53 mL, 4.7 mmol) in dry DMF (2 mL) was heated at 80° C. in a sealed tube for 16 h. The reaction mixture was cooled to RT, water was added, and the mixture was extracted with dichloromethane (2×30 mL). The combined organic fractions were washed with water (60 mL), dried over sodium sulfate, filtered, and concentrated. Purification of the residue by column chromatography (5% ethyl acetate:hexanes) afforded 1.0 g (64%) of the title compound. $^1$H NMR (300 MHz, CDCl$_3$): δ 1.30 (s, 9H), 7.54 (d, J=8.1 Hz, 1H), 7.87 (d, J=8.1 Hz, 1H), 10.29 (s, 1H).

Step E: 3-bromo-2-tert-butylsulfanyl-4-iodo-benzaldehyde oxime

A mixture of 3-bromo-2-tert-butylsulfanyl-4-iodo-benzaldehyde (1.5 g, 3.8 mmol) and hydroxylamine hydrochloride in ethanol (20 mL) and water (4 mL) was heated to reflux for 2 h. The reaction mixture was cooled and concentrated. The residue was treated with water (40 mL) and then saturated aqueous sodium bicarbonate solution until the pH was ~8.0. The mixture was extracted with ethyl acetate (2×40 mL). The combined organic fractions were dried over anhydrous sodium sulfate, filtered and concentrated. Purification by column chromatography (25% ethyl acetate:hexanes) afforded 1.1 g (70%) of the title compound. $^1$H NMR (300 MHz, CDCl$_3$): δ 1.34 (s, 9H), 7.41 (d, J=8.7 Hz, 1H), 7.77 (d, J=8.7 Hz, 1H), 8.47 (s, 1H), 8.51 (br. s, 1H); MS (ESI): 414, 416 [M+H]$^+$.

Step F: 7-bromo-6-iodo-benzo[d]isothiazole (Title Compound)

A mixture of 3-bromo-2-tert-butylsulfanyl-4-iodo-benzaldehyde oxime (1.0 g, 2.4 mmol) and p-toluenesulfonic acid (0.19 g, 1 mmol) in n-butanol (50 mL) were heated to reflux for 16 h. The reaction mixture was cooled and concentrated. Water (40 mL) was added to the residue, followed by saturated sodium bicarbonate solution. The mixture was extracted with dichloromethane (3×40 mL). The combined organic fractions were washed with water, dried over anhydrous sodium sulfate, filtered, and concentrated. Purification of the residue by column chromatography (5% ethyl acetate:hexanes) afforded 0.23 g (28%) of the title compound as a solid. $^1$H NMR (300 MHz, CDCl$_3$): δ 7.36 (d, J=7.8 Hz, 1H), 7.69 (d, J=7.8 Hz, 1H), 8.99 (s, 1H).

Intermediate 63: 7-bromo-6-iodo-benzothiazole

Step A: 7-bromo-benzothiazol-6-ylamine

To a solution of benzothiazol-6-ylamine (6.4 g, 42.6 mmol) in glacial acetic acid (40 mL) was added bromine (2.18 mL) in glacial acetic acid (10 mL) dropwise. The reaction mixture was stirred at RT for 1 h. Water (160 mL) was added to the reaction mixture and the solid formed was extracted with ethyl acetate (3×40 mL). The combined organic fractions were washed with saturated aqueous sodium bicarbonate solution (200 mL), water (100 mL), and brine (20 mL), dried over anhydrous sodium sulfate, and concentrated. Purification of the residue by column chromatography (20% ethyl acetate:hexanes) afforded 6.5 g (67%) of the title compound as a yellow solid. $^1$H NMR (300 MHz, CDCl$_3$): δ 4.31 (br. s, 2H), 7.02 (d, J=8.4 Hz, 1H), 7.92 (d, J=8.4 Hz, 1H), 8.80 (s, 1H).

Step B: 7-bromo-6-iodo-benzothiazole (Title Compound)

To a suspension of 7-bromo-benzothiazol-6-ylamine (7.6 g, 33.3 mmol) in water (60 mL) was added concentrated hydrochloric acid (6 mL, 72 mmol). The mixture was cooled to 0° C. and stirred for 10 min. A cooled (0° C.) solution of sodium nitrite (5.0 g, 73 mmol) in water (10 mL) was added dropwise to the reaction mixture keeping the internal temperature below 5° C. The mixture was stirred for further 10 min. A solution of potassium iodide (12.1 g, 73 mmol) in water (15 mL) was added to the reaction mixture and was stirred vigorously for 10 min, and then water (200 mL) and 20% aqueous sodium thiosulfate solution (100 mL) were added. The solid formed was extracted with ethyl acetate (3×70 mL). The combined organic fractions were washed with water (100 mL), dried over anhydrous sodium sulfate, and concentrated. Purification of the residue by column chromatography (25% ethyl acetate:hexanes) afforded 0.3 g (5%) of the title compound, plus some impure title compound. The impure title compound was recrystallized 2× from 1:4 DCM: hexanes to afford a further 0.71 g (9%) of the title compound. $^1$H NMR (300 MHz, CDCl$_3$): δ 8.99 (s, 1H), 7.95 (d, J=8.4, 1H), 7.77 (d, J=8.4 Hz, 1H).

Intermediate 64:
7-bromo-5-iodo-1,2,3-benzothiadiazole

Step A: 7-bromo-1,2,3-benzothiadiazol-4-amine

A mixture of 1,2,3-benzothiadiazol-4-amine (200.0 mg, 1.323 mmol) and NBS (341.4 mg, 1.918 mmol) in THF (10 mL) was stirred at RT overnight. The solution was adsorbed onto silica gel and purified by ISCO chromatography (10 to 30% EtOAc:heptane) to afford 80 mg (30%) of the title compound as a yellow solid. $^1$H NMR (400 MHz, DMSO-d$_6$): δ 6.74 (d, J=8.3 Hz, 1 H), 6.97 (s, 2 H), 7.60 (d, J=8.3 Hz, 1 H).

Step B:
7-bromo-5-iodo-1,2,3-benzothiadiazol-4-amine

A mixture of 7-bromo-1,2,3-benzothiadiazol-4-amine (80.0 mg, 0.348 mmol) and NIS (117.3 mg, 0.522 mmol) in THF (6 ml) was stirred at RT overnight. The solution was adsorbed onto silica gel and purified by ISCO chromatography (10 to 30% EtOAc:heptane) to afford 95 mg (77%) of the title compound as a yellow solid. $^1$H NMR (400 MHz, DMSO-d$_6$): δ 6.89 (s, 2 H), 8.05 (s, 1 H).

Step C: 7-bromo-5-iodo-1,2,3-benzothiadiazole
(Title Compound)

To a solution of 7-bromo-5-iodo-1,2,3-benzothiadiazol-4-amine (95 mg, 0.267 mmol) in THF (6 mL) was added tert-butyl nitrite (0.127 mL, 1.067 mmol) at RT, and the reaction was stirred for 30 min. The solution was adsorbed onto silica gel and purified by ISCO chromatography (1% EtOAc:heptane) to afford 55 mg (60%) of the title compound as a brown solid. $^1$H NMR (400 MHz, CDCl$_3$): δ 8.09 (d, J=1.0 Hz, 1 H), 8.94 (d, J=1.3 Hz, 1 H).

Intermediate 65: 7-bromo-2-chloro-benzothiozole

To a suspension of 7-bromo-2-mercaptobenzothiozole (8.0 g, 32.7 mmol) in dichloromethane (70 mL) was added sulfuryl chloride (36 mL). The resultant mixture was stirred at RT. After completion of the reaction as judged by TLC, the reaction mixture was poured into ice cold water and stirred for 5 min. The organic layer was separated and the aqueous layer was extracted with dichloromethane. The combined organic fractions were washed with saturated aqueous sodium bicarbonate solution, water, and brine, dried over sodium sulfate, filtered, and concentrated. Purification by column chromatography afforded 6.0 g (74%) of the title compound. $^1$H NMR (300 MHz, CDCl$_3$): δ 7.23-7.28 (t, J=8.1 Hz, 1H), 7.42 (dd, J=1.0, 1.2 Hz, 1H), 7.77 (dd, J=1.2, 1.0 Hz, 1H).

Intermediate 66: {7-[bis(tert-butoxycarbonyl) amino]-4-[1-(trans-4-{[tert-butyl(dimethyl)silyl] oxy}cyclohexyl)-1H-pyrazol-4-yl]furo[2,3-c]pyridin-2-yl}boronic acid Step A: 4-iodo-furo[2,3-c]pyridin-7-ylamine To a solution of furo[2,3-c]pyridine-7-ylamine (1.5 g, 11.2 mmol) in acetonitrile (40 mL) was added NIS (3.02 g, 13.4 mmol) portionwise over a period of 15 min. The resultant mixture was stirred at RT for 16 h. The reaction mixture was quenched with 20% aqueous sodium thiosulfate solution (20 mL) and stirred for 10 min. The mixture was extracted with ethyl acetate (70 mL). The organic layer was washed with aqueous 20% sodium thiosulfate solution (20 mL), water (2×50 mL), and brine (40 mL), dried over sodium sulfate, filtered, and concentrated. Purification of the residue by column chromatography (25% ethyl acetate:hexanes) afforded 2.5 g (86%) of the title compound.

Step B: 4-iodo-furo[2,3-c]pyridin-7-yl-di-tert-butoxycarbonylamine

To a solution of 4-iodo-furo[2,3-c]pyridin-7-ylamine (1.7 g, 6.54 mmol) in DCM (50 mL) was added di-tert-butyldicarbonate (4.3 g, 19.6 mmol) in DCM (50 mL) over a period of 15 min followed by DMAP (100 mg). The mixture was stirred at RT overnight. Water (50 mL) was added. The organic fraction was washed with water (2×20 mL), dried over sodium sulfate, filtered, and concentrated. Purification of the residue by column chromatography (10% ethyl acetate:hexanes) afforded 2.3 g (77%) of the title compound as a light brown solid. $^1$H NMR (300 MHz, CDCl$_3$): δ 1.39 (s, 18 H), 6.76 (d, J=1.2 Hz, 1H), 7.8 (d, J=1.2 Hz, 1H), 8.51 (s, 1H).

Step C: di-tert-butyl {4-[1-(trans-4-{[tert-butyl(dimethyl)silyl]oxy}cyclohexyl)-1H-pyrazol-4-yl]furo[2,3-c]pyridin-7-yl}imidodicarbonate A mixture of di-tert-butyl (4-iodofuro[2,3-c]pyridin-7-yl) imidodicarbonate (1.2 g, 2.6 mmol), [1-(trans-4-{[tert-butyl (dimethyl)silyl]oxy}cyclohexyl)-1H-pyrazol-4-yl]boronic acid (1.06 g, 3.26 mmol), 1,1'-bis(diphenylphosphino)ferrocenepalladium (II) dichloride dichloromethane complex (213 mg, 0.261 mmol) and potassium carbonate (0.901 g, 6.52 mmol) in 1,4-dioxane (10 mL) and water (5 mL) was degassed with nitrogen for 10 min. The mixture was then heated to 70° C. for 20 min. Ethyl acetate was added, and the layers separated. The combined organic fractions were dried over sodium sulfate, filtered, and concentrated. Purification of the residue by ISCO chromatography (0% to 35% EtOAc: heptane) afforded 1.15 g (72%) of the title compound as an off-white solid. $^1$H NMR (400 MHz, CDCl$_3$): δ 8.38 (s, 1 H), 7.89 (s, 1 H), 7.82-7.77 (m, 2 H), 7.02 (d, J=2.0 Hz, 1 H), 4.21 (tdd, J=3.9, 7.7, 11.5 Hz, 1 H), 3.82-3.66 (m, 1 H), 2.33-2.17 (m, 2 H), 2.09-2.01 (m, 2 H), 2.00-1.87 (m, 2 H), 1.59-1.49 (m, 2 H), 1.40 (s, 18 H), 0.91 (s, 9 H), 0.09 (s, 6 H); MS (ESI): 613.46 [M+H]$^+$.

Step D: {7-[bis(tert-butoxycarbonyl)amino]-4-[1-(trans-4-{[tert-butyl(dimethyl)silyl]oxy}cyclohexyl)-1H-pyrazol-4-yl]furo[2,3-c]pyridin-2-yl}boronic acid (Title Compound)

To a cooled (−78° C.) solution of di-tert-butyl{4-[1-(trans-4-{[tert-butyl(dimethyl)silyl]oxy}cyclohexyl)-1H-pyrazol-4-yl]furo[2,3-c]pyridin-7-yl}imidodicarbonate (1 g, 2 mmol) in anhydrous THF (10 mL) was added lithium diisopropylamide (2 M in THF, 1.47 mL, 2.94 mmol), and the mixture stirred for 30 min. Boric acid, trimethyl ester (0.371 mL, 3.26 mmol) was added, and the mixture stirred for 10 min before warming to 0° C. The mixture was quenched with water (0.2 mL) and warmed to RT. The THF was removed by rotary evaporation, and the residue was partitioned between ethyl acetate and water. Following separation of the layers, the organic layer was dried over sodium sulfate and evaporated. To the resulting foam was added heptane, and the solution was stirred until the particles were reduced to a powdery solid. The mixture was filtered and washed with heptane (10×). The solid was dried under vacuum to afford 0.6 g (60%) of the title compound as a beige solid. $^1$H NMR (400 MHz, CD$_3$OD): δ 8.23 (s, 1 H), 8.22 (s, 1 H), 8.01 (s, 1 H), 7.07 (s, 1 H), 4.39-4.18 (m, 1 H), 3.93-3.70 (m, 1 H), 2.26-2.13 (m, 2 H), 2.11-1.92 (m, 4 H), 1.60-1.53 (m, 2 H), 1.33 (s, 18 H), 0.93 (s, 9 H), 0.12 (s, 6 H).

Intermediate 67: di-tert-butyl {4-[1-(trans-4-{[tert-butyl(dimethyl)silyl]oxy}cyclohexyl)-1H-pyrazol-4-yl]-2-(trimethylstannanyl)furo[2,3-c]pyridin-7-yl}imidodicarbonate To a cooled (−78° C.) solution of di-tert-butyl {4-[1-(trans-4-{[tert-butyl(dimethyl)silyl]oxy}cyclohexyl)-1H-pyrazol-4-yl]furo[2,3-c]pyridin-7-yl}imidodicarbonate (400 mg, 0.653 mmol) in anhydrous THF (10 mL) was added lithium diisopropylamide (2 M in THF, 1.6 mL, 3.3 mmol), and the mixture stirred for 30 minutes. Chlorotrimethylstannane (1 M in THF, 3.92 mL, 3.92 mmol) was added, and the mixture warmed to RT. The mixture was then cooled to −78° C., quenched by addition of glacial acetic acid (0.2 mL), and warmed to RT. The solution was adsorbed onto silica gel and purified by ISCO chromatography (10 to 20% EtOAc:heptane) to afford 347 mg (69%) of the title compound as a tan solid. $^1$H NMR (400 MHz, CDCl$_3$): δ 0.10 (s, 6 H), 0.45 (s, 9 H), 0.92 (s, 9 H), 1.39 (s, 18 H), 1.50-1.62 (m, 2 H), 1.87-2.09 (m, 4 H), 2.24 (d, J=12.1 Hz, 2 H), 3.69-3.80 (m, 1 H), 4.21 (tt, J=11.5, 3.9 Hz, 1 H), 7.08-7.11 (m, 1 H), 7.78 (s, 1 H), 7.88-7.91 (m, 1 H), 8.31 (s, 1 H).

The following Intermediate was prepared by a procedure analogous to Intermediate 58.

EXAMPLES

Example 1

2-{(3,5-Bis-trifluoromethyl)phenyl}-4-(1-piperidin-4-yl-1H-pyrazol-4-yl)-furo[2,3-c]pyridin-7-ylamine

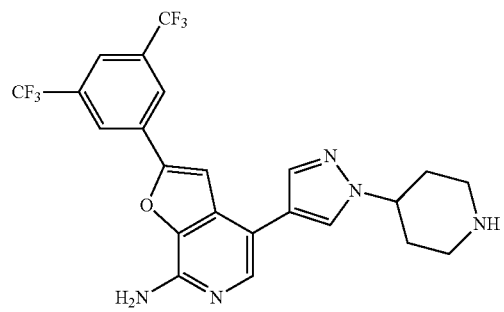 [SMILES: Nc1ncc(-c2cnn(C3CCNCC3)c2)c2cc(-c3cc(C(F)(F)F)cc(C(F)(F)F)c3)oc12]

Step A: 2-{(3,5-Bis(trifluoromethyl)phenyl}-7-chlorofuro[2,3-c]pyridine

In a three-neck flask was placed a mixture of 7-chloro-2-iodofuro[2,3-c]pyridine (1.00 g, 3.58 mmol), 3,5-bis(trifluoromethyl)phenyl boronic acid (0.92 g, 3.6 mmol), 1,4-dioxane/water (50 mL/10 mL) and K$_2$CO$_3$ (0.74 g, 5.38 mmol). After the suspension was degassed with nitrogen for 15 min, (PPh$_3$)$_2$PdCl$_2$ (0.12 g, 0.17 mmol) was added and the mixture was degassed with nitrogen for 5 min. The resultant mixture was stirred at 50° C. for 48 h under nitrogen. The mixture was then cooled to RT and the solvent was evaporated to give a black residue, which was purified by flash chromatography (2% MeOH:DCM) to afford 965 mg (74%) of the title compound as a white crystalline. $^1$H NMR (300 MHz, CDCl$_3$): δ 7.06 (s, 1H), 7.50 (m, 4H), 7.94 (dd, J=1.5 Hz, 2.4 Hz, 1H), 8.19 (d, J=5.1 Hz, 1H).

Step B: 2-{(3,5-Bis-trifluoromethyl)phenyl}-furo[2,3-c]pyridin-7-ylamine

2-{(3,5-Bis(trifluoromethyl)phenyl}-7-chlorofuro[2,3-c]pyridine (0.765 g, 2.09 mmol) was dissolved in 2-propanol (100 mL). To this solution was added anhydrous hydrazine (10 mL, 312 mmol) and the resultant mixture was refluxed for 24 h. The reaction mixture was cooled to RT and the 2-propanol and excess hydrazine were removed on a rotary evaporator. The white residue was suspended in 2-propanol (150

| Int # | NMR Data | Compound Name | MS (ESI) [M + H]$^+$ | HPLC t$_R$ (min) |
|---|---|---|---|---|
| 68 | $^1$H NMR (400 MHz, CDCl$_3$): δ 7.75 (s, 1H), 7.54 (d, J = 0.5 Hz, 1H), 7.46 (d, J = 0.5 Hz, 1H),4.78 (s, 2H), 4.17 (tt, J = 11.5, 3.9 Hz, 1H), 3.50-3.87 (m, 1H), 2.24 (d, J = 12.1 Hz, 2H), 2.00-2.08 (m, 2H), 1.99 (s, 3H), 1.82-1.95 (m, 2H), 1.43-1.66 (m, 2H), 0.91 (s, 9H), 0.09 (s, 6H) | 4-[1-(trans-4-{[tert-butyl(dimethyl)silyl]oxy}cyclohexyl)-1H-pyrazol-4-yl]-2-chloro-3-methylfuro[2,3-c]pyridin-7-amine | 461.01, 463.06 | 3.76 (ZQ3: nonpolar_4 min) | mL) and water (2 mL). Raney Ni (5.0 g) was added and the mixture was refluxed for 2 h. The reaction mixture was cooled to RT and the solution was decanted from the catalyst. The Raney Ni residue was washed with methanol (4×100 mL). The combined organic layers were filtered through a glass filter paper and the filtrate was evaporated on a rotary evaporator to give a colorless crude solid, which was purified by flash chromatography (2% MeOH:DCM) to afford 0.42 g (58%) of the title compound. $^1$H NMR (300 MHz, CD$_3$OD): δ 6.93 (d, J=5.4 Hz, 1H), 7.51 (s, 1H), 7.70 (d, J=6.0 Hz, 1H), 7.99 (s, 1H), 8.55 (s, 2H).

Step C: 2-{(3,5-Bis-trifluoromethyl-phenyl}-4-bromo-furo[2,3-c]pyridin-7-ylamine A solution of 2-(3,5-bis-trifluoromethyl-phenyl)-furo[2,3-c]pyridin-7-ylamine (0.402 g, 1.16 mmol) in a DCM (100 mL) and MeOH (10 mL) was cooled to between −10 and −5° C. and N-bromosuccinimide (0.207 g, 1.16 mmol) was added in one portion. This mixture was stirred at this temperature for 1.5 h. The reaction mixture was quenched with aqueous 20% sodium thiosulfate solution (10 mL) at −5° C. The dichloromethane layer was separated and the aqueous layer was washed with dichloromethane (2×50 mL). All organic layers were combined, washed with water (50 mL) then with brine (20 mL). The organic solution was dried over anhydrous sodium sulfate, filtered and concentrated to give a brown solid, which was purified by flash chromatography (1% MeOH:DCM) to give 0.449 (91%) of the title compound as a light-brown solid. $^1$H NMR (300 MHz, CD$_3$OD): δ 7.53 (br, 1H), 7.77 (br, 1H), 8.00 (br, 1H), 8.57 (br, 2H).

Step D: tert-butyl 4-(4-{7-amino-2-[3,5-bis(trifluoromethyl)phenyl]furo[2,3-c]pyridin-4-yl}-1H-pyrazol-1-yl)piperidine-1-carboxylate A solution of 2-(3,5-bis-trifluoromethyl-phenyl)-4-bromo-furo[2,3-c]pyridin-7-ylamine (0.449 g, 1.06 mmol) and tert-butyl 4-[4-(4,4,5,5-tetramethyl-1,3,2-dioxaborolan-2-yl)-1H-pyrazol-1-yl]piperidine-1-carboxylate (0.419 g, 1.11 mmol) in 1,4-dioxane (60 mL) and water (12 mL) was stirred for 10 min and degassed with nitrogen for 15 min. To this stirred mixture was added Pd(PPh$_3$)$_2$Cl$_2$ (100 mg, 0.14 mmol) and the solution was degassed with nitrogen for an additional 5 min. Na$_2$CO$_3$ (168 mg, 1.59 mmol) was added and resulting mixture was stirred at 95° C. for 4 h. The reaction mixture was cooled to RT and the solvent was removed on a rotary evaporator to give the crude compound, which was purified by flash chromatography (2% MeOH:DCM) to afford 229 mg (36%) of the title compound. $^1$H NMR (300 MHz, CDCl$_3$): δ 1.45 (s, 9H), 2.10 (m, 2H), 2.22 (m, 2H), 2.97 (t, J=13.2 Hz, 2H), 4.35 (m, 3H), 5.59 (br, 2H), 7.34 (s, 1H), 7.71 (s, 1H), 7.81 (s, 1H), 7.92 (d, J=5.1 Hz, 2H), 8.32 (s, 2H). MS (ESI): 596 [M+H]$^+$.

Step E: 2-{(3,5-bis-trifluoromethyl)phenyl}-4-(1-piperidin-4-yl-1H-pyrazol-4-yl)-furo[2,3-c]pyridin-7-ylamine hydrochloride (Title Compound)

tert-butyl 4-(4-{7-amino-2-[3,5-bis(trifluoromethyl)phenyl]furo[2,3-c]pyridin-4-yl}-1H-pyrazol-1-yl)piperidine-1-carboxylate (229 mg, 0.385 mmol) was dissolved in dichloromethane (4 mL). This mixture was cooled to 0° C. and HCl (4.0 M in 1,4-dioxane, 3 mL, 12 mmol) was slowly added by syringe. The reaction mixture was stirred overnight. The solvent was removed on a rotary evaporator to give 214 mg (99%) of the title compound as the hydrochloride salt. $^1$H NMR (300 MHz, D$_2$O): δ 2.23 (m, 4H), 3.18 (m, 2H), 3.57 (m, 2H), 4.53 (m, 1H), 7.40 (s, 1H), 7.47 (s, 1 H), 7.68 (s, 1H), 7.90 (s, 1H), 8.01 (s, 1H), 8.07 (s, 2H); MS (ESI): 496.13 [M+H]$^+$; HPLC t$_R$=1.86 min.

The following examples were prepared using procedures similar for the preparation of Example 1 above:

| Ex. # | Structure and NMR Data | Compound Name | MS (ESI) [M + H]$^+$ | HPLC t$_R$ (min) |
|---|---|---|---|---|
| Ex. 2 | 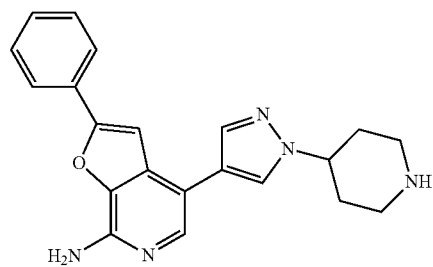 [SMILES: Nc1ncc(-c2cnn(C3CCNCC3)c2)c2cc(-c3ccccc3)oc12]<br>$^1$H NMR (300 MHz, D$_2$O): δ 2.17 (m, 4H), 3.16 (m, 2H), 3.57 (m, 3H), 7.08 (s, 1H), 7.35 (m, 3H), 7.41 (s, 1H), 7.63 (d, J = 8.1 Hz, 2H), 7.71 (s, 1H), 7.91 (s, 1H) | 2-phenyl-4-[1-(piperidin-4-yl)-1H-pyrazol-4-yl]furo[2,3-c]pyridin-7-amine | 360 | — |

-continued

| Ex. # | Structure and NMR Data | Compound Name | MS (ESI) [M + H]+ | HPLC t_R (min) |
|---|---|---|---|---|
| Ex. 3 | ¹H NMR (300 MHz, D₂O): δ 2.18 (m, 4H), 3.18 (m, 2H), 3.60 (m, 2H), 4.48 (m, 1H), 6.72 (m, 1H) 7.13 (m, 2H), 7.33 (m, 2H), 7.55 (m, 4H), 7.74 (s, 1H), 7.89 (d, J = 8.7 Hz, 1H) | 2-(naphthalen-1-yl)-4-[1-(piperidin-4-yl)-1H-pyrazol-4-yl]furo[2,3-c]pyridin-7-amine | 410 | — |
| Ex. 4 | ¹H NMR (300 MHz, CDCl₃ + CD₃OD): δ 2.43 (m, 4H), 2.85 (m, 2H), 3.36 (m, 3H), 6.55 (m, 1H), 6.82 (m, 1H), 7.41 (m, 2H), 7.52 (s, 1H), 7.62 (s, 1H), 7.82 (m, 1H) | 2-(2,3-dichlorophenyl)-4-[1-(piperidin-4-yl)-1H-pyrazol-4-yl]furo[2,3-c]pyridin-7-amine | 427.77, 429.69 | 1.91 |
| Ex. 5 | ¹H NMR (300 MHz, CD₃OD): δ 2.38 (m, 4H), 3.58 (m, 4H), 4.10 (s, 3H), 4.71 (m, 1H), 7.30 (m, 2H), 7.65 (s, 1H), 7.80 (s, 1H), 7.97 (m, 2H), 8.26 (s, 1H) | 2-(3-fluoro-2-methoxyphenyl)-4-[1-(piperidin-4-yl)-1H-pyrazol-4-yl]furo[2,3-c]pyridin-7-amine dihydrochloride | 407.87 | 1.73 |
| Ex. 6 | ¹H NMR (400 MHz, D₂O): δ ppm 2.11-2.35 (m, 4H) 3.20 (td, J = 13.01, 2.78 Hz, 2H) 3.57 (d, J = 13.64 Hz, 2H) 4.47-4.58 (m, 1H) 7.19 (s, 1H) 7.35-7.41 (m, 1H) 7.42 (s, 1H) 7.54 (d, J = 7.83 Hz, 1H) 7.69 (s, 1H) 7.76 (d, J = 7.83 Hz, 1H) 7.80 (s, 1 H) 7.97 (s, 1H) | 4-[1-(piperidin-4-yl)-1H-pyrazol-4-yl]-2-[3-(trifluoromethyl)phenyl]furo[2,3-c]pyridin-7-amine | 428.14 | 1.95 |

| Ex. # | Structure and NMR Data | Compound Name | MS (ESI) [M + H]+ | HPLC $t_R$ (min) |
|---|---|---|---|---|
| Ex. 7 | 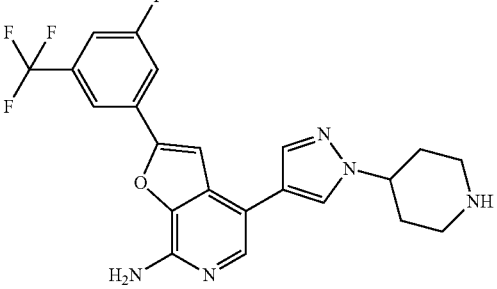<br>¹H NMR (300 MHz, D₂O): δ 2.25 (m, 4H), 3.20 (m, 2H), 3.55 (m, 2H), 4.55 (m, 1H), 7.29 (s, 1H), 7.30 (s, 1H), 7.49 (s, 1H), 7.51 (s, 1H), 7.67 (s, 1H), 7.73 (s, 1H), 8.02 (s, 1H) | 2-[3-fluoro-5-(trifluoromethyl)phenyl]-4-[1-(piperidin-4-yl)-1H-pyrazol-4-yl]furo[2,3-c]pyridin-7-amine | 446.15 | 2.02 |
| Ex. 8 | 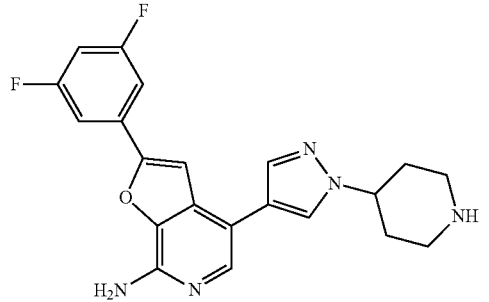 [SMILES: Nc1ncc(-c2cnn(C3CCNCC3)c2)c2cc(-c3cc(F)cc(F)c3)oc12]<br>¹H NMR (300 MHz, D₂O): δ 2.26 (m, 4H), 3.19 (m, 2H), 3.58 (m, 2H), 4.61 (m, 1H), 6.91 (m, 1H), 7.27 (m, 3H), 7.55 (s, 1H), 7.79 (s, 1H) | 2-(3,5-difluorophenyl)-4-[1-(piperidin-4-yl)-1H-pyrazol-4-yl]furo[2,3-c]pyridin-7-amine | 396.13 | 1.86 |

Example 9 methyl-2-phenyl-4-[1-(piperidin-4-yl)-1H-pyrazol-4-yl]furo[2,3-c]pyridin-7-amine hydrochloride

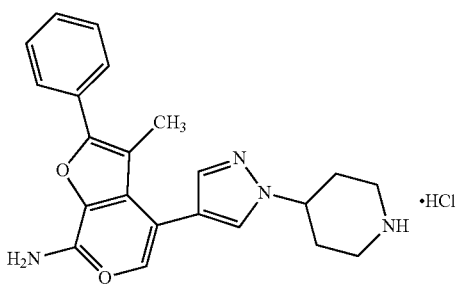

Step A: tert-butyl 4-[4-(7-amino-2-chloro-3-methyl-furo[2,3-c]pyridin-4-yl)-1H-pyrazol-1-yl]piperidine-1-carboxylate A vial was charged with 2-chloro-4-iodo-3-methylfuro[2,3-c]pyridin-7-amine (100 mg, 0.32 mmol), tert-butyl 4-[4-(4,4,5,5-tetramethyl-1,3,2-dioxaborolan-2-yl)-1H-pyrazol-1-yl]piperidine-1-carboxylate (140 mg, 0.39 mmol), Cs₂CO₃ (150 mg, 0.48 mmol), Pd(dppf)Cl₂ (20 mg, 0.027 mmol, 8 mole %), and 2-dicyclohexylphosphino-2',4',6'-triisopropyl-biphenyl (40 mg, 0.080 mmol, 26 mole %) in DME (5 mL) and H₂O (0.5 mL). The vial was purged with N₂ and heated at 100° C. in a microwave reactor for 1 h. Water (20 mL) was added, and the mixture was extracted with EtOAc (3×20 mL). The combined organic extracts were dried over Na₂SO₄, filtered and concentrated in vacuo. The residue was purified by preparative TLC (EtOAc) to afford 85 mg (62%) of the title compound. ¹H NMR (400 MHz, CDCl₃): δ 7.67 (s, 1H), 7.48 (s, 1H), 7.39 (s, 1H), 4.66 (s, 2H), 4.23 (m, 4H), 2.85 (m, 1H), 2.14 (m, 2H), 2.10 (m, 1H), 1.94 (s, 3H), 1.87 (m, 1H), 1.41 (s, 9H).

Step B: 3-methyl-2-phenyl-4-[1-(piperidin-4-yl)-1H-pyrazol-4-yl]furo[2,3-c]pyridin-7-amine (Title Compound)

A vial was charged with tert-butyl-4-[4-(7-amino-2-chloro-3-methylfuro[2,3-c]pyridin-4-yl)-1H-pyrazol-1-yl]piperidine-1-carboxylate (50 mg, 0.116 mmol), phenylboronic acid (45 mg, 0.174 mmol) in DME (3 mL) and H₂O (0.3 mL) along with Cs₂CO₃ (55 mg, 0.174 mmol), Pd(dppf)Cl₂ (20 mg, 0.027 mmol), 2-dicyclohexylphosphino-2',4',6'-triisopropylbiphenyl (40 mg, 0.08 mmole) under N₂. The mixture was heated at 100° C. in a microwave reactor for 40 min. Water (20 mL) was added, and the mixture was extracted with EtOAc (3×20 mL). The combined organic extracts were dried over Na₂SO₄, filtered and concentrated in vacuo. The residue was purified by preparative TLC (EtOAc) to afford the N-Boc protected intermediate. This was dissolved in EtOAc, treated with 4 M HCl in EtOAc (5 mL) and stirred for 60 min. The mixture was filtered to provide 24 mg (56%) of the title compound. ¹H NMR (400 MHz, CD₃OD): δ 8.10 (s, 1H), 7.88 (s, 2H), 7.76 (s, 1H), 7.55 (m, 4H), 4.73 (m, 1H), 3.59 (m, 2H), 3.33 (m, 2H), 2.40 (m, 4H), 2.22 (s, 3H); MS (ESI): 374.28 [M+H]⁺.

The following Examples were prepared using procedures analogous to Example 9.

| Ex. # | Structure and NMR Data | Compound Name | MS (ESI) [M + H]+ |
|---|---|---|---|
| Ex. 10 | 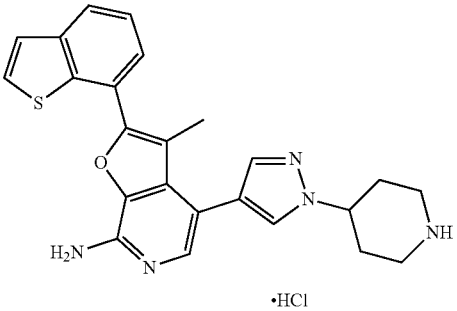 [SMILES: Cc1c(-c2cccc3ccsc23)oc2c(N)ncc(-c3cnn(C4CCNCC4)c3)c12 ; Cl]<br>•HCl<br>¹H NMR (400 MHz, DMSO-d₆, D₂O) δ: 8.60 (s, 1H), 8.12 (s, 1H), 8.09 (d, 1H), 7.91 (d, 1H), 7.74 (s, 1H), 7.62 (d, 1H), 7.60 (d, 1H), 7.58 (s, 1H), 4.55 (m, 1H), 3.58 (m, 2H), 3.05 (m, 2H), 2.21 (m, 4H), 2.05 (s, 3H) | 2-(1-benzothiophen-7-yl)-3-methyl-4-[1-(piperidin-4-yl)-1H-pyrazol-4-yl]furo[2,3-c]pyridin-7-amine hydrochloride | 430.1 |
| Ex. 11 | 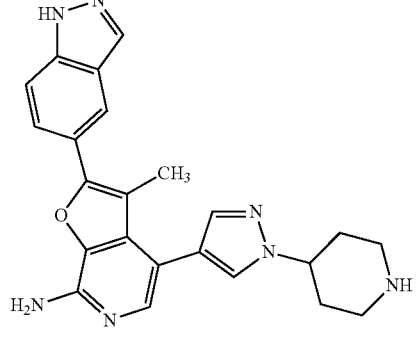<br>•HCl<br>¹H NMR (400 MHz, DMSO-d₆, D₂O) δ: 8.24 (s, 1H), 8.18 (s, 1H), 8.01 (s, 1H), 7.83 (m, 1H), 7.68 (m, 2H), 7.44 (s, 1H), 4.52 (m, 1H), 3.38 (m, 2H), 3.05 (m, 2H), 3.20 (m, 4H), 3.10 (s, 3H) | 2-(1H-indazol-5-yl)-3-methyl-4-[1-(piperidin-4-yl)-1H-pyrazol-4-yl]furo[2,3-c]pyridin-7-amine hydrochloride | 414.1 |

Example 12

3-chloro-2-phenyl-4-[1-(piperidin-4-yl)-1H-pyrazol-4-yl]furo[2,3-c]pyridin-7-amine hydrochloride

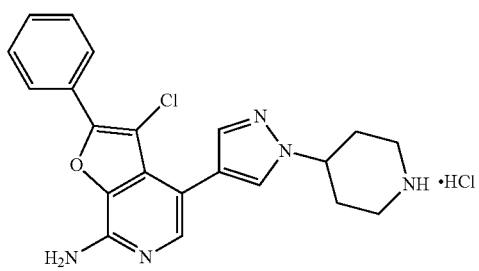 [SMILES: Nc1ncc(-c2cnn(C3CCNCC3)c2)c2c(Cl)c(-c3ccccc3)oc12 ; Cl]

Step A: tert-butyl 4-[4-(7-amino-3-chloro-2-phenyl-furo[2,3-c]pyridin-4-yl)-1H-pyrazol-1-yl]piperidine-1-carboxylate A solution of phenylboronic acid (35.0 mg, 287 μmol), tert-butyl 4-[4-(7-amino-3-chlorofuro[2,3-c]pyridin-4-yl)-1H-pyrazol-1-yl]piperidine-1-carboxylate (65 mg, 144 μmol), (1,1'-bis(diphenylphosphino)ferrocene)palladium dichloride (10.5 mg, 14.4 μmol), potassium carbonate (29.8 mg, 216 μmol) in 1,4-dioxane (785 μL) and H₂O (259 μL) was evacuated and filled with argon three times. The mixture was irradiated in a microwave reactor at 100° C. for 40 min. The reaction mixture was partitioned between EtOAc and brine/water and separated. The aqueous layer was extracted with EtOAc (3×) and the combined organic extracts were washed with brine, dried over sodium sulfate, filtered, and concentrated. The residue was purified by flash chromatography (60 to 100% EtOAc:hexanes) to afford tert-butyl 4-[4-(7-amino- 3-chloro-2-phenylfuro[2,3-c]pyridin-4-yl)-1H-pyrazol-1-yl]piperidine-1-carboxylate. MS (ESI): 494.16 [M+H]⁺; HPLC $t_R$=3.11 min.

Step B: 3-chloro-2-phenyl-4-[1-(piperidin-4-yl)-1H-pyrazol-4-yl]furo[2,3-c]pyridin-7-amine hydrochloride (Title Compound)

A solution of tert-butyl 4-[4-(7-amino-3-chloro-2-phenyl-furo[2,3-c]pyridin-4-yl)-1H-pyrazol-1-yl]piperidine-1-carboxylate in DCM (1.0 mL) was treated with HCl (1 M in Et₂O, 2.0 mL, 2.0 mmol) and stirred at RT. The reaction was concentrated in vacuo to provide 43 mg (76%) of the title compound. ¹H NMR (400 MHz, CD₃OD) δ 6.94-6.98 (m, 2H), 6.80 (s, 1H), 6.53 (s, 1H), 6.32-6.36 (m, 4H), 3.40 (tt, J=9.98, 4.93 Hz, 1H), 2.34 (dt, J=13.26, 3.35 Hz, 2H), 1.94-2.00 (m, 2H), 1.05-1.15 (m, 4H); MS (ESI): 394.14 [M+H]⁺; HPLC $t_R$=0.97 min (TOF: polar_3 min).

The following examples were prepared analogously, using procedures similar to Example 12 above.

| Ex. # | Structure and NMR Data | Compound Name | HPLC $t_R$ (min) | MS (ESI) [M + H]⁺ |
|---|---|---|---|---|
| Ex. 13 | 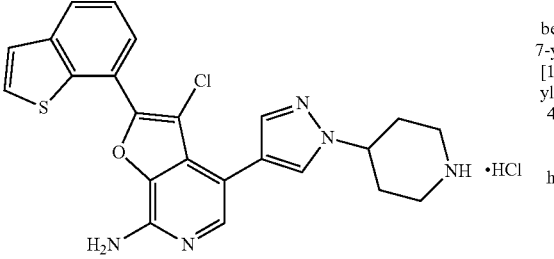 ¹H NMR (400 MHz, CD₃OD) δ 8.08-8.13 (m, 2H), 8.04 (d, J = 7.58 Hz, 1H), 7.83 (s, 1H), 7.77 (d, J = 5.56 Hz, 1H), 7.68 (s, 1H), 7.54-7.63 (m, 2H), 4.61-4.74 (m, 1H), 3.56-3.64 (m, 2H), 3.20-3.29 (m, 2H), 2.29-2.44 (m, 4H). | 2-(1-benzothiophen-7-yl)-3-chloro-4-[1-(piperidin-4-yl)-1H-pyrazol-4-yl]furo[2,3-c]pyridin-7-amine hydrochloride | 1.02 min (TOF: polar_3 min) | 450.10 |
| Ex. 14 | 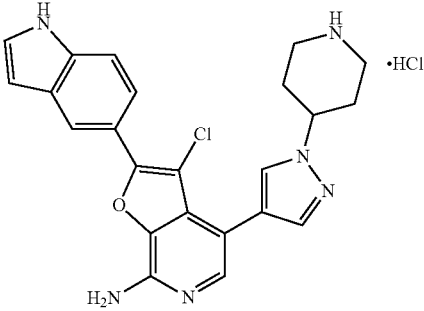 [SMILES: Nc1ncc(-c2cnn(C3CCNCC3)c2)c2c(Cl)c(-c3ccc4[nH]ccc4c3)oc12 ; Cl] ¹H NMR (400 MHz, CD₃OD) δ 8.43 (s, 1H), 8.05 (s, 1H), 7.98 (m, 1H), 7.75 (s, 1H), 7.50-7.54 (m, 2H), 7.35 (s, 1H), 6.58 (s, 1H), 4.69 (m, 1H), 3.63-3.59 (m, 2H), 3.30-3.26 (m, 2H), 2.38 (m, 4H). | 3-chloro-2-(1H-indol-5-yl)-4-[1-(piperidin-4-yl)-1H-pyrazol-4-yl]furo[2,3-c]pyridin-7-amine hydrochloride | — | 433.14 |
| Ex. 15 | 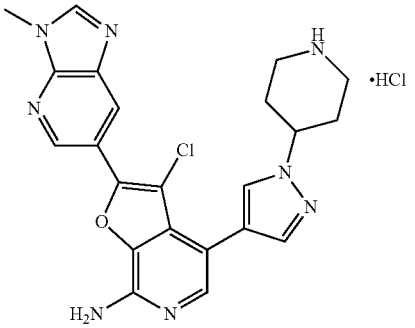 [SMILES: Cn1cnc2cc(-c3oc4c(N)ncc(-c5cnn(C6CCNCC6)c5)c4c3Cl)cnc21 ; Cl] ¹H NMR (400 MHz, DMSO-d6, D₂O) δ 9.24 (s, 1H), 8.87-8.85 (m, 2H), 8.08 (s, 1H), 7.73-7.71 (m, 2H), 4.55 (m, 1H), 3.96 (s, 3H), 3.37-3.34 (m, 2H), 3.12-3.09 (m, 2H), 2.23-2.20 (m, 4H). | 3-chloro-2-(3-methyl-3H-imidazo[4,5-b]pyridine-6-yl)-4-[1-(piperidin-4-yl)-1H-pyrazol-4-yl]furo[2,3-c]pyridin-7-amine hydrochloride | — | 449.25 |

-continued

| Ex. # | Structure and NMR Data | Compound Name | HPLC $t_R$ (min) | MS (ESI) $[M + H]^+$ |
|---|---|---|---|---|
| Ex. 16 | 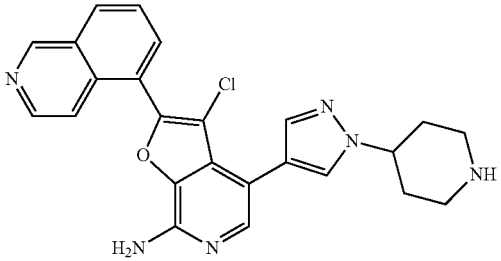 [SMILES: Nc1ncc(-c2cnn(C3CCNCC3)c2)c2c(Cl)c(-c3cccc4cnccc34)oc12] ¹H NMR (400 MHz, CD₃OD): δ: 9.79-9.80 (d, J = 1.2 Hz, 1H), 9.13 (s, 1H), 8.77-8.79 (d, J = 9.2 Hz, 1H), 8.65-8.67 (d, J = 8 Hz, 2H), 8.54-8.56 (d, J = 6 Hz, 1H), 8.10 (s, 1H), 7.81 (s, 1H), 7.65 (m, 1H), 4.65-4.68 (m, 1H), 3.57-3.61 (m, 2H), 3.25-3.25 (m, 2H), 2.36-2.39 (m, 4H) | 3-chloro-2-(isoquinoolin-5-yl)-4-[1-(piperidin-4-yl)-1H-pyrazol-4-yl]furo[2,3-c]pyridin-7-amine | — | 445.1 |

Example 17

4-{4-[7-amino-2-(1-benzothiophen-7-yl)furo[2,3-c]pyridine-4-yl]-1H-pyrazol-1-yl}piperidine hydrochloride

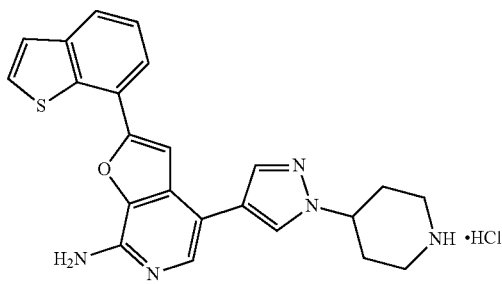 [SMILES: Nc1ncc(-c2cnn(C3CCNCC3)c2)c2cc(-c3cccc4ccsc34)oc12 ; Cl]

Step A: tert-butyl 4-{4-[7-amino-2-(1-benzothiophen-7-yl)furo[2,3-c]pyridine-4-yl]-1H-pyrazol-1-yl}piperidine-1-carboxylate A solution of 7-benzothiophene boronic acid, 4-[4-(7-amino-2-chloro-furo[2,3-c]pyridin-4-yl)-pyrazol-1-yl]-piperidine-1-carboxylic acid tert-butyl ester (150 mg, 359 μmol), Pd(dppf)Cl₂ (2.63 mg, 3.59 μmol), K₂CO₃, (74.4 mg, 538 μmol) in 1,4-dioxane (1.96 mL), and H₂O (647 μL) was degassed and refilled with argon (3×). The reaction was heated in a microwave reactor at 100° C. for 70 min. The reaction was diluted with water, extracted with EtOAc (3×) and the combined extracts were dried over Na₂SO₄, then concentrated in vacuo to give a solid. The solid was purified by flash chromatography (60-100% EtOAc:hexanes) to afford 96 mg (64%) of the title compound. ¹H NMR (400 MHz, CDCl₃): δ 8.03 (d, J=7.33 Hz, 1 H), 7.88-7.99 (m, 3 H), 7.75 (s, 1 H), 7.61 (d, J=5.31 Hz, 1 H), 7.56 (t, J=7.71 Hz, 1 H), 7.50 (d, J=5.56 Hz, 1 H), 7.44 (s, 1 H), 5.53 (br s, 2 H), 4.25-4.48 (m, 3 H), 2.90-3.01 (m, 2 H), 2.24 (d, J=15.16 Hz, 2 H), 1.97-2.11 (m, 2 H), 1.51 (s, 9 H); MS (ESI): 516.16 [M+H]⁺; HPLC $t_R$=2.66 min.

Step B: 4-{4-[7-amino-2-(1-benzothiophen-7-yl)furo[2,3-c]pyridin-4-yl]-1H-pyrazol-1-yl}Piperidine (Title Compound)

A solution of tert-butyl 4-{4-[7-amino-2-(1-benzothiophen-7-yl)furo[2,3-c]pyridine-4-yl]-1H-pyrazol-1-yl}piperidine-1-carboxylate in DCM (1.50 mL) was treated with HCl (1 M in Et₂O, 5.00 mL, 5.00 mmol) and stirred for 30 min. The reaction was concentrated in vacuo to afford 86 mg (71%) of the title compound. ¹H NMR (400 MHz, CD₃OD) δ 7.08 (s, 1 H), 7.00 (d, J=7.58 Hz, 1 H), 6.82 (d, J=7.83 Hz, 1 H), 6.79 (s, 1 H), 6.59 (s, 1 H), 6.50-6.54 (m, 2 H), 6.36 (t, J=7.71 Hz, 1 H), 6.32 (d, J=5.56 Hz, 1 H), 3.39-3.52 (m, 1 H), 2.36 (d, J=13.14 Hz, 2 H), 1.96-2.02 (m, 2 H), 1.09-1.19 (m, 4 H); MS (ESI): 416.12 [M+H]⁺; HPLC $t_R$=2.19 min.

Example 18

2-(1H-indazol-5-yl)-4-[1-(piperidin-4-yl)-1H-pyrazol-4-yl]furo[2,3-c]pyridin-7-amine hydrochloride

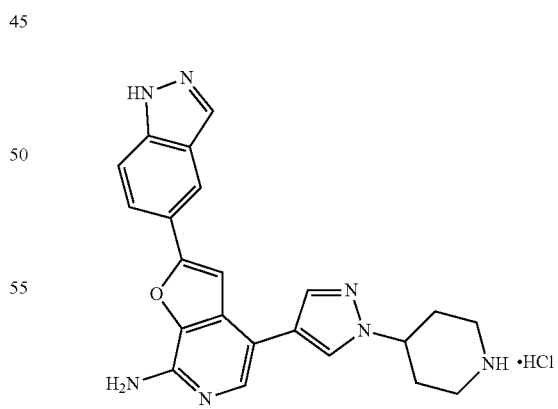

Step A: tert-butyl 4-{4-[7-amino-2-(1H-indazol-5-yl)furo[2,3-c]pyridine-4-yl]-1H-pyrazol-1-yl}piperidine-1-carboxylate A vial was charged with tert-butyl 4-[4-(7-amino-2-chlorofuro[2,3-c]pyridin-4-yl)-1H-pyrazol-1-yl]piperidine-1- carboxylate (50 mg, 0.12 mmol), 5-indazole boronic acid (45 mg, 0.18 mmol), Cs$_2$CO$_3$ (55 mg, 0.174 mmol), Pd(dppf)Cl$_2$ (20 mg) and 2-dicyclohexylphosphino-2',4',6'-triisopropylbiphenyl (40 mg) in DME (3 mL) and H$_2$O (0.3 mL) under N$_2$. The mixture was heated to 100° C. for 40 min in a microwave reactor. Water (20 mL) was added, and the mixture was extracted with EtOAc (3×20 mL). The combined organic layers were dried over Na$_2$SO$_4$, filtered and concentrated in vacuo. The residue was purified by preparative TLC (EtOAc) to afford the desired N-Boc protected intermediate, which was used immediately.

Step B: 2-(1H-indazol-5-yl)-4-[1-(piperidin-4-yl)-1H-pyrazol-4-yl]furo[2,3-c]pyridine-7-amine hydrochloride (Title Compound)

A solution of crude tert-butyl 4-{4-[7-amino-2-(1H-indazol-5-yl)furo[2,3-c]pyridine-4-yl]-1H-pyrazol-1-yl}piperidine-1-carboxylate (from Step A) in EtOAc was treated with HCl (4 M in EtOAc, 5 mL, 5 mmol) for 60 min. The reaction was filtered to afford 24 mg (60%) of the title compound. $^1$H NMR (400 MHz, CD$_3$OD): δ 8.89 (s, 1 H), 8.41 (s, 1 H), 8.08 (s, 1 H), 8.04 (d, J=7.07 Hz, 1 H), 7.89 (s, 1 H), 7.86 (s, 1 H), 7.78 (d, J=8.59 Hz, 1 H), 7.57-7.63 (m, 1 H), 4.67-4.77 (m, 1 H), 3.57-3.65 (m, 2 H), 3.22-3.29 (m, 2 H), 2.37-2.46 (m, 4 H); MS (ESI): 400.09 [M+H]$^+$; HPLC t$_R$=1.81 min.

The Examples in the table below were prepared from tert-butyl 4-[4-(7-amino-2-chlorofuro[2,3-c]pyridine-4-yl)-1H-pyrazol-1-yl]piperidine-1-carboxylate and an appropriate boronic acid or ester using procedures analogous to Examples 17 or 18 above.

| Ex. # | Structure and NMR Data | Compound Name | MS (ESI) [M + H]$^+$ | HPLC t$_R$ (min) |
|---|---|---|---|---|
| Ex. 19 | 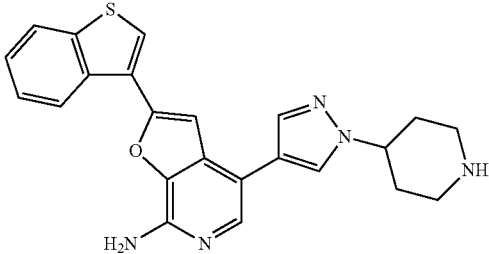 [SMILES: Nc1ncc(-c2cnn(C3CCNCC3)c2)c2cc(-c3csc4ccccc34)oc12]<br>$^1$H NMR (400 MHz, CD$_3$OD): δ 8.59 (d, J = 8.08 Hz, 1 H), 8.57 (s, 1 H), 8.41 (s, 1 H), 8.08 (s, 1 H), 8.05 (d, J = 8.08 Hz, 1 H), 7.86 (s, 1 H), 7.74 (s, 1 H), 7.62 (td, J = 7.58, 1.01 Hz, 1H), 7.50-7.55 (m, 1 H), 4.67-4.78 (m, 1 H), 3.57-3.69 (m, 2 H), 3.24-3.33 (m, 2 H), 2.37-2.45 (m, 4 H) | 2-(1-benzothiophen-3-yl)-4-[1-(piperidin-4-yl)-1H-pyrazol-4-yl]furo[2,3-c]pyridine-7-amine | 416.05 | 2.20 |
| Ex. 20 | 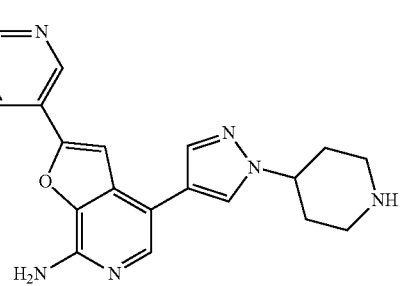<br>$^1$H NMR (400 MHz, CD$_3$OD): δ 8.59 (s, 1 H), 8.56 (d, J = 9.35 Hz, 1 H), 8.38 (s, 1 H), 7.91-7.97 (m, 2 H), 7.80 (s, 1 H), 7.15 (d, J = 9.09 Hz, 1 H), 4.64 (dt, J = 14.78, 7.52 Hz, 1 H), 3.53 (d, J = 13.39 Hz, 2 H), 3.14-3.21 (m, 2 H), 2.28-2.36 (m, 4 H) | 2-(6-aminopyridin-3-yl)-4-[1-(piperidin-4-yl)-1H-pyrazol-4-yl]furo[2,3-c]pyridine-7-amine | 376.15 | 1.61 |

| Ex. # | Structure and NMR Data | Compound Name | MS (ESI) [M + H]+ | HPLC $t_R$ (min) |
|---|---|---|---|---|
| Ex. 21 | 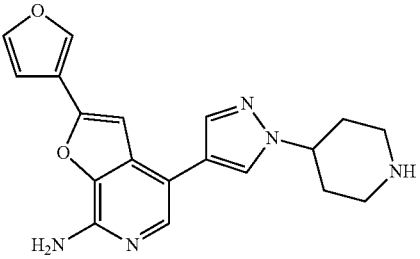<br>¹H NMR (400 MHz, CD₃OD): δ 8.34 (d, J = 10.86 Hz, 2 H), 8.03 (s, 1 H), 7.83 (s, 1 H), 7.74 (t, J = 1.64 Hz, 1 H), 7.55 (s, 1 H), 7.09 (dd, J = 1.77, 0.76 Hz, 1 H), 4.70 (quin, J = 7.45 Hz, 1 H), 3.61 (dt, J = 13.26, 3.35 Hz, 2 H), 3.22-3.30 (m, 2 H), 2.35-2.44 (m, 4 H) | 2-(furan-3-yl)-4-[1-(piperidin-4-yl)-1H-pyrazol-4-yl]furo[2,3-c]pyridine-7-amine | 350.09 | 1.76 |
| Ex. 22 | 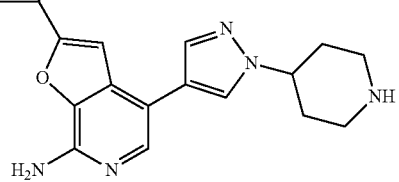<br>¹H NMR (400 MHz, CD₃OD): δ 8.35 (s, 1 H), 8.17 (d, J = 7.83 Hz, 1 H), 8.10 (s, 1 H), 8.08 (s, 1 H), 7.90 (s, 1 H), 7.85-7.88 (m, 1 H), 7.72 (t, J = 8.08 Hz, 1 H), 7.51 (dd, J = 8.46, 1.14 Hz, 1 H), 4.63-4.77 (m, 1 H), 3.64 (d, J = 12.63 Hz, 2 H), 3.22-3.31 (m, 2 H), 2.37-2.45 (m, 4 H) | 4-[1-(piperidin-4-yl)-1H-pyrazol-4-yl]-2-[3-(trifluoromethoxy)phenyl]furo[2,3-c]pyridine-7-amine | 444.09 | 2.27 |
| Ex. 23 | 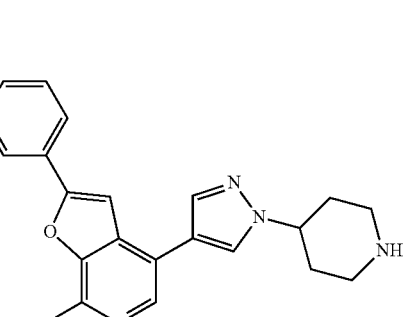<br>¹H NMR (400 MHz, CD₃OD): δ 8.39 (s, 1 H), 8.05 (s, 1 H), 8.00 (t, J = 1.77 Hz, 1 H), 7.94 (d, J = 8.34 Hz, 1 H), 7.83 (s, 1 H), 7.78 (s, 1 H), 7.56 (t, J = 7.96 Hz, 1 H), 7.38 (dd, 1 H), 4.70 (quin, J = 7.45 Hz, 1 H), 3.62 (dt, J = 13.01, 3.22 Hz, 2 H), 3.21-3.30 (m, 2 H), 3.06 (s, 3 H), 2.36-2.45 (m, 4 H) | N-(3-{7-amino-4-[1-(piperidin-4-yl)-1H-pyrazol-4-yl]furo[2,3-c]pyridine-2-yl}phenyl)methanesulfonamide | 453.08 | 1.88 |

-continued

| Ex. # | Structure and NMR Data | Compound Name | MS (ESI) [M + H]+ | HPLC $t_R$ (min) |
|---|---|---|---|---|
| Ex. 24 | 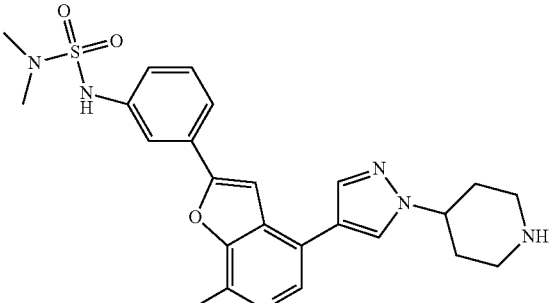<br>¹H NMR (400 MHz, CD₃OD): δ 8.35 (s, 1 H), 8.05 (s, 1 H), 7.95 (t, J = 1.77 Hz, 1 H), 7.87 (dd, J = 6.69, 1.64 Hz, 1 H), 7.82 (s, 1 H), 7.72 (s, 1 H), 7.52 (t, J = 7.96 Hz, 1 H), 7.33-7.40 (m, 1 H), 4.64-4.75 (m, 1 H), 3.62 (dt, J = 13.26, 3.73 Hz, 2 H), 3.21-3.29 (m, 2 H), 2.84 (s, 6 H), 2.35-2.43 (m, 4 H) | N'-(3-{7-amino-4-[1-(piperidin-4-yl)-1H-pyrazol-4-yl]furo[2,3-c]pyridine-2-yl}phenyl)-N,N-dimethylsulfuric diamide | 482.08 | 2.00 (TOF: polar_3 min) |
| Ex. 25 | 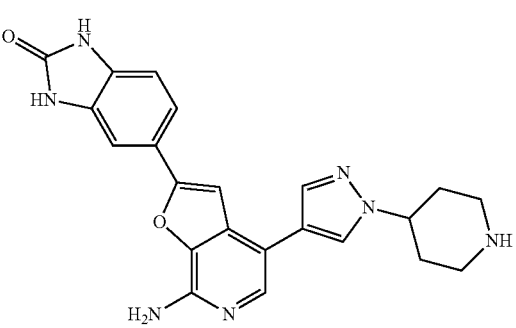 [SMILES: Nc1ncc(-c2cnn(C3CCNCC3)c2)c2cc(-c3ccc4[nH]c(=O)[nH]c4c3)oc12]<br>¹H NMR (400 MHz, DMSO-d₆): δ 10.98 (s, 1 H), 10.92 (s, 1 H), 8.29 (s, 1 H), 7.95-7.99 (m, 2 H), 7.74 (dd, J = 8.08, 1.77 Hz, 1 H), 7.63 (s, 1H), 7.59 (s, 1 H), 7.06 (d, 1 H), 6.39 (br. s., 2 H), 4.31-4.45 (m, 1 H), 4.04-4.15 (m, 2 H), 2.95 (br. s., 2 H), 2.03-2.11 (m, 3 H), 1.90 (qd, J = 12.21, 4.29 Hz, 2 H) | 5-{7-amino-4-[1-(piperidin-4-yl)-1H-pyrazol-4-yl]furo[2,3-c]pyridine-2-yl}-1,3-dihydro-2H-benzimidazol-2-one | 416.05 | 1.78 |
| Ex. 26 | 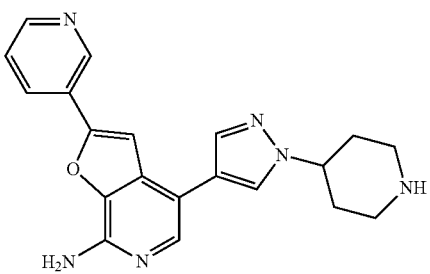 [SMILES: Nc1ncc(-c2cnn(C3CCNCC3)c2)c2cc(-c3cccnc3)oc12]<br>¹H NMR (400 MHz, CD₃OD): δ 9.05 (d, J = 7.83 Hz, 1 H), 8.90 (d, J = 4.80 Hz, 1 H), 8.45 (s, 1 H), 8.29 (s, 1 H), 8.05-8.12 (m, 2 H), 7.90 (s, 1 H), 7.52-7.61 (m, 1 H), 4.68-4.77 (m, 1 H), 3.61 (d, J = 16.17 Hz, 2 H), 3.20-3.29 (m, 2 H), 2.37-2.47 (m, 4 H) | 4-[1-(piperidin-4-yl)-1H-pyrazol-4-yl]-2-(yridine-3-yl)furo[2,3-c]pyridine-7-amine | 361.16 | 1.48 |

-continued

| Ex. # | Structure and NMR Data | Compound Name | MS (ESI) [M + H]+ | HPLC t_R (min) |
|---|---|---|---|---|
| Ex. 27 | <sup>1</sup>H NMR (400 MHz, CD<sub>3</sub>OD): δ 8.31 (s, 1 H), 8.02 (s, 1 H), 7.88 (d, J = 2.53 Hz, 1 H), 7.83 (s, 1 H), 7.60 (s, 1 H), 7.03 (d, J = 2.27 Hz, 1 H), 4.63-4.74 (m, 1 H), 3.61 (dt, J = 13.20, 3.13 Hz, 2 H), 3.22-3.29 (m, 2 H), 2.31-2.44 (m, 4 H) | 4-[1-(piperidin-4-yl)-1H-pyrazol-4-yl]-2-(1H-pyrazol-5-yl)furo[2,3-c]pyridine-7-amine | 350.09 | 1.67 |
| Ex. 28 | <sup>1</sup>H NMR (400 MHz, CD<sub>3</sub>OD): δ 8.35 (s, 1 H), 8.25 (dd, J = 3.03, 1.26 Hz, 1 H), 8.04 (s, 1 H), 7.82 (s, 1 H), 7.78 (dd, J = 5.05, 1.26 Hz, 1 H), 7.67 (dd, J = 5.18, 2.91 Hz, 1 H), 7.62 (s, 1 H), 4.69 (quin, J = 7.52 Hz, 1 H), 3.61 (dt, J = 13.33, 3.44 Hz, 2 H), 3.22-3.30 (m, 2 H), 2.35-2.43 (m, 4 H) | 4-[1-(piperidin-4-yl)-1H-pyrazol-4-yl]-2-(thiophen-3-yl)furo[2,3-c]pyridine-7-amine | 366.05 | 1.83 |
| Ex. 29 | <sup>1</sup>H NMR (400 MHz, CD<sub>3</sub>OD): δ 8.39 (s, 1 H), 8.03 (br. s., 1 H), 7.95 (d, J = 7.33 Hz, 1 H), 7.72-7.81 (m, 3 H), 7.44 (s, 1 H), 7.16-7.22 (m, 1 H), 6.58-6.62 (m, 1 H), 4.70 (dt, J = 14.34, 7.36 Hz, 1 H), 3.57-3.64 (m, 2 H), 3.22-3.32 (m, 2 H), 2.35-2.44 (m, 4 H) | 2-(1H-indol-6-yl)-4-[1-(piperidin-4-yl)-1H-pyrazol-4-yl]furo[2,3-c]pyridin-7-amine | 399.13 | 1.98 |

| Ex. # | Structure and NMR Data | Compound Name | MS (ESI) [M + H]+ | HPLC t_R (min) |
|---|---|---|---|---|
| Ex. 30 | 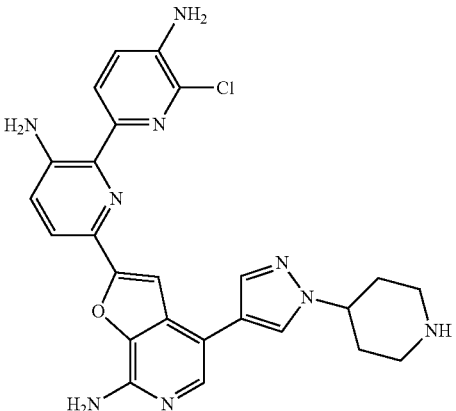<br>¹H NMR (400 MHz, CD₃OD): δ 8.46 (d, J = 8.59 Hz, 1 H), 8.33 (s, 1 H), 8.04 (s, 1 H), 7.91 (d, J = 8.34 Hz, 1 H), 7.79 (s, 1 H), 7.62 (s, 1 H), 7.37 (d, J = 8.59 Hz, 1 H), 7.27 (d, J = 8.59 Hz, 1 H), 4.79 (br. s., 1 H), 3.58-3.68 (m, 2 H), 3.26 (br. s., 2 H), 2.35-2.44 (m, 4 H) | 6-{7-amino-4-[1-(piperidin-4-yl)-1H-pyrazol-4-yl]furo[2,3-c]pyridin-2-yl}-6'-chloro-2,2'-bipyridine-3,5'-diamine | 502.07 | 2.04 |
| Ex. 31 | 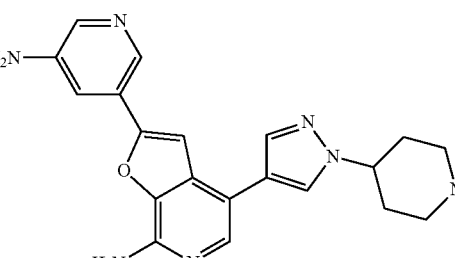<br>¹H NMR (400 MHz, CD₃OD): δ 8.73 (s, 1 H), 8.50 (s, 1 H), 8.32-8.36 (m, 1 H), 8.28 (s, 1 H), 8.13 (d, J = 2.53 Hz, 1 H), 8.05 (s, 1 H), 7.91 (s, 1 H), 4.65-4.79 (m, 1 H), 3.61 (d, J = 13.39 Hz, 2 H), 3.27 (br. s., 2 H), 3.28-2.46 (m, 4 H) | 2-(5-aminopyridin-3-yl)-4-[1-(piperidin-4-yl)-1H-pyrazol-4-yl]furo[2,3-c]pyridine-7-amine | 376.15 | 1.60 |
| Ex. 32 | 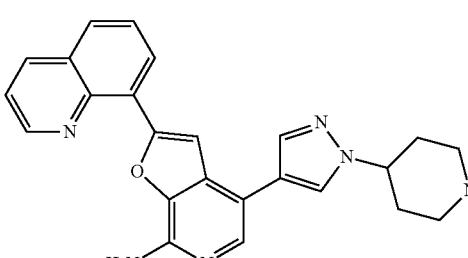<br>¹H NMR (400 MHz, CD₃OD): δ 9.13 (dd, J = 4.29, 1.77 Hz, 1 H), 8.71 (dd, J = 7.58, 1.26 Hz, 1 H), 8.55 (s, 1 H), 8.48 (dd, J = 8.46, 1.64 Hz, 1 H), 8.32 (s, 1 H), 8.15 (dd, J = 8.34, 1.01 Hz, 1 H), 8.06 (s, 1 H), 7.75-7.85 (m, 2 H), 7.67 (dd, J = 8.34, 4.29 Hz, 1 H), 2.42 (dd, J = 9.09, 3.54 Hz, 3 H), 2.22 (t, J = 10.86 Hz, 6 H) | 4-[1-(piperidin-4-yl)-1H-pyrazol-4-yl]-2-(quinolin-8-yl)furo[2,3-c]pyridine-7-amine | 411.18 | 1.96 (TOF: polar_3 min) |

| Ex. # | Structure and NMR Data | Compound Name | MS (ESI) [M + H]+ | HPLC $t_R$ (min) |
|---|---|---|---|---|
| Ex. 33 | 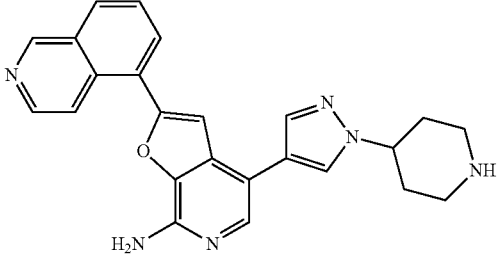 [SMILES: Nc1ncc(-c2cnn(C3CCNCC3)c2)c2cc(-c3cccc4cnccc34)oc12]<br>1H NMR (400 MHz, CD3OD): δ 9.92 (s, 1 H), 9.13 (d, J = 6.82 Hz, 1 H), 8.86 (d, J = 6.57 Hz, 1 H), 8.73 (dd, J = 14.91, 7.33 Hz, 2 H), 8.48 (s, 1 H), 8.22 (t, J = 7.83 Hz, 1 H), 8.09 (s, 1 H), 8.04 (s, 1 H), 7.93 (s, 1 H), 4.73 (dt, J = 14.53, 7.39 Hz, 1 H), 3.62 (dt, J = 12.88, 3.16 Hz, 2 H), 3.24-3.29 (m, 2 H), 2.37-2.44 (m, 4 H) | 2-(isoquinolin-5-yl)-4-[1-(piperidin-4-yl)-1H-pyrazol-4-yl]furo[2,3-c]pyridine-7-amine | 411.20 | 0.80 (TOF: polar_3 min) |
| Ex. 34 | 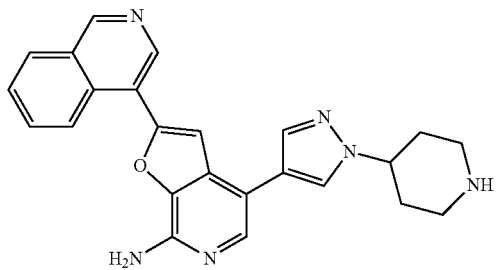 [SMILES: Nc1ncc(-c2cnn(C3CCNCC3)c2)c2cc(-c3cncc4ccccc34)oc12]<br>1H NMR (400 MHz, CD3OD): δ 9.87 (s, 1 H), 9.26 (s, 1 H), 8.92 (d, J = 8.59 Hz, 1 H), 8.62 (d, J = 8.34 Hz, 1 H), 8.50 (br. s., 1 H), 8.34-8.41 (m, 1 H), 8.11-8.20 (m, 2 H), 8.09 (s, 1 H), 7.94 (s, 1 H), 4.74 (br. s., 1 H), 3.61 (d, J = 12.63 Hz, 2 H), 3.27 (br. s., 2 H), 2.41 (br. s., 4 H) | 2-(isoquinolin-4-yl)-4-[1-(piperidin-4-yl)-1H-pyrazol-4-yl]furo[2,3-c]pyridine-7-amine | 411.19 | 0.88 (TOF: polar_3 min) |
| Ex. 35 | 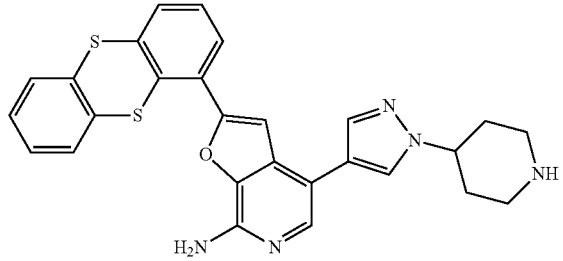 [SMILES: Nc1ncc(-c2cnn(C3CCNCC3)c2)c2cc(-c3cccc4c3Sc3ccccc3S4)oc12]<br>1H NMR (400 MHz, CD3OD): δ 7.08 (s, 1 H), 6.79 (s, 1 H), 6.68 (dd, J = 7.58, 1.26 Hz, 1 H), 6.61 (s, 1 H), 6.47-6.51 (m, 2 H), 6.30 (dd, J = 7.83, 1.26 Hz, 1 H), 6.21-6.27 (m, 2 H), 6.00-6.12 (m, 2 H), 3.38-3.49 (m, 1 H), 2.34 (dt, J = 12.95, 3.25 Hz, 2 H), 1.94-2.02 (m, 2 H), 1.09-1.18 (m, 4 H) | 4-[1-(piperidin-4-yl)-1H-pyrazol-4-yl]-2-(thianthren-1-yl)furo[2,3-c]pyridine-7-amine | 498.12 | 1.03 (TOF: polar_3 min) |

| Ex. # | Structure and NMR Data | Compound Name | MS (ESI) [M + H]+ | HPLC $t_R$ (min) |
|---|---|---|---|---|
| Ex. 36 | 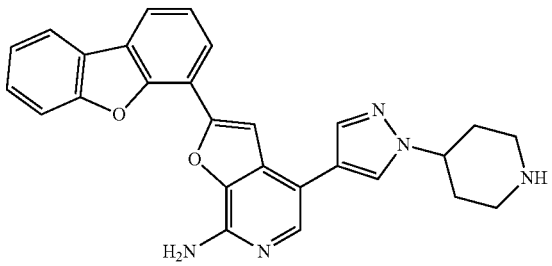 [SMILES: Nc1ncc(-c2cnn(C3CCNCC3)c2)c2cc(-c3cccc4c3oc3ccccc34)oc12]<br>¹H NMR (400 MHz, CD₃OD): δ 8.36 (s, 1 H), 8.34 (s, 1 H), 8.32 (s, 1 H), 8.28 (s, 1 H), 8.15 (s, 1 H), 8.09 (s, 1 H), 8.01 (s, 1 H), 7.82-7.88 (m, 1 H), 7.62 (t, J = 7.58 Hz, 2 H), 7.49 (s, 1 H), 4.76 (br. s., 1 H), 3.70-3.77 (m, 1 H), 3.59 (d, J = 5.31 Hz, 1 H), 3.27 (br. s., 2 H), 2.42-2.48 (m, 4 H) | 2-(dibenzo[b,d]furan-4-yl)-4-[1-(piperidin-4-yl)-1H-pyrazol-4-yl]furo[2,3-c]pyridine-7-amine | 450.18 | 0.99 (TOF: polar_3 min) |
| Ex. 37 | 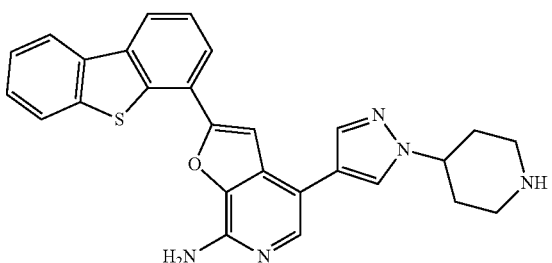<br>¹H NMR (400 MHz, CD₃OD): δ ppm 8.50 (d, J = 7.33 Hz, 1 H), 8.33-8.41 (m, 3 H), 8.09 (s, 1 H), 8.04 (d, J = 5.56 Hz, 1 H), 7.86 (s, 1 H), 7.80-7.83 (m, 1 H), 7.76 (t, J = 6.57 Hz, 1 H), 7.55-7.62 (m, 2 H), 4.74 (br. s., 1 H), 3.63 (br. s., 2 H), 3.27 (br. s., 2 H), 2.43 (br. s., 4 H) | 2-(dibenzo[b,d]thiophen-4-yl)-4-[1-(piperidin-4-yl)-1H-pyrazol-4-yl]furo[2,3-c]pyridine-7-amine | 466.16 | 1.12 (TOF: polar_3 min) |
| Ex. 38 | 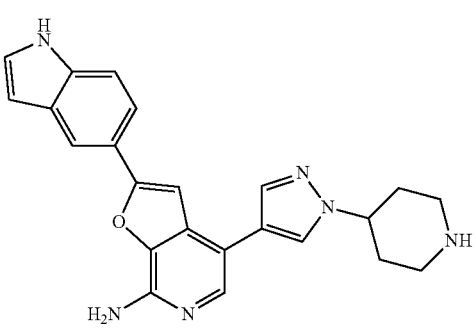 [SMILES: Nc1ncc(-c2cnn(C3CCNCC3)c2)c2cc(-c3ccc4[nH]ccc4c3)oc12]<br>¹H NMR (400 MHz, CD₃OD): δ 8.41 (d, J = 1.01 Hz, 1 H), 8.36 (s, 1 H), 8.05 (s, 1 H), 7.89 (dd, J = 8.59, 1.52 Hz, 1 H), 7.79 (s, 1 H), 7.59 (s, 1 H), 7.55 (d, J = 8.59 Hz, 1 H), 7.37 (s, 1 H), 6.61 (d, J = 3.28 Hz, 1 H), 4.65-4.76 (m, 1 H), 3.63 (dt, J = 13.07, 3.44 Hz, 2 H), 3.20-3.29 (m, 2 H), 2.35-2.45 (m, 4 H) | 2-(1H-indol-5-yl)-4-[1-(piperidin-4-yl)-1H-pyrazol-4-yl]furo[2,3-c]pyridin-7-amine | 399.16 | 1.12 (TOF: polar_3 min) |

| Ex. # | Structure and NMR Data | Compound Name | MS (ESI) [M + H]+ | HPLC t$_R$ (min) |
|---|---|---|---|---|
| Ex. 39 | 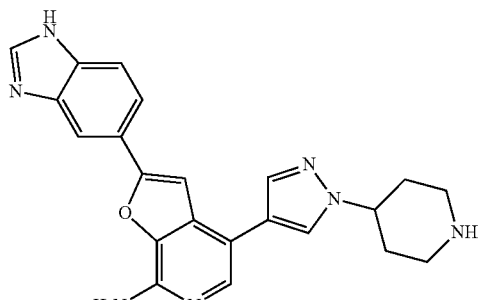<br><br>¹H NMR (400 MHz, CD₃OD): δ 9.54 (s, 1 H), 8.75 (s, 1 H), 8.44-8.51 (m, 2 H), 8.04-8.12 (m, 3 H), 7.88 (s, 1 H), 4.69-4.79 (m, 1 H), 3.57-3.69 (m, 2 H), 3.28-3.34 (m, 2 H), 2.37-2.47 (m, 4 H) | 2-(1H-benzimidazol-5-yl)-4-[1-(piperidin-4-yl)-1H-pyrazol-4-yl]furo[2,3-c]pyridine-7-amine | 400.09 | 1.81 (TOF: polar_3 min) |
| Ex. 40 | 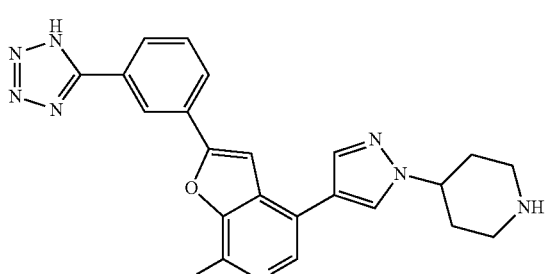<br><br>¹H NMR (400 MHz, CD₃OD): δ 8.91 (s, 1 H), 8.41 (s, 1 H), 8.35 (d, J = 8.08 Hz, 1 H), 8.17 (d, J = 7.83 Hz, 1 H), 8.06 (s, 1 H), 7.95 (s, 1 H), 7.86 (s, 1 H), 7.81 (t, J = 7.83 Hz, 1 H), 4.71 (dt, J = 14.91, 7.45 Hz, 1 H), 3.63 (dt, J = 12.95, 3.13 Hz, 2 H), 3.27 (d, J = 7.58 Hz, 2 H), 2.38-2.46 (m, 4 H) | 4-[1-(piperidin-4-yl)-1H-pyrazol-4-yl]-2-[3-(1H-tetrazol-5-yl)phenyl]furo[2,3-c]pyridine-7-amine | 428.05 | 1.91 (TOF: polar_3 min) |
| Ex. 41 | 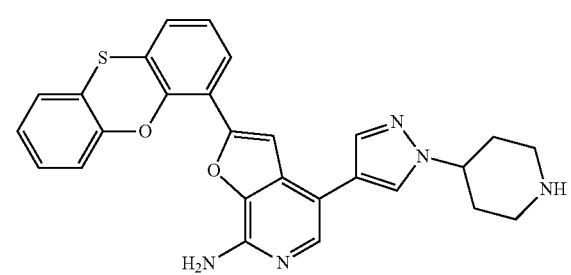 [SMILES: Nc1ncc(-c2cnn(C3CCNCC3)c2)c2cc(-c3cccc4c3Oc3ccccc3S4)oc12]<br><br>¹H NMR (400 MHz, CDCl₃): δ 8.33 (s, 1 H), 8.03-8.11 (m, 2 H), 7.94 (s, 1 H), 7.83 (s, 1 H), 7.36-7.42 (m, 1 H), 7.23-7.33 (m, 3 H), 7.10-7.21 (m, 2 H), 4.72 (tt, J = 9.92, 4.86 Hz, 1 H), 3.59-3.68 (m, 2 H), 3.20-3.30 (m, 2 H), 2.35-2.46 (m, 4 H) | 2-(phenoxathiin-4-yl)-4-[1-(piperidin-4-yl)-1H-pyrazol-4-yl]furo[2,3-c]pyridine-7-amine | 482.01 | 2.32 (TOF: polar_3 min) |

| Ex. # | Structure and NMR Data | Compound Name | MS (ESI) [M + H]+ | HPLC $t_R$ (min) |
|---|---|---|---|---|
| Ex. 42 | 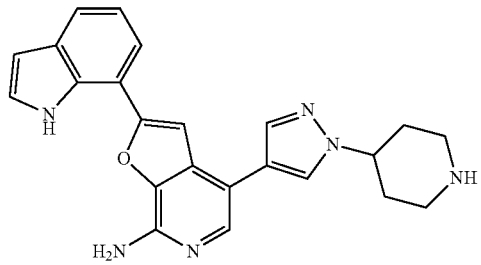 [SMILES: Nc1ncc(-c2cnn(C3CCNCC3)c2)c2cc(-c3cccc4cc[nH]c34)oc12]<br><br>¹H NMR (400 MHz, CD₃OD): δ 8.37 (s, 1 H), 8.07 (s, 1 H), 7.97 (d, J = 6.82 Hz, 1 H), 7.84 (s, 1 H), 7.77-7.83 (m, 2 H), 7.47 (d, J = 3.28 Hz, 1 H), 7.23 (t, J = 7.71 Hz, 1 H), 6.66 (d, J = 3.28 Hz, 1 H), 4.64-4.76 (m, 1 H), 3.58-3.66 (m, 2 H), 3.21-3.28 (m, 2 H), 2.33-2.46 (m, 4 H) | 2-(1H-indol-7-yl)-4-[1-(piperidin-4-yl)-1H-pyrazol-4-yl]furo[2,3-c]pyridin-7-amine | 398.92 | 2.10 (TOF: polar_3 min) |
| Ex. 43 | 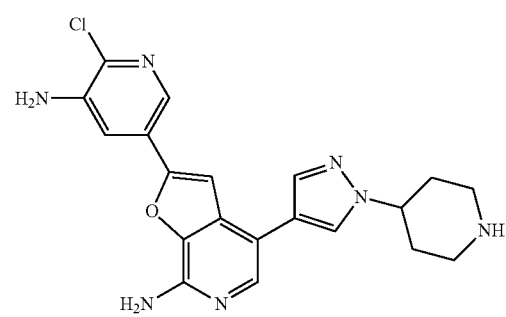 [SMILES: Nc1cc(-c2cc3c(-c4cnn(C5CCNCC5)c4)cnc(N)c3o2)cnc1Cl]<br><br>¹H NMR (400 MHz, CD₃OD): δ 8.38 (s, 1 H), 8.33 (d, J = 1.52 Hz, 1 H), 8.00 (s, 1 H), 7.86 (s, 1 H), 7.82 (d, J = 2.02 Hz, 1 H), 7.78 (s, 1 H), 4.73 (dt, J = 14.91, 7.71 Hz, 1 H), 3.59-3.66 (m, 2 H), 3.26-3.36 (m, 2 H), 2.39-2.47 (m, 4 H) | 2-(5-amino-6-chloropyridin-3-yl)-4-[1-(piperidin-4-yl)-1H-pyrazol-4-yl]furo[2,3-c]pyridine-7-amine | 409.98 | 1.83 (TOF: polar_3 min) |
| Ex. 44 | 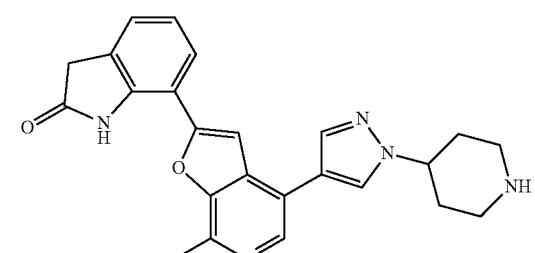<br><br>¹H NMR (400 MHz, CD₃OD): δ 8.31 (s, 1 H), 8.06 (s, 1 H), 7.93 (d, J = 8.84 Hz, 1 H), 7.83 (s, 1 H), 7.69-7.74 (m, 1 H), 7.44 (dd, J = 7.33, 1.26 Hz, 1 H), 7.17-7.23 (m, 1 H), 4.60-4.72 (m, 1 H), 3.66 (s, 2 H), 3.62 (dt, J = 13.07, 3.57 Hz, 2 H), 3.21-3.28 (m, 2 H), 2.33-2.43 (m, 4 H) | 7-{7-amino-4-[1-(piperidin-4-yl)-1H-pyrazol-4-yl]furo[2,3-c]pyridin-2-yl}-1,3-dihydro-2H-indol-2-one | 415.03 | 1.88 (TOF: polar_3 min) |

| Ex. # | Structure and NMR Data | Compound Name | MS (ESI) [M + H]+ | HPLC $t_R$ (min) |
|---|---|---|---|---|
| Ex. 45 | 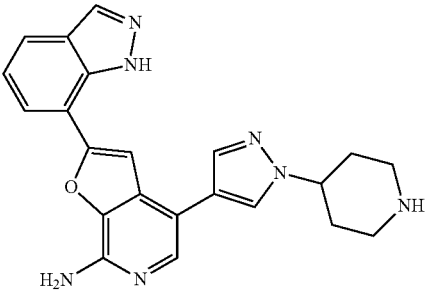 [SMILES: Nc1ncc(-c2cnn(C3CCNCC3)c2)c2cc(-c3cccc4cn[nH]c34)oc12]<br>¹H NMR (400 MHz, CD₃OD): δ 8.40 (s, 1 H), 8.25-8.32 (m, 2 H), 8.09 (s, 1 H), 8.04 (d, J = 8.08 Hz, 1 H), 7.97 (s, 1 H), 7.87 (s, 1 H), 7.39 (t, J = 7.71 Hz, 1 H), 4.64-4.77 (m, 1 H), 3.62 (dt, J = 13.39, 3.79 Hz, 2 H), 3.23-3.29 (m, 2 H), 2.36-2.45 (m, 4 H) | 2-(1H-indazol-7-yl)-4-[1-(piperidin-4-yl)-1H-pyrazol-4-yl]furo[2,3-c]pyridin-7-amine | 400.09 | 1.93 |
| Ex. 46 | 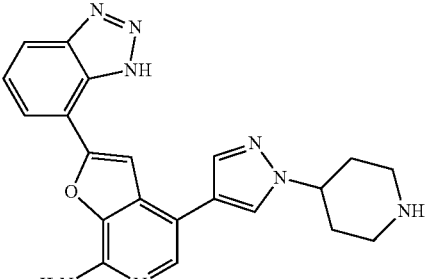<br>¹H NMR (400 MHz, CD₃OD): δ 8.34 (s, 1 H), 8.18-8.23 (m, 2 H), 8.01-8.05 (m, 2 H), 7.91-7.96 (m, 1 H), 7.66 (dd, J = 8.08, 7.58 Hz, 1 H), 4.61-4.71 (m, 1 H), 3.62 (dt, J = 13.26, 3.73 Hz, 2 H), 3.21-3.28 (m, 2 H), 2.34-2.36 (m, 4 H) | 2-(1H-benzotriazol-7-yl)-4-[1-(piperidin-4-yl)-1H-pyrazol-4-yl]furo[2,3-c]pyridine-7-amine | 401.19 | 0.89 (TOF: polar_3 min) |
| Ex. 47 | 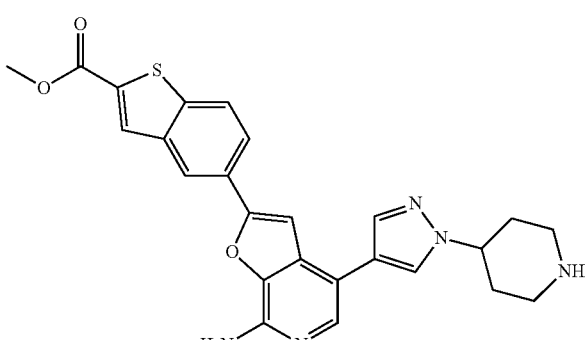<br>¹H NMR (400 MHz, CD₃OD): δ ppm 8.58 (d, J = 1.26 Hz, 1 H), 8.31 (s, 1 H), 8.10-8.15 (m, 2 H), 8.02-8.07 (m, 2 H), 7.77 (s, 1 H), 7.73 (s, 1 H), 4.64-4.74 (m, 1 H), 3.95 (s, 3 H), 3.60-3.69 (m, 2 H), 3.23-3.30 (m, 2 H), 2.36-2.46 (m, 4 H) | methyl 5-{7-amino-4-[1-(piperidin-4-yl)-1H-pyrazol-4-yl]furo[2,3-c]pyridine-2-yl}-1-benzothiophene-2-carboxylate | 474.14 | 0.92 (TOF: polar_3 min) |

| Ex. # | Structure and NMR Data | Compound Name | MS (ESI) [M + H]+ | HPLC $t_R$ (min) |
|---|---|---|---|---|
| Ex. 48 | 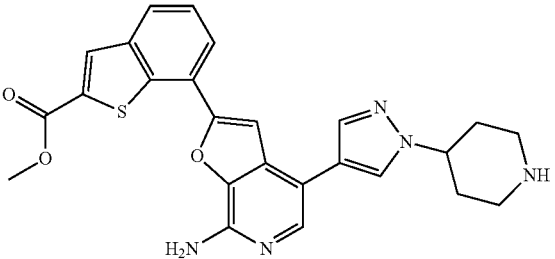 [SMILES: COC(=O)c1cc2cccc(-c3cc4c(-c5cnn(C6CCNCC6)c5)cnc(N)c4o3)c2s1]<br>¹H NMR (400 MHz, CD₃OD): δ 8.17 (s, 1 H), 8.14 (d, J = 7.58 Hz, 1 H), 8.02 (s, 1 H), 7.95 (d, J = 8.08 Hz, 1 H), 7.88 (s, 1 H), 7.66 (s, 1 H), 7.45-7.52 (m, 2 H), 4.55-4.66 (m, 1 H), 3.87 (s, 3H), 3.50-3.57 (m, 2 H), 3.37 (dt, J = 13.07, 6.47 Hz, 1 H), 3.15-3.20 (m, 1 H), 2.28-2.36 (m, 4 H) | methyl 7-{7-amino-4-[1-(piperidin-4-yl)-1H-pyrazol-4-yl]furo[2,3-c]pyridine-2-yl}-1-benzothiophene-2-carboxylate | 474.14 | 0.95 (TOF: polar_3 min) |
| Ex. 49 | 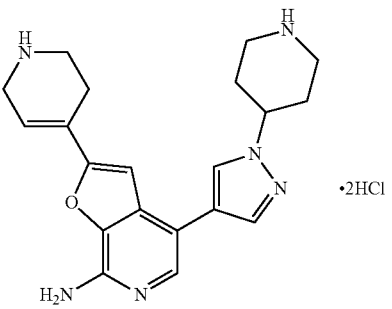 [SMILES: Nc1ncc(-c2cnn(C3CCNCC3)c2)c2cc(C3=CCNCC3)oc12 ; "·2HCl"]<br>¹H NMR (400 MHz, DMSO-d₆): δ 9.63 (m, 2 H), 9.27 (m, 1 H), 9.06 (m, 1H), 8.62 (m, 1H), 8.52 (s, 1H), 8.07 (s, 1H), 7.99 (s, 1H), 7.52 (s, 1H), 6.77 (s, 1H), 4.53 (m, 1H), 3.86 (m, 2H), 3.33 (m, 4H), 3.05 (m, 2H), 2.78 (m, 2H), 2.21 (m, 4H) | 4-[1-(piperidin-4-yl)-1H-pyrazol-4-yl]-2-(1,2,3,6-tetrahydropyridin-4-yl)furo[2,3-c]pyridin-7-amine dihydrochloride | 365.1 | — |

Example 50

1-(4-{4-[7-amino-2-(isoquinolin-5-yl)furo[2,3-c]pyridin-4-yl]-1H-pyrazol-1-yl}piperidin-1-yl)-2-methoxyethanone

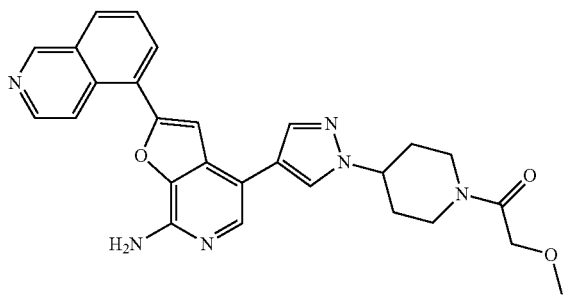 [SMILES: COCC(=O)N1CCC(n2cc(-c3cnc(N)c4oc(-c5cccc6cnccc56)cc34)cn2)CC1]

A solution of 2-isoquinolin-5-yl-4-(1-piperidin-4-yl-1H-pyrazol-4-yl)-furo[2,3-c]pyridin-7-ylamine (30 mg, 0.07 mmol), methoxyacetyl chloride (8.02 µL, 0.0877 mmol), and DIPEA (28.0 µL, 0.161 mmol) in DCM (0.94 mL) stirred overnight at RT. The reaction was diluted with DCM, washed with water and brine, dried over Na₂SO₄ and concentrated in vacuo. Purification by flash chromatography (10% 7 N NH₃/MeOH:EtOAc) afforded 20 mg (60%) of the title compound. ¹H NMR (400 MHz, CDCl₃): δ 1.97-2.21 (m, 4 H) 2.31 (br s, 2 H) 2.81-2.94 (m, 1 H) 3.17-3.32 (m, 1 H) 3.41-3.51 (m, 3 H) 4.06-4.25 (m, 3 H) 4.46 (tt, J=11.34, 4.07 Hz, 1 H) 4.76 (d, J=12.88 Hz, 1 H) 5.01 (br s, 2 H) 7.22 (s, 1 H) 7.69-7.80 (m, 2 H) 7.84-7.91 (m, 1 H) 8.03 (s, 1 H) 8.08-8.18 (m, 2 H) 8.22 (d, J=6.06 Hz, 1 H) 8.61-8.70 (m, 1 H) 9.37 (s, 1 H); MS (ESI): 483.11 [M+H]⁺; HPLC $t_R$=0.89 min (TOF, polar_3 min).

The following Examples were prepared by a procedure analogous to Example 50.

| Ex # | Structure | Compound Name | MS (ESI) [M + H]+ | HPLC t_R TOF: polar_3 min (min) |
|---|---|---|---|---|
| Ex. 51 | 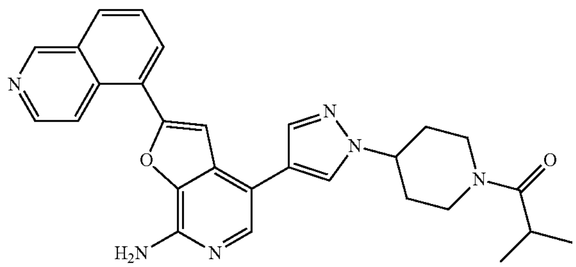 [SMILES: CC(C)C(=O)N1CCC(n2cc(-c3cnc(N)c4oc(-c5cccc6cnccc56)cc34)cn2)CC1] | 1-(4-{4-[7-amino-2-(isoquinolin-5-yl)furo[2,3-c]pyridin-4-yl]-1H-pyrazol-1-yl}piperidin-1-yl)-2-methylpropan-1-one | 481.20 | 0.99 |

$^1$H NMR (400 MHz, CDCl$_3$) δ 1.93-2.14 (m, 6H) 2.20-2.44 (m, 2H) 2.68-2.95 (m, 2H) 3.20-3.33 (m, 1H) 3.51 (s, 2H) 4.14 (d, J = 12.63 Hz, 1H) 4.46 (tt, J = 11.37, 4.04 Hz, 1H) 4.84 (d, J = 12.88 Hz, 1H) 4.92 (s, 2H) 7.20-7.25 (m, 1H) 7.74 (d, J = 0.75 Hz, 2H) 7.898 (d, J = 0.76 Hz, 1H) 8.05 (s, 1H) 8.09-8.19 (m, 2H) 8.24 (s, 1H) 8.66 (d, J = 6.06 Hz, 1H) 9.37 (d, J = 0.76Hz, 1H)

| Ex. 52 | | (4-{4-[7-amino-2-(isoquinolin-5-yl)furo[2,3-c]pyridin-4-yl]-1H-pyrazol-1-yl}piperidin-1-yl)(cyclopropyl)methanone | 479.19 | 0.97 |

$^1$H NMR (400 MHz, CDCl$_3$): ppm 9.34 (d, J = 1.0 Hz, 1H), 8.63 (d, J = 6.1 Hz, 1H), 8.21 (dt, J = 6.1, Hz, 1H), 8.06-8.16 (m, 2H), 8.02 (s, 1H), 7.86 (d, J = 0.8 Hz, 1H), 7.67-7.77 (m, 2H), 7.21 (s, 1H), 4.95 (s, 2H), 4.62-4.85 (m, 1H), 4.26-4.54 (m, 1H), 3.15-3.43 (m, 1H), 2.60-2.98 (m, 1H), 2.17-2.45 (m, 2H), 1.93-2.12 (m, 2H), 1.80 (tt, J = 8.0, 4.8 Hz, 1H), 1.10-1.34 (m, 1H), 0.89-1.06 (m, 2H), 0.72-0.86 (m, 2H)

| Ex # | Structure | Compound Name | MS (ESI) [M + H]+ | HPLC $t_R$ TOF: polar_3 min (min) |
|---|---|---|---|---|
| Ex. 53 | 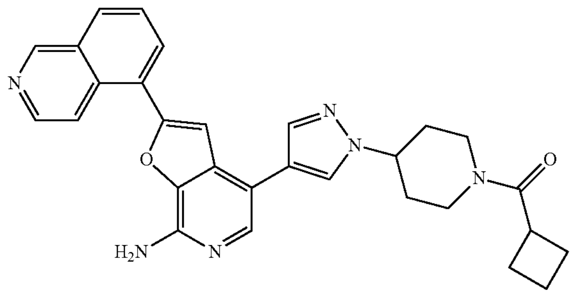 [SMILES: Nc1ncc(-c2cnn(C3CCN(C(=O)C4CCC4)CC3)c2)c2cc(-c3cccc4cnccc34)oc12] | (4-{4-[7-amino-2-(isoquinolin-5-yl)furo[2,3-c]pyridin-4-yl]-1H-pyrazol-1-yl}piperidin-1-yl)(cyclobutyl)methanone | 493.20 | 1.02 |

$^1$H NMR (400 MHz, CDCl$_3$): δ 9.35 (d, J = 0.8 Hz, 1H), 8.64 (d, J = 6.1 Hz, 1H), 8.21 (dt, J = 6.1, 0.9 Hz, 1H), 8.06-8.16 (m, 2H), 8.02 (s, 1H), 7.85 (d, J = 0.8 Hz, 1H), 7.64-7.78 (m, 2H), 7.20 (s, 1H), 4.94 (s, 2H), 4.77 (d, J = 13.6 Hz, 1H), 4.41 (tt, J = 11.4, 4.0 Hz, 1H), 3.89 (d, J = 13.6 Hz, 1H), 3.23-3.38 (m, 1H), 3.08-3.21 (m, 1H), 2.67-2.89 (m, 1H), 2.32-2.47 (m, 2H), 2.11-2.30 (m, 4H), 1.81-2.01 (m, 3H)

Example 54

2-(piperidin-4-yl)-4-[1-(piperidin-4-yl)-1H-pyrazol-4-yl]furo[2,3-c]pyridin-7-amine

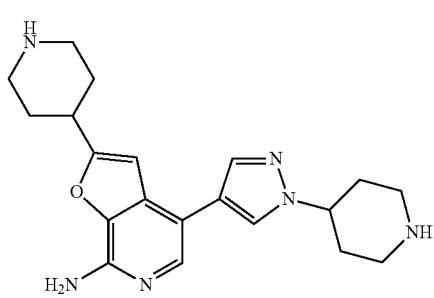 [SMILES: Nc1ncc(-c2cnn(C3CCNCC3)c2)c2cc(C3CCNCC3)oc12]

A suspension of 4-[1-(piperidin-4-yl)-1H-pyrazol-4-yl]-2-(1,2,3,6-tetrahydropyridin-4-yl)furo[2,3-c]pyridin-7-amine (30 mg, 0.082 mmol) and 10% Pd/C (5 mg) in MeOH (10 mL) was stirred at RT under a H$_2$ balloon for 2 h. The reaction mixture was filtered and concentrated to afford the title compound. $^1$H NMR (400 MHz, CD$_3$OD): δ 8.29 (s, 1H), 7.89 (s, 1H), 7.73 (s, 1H), 7.19 (s, 1H), 4.62 (m, 1H), 3.49 (m, 4H), 3.34 (m, 1H), 3.15 (m, 4H), 2.29 (m, 6H), 2.07 (m, 2H); MS (ESI): 367.1 [M+H]$^+$.

Example 55

5-{7-amino-4-[1-(piperidin-4-yl)-1H-pyrazol-4-yl]furo[2,3-c]pyridin-2-yl}-1,2-dihydro-3H-indazol-3-one trifluoroacetic acid salt

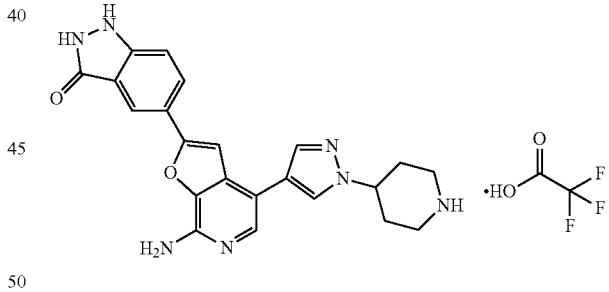

Step A: 5-{7-amino-4-[1-(piperidin-4-yl)-1H-pyrazol-4-yl]furo[2,3-c]pyridin-2-yl}-2-chlorobenzoic acid hydrochloride A suspension of 1-{4-[4-(7-amino-2-chlorofuro[2,3-c]pyridin-4-yl)-1H-pyrazol-1-yl]piperidin-1-yl}ethanone (125 mg, 0.347 mmol), 4-chloro-3-(methoxycarbonyl)phenylboronic acid (89.4 mg, 0.417 mmol), and Pd(PPh$_3$)$_4$ (40.1 mg, 0.0347 mmol) in 1.0 M aqueous sodium carbonate (1.74 mL, 1.74 mmol) and 1,4-dioxane (1.63 mL) was heated to 120° C. in a microwave for 30 min. The reaction mixture was then diluted with ethyl acetate (10 mL) and acidified with aqueous 1 N hydrochloric acid (5 mL), causing formation of a precipitate. The precipitate was collected by vacuum filtration and then triturated from DMSO and methanol (10 mL, ~1:10) to afford 55 mg (29%) of the title compound as a yellow solid. $^1$H NMR (400 MHz, DMSO-$d_6$): δ 8.45 (d, J=1.5 Hz, 1H), 8.29 (s, 1H), 8.22 (dd, J=1.8, 8.3 Hz, 1H), 8.00 (d, J=8.1 Hz, 2H), 7.91 (s, 1H), 7.75 (d, J=8.6 Hz, 1H), 6.56 (br s, 2H), 4.61-4.30 (m, 2H), 3.94 (br s, 1H), 3.24 (br s, 1H), 2.74 (br s, 1H), 2.26-1.63 (m, 7H); MS (ESI): 480.10 [M+H]$^+$; HPLC $t_R$=2.35 min (ZQ3, polar_4 min).

Step B: 5-{7-amino-4-[1-(piperidin-4-yl)-1H-pyrazol-4-yl]furo[2,3-c]pyridin-2-yl}-1,2-dihydro-3H-indazol-3-one trifluoroacetic acid salt (Title Compound)

A solution of 5-{4-[1-(1-acetylpiperidin-4-yl)-1H-pyrazol-4-yl]-7-aminofuro[2,3-c]pyridin-2-yl}-2-chlorobenzoic acid hydrochloride (29 mg, 0.056 mmol) and hydrazine hydrate (50 μL, 1 mmol) in n-BuOH (500 μL, 5 mmol) was heated to 150° C. in a microwave for 6 h. Upon cooling, the reaction mixture was concentrated. Purification by MDP afforded 9 mg (30%) of the title compound as a brown solid. $^1$H NMR (400 MHz, DMSO-$d_6$): δ 11.94 (br s, 1 H), 8.77 (br s, 1 H), 8.60-8.41 (m, 3 H), 8.34 (br s, 1 H), 8.16 (s, 1 H), 8.10 (dd, J=1.4, 9.0 Hz, 1H), 7.97 (s, 1H), 7.90 (s, 1H), 7.49 (d, J=8.8 Hz, 1H), 4.75-4.39 (m, 1H), 3.48 (br s, 2H), 3.15 (br s, 2H), 2.35-2.04 (m, 4H); MS (ESI): 416.17 [M+H]$^+$; HPLC $t_R$=2.53 min (ZQ3, VV POLAR_5 min).

Example 56

4-(1-methyl-1H-pyrazol-4-yl)-2-phenylfuro[2,3-d]pyridin-7-amine

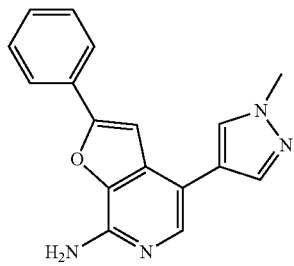 [SMILES: Cn1cc(-c2cnc(N)c3oc(-c4ccccc4)cc23)cn1]

A mixture of 1-methyl-4-(4,4,5-trimethyl-1,3,2-dioxaborolan-2-yl)-1H-pyrazole (115 mg, 0.595 mmol) and 4-iodo-2-phenylfuro[2,3-c]pyridin-7-amine (100.0 mg, 0.297 mmol) in 1,4-dioxane (2.0 mL) and H$_2$O (0.5 mL) was treated with potassium carbonate (62 mg, 0.45 mmol) and (1,1'-bis(diphenylphosphino)ferrocene)palladium dichloride (2 mg, 0.03 mmol) under an atmosphere of nitrogen. The mixture was heated in a microwave reactor at 100° C. for 40 min. The reaction mixture was partitioned between EtOAc and brine/water and separated. The aqueous phase was extracted with EtOAc (3×) and the combined organic extracts were washed with brine, dried over sodium sulfate, filtered, and concentrated. The product mixture was purified by flash chromatography (0 to 4% 7 N NH$_3$/MeOH:EtOAc) to afford 86 mg (99%) of the title compound. $^1$H NMR (400 MHz, CD$_3$OD): δ 6.73-6.78 (m, 3H), 6.59 (s, 2H), 6.20-6.27 (m, 2H), 6.14-6.19 (m, 2H), 2.71 (s, 3H). MS (ESI): 291.11 [M+H]$^+$; HPLC $t_R$=1.02 min (TOF: polar_3 min).

Example 57

2-(1-benzothiophen-7-yl)-4-[1-(1-methylpiperidin-4-yl)-1H-pyrazol-4-yl]furo[2,3-c]pyridin-7-amine

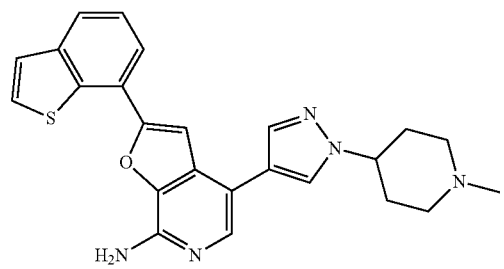 [SMILES: CN1CCC(n2cc(-c3cnc(N)c4oc(-c5cccc6ccsc56)cc34)cn2)CC1]

A solution of 1-methyl-4-[4-(4,4,5,5-tetramethyl-1,3,2-dioxaborolan-2-yl)-1H-pyrazol-1-yl]piperidine (42.0 mg, 0.14 mmol) and 2-(1-benzothiophen-7-yl)-4-iodofuro[2,3-c]pyridin-7-amine (47.1 mg, 0.12 mmol) in 1,4-dioxane (0.81 mL) and H$_2$O (0.2 mL) was charged with potassium carbonate (25 mg, 0.18 mmol) and (1,1'-bis(diphenylphosphino)ferrocene) palladium dichloride (0.9 mg, 0.01 mmol) under an atmosphere of nitrogen. The mixture was irradiated in a Biotage microwave reactor at 100° C. for 100 min. The reaction mixture was concentrated in vacuo to a solid. Purification by flash chromatography (0 to 10% 7 N NH$_3$/MeOH:EtOAc afforded 17 mg (33%) of the title compound. $^1$H NMR (400 MHz, CD$_3$OD): δ 8.11 (d, J=7.58 Hz, 1H), 8.07 (s, 1H), 7.93 (d, J=8.08 Hz, 1H), 7.88 (d, J=7.07 Hz, 2H), 7.70 (d, J=5.31 Hz, 1H), 7.45-7.55 (m, 3H), 4.27 (dt, J=15.35, 7.86 Hz, 1H), 3.06 (d, J=11.62 Hz, 2H), 2.38 (s, 3H), 2.25-2.34 (m, 2H), 2.13-2.22 (m, 4H); MS (ESI): 431.17 [M+H]$^+$; HPLC $t_R$=0.90 min (TOF: polar_3 min).

The following Example was prepared analogously, using procedures similar to Example 57 above.

Example 58

1-(4-{4-[7-amino-2-(1-benzothiophen-7-yl)furo[2,3-c]pyridin-4-yl]-1H-pyrazol-1-yl}piperidin-1-yl)propan-1-one

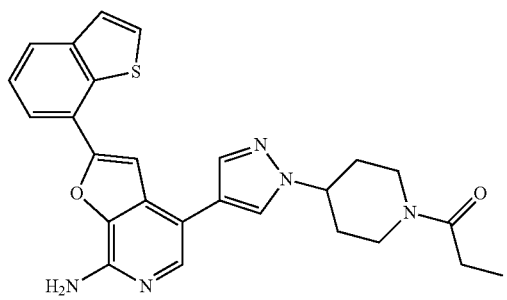 [SMILES: CCC(=O)N1CCC(n2cc(-c3cnc(N)c4oc(-c5cccc6ccsc56)cc34)cn2)CC1]

$^1$H NMR (400 MHz, CD$_3$OD): δ 8.15 (d, J=7.58 Hz, 1H), 8.13 (s, 1H), 7.97 (d, J=8.08 Hz, 1H), 7.91 (s, 2H), 7.73 (d, J=5.56 Hz, 1H), 7.50-7.59 (m, 3H), 4.72 (d, J=13.64 Hz, 1H), 4.55 (tt, J=4.17, 11.49 Hz, 1H), 4.15 (d, J=13.89 Hz, 1H), 3.35

(br s, 1H), 2.80-2.94 (m, 1H), 2.49 (q, J=7.41 Hz, 2H), 2.17-2.31 (m, 2H), 1.94-2.16 (m, 2H), 1.12-1.21 (m, 3H); MS (ESI): 473.17 [M+H]⁺; HPLC t$_R$=1.11 min (TOF: polar_3 min).

Example 59 ethyl {4-[7-amino-2-(isoquinolin-5-yl)furo[2,3-c]pyridin-4-yl]-1H-pyrazol-1-yl}acetate

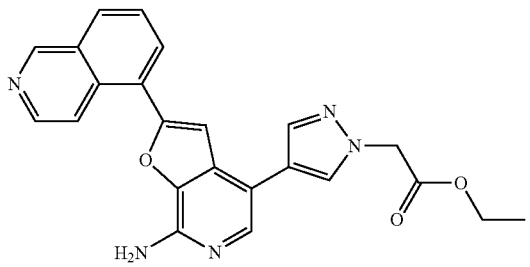 [SMILES: CCOC(=O)Cn1cc(-c2cnc(N)c3oc(-c4cccc5cnccc45)cc23)cn1]

A solution of isoquinoline-5-boronic acid (53.9 mg, 0.312 mmol) and ethyl[4-(7-amino-2-chlorofuro[2,3-c]pyridin-4-yl)-1H-pyrazol-1-yl]acetate (50.0 mg, 0.156 mol) in 1,4-dioxane (0.85 mL) and H$_2$O (0.3 mL) was charged with potassium carbonate (32 mg, 0.23 mmol) and (1,1'-bis(diphenylphosphino)ferrocene)palladium dichloride (1 mg, 0.002 mmol) under an atmosphere of nitrogen. The mixture was heated in a microwave reactor at 100° C. for 40 min. Purification of the residue by flash chromatography (0 to 5% 7 N NH$_3$/MeOH:EtOAc) afforded 27 mg (41%) of the title compound. ¹H NMR (400 MHz, CD$_3$OD) δ 9.36 (s, 1H), 8.57-8.63 (m, 1H), 8.52 (d, J=6.06 Hz, 1H), 8.37 (d, J=7.33 Hz, 1H), 8.27 (d, J=8.08 Hz, 1H), 8.18 (s, 1H), 7.98 (d, J=7.58 Hz, 2H), 7.85 (t, J=7.83 Hz, 1H), 7.55-7.62 (m, 1H), 7.53 (s, 1H), 4.28 (q, J=7.16 Hz, 2 H), 1.95 (s, 2H), 1.32 (t, 3H); MS (ESI): 415.16 [M+H]⁺; HPLC t$_R$=0.94 min (TOF: polar_3 min).

The following Examples were prepared using procedures analogous to Example 59.

| Ex. # | Structure | Compound Name | MS (ESI) [M+H]⁺ | HPLC t$_R$ TOF: polar_3 min (min) |
|---|---|---|---|---|
| Ex. 60 | 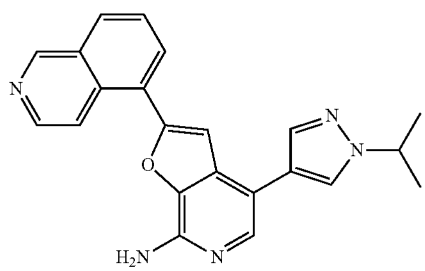 [SMILES: CC(C)n1cc(-c2cnc(N)c3oc(-c4cccc5cnccc45)cc23)cn1] | 2-(isoquinolin-5-yl)-4-[1-(propan-2-yl)-1H-pyrazol-4-yl]furo[2,3-c]pyridin-7-amine | 371.16 | 0.95 |
| | ¹H NMR (400 MHz, CD$_3$OD) δ 10.01 (s, 1H), 9.21 (d, J = 7.07 Hz, 1H), 8.90 (dd, J = 7.45, 1.14 Hz, 1H), 8.77 (dd, J = 7.58, 2.78 Hz, 2H), 8.35 (s, 1H), 8.23-8.32 (m, 1H), 8.08 (s, 1H), 8.03 (s, 1H), 7.93 (s, 1H), 4.69 (dt, J = 13.52, 6.63 Hz, 1H), 1.61 (d, J = 6.57 Hz, 6H) | | | |
| Ex. 61 | 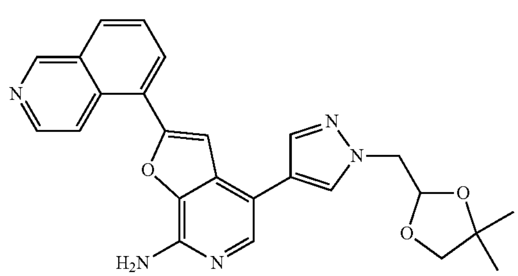 [SMILES: CC1(C)COC(Cn2cc(-c3cnc(N)c4oc(-c5cccc6cnccc56)cc34)cn2)O1] | 4-{1-[(2,2-dimethyl-1,3-dioxolan-4-yl)methyl]-1H-pyrazol-4-yl}-2-(isoquinolin-5-yl)furo[2,3-c]pyridin-7-amine | 443.19 | 0.97 |
| | ¹H NMR (400 MHz, CD$_3$OD) δ 4.49-4.57 (m, 1H), 4.31-4.43 (m, 1H), 4.12 (dd, J = 8.59, 6.32 Hz, 1H), 3.85 (dd, J = 8.59, 6.06 Hz, 1H), 1.36 (d, J = 17.68 Hz, 6H) | | | |

| Ex. # | Structure | Compound Name | MS (ESI) [M+H]+ | HPLC tR TOF: polar_3 min (min) |
|---|---|---|---|---|
| Ex. 62 | 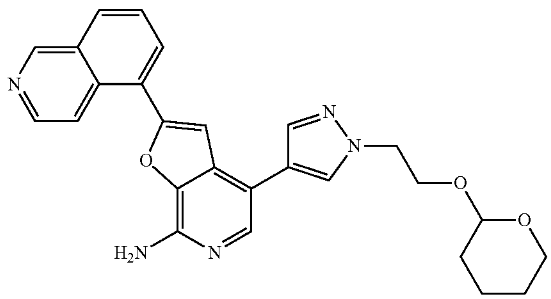 [SMILES: Nc1ncc(-c2cnn(CCOC3CCCCO3)c2)c2cc(-c3cccc4cnccc34)oc12] | 2-(isoquinolin-5-yl)-4-{1-[2-(tetrahydro-2H-pyran-2-yloxy)ethyl]-1H-pyrazol-4-yl}furo[2,3-c]pyridin-7-amine | 457.20 | 0.99 |

¹H NMR (400 MHz, CD₃OD) δ 9.29 (s, 1H), 8.53 (d, J = 6.06 Hz, 1H), 8.43 (d, J = 6.06 Hz, 1H), 8.28 (d, J = 7.33 Hz, 1H), 8.19 (d, J = 8.34 Hz, 1H), 8.11 (s, 1H), 7.88-7.90 (m, 1H), 7.78 (t, J = 7.71 Hz, 1H), 7.41 (s, 1H), 4.57 (t, J = 3.54 Hz, 1H), 4.38-4.44 (m, 1H), 4.04-4.13 (m, 1H), 3.82 (dt, J = 10.86, 5.18 Hz, 1H), 3.58-3.66 (m, 1H), 3.38-3.44 (m, 1H), 1.33-1.81 (m, 7H).

| Ex. # | Structure | Compound Name | MS (ESI) [M+H]+ | HPLC tR TOF: polar_3 min (min) |
|---|---|---|---|---|
| Ex. 63 | | 4-[1-(trans-4-{[tert-butyl(dimethyl)silyl]oxy}cyclohexyl)-1H-pyrazol-4-yl]-2-(isoquinolin-5-yl)furo[2,3-c]pyridin-7-amine | 541.27 | 1.48 |

Example 64

4-[1-(azetidin-3-yl)-1H-pyrazol-4-yl]-2-(isoquinolin-5-yl)furo[2,3-c]pyridin-7-amine

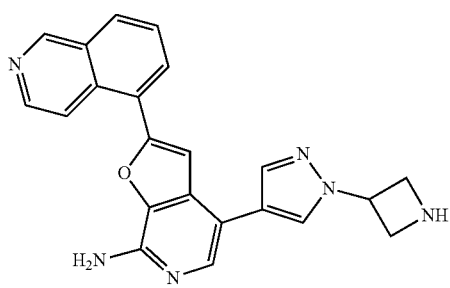 [SMILES: Nc1ncc(-c2cnn(C3CNC3)c2)c2cc(-c3cccc4cnccc34)oc12]

Step A: tert-butyl 3-{4-[7-amino-2-(isoquinolin-5-yl)furo[2,3-c]pyridin-4-yl]-1H-pyrazol-1-yl}azetidine-1-carboxylate The title compound was prepared by a procedure analogous to Example 60.

Step B: 4-[1-(azetidin-3-yl)-1H-pyrazol-4-yl]-2-(isoquinolin-5-yl)furo[2,3-c]pyridin-7-amine (Title Compound)

A solution of tert-butyl 3-{4-[7-amino-2-(isoquinolin-5-yl)furo[2,3-c]pyridin-4-yl]-1H-pyrazol-1-yl}azetidine-1-carboxylate in DCM (10 mL) was treated with HCl (4 M in 1,4-dioxane, 2.57 mL, 10.3 mmol) and stirred at RT for 16 h. The reaction was then concentrated in vacuo to a solid which was purified by MDP to afford 1.3 mg (1%) of the title compound. ¹H NMR (400 MHz, CD₃OD) δ 9.77 (br. s, 1H), 8.93 (d, J=6.32 Hz, 1H), 8.70 (d, J=7.33 Hz, 2H), 8.59 (d, J=8.34 Hz, 1H), 8.41 (s, 1H), 8.21 (s, 1H), 8.11 (t, J=7.96 Hz, 1H), 7.91 (d, J=4.29 Hz, 2H), 5.58 (s, 1H), 4.63 (dd, 4H); MS (ESI): 383.15 [M+H]+; HPLC $t_R$=0.72 min (TOF: polar_3 min).

Example 65 trans-4-{4-[7-amino-2-(isoquinolin-5-yl)furo[2,3-c]pyridin-4-yl]-1H-pyrazol-1-yl}cyclohexanol

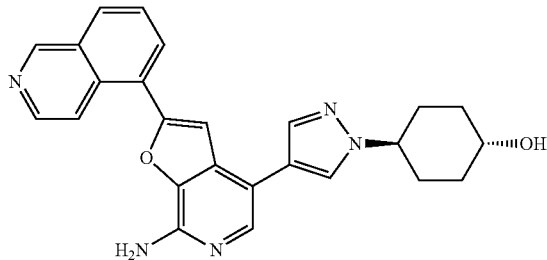 [SMILES: Nc1ncc(-c2cnn([C@H]3CC[C@H](O)CC3)c2)c2cc(-c3cccc4cnccc34)oc12]

4-[1-(trans-4-{[tert-butyl(dimethyl)silyl]oxy}cyclohexyl)-1H-pyrazol-4-yl]-2-(isoquinolin-5-yl)furo[2,3-c]pyridin-7-amine (25 mg, 0.046 mmol) was dissolved in THF (1.00 mL) and tetra-n-butylammonium fluoride (1.0 M in THF, 1.00 mL, 1.00 mmol) was added and stirred at RT for 16 h. The reaction was then washed with sodium bicarbonate and water (2×). The organic layer was collected, dried over sodium sulfate, filtered, and then concentrated in vacuo to a solid. Purification by flash chromatography (0 to 5% 7 N NH$_3$/MeOH:EtOAc) afforded 5.5 mg (28%) of the title compound. $^1$H NMR (400 MHz, CD$_3$OD): δ 9.33 (d, J=0.51 Hz, 1H), 8.57 (d, J=6.06 Hz, 1H), 8.49 (d, J=6.06 Hz, 1H), 8.35 (dd, J=7.33, 1.26 Hz, 1H), 8.24 (d, J=8.08 Hz, 1H), 8.11 (s, 1H), 7.92 (s, 1H), 7.90 (d, J=0.76 Hz, 1H), 7.83 (dd, J=8.21, 7.45 Hz, 1H), 7.50 (s, 1 H), 4.25 (tt, J=11.84, 3.82 Hz, 1H), 3.69 (tt, J=10.89, 4.26 Hz, 1H), 2.07-2.22 (m, 4H), 1.95-2.05 (m, 2H), 1.45-1.57 (m, 2H); MS (ESI): 427.19 [M+H]+; HPLC $t_R$=0.87 min (TOF: polar_3 min).

Example 66

3-{4-[7-amino-2-(isoquinolin-5-yl)furo[2,3-c]pyridin-4-yl]-1H-pyrazol-1-yl}propane-1,2-diol

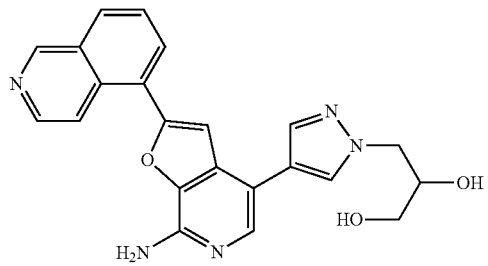 [SMILES: Nc1ncc(-c2cnn(CC(O)CO)c2)c2cc(-c3cccc4cnccc34)oc12]

4-{1-[(2,2-dimethyl-1,3-dioxolan-4-yl)methyl]-1H-pyrazol-4-yl}-2-(isoquinolin-5-yl)furo[2,3-c]pyridin-7-amine (25.0 mg, 0.0566 mmol) was dissolved in MeOH (0.5 mL, 10 mmol) and HCl (4 M in 1,4-dioxane, 0.30 mL, 1.2 mmol) was added. The reaction stirred at RT for 16 h. The product mixture was then concentrated in vacuo to a solid. Purification by flash chromatography (0 to 10% 7 N NH$_3$/MeOH:EtOAc) afforded 1 mg (4%) of the title compound. $^1$H NMR (400 MHz, CD$_3$OD) δ 9.35 (s, 1 H), 8.59 (d, J=6.06 Hz, 1 H), 8.51 (d, J=6.06 Hz, 1H), 8.37 (dd, J=7.33, 1.26 Hz, 1H), 8.26 (d, J=8.34 Hz, 1H), 8.12 (s, 1H), 7.94 (d, J=3.79 Hz, 2H), 7.81-7.89 (m, 1H), 7.54 (s, 1H), 4.40 (dd, J=14.02, 4.17 Hz, 1H), 4.19-4.27 (m, 1H), 4.01-4.12 (m, 1H), 3.52-3.61 (m, 2H); MS (ESI): 402.15 [M+H]+; HPLC $t_R$=0.79 min (TOF: polar_3 min).

Example 67

2-{4-[7-amino-2-(isoquinolin-5-yl)furo[2,3-c]pyridin-4-yl]-1H-pyrazol-1-yl}ethanol

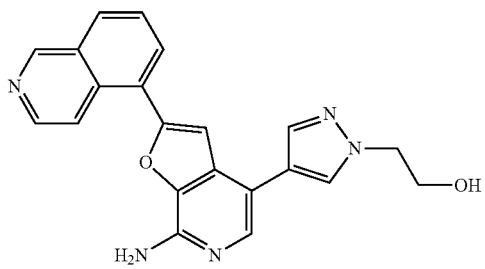 [SMILES: Nc1ncc(-c2cnn(CCO)c2)c2cc(-c3cccc4cnccc34)oc12]

2-(isoquinolin-5-yl)-4-{1-[2-(tetrahydro-2H-pyran-2-yloxy)ethyl]-1H-pyrazol-4-yl}furo[2,3-c]pyridin-7-amine (20.0 mg, 0.0439 mmol) was dissolved in MeOH (0.5 mL) and HCl (4 M in 1,4-dioxane, 0.50 mL, 2.0 mmol) was added. The reaction stirred at RT for 16 h. The reaction was concentrated in vacuo to a solid. Purification by flash chromatography (0 to 10% 7 N NH$_3$/MeOH:EtOAc) afforded 1.6 mg (10%) of the title compound. $^1$H NMR (400 MHz, CD$_3$OD): δ 9.36 (s, 1H), 8.60 (d, J=6.06 Hz, 1H), 8.52 (d, J=6.32 Hz, 1H), 8.38 (dd, J=7.33, 1.26 Hz, 1H), 8.27 (d, J=8.34 Hz, 1H), 8.14 (s, 1H), 7.96 (d, J=1.01 Hz, 2H), 7.82-7.89 (m, 1H), 7.55 (s, 1H), 4.32-4.38 (m, 2H), 3.97 (t, 2H); MS (ESI): 372.14 [M+H]+; HPLC $t_R$=0.82 min (TOF: polar_3 min).

Example 68

2-(isoquinolin-5-yl)-4-{1-[1-(2-methoxyethyl)piperidin-4-yl]-1H-pyrazol-4-yl}furo[2,3-c]pyridin-7-amine

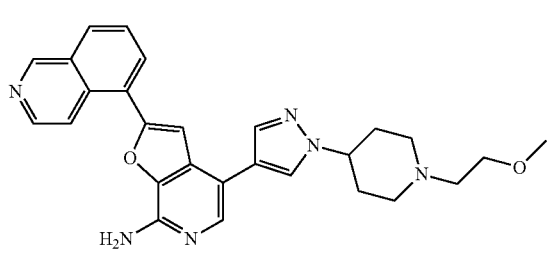 [SMILES: COCCN1CCC(n2cc(-c3cnc(N)c4oc(-c5cccc6cnccc56)cc34)cn2)CC1]

A vial was charged with 1-(2-methoxyethyl)-4-[4-(4,4,5,5-tetramethyl-1,3,2-dioxaborolan-2-yl)-1H-pyrazol-1-yl]piperidine (32.4 mg, 96.8 μmol) and 4-iodo-2-(isoquinolin-5-yl)furo[2,3-c]pyridin-7-amine (25.0 mg, 64.6 μmol) in 1,4-dioxane (0.43 mL) and H$_2$O (0.1 mL), potassium carbonate (13 mg, 97.0 μmol) and (1,1'-bis(diphenylphosphino)ferrocene) palladium dichloride (5 mg, 6 μmol) was evacuated and filled with argon three times. The mixture was heated in a microwave reactor at 100° C. for 40 min. The reaction mixture was partitioned between EtOAc and brine/water and separated. The aqueous layer was extracted with EtOAc (3×) and the combined organic extracts were washed with brine, dried over sodium sulfate, filtered, and concentrated. Purification by flash chromatography (0 to 10% 7 N NH$_3$/MeOH: EtOAc) afforded 1.9 mg (6%) of the title compound. $^1$H NMR (400 MHz, CD$_3$OD): δ 9.33 (s, 1 H), 8.57 (d, J=6.06 Hz, 1 H), 8.49 (d, J=6.06 Hz, 1 H), 8.34 (dd, J=7.33, 1.26 Hz, 1 H), 8.23 (d, J=8.34 Hz, 1 H), 8.13 (s, 1 H), 7.92 (d, J=9.09 Hz, 2 H), 7.82 (t, J=7.71 Hz, 1 H), 7.49 (s, 1 H), 4.25 (dt, J=15.54, 7.89 Hz, 1 H), 3.58 (t, J=5.56 Hz, 2 H), 3.37 (s, 3 H), 3.15 (d, J=12.13 Hz, 2 H), 2.66 (t, J=5.56 Hz, 2 H), 2.26-2.35 (m, 2 H), 2.13-2.20 (m, 4 H); MS (ESI): 469.23 [M+H]$^+$; HPLC t$_R$=0.77 min (TOF: polar_3 min).

The following examples were prepared analogously, using procedures similar to Example 68 above.

| Ex. # | Structure and NMR Data | Compound Name | HPLC tR (min) | MS (ESI) [M + H]$^+$ |
|---|---|---|---|---|
| Ex. 69 | $^1$H NMR (400 MHz, CD$_3$OD): δ 9.37 (s, 1H), 8.61 (d, J = 6.32 Hz, 1H), 8.53 (d, J = 6.32 Hz, 1H), 8.39 (d, J = 7.33 Hz, 1 H), 8.28 (d, J = 7.83 Hz, 1H), 8.08 (br. s., 2H), 7.98 (s, 1H), 7.86 (t, J = 7.83 Hz, 1H), 7.55 (s, 1H) | 2-(isoquinolin-5-yl)-4-(1H-pyrazol-4-yl)furo[2,3-c]pyridin-7-amine | 0.80 min (TOF: polar_3 min) | 328.10 |
| Ex. 70 | $^1$H NMR (400 MHz, CD$_3$OD): δ 9.37 (s, 1H), 8.58-8.64 (m, 1H), 8.52 (d, J = 6.32 Hz, 1H), 8.38 (d, J = 7.33 Hz, 1 H), 8.28 (d, J = 8.08 Hz, 1H), 8.10 (s, 1 H), 7.95 (s, 1H), 7.92 (s, 1H), 7.86 (t, J = 7.71 Hz, 1H), 7.54 (s, 1H), 4.00 (s, 3H) | 2-(isoquinolin-5-yl)-4-(1-methyl-1H-pyrazol-4-yl)furo[2,3-c]pyridin-7-amine | 2.49 min (TOF: polar_3 min) | 342.04 |
| Ex. 71 | $^1$H NMR (400 MHz, CD$_3$OD): δ 9.37 (s, 1H), 8.57-8.64 (m, 1H), 8.54 (d, J = 6.06 Hz, 1H), 8.40 (d, J = 7.33 Hz, 1 H), 8.28 (d, J = 8.34 Hz, 1H), 8.15 (s, 1 H), 7.95 (d, J = 10.86 Hz, 2H), 7.87 (t, J = 7.71 Hz, 1H), 7.56 (s, 1H), 4.30 (q, J = 7.33 Hz, 2H), 1.55 (t, 3H) | 4-(1-ethyl-1H-pyrazol-4-yl)-2-(isoquinolin-5-yl)furo[2,3-c]pyridin-7-amine | 2.62 min (TOF: polar_3 min) | 356.03 |

| Ex. # | Structure and NMR Data | Compound Name | HPLC tR (min) | MS (ESI) [M + H]+ |
|---|---|---|---|---|
| Ex. 72 | 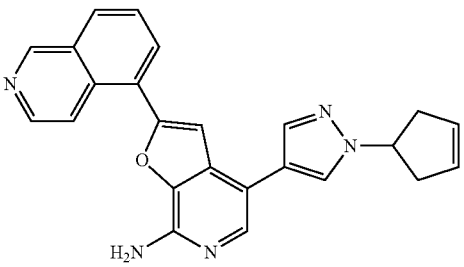 [SMILES: Nc1ncc(-c2cnn(C3CC=CC3)c2)c2cc(-c3cccc4cnccc34)oc12]<br>¹H NMR (400 MHz, CD₃OD): δ 9.11 (s, 1H), 8.40 (d, J = 6.06 Hz, 1H), 8.26 d, J = 6.06 Hz, 1H), 8.12 (dd, J = 7.33, 1.01 Hz, 1H), 7.98 (d, J = 8.34 Hz, 1H), 7.91 (s, 1H), 7.74 (s, 2H), 7.57-7.65 (m, 1 H), 7.17 (s, 1H), 5.78 (s, 2H), 5.04-5.13 (m, 1H), 2.94 (d, J = 8.34 Hz, 1H), 2.90 (d, J = 8.59 Hz, 1H), 2.73-2.77 (m, 1H), 2.69-2.73 (m, 1H) | 4-[1-(cyclopent-3-en-1-yl)-1H-pyrazol-4-yl]-2-(isoquinolin-5-yl)furo[2,3-c]pyridin-7-amine | 1.01 min (TOF: polar_3 min) | 395.17 |
| Ex. 73 | 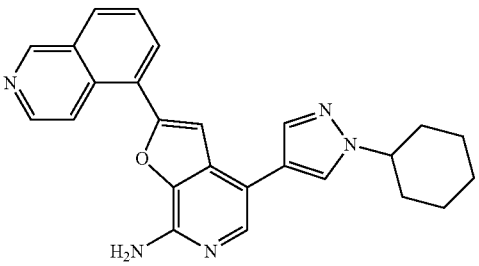 [SMILES: Nc1ncc(-c2cnn(C3CCCCC3)c2)c2cc(-c3cccc4cnccc34)oc12]<br>¹H NMR (400 MHz, CD₃OD): δ 9.37 (s, 1H), 8.58-8.63 (m, 1H), 8.53 (d, J = 6.32 Hz, 1H), 8.39 (dd, J = 1.01, 7.33 Hz, 1H), 8.28 (d, J = 8.08 Hz, 1H), 8.14 (s, 1H), 7.96 (s, 1H), 7.92 (d, J = 0.76 Hz, 1H), 7.87 (d, J = 8.08 Hz, 1H), 7.54 (s, 1H), 4.19-4.30 (m, 1H), 2.14-2.22 (m, 2H), 1.75-2.01 (m, 6H), 1.46-1.61 (m, 2H) | 4-(1-cyclohexyl-1H-pyrazol-4-yl)-2-(isoquinolin-5-yl)furo[2,3-c]pyridin-7-amine | 1.10 min (TOF: polar_3 min) | 410.17 |
| Ex. 74 | 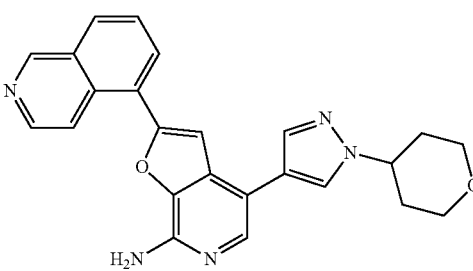<br>¹H NMR (400 MHz, CD₃OD): δ 9.36 (s, 1H), 8.60 (d, J = 6.06 Hz, 1H), 8.52 (d, J = 6.06 Hz, 1H), 8.39 (dd, J = 7.33, 1.01 Hz, 1H), 8.27 (d, J = 8.34 Hz, 1H), 8.18 (d, J = 0.51 Hz, 1H), 7.96 (s, 1H), 7.95 (d, J = 0.76 Hz, 1H), 7.85 (dd, J = 8.08, 7.33 Hz, 1H), 7.55 (s, 1H), 4.51 (tt, J = 11.49, 4.42 Hz, 1H), 4.06-4.15 (m, 2H), 3.61 (td, J = 11.75, 2.27 Hz, 2H), 2.08-2.26 (m, 4H) | 2-(isoquinolin-5-yl)-4-[1-(tetrahydro-2H-pyran-4-yl)-1H-pyrazol-4-yl]furo[2,3-c]pyridin-7-amine | 0.94 min (TOF: polar_3 min) | 412.17 |

| Ex. # | Structure and NMR Data | Compound Name | HPLC tR (min) | MS (ESI) [M + H]+ |
|---|---|---|---|---|
| Ex. 75 | ¹H NMR (400 MHz, CD₃OD): δ ppm 1.39 (s, 3H), 1.73 (td, J = 12.13, 5.81 Hz, 2H), 1.85 (d, J = 12.38 Hz, 2H), 2.06-2.19 (m, 4H), 4.25-4.38 (m, 1 H), 7.55 (s, 1H), 7.81-7.89 (m, 1H), 7.95 (d, J = 7.58 Hz, 2H), 8.17 (s, 1H), 8.27 (d, J = 8.34 Hz, 1H), 8.39 (dd, J = 7.33, 1.01 Hz, 1H), 8.53 (d, J = 6.06 Hz, 1H), 8.60 (d, J = 6.32 Hz, 1H), 9.36 (s, 1H) | trans-4-{4-[7-amino-2-(isoquinolin-5-yl)furo[2,3-c]pyridin-4-yl]-1H-pyrazol-1-yl}-1-methylcyclohexanol | 0.95 min (TOF: polar_3 min) | 440.12 |
| Ex. 76 | ¹H NMR (400 MHz, CD₃OD): 1.29 (s, 3H), 1.65 (td, J = 13.71, 3.92 Hz, 2H), 1.86 (d, J = 12.88 Hz, 2H), 1.94-2.04 (m, 2H), 2.21-2.36 (m, 2H), 4.17-4.31 (m, 1H), 7.51 (s, 1H) 7.84 (dd, J = 8.21, 7.45 Hz, 1H), 7.89-7.97 (m, 2 H), 8.13 (s, 1H), 8.26 (d, J = 8.08 Hz, 1 H), 8.37 (dd, J = 7.33, 1.01 Hz, 1H), 8.51 (d, J = 6.32 Hz, 1H), 8.59 (d, J = 6.06 Hz, 1H), 9.35 (s, 1H) | cis-4-{4-[7-amino-2-(isoquinolin-5-yl)furo[2,3-c]pyridin-4-yl]-1H-pyrazol-1-yl}-1-methylcyclohexanol | 0.95 min (TOF: polar_3 min) | 440.21 |
| Ex. 77 | ¹H NMR (400 MHz, CD₃OD): δ 9.35 (s, 1H), 8.59 (d, J = 6.32 Hz, 1H), 8.51 (d, J = 6.06 Hz, 1H), 8.38 (dd, J = 7.33, 1.01 Hz, 1H), 8.26 (d, J = 8.34 Hz, 1H), 8.16 (s, 1H), 7.94 (d, J = 8.34 Hz, 2H), 7.85 (dd, J = 8.08, 7.33 Hz, 1H), 7.54 (s, 1H), 4.21-4.33 (m, 1H), 3.04 (d, J = 11.87 Hz, 2H), 2.36 (s, 3H), 2.22-2.32 (m, 2H), 2.18 (m, J = 3.03 Hz, 4H). | 2-(isoquinolin-5-yl)-4-[1-(1-methylpiperidin-4-yl)-1H-pyrazol-4-yl]furo[2,3-c]pyridin-7-amine | 0.75 min (TOF: polar_3 min) | 425.20 |

-continued

| Ex. # | Structure and NMR Data | Compound Name | HPLC tR (min) | MS (ESI) [M + H]+ |
|---|---|---|---|---|
| Ex. 78 | 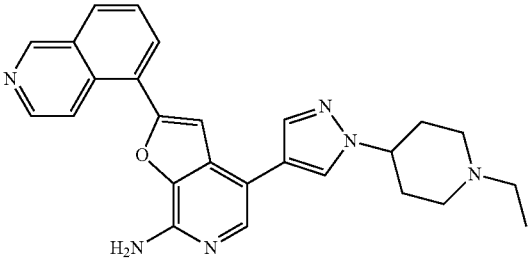 [SMILES: CCN1CCC(n2cc(-c3cnc(N)c4oc(-c5cccc6cnccc56)cc34)cn2)CC1]<br><br>¹H NMR (400 MHz, CD₃OD) δ 9.34 (s, 1H), 8.55-8.59 (m, 1H), 8.48-8.52 (m, 1H), 8.36 (dd, J = 7.33, 1.01Hz, 1H), 8.24 (d, J = 8.34 Hz, 1H), 8.14 (s, 1H), 7.92 (d, J = 8.34 Hz, 2H), 7.79-7.86 (m, 1H), 7.51 (s, 1H), 4.21-4.32 (m, 1H), 3.10-3.18 (m, 2H), 2.52 (q, J = 7.16 Hz, 2H), 2.12-2.27 (m, 6H), 1.15 (t, 3H). | 4-[1-(1-ethylpiperidin-4-yl)-1H-pyrazol-4-yl]-2-(isoquinolin-5-yl)furo[2,3-c]pyridin-7-amine | 0.77 min (TOF: polar_3 min). | 439.22 |
| Ex. 79 | 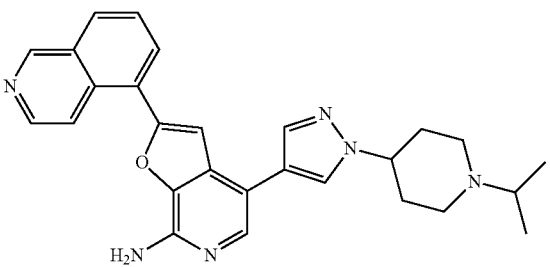 [SMILES: CC(C)N1CCC(n2cc(-c3cnc(N)c4oc(-c5cccc6cnccc56)cc34)cn2)CC1]<br><br>¹H NMR (400 MHz, CD₃OD) δ 9.30 (s, 1H), 8.55 (d, J = 6.06 Hz, 1H), 8.44-8.49 (m, 1H), 8.31 (dd, J = 7.33, 1.26 Hz, 1H), 8.19 (d, J = 8.34 Hz, 1H), 8.09 (s, 1H), 7.90 (d, J = 7.83 Hz, 2H), 7.79 (t, J = 7.83 Hz, 1H), 7.44 (s, 1H), 4.16-4.26 (m, 1H), 3.06 (d, J = 11.87 Hz, 2H), 2.81 (spt, J = 6.57 Hz, 1H), 2.30-2.46 (m, 2H), 2.05-2.22 (m, 4H), 1.12 (d, J = 8.0 Hz, 6H). | 2-(isoquinolin-5-yl)-4-{1-[1-(propan-2-yl)piperidin-4-yl]-1H-pyrazol-4-yl}furo[2,3-c]pyridin-7-amine | 0.77 min (TOF: polar_3 min) | 454.24 |
| Ex. 80 | 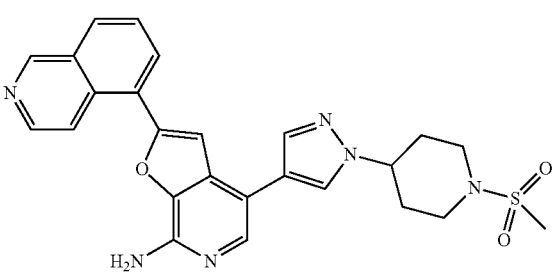 [SMILES: CS(=O)(=O)N1CCC(n2cc(-c3cnc(N)c4oc(-c5cccc6cnccc56)cc34)cn2)CC1]<br><br>¹H NMR (400MHz, CDCl₃) 9.38 (s, 1 H), 8.67 (d, J = 6.1 Hz, 1H), 8.26-8.05 (m, 3H), 7.96 (s, 1H), 7.87 (s, 1 H), 7.82-7.66 (m, 2H), 7.25 (s, 1H), 5.53 (br s, 2H), 4.49-4.25 (m, 1H), 4.06-3.92 (m, 2H), 3.10-2.90 (m, 2 H), 2.88 (s, 3H), 2.46-2.09 (m, 4H). | 2-(isoquinolin-5-yl)-4-{1-[1-(methylsulfonyl)piperidin-4-yl]-1H-pyrazol-4-yl}furo[2,3-c]pyridin-7-amine | 0.92 min (TOF: polar_3 min) | 489.17 |

| Ex. # | Structure and NMR Data | Compound Name | HPLC tR (min) | MS (ESI) [M + H]+ |
|---|---|---|---|---|
| Ex. 81 | 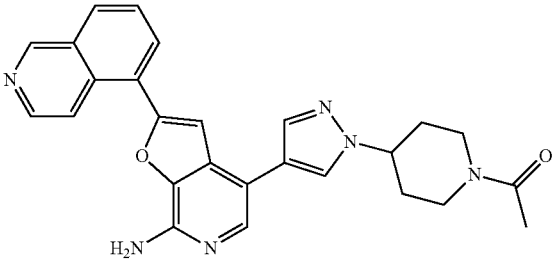 [SMILES: CC(=O)N1CCC(n2cc(-c3cnc(N)c4oc(-c5cccc6cnccc56)cc34)cn2)CC1]<br>¹H NMR (400 MHz, DMSO-d₆) δ 9.46 (s, 1H), 8.66 (d, J = 6.06 Hz, 1H), 8.54 (d, J = 6.06 Hz, 1H), 8.42 (dd, J = 7.33, 1.01 Hz, 1H), 8.29-8.34 (m, 2H), 8.06 (s, 1H), 8.01 (s, 1H), 7.85-7.90 (m, 1H), 7.76 (s, 1H), 6.43-6.49 (m, 2H), 4.42-4.54 (m, 2H), 3.96 (d, J = 14.15 Hz, 1H), 3.19-3.28 (m, 1H), 2.75 (td, J = 12.69, 2.40 Hz, 1H), 1.80-2.16 (m, 7H). | 1-(4-{4-[7-amino-2-(isoquinolin-5-yl)furo[2,3-c]pyridin-4-yl]-1H-pyrazol-1-yl}piperidin-1-yl)ethanone | 0.87 min (TOF: polar_3 min) | 454.20 |
| Ex. 82 | 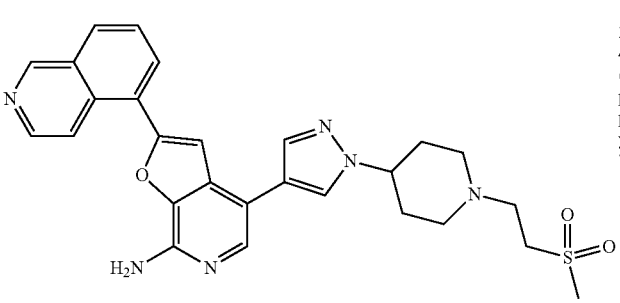<br>¹H NMR (400 MHz, CDCl₃): δ 9.39 (s, 1H), 8.68 (d, J = 6.06 Hz, 1H), 8.12-8.21 (m, 3H), 7.95 (s, 1H), 7.86 (s, 1H), 7.76 (dd, J = 8.08, 7.33 Hz, 1H), 7.73 (s, 1H), 7.26 (s, 1H), 5.50 (br. s., 2H), 4.18-4.29 (m, 1H), 3.17-3.22 (m, 2H), 3.13 (d, J = 11.37 Hz, 2H), 3.08 (s, 3H), 2.98 (t, J = 6.44 Hz, 2H), 2.24-2.38 (m, 4H), 2.09-2.21 (m, 2H) | 2-(isoquinolin-5-yl)-4-(1-{1-[2-(methylsulfonyl)ethyl]piperidin-4-yl}-1H-pyrazol-4-yl)furo[2,3-c]pyridin-7-amine | 0.7 min (TOF: polar_3 min) | 517.19 |
| Ex. 83 | 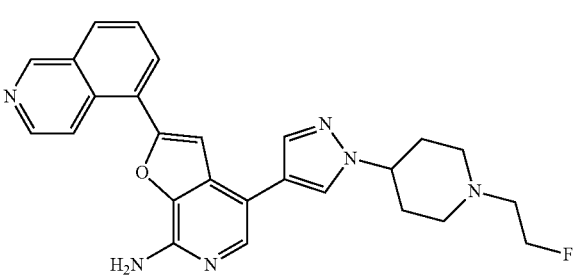 [SMILES: Nc1ncc(-c2cnn(C3CCN(CCF)CC3)c2)c2cc(-c3cccc4cnccc34)oc12]<br>¹H NMR (400 MHz, CD₃OD): δ 9.34 (s, 1H), 8.58 (d, J = 6.06 Hz, 1H), 8.50 (d, J = 6.06 Hz, 1H), 8.34-8.38 (m, 1H), 8.25 (d, J = 8.08 Hz, 1H), 8.15 (s, 1H), 7.93 (d, J = 7.83 Hz, 2H), 7.83 (t, J = 7.83 Hz, 1H), 7.51 (s, 1H), 4.65-4.70 (m, 1H), 4.54-4.58 (m, 1H), 4.22-4.33 (m, 1H), 3.17 (d, J = 12.13 Hz, 2H), 2.81-2.86 (m, 1H), 2.73-2.79 (m, 1H), 2.33-2.42 (m, 2H), 2.15-2.23 (m, 4H) | 4-{1-[1-(2-fluoroethyl)piperidin-4-yl]-1H-pyrazol-4-yl}-2-(isoquinolin-5-yl)furo[2,3-c]pyridin-7-amine | 0.76 min (TOF: polar_3 min) | 457.21 |

-continued

| Ex. # | Structure and NMR Data | Compound Name | HPLC tR (min) | MS (ESI) [M + H]+ |
|---|---|---|---|---|
| Ex. 84 | 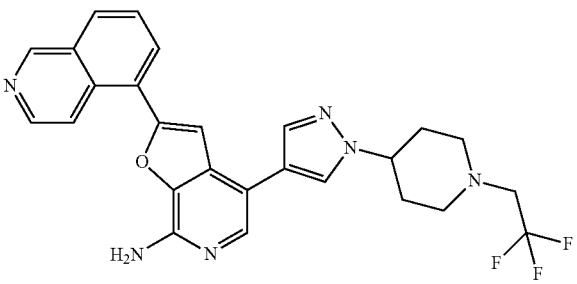 [SMILES: Nc1ncc(-c2cnn(C3CCN(CC(F)(F)F)CC3)c2)c2cc(-c3cccc4cnccc34)oc12]<br>¹H NMR (400 MHz, CD₃OD): δ 9.30 (s, 1H), 8.54 (d, J = 6.32 Hz, 1H), 8.46 (d, J = 6.32 Hz, 1H), 8.31 (d, J= 7.33 Hz, 1 H), 8.19 (d, J = 8.08 Hz, 1H), 8.10 (s, 1 H), 7.89 (d, J = 4.55 Hz, 2H), 7.79 (t, J = 7.71 Hz, 1H), 7.45 (s, 1H), 4.18-4.29 (m, 1H), 3.09-3.19 (m, 2H), 2.56-2.66 (m, 2H), 2.07-2.25 (m, 4H), 2.01 (s, 2H) | 2-(isoquinolin-5-yl)-4-{1-[1-(2,2,2-trifluoroethyl)piperidin-4-yl]-1H-pyrazol-4-yl}furo[2,3-c]pyridin-7-amine | 1.07 min (TOF: polar_3 min) | 494.20 |

Example 85

2-(4-{-4-[7-amino-2-(isoquinolin-5-yl)furo[2,3-c]pyridin-4-yl]-1H-pyrazol-1-yl}piperidin-1-yl)ethanol

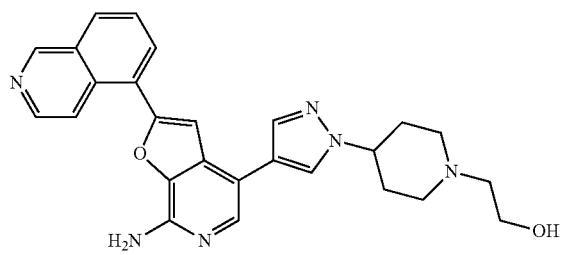 [SMILES: Nc1ncc(-c2cnn(C3CCN(CCO)CC3)c2)c2cc(-c3cccc4cnccc34)oc12]

Step A: 4-{1-[1-(2-{[tert-butyl(dimethyl)silyl]oxy}ethyl)piperidin-4-yl]-1H-pyrazol-4-yl}-2-(isoquinolin-5-yl)furo[2,3-c]pyridin-7-amine The title compound was prepared by a procedure analogous to Example 68.

Step B: 2-(4-{4-[7-amino-2-(isoquinolin-5-yl)furo[2,3-c]pyridin-4-yl]-1H-pyrazol-1-yl}piperidin-1-yl)ethanol (Title Compound)

4-{1-[1-(2-{[tert-butyl(dimethyl)silyl]oxy}ethyl)piperidin-4-yl]-1H-pyrazol-4-yl}-2-(isoquinolin-5-yl)furo[2,3-c]pyridin-7-amine (60.8 mg, 0.112 mmol) was dissolved in THF (1.2 mL) and tetra-n-butylammonium fluoride (1.0 M in THF, 1.35 mL, 1.35 mmol) was added to the reaction. The reaction stirred 16 h at RT. The reaction was washed with sodium carbonate (2×), brine 2× and extracted with EtOAc (3×). The organic layers were collected, dried with sodium sulfate, filtered and then concentrated in vacuo to a solid. Purification by flash chromatography (0 to 15% NH₃/MeOH: EtOAc) afforded 10.1 mg (34%) of the title compound. ¹H NMR (400 MHz, CD₃OD): δ 9.32 (s, 1 H), 8.54-8.58 (m, 1 H), 8.49 (d, J=6.32 Hz, 1 H), 8.34 (dd, J=7.33, 1.01 Hz, 2 H), 8.23 (d, J=8.08 Hz, 1 H), 8.13 (s, 1 H), 7.91 (d, J=7.07 Hz, 1 H), 7.81 (dd, J=8.08, 7.33 Hz, 1 H), 7.49 (s, 1 H), 4.18-4.32 (m, 1 H), 3.71 (t, J=6.06 Hz, 2 H), 3.14 (d, J=12.13 Hz, 2 H), 2.60 (t, J=6.06 Hz, 2 H), 2.25-2.36 (m, 2 H), 2.12-2.24 (m, 4 H); MS (ESI): 455.21 [M+H]⁺; HPLC t_R=0.74 min (TOF: polar_3 min).

Example 86

1-(4-{4-[7-amino-2-(1H-pyrrolo[2,3-c]pyridin-3-yl)furo[2,3-c]pyridin-4-yl]-1H-pyrazol-1-yl}piperidin-1-yl)ethanone

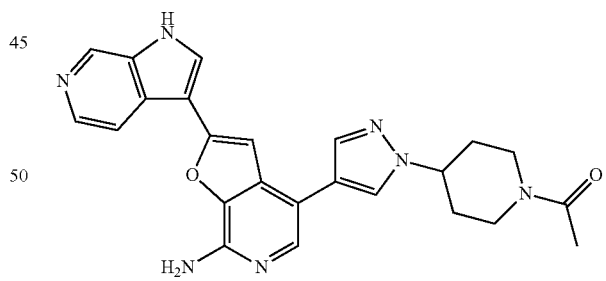

A mixture of 1-{4-[4-(7-amino-2-chlorofuro[2,3-c]pyridin-4-yl)-1H-pyrazol-1-yl]piperidin-1-yl}ethanone (45 mg, 0.13 mmol), [1-(tert-butoxycarbonyl)-1H-pyrrolo[2,3-c]pyridin-3-yl]boronic acid (65 mg, 0.26 mmol), Na₂CO₃ (55 mg, 0.52 mmol) and Pd(PPh₃)₄ (10 mg, 0.0087 mmol) in 4:1 dioxane:water (5 mL) was degassed with N₂ for 1 min, and then heated to 120° C. in a microwave reactor for 30 min. The mixture was filtered and the filtrate was purified by preparative TLC (5:1 DCM:MeOH) to afford 16 mg (29%) of the title compound. ¹H NMR (400 MHz, CD₃OD): δ 8.79 (s, 1H), 8.28-8.27 (m, 3H), 8.16 (s, 1H), 7.93 (s, 1H), 7.86 (s, 1H), 7.25 (s, 1H), 4.71-4.68 (m, 1H), 4.57-4.54 (m, 1H), 4.13-4.09

(m, 1H), 3.37 (m, 1H), 2.85 (m, 1H), 2.21 (m, 1H), 2.13 (s, 3H), 1.95 (m, 1H); MS (ESI): 442.1 [M+H]⁺; HPLC $t_R$=2.08 min (ZQ3: polar_4 min).

Example 87

4-(1H-pyrazol-4-yl)-2-(1H-pyrrolo[2,3-c]pyridin-3-yl)furo[2,3-c]pyridin-7-amine trifluoroacetic acid salt

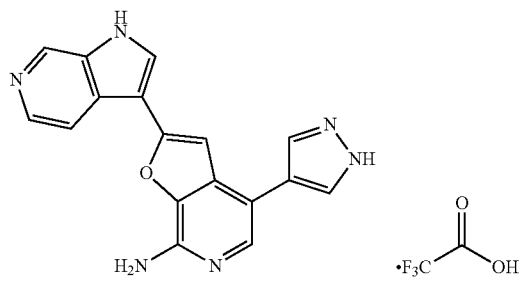

A solution of 2-chloro-4-(1H-pyrazol-4-yl)furo[2,3-c]pyridin-7-amine (12 mg, 0.051 mmol), [1-(tert-butoxycarbonyl)-1H-pyrrolo[2,3-c]pyridin-3-yl]boronic acid (16 mg, 0.061 mmol), and Pd(PPh₃)₄ (5.9 mg, 0.0051 mmol) in 1,4-dioxane (200 μL) and 1.0 M aqueous sodium carbonate (200 μL) was heated to 120° C. in a microwave for 60 min. The reaction mixture was concentrated. Purification by MDP afforded 1.4 mg (6%) of the title compound as a white solid. ¹H NMR (400 MHz, CD₃OD): δ 9.25 (s, 1 H), 8.98 (s, 1 H), 8.95 (d, J=6.3 Hz, 1 H), 8.46 (d, J=6.6 Hz, 1 H), 8.19 (s, 2 H), 7.87 (s, 1 H), 7.76 (s, 1 H); MS (ESI): 317.05 [M+H]⁺; HPLC $t_R$=1.13 min (ZQ3, polar_4 min).

The following Examples were prepared by a procedure analogous to Example 87.

| Ex. # | Structure and NMR Data | Compound Name | MS (ESI) [M + H]⁺ | HPLC $t_R$ (min) |
|---|---|---|---|---|
| 88 | ¹H NMR (400 MHz, CD₃OD): δ 9.26 (s, 1H), 8.97 (s, 1H), 8.95 (dd, J = 0.8, 6.6 Hz, 1H), 8.46 (dd, J = 0.8, 6.6 Hz, 1H), 8.22 (s, 1H), 7.99 (d, J = 0.8 Hz, 1H), 7.84 (s, 1H), 7.74 (s, 1 H), 4.03 (s, 3H) | 4-(1-methyl-1H-pyrazol-4-yl)-2-(1H-pyrrolo[2,3-c]pyridin-3-yl)furo[2,3-c]pyridin-7-amine trifluoroacetic acid salt | 331.18 | 2.52 (ZQ3: VVPOLAR_5 min) |
| 89 | ¹H NMR (400 MHz, CD₃OD): δ 9.25 (s, 1H), 8.99 (s, 1H), 8.95 (dd, J = 0.8, 6.6 Hz, 1H), 8.46 (dd, J = 0.8, 6.6 Hz, 1H), 8.26 (s, 1H), 8.00 (d, J = 0.8 Hz, 1H), 7.84 (s, 1H), 7.74 (s, 1H), 4.38-4.12 (m, 1H), 2.17 (br. s., 2 H), 2.05-1.66 (m, 5H), 1.64-1.42 (m, 2H), 1.43-1.19 (m, 1H) | 4-(1-cyclohexyl-1H-pyrazol-4-yl)-2-(1H-pyrrolo[2,3-c]pyridin-3-yl)furo[2,3-c]pyridin-7-amine | 399.17 | 2.75 (ZQ3: VVPOLAR_5 min) |

| Ex. # | Structure and NMR Data | Compound Name | MS (ESI) [M + H]+ | HPLC t_R (min) |
|---|---|---|---|---|
| 90 | *(structure)*<br><br>¹H NMR (400 MHz, CD₃OD): δ 9.25 (s, 1H), 8.99 (s, 1H), 8.96 (dd, J = 0.8, 6.6 Hz, 1H), 8.46 (dd, J = 0.8, 6.6Hz, 1H), 8.26 (s, 1H), 8.01 (d, J = 0.5Hz, 1H), 7.84 (s, 1H), 7.75 (s, 1 H), 4.66 (spt, J = 6.7 Hz, 1H), 1.59 (d, J= 6.8 Hz, 6H) | 4-[1-(propan-2-yl)-1H-pyrazol-4-yl]-2-(1H-pyrrolo[2,3-c]pyridin-3-yl)furo[2,3-c]pyridin-7-amine | 359.17 | 2.63 (ZQ3: VVPOLAR_5 min) |

The following Examples were prepared from 1-{4-[4-(7-amino-2-chlorofuro[2,3-c]pyridin-4-yl)-1H-pyrazol-1-yl]piperidin-1-yl}ethanone and an appropriate boronic acid or ester by a procedure analogous to Example 86. Boronic esters were prepared as needed from the corresponding aryl bromides or iodides by a procedure analogous to Intermediate 59, Step E.

| Ex # | Structure and ¹H NMR | Compound Name | HPLC t_R (min) | MS (ESI) [M+H]+ |
|---|---|---|---|---|
| Ex. 91 | *(structure)*<br><br>¹H NMR (400 MHz, CD₃OD): δ 8.70 (s, 2H), 8.21 (s, 1H), 8.05 (br. s., 1H), 7.97 (d, J = 5.56 Hz, 2H), 7.93 (s, 1H), 4.73 (d, J = 11.37 Hz, 1H), 4.56 (t, J = 11.75 Hz, 1H), 4.13 (d, J = 12.13 Hz, 1 H), 2.83-2.95 (m, 1H), 1.98-2.31 (m, 8H). | 1-[4-(4-{7-amino-2-[3,5-bis(trifluoromethyl)phenyl]furo[2,3-c]pyridin-4-yl}-1H-pyrazol-1-yl)piperidin-1-yl]ethanone | 1.22 (TOF: polar_3 min) | 538.12 |

| Ex # | Structure and ¹H NMR | Compound Name | HPLC t_R (min) | MS (ESI) [M+H]+ |
|---|---|---|---|---|
| Ex. 92 | 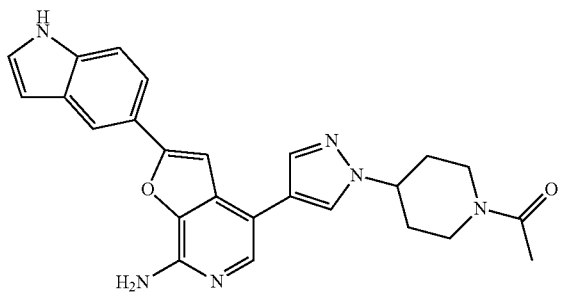 [SMILES: CC(=O)N1CCC(n2cc(-c3cnc(N)c4oc(-c5ccc6[nH]ccc6c5)cc34)cn2)CC1]<br>¹H NMR (400 MHz, CD₃OD): δ 8.19 (d, J = 1.01 Hz, 1H), 7.88 (s, 1H), 7.79 (s, 1H), 7.76 (s, 1H), 7.70 (dd, J = 8.59, 1.77 Hz, 1H), 7.45 (d, J = 8.34 Hz, 1H), 7.29 (d, J = 3.03 Hz, 1H), 7.13 (s, 1H), 6.53 (d, J = 2.53 Hz, 1H), 4.56-4.66 (m, 1H), 4.32 (tt, 1H), 3.86-3.97 (m, 1H), 3.09-3.21 (m, 1H), 2.62-2.76 (m, 1H), 1.82-2.09 (m, 7H) | 1-(4-{4-[7-amino-2-(1H-indol-5-yl)furo[2,3-c]pyridin-4-yl]-1H-pyrazol-1-yl}piperidin-1-yl)ethanone | 0.96 (TOF: polar_3 min) | 441.47 |
| Ex. 93 | 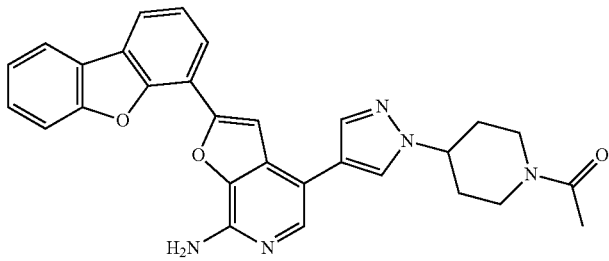 [SMILES: CC(=O)N1CCC(n2cc(-c3cnc(N)c4oc(-c5cccc6c5oc5ccccc56)cc34)cn2)CC1]<br>¹H NMR (400 MHz, DMSO-d₆): δ 8.35 (s, 1H), 8.23-8.32 (m, 3H), 7.97-8.01 (m, 2H), 7.95 (d, J = 8.08 Hz, 1H), 7.88 (s, 1H), 7.59-7.66 (m, 2H), 7.46-7.53 (m, 1H), 6.71 (br. s., 2H), 4.52-4.61 (m, 1H), 4.50 (br. s., 1H), 3.98 (d, J = 13.64 Hz, 1H), 3.21-3.28 (m, 1H), 2.78 (td, J = 12.76, 2.53 Hz, 1H), 2.09-2.19 (m, 2H), 2.08 (s, 3H), 1.82-2.06 (m, 2H) | 1-(4-{4-[7-amino-2-(dibenzo[b,d]furan-4-yl)furo[2,3-c]pyridin-4-yl]-1H-pyrazol-1-yl}piperidin-1-yl)ethanone | 1.15 (TOF: polar_3 min) | 493.20 |
| Ex. 94 | 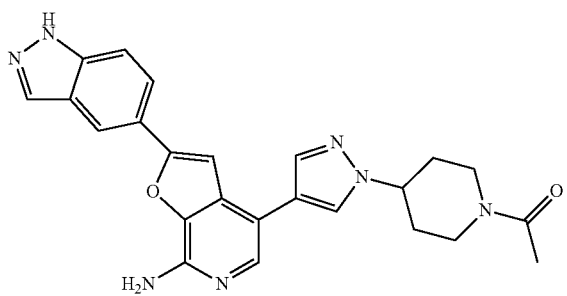 [SMILES: CC(=O)N1CCC(n2cc(-c3cnc(N)c4oc(-c5ccc6[nH]ncc6c5)cc34)cn2)CC1]<br>¹H NMR (400 MHz, CD₃OD): δ 8.53 (br. s., 1H), 8.14-8.20 (m, 2H), 8.08-8.13 (m, 1H), 7.95 (s, 1H), 7.88-7.92 (m, 1H), 7.69 (d, J = 8.84 Hz, 1H), 7.46 (s, 1H), 4.68-4.75 (m, 1H), 4.51-4.61 (m, 1H), 4.10-4.17 (m, 1H), 3.35-3.43 (m, 1H), 2.83-2.94 (m, 1H), 2.20 (s, 7H) | 1-(4-{4-[7-amino-2-(1H-indazol-5-yl)furo[2,3-c]pyridin-4-yl]-1H-pyrazol-1-yl}piperidin-1-yl)ethanone | 0.92 (TOF: polar_3 min) | 442.17 |

| Ex # | Structure and ¹H NMR | Compound Name | HPLC $t_R$ (min) | MS (ESI) [M+H]⁺ |
|---|---|---|---|---|
| Ex. 95 | 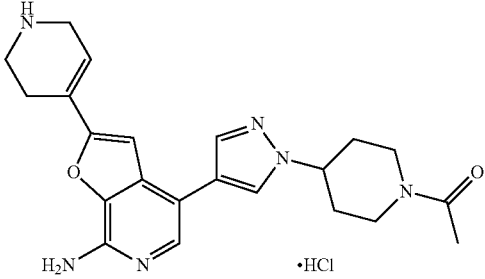 [SMILES: CC(=O)N1CCC(n2cc(-c3cnc(N)c4oc(C5=CCNCC5)cc34)cn2)CC1 ; Cl]<br>¹H NMR (400 MHz, CDCl₃): δ 7.84 (s, 1H), 7.71 (d, J = 0.4 Hz, 1H), 7.57 (d, J = 0.4 Hz, 1H), 6.59 (t, J = 1.2 Hz, 1H), 6.55 (s, 1H), 4.69-4.72 (m, 3H), 4.30-4.39 (m, 1H), 3.89-3.95 (m, 1H), 3.54-3.55 (m, 2H), 3.17-3.25 (m, 1H), 3.06 (t, J = 5.6 Hz, 2H), 2.68-2.74 (m, 1H), 2.40 (m, 2H), 2.14-2.25 (m, 3H), 2.08 (s, 3H), 1.95-2.00 (m, 1H), 1.17-1.20 (m, 1H) | 1-(4-{4-[7-amino-2-(1,2,3,6-tetrahydropyridin-4-yl)furo[2,3-c]pyridin-4-yl]-1H-pyrazol-1-yl}piperidin-1-yl)ethanone hydrochloride | — | 407.1 |
| Ex. 96 | 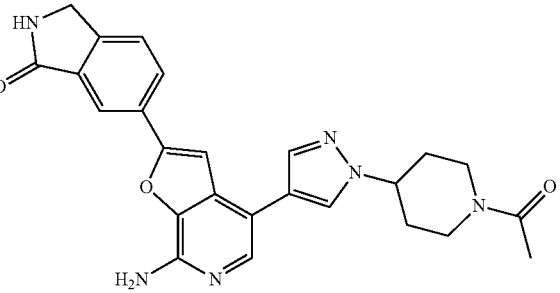<br>¹H NMR (400 MHz, CD₃OD): δ 8.25 (s, 1H), 8.16 (d, J = 7.58 Hz, 1H), 8.07 (s, 1H), 7.85 (d, J = 19.20 Hz, 2H), 7.60 (d, J = 7.83 Hz, 1H), 7.44 (s, 1H), 4.64-4.73 (m, 1H), 4.46-4.55 (m, 1H), 4.45 (s, 2H), 3.32-3.39 (m, 1H), 2.85 (td, J = 12.95, 2.40 Hz, 1H), 1.96-2.26 (m, 8H) | 6-{4-[1-(1-acetylpiperidin-4-yl)-1H-pyrazol-4-yl]-7-aminofuro[2,3-c]pyridin-2-yl}-2,3-dihydro-1H-isoindol-1-one | 0.88 (TOF: polar_3 min) | 457.17 |
| Ex. 97 | 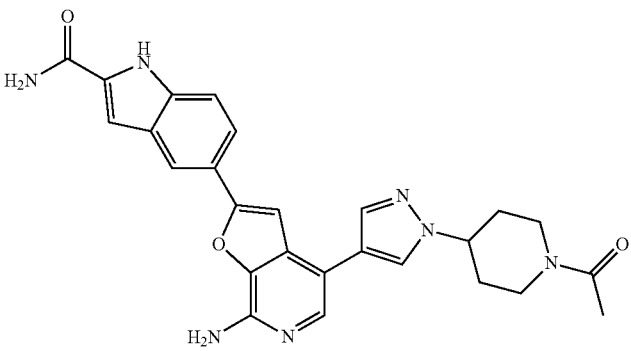 [SMILES: CC(=O)N1CCC(n2cc(-c3cnc(N)c4oc(-c5ccc6[nH]c(C(N)=O)cc6c5)cc34)cn2)CC1]<br>¹H NMR (400 MHz, CD₃OD): δ 8.34 (s, 1H), 8.12 (s, 1H), 7.90-7.93 (m, 2H), 7.86 (s, 1H), 7.56 (d, J = 8.84 Hz, 1H), 7.34 (s, 1H), 7.23 (d, J = 1.01 Hz, 1H), 4.65-4.75 (m, 1H), 4.52 (tt, J = 11.46, 4.20 Hz, 1H), 4.05-4.14 (m, 1H), 3.32-3.38 (m, 1H), 2.85 (td, J = 12.95, 2.40 Hz, 1H), 1.99-2.26 (m, 7H) | 5-{4-[1-(1-acetylpiperidin-4-yl)-1H-pyrazol-4-yl]-7-aminofuro[2,3-c]pyridin-2-yl}-1H-indole-2-carboxamide | 0.92 (TOF: polar_3 min) | 484.19 |

| Ex # | Structure and ¹H NMR | Compound Name | HPLC t$_R$ (min) | MS (ESI) [M+H]⁺ |
|---|---|---|---|---|
| Ex. 98 | 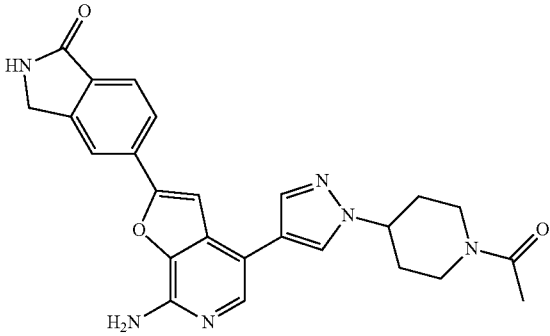 [SMILES: CC(=O)N1CCC(n2cc(-c3cnc(N)c4oc(-c5ccc6c(c5)CNC6=O)cc34)cn2)CC1]<br>¹H NMR (400 MHz, CD₃OD): δ 8.25 (s, 1H), 8.16 (d, J = 7.58 Hz, 2H), 8.07 (s, 1 H), 7.85 (d, J = 19.20 Hz, 1H), 7.60 (d, J = 7.83 Hz, 1H), 7.44 (s, 1H), 4.64-4.73 (m, 1H), 4.46-4.55 (m, 1H), 4.45 (s, 2H), 3.32-3.39 (m, 1H), 2.85 (td, J = 12.95, 2.40 Hz, 1H), 1.96-2.26 (m, 8H) | 5-{4-[1-(1-acetylpiperidin-4-yl)-1H-pyrazol-4-yl]-7-aminofuro[2,3-c]pyridin-2-yl}-2,3-dihydro-1H-isoindol-1-one | 0.88 (TOF: polar_3 min) | 457.17 |
| Ex. 99 | 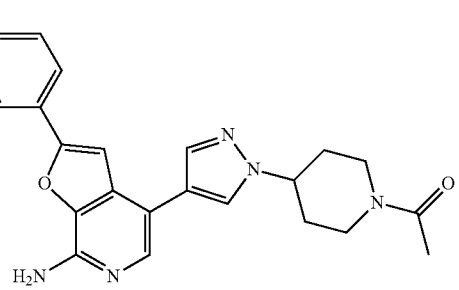<br>¹H NMR (400 MHz, CD₃OD): δ 1.98-2.19 (m, 2H), 2.20 (s, 3H), 2.22-2.29 (m, 2H), 2.88 (td, J = 12.95, 2.65 Hz, 1H), 3.35-3.41 (m, 1H), 4.09-4.17 (m, 1H), 4.55 (tt, J = 11.46, 4.20 Hz, 1H), 4.68-4.76 (m, 1H), 7.55-7.58 (m, 1 H), 7.83-7.87 (m, 1H), 7.89-7.93 (m, 2H), 7.95 (d, J = 0.51 Hz, 1H), 8.12 (s, 1H), 8.17 (s, 1H), 8.23 (s, 1H) | 1-(4-{4-[7-amino-2-(1H-indazol-6-yl)furo[2,3-c]pyridin-4-yl]-1H-pyrazol-1-yl}piperidin-1-yl)ethanone | 0.93 (TOF: polar_3 min) | 442.16 |
| Ex. 100 | 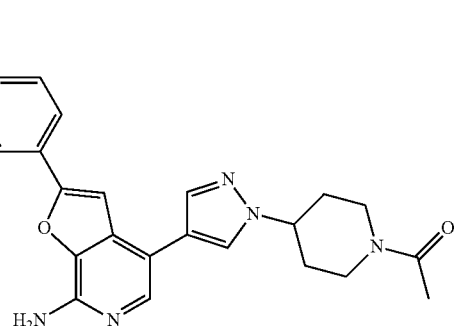<br>¹H NMR (400 MHz, CD₃OD): δ 8.60 (s, 1H), 8.54 (dd, J = 7.83, 1.52 Hz, 1H), 8.34 (s, 1H), 8.07 (s, 1H), 8.04 (s, 1H), 8.02 (d, J = 8.34 Hz, 1H), 7.86 (s, 1H), 4.72 (d, J = 13.64 Hz, 1H), 4.59 (tt, J = 11.46, 4.07 Hz, 1H), 4.14 (d, J = 12.13 Hz, 1H), 3.35-3.43 (m, 1H), 2.90 (td, 1H), 1.98-2.32 (m, 7H) | 5-{4-[1-(1-acetylpiperidin-4-yl)-1H-pyrazol-4-yl]-7-aminofuro[2,3-c]pyridin-2-yl}-1H-isoindole-1,3(2H)-dione | 0.92 (TOF: polar_3 min) | 471.15 |

-continued

| Ex # | Structure and ¹H NMR | Compound Name | HPLC t_R (min) | MS (ESI) [M+H]+ |
|---|---|---|---|---|
| Ex. 101 | 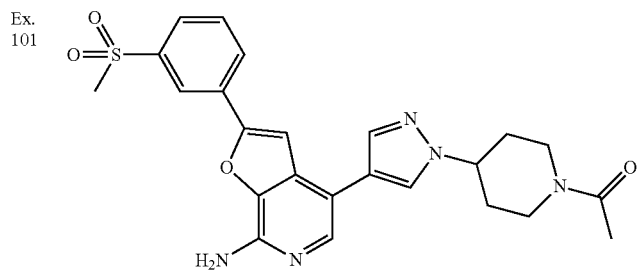<br>¹H NMR (400 MHz, DMSO-d₆): δ 8.61 (t, J = 1.6 Hz, 1H), 8.47-8.39 (m, 1H), 8.29 (s, 1H), 8.02 (s, 1H), 8.01-7.97 (m, 2H), 7.96 (s, 1H), 7.88-7.80 (m, 1H), 6.48 (s, 2H), 4.63-4.33 (m, 2H), 4.09 (q, J = 5.3 Hz, 1H), 3.95 (br. s., 1H), 3.33 (s, 3H), 3.29-3.18 (m, 1H), 2.82-2.65 (m, 1H), 2.19-2.03 (m, 4H), 2.04-1.70 (m, 2H) | 1-[4-(4-{7-amino-2-[3-(methylsulfonyl) phenyl]furo[2,3-c]pyridin-4-yl}-1H-pyrazol-1-yl)piperidin-1-yl]ethanone | 2.51 (ZQ3: polar_4 min) | 480.15 |
| Ex. 102 | 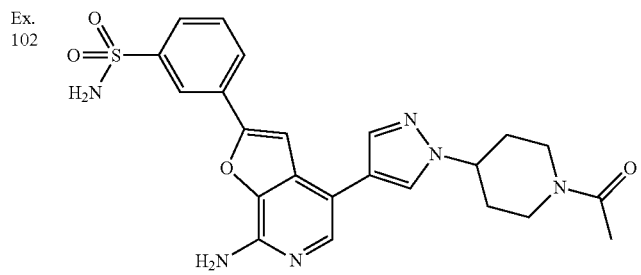<br>¹H NMR (400 MHz, DMSO-d₆): δ 8.51 (t, J = 1.6 Hz, 1H), 8.39-8.22 (m, 2H), 8.01 (s, 1H), 7.98 (d, J = 0.8 Hz, 1H), 7.93-7.87 (m, J = 1.2, 1.2, 8.2 Hz, 1H), 7.86 (s, 1H), 7.77 (t, J = 7.8 Hz, 1H), 7.48 (s, 2H), 6.42 (s, 2H), 4.62-4.33 (m, 2H), 4.14-3.86 (m, 1H), 3.30-3.13 (m, 1H), 2.91-2.61 (m, 1H), 2.24-2.03 (m, 5H), 2.04-1.91 (m, 1H), 1.91-1.75 (m, 1H) | 3-{4-[1-(1-acetylpiperidin-4-yl)-1H-pyrazol-4-yl]-7-aminofuro[2,3-c]pyridin-2-yl}benzene sulfonamide | 2.44 (ZQ3: polar_4 min) | 481.15 |
| Ex. 103 | 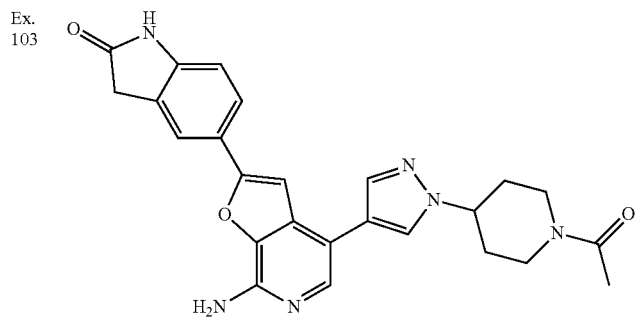 | 5-{4-[1-(1-acetylpiperidin-4-yl)-1H-pyrazol-4-yl]-7-aminofuro[2,3-c]pyridin-2-yl}-1,3-dihydro-2H-indol-2-one | 0.87 (TOF: polar_3 min) | 457.20 |

-continued

| Ex # | Structure and ¹H NMR | Compound Name | HPLC t_R (min) | MS (ESI) [M+H]⁺ |
|---|---|---|---|---|
| Ex. 104 | 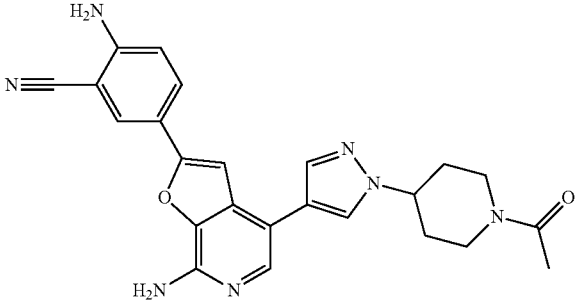 [SMILES: CC(=O)N1CCC(n2cc(-c3cnc(N)c4oc(-c5ccc(N)c(C#N)c5)cc34)cn2)CC1]  ¹H NMR (400 MHz, CD₃OD): δ 8.14 (s, 1H), 8.11 (d, J = 2.02 Hz, 1H), 7.99 (dd, J = 8.84, 2.02 Hz, 1H), 7.92 (s, 1H), 7.88 (s, 1H), 7.30 (s, 1H), 6.96 (d, 1H), 4.72 (d, J = 14.15 Hz, 1H), 4.50-4.59 (m, 1H), 4.13 (d, J = 14.40 Hz, 1H), 3.38-3.45 (m, 1H), 2.88 (td, J = 13.07, 3.16 Hz, 1H), 2.01-2.25 (m, 7H) | 5-{4-[1-(1-acetylpiperidin-4-yl)-1H-pyrazol-4-yl]-7-aminofuro[2,3-c]pyridin-2-yl}-2-aminobenzonitrile | 0.92 min (TOF: polar_3 min) | 442.16 |
| Ex. 105 | 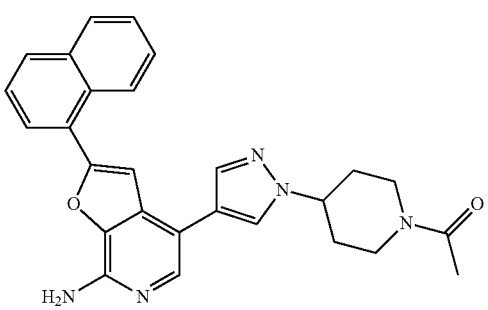 [SMILES: CC(=O)N1CCC(n2cc(-c3cnc(N)c4oc(-c5cccc6ccccc56)cc34)cn2)CC1]  ¹H NMR (400 MHz, CD₃OD): δ 8.45 (d, J = 8.6 Hz, 1H), 8.14 (s, 1H), 8.06-7.95 (m, 3H), 7.95-7.87 (m, 2H), 7.69-7.47 (m, 3H), 7.38 (s, 1H), 4.75-4.59 (m, 1H), 4.52 (tt, J = 4.1, 11.4 Hz, 1H), 4.17-4.00 (m, 1H), 3.31-3.26 (m, 1H), 2.84 (td, J = 2.8, 13.0 Hz, 1H), 2.27-2.13 (m, 5H), 2.13-1.92 (m, 2H) | 1-(4-{4-[7-amino-2-(naphthalen-1-yl)furo[2,3-c]pyridin-4-yl]-1H-pyrazol-1-yl}piperidin-1-yl)ethanone | 1.07 (TOF: polar_3 min) | 452.26 |
| Ex. 106 | 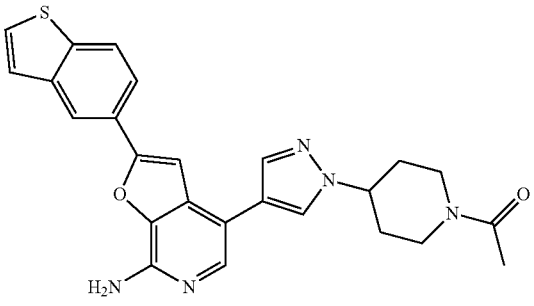  ¹H NMR (400 MHz, CD₃OD): δ 8.52 (t, J = 1.2 Hz, 1H), 8.14-8.8.14 (d, J = 0.8 Hz, 1H), 8.00-8.01 (d, J = 1.6 Hz, 2H), 7.91-7.91 (d, J = 0.8 Hz, 1H), 7.86 (s, 1H), 7.65-7.66 (d, J = 5.2 Hz, 1H), 7.506 (s, 1H), 7.46-7.48 (d, J = 6.4 Hz, 1H), 4.63-4.72 (m, 1H), 4.44-4.54 (m, 1H), 4.02-4.12 (m, 1H), 3.31-3.38 (m, 1H), 2.76-2.86 (m, 1H), 2.21-2.39 (m, 2H), 2.16 (s, 3H), 1.89-2.15 (m, 2H) | 1-(4-{4-[7-amino-2-(1-benzothiophen-5-yl)furo[2,3-c]pyridin-4-yl]-1H-pyrazol-1-yl}piperidin-1-yl)ethanone | 2.52 (ZQ3: polar_4 min) | 458.14 |

-continued

| Ex # | Structure and ¹H NMR | Compound Name | HPLC $t_R$ (min) | MS (ESI) [M+H]⁺ |
|---|---|---|---|---|
| Ex. 107 | 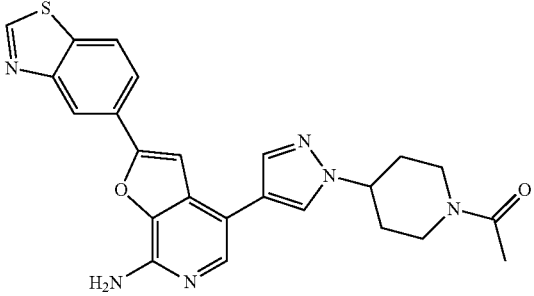 [SMILES: CC(=O)N1CCC(n2cc(-c3cnc(N)c4oc(-c5ccc6scnc6c5)cc34)cn2)CC1]  ¹H NMR (400 MHz, CD₃OD): δ 9.31 (s, 1H), 8.69 (s, 1H), 8.13 (m, 3H), 7.91 (s, 1H), 7.86 (s, 1H), 7.59 (s, 1H), 4.65-4.69 (m, 1H), 4.50-4.58 (m, 1H), 4.06-4.10 (m, 1H), 3.37-3.33 (m, 1H), 2.79-2.91 (m, 1H), 2.19-2.23 (m, 2H), 2.16 (s, 3H), 1.97-2.12 (m, 2H) | 1-(4-{4-[7-amino-2-(1,3-benzothiazol-5-yl)furo[2,3-c]pyridin-4-yl]-1H-pyrazol-1-yl}piperidin-1-yl)ethanone | 2.38 (ZQ3: polar_4 min) | 459.11 |
| Ex. 108 | 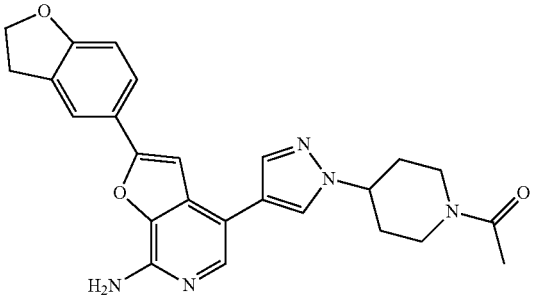  ¹H NMR (400 MHz, DMSO-d₆): δ 8.24 (s, 1H), 7.98 (d, J = 1.3 Hz, 1H), 7.97 (s, 1H), 7.94 (d, J = 0.5 Hz, 1H), 7.86 (dd, J = 1.8, 8.3 Hz, 1H), 7.52 (s, 1H), 6.93 (d, J = 8.3 Hz, 1H), 6.25 (s, 2H), 4.63 (t, J = 8.7 Hz, 2H), 4.57-4.37 (m, 2H), 3.95 (d, J = 1.8 Hz, 1H), 3.30-3.17 (m, 3H), 2.74 (s, 1H), 2.21-2.03 (m, 5H), 2.03-1.75 (m, 2H) | 1-(4-{4-[7-amino-2-(2,3-dihydro-1-benzofuran-5-yl)furo[2,3-c]pyridin-4-yl]-1H-pyrazol-1-yl}piperidin-1-yl)ethanone | 2.42 (ZQ3: polar_4 min) | 442.08 |
| Ex. 109 | 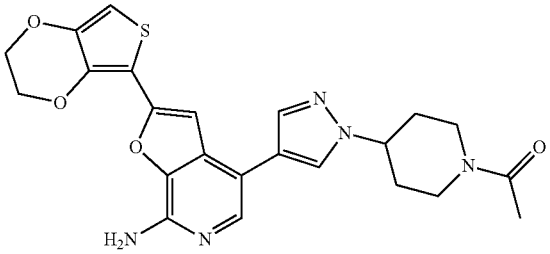 [SMILES: CC(=O)N1CCC(n2cc(-c3cnc(N)c4oc(-c5scc6c5OCCO6)cc34)cn2)CC1]  ¹H NMR (400 MHz, CD₃OD): δ 8.07 (s, 1H), 7.83 (S, 2H), 7.08 (s, 1H), 6.63 (s, 1H), 4.51-4.70 (m, 2H), 4.41-4.43 (m, 2H), 4.25-4.31 (m, 2H), 4.03-4.12 (m, 1H), 3.30-3.40 (m, 1H), 2.75-2.90 (m, 1H), 2.19-2.24 (m, 2H), 2.18 (s, 3H), 1.90-2.14 (m, 2H) | 1-(4-{4-[7-amino-2-(2,3-dihydrothieno[3,4-b][1,4]dioxin-5-yl)furo[2,3-c]pyridin-4-yl]-1H-pyrazol-1-yl}piperidin-1-yl)ethanone | 2.36 (ZQ3: polar_4 min) | 466.12 |

| Ex # | Structure and ¹H NMR | Compound Name | HPLC t_R (min) | MS (ESI) [M+H]⁺ |
|---|---|---|---|---|
| Ex. 110 | 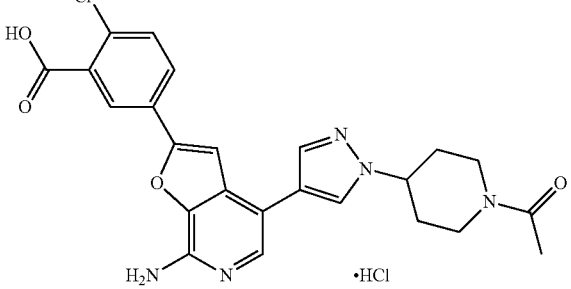<br>¹H NMR (400 MHz, DMSO-d₆): δ 8.45 (d, J = 1.5 Hz, 1H), 8.29 (s, 1H), 8.22 (dd, J = 1.8, 8.3 Hz, 1H), 8.00 (d, J = 8.1 Hz, 2H), 7.91 (s, 1H), 7.75 (d, J = 8.6 Hz, 1H), 6.56 (br. s., 2H), 4.61-4.30 (m, 2H), 3.94 (br. s., 1H), 3.24 (br. s., 1H), 2.74 (br. s., 1H), 2.26-1.63 (m, 7H) | 5-{4-[1-(1-acetylpiperidin-4-yl)-1H-pyrazol-4-yl]-7-aminofuro[2,3-c]pyridin-2-yl}-2-chlorobenzoic acid hydrochloride | 2.35 (ZQ3: polar_4 min) | 480.10 |
| Ex. 111 | 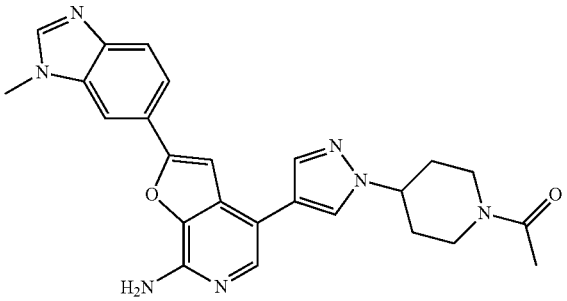 [SMILES: CC(=O)N1CCC(n2cc(-c3cnc(N)c4oc(-c5ccc6ncn(C)c6c5)cc34)cn2)CC1]<br>¹H NMR (400 MHz, CD₃OD): δ 8.20 (s, 1H), 8.13 (s, 1H), 8.06 (s, 1H), 7.90-7.92 (m, 1H), 7.84 (s, 1H), 7.78 (s, 1H), 7.66-7.68 (d, J = 8.4 Hz 1H), 7.428 (s, 1H), 4.03-4.63 (m, 1H), 4.50-4.82 (m, 1H), 3.96-4.03 (m, 1H), 3.90 (s, 3H), 3.28-3.30 (m, 1H), 2.70-2.81 (m, 1H), 2.10-2.20 (m, 2H), 2.09 (s, 3H), 1.85-2.05 (m, 2H) | 1-(4-{4-[7-amino-2-(1-methyl-1H-benzimidazol-6-yl)furo[2,3-c]pyridin-4-yl]-1H-pyrazol-1-yl}piperidin-1-yl)ethanone | 2.24 (ZQ3: polar_4 min | 456.16 |
| Ex. 112 | 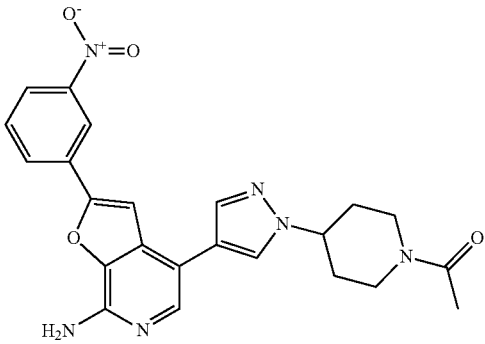 [SMILES: CC(=O)N1CCC(n2cc(-c3cnc(N)c4oc(-c5cccc([N+](=O)[O-])c5)cc34)cn2)CC1]<br>¹H NMR (400 MHz, CD₃OD): δ ppm 9.36 (s, 1H), 8.30 (d, J = 7.8 Hz, 1H), 8.20 (d, J = 8.1 Hz, 1H), 7.88 (s, 1H), 7.67-7.78 (m, 2H), 7.66 (s, 1H), 4.24 (tt, J = 11.7, 3.9 Hz, 1H), 3.56-3.80 (m, 1H), 2.05-2.28 (m, 4H), 1.86-2.03 (m, 2H), 1.42-1.60 (m, 2H) | 1-(4-{4-[7-amino-2-(3-nitrophenyl)furo[2,3-c]pyridin-4-yl]-1H-pyrazol-1-yl}piperidin-1-yl)ethanone | 2.47 (ZQ3: polar_4 min) | 447.05 |

| Ex # | Structure and ¹H NMR | Compound Name | HPLC t_R (min) | MS (ESI) [M+H]+ |
|---|---|---|---|---|
| Ex. 113 | 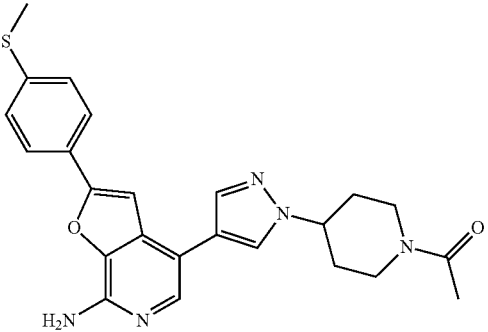 [SMILES: CSc1ccc(-c2cc3c(-c4cnn(C5CCN(C(C)=O)CC5)c4)cnc(N)c3o2)cc1]<br>¹H NMR (400 MHz, CD₃OD): δ 8.23-8.27 (dd, J = 6.2n Hz, J = 2 Hz, 2H), 8.25 (s, 1H), 8.06-8.08 (dd, J = 6.2 Hz, J = 2 Hz, 2H), 7.89-7.92 (d, J = 10 Hz, 2H), 7.72 (s, 1H), 4.62-4.80 (m, 1H), 4.47-4.59 (m, 1H), 4.03-4.13 (m, 1H), 3.33-3.43 (m, 1H), 3.17 (s, 3H), 2.78-2.89 (m, 1H), 2.18-2.22 (m, 2H), 2.17 (s, 3H), 1.94-1.16 (m, 2H) | 1-[4-(4-{7-amino-2-[4-(methylsulfanyl)phenyl]furo[2,3-c]pyridin-4-yl}-1H-pyrazol-1-yl)piperidin-1-yl]ethanone | 2.48 (ZQ3: polar_4 min) | 448.14 |
| Ex. 114 | 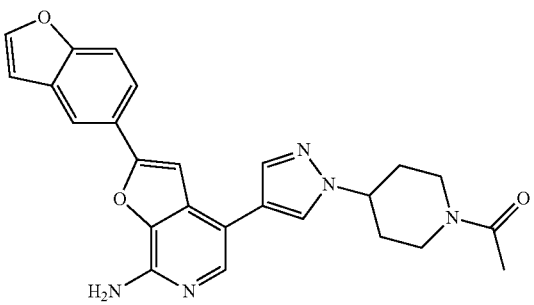<br>¹H NMR (400 MHz, CD₃OD): δ 8.33 (s, 1H), 8.15 (s, 1H), 8.00-8.02 (dd, J = 8.8 Hz, J = 1.6 Hz, 1H), 7.92 (s, 1H), 7.87 (s, 1H), 7.84 (s, 1H), 7.61-7.64 (d, J = 8.4 Hz, 1H), 7.44 (s, 1H), 6.94-6.95 (dd, J = 2.04 Hz J = 0.8 Hz, 1H), 4.50-4.68 (m, 3H), 4.08-4.12 (m, 1H), 3.34-3.38 (m, 1H), 2.22-2.28 (m, 2H), 2.21 (s, 3H), 1.92-2.20 (m, 2H) | 1-(4-{4-[7-amino-2-(1-benzofuran-5-yl)furo[2,3-c]pyridin-4-yl]-1H-pyrazol-1-yl}piperidin-1-yl)ethanone | 2.48 (ZQ3: polar_4 min) | 442.16 |
| Ex. 115 | 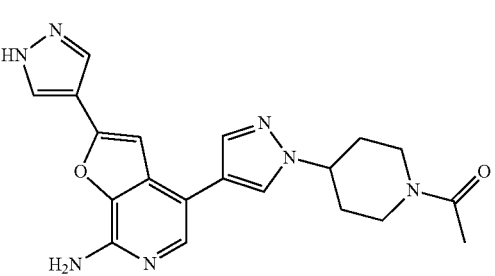 [SMILES: CC(=O)N1CCC(n2cc(-c3cnc(N)c4oc(-c5cn[nH]c5)cc34)cn2)CC1]<br>¹H NMR (400 MHz, CD₃OD): δ 8.28 (s, 1H), 8.12-8.12 (d, J = 0.8 Hz, 2H), 7.89-7.89 (d, J = 0.4 Hz, 1H), 7.84 (s, 1H), 7.20 (s, 1H), 4.53-4.70 (m, 1H), 4.48-4.55 (m, 1H), 4.05-4.15 (m, 1H), 3.33-3.34 (m, 1H), 2.82-2.91 (m, 1H), 2.21-2.31 (m, 2H), 2.16 (s, 3H), 1.91-2.15 (m, 2H) | 1-(4-{4-[7-amino-2-(1H-pyrazol-4-yl)furo[2,3-c]pyridin-4-yl]-1H-pyrazol-1-yl}piperidin-1-yl)ethanone | 2.19 (ZQ3: polar_4 min) | 392.18 |

| Ex # | Structure and ¹H NMR | Compound Name | HPLC t_R (min) | MS (ESI) [M+H]⁺ |
|---|---|---|---|---|
| Ex. 116 | ¹H NMR (400 MHz, CD₃OD): δ 8.05 (s, 1H), 7.82 (s, 1H), 7.77 (s, 1H), 7.20-7.32 (m, 4H), 6.74-6.77 (dd, J = 8 Hz, J = 1.6 Hz, 1H), 4.56-4.63 (m, 1H), 4.38-4.49 (m, 1H), 3.95-4.05 (m, 1H), 3.24-3.28 (m, 1H), 2.94 (s, 6H), 2.70-2.80 (m, 1H), 2.11-2.16 (m, 2H), 2.08 (s, 3H), 1.88-2.08 (m, 2H) | 1-[4-(4-{7-amino-2-[3-(dimethylamino)phenyl]furo[2,3-c]pyridin-4-yl-1H-pyrazol-1-yl)piperidin-1-yl]ethanone | 2.47 (ZQ3: polar_4 min) | 445.22 |
| Ex. 117 | ¹H NMR (400 MHz, CD₃OD): δ 8.02 (s, 1H), 7.79 (s, 1H), 7.75 (s, 1H), 7.47-7.49 (d, 1H), 7.43 (s, 1H), 7.24 (s, 1H), 6.83-6.85 (d, J = 8.4 Hz, 1H), 5.93 (s, 2H), 4.57-4.60 (m, 1H), 4.37-4.46 (m, 1H), 3.98-4.01 (d, J = 14 Hz, 1H), 3.24-3.26 (m, 1H), 2.70-2.78 (m, 1H), 2.06-2.10 (m, 2H), 2.02 (s, 3H), 1.97-2.02 (m, 1H), 1.85-1.96 (m, 1H) | 1-(4-{4-[7-amino-2-(1,3-benzodioxol-5-yl)furo[2,3-c]pyridin-4-yl]-1H-pyrazol-1-yl}piperidin-1-yl)ethanone | 2.41 (ZQ3: polar_4 min) | 446.13 |
| Ex. 118 | ¹H NMR (400 MHz, CD₃OD): δ 8.72 (d, J = 2 Hz, 1H), 8.12-8.13 (d, J = 0.8 Hz, 1H), 8.07-8.10 (m, 1H), 7.90 (d, J = 0.4 Hz, 1H), 7.84 (s, 1H), 7.26 (s, 1H), 6.89-6.91 (d, J = 9.2 Hz, 1H), 4.67-4.72 (m, 1H), 4.49-4.57 (m, 1H), 4.07-4.17 (m, 1H), 3.64-3.67 (m, 4H), 3.30-3.38 (m, 1H), 2.80-2.90 (m, 1H), 2.18-2.25 (m, 2H); 2.171 (s, 3H), 1.97 (m, 2H), 1.62-1.78 (m, 6H) | 1-[4-(4-{7-amino-2-[6-(piperidin-1-yl)pyridin-3-yl]furo[2,3-c]pyridin-4-yl}-1H-pyrazol-1-yl)piperidin-1-yl]ethanone | 2.47 (ZQ3: polar_4 min) | 486.20 |

-continued

| Ex # | Structure and ¹H NMR | Compound Name | HPLC $t_R$ (min) | MS (ESI) [M+H]⁺ |
|---|---|---|---|---|
| Ex. 119 | 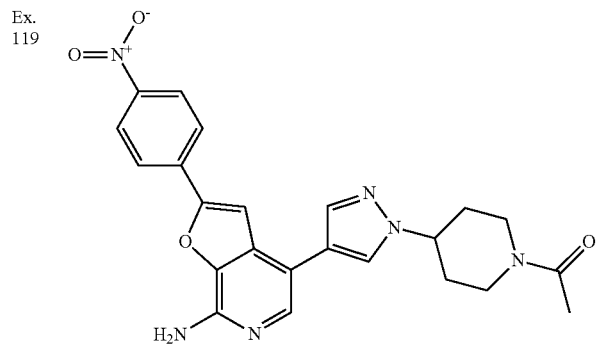<br>¹H NMR (400 MHz, DMSO-d₆): δ 9.35 (d, J = 1.6 Hz, 1H), 8.79-8.82 (dd, J = 8.4 Hz, J = 2 Hz, 1H), 8.54-8.56 (d, J = 8.4 Hz, 1H), 8.28 (s, 1H), 8.19 (s, 1H), 8.04 (s, 1H), 7.99 (s, 1H), 6.63 (s, 2H), 4.48-4.52 (m, 2H), 3.94-3.97 (m, 1H), 2.71-2.78 (m, 1H), 2.10-2.16 (m, 2H), 2.063 (s, 3H), 1.85-1.98 (m, 3H) | 1-(4-{4-[7-amino-2-(6-nitropyridin-3-yl)furo[2,3-c]pyridin-4-yl]-1H-pyrazol-1-yl}piperidin-1-yl)ethanone | 2.33 (ZQ3: polar_4 min) | 448.13 |
| Ex. 120 | 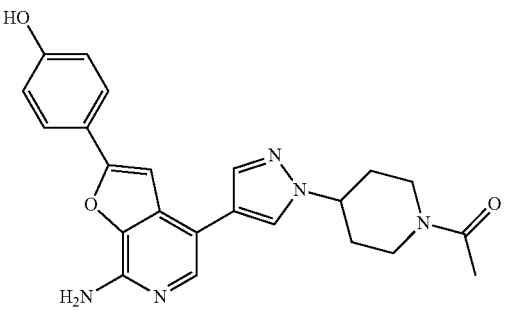 [SMILES: CC(=O)N1CCC(n2cc(-c3cnc(N)c4oc(-c5ccc(O)cc5)cc34)cn2)CC1]<br>¹H NMR (400 MHz, CD₃OD): δ 8.12 (d J = 0.8 Hz, 1H), 7.87-7.89 (m, 3H), 7.84 (s, 1H), 7.24 (s, 1H), 6.89-6.91 (dd, J = 6.8 Hz, J = 2 Hz, 2H), 4.65-4.71 (m, 1H), 4.47-4.56 (m, 1H), 4.07-4.13 (m, 1H), 4.33-4.17 (m, 1H), 2.80-2.90 (m, 1H), 2.18-2.24 (m, 2H), 2.17 (s, 3H), 1.98-2.12 (m, 2H)) | 1-(4-{4-[7-amino-2-(4-hydroxyphenyl)furo[2,3-c]pyridin-4-yl]-1H-pyrazol-1-yl}piperidin-1-yl)ethanone | 2.29 (ZQ3: polar_4 min) | 418.16 |

| Ex # | Structure and $^1$H NMR | Compound Name | HPLC $t_R$ (min) | MS (ESI) [M+H]$^+$ |
|---|---|---|---|---|
| Ex. 121 | 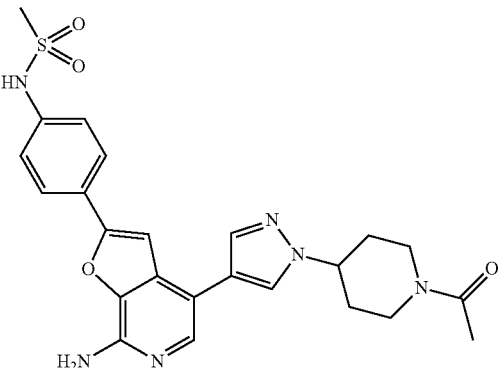<br>$^1$H NMR (400 MHz, CD$_3$OD): δ 8.12 (d, J = 0.8 Hz, 1H), 8.00-8.02 (d, J = 8.8 Hz, 2H), 7.90 (d, J = 0.8 Hz, 1H), 7.85 (s, 1H), 7.38 (t, J = 8.4 Hz, 3H), 4.65-4.71 (m, 1H), 4.48-4.56 (m, 1H), 4.06-4.15 (m, 1H), 3.33 (s, 1H), 3.02 (s, 3H), 2.80-2.90 (m, 1H), 2.18-2.25 (m, 2H), 2.17 (s, 3H), 1.98-2.15 (m, 2H) | N-(4-{4-[1-(1-acetylpiperidin-4-yl)-1H-pyrazol-4-yl]-7-aminofuro[2,3-c]pyridin-2-yl}phenyl)methanesulfonamide | 2.35 (ZQ3: polar_4 min) | 495.16 |
| Ex. 122 | 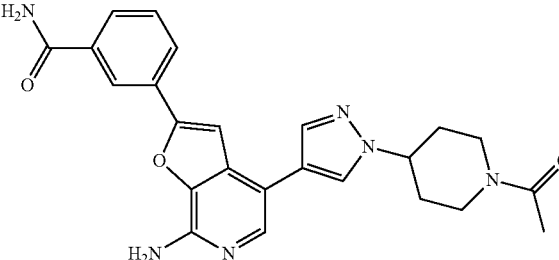<br>$^1$H NMR (400 MHz, CD$_3$OD): δ 8.54-8.55 (d, J = 1.6 Hz, 1H), 8.21-8.24 (m, 1H), 8.15 (d, J = 0.4 Hz, 1H), 7.92-7.95 (m, 2H), 7.89 (s, 1H), 7.62 (t, J = 8 Hz, 1H), 7.58 (s, 1H), 4.67-4.72 (m, 1H), 4.50-4.58 (m, 1H), 4.07-4.15 (m, 1H), 3.33-3.38 (m, 1H), 2.80-2.90 (m, 1H), 2.21-2.27 (m, 2H), 2.173 (s, 3H), 1.99-2.15 (m, 2H) | 3-{4-[1-(1-acetylpiperidin-4-yl)-1H-pyrazol-4-yl]-7-aminofuro[2,3-c]pyridin-2-yl}benzamide | 2.25 (ZQ3: polar_4 min) | 445.16 |
| Ex. 123 | 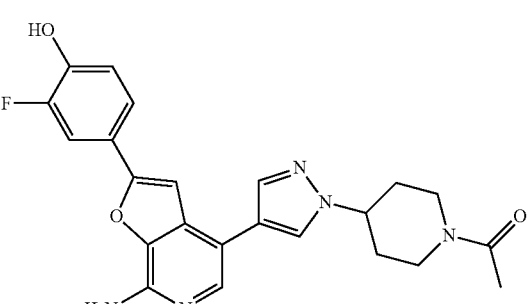<br>$^1$H NMR (400 MHz, CD$_3$OD): δ 8.12 (s, 1H), 7.90 (s, 1H), 7.85 (s, 1H), 7.76-7.80 (dd, J = 12 Hz, J = 12 Hz, 1H), 7.68-7.71 (m, 1H), 7.33 (s, 1H), 7.03 (t, J = 8.8 Hz, 1H), 4.67-4.71 (m, 1H), 4.49-4.63 (m, 1H), 4.08-4.12 (m, 1H), 3.33-3.37 (m, 1H), 2.82-2.88 (m, 1H), 2.20-2.27 (m, 2H), 2.17 (s, 3H), 1.90-2.11 (m, 2H) | 1-(4-{4-[7-amino-2-(3-fluoro-4-hydroxyphenyl)furo[2,3-c]pyridin-4-yl]-1H-pyrazol-1-yl}piperidin-1-yl)ethanone | 2.32 (ZQ3: polar_4 min) | 436.14 |

| Ex # | Structure and ¹H NMR | Compound Name | HPLC t_R (min) | MS (ESI) [M+H]⁺ |
|---|---|---|---|---|
| Ex. 124 | 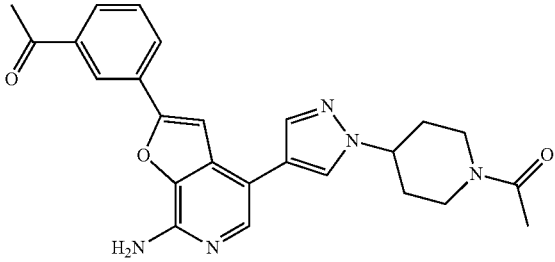 [SMILES: CC(=O)c1cccc(-c2cc3c(-c4cnn(C5CCN(C(C)=O)CC5)c4)cnc(N)c3o2)c1]<br>¹H NMR (400 MHz, CD₃OD): δ 8.55 (s, 1H), 8.20-8.22 (d, J = 7.6 Hz, 1H), 8.09 (s, 1H), 7.97-7.99 (d, J = 8 Hz, 1H), 7.86 (s, 1H), 7.82 (s, 1H), 7.58 (t, J = 8 Hz, 1H), 7.53 (s, 1H), 4.60-4.67 (m, 1H), 4.42-4.50 (m, 1H), 4.01-4.07 (m, 1H), 3.28-3.30 (m, 1H), 2.75-2.83 (m, 1H), 2.64 (s, 3H), 2.11-2.20 (m, 2H), 2.09 (s, 3H), 1.90-2.08 (m, 2H) | 1-(4-{4-[2-(3-acetylphenyl)-7-aminofuro[2,3-c]pyridin-4-yl]-1H-pyrazol-1-yl}piperidin-1-yl)ethanone | 2.38 (ZQ3: polar_4 min) | 444.15 |
| Ex. 125 | 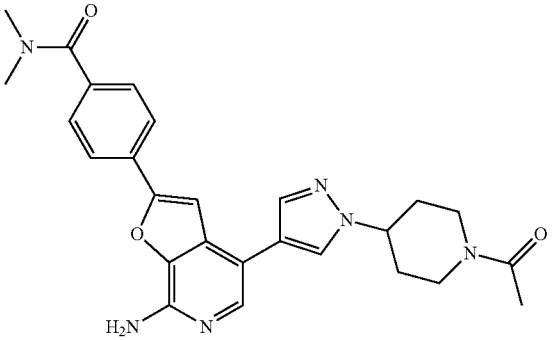 [SMILES: CC(=O)N1CCC(n2cc(-c3cnc(N)c4oc(-c5ccc(C(=O)N(C)C)cc5)cc34)cn2)CC1]<br>¹H NMR (400 MHz, CD₃OD): δ 8.06-8.10 (m, 3H), 7.86 (s, 1H), 7.79 (s, 1H), 7.55 (s, 1H), 7.49-7.51 (d, J = 8.4 Hz, 2H), 4.63-4.81 (m, 1H), 4.43-4.60 (m, 1H), 4.01-4.04 (m, 1H), 3.23-3.30 (m, 1H), 3.05 (s, 3H), 2.97 (s, 3H), 2.75-2.81 (m, 1H), 2.09-2.16 (m, 2H), 2.07 (s, 3H), 1.86-2.05 (m, 2H) | 4-{4-[1-(1-acetylpiperidin-4-yl)-1H-pyrazol-4-yl]-7-aminofuro[2,3-c]pyridin-2-yl}-N,N-dimethylbenzamide | 2.28 (ZQ3: polar_4 min) | 473.19 |
| Ex. 126 | 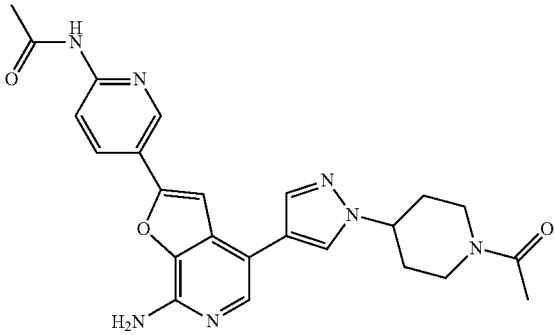 [SMILES: CC(=O)Nc1ccc(-c2cc3c(-c4cnn(C5CCN(C(C)=O)CC5)c4)cnc(N)c3o2)cn1]<br>¹H NMR (400 MHz, CD₃OD): δ 7.62-7.63 (d, J = 3.2 Hz, 1H), 7.02-7.04 (dd, J = 8.8 Hz, J = 2.4 Hz, 1H), 6.90-6.92 (m, 1H), 6.80 (s, 1H), 6.55-6.58 (d, J = 12.4 Hz, 2H), 6.18 (s, 1H), 3.30-3.37 (m, 1H), 3.15-3.23 (m, 1H), 2.71-2.79 (m, 1H), 2.01 (s, 3H), 1.97 (s, 3H), 1.47-1.58 (m, 1H), 0.80-0.90 (m, 3H), 0.52-0.63 (m, 2H) | N-(5-{4-[1-(1-acetylpiperidin-4-yl)-1H-pyrazol-4-yl]-7-aminofuro[2,3-c]pyridin-2-yl}pyridin-2-yl)acetamide | 2.25 (ZQ3: polar_4 min) | 460.13 |

| Ex # | Structure and ¹H NMR | Compound Name | HPLC $t_R$ (min) | MS (ESI) [M+H]⁺ |
|---|---|---|---|---|
| Ex. 127 | ¹H NMR (400 MHz, CD₃OD): δ 8.10-8.15 (m, 3H), 7.87-7.90 (d, J = 14 Hz, 2H), 7.57-7.60 (m, 2H), 7.45-7.48 (dd, J = 8 Hz, J = 1.6 Hz, 1H), 4.62-4.71 (m, 1H), 4.42-4.68 (m, 1H), 3.98-4.16 (m, 1H), 3.23-3.96 (m, 9H), 2.78-2.89 (m, 1H), 2.21-2.29 (m, 2H), 2.15 (s, 3H), 1.87-2.13 (m, 2H) | 1-[4-(4-{7-amino-2-[3-(morpholin-4-ylcarbonyl)phenyl]furo[2,3-c]pyridin-4-yl}-1H-pyrazol-1-yl)piperidin-1-yl]ethanone | 2.30 (ZQ3: polar_4 min) | 515.21 |
| Ex. 128 | ¹H NMR (400 MHz, CD₃OD): δ 8.14-8.15 (d, J = 0.8 Hz, 1H), 8.08-8.11 (d, J = 8.4 Hz, 2H), 7.92 (d, J = 0.8 Hz, 3H), 7.87 (s, 1H), 7.79 (s, 1H), 7.50 (s, 1H), 6.76 (d, J = 2 Hz, 1H), 4.68-4.72 (m, 1H), 4.50-4.58 (m, 1H), 4.07-4.15 (m, 1H), 3.37-3.39 (m, 1H), 2.80-2.90 (m, 1H), 2.21-2.27 (m, 2H), 2.173 (s, 3H), 1.99-2.15 (m, 2H) | 1-[4-(4-{7-amino-2-[4-(1H-pyrazol-5-yl)phenyl]furo[2,3-c]pyridin-4-yl}-1H-pyrazol-1-yl)piperidin-1-yl]ethanone | 2.35 (ZQ3: polar_4 min) | 468.17 |

| Ex # | Structure and ¹H NMR | Compound Name | HPLC $t_R$ (min) | MS (ESI) [M+H]+ |
|---|---|---|---|---|
| Ex. 129 | 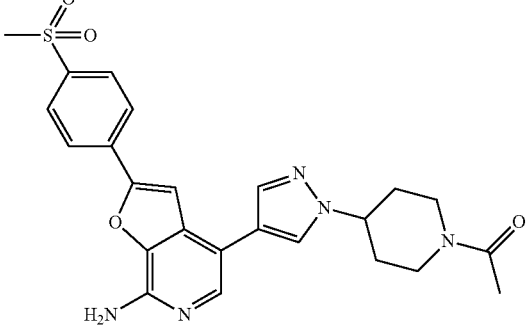<br>¹H NMR (400 MHz, CD₃OD): δ 8.12 (d, J = 0.8 Hz, 1H), 7.94-7.96 (d, J = 8.4 Hz, 2H), 7.90 (d, J = 0.4 Hz, 1H), 7.85 (s, 1H), 7.40 (s, 1H), 7.35-7.37 (d, J = 8.4 Hz, 2H), 4.62-4.70 (m, 1H), 4.48-4.57 (m, 1H), 4.07-4.11 (m, 1H), 3.30-3.32 (m, 1H), 2.79-2.91 (m, 1H), 2.221 (s, 3H), 2.18-2.25 (m, 2H), 2.179 (s, 3H), 1.97-2.15 (m, 2H) | 1-[4-(4-{7-amino-2-[4-(methylsulfonyl)phenyl]furo[2,3-c]pyridin-4-yl}-1H-pyrazol-1-yl)piperidin-1-yl]ethanone | 2.33 (ZQ3: polar_4 min) | 480.10 |
| Ex. 130 | 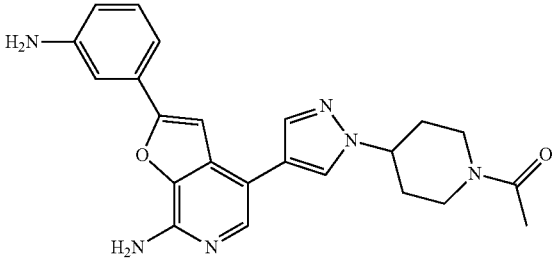 [SMILES: CC(=O)N1CCC(n2cc(-c3cnc(N)c4oc(-c5cccc(N)c5)cc34)cn2)CC1]<br>¹H NMR (400 MHz, CD₃OD): δ 8.12 (s, 1H), 7.89 (s, 1H), 7.85 (s, 1H), 7.33-7.36 (m, 3H), 7.22 (t, J = 8 Hz, 1H), 6.77-6.80 (dd, J = 8 Hz, J = 1.2 Hz, 1H), 4.67-4.71 (m, 1H), 4.49-4.60 (m, 1H), 4.08-4.11 (m, 1H), 3.33-3.37 (m, 1H), 2.81-2.89 (m, 1H), 2.17-2.25 (m, 2H), 2.15 (s, 3H), 1.88-2.08 (m, 2H) | 1-(4-{4-[7-amino-2-(3-aminophenyl)furo[2,3-c]pyridin-4-yl]-1H-pyrazol-1-yl}piperidin-1-yl)ethanone | 2.28 (ZQ3: polar_4 min) | 417.16 |
| Ex. 131 | 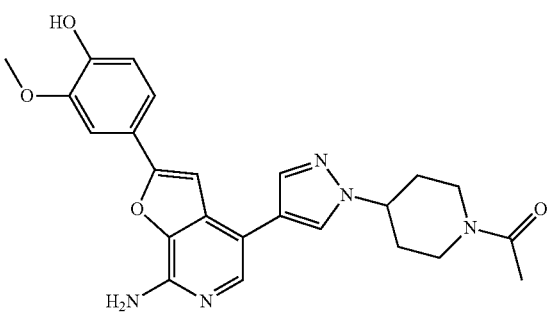 [SMILES: COc1cc(-c2cc3c(-c4cnn(C5CCN(C(C)=O)CC5)c4)cnc(N)c3o2)ccc1O]<br>¹H NMR (400 MHz, CD₃OD): δ 8.12-8.13 (d, J = 0.4 Hz, 1H), 7.91-7.91 (d, J = 0.8 Hz, 1H), 7.848 (s, 1H), 7.59-7.60 (d, J = 2 Hz, 1H), 7.52-7.54 (m, 1H), 7.29 (s, 1H), 6.90-6.92 (d, J = 8 Hz, 1H), 4.67-4.72 (m, 1H), 4.49-4.57 (m, 1H), 4.07-4.17 (m, 1H), 3.985 (s, 3H), 3.35-3.40 (m, 1H), 2.80-2.90 (m, 1H), 2.18-2.25 (m, 2H), 2.171 (s, 3H), 1.97-2.12 (m, 2H) | 1-(4-{4-[7-amino-2-(4-hydroxy-3-methoxyphenyl)furo[2,3-c]pyridin-4-yl]-1H-pyrazol-1-yl}piperidin-1-yl)ethanone | 2.31 (ZQ3: polar_4 min) | 448.16 |

| Ex # | Structure and ¹H NMR | Compound Name | HPLC $t_R$ (min) | MS (ESI) [M+H]⁺ |
|---|---|---|---|---|
| Ex. 132 | ¹H NMR (400 MHz, CD₃OD): δ 8.12 (s, 1H), 7.89 (s, 1H), 7.85 (s, 1H), 7.49-7.51 (d, J = 8 Hz, 1H), 7.41 (s, 1H), 7.37 (s, 1H), 7.30 (t, J = 8Hz, 1H), 6.84-8.87 (dd, J = 8.4 Hz, J = 0.8Hz, 1H), 4.66-4.69 (m, 1H), 4.46-4.60 (m, 1H), 4.07-4.10 (m, 1H), 3.33-3.35 (m, 1H), 2.80-2.88 (m, 1H), 2.19-2.22 (m, 2H), 2.16 (s, 3H), 1.95-2.10 (m, 2H) | 1-(4-{4-[7-amino-2-(3-hydroxyphenyl)furo[2,3-c]pyridin-4-yl]-1H-pyrazol-1-yl}piperidin-1-yl)ethanone | 2.31 (ZQ3: polar_4 min) | 418.16 |
| Ex. 133 | ¹H NMR (400 MHz, CD₃OD): δ 8.14 (s, 1H), 7.94 (t, J = 1.6 Hz, 1H), 7.91 (s, 1H), 7.87 (s, 1H), 7.79-7.80 (d, J = 0.8 Hz, 1H), 7.50 (s, 1H), 7.42 (t, J = 7.6 Hz, 1H), 7.33-7.34 (m, 1H), 4.67-4.72 (m, 1H), 4.47-4.57 (m, 1H), 4.05-4.15 (m, 1H), 3.30-3.38 (m, 1H), 2.80-2.88 (m, 1H), 2.57 (s, 3H), 2.18-2.24 (m, 2H), 2.19 (s, 3H), 1.97-2.12 (m, 2H) | 1-[4-(4-{7-amino-2-[3-(methylsulfanyl)phenyl]furo[2,3-c]pyridin-4-yl}-1H-pyrazol-1-yl)piperidin-1-yl]ethanone | 2.49 (ZQ3 : polar_4 min) | 448.14 |
| Ex. 134 | ¹H NMR (400 MHz, CD₃OD): δ 8.41 (t, J = 1.6 Hz, 1H), 8.34-8.36 (d, J = 6.4 Hz, 1H), 8.17 (s, 1H), 7.93 (s, 1H), 7.89 (s, 1H), 7.82-7.83 (m, 1H), 7.76-7.78 (d, J = 8 Hz, 1H), 7.69 (s, 1H), 4.63-4.70 (m, 1H), 4.46-4.60 (m, 1H), 4.05-4.16 (m, 1H), 3.32-3.36 (m, 1H), 2.82-2.93 (m, 1H), 2.75 (s, 6H), 2.18-2.25 (m, 2H), 2.17 (s, 3H), 1.93-2.09 (m, 2H) | 3-{4-[1-(1-acetylpiperidin-4-yl)-1H-pyrazol-4-yl]-7-aminofuro[2,3-c]pyridin-2-yl}-N,N-dimethylbenzenesulfonamide | 2.42 (ZQ3: polar_4 min) | 509.13 |

-continued

| Ex # | Structure and ¹H NMR | Compound Name | HPLC $t_R$ (min) | MS (ESI) [M+H]⁺ |
|---|---|---|---|---|
| Ex. 135 | 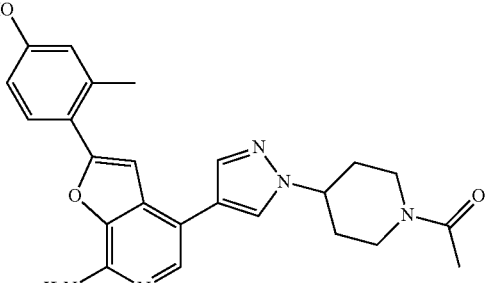<br>¹H NMR (400 MHz, CD₃OD): δ 8.09 (d, J = 0.4Hz, 1H), 7.86-7.87 (d, J = 0.4 Hz, 1H), 7.84 (s, 1H), 7.72-7.75 (d, J = 8.4 Hz, 1H), 7.01 (s, 1H), 6.74-6.74 (m, 2H), 4.59-4.73 (m, 1H), 4.47-4.56 (m, 1H), 4.05-4.19 (m, 1H), 3.40-3.41 (m, 1H), 2.77-2.89 (m, 1H), 2.50 (s, 3H), 2.22-2.29 (m, 2H), 2.10 (s, 3H), 1.93-2.09 (m, 2H) | 1-(4-{4-[7-amino-2-(4-hydroxy-2-methylphenyl)furo[2,3-c]pyridin-4-yl]-1H-pyrazol-1-yl}piperidin-1-yl)ethanone | 2.58 (ZQ3: polar_4 min) | 432.12 |
| Ex. 136 | 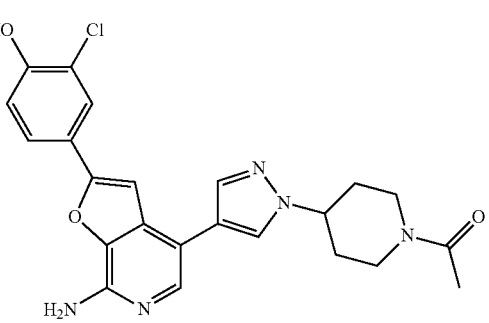<br>¹H NMR (400 MHz, CD₃OD): δ 8.11 (s, 1H), 8.01-8.02 (d, J = 2 Hz, 1H), 7.88 (s, 1H), 7.84 (s, 1H), 7.78-7.80 (m, 1H), 7.32 (s, 1H), 7.00-7.02 (d, J = 8.4 Hz, 1H), 4.65-4.70 (m, 1H), 4.48-4.52 (m, 1H), 4.06-4.12 (m, 1H), 3.31-3.36 (m, 1H), 2.77-2.88 (m, 1H), 2.18-2.23 (m, 2H), 2.156 (s, 3H), 1.95-2.11 (m, 2H) | 1-(4-{4-[7-amino-2-(3-chloro-4-hydroxyphenyl)furo[2,3-c]pyridin-4-yl]-1H-pyrazol-1-yl}piperidin-1-yl)ethanone | 2.59 (ZQ3: polar_4 min) | 452.04 |
| Ex. 137 | 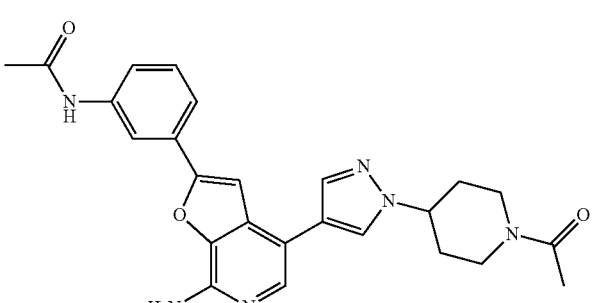<br>¹H NMR (400 MHz, CD₃OD): δ 8.14 (s, 1H), 7.97-8.00 (d, J = 8.8 Hz, 2H), 7.90 (s, 1H), 7.83 (s, 1H), 7.70-7.73 (d, J = 8.8 Hz, 2H), 7.41 (s, 1H), 4.62-4.70 (m, 1H), 4.48-4.53 (m, 1H), 4.05-4.11 (m, 1H), 3.30-3.35 (m, 1H), 2.80-2.90 (m, 1H), 2.17-2.25 (m, 2H), 2.16 (s, 3H), 2.15 (s, 3H), 1.95-2.12 (m, 2H) | N-(3-{4-[1-(1-acetylpiperidin-4-yl)1H-pyrazol-4-yl]-7-aminofuro[2,3-c]pyridin-2-yl}phenyl)acetamide | 2.52 (ZQ3: polar_4 min) | 459.14 |

-continued

| Ex # | Structure and ¹H NMR | Compound Name | HPLC $t_R$ (min) | MS (ESI) [M+H]⁺ |
|---|---|---|---|---|
| Ex. 138 | 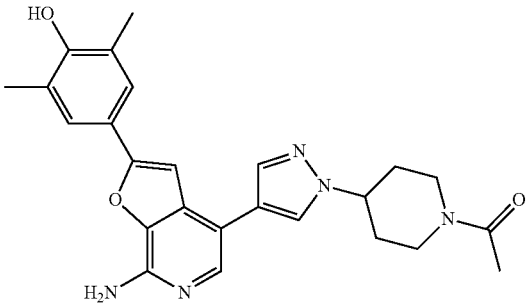 [SMILES: CC(=O)N1CCC(n2cc(-c3cnc(N)c4oc(-c5cc(C)c(O)c(C)c5)cc34)cn2)CC1]<br><br>¹H NMR (400 MHz, DMSO-d₆): δ 8.77 (s, 1H), 8.24 (s, 1H), 7.94 (d, J = 3.2 Hz, 2H), 7.67 (s, 2H), 7.43 (s, 1H), 6.23 (s, 2H), 4.40-4.51 (m, 2H), 3.90-3.95 (m, 1H), 3.19-3.25 (m, 1H), 2.67-2.76 (m, 1H), 2.24 (s, 6H), 2.05-2.12 (m, 5H), 1.78-2.01 (m, 2H) | 1-(4-{4-[7-amino-2-(4-hydroxy-3,5-dimethylphenyl)furo[2,3-c]pyridin-4-yl]-1H-pyrazol-1-yl}piperidin-1-yl)ethanone | 2.60 (ZQ3: polar_4 min) | 446.11 |
| Ex. 139 | 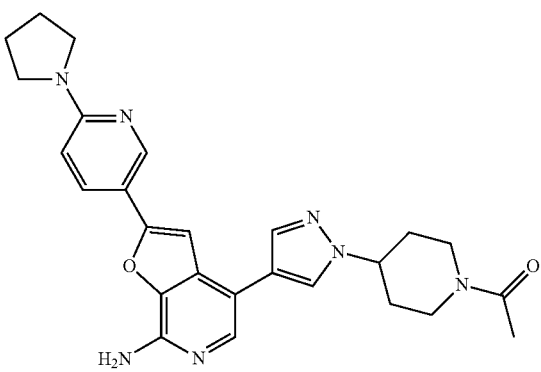 [SMILES: CC(=O)N1CCC(n2cc(-c3cnc(N)c4oc(-c5ccc(N6CCCC6)nc5)cc34)cn2)CC1]<br><br>¹H NMR (400 MHz, CD₃OD): δ 8.68 (dd, J = 2.4 Hz, J = 0.4 Hz, 1H), 8.12-8.13 (d, J = 0.4 Hz, 1H), 8.08-8.11 (dd, J = 8.8 Hz, J = 2.4 Hz, 1H), 7.90 (d, J = 0.8 Hz, 1H), 7.84 (s, 1H), 7.24 (s, 1H), 6.61-6.63 (d, J = 8.8 Hz, 1H), 4.52-4.65 (m, 1H), 4.47-4.59 (m, 1H), 4.01-4.18 (m, 1H), 3.52-3.54 (m, 5H), 3.31 (m, 1H), 2.80-2.90 (m, 1H), 2.16-2.25 (m, 5H), 2.05-2.08 (m, 3H), 1.98-2.05 (m, 2H) | 1-[4-(4-{7-amino-2-[6-(pyrrolidin-1-yl)pyridin-3-yl]furo[2,3-c]pyridin-4-yl}-1H-pyrazol-1-yl)piperidin-1-yl]ethanone | 2.22 (ZQ3: polar_4 min) | 472.15 |

-continued

| Ex # | Structure and ¹H NMR | Compound Name | HPLC t_R (min) | MS (ESI) [M+H]+ |
|---|---|---|---|---|
| Ex. 140 | ¹H NMR (400 MHz, CD₃OD): δ 8.07 (d, J = 0.8Hz, 1H), 7.86-7.87 (d, J = 0.84 Hz, 1H), 7.80 (s, 1H), 7.61-7.67 (m, 2H), 7.10 (s, 1H), 6.75-6.78 (d, J = 8.4 Hz, 1H), 4.62-4.70 (m, 1H), 4.48-4.57 (m, 1H), 4.07-4.25 (m, 1H), 3.30-3.42 (m, 1H), 2.79-2.91 (m, 1H), 2.53 (s, 3H), 2.18-2.25 (m, 2H), 2.167 (s, 3H), 1.91-2.15 (m, 2H) | 1-(4-{4-[7-amino-2-(4-amino-3-methylphenyl)furo[2,3-c]pyridin-4-yl]-1H-pyrazol-1-yl}piperidin-1-yl)ethanone | 2.22 (ZQ3: polar_4 min) | 431.1 |
| Ex. 141 | ¹H NMR (400 MHz, CD₃OD): δ 8.10 (s, 1H), 7.97-8.00 (dd, J = 7.6 Hz, J = 1.2 Hz, 1H), 7.88 (t, J = 1.2 Hz, 2H), 7.58-7.60 (m, 1H), 7.47-7.48 (m, 1H), 7.39-7.40 (m, 1H), 7.30 (s, 1H), 4.60-4.71 (m, 1H), 4.48-4.56 (m, 1H), 4.06-4.13 (m, 1H), 3.32-3.40 (m, 1H), 2.80-2.90 (m, 1H), 2.18-2.25 (m, 1H), 2.181 (s, 3H), 2.160 (s, 3H), 1.85-2.11 (m, 3H) | N-(2-{4-[1-(1-acetylpiperidin-4-yl)-1H-pyrazol-4-yl]-7-aminofuro[2,3-c]pyridin-2-yl}phenyl)acetamide | 2.15 (ZQ3: polar_4 min) | 459.13 |
| Ex. 142 | ¹H NMR (400 MHz, CD₃OD): δ 8.02 (s, 1H), 7.77 (s, 1H), 7.71 (s, 1H), 6.79 (s, 1H), 6.73-6.75 (m, 1H), 4.56-4.63 (m, 1H), 4.42-4.52 (m, 1H), 3.99-4.02 (m, 1H), 3.26-3.28 (m, 1H), 2.72-2.78 (m, 1H), 2.39 (m, 2H), 2.22-2.23 (m, 2H), 2.08-2.13 (m, 5H), 1.76-2.05 (m, 2H), 1.72-1.76 (m, 2H), 1.65-1.67 (m, 2H) | 1-(4-{4-[7-amino-2-(cyclohex-1-en-1-yl)furo[2,3-c]pyridin-4-yl]-1H-pyrazol-1-yl}piperidin-1-yl)ethanone | 2.34 (ZQ3: polar_4 min) | 406.14 |

-continued

| Ex # | Structure and $^1$H NMR | Compound Name | HPLC $t_R$ (min) | MS (ESI) [M+H]$^+$ |
|---|---|---|---|---|
| Ex. 143 | 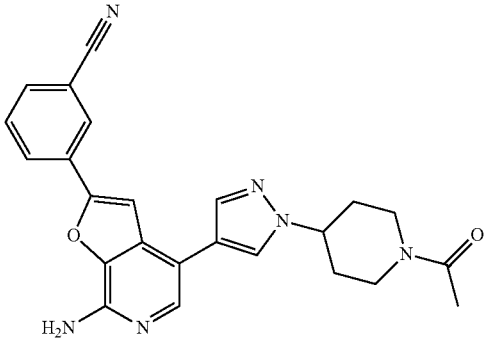 [SMILES: CC(=O)N1CCC(n2cc(-c3cnc(N)c4oc(-c5cccc(C#N)c5)cc34)cn2)CC1] $^1$H NMR (400 MHz, CD$_3$OD): 8.47 (t, J = 1.6 Hz, 1H), 8.34-8.36 (d, J = 8 Hz, 1H), 8.17 (s, 1H), 7.94 (d, J = 0.8 Hz, 1H), 7.89 (s, 1H), 7.79-7.81 (m, 1H), 7.69-7.73 (m, 2H), 4.67-4.72 (m, 1H), 4.50-4.58 (m, 1H), 4.08-4.13 (m, 1H), 3.31-3.38 (m, 1H), 2.80-2.90 (m, 1H), 2.20-2.26 (m, 2H), 2.175 (s, 3H), 1.96-2.12 (m, 2H) | 3-{4-[1-(1-acetylpiperidin-4-yl)-1H-pyrazol-4-yl]-7-aminofuro[2,3-c]pyridin-2-yl}benzonitrile | 2.29 (ZQ3: polar_4 min) | 427.08 |
| Ex. 144 | 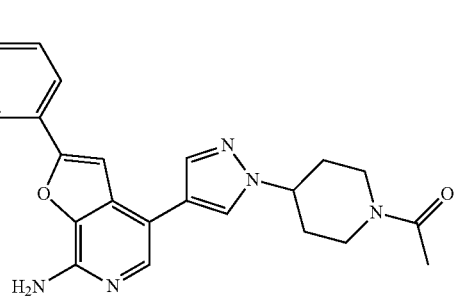 $^1$H NMR (400 MHz, CD$_3$OD): δ 8.14 (s, 1H), 7.90-7.91 (d, J = 0.8 Hz, 1H), 7.87 (s, 1H), 7.71-7.72 (m, 1H), 7.51-7.52 (d, J = 1.6 Hz, 1H), 7.43 (s, 1H), 7.37-7.39 (m, 1H), 4.63-4.72 (m, 1H), 4.49-4.57 (m, 1H), 4.07-4.15 (m, 1H), 3.31-3.35 (m, 3H), 2.78-2.90 (m, 1H), 2.18-2.25 (m, 2H), 2.17 (s, 3H), 1.95-2.20 (m, 2H) | 6-{4-[1-(1-acetylpiperidin-4-yl)-1H-pyrazol-4-yl]-7-aminofuro[2,3-c]pyridin-2-yl}-1,3-dihydro-2H-indol-2-one | 2.16 (ZQ3: polar_4 min) | 457.09 |
| Ex. 145 | 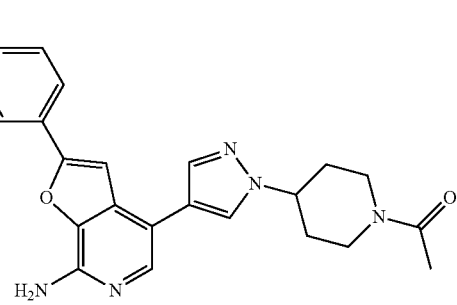 $^1$H NMR (400 MHz, CD$_3$OD): δ 8.29 (s, 1H), 8.23 (s, 1H), 8.16 (s, 1H), 7.92 (s, 1H), 7.87 (s, 1H), 7.82 (d, J = 0.8 Hz, 1H), 7.74 (d, J = 1.2 Hz, 1H), 7.51 (s, 1H), 4.63-4.72 (m, 1H), 4.43-4.59 (m, 1H), 4.24 (s, 3H), 4.05-4.15 (m, 1H), 3.31-3.41 (m, 1H), 2.78-2.90 (m, 1H), 2.18-2.26 (m, 2H), 2.17 (s, 3H), 1.93-2.16 (m, 2H) | 1-(4-{4-[7-amino-2-(2-methyl-2H-indazol-5-yl)furo[2,3-c]pyridin-4-yl]-1H-pyrazol-1-yl}piperidin-1-yl)ethanone | 2.21 (ZQ3: polar_4 min) | 456.14 |

| Ex # | Structure and $^1$H NMR | Compound Name | HPLC $t_R$ (min) | MS (ESI) [M+H]$^+$ |
|---|---|---|---|---|
| Ex. 146 | 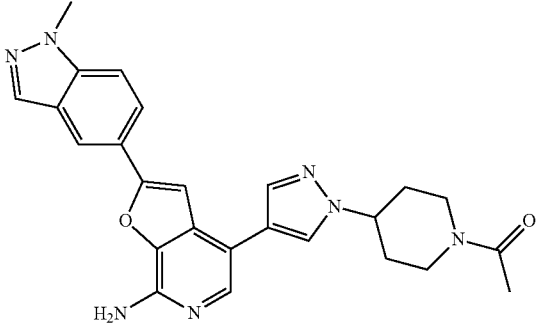 [SMILES: CC(=O)N1CCC(n2cc(-c3cnc(N)c4oc(-c5ccc6c(cnn6C)c5)cc34)cn2)CC1]<br>$^1$H NMR (400 MHz, CD$_3$OD): δ 8.41 (s, 1H), 8.09 (s, 1H), 8.04-8.06 (m, 2H), 7.87 (s, 1H), 7.81 (s, 1H), 7.61-7.63 (d, J = 8.8 Hz, 1H), 7.40 (s, 1H), 4.62-4.66 (m, 1H), 4.45-4.49 (m, 1H), 4.05 (m, 4H), 3.29-3.32 (m, 1H), 2.77-2.83 (m, 1H), 2.10-2.16 (m, 5H), 1.94-2.08 (m, 2H) | 1-(4-{4-[7-amino-2-(1-methyl-1H-indazol-5-yl)furo[2,3-c]pyridin-4-yl]-1H-pyrazol-1-yl}piperidin-1-yl)ethanone | 2.25 (ZQ3: polar_4 min) | 456.12 |
| Ex. 147 | 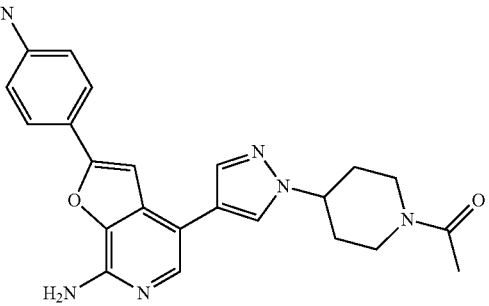<br>$^1$H NMR (400 MHz, CD$_3$OD): δ 8.59 (dd, J = 2.4 Hz, J = 0.8 Hz, 1H), 8.12 (d, J = 0.8 Hz, 1H), 8.04-8.07 (dd, J = 8.8 Hz, J = 2.4 Hz, 1H), 7.90 (d, J = 0.8 Hz, 1H), 7.85 (s, 1H), 7.27 (s, 1H), 6.67-6.70 (dd, J = 8.8 Hz, J = 0.8 Hz, 1H), 4.62-4.72 (m, 1H), 4.48-4.56 (m, 1H), 4.05-4.12 (m, 1H), 3.30-3.35 (m, 1H), 2.80-2.90 (m, 1H), 2.17-2.25 (m, 2H), 2.17 (s, 3H), 1.95-2.12 (m, 2H) | 1-(4-{4-[7-amino-2-(6-aminopyridin-3-yl)furo[2,3-c]pyridin-4-yl]-1H-pyrazol-1-yl}piperidin-1-yl)ethanone | 2.15 (ZQ3: polar_4 min) | 418.14 |
| Ex. 148 | 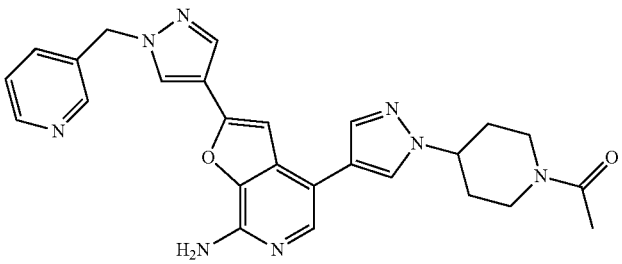 [SMILES: CC(=O)N1CCC(n2cc(-c3cnc(N)c4oc(-c5cnn(Cc6cccnc6)c5)cc34)cn2)CC1]<br>$^1$H NMR (400 MHz, CD$_3$OD): δ 8.47 (s, 1H), 8.42-8.44 (dd, J = 4.8 Hz, J = 1.24 Hz, 1H), 8.29 (s, 1H), 8.02 (s, 2H), 7.80 (s, 1H), 7.76 (s, 1H), 7.72-7.74 (d, J = 8 Hz, 1H), 7.36-7.39 (dd, J = 8 Hz, J = 5.2 Hz, 1H), 7.11 (s, 1H), 5.42 (s, 2H), 4.54- 4.62 (m, 1H), 4.38-4.49 (m, 1H), 3.83-4.06 (m, 1H), 3.27-3.29 (m, 1H), 2.70-2.83 (m, 1H), 2.11- 2.20 (m, 2H), 2.10 (s, 3H), 1.80-2.08 (m, 2H) | 1-[4-(4-{7-amino-2-[1-(pyridin-3-ylmethyl)-1H-pyrazol-4-yl]furo[2,3-c]pyridin-4-yl}-1H-pyrazol-1-yl)piperidin-1-yl]ethanone | 2.24 (ZQ3: polar_4 min) | 483.10 |

-continued

| Ex # | Structure and ¹H NMR | Compound Name | HPLC t_R (min) | MS (ESI) [M+H]+ |
|---|---|---|---|---|
| Ex. 149 | 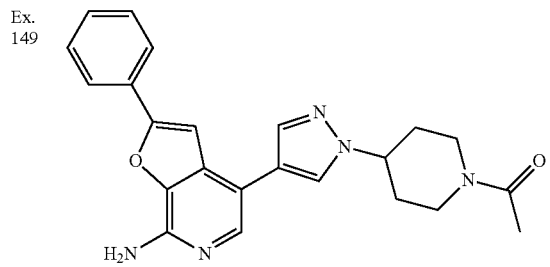  ¹H NMR (400 MHz, DMSO-d₆): δ 8.27 (s, 1H), 8.18-8.04 (m, 2H), 7.99 (s, 1H), 7.96 (s, 1H), 7.72 (s, 1H), 7.59-7.50 (m, 2H), 7.51-7.42 (m, 1H), 6.35 (s, 2H), 4.64-4.31 (m, 2H), 4.09-3.84 (m, J = 13.9 Hz, 1H), 3.29-3.16 (m, 1H), 2.75 (td, J = 2.3, 12.8 Hz, 1H), 2.24-2.02 (m, 5H), 2.04-1.75 (m, 2H) | 1-{4-[4-(7-amino-2-phenylfuro[2,3-c]pyridin-4-yl)-1H-pyrazol-1-yl]piperidin-1-yl}ethanone | 2.40 (ZQ3: polar_4 min) | 402.09 |
| Ex. 150 | 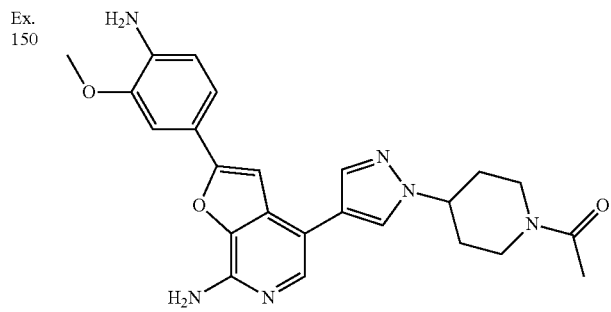  ¹H NMR (400 MHz, DMSO-d₆): δ 8.22 (s, 1H), 7.99-7.86 (m, 2H), 7.49 (d, J = 1.8 Hz, 1H), 7.46 (dd, J = 1.8, 8.1 Hz, 1H), 7.36 (s, 1H), 6.73 (d, J = 8.3 Hz, 1H), 6.20 (s, 2H), 5.24 (s, 2H), 4.59-4.35 (m, 2H), 4.05-3.87 (m, 4H), 3.28-3.14 (m, 1H), 2.82-2.66 (m, 1H), 2.06 (s, 5H), 2.04-1.91 (m, 1H), 1.90-1.77 (m, 1H) | 1-(4-{4-[7-amino-2-(4-amino-3-methoxyphenyl)furo[2,3-c]pyridin-4-yl]-1H-pyrazol-1-yl}piperidin-1-yl)ethanone | 2.31 (ZQ3: polar_4 min) | 447.10 |
| Ex. 151 | 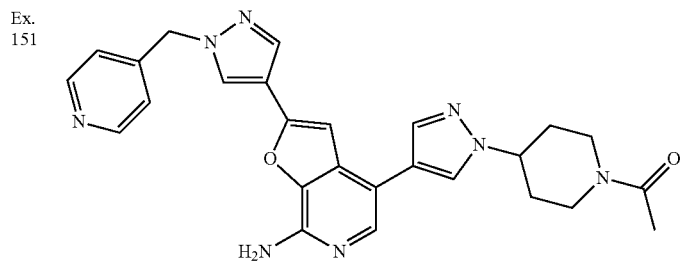  ¹H NMR (400 MHz, CD₃OD): δ 8.51-8.53 (dd, J = 4.8 Hz, J = 2 Hz, 2H), 8.36 (s, 1H), 8.13-8.14 (d, J = 0.4 Hz, 1H), 8.10 (s, 1H), 7.88 (s, 1H), 7.854 (s, 1H), 7.26-7.27 (dd, J = 4.4 Hz, J = 1.6 Hz, 2H), 7.20 (s, 1H), 5.53 (s, 2H), 4.65-4.72 (m, 1H), 4.47-4.58 (m, 1H), 4.12-4.03 (m, 1H), 3.36 (s, 1H), 2.84-2.85 (m, 1H), 2.13-2.26 (m, 2H), 2.12 (s, 3H), 1.88-2.11 (m, 2H) | 1-[4-(4-{7-amino-2-[1-(pyridin-4-ylmethyl)-1H-pyrazol-4-yl]furo[2,3-c]pyridin-4-yl}-1H-pyrazol-1-yl)piperidin-1-yl]ethanone | 2.23 (ZQ3: polar_4 min) | 483.12 |

-continued

| Ex # | Structure and ¹H NMR | Compound Name | HPLC t$_R$ (min) | MS (ESI) [M+H]$^+$ |
|---|---|---|---|---|
| Ex. 152 | 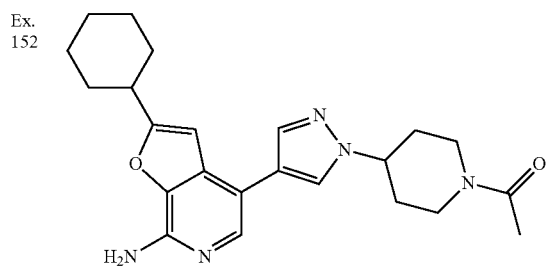<br>¹H NMR (400 MHz, CD$_3$OD): δ 8.06-8.08 (d, J = 8.4 Hz, 1H), 7.83-7.85 (m, 1H), 7.79-7.80 (d, J = 3.2 Hz, 1H), 6.70-6.84 (m, 1H), 4.65-4.70 (m, 1H), 4.47-4.53 (m, 1H), 4.05-4.12 (m, 1H), 3.35-3.40 (m, 1H), 2.80-2.90 (m, 2H), 2.13-2.20 (m, 7H), 1.97-2.10 (m, 3H), 1.67-1.90 (m, 3H), 1.28-1.62 (m, 4H) | 1-{4-[4-(7-amino-2-cyclohexylfuro[2,3-c]pyridin-4-yl)-1H-pyrazol-1-yl]piperidin-1-yl}ethanone | 2.45 (ZQ3: polar_4 min) | 408.13 |
| Ex. 153 | 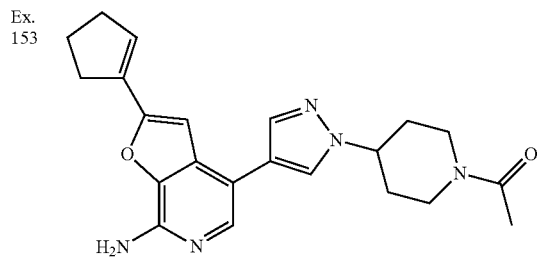<br>¹H NMR (400 MHz, CD$_3$OD): δ 8.08 (d, J = 0.4 Hz, 1H), 7.85 (d, J = 0.8 Hz, 1H), 7.82 (s, 1H), 6.85 (s, 1H), 6.59 (t, J = 2 Hz, 1H), 4.65-4.70 (m, 1H), 4.49-4.52 (m, 1H), 4.15-4.22 (m, 1H), 3.30-3.36 (m, 1H), 2.77-2.84 (m, 4H), 2.61-2.64 (m, 2H), 2.18-2.22 (m, 5H), 2.07-2.14 (m, 2H), 1.90-2.05 (m, 1H) | 1-(4-{4-[7-amino-2-(cyclopent-1-en-1-yl)furo[2,3-c]pyridin-4-yl]-1H-pyrazol-1-yl}piperidin-1-yl)ethanone | 2.39 (ZQ3: polar_4 min) | 392.14 |
| Ex. 154 | 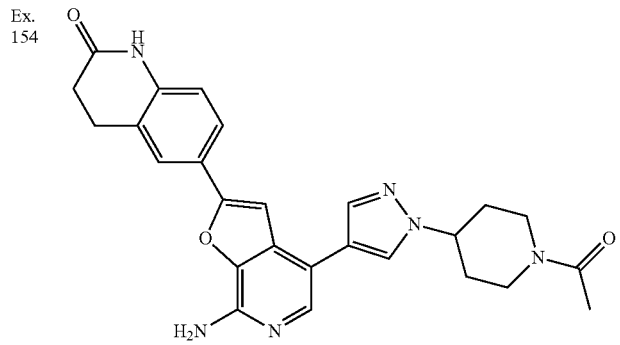<br>¹H NMR (400 MHz, CD$_3$OD): δ 8.13 (d, J = 0.4 Hz, 1H), 7.90 (t, J = 1.6 Hz, 2H), 7.85-7.87 (m, 2H), 7.37 (s, 1H), 6.98-7.00 (d, J = 8 Hz, 1H), 4.68-4.72 (m, 1H), 4.50-4.58 (m, 1H), 4.07-4.15 (m, 1H), 3.30-3.35 (m, 1H), 3.05-3.10 (m, 2H), 2.80-2.90 (m, 1H), 2.60-2.67 (m, 2H), 2.20-2.23 (m, 2H), 2.17 (s, 3H), 1.99-2.15 (m, 2H) | 6-{4-[1-(1-acetylpiperidin-4-yl)-1H-pyrazol-4-yl]-7-aminofuro[2,3-c]pyridin-2-yl}-3,4-dihydroquinolin-2(1H)-one | 2.27 (ZQ3: polar_4 min) | 471.09 |

| Ex # | Structure and ¹H NMR | Compound Name | HPLC $t_R$ (min) | MS (ESI) [M+H]⁺ |
|---|---|---|---|---|
| Ex. 155 | 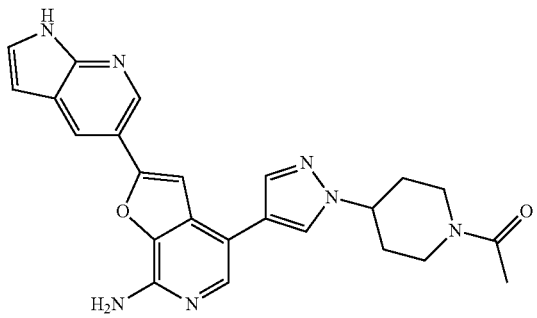 [SMILES: CC(=O)N1CCC(n2cc(-c3cnc(N)c4oc(-c5cnc6[nH]ccc6c5)cc34)cn2)CC1]  ¹H NMR (400 MHz, CD₃OD): δ 8.89 (d, J = 2 Hz, 1H), 8.63-8.64 (d, J = 2 Hz, 1H), 8.15 (d, J = 0.4 Hz, 1H), 7.92 (d, J = 0.8 Hz, 1H), 7.87 (s, 1H), 7.48 (t, J = 4 Hz, 2H), 6.60-6.61 (d, J = 3.6 Hz, 1H), 4.67-4.73 (m, 1H), 4.47-4.56 (m, 1H), 4.07-4.13 (m, 1H), 3.34 (s, 1H), 2.80-2.90 (m, 1H), 2.20-2.26 (m, 2H), 2.17 (s, 3H), 1.97-2.13 (m, 2H) | 1-(4-{4-[7-amino-2-(1H-pyrrolo[2,3-b]pyridin-5-yl)furo[2,3-c]pyridin-4-yl]-1H-pyrazol-1-yl}piperidin-1-yl)ethanone | 2.29 (ZQ3: polar_4 min) | 442.07 |
| Ex. 156 | 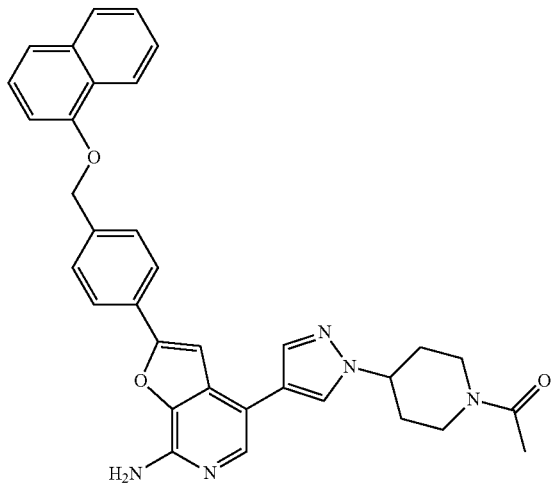 [SMILES: CC(=O)N1CCC(n2cc(-c3cnc(N)c4oc(-c5ccc(COc6cccc7ccccc67)cc5)cc34)cn2)CC1]  ¹H NMR (400 MHz, CD₃OD): δ 8.29-8.31 (d, J = 10 Hz, 1H), 8.13 (d, J = 0.8 Hz, 1H), 8.08-8.10 (m, 2H), 7.91 (d, J = 0.4 Hz, 1H), 7.87 (s, 1H), 7.80-7.81 (m, 1H), 7.68-7.70 (d, J = 8.8 Hz, 2H), 7.39-7.49 (m, 4H), 7.35-7.37 (m, 1H), 6.99-7.01 (dd, J = 7.6Hz, J = 0.8 Hz, 1H), 5.35 (s, 2H), 4.65-4.71 (m, 1H), 4.47-4.56 (m, 1H), 4.03-4.13 (m, 1H), 3.34 (s, 1H), 2.80-2.90 (m, 1H), 2.17-2.26 (m, 2H), 2.17 (s, 3H), 1.95-2.13 (m, 2H) | 1-{4-[4-(7-amino-2-{4-[(naphthalen-1-yloxy)methyl]phenyl}furo[2,3-c]pyridin-4-yl)-1H-pyrazol-1-yl]piperidin-1-yl}ethanone | 2.81 (ZQ3: polar_4 min) | 558.13 |

| Ex # | Structure and ¹H NMR | Compound Name | HPLC $t_R$ (min) | MS (ESI) [M+H]⁺ |
|---|---|---|---|---|
| Ex. 157 | 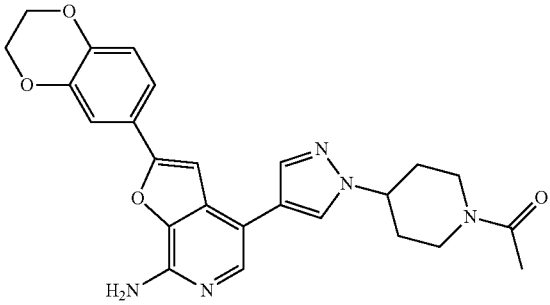 [SMILES: CC(=O)N1CCC(n2cc(-c3cnc(N)c4oc(-c5ccc6c(c5)OCCO6)cc34)cn2)CC1]<br>¹H NMR (400 MHz, CD₃OD): δ 8.13 (d, J = 0.4 Hz, 1H), 7.88-7.89 (d, J = 0.8 Hz, 1H), 7.84 (s, 1H), 7.52-7.55 (m, 1H), 7.50-7.51 (d, J = 2 Hz, 1H), 7.30 (s, 1H), 6.93-6.96 (d, J = 8.4 Hz, 1H), 4.67-4.73 (m, 1H), 4.47-4.53 (m, 1H), 4.29-4.31 (m, 4H), 4.07-4.10 (m, 1H), 3.33-3.35 (m, 1H), 2.79-2.87 (m, 1H), 2.17-2.23 (m, 2H), 2.17 (s, 3H), 1.97-2.13 (m, 2H) | 1-(4-{4-[7-amino-2-(2,3-dihydro-1,4-benzodioxin-6-yl)furo[2,3-c]pyridin-4-yl]-1H-pyrazol-1-yl}piperidin-1-yl)ethanone | 2.40 (ZQ3: polar_4 min) | 460.07 |
| Ex. 158 | 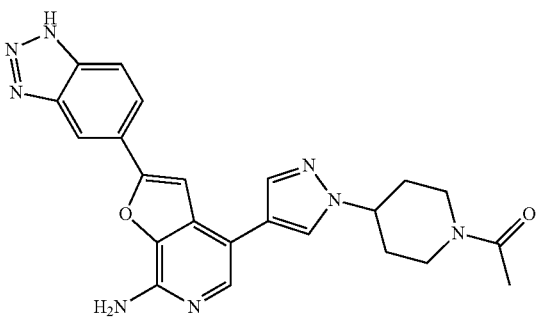 [SMILES: CC(=O)N1CCC(n2cc(-c3cnc(N)c4oc(-c5ccc6[nH]nnc6c5)cc34)cn2)CC1]<br>¹H NMR (400 MHz, DMSO-d₆): δ 8.28 (s, 1H), 8.13-8.26 (m, 1H), 7.98-7.99 (d, J = 4.2 Hz, 2H), 7.86-7.92 (m, 1H), 6.46 (s, 2H), 4.42-4.51 (m, 2H), 4.06-4.11 (m, 1H), 3.90-3.97 (m, 1H), 3.18-3.26 (m, 1H), 2.69-2.76 (m, 2H), 2.08-2.14 (m, 2H), 2.06 (s, 3H), 1.78-2.02 (m, 2H) | 1-(4-{4-[7-amino-2-(1H-benzotriazol-5-yl)furo[2,3-c]pyridin-4-yl]-1H-pyrazol-1-yl}piperidin-1-yl)ethanone | 0.88 (TOF: polar_3 min) | 444.21 |
| Ex. 159 | 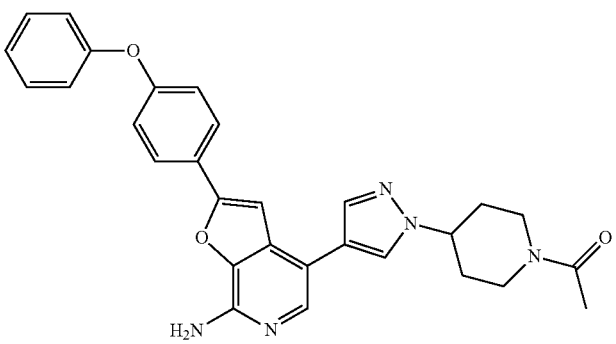 [SMILES: CC(=O)N1CCC(n2cc(-c3cnc(N)c4oc(-c5ccc(Oc6ccccc6)cc5)cc34)cn2)CC1]<br>¹H NMR (400 MHz, CD₃OD): δ 8.11 (d, J = 0.8 Hz, 1H), 7.99-8.01 (dd, J = 6.8 Hz, J = 2.0 Hz, 2H), 7.89 (d, J = 0.8 Hz, 1H), 7.84 (s, 1H), 7.38-7.42 (m, 2H), 7.36 (s, 1H), 7.16-7.20 (m, 1H), 7.05-7.07 (m, 4H), 4.64-4.71 (m, 1H), 4.45-4.53 (m, 1H), 4.07-4.10 (m, 1H), 3.34 (s, 1H), 2.79-2.87 (m, 1H), 2.17-2.23 (m, 2H), 2.16 (s, 3H), 1.93-2.13 (m, 2H) | 1-(4-{4-[7-amino-2-(4-phenoxyphenyl)furo[2,3-c]pyridin-4-yl]-1H-pyrazol-1-yl}piperidin-1-yl)ethanone | 1.14 (TOF: polar_3 min) | 494.22 |

-continued

| Ex # | Structure and ¹H NMR | Compound Name | HPLC t_R (min) | MS (ESI) [M+H]+ |
|---|---|---|---|---|
| Ex. 160 | 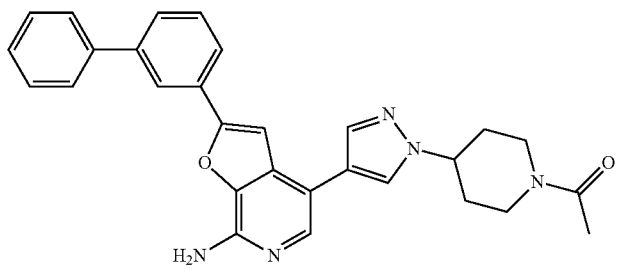 [SMILES: CC(=O)N1CCC(n2cc(-c3cnc(N)c4oc(-c5cccc(-c6ccccc6)c5)cc34)cn2)CC1]<br>¹H NMR (400 MHz, CD₃OD): δ : 8.30 (s, 1H), 8.13-8.14 (d, J = 0.8 Hz, 1H), 7.99-8.02 (m, 1H), 7.91 (d, J = 0.4 Hz, 1H), 7.86 (s, 1H), 7.71-7.73 (m, 2H), 7.67-7.69 (m, 1H), 7.54-7.58 (m, 2H), 7.50 (m, 2H), 7.38-7.48 (m, 1H), 4.64-4.71 (m, 1H), 4.45-4.53 (m, 1H), 4.07-4.13 (m, 1H), 3.30-3.34 (m, 1H), 2.79-2.87 (m, 1H), 2.17-2.23 (m, 2H), 2.16 (s, 3H), 1.96-2.13 (m, 2H) | 1-(4-{4-[7-amino-2-(biphenyl-3-yl)furo[2,3-c]pyridin-4-yl]-1H-pyrazol-1-yl}piperidin-1-yl)ethanone | 1.16 (TOF: polar_3 min) | 478.22 |
| Ex. 161 | 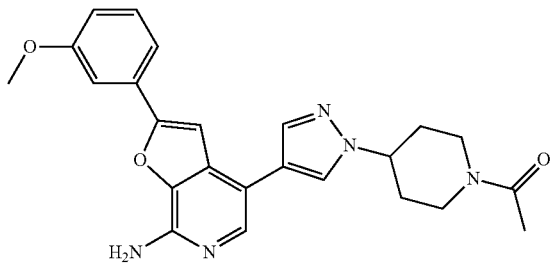 [SMILES: COc1cccc(-c2cc3c(-c4cnn(C5CCN(C(C)=O)CC5)c4)cnc(N)c3o2)c1]<br>¹H NMR (400 MHz, CD₃OD): δ 8.11 (s, 1H), 7.89 (d, J = 0.4 Hz, 1H), 7.85 (s, 1H), 7.57-7.61 (m, 2H), 7.44 (s, 1H), 7.38 (t, J = 8 Hz, 1H), 6.97-6.99 (m, 1H), 4.65-4.71 (m, 1H), 4.47-4.53 (m, 1H), 4.07-4.15 (m, 1H), 3.87 (s, 3H), 3.31-3.36 (m, 1H), 2.79-2.87 (m, 1H), 2.17-2.23 (m, 2H), 2.15 (s, 3H), 1.93-2.11 (m, 2H) | 1-(4-{4-[7-amino-2-(3-methoxyphenyl)furo[2,3-c]pyridin-4-yl]-1H-pyrazol-1-yl}piperidin-1-yl)ethanone | 1.04 (TOF: polar_3 min) | 428.25 |
| Ex. 162 | 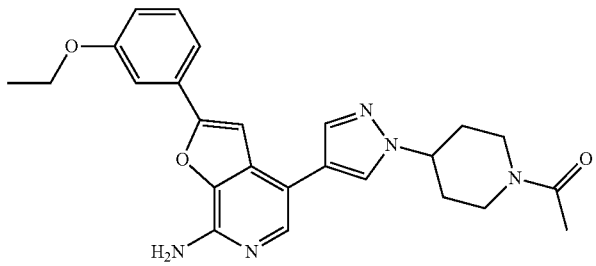 [SMILES: CCOc1cccc(-c2cc3c(-c4cnn(C5CCN(C(C)=O)CC5)c4)cnc(N)c3o2)c1]<br>¹H NMR (400 MHz, CD₃OD): δ 8.13 (s, 1H), 7.90 (s, 1H), 7.85 (s, 1H), 7.58-7.60 (m, 2H), 7.44 (s, 1H), 7.38 (t, J = 8 Hz, 1H), 6.96-6.98 (d, J = 8 Hz, 1H), 4.67-4.71 (m, 1H), 4.47-4.53 (m, 1H), 4.07-4.15 (m, 3H), 3.35 (m, 1H), 2.79-2.87 (m, 1H), 2.17-2.23 (m, 2H), 2.16 (s, 3H), 1.97-2.13 (m, 2H), 1.42 (t, J = 6.4 Hz, 3H) | 1-(4-{4-[7-amino-2-(3-ethoxyphenyl)furo[2,3-c]pyridin-4-yl]-1H-pyrazol-1-yl}piperidin-1-yl)ethanone | 1.02 (TOF: polar_3 min) | 432.22 |

| Ex # | Structure and ¹H NMR | Compound Name | HPLC t$_R$ (min) | MS (ESI) [M+H]⁺ |
|---|---|---|---|---|
| Ex. 163 | 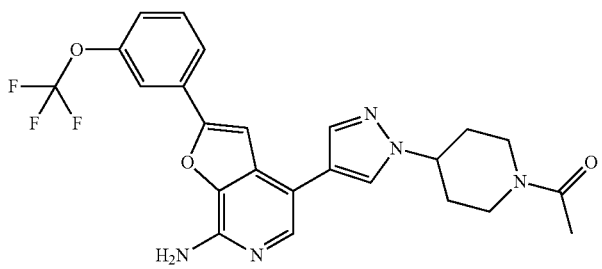 [SMILES: CC(=O)N1CCC(n2cc(-c3cnc(N)c4oc(-c5cccc(OC(F)(F)F)c5)cc34)cn2)CC1]<br>¹H NMR (400 MHz, CD₃OD): δ 8.15 (d, J = 0.4 Hz, 1H), 8.04-8.07 (m, 1H), 7.98 (s, 1H), 7.92 (d, J = 0.8 Hz, 1H), 7.89 (s, 1H), 7.59-7.63 (m, 2H), 7.35-7.37 (dd, J = 8Hz, J = 1.2 Hz, 1H), 4.67-4.71 (m, 1H), 4.49-4.54 (m, 1H), 4.06-4.13 (m, 1H), 3.34 (s, 1H), 2.80-2.90 (m, 1H), 2.21-2.25 (m, 2H), 2.17 (s, 3H), 1.97-2.13 (m, 2H) | 1-[4-(4-{7-amino-2-[3-(trifluoromethoxy)phenyl]furo[2,3-c]pyridin-4-yl}-1H-pyrazol-1-yl)piperidin-1-yl]ethanone | 1.10 (TOF: polar_3 min) | 487.18 |
| Ex. 164 | 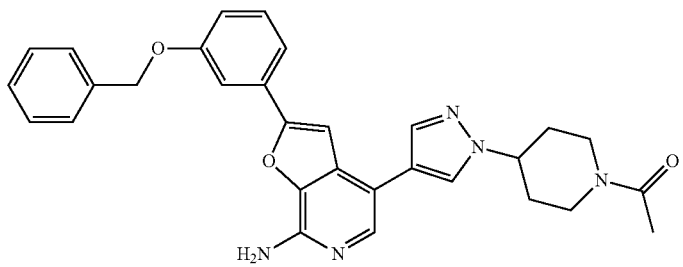 [SMILES: CC(=O)N1CCC(n2cc(-c3cnc(N)c4oc(-c5cccc(OCc6ccccc6)c5)cc34)cn2)CC1]<br>¹H NMR (400 MHz, CD₃OD): δ 8.13 (s, 1H), 7.91 (s, 1H), 7.86 (s, 1H), 7.69-7.70 (d, J = 2.4 Hz, 1H), 7.62-7.64 (m, 1H), 7.47-7.50 (m, 3H), 7.37-7.41 (m, 3H), 7.32-7.34 (m, 1H), 7.06-7.08 (m, 1H), 5.18 (s, 2H), 4.67-4.71 (m, 1H), 4.45-4.54 (m, 1H), 4.05-4.12 (m, 1H), 3.31-3.35 (m, 1H), 2.69-2.76 (m, 1H), 2.19-2.22 (m, 2H), 2.16 (s, 3H), 1.98-2.12 (m, 2H) | 1-[4-(4-{7-amino-2-[3-(benzyloxy)phenyl]furo[2,3-c]pyridin-4-yl}-1H-pyrazol-1-yl)piperidin-1-yl]ethanone | 1.18 (TOF: polar_3 min) | 509.23 |
| Ex. 165 | 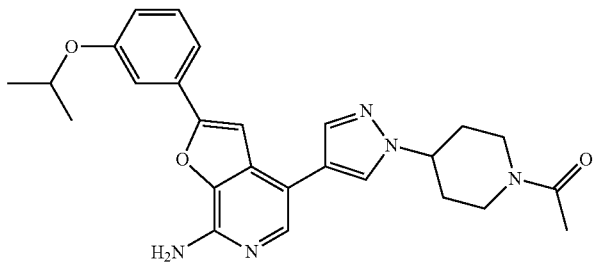 [SMILES: CC(=O)N1CCC(n2cc(-c3cnc(N)c4oc(-c5cccc(OC(C)C)c5)cc34)cn2)CC1]<br>¹H NMR (400 MHz, CD₃OD): δ 8.14 (d, J = 0.4 Hz, 1H), 7.91 (d, J = 0.8 Hz, 1H), 7.87 (s, 1H), 7.58-7.61 (m, 2H), 7.46 (s, 1H), 7.37-7.39 (m, 1H), 6.97-7.00 (m, 1H), 4.70-4.75 (m, 1H), 4.65-4.70 (m, 1H), 4.49-4.57 (m, 1H), 4.07-4.12 (m, 1H), 3.30-3.35 (m, 1H), 2.80-2.90 (m, 1H), 2.17-2.25 (m, 2H), 2.17 (s, 3H), 1.97-2.13 (m, 2H), 1.35-1.36 (d, J = 6 Hz, 6H) | 1-[4-(4-{7-amino-2-[3-(propan-2-yloxy)phenyl]furo[2,3-c}pyridin-4-yl}-1H-pyrazol-1-yl)piperidin-1-yl}ethanone | 1.10 (TOF: polar_3 min) | 460.25 |

| Ex # | Structure and ¹H NMR | Compound Name | HPLC $t_R$ (min) | MS (ESI) [M+H]⁺ |
|---|---|---|---|---|
| Ex. 166 | 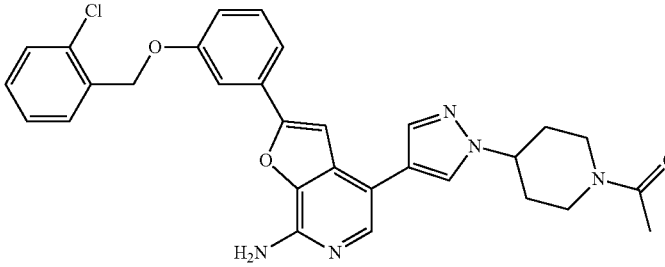<br>¹H NMR (400 MHz, CD₃OD): δ 8.12 (s, 1H), 7.90 (d, J = 0.4 Hz, 1H), 7.86 (s, 1H), 7.69-7.70 (m, 1H), 7.60-7.66 (m, 2H), 7.39-7.46 (m, 3H), 7.32-7.34 (m, 2H), 7.05-7.07 (m, 1H), 5.26 (s, 2H), 4.67-4.71 (m, 1H), 4.47-4.55 (m, 1H), 4.05-4.11 (m, 1H), 3.31-3.34 (m, 1H), 2.77-2.86 (m, 1H), 2.19-2.24 (m, 2H), 2.15 (s, 3H), 1.93-2.12 (m, 2H) | 1-{4-[4-(7-amino-2-{3-[(2-chlorobenzyl)oxy]phenyl}furo[2,3-c]pyridin-4-yl)-1H-pyrazol-1-yl]piperidin-1-yl}ethanone | 1.21 (TOF: polar_3 min) | 544.19 |
| Ex. 167 | 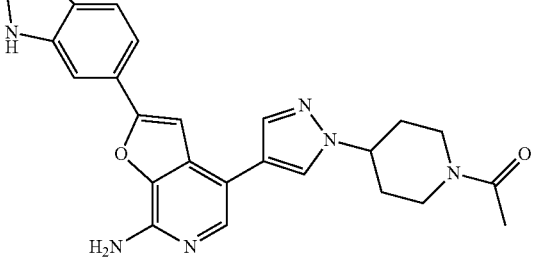<br>¹H NMR (400 MHz, CD₃OD): δ 8.15 (s, 1H), 8.08 (s, 1H), 7.92 (s, 1H), 7.85 (s, 1H), 7.70-7.72 (m, 1H), 7.65-7.67 (d, J = 8.4 Hz, 1H), 7.36-7.37 (d, J = 4 Hz, 2H), 6.51 (d, J = 3.2 Hz, 1H), 4.67-4.72 (m, 1H), 4.50-4.60 (m, 1H), 4.06-4.16 (m, 1H), 3.30-3.36 (m, 1H), 2.80-2.90 (m, 1H), 2.18-2.22 (m, 2H), 2.17 (s, 3H), 1.97-2.12 (m, 2H) | 1-(4-{4-[7-amino-2-(1H-indol-6-yl)furo[2,3-c]pyridin-4-yl]-1H-pyrazol-1-yl}piperidin-1-yl)ethanone | 1.00 (TOF: polar_3 min) | 442.20 |
| Ex. 168 | 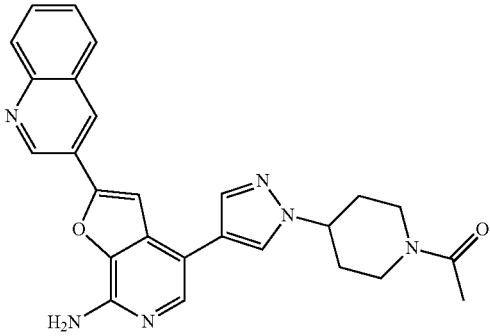 [SMILES: CC(=O)N1CCC(n2cc(-c3cnc(N)c4oc(-c5cnc6ccccc6c5)cc34)cn2)CC1]<br>¹H NMR (400 MHz, CD₃OD): δ 9.43-9.44 (d, J = 2 Hz, 1H), 8.87 (d, J = 1.6 Hz, 1H), 8.13 (s, 1H), 8.02 (t, J = 8.8 Hz, 2H), 7.91 (s, 1H), 7.86 (s, 1H), 7.78-7.80 (d, J = 7.2 Hz, 1H), 7.73 (s, 1H), 7.63-7.67 (m, 1H), 4.65-4.71 (m, 1H), 4.45-4.54 (m, 1H), 4.07-4.12 (m, 1H), 3.30-3.36 (m, 1H), 2.80-2.90 (m, 1H), 2.17-2.25 (m, 2H), 2.16 (s, 3H), 1.97-2.12 (m, 2H) | 1-(4-{4-[7-amino-2-(quinolin-3-yl)furo[2,3-c]pyridin-4-yl]-1H-pyrazol-1-yl}piperidin-1-yl)ethanone | 0.97 (TOF: polar_3 min) | 452.23 |

-continued

| Ex # | Structure and ¹H NMR | Compound Name | HPLC $t_R$ (min) | MS (ESI) [M+H]⁺ |
|---|---|---|---|---|
| Ex. 169 | 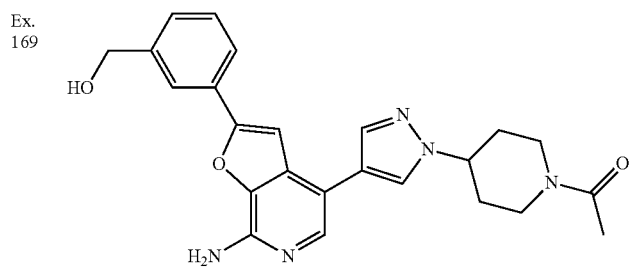<br>¹H NMR (400 MHz, CD₃OD): δ 8.13 (d, J = 0.4 Hz, 1H), 8.02 (s, 1H), 7.93-7.95 (m, 1H), 7.90 (d, J = 0.4 Hz, 1H), 7.86 (s, 1H), 7.42-7.49 (m, 3H), 4.63-4.69 (m, 3H), 4.47-4.56 (m, 1H), 4.04-4.11 (m, 1H), 3.33-3.36 (m, 1H), 2.79-2.88 (m, 1H), 2.19-2.24 (m, 2H), 2.158 (s, 3H), 1.93-2.11 (m, 2H) | 1-[4-(4-{7-amino-2-[3-(hydroxymethyl)phenyl]furo[2,3-c]pyridin-4-yl}-1H-pyrazol-1-yl)piperidin-1-yl]ethanone | 0.90 (TOF: polar_3 min) | 432.22 |
| Ex. 170 | 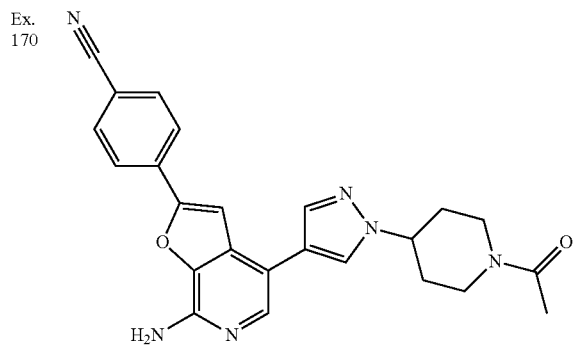<br>¹H NMR (400 MHz, CD₃OD): δ 8.19 (s, 1H), 8.17 (s, 1H), 8.13 (s, 1H), 7.91 (s, 1H), 7.88 (s, 1H), 7.85 (s, 1H), 7.83 (s, 1H), 7.68 (s, 1H), 4.65-4.71 (m, 1H), 4.48-4.56 (m, 1H), 4.07-4.11 (m, 1H), 3.31-3.36 (m, 1H), 2.80-2.90 (m, 1H), 2.18-2.25 (m, 2H), 2.171 (s, 3H), 1.97-2.12 (m, 2H) | 4-{4-[1-(1-acetylpiperidin-4-yl)-1H-pyrazol-4-yl]-7-aminofuro[2,3-c]pyridin-2-yl}benzonitrile | 0.96 (TOF: polar_3 min) | 427.20 |
| Ex. 171 | 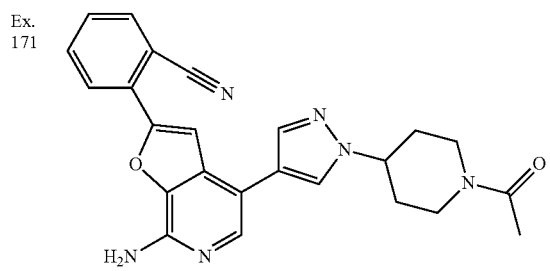<br>¹H NMR (400 MHz, CD₃OD): δ 8.26-8.28 (dd, J = 8 Hz, J = 0.8 Hz, 1H), 8.09 (d, J = 0.8 Hz, 1H), 7.90-7.92 (m, 2H), 7.85-7.87 (m, 1H), 7.81-7.83 (m, 2H), 7.59-7.63 (m, 1H), 4.62-4.70 (m, 1H), 4.48-4.57 (m, 1H), 4.04-4.11 (m, 1H), 3.33-3.36 (m, 1H), 2.80-2.90 (m, 1H), 2.21-2.26 (m, 2H), 2.166 (s, 3H), 1.96-2.13 (m, 2H) | 2-{4-[1-(1-acetylpiperidin-4-yl)-1H-pyrazol-4-yl]-7-aminofuro[2,3-c]pyridin-2-yl}benzonitrile | 0.95 (TOF: polar_3 min) | 427.20 |

-continued

| Ex # | Structure and ¹H NMR | Compound Name | HPLC $t_R$ (min) | MS (ESI) [M+H]⁺ |
|---|---|---|---|---|
| Ex. 172 | 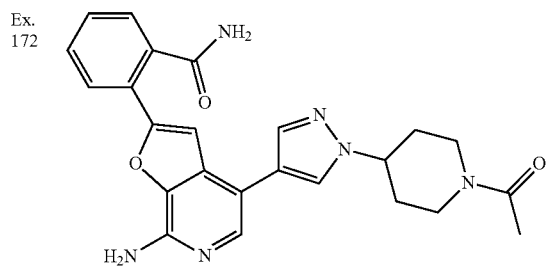<br>¹H NMR (400 MHz, CD₃OD): δ 8.07-8.08 (d, J = 0.8 Hz, 1H), 8.02-8.04 (m, 1H), 7.86 (s, 2H), 7.60-7.62 (m, 1H), 7.53-7.60 (m, 2H), 7.36 (s, 1H), 4.62-4.70 (m, 1H), 4.48-4.57 (m, 1H), 4.04-4.11 (m, 1H), 3.33-3.36 (m, 1H), 2.78-2.90 (m, 1H), 2.18-2.22 (m, 2H), 2.16 (s, 3H), 1.93-2.12 (m, 2H) | 2-{4-[1-(1-acetylpiperidin-4-yl)-1H-pyrazol-4-yl]-7-aminofuro[2,3-c]pyridin-2-yl}benzamide | 0.84 (TOF: polar_3 min) | 445.23 |
| Ex. 173 | 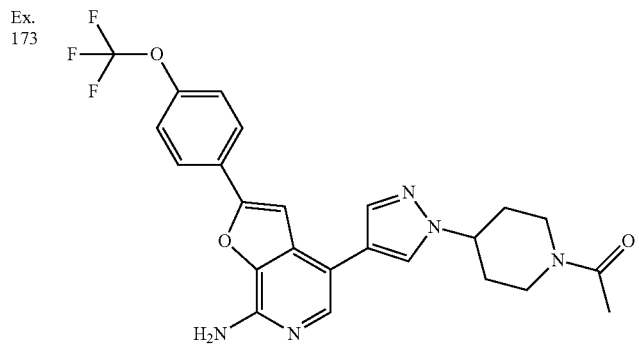<br>¹H NMR (400 MHz, CD₃OD): δ 8.11-8.13 (m, 3H), 7.89 (d, J = 0.4 Hz, 1H), 7.86 (s, 1H), 7.50 (s, 1H), 7.38-7.40 (dd, J = 9.2 Hz, J = 0.8 Hz, 2H), 4.65-4.71 (m, 1H), 4.45-4.53 (m, 1H), 4.05-4.11 (m, 1H), 3.31-3.36 (m, 1H), 2.78-2.86 (m, 1H), 2.17-2.23 (m, 2H), 2.15 (s, 3H), 1.92-2.11 (m, 2H) | 1-[4-(4-{7-amino-2-[4-(trifluoromethoxy)phenyl]furo[2,3-c]pyridin-4-yl}-1H-pyrazol-1-yl)piperidin-1-yl]ethanone | 1.11 (TOF: polar_3 min) | 486.21 |
| Ex. 174 | 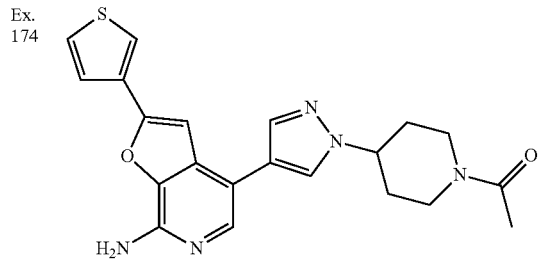<br>¹H NMR (400 MHz, CD₃OD): δ 8.09-8.10 (d, J = 0.8 Hz, 1H), 8.02-8.03 (dd, J = 3.2 Hz, J = 1.2 Hz, 1H), 7.88 (d, J = 0.4 Hz, 1H), 7.84 (s, 1H), 7.65-7.66 (dd, J = 5.2 Hz, J = 1.2 Hz, 1H), 7.54-7.56 (dd, J = 5.2 Hz, J = 2.8 Hz, 1H), 7.27 (s, 1H), 4.65-4.71 (m, 1H), 4.45-4.53 (m, 1H), 4.05-4.11 (m, 1H), 3.31-3.36 (m, 1H), 2.78-2.86 (m, 1H), 2.17-2.23 (m, 2H), 2.15 (s, 3H), 1.92-2.11 (m, 2H) | 1-(4-{4-[7-amino-2-(thiophen-3-yl)furo[2,3-c]pyridin-4-yl]-1H-pyrazol-1-yl}piperidin-1-yl)ethanone | 0.97 (TOF: polar_3 min) | 408.19 |

| Ex # | Structure and ¹H NMR | Compound Name | HPLC $t_R$ (min) | MS (ESI) [M+H]⁺ |
|---|---|---|---|---|
| Ex. 175 | 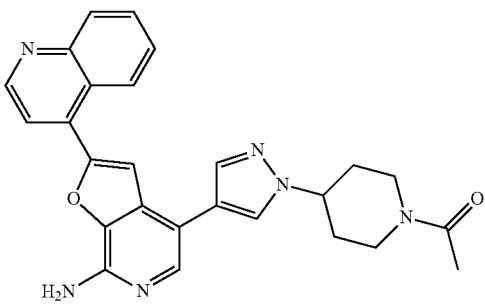 [SMILES: CC(=O)N1CCC(n2cc(-c3cnc(N)c4oc(-c5ccnc6ccccc56)cc34)cn2)CC1]<br>¹H NMR (400 MHz, CD₃OD): δ 8.97 (d, J = 4.4 Hz, 1H), 8.65-8.68 (m, 1H), 8.21-8.22 (d, J = 0.8 Hz, 1H), 8.14-8.17 (m, 1H), 8.03-8.05 (d, J = 4.8 Hz, 1H), 7.96 (d, J = 0.4 Hz, 1H), 7.919 (s, 1H), 7.85-7.91 (m, 1H), 7.77-7.80 (m, 2H), 4.65-4.70 (m, 1H), 4.50-4.55 (m, 1H), 4.07-4.12 (m, 1H), 3.30-3.36 (m, 1H), 2.80-2.90 (m, 1H), 2.17-2.20 (m, 2H), 2.16 (s, 3H), 1.97-2.10 (m, 2H) | 1-(4-{4-[7-amino-2-(quinolin-4-yl)furo[2,3-c]pyridin-4-yl]-1H-pyrazol-1-yl}piperidin-1-yl)ethanone | 2.02 (ZQ3: polar_4 min) | 453.08 |
| Ex. 176 | 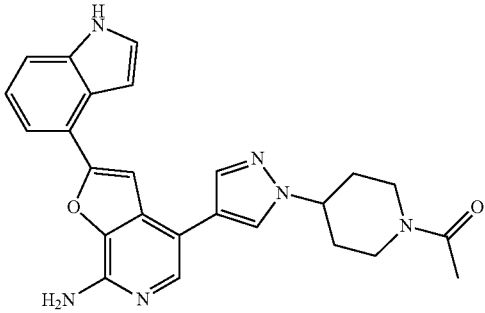 [SMILES: CC(=O)N1CCC(n2cc(-c3cnc(N)c4oc(-c5cccc6[nH]ccc56)cc34)cn2)CC1]<br>¹H NMR (400 MHz, DMSO-d₆): δ 11.54 (s, 1H), 8.42 (s, 1H), 8.02 (s, 1H), 7.98 (s, 1H), 7.89-7.91 (d, J = 7.6 Hz, 1H), 7.73 (s, 1H), 7.58-7.59 (m, 1H), 7.36-7.56 (m, 1H), 7.33-7.36 (d, J = 13.2 Hz, 1H), 7.24-7.28 (m, 2H), 7.10 (s, 1H), 4.48-4.53 (m, 2H), 3.94-3.97 (d, J = 13.6 Hz, 1H), 3.20-3.23 (m, 1H), 2.71-2.77 (m, 1H), 2.05-2.21 (m, 5H), 1.89-2.02 (m, 2H) | 1-(4-{4-[7-amino-2-(1H-indol-4-yl)furo[2,3-c]pyridin-4-yl]-1H-pyrazol-1-yl}piperidin-1-yl)ethanone | 2.10 (ZQ3: polar_4 min) | 441.12 |

| Ex # | Structure and ¹H NMR | Compound Name | HPLC $t_R$ (min) | MS (ESI) [M+H]⁺ |
|---|---|---|---|---|
| Ex. 177 | ¹H NMR (400 MHz, CD₃OD): δ 8.76 (s, 1H), 8.20 (s, 1H), 7.91 (s, 1H), 7.87-7.89 (d, J = 7.2 Hz, 1H), 7.77 (s, 1H), 7.69 (s, 1H), 7.62-7.64 (m, 1H), 7.45-7.47 (m, 1H), 4.60-4.70 (m, 2H), 3.97-4.05 (m, 1H), 3.25 (s, 1H), 2.73-2.81 (m, 1H), 2.11-2.18 (m, 2H), 2.089 (s, 3H), 1.89-2.05 (m, 2H) | 1-(4-{4-[7-amino-2-(1H-indazol-4-yl)furo[2,3-c]pyridin-4-yl]-1H-pyrazol-1-yl}piperidin-1-yl)ethanone | 1.71 (ZQ3: polar_4 min) | 442.07 |
| Ex. 178 | ¹H NMR (400 MHz, CD₃OD): δ 8.21 (s, 1H), 8.18 (d, J = 0.4 Hz, 1H), 8.11-8.13 (m, 1H), 7.91-7.92 (d, J = 0.4 Hz, 1H), 7.86 (s, 1H), 7.59-7.61 (m, 2H), 7.56 (s, 1H), 4.65-4.71 (m, 1H), 4.50-4.60 (m, 1H), 4.24 (s, 2H), 4.05-4.13 (m, 1H), 3.31-3.37 (m, 1H), 2.80-2.90 (m, 1H), 2.18-2.26 (m, 2H), 2.17 (s, 3H), 1.97-2.12 (m, 2H) | 1-[4-(4-{7-amino-2-[3-(aminomethyl)phenyl]furo[2,3-c]pyridin-4-yl}-1H-pyrazol-1-yl)piperidin-1-yl]ethanone | 1.98 (ZQ3: polar_4 min) | 430.10 |
| Ex. 179 | ¹H NMR (400 MHz, CD₃OD): δ 8.27 (s, 1H), 8.11-8.13 (d, J = 8 Hz, 2H), 7.97 (s, 1H), 7.79 (s, 1H), 7.72 (s, 1H), 7.54-7.56 (d, J = 8 Hz, 2H), 4.65-4.71 (m, 1H), 4.50-4.60 (m, 1H), 4.05-4.13 (m, 1H), 4.018 (s, 2H), 3.31-3.38 (m, 1H), 2.80-2.904 (m, 1H), 2.17-2.25 (m, 2H), 2.16 (s, 3H), 1.97-2.12 (m, 2H) | (4-{4-[1-(1-acetylpiperidin-4-yl)-1H-pyrazol-4-yl]-7-aminofuro[2,3-c]pyridin-2-yl}phenyl)acetonitrile | 1.97 (ZQ3: polar_4 min) | 441.11 |

-continued

| Ex # | Structure and ¹H NMR | Compound Name | HPLC $t_R$ (min) | MS (ESI) [M+H]⁺ |
|---|---|---|---|---|
| Ex. 180 | 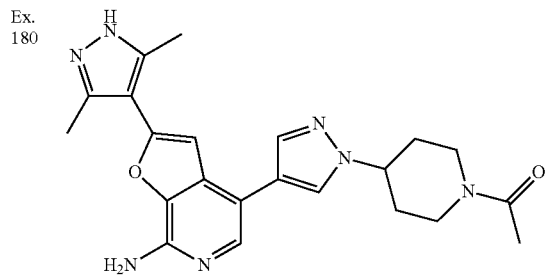 | 1-(4-{4-[7-amino-2-(3,5-dimethyl-1H-pyrazol-4-yl)furo[2,3-c]pyridin-4-yl]-1H-pyrazol-1-yl}piperidin-1-yl)ethanone | 0.83 (TOF: polar_3 min) | 420.25 |
|  | ¹H NMR (400 MHz, CD₃OD): δ 8.13 (s, 1H), 7.13 (s, 1H), 7.69 (s, 1H), 6.93 (s, 1H), 4.55 (m, 2H), 3.98-4.01 (m, 1H), 3.25-3.30 (m, 1H), 2.72-2.80 (m, 1H), 2.45 (s, 6H), 2.08-2.15 (m, 2H), 2.06 (s, 3H), 1.82-1.98 (m, 2H) | | | |
| Ex. 181 | 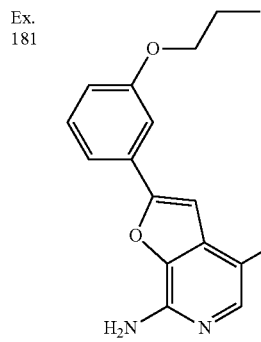 | 1-(4-{4-[7-amino-2-(3-propoxyphenyl)furo[2,3-c]pyridin-4-yl]-1H-pyrazol-1-yl}piperidin-1-yl)ethanone | 2.33 (ZQ3: polar_4 min) | 460.10 |
|  | ¹H NMR (400 MHz, DMSO-d₆): δ 8.25 (s, 1H), 7.97 (s, 1H), 7.96 (d, J = 0.4 Hz, 1H), 7.73 (s, 1H), 7.66 (t, J = 1.2 Hz, 2H), 7.42-7.45 (m, 1H), 6.98-7.02 (m, 1H), 6.37 (s, 2H), 4.40-4.51 (m, 2H), 4.01-4.04 (m, 2H), 3.90-3.96 (m, 1H), 3.15-3.21 (m, 1H), 2.67-2.76 (m, 1H), 2.05-2.12 (m, 5H), 1.90-2.01 (m, 2H), 1.72-1.80 (m, 2H), 1.016 (t, J = 7.2 Hz, 3H) | | | |

| Ex # | Structure and ¹H NMR | Compound Name | HPLC t_R (min) | MS (ESI) [M+H]⁺ |
|---|---|---|---|---|
| Ex. 182 | 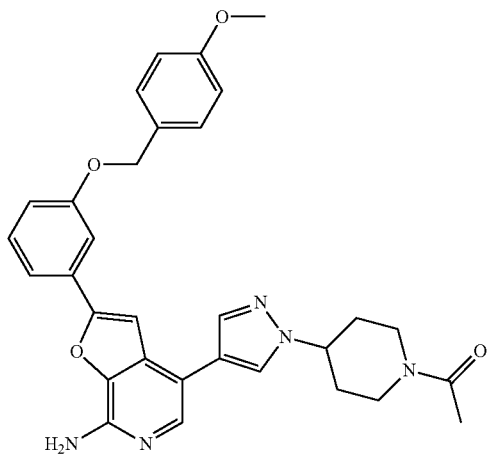 [SMILES: COc1ccc(COc2cccc(-c3cc4c(-c5cnn(C6CCN(C(C)=O)CC6)c5)cnc(N)c4o3)c2)cc1]<br>¹H NMR (400 MHz, CD₃OD): δ 8.15 (s, 1H), 7.91 (d, J = 0.4 Hz, 1H), 7.87 (s, 1H), 7.69 (d, J = 2.4 Hz, 1H), 7.61-7.66 (m, 1H), 7.48 (s, 1H), 7.33-7.42 (m, 3H), 7.05-7.09 (m, 1H), 6.95 (s, 1H), 6.93 (dd, J = 8 Hz, J = 2 Hz, 1H), 5.10 (s, 2H), 4.65-4.7 (m, 1H), 4.47-4.56 (m, 1H), 4.06-4.14 (m, 1H), 3.80 (s, 3H), 3.30-3.32 (m, 1H), 2.80-2.90 (m, 1H), 2.18-2.25 (m, 2H), 2.17 (s, 3H), 1.97-2.12 (m, 2H) | 1-{4-[4-(7-amino-2-{3-[(4-methoxybenzyl)oxy]phenyl}furo[2,3-c]pyridin-4-yl)-1H-pyrazol-1-yl]piperidin-1-yl}ethanone | 2.53 (ZQ3: polar_4 min) | 538.06 |
| Ex. 183 | 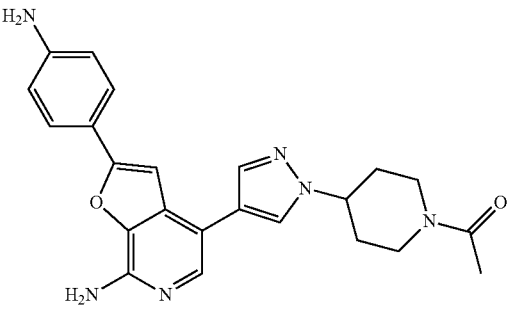 [SMILES: CC(=O)N1CCC(n2cc(-c3cnc(N)c4oc(-c5ccc(N)cc5)cc34)cn2)CC1]<br>¹H NMR (400 MHz, CD₃OD): δ 8.11 (s, 1H), 7.88 (s, 1H), 7.826 (s, 1H), 7.75-7.77 (m, 2H), 7.13 (s, 1H), 6.76-6.78 (dd, J = 6.8 Hz, J = 2.0 Hz, 2H), 4.65-4.71 (m, 1H), 4.49-4.54 (m, 1H), 4.07-4.13 (m, 1H), 4.30-4.35 (m, 1H), 2.80-2.90 (m, 1H), 2.18-2.25 (m, 2H), 2.17 (s, 3H), 1.97-2.12 (m, 2H) | 1-(4-{4-[7-amino-2-(4-aminophenyl)furo[2,3-c]pyridin-4-yl]-1H-pyrazol-1-yl}piperidin-1-yl)ethanone | 2.29 (ZQ3: polar_4 min) | 417.01 |

| Ex # | Structure and ¹H NMR | Compound Name | HPLC $t_R$ (min) | MS (ESI) [M+H]⁺ |
|---|---|---|---|---|
| Ex. 184 | 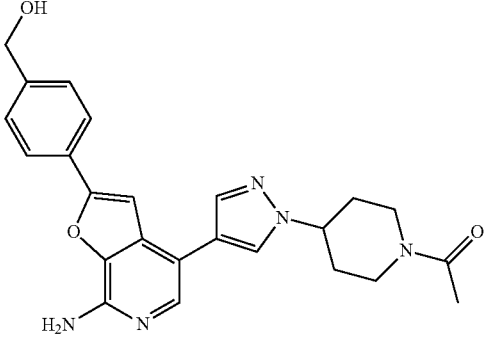 [SMILES: CC(=O)N1CCC(n2cc(-c3cnc(N)c4oc(-c5ccc(CO)cc5)cc34)cn2)CC1]<br>¹H NMR (400 MHz, CD₃OD): δ 8.14 (s, 1H), 8.04 (d, J = 2 Hz, 1H), 8.02 (s, 1H), 7.91 (d, J = 0.4 Hz, 1H), 7.87 (s, 1H), 7.49-7.51 (d, J = 8.4 Hz, 2H), 7.45 (s, 1H), 4.70-4.71 (m, 1H), 4.67 (s, 2H), 4.50-4.60 (m, 1H), 4.09-4.12 (m, 1H), 3.33-3.38 (m, 1H), 2.80-2.90 (m, 1H), 2.19-2.25 (m, 2H), 2.16 (s, 3H), 1.97-2.12 (m, 2H) | 1-[4-(4-{7-amino-2-[4-(hydroxymethyl) phenyl]furo[2,3-c]pyridin-4-yl}-1H-pyrazol-1-yl)piperidin-1-yl]ethanone | 2.27 (ZQ3: polar_4 min) | 431.99 |
| Ex. 185 | 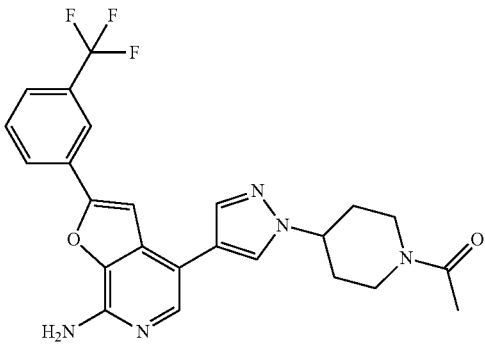 [SMILES: CC(=O)N1CCC(n2cc(-c3cnc(N)c4oc(-c5cccc(C(F)(F)F)c5)cc34)cn2)CC1]<br>¹H NMR (400 MHz, CDCl₃): δ 8.07 (s, 1H), 7.99-8.01 (d, J = 8 Hz, 1H), 7.90 (s, 1H), 7.76 (s, 1H), 7.60-7.62 (d, J = 10 Hz, 2H), 7.55 (t, J = 8 Hz, 1H), 7.13 (s, 1H), 4.72-4.75 (d, J = 14 Hz, 1H), 4.34-4.40 (m, 1H), 3.93-3.96 (d, J = 12.8 Hz, 1H), 3.21 (m, 1H), 2.70-2.76 (m, 1H), 2.17-2.26 (m, 2H), 2.10 (s, 3H), 1.95-2.03 (m, 2H) | 1-[4-(4-{7-amino-2-[3-(trifluoromethyl) phenyl]furo[2,3-c]pyridin-4-yl}-1H-pyrazol-1-yl)piperidin-1-yl]ethanone | 2.56 (ZQ3: polar_4 min) | 469.85 |

-continued

| Ex # | Structure and ¹H NMR | Compound Name | HPLC $t_R$ (min) | MS (ESI) [M+H]⁺ |
|---|---|---|---|---|
| Ex. 186 | 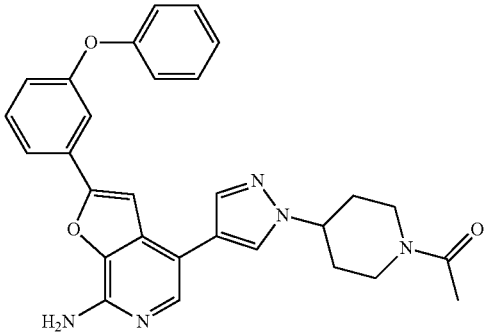 [SMILES: CC(=O)N1CCC(n2cc(-c3cnc(N)c4oc(-c5cccc(Oc6ccccc6)c5)cc34)cn2)CC1]<br>¹H NMR (400 MHz, DMSO-d₆) δ 8.27 (s, 1H), 7.98 (d, J = 10.1 Hz, 2H), 7.94-7.84 (m, 2H), 7.80 (s, 1H), 7.57 (t, J = 8.0 Hz, 1H), 7.49-7.32 (m, 2H), 7.16 (t, J = 7.3 Hz, 1H), 7.11-6.96 (m, 3H), 6.43 (br. s., 2H), 4.48 (d, J = 11.1 Hz, 2H), 3.94 (br. s., 1H), 3.29-3.13 (m, 1H), 2.83-2.63 (m, 1H), 2.21-2.07 (m, 2H), 2.06 (s, 3H), 2.04-1.76 (m, 2H) | 1-(4-{4-[7-amino-2-(3-phenoxyphenyl)furo[2,3-c]pyridin-4-yl]-1H-pyrazol-1-yl}piperidin-1-yl)ethanone | 2.63 (ZQ3: polar_4 min) | 493.90 |
| Ex. 187 | 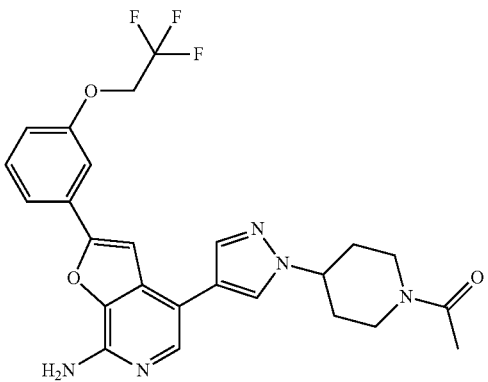 [SMILES: CC(=O)N1CCC(n2cc(-c3cnc(N)c4oc(-c5cccc(OCC(F)(F)F)c5)cc34)cn2)CC1]<br>¹H NMR (400 MHz, DMSO-d₆) δ 8.26 (s, 1H), 8.06-7.91 (m, 2H), 7.86-7.70 (m, 3H), 7.52 (t, J = 8.0 Hz, 1H), 7.16 (dd, J = 2.1, 8.2 Hz, 1H), 6.39 (s, 2H), 4.87 (q, J = 8.8 Hz, 2H), 4.60-4.31 (m, 2H), 3.94 (br. s., 1H), 3.42-3.12 (m, 3H), 2.82-2.69 (m, 2H), 2.23-2.08 (m, 2H), 2.06 (s, 4H), 2.03-1.74 (m, 3H) | 1-[4-(4-{7-amino-2-[3-(2,2,2-trifluoroethoxy)phenyl]furo[2,3-c]pyridin-4-yl}-1H-pyrazol-1-yl)piperidin-1-yl]ethanone | 2.57 (ZQ3: polar_4 min) | 499.91 |

| Ex # | Structure and ¹H NMR | Compound Name | HPLC $t_R$ (min) | MS (ESI) [M+H]⁺ |
|---|---|---|---|---|
| Ex. 188 | 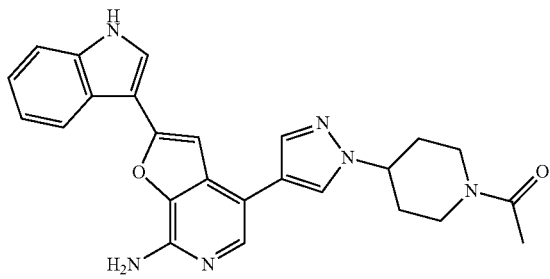 [SMILES: CC(=O)N1CCC(n2cc(-c3cnc(N)c4oc(-c5c[nH]c6ccccc56)cc34)cn2)CC1]<br>¹H NMR (400 MHz, CD₃OD): δ 8.03 (s, 1H), 7.80-7.82 (d, J = 6 Hz, 2H), 7.52-7.54 (d, J = 8 Hz, 1H), 7.35-7.37 (d, J = 8.4 Hz, 1H), 7.30 (s, 1H), 7.12 (t, J = 8 Hz, 1H), 7.04 (s, 1H), 6.99-7.04 (m, 1H), 4.55-4.65 (m, 1H), 4.40-4.45 (m, 1H), 3.92-4.05 (m, 1H), 3.22-3.26 (m, 1H), 2.73- 2.79 (m, 1H), 2.10-2.14 (m, 2H), 2.09 (s, 3H), 1.88-2.08 (m, 2H) | 1-(4-{4-[7-amino-2-(1H-indol-3-yl)furo[2,3-c]pyridin-4-yl]-1H-pyrazol-1-yl}piperidin-1-yl)ethanone | 2.44 (ZQ3: polar_4 min) | 441.25 |
| Ex. 189 | 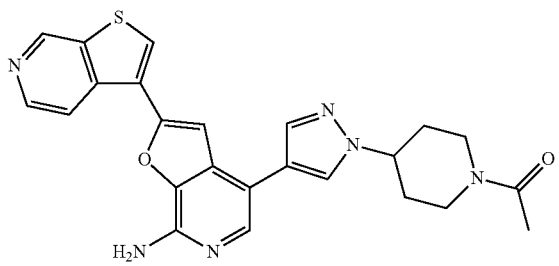 [SMILES: CC(=O)N1CCC(n2cc(-c3cnc(N)c4oc(-c5csc6cnccc56)cc34)cn2)CC1]<br>¹H NMR (400 MHz, DMSO-d₆): δ 9.40 (d, J = 1.2 Hz, 1H), 8.82 (s, 1H), 8.69 (dd, J = 5.6, 0.8 Hz, 1H), 8.65 (d, J = 5.6 Hz, 1H), 8.31 (s, 1H), 8.03 (s, 1H), 8.01 (d, J = 0.8 Hz, 1H), 7.75 (s, 1H), 6.52 (br s, 2H), 4.47-4.56 (m, 2H), 3.94-4.01 (m, 1H), 3.21-3.30 (m, 1H), 2.72-2.81 (m, 1H), 2.08-2.18 (m, 2H), 2.07 (s, 3H), 1.93-2.06 (m, 1H), 1.81-1.92 (m, 1H) | 1-(4-{4-[7-amino-2-(thieno[2,3-c]pyridin-3-yl)furo[2,3-c]pyridin-4-yl]-1H-pyrazol-1-yl}piperidin-1-yl)ethanone | 0.88 (TOF: polar_3 min) | 459.13 |
| Ex. 190 | 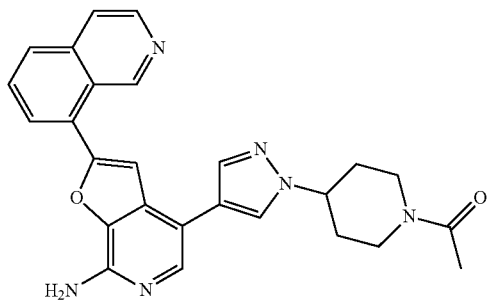 [SMILES: CC(=O)N1CCC(n2cc(-c3cnc(N)c4oc(-c5cccc6ccncc56)cc34)cn2)CC1]<br>¹H NMR (400 MHz, CD₃OD): δ 9.77 (s, 1H), 8.47-8.48 (d, J = 5.6 Hz, 1H), 8.10 (m, 2H), 8.00-8.02 (d, J = 8.4 Hz, 1H), 7.82-7.87 (m, 4H), 7.50 (s, 1H), 4.58-4.61 (m, 1H), 4.44-4.50 (m, 1H), 3.97-4.05 (m, 1H), 3.27-3.30 (m, 1H), 2.71-2.80 (m, 1H), 2.08-2.17 (m, 2H), 2.05 (s, 3H), 1.88-1.97 (m, 2H) | 1-(4-{4-[7-amino-2-(isoquinolin-8-yl)furo[2,3-c]pyridin-4-yl]-1H-pyrazol-1-yl}piperidin-1-yl)ethanone | 2.22 (ZQ3: polar_4 min) | 453.15 |

-continued

| Ex # | Structure and ¹H NMR | Compound Name | HPLC t$_R$ (min) | MS (ESI) [M+H]⁺ |
|---|---|---|---|---|
| Ex. 191 | ¹H NMR (400 MHz, CDCl₃): δ : 7.88 (s, 1H), 7.78 (s, 1H), 7.64 (s, 1H), 7.62 (s, 1H), 7.23 (s, 1H), 7.17-7.31 (m, 1H), 7.04-7.06 (d, J = 7.6 Hz, 1H), 5.02-5.10 (s, 2H), 4.70-4.74 (d, J = 13.2 Hz, 1H), 4.35-4.41 (m, 1H), 3.93-3.96 (d, J = 13.2 Hz, 1H), 3.20-3.26 (m, 1H), 2.72-2.78 (m, 1H), 2.17-2.26 (m, 2H), 2.10 (s, 3H), 1.95-2.04 (m, 2H) | 1-(4-{4-[7-amino-2-(2,2-difluoro-1,3-benzodioxol-4-yl)furo[2,3-c]pyridin-4-yl]-1H-pyrazol-1-yl}piperidin-1-yl)ethanone | 2.55 (ZQ3: polar_4 min) | 482.10 |
| Ex. 192 | ¹H NMR (400 MHz, CD₃OD): δ 8.94 (s, 1H), 8.12 (s, 1H), 7.88 (s, 1H), 7.79-7.82 (m, 2H), 7.63-7.65 (d, J = 8.8 Hz, 1H), 7.50 (s, 1H), 7.36 (t, J = 8 Hz, 1H), 4.62-4.66 (m, 1H), 4.43-4.53 (m, 1H), 4.25 (s, 3H), 4.04-4.07 (d, J = 13.6 Hz, 1H), 3.25-3.29 (m, 1H), 2.70-2.90 (m, 1H), 2.13-2.16 (m, 2H), 2.12 (s, 3H), 1.91-2.08 (m, 2H) | 1-(4-{4-[7-amino-2-(2-methyl-2H-indazol-4-yl)furo[2,3-c]pyridin-4-yl]-1H-pyrazol-1-yl}piperidin-1-yl)ethanone | 2.33 (ZQ3: polar_4 min) | 456.12 |
| Ex. 193 | ¹H NMR (400 MHz, CDCl₃): δ 7.94 (s, 1H), 7.79 (s, 1H), 7.71-7.73 (d, J = 7.2 Hz, 1H), 7.66 (s, 1H), 7.52-7.56 (m, 3H), 7.02 (s, 1H), 4.74-4.78 (d, J = 13.2 Hz, 1H), 4.37-4.43 (m, 1H), 3.96-3.99 (d, J = 14 Hz 1H), 3.21-3.29 (m, 1H), 2.73-2.81 (m, 1H), 2.35 (s, 3H), 2.19-2.26 (m, 2H), 2.13 (s, 3H), 1.97-2.07 (m, 2H) | 1-(4-{4-[2-(2-acetylphenyl)-7-aminofuro[2,3-c]pyridin-4-yl]-1H-pyrazol-1-yl}piperidin-1-yl)ethanone | 2.27 (ZQ3: polar_4 min) | 444.14 |

-continued

| Ex # | Structure and ¹H NMR | Compound Name | HPLC t_R (min) | MS (ESI) [M+H]⁺ |
|---|---|---|---|---|
| Ex. 194 | 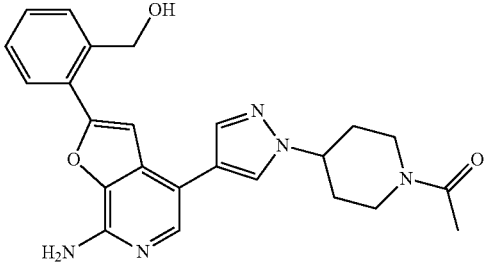 [SMILES: CC(=O)N1CCC(n2cc(-c3cnc(N)c4oc(-c5ccccc5CO)cc34)cn2)CC1]<br>¹H NMR (400 MHz, CD₃OD): δ 8.11 (s, 1H), 7.93-7.96 (m, 1H), 7.88-7.89 (d, J = 4.2 Hz, 2H), 7.64-7.66 (m, 1H), 7.45-7.51 (m, 2H), 7.38 (s, 1H), 4.85-4.87 (m, 2H), 4.61-4.71 (m, 1H), 4.48-4.57 (m, 1H), 4.02-4.12 (m, 1H), 3.32-3.36 (m, 1H), 2.78-2.90 (m, 1H), 2.16-2.15 (m, 2H), 2.16 (s, 3H), 1.90-2.13 (m, 2H) | 1-[4-(4-{7-amino-2-[2-(hydroxymethyl)phenyl]furo[2,3-c]pyridin-4-yl}-1H-pyrazol-1-yl)piperidin-1-yl]ethanone | 2.27 (ZQ3: polar_4 min) | 432.12 |
| Ex. 195 | 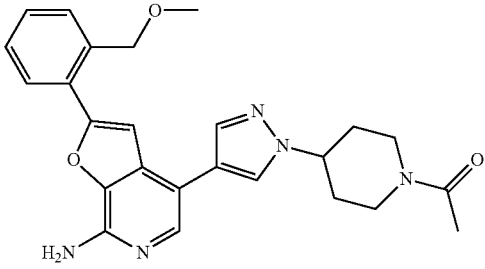 [SMILES: COCc1ccccc1-c1cc2c(-c3cnn(C4CCN(C(C)=O)CC4)c3)cnc(N)c2o1]<br>¹H NMR (400 MHz, CDCl₃): δ 7.93 (s, 1H), 7.82 (s, 2H), 7.689 (s, 1H), 7.54-7.55 (d, J = 4.2 Hz, 1H), 7.43-7.45 (m, 2H), 7.164 (s, 1H), 4.74-4.77 (d, J = 13.6 Hz, 1H), 4.60 (s, 2H), 4.37-4.42 (m, 1H), 3.95-3.99 (d, J = 13.6 Hz, 1H), 3.43 (s, 3H), 3.25 (t, J = 12.4 Hz, 1H), 2.75-2.78 (m, 1H), 2.20-2.29 (m, 2H), 2.36 (s, 3H), 1.96-2.04 (m, 2H) | 1-[4-(4-{7-amino-2-[2-(methoxymethyl)phenyl]furo[2,3-c]pyridin-4-yl}-1H-pyrazol-1-yl)piperidin-1-yl]ethanone | 2.41 (ZQ3: polar_4 min) | 446.10 |
| Ex. 196 | 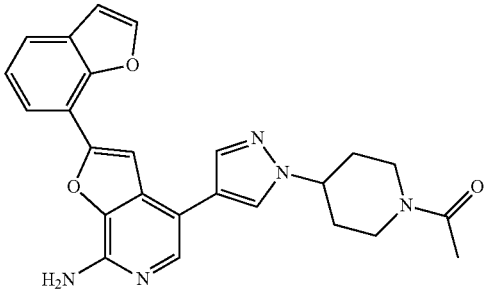 [SMILES: CC(=O)N1CCC(n2cc(-c3cnc(N)c4oc(-c5cccc6ccoc56)cc34)cn2)CC1] | 1-(4-{4-[7-amino-2-(1-benzofuran-7-yl)furo[2,3-c]pyridin-4-yl]-1H-pyrazol-1-yl}piperidin-1-yl)ethanone | 2.51 (ZQ3: polar_4 min) | 442.07 |

| Ex # | Structure and ¹H NMR | Compound Name | HPLC $t_R$ (min) | MS (ESI) [M+H]⁺ |
|---|---|---|---|---|
| Ex. 197 | 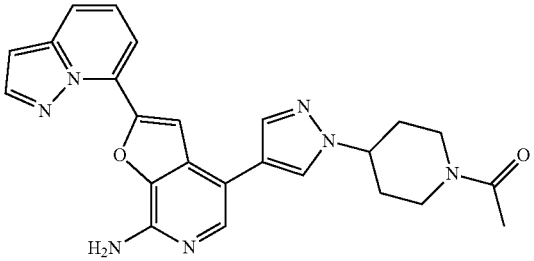 ¹H NMR (400 MHz, DMSO-d₆): δ 8.55 (s, 1H), 8.39 (s, 1H), 8.33 (d, J = 2.3 Hz, 1H), 8.03 (s, 1H), 8.01 (d, J = 1.5 Hz, 1H), 7.98 (d, J = 0.5 Hz, 1H), 7.94 (s, 1H), 7.55 (dd, J = 7.3, 8.6Hz, 1H), 6.94 (d, J = 2.3Hz, 1H), 4.72-4.38 (m, 2H), 4.04-3.89 (m, 1H), 3.32-3.15 (m, 1H), 2.84-2.65 (m, 1H), 2.20-2.03 (m, 5H), 2.03-1.88 (m, 1H), 1.88-1.71 (m, 1H) | 1-(4-{4-[7-amino-2-(pyrazolo[1,5-a]pyridin-7-yl)furo[2,3-c]pyridin-4-yl]-1H-pyrazol-1-yl}piperidin-1-yl)ethanone | 2.41 (ZQ3: polar_4 min) | 442.16 |

Example 198

1-{4-[4-(7-amino-2-cyclopentylfuro[2,3-c]pyridin-4-yl)-1H-pyrazol-1-yl]piperidin-1-yl}ethanone

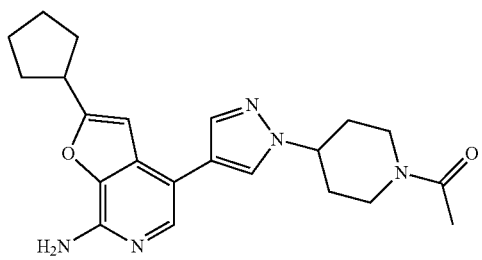 [SMILES: CC(=O)N1CCC(n2cc(-c3cnc(N)c4oc(C5CCCC5)cc34)cn2)CC1]

1-{4-[4-(7-Amino-2-cyclopent-1-enyl-furo[2,3-c]pyridin-4-yl)-pyrazol-1-yl]-piperidin-1-yl}-ethanone (80 mg, 0.2 mmol) and10% Pd/C (20 mg) were suspended in dry THF (30 mL) and the solution was stirred at rt under a hydrogen balloon overnight. The Pd/C was filtered and the filtrate was concentrated. The residue was purified by preparative TLC (5:1 DCM:MeOH) to afford 32 mg (40%) of the title compound. ¹H NMR (400 MHz, CD₃OD): δ 8.03 (d, J=0.8 Hz, 1H), 7.80-7.81 (d, J=0.8 Hz, 1H), 7.79 (s, 1H), 6.70 (s, 1H), 4.62-4.70 (m, 1H), 4.49-4.51 (m, 1H), 4.10-4.22 (m, 1H), 3.31-3.33 (m, 1H), 2.76-2.85 (m, 1H), 2.15-2.20 (m, 2H), 2.14 (s, 3H), 2.08-2.14 (m, 2H), 1.92-2.08 (m, 2H), 1.85-1.88 (m, 5H), 1.70-1.78 (m, 2H); MS (ESI): 394.16 [M+H]⁺; HPLC $t_R$=2.40 min (ZQ3: polar_4 min).

Example 199

1-[4-(4-{7-amino-2-[3-(Pyridin-2-ylmethoxy)phenyl]furo[2,3-c]pyridin-4-yl}-1H-pyrazol-1-yl)piperidin-1-yl]ethanone

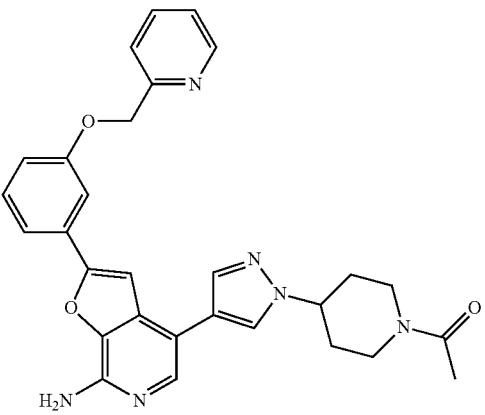 [SMILES: CC(=O)N1CCC(n2cc(-c3cnc(N)c4oc(-c5cccc(OCc6ccccn6)c5)cc34)cn2)CC1]

1-(4-{4-[7-Amino-2-(3-hydroxy-phenyl)-furo[2,3-c]pyridin-4-yl]-pyrazol-1-yl}-piperidin-1-yl)-ethanone (50 mg, 0.12 mmol) was dissolved in acetone (10 mL) and potassium carbonate (50 mg, 0.36 mmol) and 2-bromomethyl-pyridine (24 mg, 0.14 mmol) was added. The solution was stirred at RT overnight. After filtration the filtrate was concentrated and the residue was purified by preparative TLC (10% MeOH:DCM) to afford 8 mg (13%) of the title compound. ¹H NMR (400 MHz, CD₃OD): δ 8.56-8.57 (d, J=4 Hz, 1H), 8.17 (s, 1H), 7.85-7.93 (m, 3H), 7.74 (s, 1H), 7.66-7.68 (d, J=7.2 Hz, 2H), 7.54 (s, 1H), 7.39-7.43 (m, 2H), 7.10-7.12 (d, J=8 Hz, 1H), 5.29 (s, 2H), 4.65-4.72 (m, 1H), 4.49-4.60 (m, 1H), 4.06-4.14 (m, 1H), 3.33-3.35 (m, 1H), 2.80-2.88 (m, 1H), 2.20-2.27 (m, 2H), 2.16 (s, 3H), 1.95-2.11 (m, 2H); MS (ESI): 509.11 [M+H]⁺; HPLC $t_R$=2.18 min (ZQ3: polar_4 min).

The following Examples were prepared by from 1-(4-{4-[7-amino-2-(3-hydroxy-phenyl)-furo[2,3-c]pyridin-4-yl]-pyrazol-1-yl}-piperidin-1-yl)-ethanone by a procedure analogous to Example 199.

| Ex. # | Structure | Compound Name | HPLC $t_R$ (min) | MS (ESI) [M + H]+ |
|---|---|---|---|---|
| Ex. 200 | 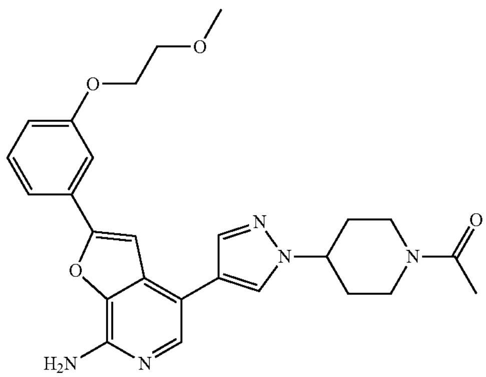 [SMILES: COCCOc1cccc(-c2cc3c(-c4cnn(C5CCN(C(C)=O)CC5)c4)cnc(N)c3o2)c1] | 1-[4-(4-{7-amino-2-[3-(2-methoxyethoxy)phenyl]furo[2,3-c]pyridin-4-yl}-1H-pyrazol-1-yl)piperidin-1-yl]ethanone | 2.21 (ZQ3: polar_4 min) | 476.13 |

$^1$H NMR (400 MHz, DMSO-d$_6$): δ 8.30 (s, 1H), 8.01-8.02 (d, J = 6 Hz, 2H), 7.79 (s, 1H), 7.71-7.75 (m, 2H), 7.49 (t, J = 8 Hz, 1H), 7.06-7.09 (dd, J = 8 Hz, J = 2 Hz, 1H), 6.43 (s, 2H), 4.47-4.56 (m, 2H), 4.23-4.26 (m, 2H), 4.13-4.14 (d, J = 4.2 Hz, 1H), 3.74-3.76 (t, J = 4.4 Hz, 2H), 3.36-3.38 (d, J = 4.4 Hz, 3H), 3.24-3.30 (m, 1H), 2.75-2.78 (m, 1H), 2.10-2.13 (m, 5H), 1.85-1.94 (m, 2H)

| Ex. # | Structure | Compound Name | HPLC $t_R$ (min) | MS (ESI) [M + H]+ |
|---|---|---|---|---|
| Ex. 201 | | 1-{4-[4-(7-amino-2-{3-[(3-chlorobenzyl)oxy]phenyl}furo[2,3-c]pyridin-4-yl)-1H-pyrazol-1-yl]piperidin-1-yl}ethanone | 2.51 (ZQ3: polar_4 min) | 542.05 |

$^1$H NMR (400 MHz, CD$_3$OD): δ 6.92 (s, 1H), 6.66 (s, 1H), 6.57 (s, 1H), 6.47 (s, 1H), 6.40-6.42 (d, J = 8.4 Hz, 1H), 6.33 (s, 1H), 6.25 (s, 1H), 6.04-6.18 (m, 4H), 5.82-5.85 (dd, J = 8 Hz, J = 2.4 Hz, 1H), 3.92 (s, 2H), 3.38-3.42 (m, 1H), 3.20-3.31 (m, 1H), 2.80-2.84 (d, J = 12.8 Hz, 1H), 2.05-2.09 (m, 1H), 1.54-1.60 (m, 1H), 0.93-0.98 (m, 5H), 0.70-0.88 (m, 2H)

| Ex. # | Structure | Compound Name | HPLC t$_R$ (min) | MS (ESI) [M + H]$^+$ |
|---|---|---|---|---|
| Ex. 202 | 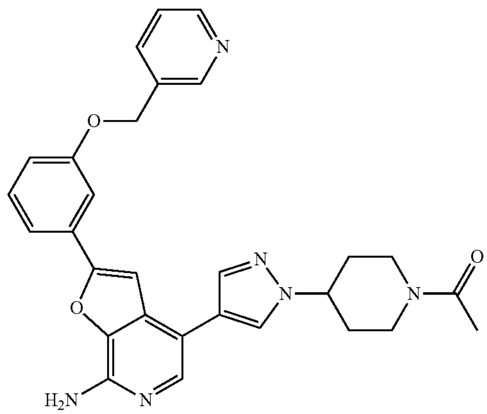 [SMILES: CC(=O)N1CCC(n2cc(-c3cnc(N)c4oc(-c5cccc(OCc6cccnc6)c5)cc34)cn2)CC1] | 1-[4-(4-{7-amino-2-[3-(pyridin-3-ylmethoxy)phenyl]furo[2,3-c]pyridin-4-yl}-1H-pyrazol-1-yl)piperidin-1-yl]ethanone | 2.06 (ZQ3: polar_4 min) | 509.06 |

$^1$H NMR (400 MHz, CD$_3$OD): δ 8.69-8.70 (d, J = 1.6 Hz, 1H), 8.52-8.53 (m, 1H), 8.16 (s, 1H), 7.99-8.01 (d, J = 8 Hz, 1H), 7.92-7.93 (d, J = 0.4 Hz, 1H), 7.86 (s, 1H), 7.75-7.76 (m, 1H), 7.67-7.69 (d, J = 8 Hz, 1H), 7.42-7.53 (m, 3H), 7.11-7.13 (m, 1H), 5.27 (s, 2H), 4.65-4.71 (m, 1H), 4.47-4.57 (m, 1H), 4.03-4.11 (m, 1H), 3.33-3.36 (m, 1H), 2.80-2.90 (m, 1H), 2.20-2.26 (m, 2H), 2.16 (s, 3H), 1.93-2.10 (m, 2H)

| Ex. # | Structure | Compound Name | HPLC t$_R$ (min) | MS (ESI) [M + H]$^+$ |
|---|---|---|---|---|
| Ex. 203 | | 1-[4-(4-{7-amino-2-[3-(pyridin-4-ylmethoxy)phenyl]furo[2,3-c]pyridin-4-yl}-1H-pyrazol-1-yl)piperidin-1-yl]ethanone | 1.82 (ZQ3: polar_4 min) | 509.06 |

$^1$H NMR (400 MHz, CD$_3$OD): δ 8.54-8.55 (dd, J = 4.8 Hz, J = 1.6 Hz, 2H), 8.15 (s, 1H), 7.92 (d, J = 0.8 Hz, 1H), 7.85 (s, 1H), 7.92-7.93 (d, J = 0.4 Hz, 1H), 7.75 (s, 1H), 7.68-7.71 (m, 1H), 7.56-7.57 (d, J = 6.4 Hz, 2H), 7.54 (s, 1H), 7.41-7.47 (m, 1H), 5.29 (s, 2H), 4.65-4.70 (m, 1H), 4.48-4.59 (m, 1H), 4.03-4.12 (m, 1H), 3.33-3.35 (m, 1H), 2.80-2.90 (m, 1H), 2.16-2.24 (m, 2H), 2.15 (s, 3H), 1.95-2.12 (m, 2H)

| Ex. # | Structure | Compound Name | HPLC $t_R$ (min) | MS (ESI) [M + H]$^+$ |
|---|---|---|---|---|
| Ex. 204 | 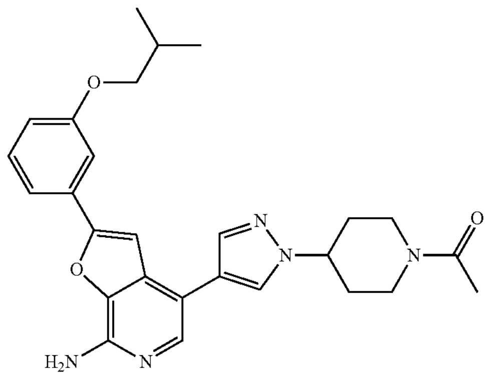 [SMILES: CC(=O)N1CCC(n2cc(-c3cnc(N)c4oc(-c5cccc(OCC(C)C)c5)cc34)cn2)CC1] | 1-[4-(4-{7-amino-2-[3-(2-methylpropoxy)phenyl]furo[2,3-c]pyridin-4-yl}-1H-pyrazol-1-yl)piperidin-1-yl]ethanone | 2.76 (ZQ3: polar_4 min) | 474.10 |

$^1$H NMR (400 MHz, CD$_3$OD): δ: 8.14 (d, J = 0.8 Hz, 1H), 7.91 (d, J = 0.8 Hz, 1H), 7.87 (s, 1H), 7.60-7.62 (m, 2H), 7.46 (s, 1H), 7.39 (t, J = 8 Hz, 1H), 6.98-7.00 (m, 1H), 4.65-4.71 (m, 1H), 4.50-4.53 (m, 1H), 4.05-4.14 (m, 1H), 3.84-3.86 (d, J = 6.4 Hz, 2H), 3.34-3.36 (m, 1H), 2.70-2.76 (m, 1H), 2.19-2.22 (m, 2H), 2.17 (s, 3H), 1.97-2.12 (m, 3H), 1.07-1.08 (d, J = 6.4 Hz, 6H)

| Ex. 205 | 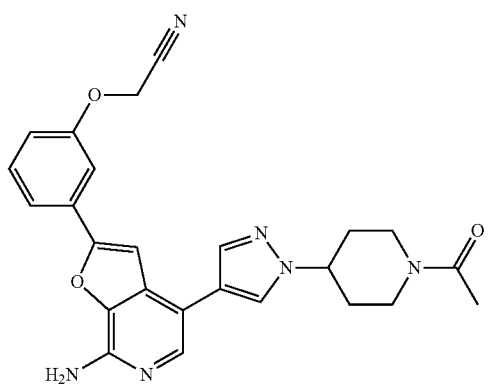 [SMILES: CC(=O)N1CCC(n2cc(-c3cnc(N)c4oc(-c5cccc(OCC#N)c5)cc34)cn2)CC1] | (3-{4-[1-(1-acetylpiperidin-4-yl)-1H-pyrazol-4-yl]-7-aminofuro[2,3-c]pyridin-2-yl}phenoxy)acetonitrile | 2.19 (ZQ3: polar_4 min) | 457.05 |

$^1$H NMR (400 MHz, DMSO-d6): δ 8.23-8.24 (d, J = 0.4 Hz, 1H), 7.96 (s, 1H), 7.94 (d, J = 0.8 Hz, 1H), 7.76-7.79 (m, 3H), 7.53 (t, J = 8 Hz, 1H), 7.14-7.17 (m, 1H), 6.39 (s, 1H), 5.16 (s, 2H), 4.41-4.54 (m, 2H), 3.91-3.95 (m, 1H), 3.18-3.24 (m, 1H), 2.01-2.03 (m, 2H), 1.962 (s, 3H), 1.809-1.954 (m, 2H)

-continued

| Ex. # | Structure | Compound Name | HPLC $t_R$ (min) | MS (ESI) [M + H]$^+$ |
|---|---|---|---|---|
| Ex. 206 | 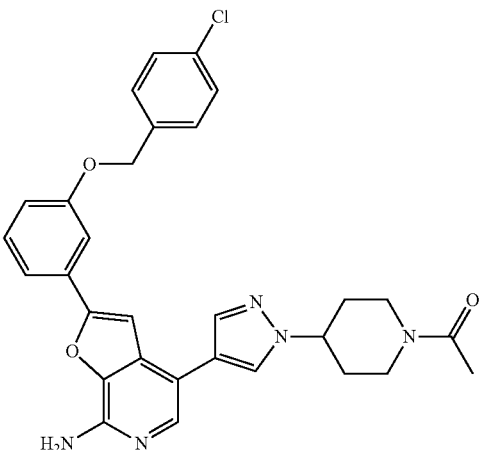 [SMILES: CC(=O)N1CCC(n2cc(-c3cnc(N)c4oc(-c5cccc(OCc6ccc(Cl)cc6)c5)cc34)cn2)CC1] | 1-{4-[4-(7-amino-2-{3-[(4-chlorobenzyl)oxy]phenyl}furo[2,3-c]pyridin-4-yl)-1H-pyrazol-1-yl]piperidin-1-yl}ethanone | 2.57 (ZQ3: polar_4 min) | 542.05 |
| | $^1$H NMR (400 MHz, CD$_3$OD): δ 8.14 (s, 1H), 7.91-7.92 (d, J = 0.8 Hz, 1H), 7.87 (s, 1H), 7.71 (d, J = 2.4 Hz, 1H), 7.65-7.67 (m, 1H), 7.48-7.50 (m, 3H), 7.39-7.44 (m, 3H), 7.06-7.10 (m, 1H), 5.18 (s, 2H), 4.65-4.71 (m, 1H), 4.48-4.58 (m, 1H), 4.05-4.12 (m, 1H), 3.34-3.37 (m, 1H), 2.70-2.80 (m, 1H), 2.16-2.25 (m, 5H), 1.97-2.12 (m, 2H) | | | |
| Ex. 207 | 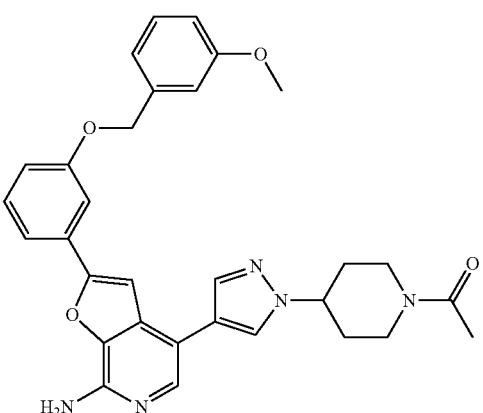 | 1-{4-[4-(7-amino-2-{3-[(3-methoxybenzyl)oxy]phenyl}furo[2,3-c]pyridin-4-yl)-1H-pyrazol-1-yl]piperidin-1-yl}ethanone | 2.54 (ZQ3: polar_4 min) | 538.09 |
| | $^1$H NMR (400 MHz, CD$_3$OD): δ 8.13 (s, 1H), 7.90 (s, 1H), 7.86 (s, 1H), 7.69 (t, J = 2 Hz, 1H), 7.61-7.63 (d, J = 7.6 Hz, 1H), 7.45 (s, 1H), 7.39 (t, J = 8 Hz, 1H), 7.29 (t, J = 8 Hz, 1H), 7.04-7.07 (m, 3H), 6.86-6.88 (m, 1H), 5.15 (s, 2H), 4.63-4.71 (m, 1H), 4.45-4.56 (m, 1H), 4.03-4.12 (m, 1H), 3.79 (s, 3H), 3.31-3.34 (m, 1H), 2.77-2.86 (m, 1H), 2.10-2.21 (m, 5H), 1.94-2.10 (m, 2H) | | | |

| Ex. # | Structure | Compound Name | HPLC t$_R$ (min) | MS (ESI) [M + H$^+$] |
|---|---|---|---|---|
| Ex. 208 | 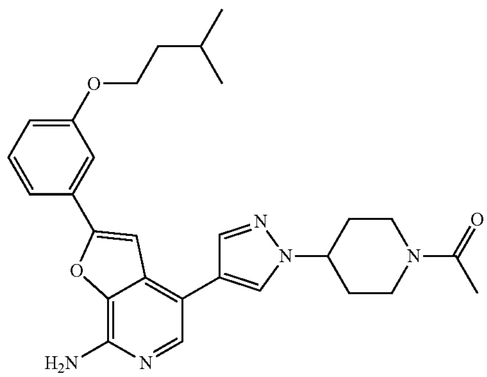 [SMILES: CC(=O)N1CCC(n2cc(-c3cnc(N)c4oc(-c5cccc(OCCC(C)C)c5)cc34)cn2)CC1] | 1-[4-(4-{7-amino-2-[3-(3-methylbutoxy)phenyl]furo[2,3-c]pyridin-4-yl}-1H-pyrazol-1-yl)piperidin-1-yl]ethanone | 2.56 (ZQ3: polar_4 min) | 488.03 |

$^1$H NMR (400 MHz, CD$_3$OD): δ 8.14 (s, 1H), 7.91 (d, J = 0.8 Hz, 1H), 7.87 (s, 1H), 7.59-7.60 (m, 2H), 7.46 (s, 1H), 7.39 (t, J = 8 Hz, 1H), 6.97-7.01 (m, 1H), 4.65-4.71 (m, 1H), 4.47-4.59 (m, 1H), 4.10-4.13 (t, J = 6.4 Hz, 3H), 3.32-3.35 (m, 1H), 2.80-2.90 (m, 1H), 2.16-2.22 (m, 2H), 2.17 (s, 3H), 1.98-2.13 (m, 2H), 1.84-1.93 (m, 1H), 1.68-1.75 (m, 2H), 0.99-1.01 (d, J = 6.8 Hz, 6H)

| Ex. # | Structure | Compound Name | HPLC t$_R$ (min) | MS (ESI) [M + H$^+$] |
|---|---|---|---|---|
| Ex. 209 | | 1-[4-(4-{7-amino-2-[3-(cyclohexylmethoxy)phenyl]furo[2,3-c]pyridin-4-yl}-1H-pyrazol-1-yl)piperidin-1-yl]ethanone | 2.73 (ZQ3: polar_4 min) | 514.10 |

$^1$H NMR (400 MHz, DMSO-d$_6$): δ 8.25 (d, J = 0.4 Hz, 1H), 7.96 (s, 1H), 7.95 (d, J = 0.8 Hz, 1H), 7.72 (s, 1H), 7.63-7.65 (m, 2H), 7.41 (t, J = 8 Hz, 1H), 6.97-7.00 (m, 1H), 6.38 (s, 2H), 4.39-4.50 (m, 2H), 3.90-3.96 (m, 1H), 3.85-3.87 (d, J = 6.4 Hz, 2H), 3.17-3.22 (m, 1H), 2.68-2.76 (m, 1H), 2.07-2.10 (m, 2H), 2.03 (s, 3H), 1.85-1.98 (m, 3H), 1.60-1.77 (m, 4H), 1.18-1.29 (m, 3H), 1.00-1.12 (m, 3H)

| Ex. # | Structure | Compound Name | HPLC $t_R$ (min) | MS (ESI) [M + H]$^+$ |
|---|---|---|---|---|
| Ex. 210 | 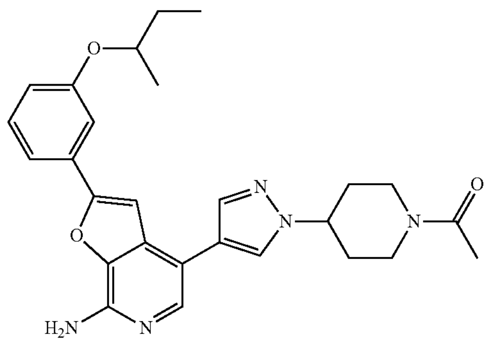 [SMILES: CCC(C)Oc1cccc(-c2cc3c(-c4cnn(C5CCN(C(C)=O)CC5)c4)cnc(N)c3o2)c1] | 1-[4-(4-{7-amino-2-[3-(butan-2-yloxy)phenyl[furo[2,3-c]pyridin-4-yl}-1H-pyrazol-1-yl)piperidin-1-yl]ethanone | 2.50 (ZQ3: polar_4 min) | 473.98 |

$^1$H NMR (400 MHz, CD$_3$OD): δ 8.14 (s, 1H), 7.91 (d, J = 0.8 Hz, 1H), 7.87 (s, 1H), 7.58-7.60 (m, 2H), 7.45 (s, 1H), 7.39 (t, J = 8 Hz, 1H), 6.96-7.00 (m, 1H), 4.63-4.71 (m, 1H), 4.49-4.52 (m, 1H), 4.07-4.12 (m, 1H), 3.54-3.61 (m, 1H), 3.31-3.35 (m, 1H), 2.80-2.90 (m, 1H), 2.19-2.27 (m, 2H), 2.17 (s, 3H), 1.97-2.12 (m, 2H), 1.63-1.80 (m, 2H), 1.31-1.32 (d, J = 6 Hz, 3H), 1.02 (t, J = 7.2 Hz, 3H)

| Ex. # | Structure | Compound Name | HPLC $t_R$ (min) | MS (ESI) [M + H]$^+$ |
|---|---|---|---|---|
| Ex. 211 | | ethyl (3-{4-[1-(1-acetylpiperidin-4-yl)-1H-pyrazol-4-yl]-7-aminofuro[2,3-c]pyridin-2-yl}phenoxy)acetate | 2.46 (ZQ3: polar_4 min) | 503.96 |

$^1$H NMR (400 MHz, CD$_3$OD): δ 8.16 (s, 1H), 7.93 (d, J = 0.4 Hz, 1H), 7.86 (s, 1H), 7.68-7.70 (d, J = 8 Hz, 1H), 7.65 (t, J = 2 Hz, 1H), 7.52 (s, 1H), 7.44 (t, J = 8 Hz, 1H), 7.02-7.04 (dd, J = 8 Hz, J = 2.8 Hz, 1H), 4.82 (s, 2H), 4.67-4.72 (m, 1H), 4.50-4.52 (m, 1H), 4.24-4.30 (q, J = 4.2 Hz, 2H), 4.06-4.12 (m, 1H), 3.30-3.36 (m, 1H), 2.80-2.90 (m, 1H), 2.20-2.25 (m, 2H), 2.17 (s, 3H), 1.97-2.12 (m, 2H), 1.30 (t, J = 7.2 Hz, 3H)

| Ex. # | Structure | Compound Name | HPLC $t_R$ (min) | MS (ESI) [M + H]+ |
|---|---|---|---|---|
| Ex. 212 | 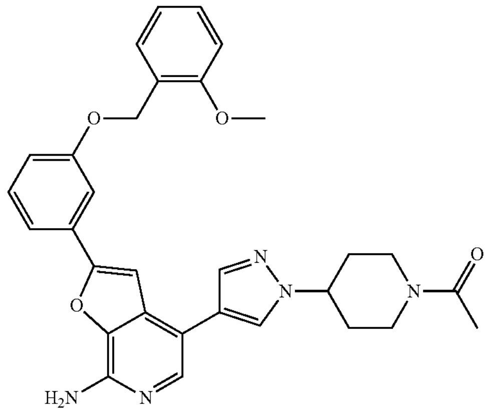 [SMILES: COc1ccccc1COc1cccc(-c2cc3c(-c4cnn(C5CCN(C(C)=O)CC5)c4)cnc(N)c3o2)c1] | 1-{4-[4-(7-amino-2-{3-[(2-methoxybenzyl)oxy]phenyl}furo[2,3-c]pyridin-4-yl)-1H-pyrazol-1-yl]piperidin-1-yl}ethanone | 2.65 (ZQ3: polar_4 min) | 538.02 |

¹H NMR (400 MHz, CD₃OD): δ 8.15 (s, 1H), 7.91 (d, J = 0.4 Hz, 1H), 7.87 (s, 1H), 7.68 (d, J = 2.4 Hz, 1H), 7.62-7.64 (m, 1H), 7.45-7.46 (m, 2H), 7.40 (t, J = 8 Hz, 1H), 7.29-7.34 (m, 1H), 7.04-7.07 (m, 1H), 7.01-7.03 (d, J = 8.4 Hz, 1H), 6.95-6.98 (m, 1H), 5.19 (s, 2H), 4.65-4.71 (m, 1H), 4.49-4.58 (m, 1H), 4.03-4.11 (m, 1H), 3.88 (s, 3H), 3.31-3.36 (m, 1H), 2.80-2.90 (m, 1H), 2.18-2.24 (m, 2H), 2.16 (s, 3H), 1.96-2.12 (m, 2H)

Example 213

1-(4-{4-[7-amino-2-(6-fluoro-1H-indol-3-yl)furo[2,3-c]pyridin-4-yl]-1H-pyrazol-1-yl}piperidin-1-yl)ethanone

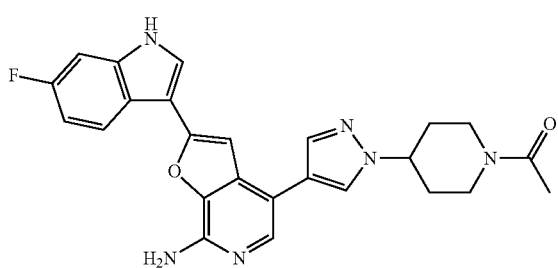 [SMILES: CC(=O)N1CCC(n2cc(-c3cnc(N)c4oc(-c5c[nH]c6cc(F)ccc56)cc34)cn2)CC1]

To a nitrogen degassed solution of 1-{4-[4-(7-amino-2-chloro-furo[2,3-c]pyridin-4-yl)-pyrazol-1-yl]-piperidin-1-yl}ethanone (0.050 g, 0.14 mmol) in 4:1 1,4-dioxane:water (10 mL) was added 6-fluoro-3-(4,4,5,5-tetramethyl-[1,3,2]dioxaborolan-2-yl)-1-triisopropylsilanyl-1H-indole (0.060 g, 0.143 mmol), potassium carbonate (0.047 g, 0.34 mmol), dichlorobis(triphenylphosphine)palladium (16 mg, 0.023 mmol). The mixture was heated at reflux for 3 h, then cooled to room temperature and concentrated. The residue was suspended in water and extracted with ethyl acetate (3×50 mL). The combined organic fractions were washed with water (15 mL), dried, and evaporated. Purification by flash chromatography (5% MeOH:DCM) afforded 18 mg (28%) of the title compound as a solid. ¹H NMR (300 MHz, CDCl₃): δ 1.99-2.14 (m, 2H), 2.17 (s, 3H), 2.24-2.34 (m, 2H), 2.81 (t, J=12 Hz, 1H), 3.29 (m, 1H), 4.02 (d, J=14.7 Hz, 1H), 4.40-4.48 (m, 1H), 4.78 (br. s, 2H), 4.78-4.82 (m, 1H), 6.97 (s, 1H), 7.07 (dt, J=9 Hz, 2.4 Hz, 1H), 7.16 (dd, J=9 Hz, 2.4 Hz, 1H), 7.70 (s, 1H), 7.78 (d, J=2.7 Hz, 1H), 7.87 (s, 1H), 7.92-7.97 (m, 2H), 8.94 (brs, 1H); MS (ESI): 459 [M+H]+.

The following Examples were prepared from 1-{4-[4-(7-amino-2-chloro-furo[2,3-c]pyridin-4-yl)-pyrazol-1-yl]-piperidin-1-yl}ethanone and an appropriate boronic acid or ester by a procedure analogous to Example 213.

| Ex. # | Structure and NMR Data | Compound Name | MS (ESI) [M + H]+ |
|---|---|---|---|
| 214 | 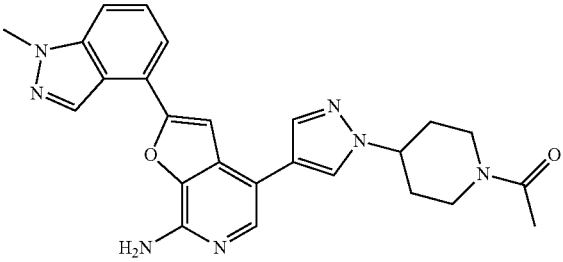<br>¹H NMR (300 MHz, CDCl₃): δ 2.01-2.18 (m, 2H), 2.20 (s, 3H), 2.22-2.38 (m, 2H), 2.77-2.84 (m, 1H), 3.24-3.38 (m, 1H), 3.99-4.10 (m, 1H), 4.15 (s, 3H), 4.40-4.58 (m, 1H), 4.78-4.85 (m, 1H), 4.91 (brs, 2H), 7.30 (s, 1H), 7.48-7.53 (m, 2H) 7.71-7.74 (m, 2H), 7.86 (s, 1H), 7.98 (s, 1H), 8.45 (s, 1H). | 1-(4-{4-[7-amino-2-(1-methyl-1H-indazol-4-yl)furo[2,3-c]pyridin-4-yl]-1H-pyrazol-1-yl}piperidin-1-yl)ethanone | 456 |
| 215 | 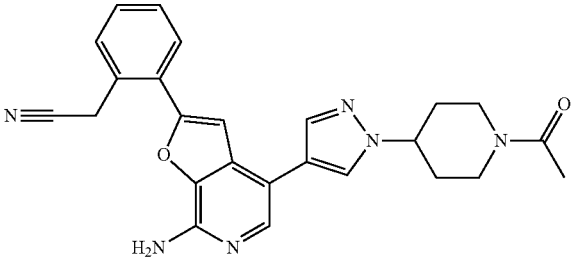<br>¹H NMR (300 MHz, CDCl₃): δ 1.90-2.03 (m, 2H), 2.18 (s, 3H), 2.20-2.29 (m, 2H), 2.71-2.85 (m, 1H), 3.21-3.36 (m, 1H), 3.98 (s, 2H), 3.99-4.05 (m, 1H), 4.38-4.50 (m, 1H), 4.70-4.85 (m, 1H), 4.99 (brs, 2H), 7.07 (s, 1H), 7.51-7.60 (m, 3H) 7.70 (s, 1H), 7.75-7.78 (m, 1H), 7.82 (s, 1H), 8.00 (s, 1H). | (2-{4-[1-(1-acetylpiperidin-4-yl)-1H-pyrazol-4-yl]-7-aminofuro[2,3-c]pyridin-2-yl}phenyl)acetonitrile | 441 |
| 216 | 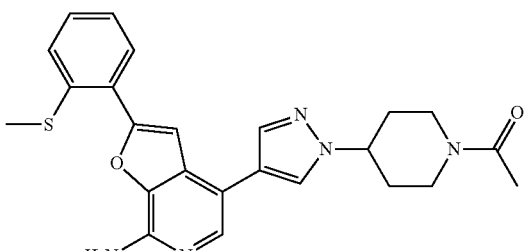<br>¹H NMR (300 MHz-CDCl₃) 11e: δ ppm = 1.99-2.01 (m, 2H), 2.15 (s, 3H), 2.22-2.38 (m, 2H), 2.54 (s, 3H), 2.76-2.84 (m, 1H), 3.22-3.32 (m, 1H), 3.97-4.02 (m, 1H), 4.38-4.45 (m, 1H), 4.76-4.77 (m, 1H), 4.80 (brs, 2H), 7.27-7.30 (m, 1H), 7.36-7.39 (m, 2H) 7.41 (s, 1H), 7.69 (s, 1H), 7.84-7.86 (m, 1H), 7.87 (s, 1H), 7.97 (s, 1H). | 1-[4-(4-{7-amino-2-[2-(methylsulfanyl)phenyl]furo[2,3-c]pyridin-4-yl}-1H-pyrazol-1-yl)piperidin-1-yl]ethanone | 448 |

| Ex. # | Structure and NMR Data | Compound Name | MS (ESI) [M + H]+ |
|---|---|---|---|
| 217 | 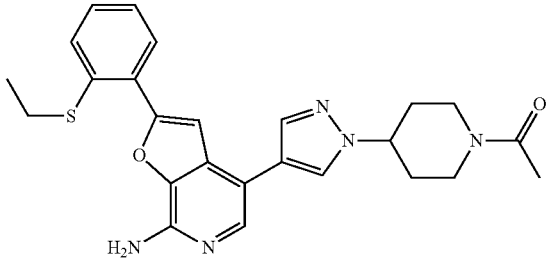<br>¹H NMR (300 MHz-CDCl₃) 11f: δ ppm = 1.27-1.37 (m, 3H), 1.95-2.07 (m, 2H), 2.12 (s, 3H), 2.20-2.32 (m, 2H), 2.79-2.84 (m, 1H), 2.97-3.04 (m, 2H), 3.22-3.27 (m, 1H), 3.96-4.02 (m, 1H), 4.36-4.45 (m, 1H), 4.45-4.74 (m, 1H), 4.80 (brs, 2H), 7.28-7.45 (m, 4H), 7.70 (s, 1H), 7.84-7.87 (m, 2H), 7.97 (s, 1H). | 1-[4-(4-{7-amino-2-[2-(ethylsulfanyl)phenyl]furo[2,3-c]pyridin-4-yl}-1H-pyrazol-1-yl)piperidin-1-yl]ethanone | 462 |
| 218 | 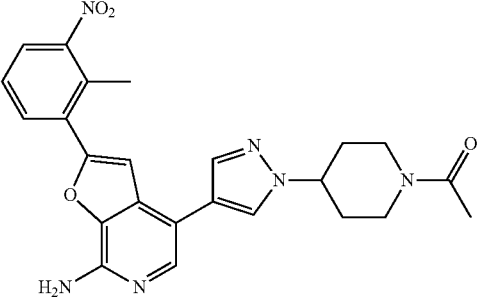<br>¹H NMR (300 MHz, CDCl₃): δ 1.99-2.09 (m, 2H), 2.15 (s, 3H), 2.21-2.32 (m, 2H), 2.62 (s, 3H), 2.76-2.84 (m, 1H), 3.22-3.32 (m, 1H), 4.00 (d, J = 14.1 Hz, 1H), 4.39-4.46 (m, 1H), 4.77-4.82 (m, 3H), 7.02 (s, 1H), 7.47 (t, J = 9.0 Hz, 1H), 7.68 (s, 1H), 7.81 (s, 1H), 7.86-7.93 (m, 2H), 8.00 (s, 1H) | 1-(4-{4-[7-amino-2-(2-methyl-3-nitrophenyl)furo[2,3-c]pyridin-4-yl]-1H-pyrazol-1-yl}piperidin-1-yl)ethanone | — |
| 219 | 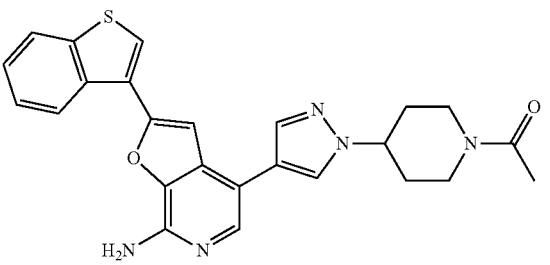<br>¹H NMR (300 MHz, CDCl₃): δ 2.01-2.10 (m, 2H), 2.16 (s, 3H), 2.24-2.34 (s, 2H), 2.76-2.86 (m, 1H), 3.23-3.33 (s, 1H), 3.98-4.03 (d, J = 15.0 Hz, 1H), 4.40-4.48 (m, 1H), 4.76 (d, J = 6.9 Hz, 1H), 4.86 (brs, 2H), 7.17 (s, 1H), 7.46-7.56 (m, 1H), 7.70 (s, 1H), 7.87 (s, 1H), 7.94-7.98 (m, 3H), 8.02 (s, 1H), 8.26 (d, J = 7.5 Hz, 1H) | 1-(4-{4-[7-amino-2-(1-benzothiophen-3-yl)furo[2,3-c]pyridin-4-yl]-1H-pyrazol-1-yl}piperidin-1-yl)ethanone | — |

| Ex. # | Structure and NMR Data | Compound Name | MS (ESI) [M + H]⁺ |
|---|---|---|---|
| 220 | 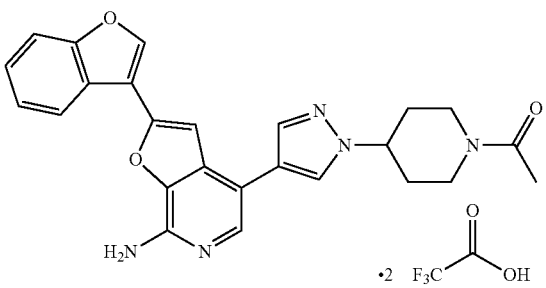<br>¹H NMR (400 MHz, DMSO-d₆): δ 8.62 (br s, 2H), 8.51 (s, 1H), 8.09 (d, J = 0.8 Hz, 1H), 8.03 (s, 1H), 8.02 (s, 1H), 7.87 (dd, J = 7.2, 0.8 Hz, 1H), 7.75 (dd, J = 8.4, 0.8 Hz, 1H), 7.68 (d, J = 0.8 Hz, 1H), 7.47-7.53 (m, 1H), 7.38-7.43 (m, 1H), 4.48-4.58 (m, 2H), 3.94-4.02 (m, 1H), 3.22-3.31 (m, 1H), 2.72-2.82 (m, 1H), 2.08-2.18 (m, 2H), 2.08 (s, 3H), 1.93-2.06 (m, 1H), 1.82-1.92 (m, 1H) | 1-(4-{4-[7-amino-2-(1-benzofuran-3-yl)furo[2,3-c]pyridin-4-yl]-1H-pyrazol-1-yl}piperidin-1-yl)ethanone bis(trifluoroacetate) | 442.15 |
| 221 | 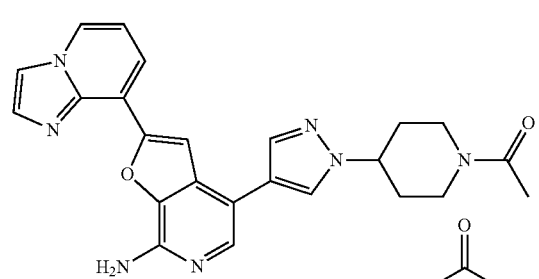<br>¹H NMR (400 MHz, DMSO-d₆): δ 8.84 (dd, J = 6.4, 1.2 Hz, 1H), 8.49 (br s, 2H), 8.39 (s, 1H), 8.37 (s, 1H), 8.26 (d, J = 6.8 Hz, 1H), 8.23 (d, J = 1.2 Hz, 1H), 7.99 (d, J = 0.4 Hz, 1H), 7.93 (s, 1H), 7.90 (s, 1H), 7.30 (t, J = 6.8 Hz, 1H), 4.55-4.63 (m, 1H), 4.48-4.55 (m, 1H), 3.94-4.01 (m, 1H), 3.22-3.31 (m, 1H), 2.73-2.82 (m, 1H), 2.08-2.18 (m, 2H), 2.07 (s, 3H), 1.93-2.03 (m, 1H), 1.79-1.92 (m, 1H) | 1-(4-{4-[7-amino-2-(imidazo[1,2-a]pyridin-8-yl)furo[2,3-c]pyridin-4-yl]-1H-pyrazol-1-yl}piperidin-1-yl)ethanone bis(trifluoroacetate) | 442.09 |

Example 222

3-{4-[1-(1-acetylpiperidin-4-yl)-1H-pyrazol-4-yl]-7-aminofuro[2,3-c]pyridin-2-yl}-1H-indole-6-carbonitrile

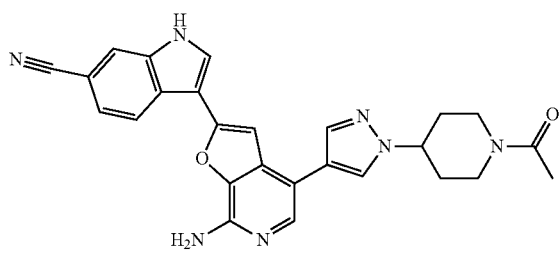 [SMILES: CC(=O)N1CCC(n2cc(-c3cnc(N)c4oc(-c5c[nH]c6cc(C#N)ccc56)cc34)cn2)CC1]

Step A: 3-bromo-1H-indole-6-carbonitrile

To a solution of 1H-indole-6-carbonitrile (1.6 g, 11.25 mmol) in DCM (60 mL) was added NBS (2.0 g, 11.25 mmol) in portions over a period of 5 minutes. The resultant mixture was stirred for 1 h. The reaction mixture was quenched with saturated sodium thiosulfate solution (25 mL) and further diluted with DCM (60 mL). The organic layer was washed with water (2×25 mL) followed by brine solution and dried over anhydrous sodium sulfate, filtered and concentrated to afford 2.50 g (99%) of the title compound. $^1$H NMR (300 MHz, CDCl$_3$): δ 7.43 (d, J=7.4 Hz, 1 H), 7.45 (s, 1 H), 7.67 (d, J=6.9 Hz, 1 H), 7.79 (s, 1 H), 8.67 (br. s., 1H).

Step B: 3-(4,4,5,5-tetramethyl-[1,3,2]dioxaborolan-2-yl)-1H-indole-6-carbonitrile A solution of trisbenzylideneacetone dipalladium (0) (242 mg, 0.26 mmole) and tricyclohexylphosphine (281 mg, 1.0 mmole) in degassed 1,4-dioxane (100 mL) was bubbled with N$_2$ for 10 minutes, 4,4,5,5,4',4',5',5'-octamethyl-[2,2']bi[[1,3,2]dioxaborolanyl] 1.37 g, 5.41 mmol), potassium acetate (728 mg, 7.43 mmol) and 3-bromo-1H-indole-6-carbonitrile (1.0 g, 4.5 mmol) were added and the resultant solution was heated at 90-95° C. overnight. The reaction mixture was cooled to room temperature, filtered to remove the catalyst and the filtrate was concentrated to a residue. The residue was triturated with hot hexanes (2×) and the solid was filtered to afford 700 mg (58%) of the title compound. $^1$H NMR (300 MHz, CDCl$_3$): δ 1.39 (s, 12 H), 7.10 (d, J=6.70 Hz, 1 H), 7.70 (s, 1 H), 7.84 (s, 1 H), 8.10 (d, J=6.40 Hz, 1 H), 8.95 (br. s, 1 H).

Step C: 3-{4-[1-(1-acetylpiperidin-4-yl)-1H-pyrazol-4-yl]-7-aminofuro[2,3-c]pyridin-2-yl}-1H-indole-6-carbonitrile (Title Compound)

The title compound was prepared in 60% yield from 1-{4-[4-(7-amino-2-chloro-furo[2,3-c]pyridin-4-yl)-4,5-dihydropyrazol-1-yl]-piperidin-1-yl}ethanone and 3-(4,4,5,5-tetramethyl-[1,3,2]dioxaborolan-2-yl)-1H-indole-6-carbonitrile by a procedure analogous to Example 213. $^1$H NMR (600 MHz, CD$_3$OD): δ 1.99-2.02 (m, 2H), 2.12 (s, 3H), 2.14-2.24 (m, 2H), 2.84-2.88 (m, 1H), 3.29-3.38 (m, 1H), 4.07-4.11 (m, 1H), 4.52-4.54 (m, 1H), 4.67-4.70 (m, 1H), 7.25 (s, 1H), 7.51 (d, J=7.8 Hz, 1H), 7.84 (s, 1H), 7.89 (s, 1H), 7.92 (s, 1H), 8.15 (s, 1H), 8.25 (s, 1H), 8.39 (d, J=8.0 Hz, 1H); MS (ESI): 466 [M+H]$^+$.

Example 223

1-(4-{4-[7-amino-2-(4-fluoro-1,2-benzothiazol-7-yl)furo[2,3-c]pyridin-4-yl]-1H-pyrazol-1-yl}piperidin-1-yl)ethanone diformate salt

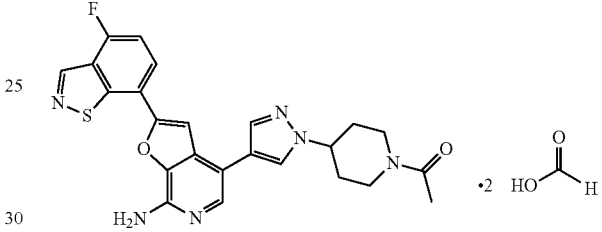

Step A: 3-bromo-2-(tert-butylsulfanyl)-6-fluorobenzaldehyde

A mixture of 3-bromo-2,6-difluorobenzaldehyde (2.00 g, 9.05 mmol), 2-methyl-2-propanethiol (0.917 mL, 8.13 mmol), and potassium carbonate (1.5 g, 11 mmol) in DMF (6 mL) was heated to 50° C. overnight in a sealed tube. The material was extracted with EtOAc, and washed with water (3×). Purification of the organic layer by column chromatography (1 to 2% EtOAc:hexanes) afforded 1.2 g (51%) of the title compound as a yellow solid. $^1$H NMR (400 MHz, CDCl$_3$): δ 1.34 (s, 9 H), 7.07-7.16 (m, 1 H), 7.91 (dd, J=9.0, 5.2 Hz, 1H), 10.56-10.63 (m, 1 H).

Step B: 7-bromo-4-fluoro-1,2-benzothiazole

A mixture of 3-bromo-2-(tert-butylsulfanyl)-6-fluorobenzaldehyde (1.20 g, 4.12 mmol) and hydroxylamine hydrochloride (1.432 g, 20.60 mmol) in isopropanol (60 mL, 800 mmol) and water (10 mL) was heated to 70° C. for 20 min. The organic solvent was removed in vacuo, and saturated aqueous sodium bicarbonate was added to bring the pH to 8.5. The material was extracted with DCM and water, and the organic layer was concentrated in vacuo. The residue was treated with p-toluenesulfonic acid (141.9 mg, 0.8242 mmol) in n-butanol (60 mL) and the solution was heated to 120° C. overnight. The solvent was removed in vacuo. The residue was purified by column chromatography (1 to 2% EtOAc:

hexanes) to afford 382 mg (40%) of the title compound as a white solid. $^1$H NMR (400 MHz, CDCl$_3$): δ 7.01 (dd, J=9.1, 8.3 Hz, 1 H), 7.60 (dd, J=8.3, 4.0 Hz, 1 H), 9.10 (s, 1 H).

Step C: 4-fluoro-7-(4,4,5,5-tetramethyl-1,3,2-dioxaborolan-2-yl)-1,2-benzothiazole A mixture of 7-bromo-4-fluoro-1,2-benzothiazole (400.0 mg, 1.724 mmol), bis(pinacolato)diboron (523 mg, 2.06 mmol), (1,1'bis-(diphenylphosphino)-ferrocene) palladium dichloride (63.0 mg, 0.0862 mmol), and potassium acetate (295 mg, 3.01 mmol) in 1,4-dioxane (30 mL) was heated to 90° C. for 2 h. The solution was concentrated in vacuo, and the residue purified by column chromatography (1 to 3% EtOAc:heptane) to afford 260 mg (54%) of the title compound as a white solid. $^1$H NMR (400 MHz, CDCl$_3$): δ 1.41 (s, 12 H), 7.08 (dd, J=9.9, 7.8 Hz, 1 H), 7.96 (dd, J=7.8, 5.3 Hz, 1 H), 9.03 (s, 1 H); MS (ESI): 280.10 [M+H]$^+$; HPLC t$_R$=1.80 min (TOF: polar_3 min).

Step D: 1-(4-{4-[7-amino-2-(4-fluoro-1,2-benzothiazol-7-yl)furo[2,3-c]pyridin-4-yl]-1H-pyrazol-1-yl}piperidin-1-yl)ethanone diformate salt (Title Compound)

A mixture of 1-{4-[4-(7-amino-2-chlorofuro[2,3-c]pyridin-4-yl)-1H-pyrazol-1-yl]piperidin-1-yl}ethanone (15.0 mg, 0.0417 mmol), 4-fluoro-7-(4,4,5,5-tetramethyl-1,3,2-dioxaborolan-2-yl)-1,2-benzothiazole (23.3 mg, 0.0824 mmol), Pd(PPh$_3$)$_4$ (4.82 mg, 0.00417 mmol), potassium carbonate (17.3 mg, 0.125 mmol) and 4:1 dioxane:H$_2$O (1 mL) was heated in a microwave reactor at 110° C. for 40 min. The crude reaction mixture was purified by preparative HPLC to afford 3.8 mg (19%) the title compound as a yellow solid. $^1$H NMR (400 MHz, CD$_3$OD): δ 1.97-2.15 (m, 2 H), 2.19 (s, 3 H), 2.19-2.30 (m, 2 H), 2.88 (td, J=13.0, 2.8 Hz, 1 H), 3.33-3.40 (m, 1 H), 4.07-4.16 (m, 1 H), 4.54 (tt, J=11.5, 4.2 Hz, 1 H), 4.65-4.74 (m, 1 H), 7.27 (dd, J=9.3, 8.3 Hz, 1 H), 7.41 (s, 1 H), 7.83 (s, 1H), 7.87 (s, 1 H), 8.09 (s, 1H), 8.20 (s, 2 H), 8.22 (dd, J=8.3, 4.5 Hz, 1 H), 9.06 (s, 1 H); MS (ESI): 477.13 [M+H]$^+$; HPLC t$_R$=1.10 min (TOF: polar_3 min).

The following Examples were prepared from 1-{4-[4-(7-amino-2-chlorofuro[2,3-c]pyridin-4-yl)-1H-pyrazol-1-yl]piperidin-1-yl}ethanone and an appropriate boronic acid or ester by a procedure analogous to Example 223, Step D.

| Ex. # | Structure and NMR Data | Compound Name | MS (ESI) [M + H]$^+$ | HPLC t$_R$ (min) |
|---|---|---|---|---|
| 224 | 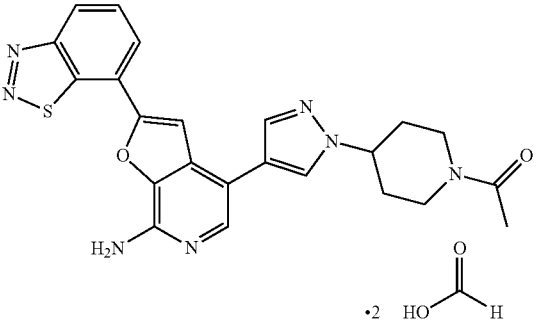<br>$^1$H NMR (400 MHz, CD$_3$OD): δ 1.98-2.16 (m, 2H), 2.18 (s, 3H), 2.19-2.30 (m, 2H), 2.88 (td, J = 12.9, 2.8 Hz, 1H), 3.33-3.41 (m, 1H), 4.07-4.16 (m, 1H), 4.55 (tdd, J = 11.4, 11.4, 4.2, 4.0 Hz, 1H), 4.66-4.75 (m, 1H), 7.65 (s, 1H), 7.86 (dd, J = 8.2, 7.5 Hz, 1H), 7.89 (s, 1H), 7.92 (s, 1H), 8.14 (s, 1H), 8.18 (s, 2H), 8.43-8.48 (m, 1H), 8.71 (d, J = 8.1 Hz, 1H) | 1-(4-{4-[7-amino-2-(1,2,3-benzothiadiazol-7-yl)furo[2,3-c]pyridin-4-yl]-1H-pyrazol-1-yl}piperidin-1-yl)ethanone diformate salt | 460.15 | 1.06 (TOF: polar_3 min) |

| Ex. # | Structure and NMR Data | Compound Name | MS (ESI) [M + H]+ | HPLC $t_R$ (min) |
|---|---|---|---|---|
| 225 | 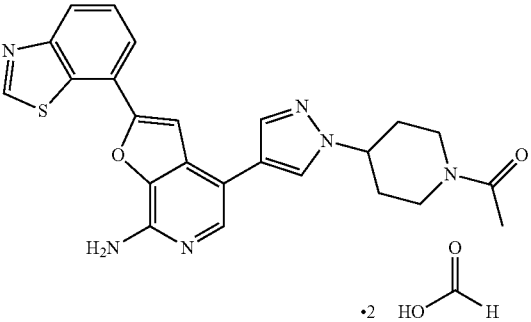<br>¹H NMR (400 MHz, CD₃OD): δ 1.98-2.15 (m, 2H), 2.18 (s, 3H), 2.19-2.28 (m, 2H), 2.87 (td, J = 12.9, 2.7 Hz, 1H), 3.33-3.40 (m, 1H), 4.05-4.17 (m, 1H), 4.55 (tt, J = 11.5, 4.1 Hz, 1 H), 4.65-4.74 (m, 1H), 7.58 (s, 1H), 7.71 (t, J = 7.8 Hz, 1H), 7.87 (s, 1H), 7.92 (s, 1H), 8.15 (s, 1H), 8.16 (s, 2H), 8.18-8.20 (m, 1H), 8.23 (d, J = 7.6 Hz, 1H), 9.37 (s, 1H) | 1-(4-{4-[7-amino-2-(1,3-benzothiazol-7-yl)furo[2,3-c]pyridin-4-yl]-1H-pyrazol-1-yl}piperidin-1-yl)ethanone diformate salt | 459.15 | 0.99 (TOF: polar_3 min) |
| 226 | 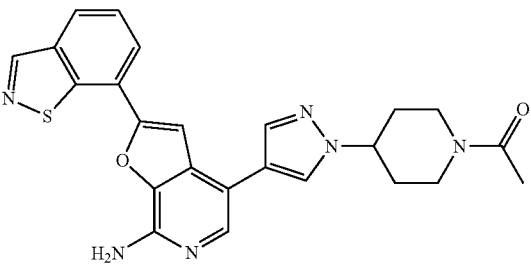<br>¹H NMR (400 MHz, DMSO-d₆): δ 9.29 (s, 1 H), 8.46 (dd, J = 7.2, 0.8 Hz, 1H), 8.37 (dd, J = 8.0, 0.8 Hz, 1H), 8.32 (s, 1H), 8.07 (s, 1H), 8.01 (d, J = 0.4 Hz, 1H), 7.90 (s, 1H), 7.75 (t, J = 7.6 Hz, 1H), 6.32 (br s, 2H), 4.47-4.56 (m, 2H), 3.94-4.02 (m, 1H), 3.21-3.30 (m, 1H), 2.72-2.82 (m, 1H), 2.08-2.18 (m, 2H), 2.08 (s, 3H), 1.93-2.06 (m, 1H), 1.81-1.92 (m, 1H) | 1-(4-{4-[7-amino-2-(1,2-benzothiazol-7-yl)furo[2,3-c]pyridin-4-yl]-1H-pyrazol-1-yl}piperidin-1-yl)ethanone | 459.13 | 1.01 (TOF: polar_3 min) |

| Ex. # | Structure and NMR Data | Compound Name | MS (ESI) [M + H]⁺ | HPLC $t_R$ (min) |
|---|---|---|---|---|
| 227 | 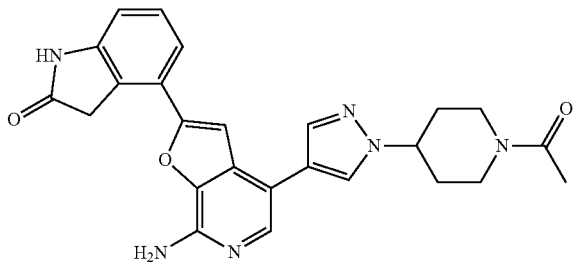<br>¹H NMR (400 MHz, DMSO-d₆): δ 10.58 (s, 1H), 8.28 (s, 1H), 8.06-7.95 (m, 2H), 7.69 (d, J = 7.1 Hz, 1H), 7.53 (s, 1H), 7.35 (t, J = 7.8 Hz, 1H), 6.91 (d, J = 7.1 Hz, 1H), 6.39 (s, 2H), 4.63-4.28 (m, 2H), 4.03 (s, 2H), 4.01-3.87 (m, 1H), 3.28-3.15 (m, 1H), 2.83-2.65 (m, 1H), 2.19-1.91 (m, 6H), 1.91-1.77 (m, 1H) | 4-{4-[1-(1-acetylpiperidin-4-yl)-1H-pyrazol-4-yl]-7-aminofuro[2,3-c]pyridin-2-yl}-1,3-dihydro-2H-indol-2-one | 457.20 | 2.29 (ZQ3: polar_4 min) |

Example 228

(4-{4-[7-amino-2-(thieno[2,3-c]pyridin-3-yl)furo[2,3-c]pyridin-4-yl]-1H-pyrazol-1-yl}piperidin-1-yl)(cyclopropyl)methanone diformate salt

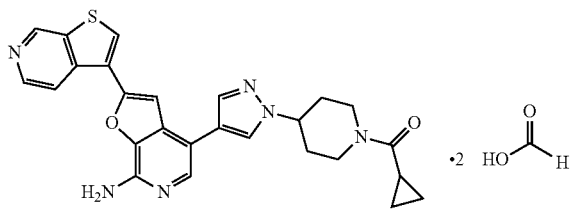

The title compound was prepared by a procedure analogous to Example 223, Step D. ¹H NMR (400 MHz, CD₃OD): δ 0.78-0.99 (m, 4 H), 1.97-2.07 (m, 2 H), 2.08-2.23 (m, 2 H), 2.23-2.34 (m, 1 H), 2.90 (t, J=12.4 Hz, 1 H), 3.34-3.47 (m, 1 H), 4.47-4.61 (m, 2 H), 4.68 (d, J=12.6 Hz, 1 H), 7.56 (s, 1 H), 7.82 (s, 1 H), 7.94 (s, 1 H), 8.19 (s, 1 H), 8.19 (s, 2 H), 8.51 (d, J=5.6 Hz, 1 H), 8.57 (d, J=5.3 Hz, 1 H), 8.70 (s, 1 H), 9.22 (br. s., 1 H); MS (ESI): 485.56 [M+H]⁺; HPLC $t_R$=0.63 min (HPLC: polar_2 min).

Example 229 trans-4-{4-[7-amino-2-(1,2,3-benzothiadiazol-7-yl)furo[2,3-c]pyridin-4-yl]-1H-pyrazol-1-yl}cyclohexanol

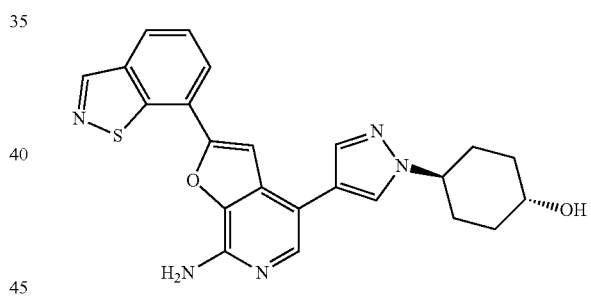

A mixture of 4-{1-[4-(tert-butyl-dimethyl-silanyloxy)-cyclohexyl]-1H-pyrazol-4-yl}-2-chloro-furo[2,3-c]pyridin-7-ylamine (179 mg, 0.400 mmol), 7-(4,4,5,5-tetramethyl-1,3,2-dioxaborolan-2-yl)-1,2,3-benzothiadiazole (105.0 mg, 0.4006 mmol), Pd(PPh₃)₄ (46.3 mg, 0.0400 mmol), potassium carbonate (166 mg, 1.20 mmol) and 4:1 1,4-dioxane: water (6 mL) was heated in a microwave reactor at 110° C. for 1 h. Aqueous 12 N hydrochloric acid (0.5 mL, 6 mmol) and methanol (2 mL) were added, and the solution was heated to 30° C. for 30 min. The organic solvent was removed in vacuo, and the material was extracted with DCM and saturated aqueous sodium bicarbonate (2×). The organic layer was purified by column chromatography (1 to 3% 7 N ammonia/methanol: DCM), followed by trituration from methanol (5 mL) and filtration to afford 80 mg (50%) of the title compound as a yellow solid. ¹H NMR (400 MHz, DMSO-d₆): δ 1.31-1.46 (m, 2 H), 1.82-2.02 (m, 4 H), 2.04-2.15 (m, 2 H), 3.48-3.61 (m, 1 H), 4.14-4.25 (m, 1 H), 4.71 (d, J=4.5 Hz, 1 H), 6.42 (s, 2 H), 7.94-8.03 (m, 3 H), 8.06 (s, 1 H), 8.26 (s, 1 H), 8.65 (dd, J=7.5, 0.6 Hz, 1 H), 8.81-8.89 (m, 1 H); MS (ESI): 433.14 [M+H]⁺; HPLC $t_R$=1.18 min (TOF: polar_3 min).

The following Examples were prepared from 4-{1-[4-(tert-butyl-dimethyl-silanyloxy)-cyclohexyl]-1H-pyrazol-4-yl}-2-chloro-furo[2,3-c]pyridin-7-ylamine and an appropriate boronic acid or ester by a procedure analogous to Example 229.

| Ex. # | Structure and NMR Data | Compound Name | MS (ESI) [M + H]⁺ | HPLC $t_R$ (min) |
|---|---|---|---|---|
| 230 | 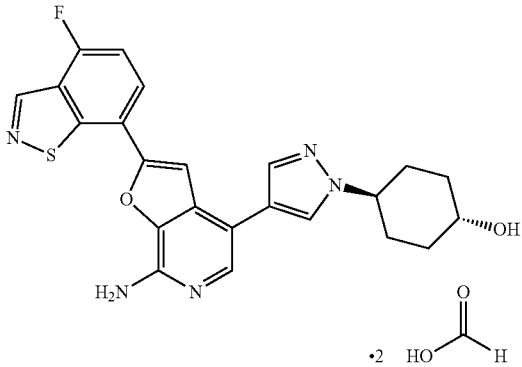<br>¹H NMR (400 MHz, CD₃OD): δ 1.46-1.58 (m, 2H), 2.00 (dtd, J = 13.0, 12.6, 12.6, 2.9 Hz, 2H), 2.09-2.25 (m, 4H), 3.66-3.76 (m, 1H), 4.21-4.32 (m, 1H), 7.29-7.37 (m, 1H), 7.49 (s, 1H), 7.88 (d, J = 3.0 Hz, 2H), 8.08 (s, 1H), 8.25-8.30 (m, 1H), 8.33 (s, 2H), 9.12 (s, 1H) | trans-4-{4-[7-amino-2-(4-fluoro-1,2-benzothiazol-7-yl)furo[2,3-c]pyridin-4-yl]-1H-pyrazol-1-yl}cyclohexanol diformate salt | 450.13 | 1.09 (TOF: polar_3 min) |
| 231 | 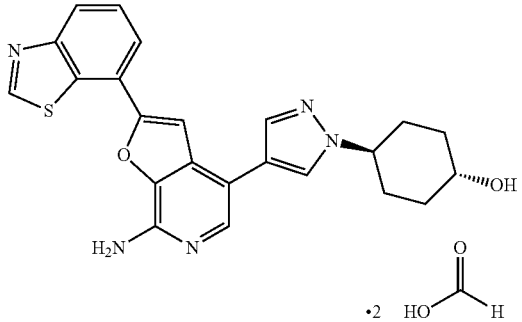<br>¹H NMR (400 MHz, CD₃OD): δ 1.45-1.59 (m, 2H), 1.99 (dtd, J = 12.8, 12.6, 12.6, 2.9 Hz, 2H), 2.08-2.25 (m, 4H), 3.71 (tdd, J = 10.9, 10.9, 4.2, 4.0 Hz, 1H), 4.27 (tt, J = 11.8, 3.8 Hz, 1H), 7.60 (s, 1H), 7.72 (t, J = 8.0 Hz, 1H), 7.86 (s, 1H), 7.90 (s, 1H), 8.13 (s, 1H), 8.16 (s, 2H), 8.18 (d, J = 8.3 Hz, 1H), 8.25 (d, J = 7.6 Hz, 1H), 9.37 (s, 1H) | trans-4-{4-[7-amino-2-(1,3-benzothiazol-7-yl)furo[2,3-c]pyridin-4-yl]-1H-pyrazol-1-yl}cyclohexanol diformate salt | 432.14 | 0.99 (TOF: polar_3 min) |

| Ex. # | Structure and NMR Data | Compound Name | MS (ESI) [M + H]⁺ | HPLC $t_R$ (min) |
|---|---|---|---|---|
| 232 | 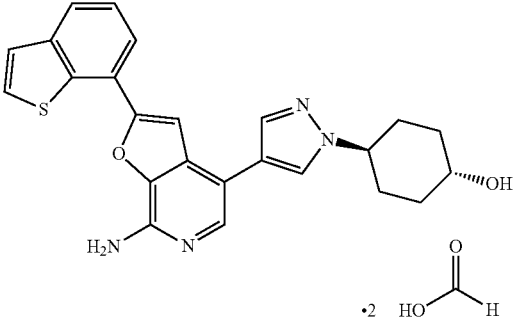<br>¹H NMR (400 MHz, CD₃OD): δ 1.45-1.59 (m, 2H), 1.91-2.05 (m, 2H), 2.08-2.24 (m, 4H), 3.70 (tdd, J = 10.9, 10.9, 4.2, 4.0 Hz, 1H), 4.26 (tt, J = 11.8, 3.8 Hz, 1H), 7.48-7.55 (m, 3H), 7.71 (d, J = 5.3 Hz, 1H), 7.83 (s, 1H), 7.87 (s, 1H), 7.93-7.98 (m, 1H), 8.08 (s, 1H), 8.12 (d, J = 7.3 Hz, 1H), 8.40 (s, 2H) | trans-4-{4-[7-amino-2-(1-benzothiophen-7-yl)furo[2,3-c]pyridin-4-yl]-1H-pyrazol-1-yl}cyclohexanol diformate salt | 431.13 | 1.07 (TOF: polar_3 min) |
| 233 | 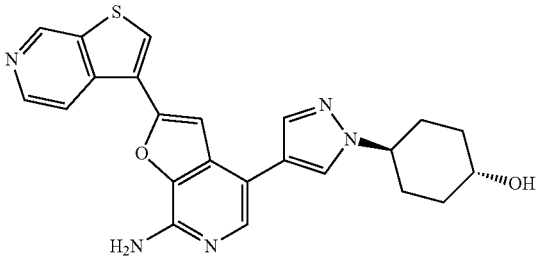<br>¹H NMR (400 MHz, DMSO-d₆): δ 9.40 (d, J = 0.76 Hz, 1H), 8.82 (s, 1H), 8.68 (dd, J = 5.56, 1.26 Hz, 1H), 8.64 (d, J = 5.56 Hz, 1H), 8.25 (s, 1H), 8.01 (s, 1H), 7.96 (s, 1H), 7.73 (s, 1H), 6.46 (s, 2H), 4.70 (br s, 1H), 4.19 (tt, J = 11.49, 3.92 Hz, 1H), 3.47-3.59 (m, 1H), 2.07 (dd, J = 12.25, 2.65 Hz, 2H), 1.80-2.01 (m, 4H), 1.38 (quin, J = 13.10 Hz, 2H) | trans-4-{4-[7-amino-2-(thieno[2,3-c]pyridin-3-yl)furo[2,3-c]pyridin-4-yl]-1H-pyrazol-1-yl}cyclohexanol | 432.13 | 2.44 (ZQ3: polar_4 min) |

| Ex. # | Structure and NMR Data | Compound Name | MS (ESI) [M + H]+ | HPLC $t_R$ (min) |
|---|---|---|---|---|
| 234 | 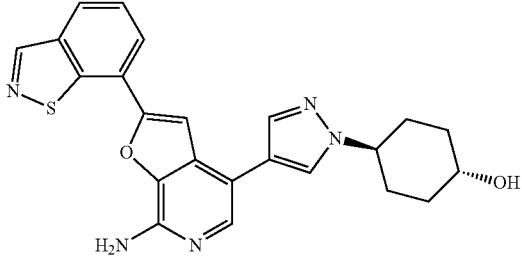 [SMILES: Nc1ncc(-c2cnn([C@H]3CC[C@H](O)CC3)c2)c2cc(-c3cccc4cnsc34)oc12]<br>¹H NMR (400 MHz, DMSO-d₆): δ 9.28 (s, 1H), 8.46 (dd, J = 7.33, 0.76 Hz, 1H), 8.36 (dd, J = 7.83, 0.76 Hz, 1H), 8.26 (d, J = 0.51 Hz, 1H), 8.05 (s, 1H), 7.96 (d, J = 0.51 Hz, 1H), 7.88 (s, 1H), 7.74 (dd, J = 7.70, 7.70 Hz, 1H), 6.30 (s, 2H), 4.70 (d, J = 4.29 Hz, 1H), 4.20 (tt, J = 11.49, 3.92 Hz, 1H), 3.49-3.60 (m, 1H), 2.08 (br d, J = 12.10 Hz, 2H), 1.82-2.02 (m, 4H), 1.32-1.46 (m, 2H) | trans-4-{4-[7-amino-2-(1,2-benzothiazol-7-yl)furo[2,3-c]pyridin-4-yl]-1H-pyrazol-1-yl}cyclohexanol | 432.25 | 2.72 (ZQ3: polar_4 min) |
| 235 | 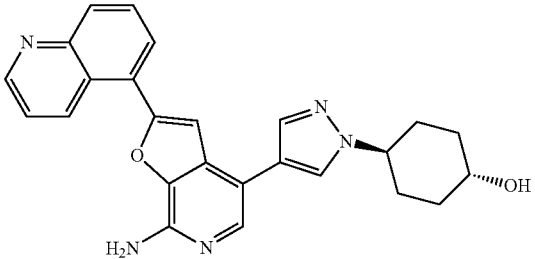<br>¹H NMR (400 MHz, CD₃OD): δ 9.02 (d, J = 8.6 Hz, 1H), 8.93 (dd, J = 1.5, 4.3 Hz, 1H), 8.18-8.12 (m, 2H), 8.10 (s, 1H), 7.92 (s, 1H), 7.89 (t, J = 15.9 Hz, 2H), 7.67 (dd, J = 4.2, 8.7 Hz, 1H), 7.46 (s, 1H), 4.24 (tt, J = 3.8, 11.8 Hz, 1H), 3.74-3.64 (m, 1H), 2.25-2.06 (m, 4H), 1.98 (dq, J = 2.8, 12.6 Hz, 2H), 1.58-1.43 (m, J = 3.0 Hz, 2H) | trans-4-{4-[7-amino-2-(quinolin-5-yl)furo[2,3-c]pyridin-4-yl]-1H-pyrazol-1-yl}cyclohexanol | 426.32 | — |

Example 236

5-{4-[1-(1-acetylpiperidin-4-yl)-1H-pyrazol-4-yl]-7-aminofuro[2,3-c]pyridin-2-yl}-1H-indazole-3-carbonitrile

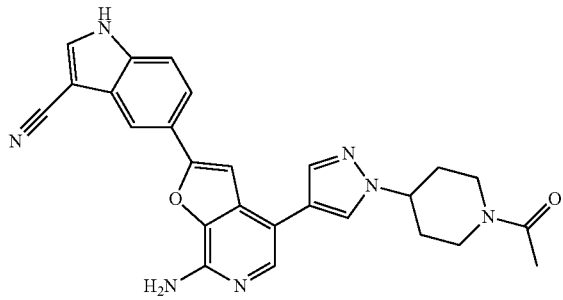 [SMILES: CC(=O)N1CCC(n2cc(-c3cnc(N)c4oc(-c5ccc6[nH]cc(C#N)c6c5)cc34)cn2)CC1]

Step A: 5-bromo-1-(tetrahydro-2H-pyran-2-yl)-1H-indazole-3-carbaldehyde

A solution of 5-bromo-1H-indazole-3-carbaldehyde (1.00 g, 4.44 mmol), dihydropyran (912 uL, 10.0 mmol), and p-toluenesulfonic acid monohydrate (16.9 mg, 0.0889 mmol) in DCM (8.8 mL) was stirred at room temperature for 24 h. The reaction was poured into saturated aqueous sodium bicarbonate (10 mL) and extracted with dichloromethane (3×5 mL). The combined organic fractions were washed with saturated aqueous sodium chloride (1×10 mL), dried over sodium sulfate, filtered, and concentrated. Purification by ISCO chromatography (10 to 40% ethyl acetate:heptane) afforded 858 mg (56%) of the title compound as a white solid. $^1$H NMR (400 MHz, DMSO-$d_6$): δ 10.17 (s, 1 H), 8.28 (d, J=1.8 Hz, 1 H), 7.92 (d, J=8.3 Hz, 1 H), 7.80-7.61 (m, 1 H), 6.08 (dd, J=2.5, 9.3 Hz, 1 H), 3.99-3.69 (m, 2 H), 2.46-2.26 (m, 1 H), 2.17-1.92 (m, 2 H), 1.87-1.67 (m, 1 H), 1.68-1.53 (m, 2 H); MS (ESI): 309.03, 311.05 [M+H]$^+$; HPLC $t_R$=3.38 min (ZQ3, nonpolar_4 min).

Step B: 5-bromo-1-(tetrahydro-2H-pyran-2-yl)-1H-indazole-3-carbonitrile

To a solution of 5-bromo-1-(tetrahydro-2H-pyran-2-yl)-1H-indazole-3-carbaldehyde (353 mg, 1.14 mmol) in MeCN (11.4 mL) was added triethylamine (223 uL, 1.60 mmol) and hydroxylamine hydrochloride (95.2 mg, 1.37 mmol). The reaction was heated to 60° C. for 16 h. The reaction mixture was then cooled to room temperature and additional triethylamine (541 uL, 3.88 mmol) was added, followed by trichloroacetyl chloride (306 uL, 2.74 mmol) dropwise. After stirring 30 min at room temperature, the reaction was heated to 65° C. for 20 h. The reaction mixture was then cooled to room temperature and poured into saturated aqueous sodium chloride (100 mL). The aqueous fraction was extracted with ethyl acetate (3×75 mL). The combined organic fractions were dried over sodium sulfate, filtered, and concentrated onto silica gel. Purification by ISCO chromatography (10 to 40% ethyl acetate:hexanes) afforded 301 mg (86%) of the title compound as a white solid. $^1$H NMR (400 MHz, DMSO-$d_6$): δ 8.19 (d, J=1.8 Hz, 1 H), 7.97 (d, J=8.3 Hz, 1 H), 7.75 (dd, J=1.9, 9.0 Hz, 1 H), 6.07 (dd, J=2.5, 9.1 Hz, 1 H), 3.97-3.60 (m, 2 H), 2.40-2.17 (m, 1 H), 2.12-1.91 (m, 2 H), 1.84-1.64 (m, 1 H), 1.66-1.47 (m, 2 H); HPLC $t_R$=3.73 min.

Step C: 1-(tetrahydro-2H-pyran-2-yl)-5-(4,4,5,5-tetramethyl-1,3,2-dioxaborolan-2-yl)-1H-indazole-3-carbonitrile A solution of 5-bromo-1-(tetrahydro-2H-pyran-2-yl)-1H-indazole-3-carbonitrile (175 mg, 0.572 mmol), bis(pinacolato)diboron (174 mg, 0.686 mmol), potassium acetate (168 mg, 1.71 mmol), and 1,1'-bis(diphenylphosphino)ferrocene-palladium(II) dichloride dichloromethane complex (35.0 mg, 0.0429 mmol) in dimethyl sulfoxide (2.3 mL) was heated to 85° C. for 3 h. The reaction mixture was poured into ethyl acetate (100 mL) and washed with water (3×50 mL) and saturated aqueous sodium chloride (1×50 mL). The organic fraction was dried over sodium sulfate, filtered, and concentrated onto silica gel. Purification by ISCO chromatography (10 to 40% ethyl acetate:heptane) afforded 55 mg (24%) of the title compound as a white solid. $^1$H NMR (400 MHz, DMSO-$d_6$): δ 8.14 (t, J=0.9 Hz, 1 H), 7.98 (dd, J=0.8, 8.6 Hz, 1 H), 7.83 (dd, J=0.8, 8.6 Hz, 1 H), 6.08 (dd, J=2.4, 9.2 Hz, 1 H), 3.98-3.62 (m, 2 H), 2.43-2.20 (m, 1 H), 2.15-1.89 (m, 2 H), 1.88-1.65 (m, 1 H), 1.67-1.52 (m, 2 H), 1.33 (s, 12 H); MS (APCI): 354.19 [M+H]$^+$; HPLC $t_R$=3.65 min (ZQ3, nonpolar_4 min).

Step D: 5-{4-[1-(1-acetylpiperidin-4-yl)-1H-pyrazol-4-yl]-7-aminofuro[2,3-c]pyridin-2-yl}-1-(tetrahydro-2H-pyran-2-yl)-1H-indazole-3-carbonitrile The title compound was prepared in 65% yield from 1-{4-[4-(7-amino-2-chlorofuro[2,3-c]pyridin-4-yl)-1H-pyrazol-1-yl]piperidin-1-yl}ethanone and 1-(tetrahydro-2H-pyran-2-yl)-5-(4,4,5,5-tetramethyl-1,3,2-dioxaborolan-2-yl)-1H-indazole-3-carbonitrile by a procedure analogous to Example 87. $^1$H NMR (400 MHz, CDCl$_3$): δ 8.39 (s, 1 H), 8.07-7.92 (m, 2 H), 7.90-7.80 (m, 2 H), 7.72 (s, 1 H), 7.19 (s, 1 H), 5.87 (dd, J=2.9, 8.2 Hz, 1 H), 4.97 (s, 2 H), 4.87-4.68 (m, 1 H), 4.60-4.28 (m, 1 H), 4.11-3.87 (m, 2 H), 3.88-3.68 (m, 1 H), 3.39-3.16 (m, 1 H), 2.95-2.69 (m, 1 H), 2.61-2.43 (m, 1 H), 2.31 (br. s, 2 H), 2.23-2.12 (m, 4 H), 2.12-1.96 (m, 2 H), 1.93-1.62 (m, 4 H); MS (ESI): 551.19 [M+H]$^+$; HPLC $t_R$=2.62 min (ZQ3, polar_4 min).

Step E: 5-{4-[1-(1-acetylpiperidin-4-yl)-1H-pyrazol-4-yl]-7-aminofuro[2,3-d]pyridin-2-yl}-1H-indazole-3-carbonitrile (Title Compound)

A solution of 5-{4-[1-(1-acetylpiperidin-4-yl)-1H-pyrazol-4-yl]-7-aminofuro[2,3-c]pyridin-2-yl}-1-(tetrahydro-2H-pyran-2-yl)-1H-indazole-3-carbonitrile (33 mg, 0.060 mmol) in 4.0 M of HCl in 1,4-Dioxane (0.30 mL) and MeOH (0.15 mL) was stirred at room temperature for 16 h. The reaction mixture was poured into saturated aqueous sodium bicarbonate (5 mL) and extracted with ethyl acetate (3×5 mL). The combined organic fractions were dried over sodium sulfate, filtered, and concentrated onto silica gel. Purification by ISCO chromatography (0 to 15% methanol:dichloromethane) afforded 3 mg (10%) of the title compound as a tan solid. $^1$H NMR (400 MHz, CD$_3$OD): δ 8.56 (s, 1 H), 8.21 (dd, J=1.5, 8.8 Hz, 1 H), 8.16 (s, 1 H), 7.99-7.85 (m, 2 H), 7.82 (d, J=8.8 Hz, 1 H), 7.60 (s, 1 H), 4.77-4.61 (m, J=13.9 Hz, 1 H), 4.63-4.42 (m, 1 H), 4.20-3.99 (m, 1 H), 3.44-3.33 (m, 1

H), 2.98-2.75 (m, 1 H), 2.34-1.95 (m, 7 H); MS (ESI): 467.08 [M+H]+; HPLC $t_R$=2.38 min (ZQ3, polar_4 min).

Example 237

1-(4-{4-[7-amino-2-(5-fluoro-1,2-benzothiazol-7-yl)furo[2,3-c]pyridin-4-yl]-1H-pyrazol-1-yl}piperidin-1-yl)ethanone diformate salt

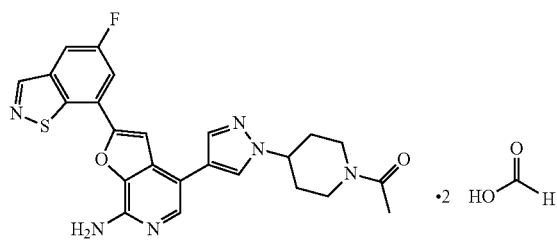

Step A: 4-amino-3-bromo-2,5-difluoro-benzonitrile

A mixture of bromine (1.65 mL, 32 mmol), water (2 mL), and 4-amino-2,5-difluorobenzonitrile (5 g, 32 mmol) in acetic acid (50 mL) was stirred at RT for 16 h. The mixture was poured into ice cooled saturated sodium bicarbonate solution, causing a solid to separate out. The solid was filtered and washed with water. The solid was then dissolved in DCM, washed with water, dried over sodium sulfate, filtered, and concentrated to afford 7 g (92%) of the title compound. $^1$H NMR (300 MHz, CDCl$_3$): δ 7.18-7.21 (m, 1H), 4.80 (br. s, 2H).

Step B: 4-amino-3-bromo-2,5-difluoro-benzaldehyde

To a solution of 4-amino-3-bromo-2,5-difluoro-benzonitrile (7 g, 30 mmol) in 95-97% formic acid (40 mL) was added Raney nickel (7 g, previously washed with water and methanol). The reaction mixture was heated to 75-85° C. for 2 h. The reaction was then cooled to room temperature and filtered through Celite, washing with dichloromethane and water. The dichloromethane layer was washed with aqueous sodium bicarbonate and brine, dried over sodium sulfate, filtered, and concentrated to afford 5 g (71%) of the title compound. $^1$H NMR (300 MHz, CDCl$_3$): δ 10.15 (s, 1H), 7.41-7.49 (m, 1H), 4.9 (br. s, 2H).

Step C: 3-bromo-2,5-fluoro-benzaldehyde

To a cooled (15° C.) solution of 4-amino-3-bromo-2,5-difluoro-benzaldehyde (5 g, 21 mmol) in acetic acid (150 mL) was added 50-52% aqueous hypophosphorous acid (5.5 mL) and then a solution of sodium nitrite (2.1 g, 31 mmol) in water (12 mL) dropwise over a period of 10 min. The reaction then stirred 2 h at RT. The reaction mixture was poured into ice water and extracted with dichloromethane. The dichloromethane extracts were washed with water, 10% aqueous sodium hydroxide solution, and water again. The organic layer was dried over sodium sulfate and concentrated in vacuo. Purification of the residue by column chromatography (10 to 20% ethyl acetate:hexanes) afforded a mixture of compounds including the title compound as the major component, which was used without further purification. $^1$H NMR (300 MHz, CDCl$_3$) δ 10.35 (s, 1H), 7.48-7.62 (m, 2H).

Step D: 3-bromo-2-tert-butylsulfanyl-5-fluoro-benzaldehyde

A mixture of 3-bromo-2,5-fluorobenzaldehyde (3 g, 13.5 mmol), potassium carbonate (2.24 g, 16.2 mmol), and 2-methyl-2-propanethiol (3 mL, 27 mmol) in DMF (15 mL) was heated to 110° C. in a sealed tube for 16 h. The reaction was cooled to room temperature, water was added, and the mixture was extracted with DCM (2×30 mL). The combined organic fractions were washed with water (3×15 mL), dried over sodium sulfate, filtered, and concentrated to afford 6.7 g of the crude title compound, which was used without further purification.

Step E: 3-bromo-2-tert-butylsulfanyl-5-fluoro-benzaldehyde oxime

A mixture of 3-bromo-2-tert-butylsulfanyl-5-fluorobenzaldehyde (4 g, 13.7 mmol) and hydroxylamine hydrochloride in isopropanol (160 mL) and water (33 mL) was heated to 90° C. for 16 h. The reaction mixture was cooled and 2-propanol was removed in vacuo. Water was added to residue, followed by saturated aqueous sodium bicarbonate until the pH was ~8. The mixture was extracted with dichloromethane (2×30 mL). The combined organic fractions were dried sodium sulfate, filtered, and concentrated to afford 3.8 g of the crude title compound, which was used without further purification.

Step F: 7-bromo-5-fluoro-1,2-benzothiazole

A mixture of 3-bromo-2-tert-butylsulfanyl-5-fluoro-benzaldehyde oxime (3.8 g, 12 mmol) and p-toluenesulfonic acid (1.1 g, 6.2 mmol) in n-butanol (60 mL) was heated to reflux for 16 h. The reaction mixture was then concentrated. The residue was treated with water and saturated aqueous sodium bicarbonate, then extracted with dichloromethane (3×20 mL). The combined organic fractions were washed with water, dried over sodium sulfate, filtered, and concentrated. Purification by column chromatography (100% hexanes) afforded 900 mg (32%) of the title compound. $^1$H NMR (300 MHz, CDCl$_3$): δ 8.97 (s, 1H), 7.68 (dd, J=2, 6 Hz, 1H), 7.50 (dd, J=2, 6 Hz, 1H).

Step G: 5-fluoro-7-(4,4,5,5-tetramethyl-1,3,2-dioxaborolan-2-yl)-1,2-benzothiazole A nitrogen degassed mixture of Pd$_2$(dba)$_3$ (60 mg, 0.065 mmol) and tricyclohexylphosphine (72 mg, 0.26 mmol) in 1,4-dioxane (40 mL) was stirred for 30 min. To this solution was added 7-bromo-5-fluoro-1,2-benzothiazole (0.50 g, 2.1 mmol), 4,4,5,5,4',4',5',5'-octamethyl-[2,2']bi[[1,3,2]dioxaborolanyl] (0.711 g, 2.8 mmol) and potassium acetate (0.34 g, 3.4 mmol) and the mixture was heated to 90° C. for 16 h. The reaction mixture was cooled to RT and filtered. The filtrate was evaporated under reduced pressure and the residue was purified by column chromatography (10% ethyl acetate:DCM) to afford 0.320 g (51%) of the title compound as a yellow-brown solid. $^1$H NMR (300 MHz, CDCl$_3$): δ 1.41 (s, 12 H), 7.74-7.77 (m, 2H), 8.87 (s, 1H).

Step H: 1-(4-{4-[7-amino-2-(5-fluoro-1,2-benzothiazol-7-yl)furo[2,3-c]pyridin-4-yl]-1H-pyrazol-1-yl}piperidin-1-yl)ethanone diformate salt (Title Compound)

The title compound was prepared by a procedure analogous to Example 223, Step D. $^1$H NMR (400 MHz, CD$_3$OD):

δ 1.99-2.13 (m, 2 H), 2.18 (s, 3 H), 2.20-2.29 (m, 2 H), 2.83-2.92 (m, 1 H), 3.34-3.40 (m, 1 H), 4.08-4.16 (m, 1 H), 4.55 (tt, J=11.5, 4.2 Hz, 1 H), 4.66-4.74 (m, 1 H), 7.64 (s, 1 H), 7.91 (s, 1 H), 7.91 (s, 1 H), 7.96 (dd, J=8.2, 2.1 Hz, 1 H), 8.14 (s, 1 H), 8.16 (dd, J=9.5, 2.1 Hz, 1 H), 8.25 (s, 2 H), 9.02 (s, 1 H); MS (ESI): 477.15 [M+H]$^+$; HPLC t$_R$=1.10 min (TOF: polar_3 min).

Example 238 trans-4-{4-[7-amino-2-(5-fluoro-1,2-benzothiazol-7-yl)furo[2,3-c]pyridin-4-yl]-1H-pyrazol-1-yl}cyclohexanol diformate salt

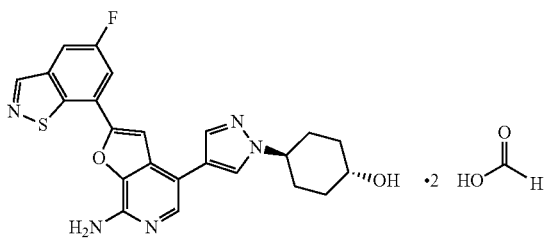

The title compound was prepared by a procedure analogous to Example 229. $^1$H NMR (400 MHz, CD$_3$OD): δ 1.48-1.58 (m, 2 H), 1.95-2.05 (m, 2 H), 2.10-2.23 (m, 4 H), 3.71 (tdd, J=10.8, 10.8, 4.5, 4.4 Hz, 1 H), 4.28 (tdd, J=11.9, 11.9, 4.0, 3.9 Hz, 1 H), 7.68 (s, 1 H), 7.91 (s, 1 H), 7.93 (s, 1 H), 7.99 (dd, J=8.3, 2.3 Hz, 1 H), 8.12 (s, 1 H), 8.21 (dd, J=9.3, 2.3 Hz, 1 H), 8.31 (s, 2 H), 9.05 (s, 1 H); MS (ESI): 450.13 [M+H]$^+$; HPLC t$_R$=1.10 min (TOF: polar_3 min).

Example 239

1-(4-{4-[7-amino-2-(6-fluoro-1,2-benzothiazol-7-yl)furo[2,3-c]pyridin-4-yl]-1H-pyrazol-1-yl}piperidin-1-ylethanone diformate salt

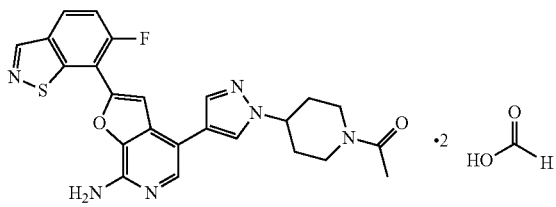 [SMILES: CC(=O)N1CCC(n2cc(-c3cnc(N)c4oc(-c5c(F)ccc6cnsc56)cc34)cn2)CC1 ; "·2" ; O=CO]

Step A: 3-bromo-2,4-difluorobenzaldehyde

To a cooled (0° C.) solution of 2,2,6,6-tetramethylpiperidine (1.64 mL, 9.75 mmol) in THF (20 mL) was added 1.6 M n-butyllithium in hexane (5.54 mL, 8.86 mmol). The solution was stirred for 20 min, then brought to −78° C. 1-bromo-2,6-difluorobenzene (1.00 mL, 8.86 mmol) in THF was added slowly, and the solution was stirred at −78° C. for 30 min. DMF (1 mL) was added slowly, and the solution was stirred at −78° C. for 20 min. Saturated aqueous ammonium chloride was added and the reaction was allowed to warm to rt. The organic solvent was removed in vacuo, and the residual material was extracted with EtOAc and washed with water (2×). The organic layer was purified by column chromatography (1 to 2% EtOAc:hexanes) to afford 350 mg (18%) of the title compound as a yellow solid. $^1$H NMR (400 MHz, CDCl$_3$): δ 6.97 (td, J=9.2, 1.5 Hz, 1 H), 7.78 (ddd, J=9.0, 7.5, 5.7 Hz, 1 H), 10.34 (s, 1 H).

Step B: 3-bromo-2-(tert-butylsulfanyl)-4-fluorobenzaldehyde

The title compound was prepared by a procedure analogous to Example 223, Step A. $^1$H NMR (400 MHz, CDCl$_3$): δ 1.27 (s, 9 H), 7.45 (ddd, J=9.9, 9.0, 0.8 Hz, 1 H), 8.13 (dd, J=9.0, 5.2 Hz, 1 H), 10.41 (s, 1 H).

Step C: 7-bromo-6-fluoro-1,2-benzothiazole

The title compound was prepared by a procedure analogous to Example 223, Step B. $^1$H NMR (400 MHz, CDCl$_3$): δ 7.02 (dd, J=9.3, 8.3 Hz, 1 H), 7.60 (dd, J=8.3, 4.0 Hz, 1 H), 9.10 (s, 1 H).

Step D: 6-fluoro-7-(4,4,5,5-tetramethyl-1,3,2-dioxaborolan-2-yl)-1,2-benzothiazole The title compound was prepared by a procedure analogous to Example 223, Step C. MS (ESI): 280.08 [M+H]$^+$; HPLC t$_R$=1.80 min (TOF: polar_3 min).

Step E: 1-(4-{4-[7-amino-2-(6-fluoro-1,2-benzothiazol-7-yl)furo[2,3-c]pyridin-4-yl]-1H-pyrazol-1-yl}piperidin-1-yl)ethanone diformate salt (Title Compound)

The title compound was prepared by a procedure analogous to Example 223, Step D. $^1$H NMR (400 MHz, CD$_3$OD): δ 1.95-2.13 (m, 2 H), 2.19 (s, 3 H), 2.19-2.29 (m, 2 H), 2.88 (td, J=12.9, 2.7 Hz, 1 H), 3.33-3.41 (m, 1 H), 4.08-4.15 (m, 1 H), 4.48-4.56 (m, 1 H), 4.66-4.74 (m, 1 H), 7.21 (t, J=8.8 Hz, 1 H), 7.29 (s, 1 H), 7.79 (s, 1 H), 7.83 (s, 1 H), 8.03 (s, 1 H), 8.14 (dd, J=8.1, 4.5 Hz, 1 H), 8.28 (s, 2 H), 9.00 (s, 1 H); MS (ESI): 477.14 [M+H]$^+$; HPLC t$_R$=1.11 min (TOF: polar_3 min).

Example 240 trans-4-{4-[7-amino-2-(6-fluoro-1,2-benzothiazol-7-yl)furo[2,3-c]pyridin-4-yl]-1H-pyrazol-1-yl}cyclohexanol diformate salt

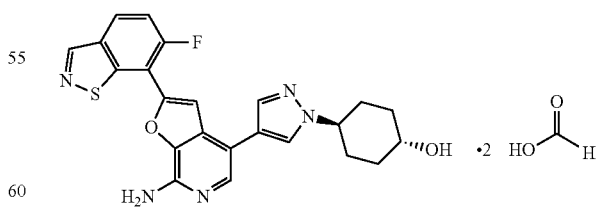

The title compound was prepared by a procedure analogous to Example 229. $^1$H NMR (400 MHz, CD$_3$OD): δ 1.48-1.58 (m, 2 H), 1.95-2.06 (m, 2 H), 2.09-2.23 (m, 4 H), 3.67-3.75 (m, 1 H), 4.27 (tt, J=11.7, 3.8 Hz, 1 H), 7.35 (t, J=8.8 Hz, 1 H), 7.51 (s, 1 H), 7.89 (d, J=2.3 Hz, 2 H), 8.10 (s, 1 H), 8.26

(s, 2 H), 8.31 (dd, J=8.0, 4.4 Hz, 1 H), 9.13 (s, 1 H); MS (ESI): 450.13 [M+H]⁺; HPLC $t_R$=1.10 min (TOF: polar_3 min).

Example 241

1-(4-{4-[7-amino-2-(1,2-benzothiazol-4-yl)furo[2,3-c]pyridin-4-yl]-1H-pyrazol-1-yl}piperidin-1-yl)ethanone diformate Salt

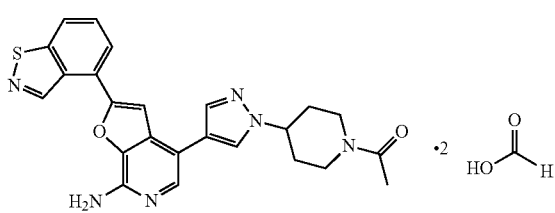 [SMILES: CC(=O)N1CCC(n2cc(-c3cnc(N)c4oc(-c5cccc6sncc56)cc34)cn2)CC1 ; "·2" ; O=CO]

Step A: 2-bromo-6-(tert-butylsulfanyl)benzaldehyde

The title compound was prepared by a procedure analogous to Example 223, Step A. ¹H NMR (400 MHz, CDCl₃): δ 1.32 (s, 9 H), 7.30-7.38 (m, 1 H), 7.59 (dd, J=7.7, 1.1 Hz, 1 H), 7.71 (d, J=8.1 Hz, 1 H), 10.58 (s, 1 H).

Step B: 4-bromo-1,2-benzothiazole

The title compound was prepared by a procedure analogous to Example 223, Step B. ¹H NMR (400 MHz, CDCl₃): δ 7.36-7.43 (m, 1 H), 7.57-7.62 (m, 1 H), 7.91 (d, J=8.1 Hz, 1 H), 9.02 (s, 1 H).

Step C: 4-(4,4,5,5-tetramethyl-1,3,2-dioxaborolan-2-yl)-1,2-benzothiazole

The title compound was prepared by a procedure analogous to Example 223, Step C. MS (ESI): 262.10 [M+H]⁺; HPLC $t_R$=1.75 min (TOF: polar_3 min).

Step D: 1-(4-{4-[7-amino-2-(1,2-benzothiazol-4-yl)furo[2,3-c]pyridin-4-yl]-1H-pyrazol-1-yl}piperidin-1-yl)ethanone diformate salt (Title Compound)

The title compound was prepared by a procedure analogous to Example 223, Step D. ¹H NMR (400 MHz, CD₃OD): δ 1.97-2.14 (m, 2 H), 2.18 (s, 3 H), 2.18-2.29 (m, 2 H), 2.80-2.91 (m, 1 H), 3.33-3.39 (m, 1 H), 4.04-4.15 (m, 1 H), 4.52 (tdd, J=11.4, 11.4, 4.2, 4.0 Hz, 1 H), 4.65-4.73 (m, 1 H), 7.62-7.70 (m, 2 H), 7.82 (s, 1 H), 7.92 (s, 1 H), 8.10 (d, J=7.3 Hz, 1H), 8.13-8.18 (m, 2 H), 8.32 (s, 2 H), 9.72 (s, 1 H); MS (ESI): 459.14 [M+H]⁺; HPLC $t_R$=1.07 min (TOF: polar_3 min).

Example 242 trans-4-{4-[7-amino-2-(1,2-benzothiazol-4-yl)furo[2,3-c]pyridin-4-yl]-1H-pyrazol-1-yl}cyclohexanol Diformate Salt

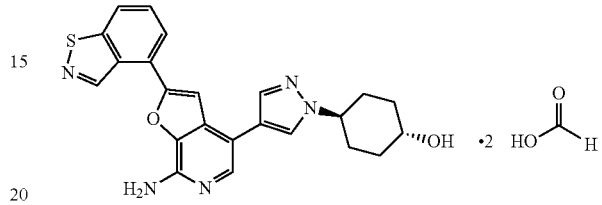

The title compound was prepared by a procedure analogous to Example 229. ¹H NMR (400 MHz, CD₃OD): δ 1.46-1.58 (m, 2 H), 1.94-2.06 (m, 2 H), 2.07-2.23 (m, 4 H), 3.70 (tdd, J=10.9, 10.9, 4.4, 4.3 Hz, 1 H), 4.26 (tt, J=11.8, 3.8 Hz, 1 H), 7.67-7.74 (m, 2 H), 7.88-7.93 (m, 2 H), 8.13-8.21 (m, 3 H), 8.39 (s, 2 H), 9.78 (d, J=1.0 Hz, 1 H); MS (ESI): 432.13 [M+H]⁺; HPLC $t_R$=1.08 min (TOF: polar_3 min).

Example 243

1-(4-{4-[7-amino-2-(5-methoxythieno[2,3-c]pyridin-3-yl)furo[2,3-c]pyridin-4-yl]-1H-pyrazol-1-yl}piperidin-1-yl)ethanone

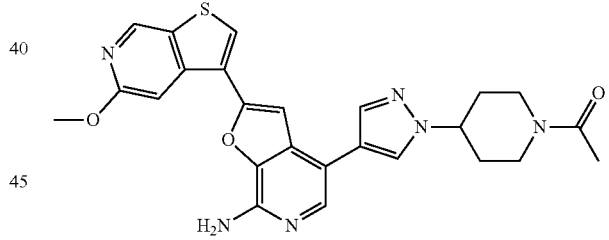

Step A: 7-chlorothieno[2,3-c]pyridine 6-oxide

To a solution of 7-chlorothieno[2,3-c]pyridine (5.00 g, 29.5 mmol) in DCM (200 mL) was added m-chloroperbenzoic acid (13.2 g, 59.0 mmol). The combined mixture was stirred at RT for 24 h. After that time, it was purified by ISCO chromatography (0 to 6% MeOH:DCM) to afford 3.18 g (58%) of the title compound as a light brown solid. ¹H NMR (400 MHz, CDCl₃): δ 8.31 (d, J=7.2 Hz, 1 H), 7.69 (d, J=5.2 Hz, 1 H), 7.57 (d, J=6.8 Hz, 1 H), 7.35 (d, J=5.2 Hz, 1 H); MS (ESI): 185.95, 187.96 [M+H]⁺; HPLC $t_R$=0.88 min (TOF: polar_3 min).

Step B: 5,7-dichlorothieno[2,3-c]pyridine

A mixture of 7-chlorothieno[2,3-c]pyridine 6-oxide (2.58 g, 13.8 mmol) and POCl₃ (20 mL) was stirred at 115° C. under N₂ for 7 h. After that time, the excess POCl₃ was removed in vacuo, and the residue was poured into ice/water (100 mL), basified by addition of 8 N NaOH followed by saturated NaHCO$_3$, and extracted with DCM (3×50 mL). The combined extracts were washed with saturated NaHCO$_3$ (50 mL), water (50 mL) and brine (50 mL), dried over MgSO$_4$, and concentrated in vacuo. The residue was purified by ISCO chromatography (0 to 40% EtOAc:heptane) to afford 1.97 g (70%) of the title compound as a beige solid. $^1$H NMR (400 MHz, DMSO-d$_6$): δ 7.82 (d, J=5.6 Hz, 1 H), 7.68 (s, 1 H), 7.37 (d, J=5.6 Hz, 1 H); MS (ESI): 203.94, 205.94 [M+H]$^+$; HPLC t$_R$=1.55 min (TOF: polar_3 min).

Step C: 5-chlorothieno[2,3-c]pyridine

A mixture of 5,7-dichlorothieno[2,3-c]pyridine (1.86 g, 8.20 mmol), AcOH (9.42 mL, 164 mmol), and concentrated HCl (3.16 mL, 38.4 mmol) was treated with tin powder (3.04 g, 24.6 mmol) at 60° C. After 3 h heating, another portion of concentrated HCl (3.16 mL) was added followed by another portion of tin powder (3.04 g). After 2 h heating, another portion of concentrated HCl (3.16 mL) was added followed by tin powder (1.03 g). After 2 h, the heating was stopped, and the reaction mixture was cooled and diluted with water (50 mL). After filtration, the residue was washed with water. The combined filtrates were extracted with EtOAc (4×100 mL). The combined extracts were washed with aqueous 1 N NaOH until the pH was >9, followed by brine (100 mL), dried over MgSO$_4$, and concentrated in vacuo. Purification by ISCO chromatography (0 to 30% EtOAc:heptane) afforded 980 mg (70%) of the title compound as a white solid. $^1$H NMR (400 MHz, CDCl$_3$): δ 8.93 (d, J=0.4 Hz, 1 H), 7.79 (d, J=6.4 Hz, 1 H), 7.75 (d, J=1.2 Hz, 1 H), 7.33 (dd, J=5.6, 0.8 Hz, 1 H); MS (ESI): 169.98, 171.98 [M+H]$^+$; HPLC t$_R$=1.29 min (TOF: polar_3 min).

Step D: 5-ethoxythieno[2,3-c]pyridine

A sealable vial was charged with 5-chlorothieno[2,3-c]pyridine (240 mg, 1.41 mmol), sodium ethoxide (557 mg, 7.78 mmol) and EtOH (6.5 mL). The reaction was heated in a microwave reactor at 175° C. for 2 h, then purified by ISCO chromatography (0 to 25% EtOAc:hexane) to afford 174 mg (69%) of the title compound as a yellow solid. $^1$H NMR (400 MHz, CDCl$_3$): δ 8.69-8.70 (m, 1 H), 7.63 (d, J=5.6 Hz, 1 H), 7.20 (dd, J=5.6, 0.8 Hz, 1 H), 7.08 (d, J=0.8 Hz, 1 H), 4.39 (quartet, J=7.2 Hz, 2 H), 1.43 (t, J=7.2 Hz, 3 H); MS (ESI): 180.04 [M+H]$^+$; HPLC t$_R$=1.39 min (TOF: polar_3 min).

Step E: thieno[2,3-c]pyridin-5-ol

A mixture of 5-ethoxythieno[2,3-c]pyridine (127 mg, 0.700 mmol), pyridine hydrochloride (827 mg, 7.00 mmol) and H$_2$O (1.2 mL) was heated in a microwave reactor at 175° C. for 2 h. The reaction mixture was concentrated in vacuo and purified by ISCO chromatography (0 to 15% MeOH:DCM) to afford 58.7 mg (55%) of the title compound as a brown solid. $^1$H NMR (400 MHz, CDCl$_3$): δ 14.04 (br s, 1 H), 8.12 (s, 1 H), 7.66 (d, J=5.6 Hz, 1 H), 7.07 (dd, J=5.6, 0.4 Hz, 1 H), 6.95 (d, J=0.8 Hz, 1 H); MS (ESI): 152.02 [M+H]$^+$; HPLC t$_R$=0.74 min (TOF: polar_3 min).

Step F: thieno[2,3-c]pyridin-5-yl trifluoromethanesulfonate

A suspension of thieno[2,3-c]pyridin-5-ol (67.0 mg, 0.443 mmol) and triethylamine (68.3 μL, 0.487 mmol) in DCM (9 mL) was charged with N-phenylbis-(trifluoromethane-sulfonimide) (171 mg, 0.474 mmol) slowly at RT. This mixture was allowed to stir at RT for 16 h. After that time, additional triethylamine (50.0 μL, 0.357 mmol) and N-phenylbis(trifluoromethanesulphonimide) (100 mg, 0.257 mmol) were added. After stirring at RT for another 8 h, the mixture was concentrated in vacuo and purified by ISCO chromatography (0 to 30% EtOAc:heptane) to afford 114 mg (91%) of the title compound as a colorless oil. $^1$H NMR (400 MHz, CDCl$_3$): δ 8.90 (s, 1 H), 7.91 (d, J=6.0 Hz, 1 H), 7.59 (d, J=0.4 Hz, 1 H), 7.45 (dd, J=5.6, 0.8 Hz, 1 H); MS (ESI): 283.99 [M+H]$^+$; HPLC t$_R$=4.09 min (ZQ3: polar_5 min).

Step G: 3-bromothieno[2,3-c]pyridin-5-yl trifluoromethanesulfonate

A sealable vial was charged with thieno[2,3-c]pyridin-5-yl trifluoromethanesulfonate (109 mg, 0.300 mmol), sodium acetate (75.3 mg, 0.900 mmol) and 1.0 M bromine in AcOH (0.900 mL, 0.900 mmol). The reaction was heated in a microwave reactor at 90° C. for 2 h. The reaction mixture was treated with aqueous Na$_2$CO$_3$ until the pH was >9, then extracted with EtOAc (3×20 mL). The combined extracts were washed with water (10 mL) and brine (10 mL), dried over MgSO$_4$, and concentrated in vacuo. The residue was purified by ISCO chromatography (0 to 25% EtOAc:heptane) to afford 60 mg (55%) of the title compound as an off-white solid. $^1$H NMR (400 MHz, DMSO-d$_6$): δ 9.26 (d, J=0.4 Hz, 1 H), 8.61 (s, 1 H), 7.92 (d, J=1.2 Hz, 1H); MS (ESI): 362.08, 384.04 [M+H]$^+$; HPLC t$_R$=4.39 min (ZQ3: polar_5 min).

Step H: 3-bromothieno[2,3-c]pyridin-5-ol

A mixture of 3-bromothieno[2,3-c]pyridin-5-yl trifluoromethanesulfonate (145 mg, 0.400 mmol), lithium hydroxide monohydrate (173 mg, 4.00 mmol) and dimethyl sulfoxide (10 mL) was heated at 75° C. for 2.5 h. The solvent was removed and the residue was neutralized with aqueous 2 N HCl. The residue was then extracted with 30% n-BuOH:EtOAc (3×50 mL). The combined organic extracts were washed with water (2×10 mL) and brine (10 mL), dried over MgSO$_4$, and concentrated in vacuo to afford 92 mg (100%) of the title compound as a yellow solid. MS (ESI): 230.01, 231.97 [M+H]$^+$; HPLC t$_R$=2.46 min (ZQ3: polar_5 min).

Step I: 3-bromo-5-methoxythieno[2,3-c]pyridine

Into a suspension of 60% sodium hydride (18.6 mg, 0.465 mmol) in DMF (1.0 mL) was added a solution of 3-bromothieno[2,3-c]pyridin-5-ol (54.0 mg, 0.232 mmol) in DMF (3 mL) at RT in 5 min under an atmosphere of nitrogen. After 30 min stirring at RT, dimethyl sulfate (26.9 μL, 0.279 mmol) was added. The combined mixture was stirred at RT for 16 h. After that time, the solvent was removed in vacuo. The residue was then purified by ISCO chromatography (0 to 5% MeOH:DCM) to afford 11.2 mg (20%) of the title compound as a beige solid. $^1$H NMR (400 MHz, DMSO-d$_6$): δ 8.95 (d, J=0.8 Hz, 1H), 8.31 (s, 1 H), 7.01 (d, J=0.8 Hz, 1 H), 3.94 (s, 3 H); MS (ESI): 243.94, 245.90 [M+H]$^+$; HPLC t$_R$=4.15 min (ZQ3: polar_5 min).

Step J: 5-methoxy-3-(4,4,5,5-tetramethyl-1,3,2-dioxaborolan-2-yl)thieno[2,3-c]pyridine To a cooled (−78° C.) solution of 3-bromo-5-methoxythieno[2,3-c]pyridine (14.7 mg, 0.0602 mmol) in THF (2.5 mL) was added dropwise 1.60 M n-BuLi in hexane (56.4 μL, 0.0903 mmol) in 5 min under an atmosphere of nitrogen.

After stirring at −78° C. for 1 h, 2-isopropoxy-4,4,5,5-tetramethyl-1,3,2-dioxaborolane (18.8 μL, 0.0903 mmol) was added dropwise. The combined mixture was stirred at −78° C. for another 1 h. The temperature was then gradually raised to RT in 40 min. The reaction was then quenched by addition of MeOH (5 mL) and purified by ISCO chromatography (0 to 20% EtOAc:hexane) to afford 6.6 mg (38%) of the title compound as a light yellow solid. $^1$H NMR (400 MHz, dioxane-$d_8$): δ 8.72 (d, J=1.2 Hz, 1 H), 8.29 (s, 1 H), 7.48 (d, J=0.8 Hz, 1 H), 3.93 (s, 3 H), 1.35 (s, 12 H); MS (ESI): 292.11 [M+H]$^+$; HPLC $t_R$=1.71 min (TOF: polar__3 min).

Step K: 1-(4-{4-[7-amino-2-(5-methoxythieno[2,3-c]pyridin-3-yl)furo[2,3-c]pyridin-4-yl]-1H-pyrazol-1-yl}piperidin-1-yl)ethanone (Title Compound)

The title compound was prepared in 15% yield using procedure analogous to Example 223, Step D. $^1$H NMR (400 MHz, CD$_3$OD): δ 8.81 (d, J=0.8 Hz, 1 H), 8.57 (s, 1 H), 8.16 (s, 1 H), 7.93 (s, 1 H), 7.90 (s, 1 H), 7.75 (d, J=0.4 Hz, 1 H), 7.42 (s, 1 H), 4.67-4.74 (m, 1 H), 4.49-4.59 (m, 1 H), 4.06-4.14 (m, 1 H), 4.04 (s, 3 H), 3.30-3.39 (m, 1 H), 2.82-2.91 (m, 1 H), 2.19-2.28 (m, 2 H), 2.18 (s, 3 H), 2.09-2.18 (m, 1 H), 1.96-2.09 (m, 1 H); MS (ESI): 489.15 [M+H]$^+$; HPLC $t_R$=1.09 min (TOF: polar__3 min).

Example 244

3-{4-[1-(1-acetylpiperidin-4-yl)-1H-pyrazol-4-yl]-7-aminofuro[2,3-c]pyridin-2-yl}-6-methylthieno[2,3-c]pyridin-5(6H)-one trifluoroacetate

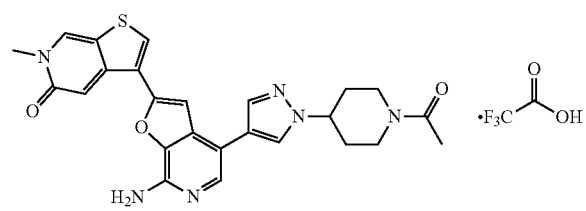

Step A: 3-bromo-6-methylthieno[2,3-c]pyridin-5(6H)-one

The title compound was prepared in 28% yield by a procedure analogous to Example 243, Step I. $^1$H NMR (400 MHz, DMSO-d$_6$): δ 8.60 (s, 1H), 8.16 (s, 1 H), 6.41 (s, 1 H), 3.58 (s, 3 H); MS (ESI): 243.94, 245.90 [M+H]$^+$; HPLC $t_R$=2.82 min (ZQ3: polar__5 min).

Step B: 6-methyl-3-(4,4,5,5-tetramethyl-1,3,2-dioxaborolan-2-yl)thieno[2,3-d]pyridin-5(6H)-one The title compound was prepared in 22% yield by a procedure analogous to Example 243, Step J. MS (ESI): 292.11 [M+H]$^+$; HPLC $t_R$=1.23 min (TOF: polar__3 min).

Step C: 3-{4-[1-(1-acetylpiperidin-4-yl)-1H-pyrazol-4-yl]-7-aminofuro[2,3-c]pyridin-2-yl}-6-methylthieno[2,3-c]pyridin-5(6H)-one Trifluoroacetate (Title Compound)

The title compound was prepared in 15% yield by a procedure analogous to Example 223, Step D. $^1$H NMR (400 MHz, DMSO-d$_6$): δ 8.82 (s, 1H), 8.70 (d, J=0.4 Hz, 1 H), 8.55 (br s, 2 H), 8.48 (s, 1 H), 8.12 (d, J=0.8 Hz, 1 H), 7.95 (s, 1 H), 7.85 (s, 1 H), 7.49 (s, 1 H), 4.47-4.56 (m, 2 H), 3.94-4.01 (m, 1 H), 3.63 (s, 3 H), 3.21-3.30 (m, 1 H), 2.72-2.81 (m, 1 H), 2.08-2.18 (m, 2 H), 2.07 (s, 3 H), 1.93-2.06 (m, 1 H), 1.81-1.92 (m, 1 H); MS (ESI): m/z=489.23 [M+H]$^+$; HPLC $t_R$=2.44 min (ZQ3: polar__5 min).

Example 245

1-(4-{4-[7-amino-2-(5-ethoxythieno[2,3-c]pyridin-3-yl)furo[2,3-c]pyridin-4-yl]-1H-pyrazol-1-yl}piperidin-1-yl)ethanone bis(trifluoroacetate)

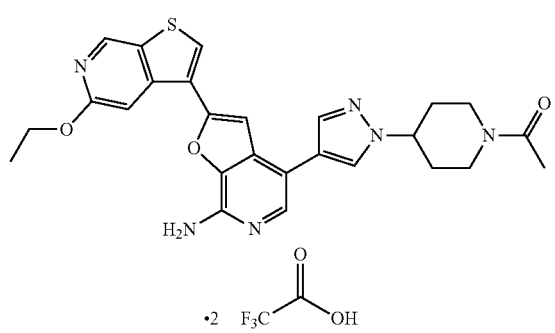

Step A: 3-bromo-5-chlorothieno[2,3-c]pyridine

The title compound was prepared in 72% yield by a procedure analogous to Example 243, Step G. The reaction time was 90 min. $^1$H NMR (400 MHz, CDCl$_3$): δ 8.91 (d, J=0.4 Hz, 1 H), 7.76 (s, 1 H), 7.75 (d, J=0.8 Hz, 1 H); MS (ESI): 247.87, 249.90, 251.86 [M+H]$^+$; HPLC $t_R$=4.12 min (ZQ3: polar__5 min).

Step B: 3-bromo-5-ethoxythieno[2,3-c]pyridine

The title compound was prepared in 16% yield by a procedure analogous to Example 243, Step D. The reaction temperature was 150° C. $^1$H NMR (400 MHz, CDCl$_3$): δ 8.66 (d, J=1.2 Hz, 1 H), 7.61 (s, 1 H), 7.09 (d, J=1.2 Hz, 1 H), 4.41 (quartet, J=7.2 Hz, 2H), 1.45 (t, J=7.2 Hz, 3 H); MS (ESI): m/z=257.97, 259.95 [M+H]$^+$; HPLC $t_R$=1.64 min (TOF: polar__3 min,).

Step C: 5-ethoxy-3-(4,4,5,5-tetramethyl-1,3,2-dioxaborolan-2-yl)thieno[2,3-c]pyridine The title compound was prepared in 46% yield by a procedure analogous to Example 243, Step J. $^1$H NMR (400 MHz, DMSO-d$_6$): δ 8.88 (d, J=1.2 Hz, 1 H), 8.51 (s, 1 H), 7.43 (d, J=0.8 Hz, 1 H), 4.35 (quartet, J=6.8 Hz, 2 H), 1.34 (s, 12 H), 1.30-1.37 (m, 3 H); MS (ESI): 306.13 [M+H]$^+$; HPLC $t_R$=1.81 min (TOF: polar__3 min).

Step D: 1-(4-{4-[7-amino-2-(5-ethoxythieno[2,3-c]pyridin-3-yl)furo[2,3-c]pyridin-4-yl]-1H-pyrazol-1-yl}piperidin-1-yl)ethanone bis(trifluoroacetate) (Title Compound)

The title compound was prepared in 24% yield by a procedure analogous to Example 223, Step D. $^1$H NMR (400 MHz, CD$_3$OD): δ 8.82 (d, J=0.8 Hz, 1 H), 8.74 (s, 1 H), 8.31

(s, 1 H), 8.02 (s, 1 H), 7.81 (s, 1 H), 7.79 (d, J=0.8 Hz, 1 H), 7.65 (s, 1 H), 4.66-4.73 (m, 1 H), 4.54-4.63 (m, 1 H), 4.45 (quartet, J=7.2 Hz, 2 H), 4.08-4.16 (m, 1 H), 3.31-3.41 (m, 1 H), 2.83-2.92 (m, 1 H), 2.18-2.28 (m, 2 H), 2.18 (s, 3 H), 2.09-2.17 (m, 1 H), 1.95-2.08 (m, 1 H), 1.45 (t, J=7.2 Hz, 3H); MS (ESI): 503.18 [M+H]$^+$; HPLC $t_R$=2.91 min (ZQ3: polar_5 min).

Example 246

1-(4-{4-[7-amino-2-(5-chlorothieno[2,3-c]pyridin-3-yl)furo[2,3-c]pyridin-4-yl]-1H-pyrazol-1-yl}piperidin-1-yl)ethanone bis(trifluoroacetate)

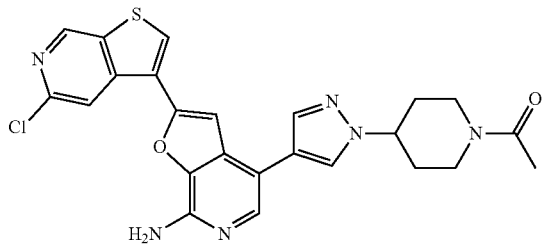

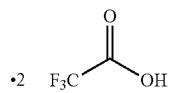

Step A: 5-chloro-3-(4,4,5,5-tetramethyl-1,3,2-dioxaborolan-2-yl)thieno[2,3-c]pyridine A solution of 3-bromo-5-chlorothieno[2,3-c]pyridine (74.6 mg, 0.300 mmol), bis(pinacolato)diboron (114 mg, 0.450 mmol), potassium acetate (58.9 mg, 0.600 mmol), and 1,1'-bis(diphenylphosphino)ferrocenepalladium(II) dichloride dichloromethane complex (12.2 mg, 0.0150 mmol) in 1,4-dioxane (1.5 mL) was heated to 85° C. under a nitrogen atmosphere for 16 h. The reaction mixture was concentrated in vacuo, and was then purified by ISCO chromatography (0 to 35% EtOAc:heptane) to afford 51 mg (58%) of the title compound as a colorless oil. $^1$H NMR (400 MHz, CDCl$_3$): δ 8.92-8.93 (m, 1 H), 8.33 (s, 1 H), 8.23 (d, J=1.2 Hz, 1 H), 1.39 (s, 12 H); MS (ESI): 296.06 [M+H]$^+$; HPLC $t_R$=1.75 min (TOF: polar_3 min).

Step B: 1-(4-{4-[7-amino-2-(5-chlorothieno[2,3-c]pyridin-3-yl)furo[2,3-c]pyridin-4-yl]-1H-pyrazol-1-yl}piperidin-1-yl)ethanone bis(trifluoroacetate) (Title Compound)

The title compound was prepared in 18% yield by a procedure analogous to Example 223, Step D. $^1$H NMR (400 MHz, DMSO-d$_6$): δ 9.30 (d, J=0.8 Hz, 1 H), 9.09 (s, 1 H), 8.79 (br s, 2 H), 8.70 (d, J=0.8 Hz, 1 H), 8.47 (d, J=0.4 Hz, 1 H), 8.14 (d, J=0.8 Hz, 1 H),), 8.05 (s, 1 H), 8.00 (s, 1 H), 4.48-4.59 (m, 2 H), 3.93-4.02 (m, 1 H), 3.22-3.32 (m, 1 H), 2.74-2.82 (m, 1 H), 2.05-2.18 (m, 2 H), 2.07 (s, 3 H), 1.80-2.04 (m, 2 H); MS (ESI): 493.29, 495.26 [M+H]$^+$; HPLC $t_R$=2.78 min (ZQ3: polar_5 min).

Example 247 trans-4-{4-[7-amino-2-(5-chlorothieno[2,3-c]pyridin-3-yl)furo[2,3-c]pyridin-4-yl]-1H-pyrazol-1-yl}cyclohexanol bis(trifluoroacetate)

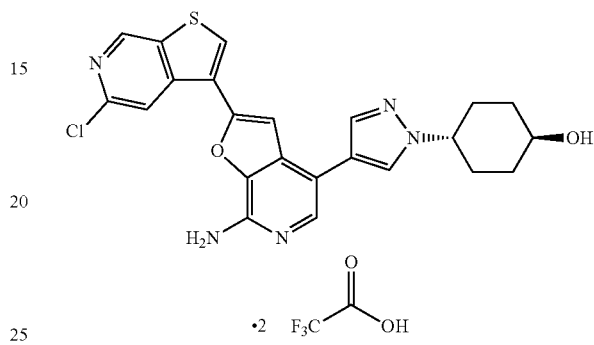

The title compound was prepared in 29% yield by a procedure analogous to Example 229. $^1$H NMR (400 MHz, DMSO-d$_6$): δ 9.30 (s, 1 H), 9.11 (s, 1 H), 8.74 (br s, 2 H), 8.72 (s, 1 H), 8.42 (s, 1 H), 8.11 (s, 1 H), 8.05 (s, 1 H), 7.99 (s, 1 H), 4.18-4.27 (m, 1 H), 3.49-3.59 (m, 1 H), 2.17-2.26 (m, 1 H), 2.04-2.12 (m, 2 H), 1.94-2.04 (m, 2 H), 1.82-1.94 (m, 2 H), 1.36-1.47 (m, 2 H); MS (ESI): 466.25, 468.28 [M+H]$^+$; HPLC $t_R$=2.79 min (ZQ3: polar_5 min).

Example 248

1-(4-{4-[7-amino-2-(5-fluorothieno[2,3-c]pyridin-3-yl)furo[2,3-c]pyridin-4-yl]-1H-pyrazol-1-yl}piperidin-1-yl)ethanone bis(trifluoroacetate)

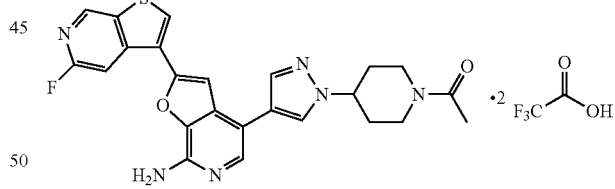

Step A: thieno[2,3-c]pyridin-5-amine

A mixture of 5-chlorothieno[2,3-c]pyridine (685 mg, 4.00 mmol), benzophenone imine (1.03 mL, 6.00 mmol), sodium tert-butoxide (595 mg, 6.00 mmol), Xantphos (358 mg, 0.600 mmol), tris(dibenzylideneacetone)dipalladium(0) (185 mg, 0.200 mmol) and toluene (40 mL) was heated at 120° C. under a nitrogen atmosphere for 3 h. After cooling, the reaction mixture was partitioned between EtOAc (50 mL) and water (50 mL). The aqueous layer was extracted with EtOAc (50 mL). The combined organic fractions were washed with water (30 mL) and brine (30 mL), dried over MgSO$_4$, and concentrated in vacuo. The residue was dissolved in THF (80 mL) and treated with aqueous 2 N hydrochloric acid (8.0 mL, 16 mmol). After 1 h at RT, the reaction mixture was diluted with water (50 mL) and extracted with EtOAc (3×30 mL). The extracts were washed with water (2×30 mL) and brine (30 mL). The aqueous layer was treated with aqueous NaOH until the pH was >9 and then extracted with EtOAc (3×50 mL). The combined organic extracts were washed with brine (30 mL), dried over $MgSO_4$, and concentrated in vacuo. The resultant solid was purified by ISCO chromatography (50% to 100% EtOAc:heptane) to afford 420 mg (70%) of the title compound as a yellow solid. $^1$H NMR (400 MHz, $CDCl_3$) δ 8.64 (s, 1 H), 7.59 (d, J=5.6 Hz, 1 H), 7.12 (d, J=5.6 Hz, 1 H), 6.88 (d, J=1.2 Hz, 1 H), 4.36 (br s, 2 H); MS (ESI): 151.03 $[M+H]^+$; HPLC $t_R$=0.43 min (TOF: polar_3 min).

Step B: 5-fluorothieno[2,3-c]pyridine

To a solution of thieno[2,3-c]pyridin-5-ylamine (24.0 mg, 0.160 mmol) in pyridine hydrofluoride (0.50 mL, 5.50 mmol) in a plastic bottle was added sodium nitrite (33.1 mg, 0.479 mmol). The reaction mixture was stirred at RT for 50 min. Another portion of sodium nitrite was added and the mixture was stirred at RT for another 30 min, then at 100° C. for 1 h. The reaction mixture was then poured into 1:1 $NH_4OH$:water (10 mL) and extracted with EtOAc (3×15 mL). The combined organic extracts were washed with water (2×10 mL) and brine (10 mL), dried over $MgSO_4$, and concentrated in vacuo. Purification by ISCO chromatography (0 to 30% EtOAc:heptane) afforded 8 mg (33%) of the title compound as a beige solid. $^1$H NMR (400 MHz, $CDCl_3$): δ 8.75 (s, 1 H), 7.81 (d, J=5.6 Hz, 1 H), 7.35 (d, J=5.2 Hz, 1 H), 7.29-7.31 (m, 1 H); MS (ESI): 154.12 $[M+H]^+$; HPLC $t_R$=3.40 min (ZQ3: polar_5 min).

Step C: 3-bromo-5-fluorothieno[2,3-c]pyridine

The title compound was prepared in 60% yield by procedure analogous to Example 243, Step G. The reaction time was 90 min. $^1$H NMR (400 MHz, DMSO-$d_6$): δ 9.04 (s, 1 H), 8.49 (s, 1 H), 7.44 (d, J=0.8, 1 H); MS (ESI): 232.03, 234.00 $[M+H]^+$; HPLC $t_R$=3.93 min (ZQ3: polar_5 min).

Step D: 5-fluoro-3-(4,4,5,5-tetramethyl-1,3,2-dioxaborolan-2-yl)thieno[2,3-c]pyridine The title compound was prepared in 27% yield by a procedure analogous to Example 246, Step A. MS (ESI): 280.09 $[M+H]^+$; HPLC $t_R$=1.69 min (TOF: polar_3 min).

Step E: 1-(4-{4-[7-amino-2-(5-fluorothieno[2,3-c]pyridin-3-yl)furo[2,3-c]pyridin-4-yl]-1H-pyrazol-1-yl}piperidin-1-yl)ethanone bis(trifluoroacetate) (Title Compound)

The title compound was prepared in 60% yield by a procedure analogous to Example 223, Step D. $^1$H NMR (400 MHz, DMSO-$d_6$): δ 9.12 (s, 1 H), 9.11 (s, 1 H), 8.79 (br s, 2 H), 8.46 (s, 1 H), 8.45 (s, 1 H), 8.13 (d, J=0.8 Hz, 1 H), 8.02 (s, 1 H), 7.99 (s, 1 H), 4.48-4.58 (m, 2 H), 3.94-4.02 (m, 1 H), 3.23-3.32 (m, 1 H), 2.72-2.82 (m, 1 H), 2.07-2.19 (m, 2 H), 2.07 (s, 3 H), 1.79-2.02 (m, 2 H); MS (ESI): 477.32 $[M+H]^+$; HPLC $t_R$=2.74 min (ZQ3: polar_5 min).

Example 249 trans-4-{4-[7-amino-2-(5-fluorothieno[2,3-c]pyridin-3-yl)furo[2,3-c]pyridin-4-yl]-1H-pyrazol-1-yl}cyclohexanol

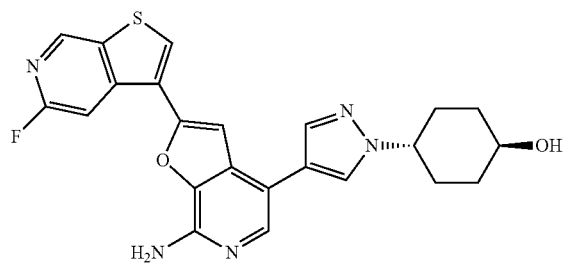 [SMILES: Nc1ncc(-c2cnn([C@H]3CC[C@H](O)CC3)c2)c2cc(-c3csc4cnc(F)cc34)oc12]

The title compound was prepared in 17% yield by a procedure analogous to Example 229. $^1$H NMR (400 MHz, DMSO-$d_6$): δ 9.09 (s, 1 H), 8.95 (s, 1 H), 8.41 (s, 1 H), 8.24 (s, 1 H), 8.02 (s, 1 H), 7.98 (d, J=0.4 Hz, 1 H), 7.76 (s, 1 H), 6.53 (br s, 2 H), 4.70 (d, J=4.8 Hz, 1 H), 4.15-4.25 (m, 1 H), 3.49-3.59 (m, 1 H), 2.06-2.12 (m, 2 H), 1.92-2.02 (m, 2 H), 1.82-1.92 (m, 2 H), 1.33-1.45 (m, 2 H); MS (ESI): 450.27 $[M+H]^+$; HPLC $t_R$=2.70 min (ZQ3: polar_5 min).

Example 250 trans-4-{4-[7-amino-2-(5-methoxythieno[2,3-c]pyridin-3-yl)furo[2,3-c]pyridin-4-yl]-1H-pyrazol-1-yl}cyclohexanol bis(trifluoroacetate)

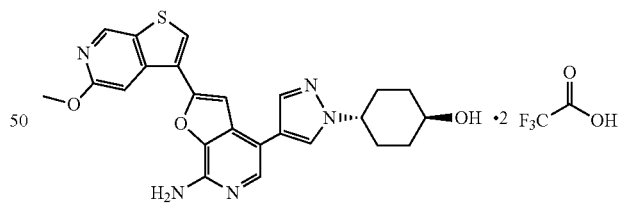

A mixture of trans-4-{-4-[7-amino-2-(5-fluorothieno[2,3-c]pyridin-3-yl)furo[2,3-c]pyridin-4-yl]-1H-pyrazol-1-yl}cyclohexanol (22.9 mg, 0.0500 mmol), sodium methoxide (14.2 mg, 0.250 mmol) and methanol (2.0 mL) was heated in a microwave reactor at 150° C. for 90 min. Purification by MDP afforded 28.8 mg (84%) of the title compound as a yellow oil. $^1$H NMR (400 MHz, DMSO-$d_6$): δ 9.03 (s, 1 H), 8.96 (s, 1 H), 8.72 (br s, 2 H), 8.46 (s, 1 H), 8.13 (d, J=0.4 Hz, 1 H), 8.03 (s, 1 H), 7.98 (s, 1 H), 7.95 (s, 1 H), 5.04-5.13 (m, 1 H), 4.33-4.42 (m, 1 H), 4.00 (s, 3 H), 3.49-3.59 (m, 1 H), 1.72-2.26 (m, 8H); MS (ESI): 462.33 [M+H]+; HPLC $t_R$=2.74 min (ZQ3: polar_5 min).

Example 251

1-(4-{4-[7-amino-2-(5-hydroxythieno[2,3-c]pyridin-3-yl)furo[2,3-c]pyridin-4-yl]-1H-pyrazol-1-yl}piperidin-1-yl)ethanone bis(trifluoroacetate)

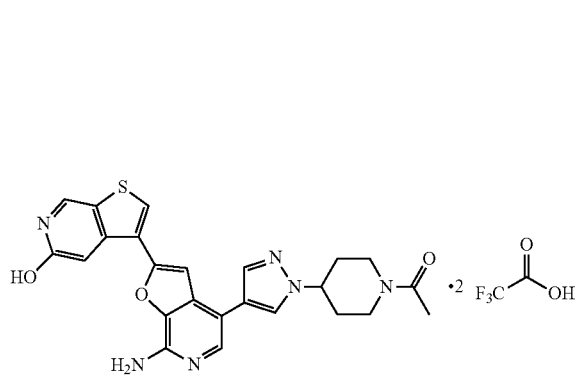 [SMILES: CC(=O)N1CCC(n2cc(-c3cnc(N)c4oc(-c5csc6cnc(O)cc56)cc34)cn2)CC1 ; O=C(O)C(F)(F)F]

Step A: 3-{7-amino-4-[1-(piperidin-4-yl)-1H-pyrazol-4-yl]furo[2,3-c]pyridin-2-yl}thieno[2,3-c]pyridin-5-ol bis(trifluoroacetate)

A mixture of 1-(4-{4-[7-amino-2-(5-methoxythieno[2,3-c]pyridin-3-yl)-furo[2,3-c]pyridin-4-yl]-pyrazol-1-yl}-piperidin-1-yl)-ethanone (50.4 mg, 0.103 mmol), pyridine hydrochloride (122 mg, 1.03 mmol) and water (10 mL) was heated in a microwave reactor at 150° C. for 2 h. Purification by MDP afforded 40 mg (59%) of the title compound as a yellow oil. MS (ESI): 433.14 [M+H]+; HPLC $t_R$=0.84 min (TOF: polar_3 min).

Step B: 1-(4-{4-[7-amino-2-(5-hydroxythieno[2,3-c]pyridin-3-yl)furo[2,3-c]pyridin-4-yl]-1H-pyrazol-1-yl}piperidin-1-yl)ethanone bis(trifluoroacetate) (Title Compound)

To a mixture of 3-{7-amino-4-[1-(piperidin-4-yl)-1H-pyrazol-4-yl]furo[2,3-c]pyridin-2-yl}thieno[2,3-c]pyridin-5-ol bis(trifluoroacetate) (40 mg, 0.061 mmol), THF (3 mL), and DMF (1.5 mL) was added triethylamine (72 µl, 0.52 mmol) followed by acetic anhydride (5.9 µl, 0.61 mmol). After stirring at RT for 1 h, the reaction mixture was concentrated in vacuo, and was then purified by MDP to afford 2.0 mg (5%) of the title compound as a yellow paste. 1H NMR (400 MHz, DMSO-d6): δ 13.72 (br s, 1 H), 8.86 (s, 1 H), 8.74 (s, 1 H), 8.56 (br s, 2 H), 8.48 (d, J=0.8 Hz, 1 H), 8.12 (d, J=0.8 Hz, 1 H), 7.96 (s, 1 H), 7.88 (s, 1 H), 7.67 (s, 1 H), 4.48-4.58 (m, 2 H), 3.94-4.01 (m, 1 H), 3.22-3.31 (m, 1 H), 2.73-2.82 (m, 1 H), 2.07-2.18 (m, 2 H), 2.07 (s, 3 H), 1.79-2.02 (m, 2 H); MS (ESI): 475.14 [M+H]+; HPLC $t_R$=0.96 min (TOF: polar_3 min).

Example 252 trans-4-{4-[7-amino-2-(2-methylthieno[2,3-c]pyridin-3-yl)furo[2,3-c]pyridin-4-yl]-1H-pyrazol-1-yl}cyclohexanol trifluoroacetate

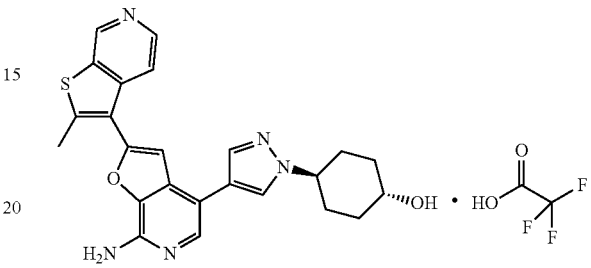

Step A: 2,3-dibromo-thieno[2,3-c]pyridine

To a cooled (−78° C.) solution of 3-bromo-thieno[2,3-c]pyridine (6.42 g, 30.0 mmol) in dry THF (150 mL) under nitrogen was added 2.0 M LDA (30.0 mL, 60.0 mmol) dropwise. The mixture was stirred at −78° C. for 1 h. A solution of NBS (10.7 g, 60 mmol) in THF (50 mL) was added to the reaction mixture dropwise keeping the temperature below −70° C. The mixture was then warmed to room temperature overnight. Saturated aqueous ammonium chloride (50 mL) was added to the mixture and layers were separated. The aqueous layer was extracted with EtOAc (2×60 mL). The combined organic fractions were washed with brine (50 mL), dried over sodium sulfate, and concentrated. Purification by column chromatography (100% DCM) afforded 4.5 g (55%) of the title compound. 1H NMR (300 MHz, CDCl3): δ 7.62 (d, J=5.4 Hz, 1H); 8.58 (d, J=5.4 Hz, 1H); 8.99 (s, 1H).

Step B: 3-bromo-2-methylthieno[2,3-c]pyridine

To a cooled (−78° C.) solution of 3-bromothieno[2,3-c]pyridine (250 mg, 1.17 mmol) in THF (10 mL) was added 1.5 M lithium diisopropylamide in cyclohexane (0.86 mL, 1.28 mmol) and the mixture stirred at −78° C. for 15 min. Methyl iodide (80 µL, 1.28 mmol) was added at −78° C. The mixture was stirred from −78° C. to room temperature and stayed at room temperature for 30 min. Saturated aqueous NH4Cl solution was added and the mixture extracted with DCM. The organic layer was washed with brine and dried over anhydrous sodium sulfate. The crude product was purified by ISCO chromatography (0 to 25% EtOAc:heptane) to afford 178 mg (67%) of the title compound as a white solid. 1H NMR (400 MHz, CD3Cl): δ 8.81 (s, 1 H), 8.39 (d, J=5.6 Hz, 1 H), 7.36 (dd, J=5.3, 0.8 Hz, 1 H), 2.41 (s, 3 H); MS (ESI): 228.30, 230.30 [M+H]+; HPLC $t_R$=0.68 min (HPLC: Analytical_2 min).

Step C: 2-methyl-3-(4,4,5,5-tetramethyl-1,3,2-dioxaborolan-2-yl)thieno[2,3-c]pyridine A solution of 3-bromo-2-methylthieno[2,3-c]pyridine (100 mg, 0.44 mmol), bis(pinacolato)diboron (557 mg, 2.19 mmol), potassium acetate (301 mg, 3.07 mmol), and 1,1'-bis(diphenylphosphino)ferrocenepalladium(II) dichloride dichloromethane complex (36 mg, 0.04 mmol) in 1,4-dioxane (2.5 mL) was heated to 105° C. for 18 h. The mixture was diluted with EtOAc and washed with saturated aqueous NaHCO$_3$, water and brine. The organic layer was dried over anhydrous Na$_2$SO$_4$. The material was purified by ISCO chromatography (0 to 20% EtOAc:heptane) to afford 50 mg (41%) of the title compound as a white solid. $^1$H NMR (400 MHz, CD$_3$Cl): δ 9.01 (s, 1 H), 8.46 (d, J=5.6 Hz, 1 H), 8.19 (d, J=5.6 Hz, 1 H), 2.88 (s, 3 H), 1.40 (s, 12 H); MS (ESI): 276.11 [M+H]$^+$; HPLC t$_R$=1.28 min (TOF: polar_3 min).

Step D: trans-4-{4-[7-amino-2-(2-methylthieno[2,3-c]pyridin-3-yl)furo[2,3-c]pyridin-4-yl]-1H-pyrazol-1-yl}cyclohexanol Trifluoroacetate (Salt) (Title Compound)

The title compound was prepared by a procedure analogous to Example 229. $^1$H NMR (400 MHz, CD$_3$OD): δ 9.45 (s, 1 H), 8.65 (d, J=6.3 Hz, 1 H), 8.54 (d, J=5.6 Hz, 1 H), 8.25-8.30 (m, 1 H), 8.01 (d, J=0.8 Hz, 1 H), 7.87 (s, 1 H), 7.67 (s, 1 H), 4.29 (tdd, J=11.8, 11.8, 3.9, 3.8 Hz, 1 H), 3.69 (tt, J=11.0, 4.2 Hz, 1 H), 3.05 (s, 3 H), 2.08-2.22 (m, 4 H), 1.94-2.05 (m, 2 H), 1.46-1.57 (m, 2 H); MS (ESI): 446.56 (M+H)$^+$; HPLC t$_R$=0.40 min (HPLC: Purity_2 min).

Example 253

1-(4-{4-[7-amino-2-(2-methylthieno[2,3-c]pyridin-3-yl)furo[2,3-c]pyridin-4-yl]-1H-pyrazol-1-yl}piperidin-1-yl)ethanone trifluoroacetate

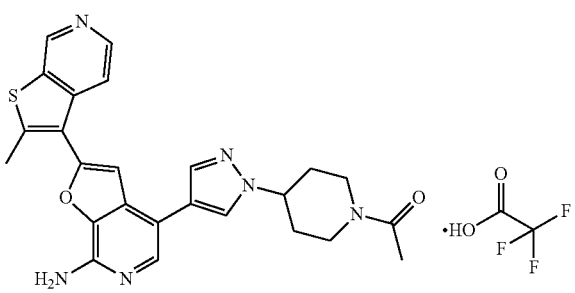

The title compound was prepared by a procedure analogous to Example 252. $^1$H NMR (400 MHz, CD$_3$OD): δ 9.50 (s, 1 H), 8.64-8.69 (m, 1 H), 8.57-8.62 (m, 1 H), 8.30-8.31 (m, 1 H), 8.03 (d, J=0.8 Hz, 1 H), 7.88 (s, 1 H), 7.69 (s, 1 H), 4.68 (dd, J=11.6, 2.0 Hz, 1 H), 4.57 (tdd, J=11.4, 11.4, 4.2, 4.0 Hz, 1 H), 4.11 (d, J=13.6 Hz, 1 H), 3.34-3.39 (m, 1 H), 3.07 (s, 3 H), 2.87 (td, J=12.8, 2.4 Hz, 1 H), 2.18-2.27 (m, 2 H), 2.17 (s, 3 H), 1.97-2.13 (m, 2 H); MS (ESI): 473.57 [M+H]$^+$; HPLC t$_R$=0.40 min (HPLC: Purity_2 min).

Example 254

1-(4-{4-[7-amino-2-(4-fluorothieno[2,3-d]pyridin-3-yl)furo[2,3-d]pyridin-4-yl]-1H-pyrazol-1-yl}piperidin-1-yl)ethanone trifluoroacetic acid salt

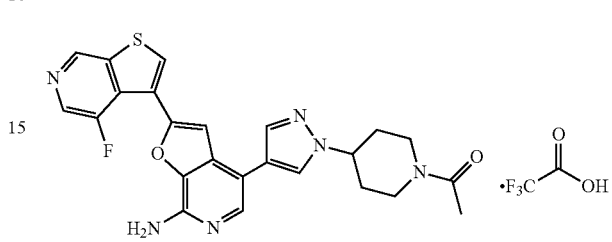

Step A: methyl 4-fluorothieno[2,3-c]pyridine-2-carboxylate

To a cooled (0° C.) solution of 3,5-difluoro-4-formylpyridine (1.00 g, 6.99 mmol) in THF (12.3 mL) was added mercaptoacetic acid methyl ester (625 μL, 6.99 mmol). The reaction stirred 1 h at 0° C. and 1 h at room temperature, and then cesium carbonate (2.28 g, 6.99 mmol) was added. The reaction then stirred a further 18 h at room temperature. The reaction mixture was then partitioned between ethyl acetate (50 mL) and brine (50 mL). The layers were separated and the organic fraction was washed with water (1×50 mL) and brine (1×25 mL), then dried over sodium sulfate, filtered, and concentrated. Purification by ISCO chromatography (20 to 40% ethyl acetate:hexanes) afforded 942 mg (64%) of the title compound as a white solid. $^1$H NMR (400 MHz, DMSO-d$_6$): δ 9.23-9.29 (m, 1 H), 8.56 (dd, J=2.0, 0.5 Hz, 1 H), 8.25 (d, J=0.8 Hz, 1 H), 3.94 (s, 3 H); MS (ESI): 212.09 [M+H]$^+$; HPLC t$_R$=3.17 min (ZQ3, polar_4 min).

Step B: 4-fluorothieno[2,3-c]pyridine-2-carboxylic acid

To a solution of methyl 4-fluorothieno[2,3-c]pyridine-2-carboxylate (0.942 g, 4.46 mmol) in THF (23 mL) was added a solution of lithium hydroxide monohydrate (0.384 g, 9.14 mmol) in water (23 mL). Methanol (2.8 mL) was then added until the solution was transparent. The reaction mixture stirred 2 h at room temperature. The reaction was then adjusted to pH ~4 by addition of 2 N aqueous HCl, causing formation of a white precipitate. THF and methanol were removed by rotary evaporation, and then the residual solid was collected by vacuum filtration, washing with water (2×25 mL). The collected white solid was dried in an oven at 50° C. to afford 765 mg (87%) of the title compound. $^1$H NMR (400 MHz, DMSO-d$_6$): δ 14.15 (br. s., 1 H), 9.23 (s, 1 H), 8.54 (s, 1 H), 8.14 (s, 1 H); MS (ESI): 198.05 [M+H]$^+$; HPLC t$_R$=2.40 min (ZQ3, polar_4 min).

Step C: 4-fluorothieno[2,3-c]pyridine

A mixture of 4-fluorothieno[2,3-c]pyridine-2-carboxylic acid (765 mg, 3.88 mmol) and copper powder (629 mg, 9.91 mmol) in diphenyl ether (3.8 mL) was heated to boiling for ~5 min. After cooling to 40° C., the reaction mixture was diluted with heptane (10 mL), filtered through a short pad of Celite, and concentrated to remove the heptane. Purification of the residue by ISCO chromatography (5 to 45% ethyl acetate:heptane) afforded 441 mg (74%) of the title compound as a white solid. $^1$H NMR (400 MHz, CDCl$_3$): δ 8.96 (d, J=1.8 Hz, 1 H), 8.34 (d, J=2.0 Hz, 1 H), 7.61-7.88 (m, 1 H), 7.38-7.57 (m, 1 H); MS (ESI): 154.07 [M+H]$^+$; HPLC t$_R$=2.97 min (ZQ3, polar_4 min).

Step D: 3-bromo-4-fluorothieno[2,3-c]pyridine

To a solution of 4-fluorothieno[2,3-c]pyridine (100 mg, 0.653 mmol) and sodium acetate (109 mg, 1.30 mmol) in acetic acid (2.65 mL) was added bromine (101 uL, 1.96 mmol). The reaction was heated in a microwave at 90° C. for 90 min. The reaction was concentrated. Purification by ISCO chromatography (5 to 40% ethyl acetate:heptane) afforded 77 mg (51%) of the title compound as a white solid. $^1$H NMR (400 MHz, CDCl$_3$): δ 8.96 (s, 1 H), 8.40 (d, J=2.3 Hz, 1 H), 7.67 (d, J=0.8 Hz, 1 H); MS (ESI): 231.99, 233.95 [M+H]$^+$; HPLC t$_R$=3.28 min (ZQ3, polar_4 min).

Step E: 4-fluoro-3-(4,4,5,5-tetramethyl-1,3,2-dioxaborolan-2-yl)thieno[2,3-c]pyridine A solution of 3-bromo-4-fluorothieno[2,3-c]pyridine (77 mg, 0.33 mmol), bis(pinacolato)diboron (126 mg, 0.498 mmol), potassium acetate (65.1 mg, 0.664 mmol), and 1,1'-bis(diphenylphosphino)ferrocenepalladium(II) dichloride dichloromethane complex (13.5 mg, 0.0166 mmol) in 1,4-dioxane (1.6 mL) was heated to 85° C. for 18 h. The reaction mixture was then diluted with dichloromethane (40 mL), filtered through a pad of Celite, and concentrated. The residue was purified by ISCO chromatography (5 to 100% ethyl acetate:hexanes) to afford 57 mg (52%) of the title compound as a light yellow oil. $^1$H NMR (400 MHz, CDCl$_3$): δ 8.96 (s, 1 H), 8.35 (d, J=2.3 Hz, 1 H), 8.24 (s, 1 H), 1.40 (s, 12 H); MS (ESI): 280.18 [M+H]$^+$; HPLC t$_R$=3.54 min (TOF, polar_3 min).

Step F: 1-(4-{4-[7-amino-2-(4-fluorothieno[2,3-c]pyridin-3-yl)furo[2,3-c]pyridin-4-yl]-1H-pyrazol-1-yl}piperidin-1-yl)ethanone trifluoroacetic Acid Salt (Title Compound)

The title compound was prepared in 32% yield from 1-{4-[4-(7-amino-2-chlorofuro[2,3-c]pyridin-4-yl)-1H-pyrazol-1-yl]piperidin-1-yl}ethanone and 4-fluoro-3-(4,4,5,5-tetramethyl-1,3,2-dioxaborolan-2-yl)thieno[2,3-c]pyridine by a procedure analogous to Example 223, Step D. $^1$H NMR (400 MHz, CD$_3$OD): δ 9.15 (s, 1 H), 8.79 (s, 1 H), 8.51 (d, J=4.0 Hz, 1 H), 8.24 (s, 1 H), 7.97 (s, 1 H), 7.82 (s, 1 H), 7.66 (d, J=1.5 Hz, 1 H), 4.64-4.74 (m, 1 H), 4.50-4.62 (m, 1 H), 4.11 (s, 1 H), 3.33-3.42 (m, 1 H), 2.77-2.97 (m, 1 H), 2.13-2.32 (m, 5 H), 1.92-2.13 (m, 2 H); MS (ESI): 477.27 [M+H]$^+$; HPLC t$_R$=2.40 min (ZQ3, polar_4 min).

Example 255

1-(4-{4-[7-amino-2-(4-fluorothieno[2,3-c]pyridin-3-yl)furo[2,3-c]pyridin-4-yl]-1H-pyrazol-1-yl}piperidin-1-yl)ethanone

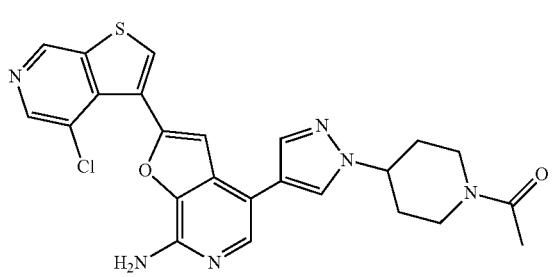 [SMILES: CC(=O)N1CCC(n2cc(-c3cnc(N)c4oc(-c5csc6cncc(Cl)c56)cc34)cn2)CC1]

Step A: methyl 4-chlorothieno[2,3-c]pyridine-2-carboxylate

The title compound was prepared in 58% yield from 3,5-dichloro-4-pyridinecarboxaldehyde by a procedure analogous to Example 254, Step A. $^1$H NMR (400 MHz, DMSO-d$_6$): δ 9.54-9.18 (m, J=0.5 Hz, 1 H), 8.64 (d, J=0.5 Hz, 1 H), 8.13 (d, J=1.0 Hz, 1 H), 3.95 (s, 3 H); MS (ESI): 227.99, 229.97 [M+H]$^+$; HPLC t$_R$=3.37 min (ZQ3, polar_4 min).

Step B: 4-chlorothieno[2,3-c]pyridine-2-carboxylic acid

The title compound was prepared in 56% yield from methyl 4-chlorothieno[2,3-c]pyridine-2-carboxylate by a procedure analogous to Example 254, Step B. $^1$H NMR (400 MHz, DMSO-d$_6$): δ 4.20 (br. s., 1 H), 9.04-9.77 (m, 1 H), 8.62 (d, J=0.5 Hz, 1 H), 8.05 (d, J=0.8 Hz, 1 H); MS (ESI): 214.03, 215.99 [M+H]$^+$; HPLC t$_R$=3.04 min (ZQ3, polar_4 min).

Step C: 4-chlorothieno[2,3-c]pyridine

The title compound was prepared in 66% yield from 4-chlorothieno[2,3-c]pyridine-2-carboxylic acid by a procedure analogous to Example 254, Step C. $^1$H NMR (400 MHz, CDCl$_3$): δ 9.05 (s, 1 H), 8.49 (s, 1 H), 7.82 (d, J=5.6 Hz, 1 H), 7.55 (dd, J=5.3, 0.8 Hz, 1 H); MS (ESI): 170.00, 172.00 [M+H]$^+$; HPLC t$_R$=3.20 min (ZQ3, polar_4 min).

Step D: 3-bromo-4-chlorothieno[2,3-c]pyridine

The title compound was prepared in 39% yield from 4-chlorothieno[2,3-c]pyridine by a procedure analogous to Example 254, Step D. $^1$H NMR (400 MHz, CDCl$_3$): δ 9.03 (s, 1 H), 8.51 (s, 1 H), 7.79 (s, 1 H); MS (ESI): 247.98, 249.97 [M+H]$^+$; HPLC t$_R$=3.50 min (ZQ3, polar_4 min).

Step E: 4-chloro-3-(4,4,5,5-tetramethyl-1,3,2-dioxaborolan-2-yl)thieno[2,3-c]pyridine The title compound was prepared in 49% yield from 3-bromo-4-chlorothieno[2,3-c]pyridine by a procedure analogous to Example 254, Step E. The title compound was judged to be 55% pure by LCMS and used without further purification. MS (ESI): 296.12, 298.12 [M+H]⁺; HPLC t_R=3.62 min (TOF, polar_3 min).

Step F: 1-(4-{4-[7-amino-2-(4-fluorothieno[2,3-c]pyridin-3-yl)furo[2,3-c]pyridin-4-yl]-1H-pyrazol-1-yl}piperidin-1-yl)ethanone (Title Compound)

The title compound was prepared in 10% yield from 1-{4-[4-(7-amino-2-chlorofuro[2,3-c]pyridin-4-yl)-1H-pyrazol-1-yl]piperidin-1-yl}ethanone and 4-chloro-3-(4,4,5,5-tetramethyl-1,3,2-dioxaborolan-2-yl)thieno[2,3-c]pyridine by a procedure analogous to Example 223, Step D. ¹H NMR (400 MHz, DMSO-d₆): δ 9.39 (s, 1 H), 8.70 (s, 1 H), 8.59 (s, 1 H), 8.25 (s, 1 H), 8.04 (s, 1 H), 7.92 (s, 1 H), 7.51 (s, 1 H), 6.28 (br. s, 2 H), 4.35-4.57 (m, 2 H), 3.93 (d, J=14.1 Hz, 1 H), 3.23 (d, J=11.6 Hz, 1 H), 2.64-2.78 (m, 1 H), 1.98-2.17 (m, 5 H), 1.73-1.97 (m, 2 H); MS (ESI): 493.21, 495.22 [M+H]⁺; HPLC t_R=2.40 min (ZQ3, polar_4 min).

Examples 256 and 257

1-(4-{4-[7-amino-2-(7-fluorothieno[2,3-c]pyridin-3-yl)furo[2,3-c]pyridin-4-yl]-1H-pyrazol-1-yl}piperidin-1-yl)ethanone trifluoroacetic acid salt and 3-{4-[1-(1-acetylpiperidin-4-yl)-1H-pyrazol-4-yl]-7-aminofuro[2,3-c]pyridin-2-yl}thieno[2,3-c]pyridin-7(6H)-one trifluoroacetic Acid Salt

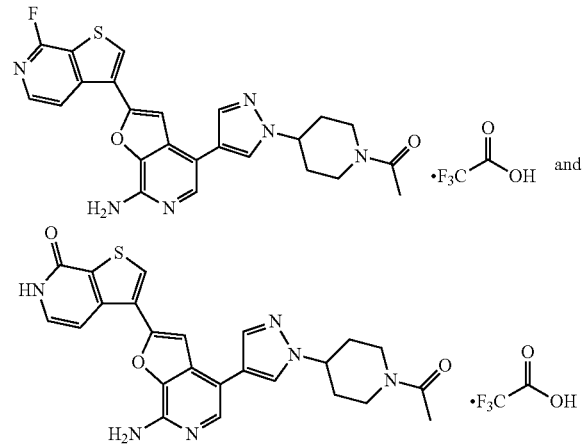

Step A: 3-bromothieno[2,3-c]pyridin-7-amine

To a solution of 3-bromo-7-chlorothieno[2,3-c]pyridine (200 mg, 0.805 mmol) in 1,4-dioxane (2.6 mL) was added 28% ammonium hydroxide (2.2 mL, 22 mmol). The mixture was heated in a microwave at 140° C. for 6 h and then concentrated. The residue was suspended in water (15 mL) and extracted with 5% methanol:dichloromethane (5×10 mL). The combined organic fractions were dried over sodium sulfate, filtered, and concentrated. Purification by ISCO chromatography (0 to 5% methanol:dichloromethane) afforded 27 mg (15%) of the title compound as a light yellow solid. ¹H NMR (400 MHz, CDCl₃): δ 8.10 (d, J=5.8 Hz, 1 H), 7.58 (s, 1 H), 7.18 (d, J=5.6 Hz, 1 H), 4.87 (br. s., 2 H); MS (ESI): 229.04, 231.00 [M+H]⁺; HPLC t_R=2.19 min (ZQ3, polar_4 min).

Step B: 3-bromo-7-fluorothieno[2,3-c]pyridine

To a solution of 3-bromothieno[2,3-c]pyridin-7-amine (51 mg, 0.22 mmol) in pyridine hydrofluoride (1.2 mL) was added sodium nitrite (23.1 mg, 0.334 mmol). The reaction stirred at room temperature for 18 h. The reaction was then neutralized by addition of saturated aqueous sodium bicarbonate (40 mL). The mixture was extracted with ethyl acetate (2×10 mL). The combined organic fractions were washed with brine (1×20 mL), dried over sodium sulfate, filtered, and concentrated to afford 33 mg (59%) of the title compound. ¹H NMR (400 MHz, CDCl₃): δ 8.20 (dd, J=5.6, 1.3 Hz, 1 H), 7.76 (s, 1 H), 7.62 (dd, J=5.6, 2.8 Hz, 1 H); MS (ESI): 232.04, 234.04 [M+H]⁺; HPLC t_R=3.49 min (ZQ3, polar_4 min).

Step C: 7-fluoro-3-(4,4,5,5-tetramethyl-1,3,2-dioxaborolan-2-yl)thieno[2,3-c]pyridine A solution of 3-bromo-7-fluorothieno[2,3-c]pyridine (33 mg, 0.14 mmol), bis(pinacolato)diboron (54.2 mg, 0.213 mmol), potassium acetate (27.9 mg, 0.284 mmol), and 1,1'-bis(diphenylphosphino)ferrocenepalladium(II) dichloride dichloromethane complex (5.8 mg, 0.0071 mmol) in 1,4-dioxane (0.71 mL) was heated to 85° C. for 18 h. The reaction mixture was then diluted with dichloromethane (40 mL), filtered through a pad of Celite, and concentrated. The residue was purified by ISCO chromatography (5 to 100% ethyl acetate:hexanes) to afford 40 mg (87%) of the title compound as a light yellow oil. ¹H NMR (400 MHz, CDCl₃): δ 8.32 (d, J=0.5 Hz, 1 H), 8.03-8.14 (m, 2 H), 1.39 (m, 12 H); MS (ESI): 280.18 [M+H]⁺; HPLC t_R=3.54 min (TOF, polar_3 min).

Step D: 1-(4-{4-[7-amino-2-(7-fluorothieno[2,3-c]pyridin-3-yl)furo[2,3-c]pyridin-4-yl]-1H-pyrazol-1-yl}piperidin-1-yl)ethanone trifluoroacetic acid salt and 3-{4-[1-(1-acetylpiperidin-4-yl)-1H-pyrazol-4-yl]-7-aminofuro[2,3-c]pyridin-2-yl}thieno[2,3-c]pyridin-7(6H)-one trifluoroacetic acid salt (Title Compounds)

The title compounds were prepared in 25% and 5% yields, respectively, from 1-{4-[4-(7-amino-2-chlorofuro[2,3-c]pyridin-4-yl)-1H-pyrazol-1-yl]piperidin-1-yl}ethanone and 7-fluoro-3-(4,4,5,5-tetramethyl-1,3,2-dioxaborolan-2-yl)thieno[2,3-c]pyridine by a procedure analogous to Example 223, Step D.

1-(4-{4-[7-amino-2-(7-fluorothieno[2,3-c]pyridin-3-yl)furo[2,3-c]pyridin-4-yl]-1H-pyrazol-1-yl}piperidin-1-yl)ethanone trifluoroacetic acid salt: ¹H NMR (400 MHz, CD₃OD): δ 8.90 (s, 1 H), 8.52 (dd, J=5.7, 2.7 Hz, 1 H), 8.33 (s, 1 H), 8.29 (dd, J=5.7, 0.9 Hz, 1 H), 8.04 (s, 1 H), 7.74-7.92 (m, 2 H), 4.65-4.77 (m, 1 H), 4.49-4.64 (m, 1 H), 3.98-4.25 (m, 1 H), 3.40 (d, J=3.0 Hz, 1 H), 2.81-2.97 (m, 1 H), 2.14-2.33 (m, 5 H), 1.95-2.14 (m, 2 H); MS (ESI): 477.23 [M+H]⁺; HPLC t_R=2.52 min (ZQ3, polar_4 min).

3-{4-[1-(1-acetylpiperidin-4-yl)-1H-pyrazol-4-yl]-7-aminofuro[2,3-c]pyridin-2-yl}thieno[2,3-c]pyridin-7(6H)-one trifluoroacetic acid salt: ¹H NMR (400 MHz, CD₃OD): δ 8.76 (s, 1 H), 8.31 (s, 1 H), 8.02 (s, 1 H), 7.83 (s, 1 H), 7.70 (s, 1 H), 7.52-7.59 (m, 1 H), 7.44-7.51 (m, 1 H), 4.69 (s, 1 H), 4.50-4.63 (m, 1 H), 4.11 (s, 1 H), 3.33-3.45 (m, 1 H), 2.78-3.01 (m, 1H), 2.15-2.32 (m, 5 H), 1.95-2.14 (m, 2 H); MS (ESI): 475.19 [M+H]⁺; HPLC t_R=2.27 min (ZQ3, polar_4 min).

Example 258

3-{4-[1-(1-acetylpiperidin-4-yl)-1H-pyrazol-4-yl]-7-aminofuro[2,3-c]pyridin-2-yl}-5-methylthieno[3,2-c]pyridin-6(5H)-one trifluoroacetic Acid Salt

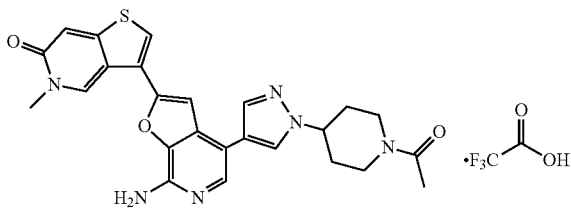

Step A: N-[(4-bromothiophen-3-yl)methyl]-2-ethoxy-3-methoxypropanamide

To a suspension of sodium hydride (162 mg, 6.74 mmol) in THF (14 mL, 170 mmol) was added 2,2-diethoxyacetamide (949 mg, 6.45 mmol) in portions, followed by 3-bromo-4-(bromomethyl)thiophene (1.50 g, 5.86 mmol) dropwise as a solution in THF (3 mL) and sodium iodide (87.8 mg, 0.586 mmol). The reaction mixture was heated to reflux for 18 h and then concentrated. The residue was then partitioned between water (40 mL) and ethyl acetate (40 mL). The layers were separated and the aqueous layer was further extracted with ethyl acetate (2×30 mL). The combined organic fractions were dried over sodium sulfate, filtered, and concentrated. Purification by ISCO chromatography (5 to 30% ethyl acetate:heptane) afforded 729 mg (35%) of the title compound as a clear, colorless oil. ¹H NMR (400 MHz, CDCl₃): δ 7.26-7.29 (m, 1 H), 7.23-7.25 (m, 1 H), 6.99 (br. s., 1 H), 4.83 (s, 1 H), 4.44 (dd, J=6.1, 0.8 Hz, 2 H), 3.21-3.98 (m, 4 H), 1.25 (t, J=6.9 Hz, 6 H); MS (ESI): 322.17, 324.15 [M+H]⁺; HPLC t_R=3.26 min (ZQ3, polar_4 min).

Step B: 3-bromothieno[3,2-c]pyridin-6(5H)-one

A solution of N-[(4-bromothiophen-3-yl)methyl]-2-ethoxy-3-methoxypropanamide (729 mg, 2.26 mmol) in acetic acid (4.5 mL) and hydrogen bromide (2.2 mL, 41 mmol) was heated to reflux for 2 h. Upon cooling a precipitate formed. The precipitate was collected by vacuum filtration, washing with acetic acid (2×10 mL) and diethyl ether (2×10 mL). The collected solid was suspended in water (10 mL) and treated with solid sodium bicarbonate until the solution pH was ~8. The solid was then collected by vacuum filtration, washing with water (2×10 mL). The collected solid was dried in an oven at 50° C. for 16 h to afford 235 mg (45%) of the title compound as a tan solid. ¹H NMR (400 MHz, DMSO-d₆): δ ppm 11.82 (br. s., 1 H), 8.07 (s, 1 H), 7.55 (s, 1 H), 7.01 (s, 1H); MS (ESI): 230.01, 231.99 [M+H]⁺; HPLC t_R=2.53 min (ZQ3, polar_4 min).

Step C: 3-bromo-5-methylthieno[3,2-c]pyridin-6(5H)-one

To a suspension of 3-bromothieno[3,2-c]pyridin-6(5H)-one (235 mg, 1.02 mmol) in DMF (3.9 mL) was added sodium hydride (25.7 mg, 1.07 mmol). The mixture stirred 1 h at room temperature, and then methyl iodide (69.9 μL, 1.12 mmol) was added. The reaction stirred a further 1 h at room temperature and then was poured into water (100 mL). The mixture was extracted with dichloromethane (3×50 mL). The combined organic fractions were washed with water (3×50 mL), dried over sodium sulfate, filtered, and concentrated. Trituration with diethyl ether (~5 mL) and filtration to collect the resultant solid afforded 120 mg (48%) of the title compound as a tan solid. ¹H NMR (400 MHz, CDCl₃): δ 7.84 (s, 1 H), 6.91 (s, 1 H), 6.89 (d, J=0.8 Hz, 1 H), 3.75 (s, 3 H); MS (ESI): 244.03, 245.98 [M+H]⁺; HPLC t_R=2.76 min (ZQ3, polar_4 min).

Step D: 5-methyl-3-(4,4,5,5-tetramethyl-1,3,2-dioxaborolan-2-yl)thieno[3,2-c]pyridin-6(5H)-one A solution of 3-bromo-5-methylthieno[3,2-c]pyridin-6(5H)-one (80 mg, 0.33 mmol), bis(pinacolato)diboron (125 mg, 0.492 mmol), potassium acetate (64.3 mg, 0.655 mmol), and 1,1'-bis(diphenylphosphino)ferrocenepalladium(II) dichloride dichloromethane complex (13.4 mg, 0.0164 mmol) in 1,4-Dioxane (1.6 mL) was heated to 85° C. for 4 h. The reaction was cooled to room temperature and concentrated. Purification by ISCO chromatography (0 to 50% acetone:heptane) afforded 26 mg (27%) of the title compound as a white solid. ¹H NMR (400 MHz, CDCl₃): δ 8.35 (br. s., 1 H), 7.54-7.69 (m, 1 H), 6.93-7.19 (m, 1 H), 3.69-3.91 (m, 3 H), 1.36 (s, 12H); MS (ESI): 292.25 [M+H]⁺; HPLC t_R=3.19 min (ZQ3, polar_4 min).

Step E: 3-{4-[1-(1-acetylpiperidin-4-yl)-1H-pyrazol-4-yl]-7-aminofuro[2,3-c]pyridin-2-yl}-5-methylthieno[3,2-c]pyridin-6(5H)-one (Title Compound)

The title compound was prepared in 30% yield from 1-{4-[4-(7-amino-2-chlorofuro[2,3-c]pyridin-4-yl)-1H-pyrazol-1-yl]piperidin-1-yl}ethanone and 5-methyl-3-(4,4,5,5-tetramethyl-1,3,2-dioxaborolan-2-yl)thieno[3,2-c]pyridin-6(5H)-one by a procedure analogous to Example 223, Step D. ¹H NMR (400 MHz, CD₃OD): δ 9.01 (s, 1 H), 8.29 (s, 1 H), 8.17 (s, 1 H), 8.03 (s, 1 H), 7.83 (s, 1 H), 7.75 (s, 1 H), 7.07 (s, 1 H), 4.69 (m, J=13.1 Hz, 1 H), 4.51-4.62 (m, 1 H), 4.11 (m, J=16.4 Hz, 1 H), 3.87 (s, 3 H), 3.33-3.42 (m, 1 H), 2.80-2.96 (m, 1 H), 2.16-2.30 (m, 5 H), 1.95-2.15 (m, 2 H); MS (ESI): 489.37 [M+H]⁺; HPLC t_R=2.32 min (ZQ3, polar_4 min).

Example 259

3-{7-amino-4-[1-(trans-4-hydroxycyclohexyl)-1H-pyrazol-4-yl]furo[2,3-c]pyridin-2-yl}-5-methylthieno[3,2-c]pyridin-6(5H)-one

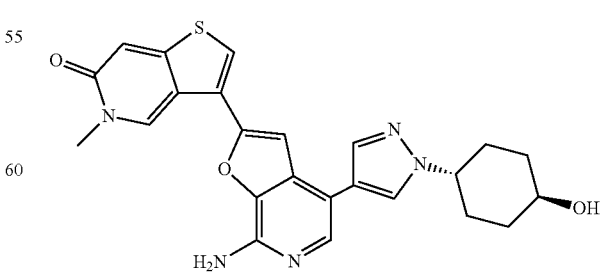

The title compound was prepared in 60% yield from 4-[1-(trans-4-{[tert-butyl(dimethyl)silyl]oxy}cyclohexyl)-1H- pyrazol-4-yl]-2-chlorofuro[2,3-c]pyridin-7-amine and 5-methyl-3-(4,4,5,5-tetramethyl-1,3,2-dioxaborolan-2-yl)thieno[3,2-c]pyridin-6(5H)-one by a procedure analogous to Example 229. ¹H NMR (400 MHz, CD₃OD): δ 8.98 (s, 1 H), 8.11 (s, 1 H), 7.99-8.03 (m, 1 H), 7.87-7.95 (m, 2 H), 7.43-7.52 (m, 1 H), 6.96-7.10 (m, 1 H), 4.16-4.37 (m, 1 H), 3.88 (s, 3 H), 3.61-3.78 (m, 1 H), 1.85-2.31 (m, 6 H), 1.39-1.69 (m, 2 H); MS (ESI): 462.28 [M+H]⁺; HPLC $t_R$=2.30 min (ZQ3, polar_4 min).

Example 260

1-(4-{4-[7-amino-2-(thieno[3,2-d]pyrimidin-7-yl)furo[2,3-c]pyridin-4-yl]-1H-pyrazol-1-yl}piperidin-1-yl)ethanone

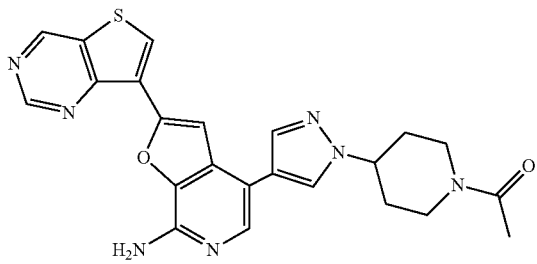 [SMILES: CC(=O)N1CCC(n2cc(-c3cnc(N)c4oc(-c5csc6cncnc56)cc34)cn2)CC1]

Step A: 7-thieno[3,2-d]pyrimidine

A stirred solution of 4-chlorothieno[3,2-d]pyrimidine (1 g, 6 mmol) in MeOH (45 mL) was sparged with nitrogen for 15 min. To this solution was added magnesium monoxide (0.75 g, 19 mmol) and 10% palladium on carbon (0.5 g, 5 mmol). After flushing out the nitrogen atmosphere with hydrogen, the reaction mixture was stirred overnight at room temperature under a hydrogen-filled balloon. Following removal of the hydrogen balloon, the reaction mixture was degassed by bubbling nitrogen through for 15 min. The crude product mixture was filtered through Celite, and solvent removed by rotary evaporation. The crude product was passed through a short column of silica gel, eluting with 9:1 methylene chloride/methanol. Evaporation of the solvent provided 0.712 g (90%) of the title compound as a crystalline white solid. ¹H NMR (400 MHz, CDCl₃): δ 9.30 (s, 1 H), 9.23 (s, 1 H), 8.04 (d, J=5.3 Hz, 1 H), 7.59 (dd, J=0.6, 5.4 Hz, 1 H); MS (ESI): 137.02 [M+H]⁺.

Step B: 7-bromothieno[3,2-d]pyrimidine

Thieno[3,2-d]pyrimidine (0.163 g, 1.20 mmol) was dissolved in acetic acid (3 mL). Sodium acetate (0.196 g, 2.39 mmol) was added while stirring, followed by bromine (0.38 g, 2.4 mmol). The reaction mixture was heated in a microwave reactor at 90° C. for 90 min. Solvent was removed by rotary evaporation, then under high vacuum. Purification by ISCO chromatography (0 to 10% methanol:DCM) afforded 0.152 g (59%) of the title compound as a yellow solid. ¹H NMR (400 MHz, CDCl₃): δ 9.36 (s, 1 H), 9.30 (s, 1 H), 8.05 (s, 1 H); MS (ESI): 214.97, 216.99 [M+H]⁺.

Step C: 7-(tributylstannanyl)thieno[3,2-d]pyrimidine

A suspension of 7-bromothieno[3,2-d]pyrimidine (0.060 g, 0.28 mmol) and bis(tri-n-butyltin) (0.21 g, 0.36 mmol) in toluene (2 mL) was degassed with nitrogen for 15 min. To this mixture was added Pd(PPh₃)₄ (0.032 g, 0.028 mmol), and the mixture was heated to 125° C. under a reflux condenser. After 1 h, the reaction was allowed to cool, then evaporated in vacuo. Purification by ISCO chromatography (5 to 25% ethyl acetate:heptane) afforded 0.045 g (38%) of the title compound as a clear oil. ¹H NMR (400 MHz, CDCl₃): δ 9.29 (s, 1 H), 9.17 (s, 1 H), 7.95-7.85 (m, 1 H), 1.60-1.53 (m, 6 H), 1.37-1.30 (m, 7 H), 1.25-1.19 (m, 5 H), 0.87 (t, J=7.3 Hz, 9 H); MS (ESI): 425.32, 427.24 [M+H]⁺.

Step D: 1-(4-{4-[7-amino-2-(thieno[3,2-d]pyrimidin-7-yl)furo[2,3-c]pyridin-4-yl]-1H-pyrazol-1-yl}piperidin-1-yl)ethanone (Title Compound)

A portion of 7-(tributylstannanyl)thieno[3,2-d]pyrimidine (0.030 g, 0.071 mmol) was dissolved in DMF (0.8 mL), and the solution was degassed with nitrogen for 10 min. To this mixture was added 1-{4-[4-(7-amino-2-chlorofuro[2,3-c]pyridin-4-yl)-1H-pyrazol-1-yl]piperidin-1-yl}ethanone (0.017 g, 0.047 mmol), Pd(PPh₃)₄ (0.0066 g, 0.0057 mmol) and cesium fluoride (0.0241 g, 0.159 mmol). The mixture was heated in a microwave reactor for 30 min at 130° C. Purification by MDP and then ISCO chromatography (0 to 20% methanol:DCM) afforded 0.006 g (30%) of the title compound an off-white solid. ¹H NMR (400 MHz, CD₃OD): δ 9.53 (s, 1 H), 9.36 (s, 1 H), 8.94 (s, 1 H), 8.15 (s, 1 H), 8.03 (s, 1 H), 7.93 (s, 1 H), 7.91 (br. s., 1 H), 4.72 (d, J=13.1 Hz, 1 H), 4.65-4.54 (m, 2 H), 4.14 (d, J=9.6 Hz, 1 H), 2.90 (dt, J=2.8, 13.0 Hz, 1 H), 2.33-2.22 (m, 2 H), 2.20 (s, 3 H), 2.19-2.11 (m, 1 H), 2.10-1.97 (m, 1 H); MS (ESI): 460.36 [M+H]⁺.

Example 261

1-(4-{4-[7-amino-2-(thieno[2,3-d]pyridazin-3-yl)furo[2,3-c]pyridin-4-yl]-1H-pyrazol-1-yl}piperidin-1-yl)ethanone diformate

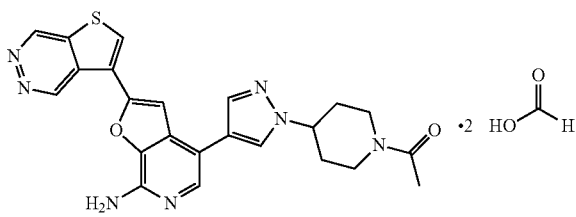 [SMILES: CC(=O)N1CCC(n2cc(-c3cnc(N)c4oc(-c5csc6cnncc56)cc34)cn2)CC1 ; O=CO]

Step A: 3-bromothieno[2,3-d]pyridazine

A solution of thieno[2,3-d]pyridazine (468.0 mg, 3.437 mmol) and sodium acetate (879.2 mg, 10.50 mmol) in acetic acid (14 mL) was charged with bromine (0.55 mL, 11 mmol) and then irradiated under microwave heating at 90° C. for 3 h. The reaction mixture was concentrated in vacuo. Purification by ISCO chromatography (1 to 15% methanol:dichloromethane) afforded 210.6 mg (27%) of the title compound as a pink solid. ¹H NMR (400 MHz, DMSO-d₆): δ 9.96 (d, J=1.52 Hz, 1H), 9.53 (d, J=1.52 Hz, 1H), 8.51 (s, 1H); MS (ESI): 214.97, 216.92 [M+H]⁺; HPLC $t_R$=2.68 min.

Step B: 2-(thieno[2,3-d]pyridazin-3-yl)furo[2,3-c]pyridin-7-amine

A suspension of {7-[bis(tert-butoxycarbonyl)amino]furo[2,3-c]pyridin-2-yl}boronic acid (200.0 mg, 0.5288 mmol), 3-bromothieno[2,3-d]pyridazine (77.1 mg, 0.358 mmol), Pd(PPh$_3$)$_4$ (21.8 mg, 0.0189 mmol), and potassium carbonate (150.5 mg, 1.089 mmol) in a 4:1 mixture of 1,4-dioxane to water (3.5 mL) was heated conventionally to 70° C. for 2.5 h. To the stirring reaction at 70° C., 4.0 M hydrochloric acid in 1,4-dioxane (2.0 mL) was added and was stirred for 1 h. The reaction mixture was cooled to ambient temperature, poured into saturated aqueous sodium bicarbonate, and extracted with dichloromethane. The combined organic layers were washed with brine, dried over anhydrous Na$_2$SO$_4$, filtered, and concentrated in vacuo. Purification by ISCO chromatography (3 to 15% methanol:dichloromethane) afforded 30.6 mg (31%) of the title compound as a yellow solid. $^1$H NMR (400 MHz, DMF-d$_7$): δ 10.43 (d, J=1.52 Hz, 1H), 10.10 (d, J=1.52 Hz, 1H), 8.92 (s, 1H), 7.83 (d, J=5.31 Hz, 1H), 7.67 (s, 1H), 6.95 (d, J=5.31 Hz, 1H), 6.66 (br s, 2H); MS (ESI): 269.13 [M+H]$^+$; HPLC t$_R$=2.16 min.

Step C: 4-iodo-2-(thieno[2,3-d]pyridazin-3-yl)furo[2,3-c]pyridin-7-amine

A solution of 2-(thieno[2,3-d]pyridazin-3-yl)furo[2,3-c]pyridin-7-amine (30.0 mg, 0.112 mmol) and N-iodosuccinimide (101.6 mg, 0.4516 mmol) in N,N-dimethylformamide (2 mL) was stirred at 40° C. for 45 min. The reaction was removed from the heat and 1.0 M aqueous sodium thiosulfate solution (2 mL) was added. The crude mixture was concentrated in vacuo. The residue was then suspended in water and the fine solid was filtered off and dried, giving 39.0 mg (88%) of the title compound as a brown solid. $^1$H NMR (400 MHz, DMSO-d$_6$): δ 10.48 (d, J=1.52 Hz, 1H), 10.02 (d, J=1.52 Hz, 1H), 9.04 (s, 1H), 7.96 (s, 1H), 7.45 (s, 1H), 6.89 (s, 2H); MS (ESI): 395.07 [M+H]$^+$; HPLC: t$_R$=2.83 min.

Step D: 1-(4-{4-[7-amino-2-(thieno[2,3-d]pyridazin-3-yl)furo[2,3-c]pyridin-4-yl]-1H-pyrazol-1-yl}piperidin-1-yl)ethanone diformate (Title Compound)

A mixture of 4-iodo-2-(thieno[2,3-d]pyridazin-3-yl)furo[2,3-c]pyridin-7-amine (7.0 mg, 0.018 mmol), 1-{4-[4-(4,4,5,5-tetramethyl-1,3,2-dioxaborolan-2-yl)-1H-pyrazol-1-yl]piperidin-1-yl}ethanone (6.80 mg, 0.0213 mmol), (1,1'-bis-(diphenylphosphino)-ferrocene) palladium dichloride (14.6 mg, 0.020 mmol), and potassium carbonate (6.14 mg, 0.0444 mmol) in 1,4-dioxane (0.5 mL) and water (0.2 mL) was irradiated under microwave heating at 120° C. for 60 min. The sample was passed through a syringe filter and purified by preparative HPLC to afford 5.2 mg (50%) of the title compound as a yellow solid. $^1$H NMR (400 MHz, CD$_3$OD): δ 10.29 (s, 1H), 9.86 (s, 1H), 8.85 (s, 1H), 8.24 (br s, 2H), 8.19 (s, 1H), 7.95 (s, 1H), 7.90 (s, 1H), 7.71 (s, 1H), 4.70 (d, J=11.87 Hz, 1H), 4.55 (t, J=11.37 Hz, 1H), 4.12 (d, J=13.64 Hz, 1H), 3.33-3.41 (m, 1H), 3.21 (q, J=7.16 Hz, 1H), 2.88 (t, J=13.01 Hz, 1H), 2.18 (s, 3H), 2.12-2.30 (m, 3H); MS (ESI): 460.29 [M+H]$^+$; HPLC t$_R$=2.40 min.

Example 262

1-(4-{4-[7-amino-2-([1,2]thiazolo[4,5-c]pyridin-7-yl)furo[2,3-c]pyridin-4-yl]-1H-pyrazol-1-yl}piperidin-1-yl)ethanone Diformate Salt

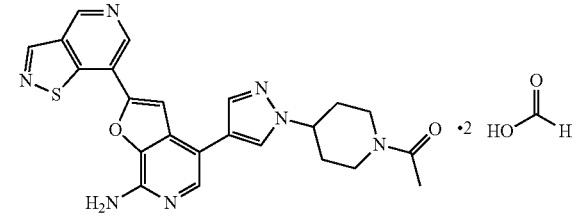 [SMILES: CC(=O)N1CCC(n2cc(-c3cnc(N)c4oc(-c5cncc6cnsc56)cc34)cn2)CC1 ; O=CO]

Step A: 4,5-dibromonicotinic Acid

A cooled (−70° C.) solution of 5-bromonicotinic acid (12.6 g, 62.5 mmol) in THF under nitrogen was treated with 2 M lithium diisopropylamide (72 mL, 144 mmol) dropwise over 1 h. The solution stirred for 2.5 h at −55° C. The mixture was then cooled to −70° C. and treated with 1,2-dibromotetrachloroethane (25 g, 77.2 mmol) in portions over 30 min. After 1 h, the reaction mixture was allowed to warm to −20° C. over 2 h and then water (75 mL) was added slowly. The organic layer was then evaporated in vacuo and the aqueous residue was diluted with water (250 mL), then washed with ethyl acetate. The aqueous layer was then acidified to pH 3 by addition of concentrated hydrochloric acid. The precipitated solid was collected by filtration and dried at 60° C. in vacuo to afford 10 g (57%) of the title compound. $^1$H NMR (300 MHz, DMSO-d$_6$) δ 8.98 (s, 1H), 8.75 (s, 1H), 3.2 (br. s, 1H).

Step B: 4,5-dibromonicotinic Acid Ethyl Ester

A suspension of 4,5-dibromonicotinic acid (10 g, 36 mmol) in acetonitrile (160 mL) under nitrogen was treated with 1,1'-carbonyldiimidazole (8.65 g, 53.4 mmol) in portions over 10 min. The resulting mixture was stirred for 3 h at room temperature. Ethanol (24 mL) was added and the mixture was heated to 55° C. for 16 h. The solution was then filtered and the filtrate evaporated in vacuo. The residual oil was dissolved in ethyl acetate and the solution was washed with water followed by brine. The organic fraction was then dried over sodium sulfate, filtered, and concentrated. The residue was purified by flash chromatography to afford 9 g (82%) of the title compound. $^1$H NMR (300 MHz, CDCl$_3$): δ 8.70 (s, 1H), 8.74 (s, 1H), 4.44 (q, J=7.1 Hz, 2H), 1.42 (t, J=7.1 Hz, 3H).

Step C: 4,5-dibromopyridine-3-carbaldehyde

To a cooled (−78° C.) solution of 4,5-dibromonicotinic acid ethyl ester (6 g, 19 mmol) in DCM was added diisobutylaluminum hydride (1 M in toluene, 38.8 mL, 38.8 mmol) dropwise. The mixture stirred for 3 h at −78° C. 1.5 N aqueous hydrochloric acid was added at −78° C. and then the mixture stirred at room temperature for 1 h. The reaction mixture was extracted with DCM. The organic fraction was washed with brine, dried over sodium sulfate, filtered, and concentrated to afford the crude title compound, which was used without further purification.

Step D: 5-bromo-4-tert-butylsulfanylpyridine-3-carbaldehyde

The crude title compound was prepared from 4,5-dibromopyridine-3-carbaldehyde by a procedure analogous to Example 237, Step D.

Step E: 5-bromo-4-tert-butylsulfanyl-pyridine-3-carbaldehyde oxime

The title compound was prepared from 5-bromo-4-tert-butylsulfanylpyridine-3-carbaldehyde by a procedure analogous to Example 237, Step E. The crude title compound was purified by column chromatography (20% ethyl acetate:hexanes). $^1$H NMR (300 MHz, CDCl$_3$): δ 9.03 (s, 1H), 8.83-8.84 (d, 2H), 1.35 (s, 9H).

Step F: 7-bromo[1,2]thiazolo[4,5-c]pyridine

The title compound was prepared in 98% yield from 5-bromo-4-tert-butylsulfanyl-pyridine-3-carbaldehyde oxime by a procedure analogous to Example 237, Step F. $^1$H NMR (300 MHz, CDCl$_3$): δ 9.34 (s, 1H), 9.16 (s, 1H), 8.65 (s, 1H).

Step G: 4-iodo-2-([1,2]thiazolo[4,5-c]pyridin-7-yl)furo[2,3-c]pyridin-7-amine

A mixture of {7-[bis(tert-butoxycarbonyl)amino]furo[2,3-c]pyridin-2-yl}boronic acid (82.6 mg, 0.219 mmol), 7-bromo[1,2]thiazolo[4,5-c]pyridine (47.0 mg, 0.218 mmol), Pd(PPh$_3$)$_4$ (12.6 mg, 0.0109 mmol), and potassium carbonate (90.6 mg, 0.656 mmol) in 4:1 1,4-dioxane:water (2 mL) was heated to 70° C. for 30 min. Aqueous 12 N hydrochloric acid (0.3 mL, 3 mmol) and methanol (6 mL) was added at 70° C., and the solution was stirred for 2 h. The organic solvents were removed in vacuo, and the material was extracted with DCM and saturated aqueous sodium bicarbonate. The organic layer was purified by column chromatography (1 to 3% 7 N ammonia/methanol:DCM). The purified intermediate was treated with NIS (15.0 mg, 0.0667 mmol) in DMF (1 mL), and the mixture was heated to 40° C. for 20 min. The material was extracted with EtOAc, and washed with aqueous 1 M sodium thiosulfate and brine (2×). The organic layer was concentrated in vacuo to afford 15 mg (17%) of the title compound as a yellow solid. MS (ESI): 395.39 [M+H]$^+$; HPLC t$_R$=1.06 min (HPLC: polar_2 min).

Step H: 1-(4-{4-[7-amino-2-([1,2]thiazolo[4,5-c]pyridin-7-yl)furo[2,3-c]pyridin-4-yl]-1H-pyrazol-1-yl}piperidin-1-yl)ethanone Diformate Salt (Title Compound)

A mixture of 4-iodo-2-([1,2]thiazolo[4,5-c]pyridin-7-yl)furo[2,3-c]pyridin-7-amine (7.0 mg, 0.018 mmol), 1-{4-[4-(4,4,5,5-tetramethyl-1,3,2-dioxaborolan-2-yl)-1H-pyrazol-1-yl]piperidin-1-yl}ethanone (8.5 mg, 0.027 mmol), Pd(PPh$_3$)$_4$ (1.0 mg, 0.00089 mmol), potassium carbonate (7.4 mg, 0.053 mmol) and 4:1 dioxane:water (1 mL) was heated in a microwave reactor at 85° C. for 20 min. The solution was used directly for HPLC purification, and the fractions containing the pure product were concentrated in vacuo to afford 3.1 mg (38%) of the title compound as a yellow solid. $^1$H NMR (400 MHz, CD$_3$OD): δ 2.03-2.16 (m, 2 H), 2.19 (s, 3 H), 2.20-2.31 (m, 2 H), 2.88 (td, J=12.9, 2.7 Hz, 1 H), 3.34-3.41 (m, 1 H), 4.08-4.17 (m, 1 H), 4.55 (tdd, J=11.4, 11.4, 4.2, 4.0 Hz, 1 H), 4.67-4.75 (m, 1 H), 7.72 (s, 1 H), 7.89 (s, 1 H), 7.92 (s, 1 H), 8.15 (s, 1 H), 8.16 (s, 2 H), 9.23 (s, 1 H), 9.28 (s, 1 H), 9.44 (s, 1 H); MS (ESI): 460.63 [M+H]$^+$; HPLC t$_R$=0.56 min (TOF: polar_3 min).

Example 263

1-(4-{4-[7-amino-2-(2-phenylthieno[2,3-c]pyridin-3-yl)furo[2,3-c]pyridin-4-yl]-1H-pyrazol-1-yl}piperidin-1-yl)ethanone trifluoroacetate

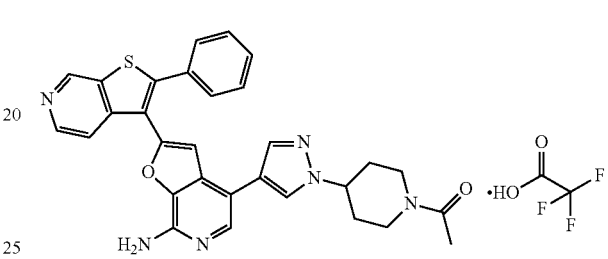

Step A: 3-bromo-2-phenylthieno[2,3-c]pyridine

A mixture of 2,3-dibromothieno[2,3-c]pyridine (500 mg, 1.71 mmol), phenylboronic acid (197 mg, 1.61 mmol), Pd(PPh$_3$)$_4$ (187 mg, 0.16 mmol), 2.0 M aqueous sodium carbonate (4 mL, 8 mmol) in DME (25 mL) was evacuated and refilled with nitrogen 3× and then heated in a microwave at 100° C. for 30 min. The reaction was diluted with EtOAc and washed with saturated aqueous sodium bicarbonate, water and brine. The organic layer was dried over anhydrous sodium sulfate and purified by ISCO chromatography (0 to 25% EtOAc:heptane) to afford 162 mg (35%) of the title compound as a white solid. $^1$H NMR (acetone-d$_6$): δ 9.24 (s, 1 H), 8.65 (d, J=5.5 Hz, 1 H), 7.82 (dd, J=7.9, 1.5 Hz, 2 H), 7.76 (d, J=5.5 Hz, 1 H), 7.55-7.61 (m, 3 H); MS (ESI): 290.36, 292.34 [M+H]$^+$; HPLC t$_R$=1.25 min (HPLC: Analytical_2 min).

Step B: 2-(2-phenylthieno[2,3-c]pyridin-3-yl)furo[2,3-c]pyridin-7-amine

The title compound was prepared by a procedure analogous to Example 261, Step B. MS (ESI): 344.56 [M+H]$^+$; HPLC t$_R$=0.65 min (HPLC: Analytical_2 min).

Step C: 4-iodo-2-(2-phenylthieno[2,3-c]pyridin-3-yl)furo[2,3-c]pyridin-7-amine

The title compound was prepared by a procedure analogous to Example 261, Step C. MS (ESI): 470.43 [M+H]$^+$; HPLC t$_R$=1.04 min (HPLC: Analytical_2 min).

Step D: 1-(4-{4-[7-amino-2-(2-phenylthieno[2,3-c]pyridin-3-yl)furo[2,3-c]pyridin-4-yl]-1H-pyrazol-1-yl}piperidin-1-yl)ethanone Trifluoroacetate (Title Compound)

The title compound was prepared by a procedure analogous to Example 261, Step D. $^1$H NMR (400 MHz, CD$_3$OD): δ 9.55 (s, 1 H), 8.71 (d, J=6.3 Hz, 1 H), 8.63 (d, J=5.8 Hz, 1 H), 8.00 (s, 1 H), 7.82 (s, 1 H), 7.74-7.78 (m, 1 H), 7.54-7.68 (m, 5 H), 7.07 (s, 1 H), 4.63-4.71 (m, 1 H), 4.50 (tt, J=11.5, 4.2 Hz, 1 H), 4.09 (d, J=14.9 Hz, 1 H), 3.33-3.35 (m, 1 H), 2.81-2.93 (m, 1 H), 2.09-2.23 (m, 5 H), 1.97-2.06 (m, 1 H), 1.84-1.94 (m, 1 H); MS (ESI): 535.62 [M+H]+; HPLC $t_R$=0.54 min (HPLC: Purity__2 min).

Example 264

3-{4-[1-(1-acetylpiperidin-4-yl)-1H-pyrazol-4-yl]-7-aminofuro[2,3-d]pyridin-2-yl}thieno[2,3-d]pyridine-2-carbonitrile trifluoroacetate

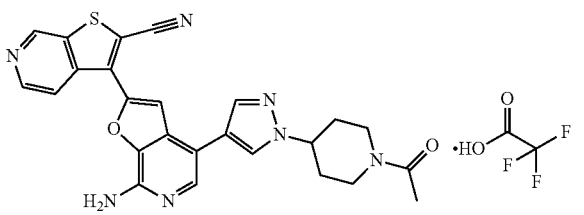

Step A: 3-bromothieno[2,3-c]pyridine-2-carboxylic acid

To a cooled (−78° C.) solution of 3-bromomthieno[2,3-c]pyridine (50 mg, 0.23 mmol) in THF (1 mL) was added 1.5 M lithium diisopropylamide in cyclohexane (0.23 mL, 0.35 mmol) and stirred at −78° C. for 15 min. The system was evacuated and refilled with carbon dioxide 3×. The mixture was stirred from −78° C. to room temperature and stayed at room temperature overnight. Saturated aqueous NH4Cl was added, causing formation of a precipitate. The precipitate was filtered and carried directly to the next step without further purification. MS (ESI): 258.41, 260.39 [M+H]+; HPLC $t_R$=0.41 min (HPLC: Analytical__2 min).

Step B: 3-bromothieno[2,3-c]pyridine-2-carboxamide

To a cooled (0° C.) mixture of 3-bromothieno[2,3-c]pyridine-2-carboxylic acid (50 mg, 0.19 mmol), DCM (1 mL) and DMF (10 μL, 0.1 mmol) was added oxalyl chloride (29 μL, 0.34 mmol). The ice bath was removed and the mixture was stirred at room temperature for 1 h. Oxalyl chloride (29 μL, 0.34 mmol) was added again and the mixture was stirred at room temperature for 1 h. The solvent was evaporated and THF (1 mL) was added. Ammonium hydroxide (0.7 mL, 20 mmol) was added to the mixture and stirred at room temperature for 1 h. The precipitate was filtered and washed with DCM and used without further purification. 1H NMR (400 MHz, CD3OD): δ 9.20-9.27 (m, 1 H), 8.61 (d, J=5.8 Hz, 1 H), 7.89 (dd, J=5.7, 0.9 Hz, 1 H); MS (ESI): 257.33, 259.35 [M+H]+; HPLC $t_R$=0.52 min (HPLC: Analytical__2 min).

Step C: 3-bromothieno[2,3-c]pyridine-2-carbonitrile

To a suspension of 3-bromothieno[2,3-c]pyridine-2-carboxamide (750 mg, 2.92 mmol) in acetonitrile (20 mL) was added phosphorus oxychloride (816 μL, 8.75 mmol) and the mixture was heated under N2 for 1 hour at 85° C. The same portion of phosphorus oxychloride was added every hour at 85° C. for a total of 6 h. The crude mixture was poured into saturated aqueous sodium carbonate on ice, to reach pH 7-8. DCM was added. The mixture was filtered to remove inorganic salts and the organic layer was separated. The DCM layer was washed with brine and dried over anhydrous Na2SO4. Purification by ISCO chromatography (100% DCM) afforded 205 mg (29%) of the title compound as a white solid. 1H NMR (400 MHz, CD3OD): δ 9.31-9.36 (m, 1 H), 8.71 (d, J=5.8 Hz, 1 H), 7.93 (dd, J=5.6, 1.0 Hz, 1 H); MS (ESI): 239.42, 241.35 [M+H]+; HPLC $t_R$=1.04 min (HPLC: Analytical__2 min).

Step D: 3-(7-aminofuro[2,3-d]pyridin-2-yl)thieno[2,3-d]pyridine-2-carbonitrile

The title compound was prepared by a procedure analogous to Example 261, Step B. MS (ESI): 294.23 [M+H]+; HPLC $t_R$=0.62 min (HPLC: Analytical__2 min).

Step E: 3-(7-amino-4-iodofuro[2,3-c]pyridin-2-yl)thieno[2,3-c]pyridine-2-carbonitrile The title compound was prepared by a procedure analogous to Example 261, Step C. MS (ESI): 419.43 [M+H]+; HPLC $t_R$=1.04 min (HPLC: Analytical__2 min).

Step F: 3-{4-[1-(1-acetylpiperidin-4-yl)-1H-pyrazol-4-yl]-7-aminofuro[2,3-c]pyridin-2-yl}thieno[2,3-c]pyridine-2-carbonitrile Trifluoroacetate (Title Compound)

The title compound was prepared by a procedure analogous to Example 261, Step D. 1H NMR (400 MHz, CD3OD): δ 9.45 (s, 1 H), 8.77 (d, J=5.8 Hz, 1 H), 8.70 (d, J=5.6 Hz, 1 H), 8.28 (s, 1 H), 8.09 (s, 1 H), 8.00 (s, 1 H), 7.89 (s, 1 H), 4.54-4.73 (m, 2 H), 4.10 (d, J=14.4 Hz, 1 H), 3.34-3.40 (m, 1 H), 2.89 (t, J=11.7 Hz, 1 H), 2.18-2.30 (m, 2 H), 2.17 (s, 3 H), 2.10 (dd, J=11.6, 4.5 Hz, 1 H), 1.96-2.06 (m, 1 H); MS (ESI): 484.59 [M+H]+; HPLC $t_R$=0.52 min (HPLC: Purity__2 min).

Example 265

1-[4-(4-{7-amino-2-[2-(3-hydroxy-3-methylbut-1-yn-1-yl)thieno[2,3-c]pyridin-3-yl]furo[2,3-c]pyridin-4-yl}-1H-pyrazol-1-yl)piperidin-1-yl]ethanone trifluoroacetate

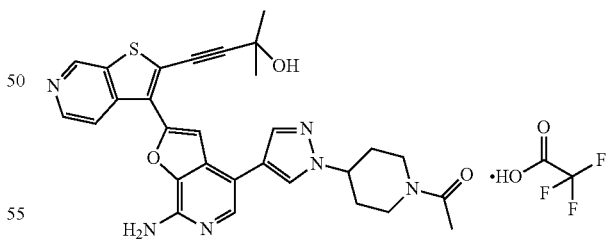

Step A: 4-(3-bromothieno[2,3-c]pyridin-2-yl)-2-methylbut-3-yn-2-ol

To a suspension of 2,3-dibromothieno[2,3-c]pyridine (400 mg, 1.37 mmol), 2-methyl-3-butyn-2-ol (121 μL, 1.24 mmol), copper (I) iodide (24 mg, 0.12 mmol) and DIPEA (2.16 mL, 12.41 mmol) in 1,4-dioxane (16 mL) was added Pd(PPh3)2Cl2 (174 mg, 0.25 mmol). The mixture was evacuated and refilled with nitrogen (3×), then stirred at 50° C. for 2 h. Solvent was evaporated and the resultant mixture was dissolved in EtOAc. The organic solution was washed with water and brine, dried over anhydrous sodium sulfate, and purified by ISCO column chromatography (0 to 5% MeOH:DCM) to afford 319 mg (87%) of the title compound as a light-yellow solid. MS (ESI): 296.38, 298.35 [M+H]$^+$; HPLC $t_R$=0.94 min (HPLC: Analytical_2 min).

Step B: 4-[3-(7-aminofuro[2,3-c]pyridin-2-yl)thieno[2,3-c]pyridin-2-yl]-2-methylbut-3-yn-2-ol The title compound was prepared by a procedure analogous to Example 261, Step B. MS (ESI): 350.48 [M+H]$^+$; HPLC $t_R$=0.62 min (HPLC: Analytical_2 min).

Step C: 4-[3-(7-amino-4-iodofuro[2,3-c]pyridin-2-yl)thieno[2,3-c]pyridin-2-yl]-2-methylbut-3-yn-2-ol The title compound was prepared by a procedure analogous to Example 261, Step D. MS (ESI): 476.49 [M+H]$^+$; HPLC $t_R$=0.90 min (HPLC: Analytical_2 min).

Step D: 1-[4-(4-{7-amino-2-[2-(3-hydroxy-3-methylbut-1-yn-1-yl)thieno[2,3-c]pyridin-3-yl]furo[2,3-c]pyridin-4-yl}-1H-pyrazol-1-yl)piperidin-1-yl]ethanone Trifluoroacetate (Title Compound)

The title compound was prepared by a procedure analogous to Example 261, Step D. $^1$H NMR (400 MHz, CD$_3$OD): δ 9.28 (br. s., 1 H), 8.80 (d, J=6.1 Hz, 1 H), 8.66 (br. s., 1 H), 8.33 (s, 1 H), 8.10 (s, 1 H), 8.01 (s, 1 H), 7.87 (s, 1 H), 4.69 (d, J=13.9 Hz, 1 H), 4.55-4.64 (m, 1 H), 4.11 (d, J=12.1 Hz, 1 H), 3.34-3.38 (m, 1 H), 2.81-2.90 (m, 1 H), 1.99-2.22 (m, 7 H), 1.64 (s, 6 H); MS (ESI): 541.65 (M+H)$^+$; HPLC $t_R$=0.53 min (HPLC: Purity_2 min).

Example 266

1-(4-{4-[7-amino-2-(1-methyl-1H-pyrrolo[2,3-c]pyridin-3-yl)-furo[2,3-c]pyridin-4-yl]-pyrazol-1-yl}-piperidin-1-yl)-ethanone

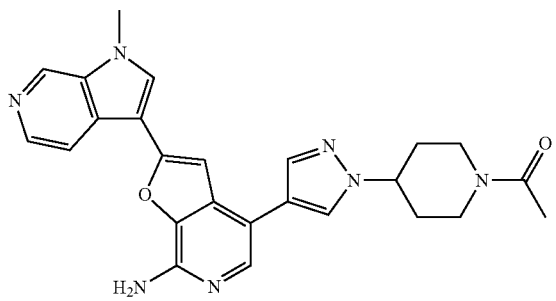 [SMILES: CC(=O)N1CCC(n2cc(-c3cnc(N)c4oc(-c5cn(C)c6cnccc56)cc34)cn2)CC1]

Step A: 2-(1-methyl-1H-pyrrolo[2,3-c]pyridin-3-yl)furo[2,3-c]pyridin-7-amine

The title compound was prepared by a procedure analogous to Example 261, Step B. $^1$H NMR (400 MHz, CD$_3$OD): δ 8.86 (s, 1 H), 8.31 (d, J=5.6 Hz, 1 H), 8.15 (dd, J=0.9, 5.7 Hz, 1 H), 8.13 (s, 1 H), 7.68 (d, J=5.6 Hz, 1 H), 7.00 (s, 1 H), 6.93 (d, J=5.6 Hz, 1 H), 4.05 (s, 3 H); MS (ESI): 265.26 [M+H]$^+$.

Step B: 4-iodo-2-(1-methyl-1H-pyrrolo[2,3-c]pyridin-3-yl)furo[2,3-c]pyridin-7-amine The title compound was prepared by a procedure analogous to Example 261, Step C. $^1$H NMR (400 MHz, CD$_3$OD): δ 8.88 (d, J=1.01 Hz, 1 H), 8.32 (d, J=1.00 Hz, 1 H), 8.14-8.20 (m, 2 H), 7.87 (s, 1 H), 6.80 (s, 1 H), 4.06 (s, 3 H); MS (ESI): 391.18 [M+H]$^+$.

Step C: 1-(4-{4-[7-Amino-2-(1-methyl-1H-pyrrolo[2,3-c]pyridin-3-yl)-furo[2,3-c]pyridin-4-yl]-pyrazol-1-yl}-piperidin-1-yl)-ethanone (Title Compound)

The title compound was prepared by a procedure analogous to Example 261, Step D. $^1$H NMR (400 MHz, CD$_3$OD): δ 8.88 (d, J=1.0 Hz, 1 H), 8.33 (d, J=5.6 Hz, 1 H), 8.26 (dd, J=0.9, 5.7 Hz, 1 H), 8.20 (s, 1 H), 8.16 (s, 1 H), 7.94 (d, J=0.5 Hz, 1 H), 7.88 (s, 1 H), 7.22 (s, 1 H), 4.72 (d, J=13.6 Hz, 1 H), 4.57 (tt, J=4.1, 11.4 Hz, 1 H), 4.14 (d, J=13.4 Hz, 1 H), 4.07 (s, 3 H), 3.42-3.37 (m, 1 H), 2.89 (dt, J=2.7, 13.1 Hz, 1 H), 2.31-2.21 (m, 2 H), 2.20 (s, 3 H), 2.18-2.10 (m, 1 H), 2.04 (dq, J=4.4, 12.0 Hz, 1 H); MS (ESI): 456.36 [M+H]$^+$.

Example 267 trans-4-{4-[7-amino-2-([1,2]thiazolo[4,5-c]pyridin-7-yl)furo[2,3-c]pyridin-4-yl]-1H-pyrazol-1-yl}cyclohexanol Diformate Salt

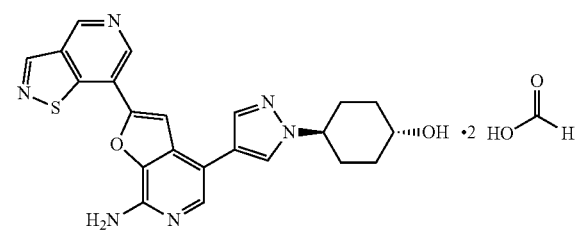 [SMILES: Nc1ncc(-c2cnn([C@H]3CC[C@H](O)CC3)c2)c2cc(-c3cncc4cnsc34)oc12 ; O=CO]

A mixture of 4-iodo-2-([1,2]thiazolo[4,5-c]pyridin-7-yl)furo[2,3-c]pyridin-7-amine (7.0 mg, 0.018 mmol), [1-(trans-4-{[tert-butyl(dimethyl)silyl]oxy}cyclohexyl)-1H-pyrazol-4-yl]boronic acid (8.6 mg, 0.027 mmol), Pd(PPh$_3$)$_4$ (1.0 mg, 0.00089 mmol), and potassium carbonate (7.4 mg, 0.053 mmol) in 4:1 1,4-dioxane:water (1 mL) was heated in a microwave reactor at 85° C. for 20 min. Aqueous 12 N hydrochloric acid (0.030 mL, 0.36 mmol) was added, and the solution was heated to 30° C. for 30 min. The solution was filtered, and purified via preparative HPLC to afford 1.6 mg (21%) of the title compound as a yellow solid. $^1$H NMR (400 MHz, CD$_3$OD): δ 1.48-1.59 (m, 2 H), 1.97-2.06 (m, 2 H), 2.11-2.24 (m, 4 H), 3.71 (tt, J=10.8, 4.2 Hz, 1 H), 4.27 (tt, J=11.8, 3.8 Hz, 1 H), 7.75 (s, 1 H), 7.91 (s, 2 H), 8.13 (s, 1 H), 8.18 (s, 2 H), 9.26 (s, 1 H), 9.29 (s, 1 H), 9.45 (s, 1 H); MS (ESI): 433.14 [M+H]$^+$; HPLC $t_R$=0.92 min (TOF: polar_3 min).

The following Examples were prepared by a procedure analogous to Example 267.

| Ex. # | Structure and NMR Data | Compound Name | MS (ESI) [M + H]+ | HPLC $t_R$ (min) |
|---|---|---|---|---|
| 268 | 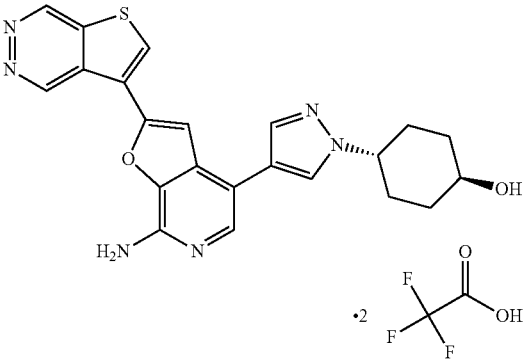<br>¹H NMR (400 MHz, CD₃OD): δ 10.44 (d, J = 1.01 Hz, 1H), 9.99 (d, J = 1.26 Hz, 1H), 9.11 (s, 1H), 8.31 (s, 1H), 8.03 (s, 1H), 8.00 (s, 1H), 7.87 (s, 1H), 4.31 (tt, J = 3.69, 11.84 Hz, 1H), 3.72 (tt, J = 4.17, 10.86 Hz, 1H), 2.10-2.26 (m, 4H), 1.96-2.08 (m, 2H), 1.47-1.63 (m, 2H) | trans-4-{4-[7-amino-2-(thieno[2,3-d]pyridazin-3-yl)furo[2,3-c]-pyridin-4-yl]-1H-pyrazol-1-yl}cyclohexanol bistrifluoroacetate | 433.14 | 0.84 (TOF: polar_3 min) |
| 269 | 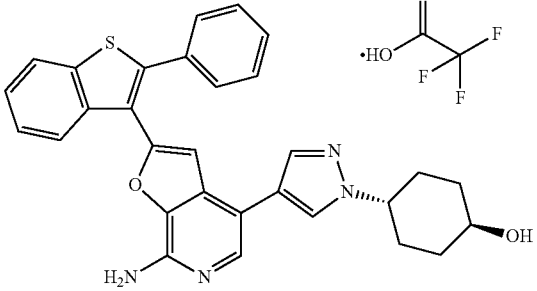<br>¹H NMR (400 MHz, CD₃OD): δ 9.56 (s, 1H), 8.71 (d, J = 6.3 Hz, 1H), 8.64 (d, J = 6.3 Hz, 1H), 7.95-8.01 (m, 1H), 7.81 (s, 1H), 7.72 (d, J = 0.5 Hz, 1H), 7.55-7.69 (m, 5H), 7.06 (s, 1H), 4.21 (tt, J = 11.8, 3.7 Hz, 1H), 3.68 (tt, J = 10.9, 4.0 Hz, 1H), 2.12 (ddd, J = 8.8, 4.8, 4.5 Hz, 4H), 1.83-1.96 (m, 2H), 1.44-1.58 (m, 2H) | trans-4-{4-[7-amino-2-(2-phenylthieno[2,3-c]pyridin-3-yl)furo[2,3-c]pyridin-4-yl]-1H-pyrazol-1-yl}cyclohexanol trifluoroacetate | 508.60 | 0.55 (UPLC: Purity_2 min) |

| Ex. # | Structure and NMR Data | Compound Name | MS (ESI) [M + H]+ | HPLC t_R (min) |
|---|---|---|---|---|
| 270 | 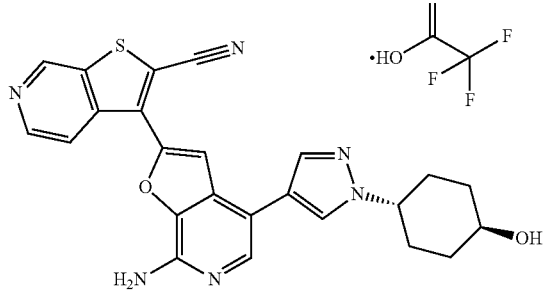<br>¹H NMR (400 MHz, CD₃OD): δ 9.45 (s, 1H), 8.77 (d, J = 5.8 Hz, 1H), 8.72 (d, J = 5.8 Hz, 1H), 8.24 (s, 1H), 8.08 (s, 1H), 7.97 (s, 1H), 7.88 (s, 1H), 4.29 (tt, J = 11.8, 3.8 Hz, 1H), 3.64-3.74 (m, 1H), 2.20 (d, J = 10.9 Hz, 2H), 2.12 (d, J = 11.9 Hz, 2H), 1.92-2.05 (m, 2H), 1.45-1.58 (m, 2H) | 3-{7-amino-4-[1-(trans-4-hydroxycyclohexyl)-1H-pyrazol-4-yl]furo[2,3-c]pyridin-2-yl}thieno[2,3-c]pyridine-2-carbonitrile trifluoroacetate | 457.56 | 0.51 (UPLC: Purity_2 min) |
| 271 | 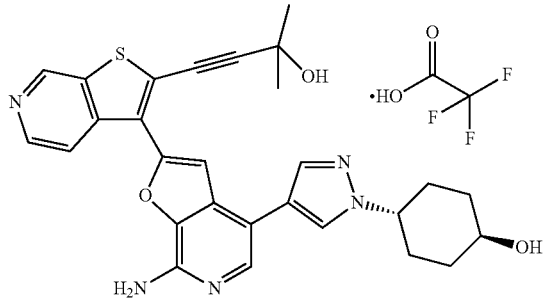<br>¹H NMR (400 MHz, CD₃OD): δ 9.33 (br. s., 1H), 8.86 (d, J = 5.8 Hz, 1H), 8.69 (br. s., 1H), 8.30 (s, 1H), 8.10 (s, 1H), 7.99 (s, 1H), 7.86 (s, 1H), 4.28-4.38 (m, 1H), 3.66-3.76 (m, 1H), 2.09-2.18 (m, 4H), 1.96-2.08 (m, 2H), 1.64 (s, 6H), 1.43-1.57 (m, 2H) | trans-4-(4-{7-amino-2-[2-(3-hydroxy-3-methylbut-1-yn-1-yl)thieno[2,3-c]pyridin-3-yl]furo[2,3-c]pyridin-4-yl}-1H-pyrazol-1-yl)cyclohexanol trifluoroacetate | 514.65 | 0.53 (UPLC: Purity_2 min) |

Example 272 trans-4-{4-[7-amino-2-(6-fluoro-1,2,3-benzothiadiazol-7-yl)furo[2,3-c]pyridin-4-yl]-1H-pyrazol-1-yl}cyclohexanol diformate salt

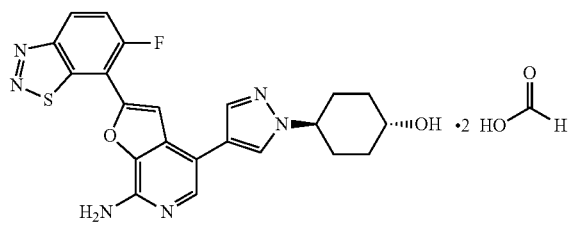 [SMILES: Nc1ncc(-c2cnn([C@H]3CC[C@H](O)CC3)c2)c2cc(-c3c(F)ccc4nnsc34)oc12 ; O=CO]

Step A: 3-bromo-2,4-difluoronitrobenzene

The title compound was prepared by a procedure analogous to Intermediate 59, Step B. ¹H NMR (400 MHz, CDCl₃): δ 7.14 (ddd, J=9.3, 7.1, 2.0 Hz, 1 H), 8.13 (ddd, J=9.3, 8.0, 5.4 Hz, 1 H).

Step B: 7-bromo-6-fluoro-1,2,3-benzothiadiazole

A mixture of 3-bromo-2,4-difluoronitrobenzene (1.00 g, 4.20 mmol) and sodium sulfide (655.9 mg, 8.404 mmol) in degassed water (20 mL) was heated to 30° C. overnight in a sealed tube. The solution was neutralized with aqueous 2 N hydrochloric acid at rt. The material was extracted with DCM and water, and the organic layer was purified by column chromatography (1% EtOAc:heptane). The purified residue was dissolved in ethanol (20 mL). Iron powder (1.173 g, 21.01 mmol) and aqueous 12 N hydrochloric acid (0.07 mL, 0.84 mmol) were added, and the mixture was heated to 70° C.

for 20 min. The solution was cooled to rt and filtered through Celite. The filtrate was concentrated in vacuo, redissolved in acetic acid (20 mL), and sodium nitrite (579.8 mg, 8.404 mmol) was added at rt. After stirring for 10 min, saturated potassium carbonate was added until bubbling stopped. The material was extracted with DCM and saturated aqueous sodium bicarbonate. The organic layer was purified via column chromatography (1% EtOAc:heptane) to afford 125 mg (13%) of the title compound as a white solid. $^1$H NMR (400 MHz, CDCl$_3$): δ 7.47 (dd, J=8.8, 8.1 Hz, 1 H), 8.56 (dd, J=9.1, 4.0 Hz, 1 H).

Step C: 2-(6-fluoro-1,2,3-benzothiadiazol-7-yl)-4-iodofuro[2,3-c]pyridin-7-amine The title compound was prepared by a procedure analogous to Example 264, Step G.

Step D: trans-4-{4-[7-amino-2-(6-fluoro-1,2,3-benzothiadiazol-7-yl)furo[2,3-c]pyridin-4-yl]-1H-pyrazol-1-yl}cyclohexanol diformate salt (Title Compound)

The title compound was prepared by a procedure analogous to Example 269. $^1$H NMR (400 MHz, CD$_3$OD): δ 1.49-1.58 (m, 2 H), 1.93-2.04 (m, 2 H), 2.10-2.17 (m, 2 H), 2.21-2.26 (m, 2 H), 3.72 (tt, J=11.0, 4.3 Hz, 1 H), 4.22-4.33 (m, 1 H), 7.62 (d, J=3.3 Hz, 1 H), 7.74-7.79 (m, 1 H), 7.84 (s, 1 H), 7.94 (s, 1 H), 7.98 (s, 1 H), 8.24 (s, 2 H), 8.73 (dd, J=9.1, 4.3 Hz, 1 H); MS (ESI): 451.13 [M+H]$^+$; HPLC $t_R$=1.01 min (TOF: polar_3 min).

Example 273

1-(4-{4-[7-amino-2-(6-fluoro-1,2,3-benzothiadiazol-7-yl)furo[2,3-c]pyridin-4-yl]-1H-pyrazol-1-yl}piperidin-1-yl)ethanone

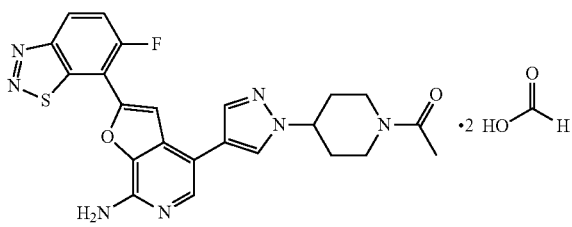 [SMILES: CC(=O)N1CCC(n2cc(-c3cnc(N)c4oc(-c5c(F)ccc6nnsc56)cc34)cn2)CC1 ; O=CO]

The title compound was prepared by a procedure analogous to Example 264, Step H. $^1$H NMR (400 MHz, CD$_3$OD): δ 2.03-2.10 (m, 1 H), 2.11-2.17 (m, 1 H), 2.20 (s, 3 H), 2.24-2.33 (m, 2 H), 2.84-2.92 (m, 1 H), 3.38-3.42 (m, 1 H), 4.07-4.14 (m, 1 H), 4.53-4.58 (m, 1 H), 4.67-4.71 (m, 1 H), 7.64 (d, J=3.0 Hz, 1 H), 7.75 (dd, J=10.6, 9.1 Hz, 1 H), 7.88 (s, 1 H), 7.96 (s, 1 H), 8.02 (s, 1 H), 8.28 (s, 2 H), 8.74 (dd, J=9.1, 4.3 Hz, 1 H); MS (ESI): 478.14 [M+H]$^+$; HPLC $t_R$=1.01 min (TOF: polar_3 min).

Example 274

1-(4-{4-[7-amino-2-(imidazol[1,2-a]pyrazin-3-yl)furo[2,3-c]pyridin-4-yl]-1H-pyrazol-1-yl}piperidin-1-yl)ethanone trifluoroacetic acid salt

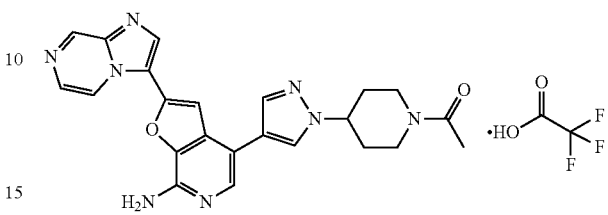

Step A: 2-(imidazo[1,2-a]pyrazin-3-yl)furo[2,3-c]pyridin-7-amine

A mixture of di-tert-butyl[2-(trimethylstannanyl)furo[2,3-c]pyridin-7-yl]imidodicarbonate (0.0994 g, 0.200 mmol) in 1,4-dioxane (1.5 mL) was degassed with nitrogen for 10 min. To this mixture was added 3-bromoimidazo[1,2-a]pyrazine (0.033 g, 0.17 mmol), Pd(FPh$_3$)$_4$ (0.0192 g, 0.0167 mmol) and cesium fluoride (0.0850 g, 0.560 mmol). The temperature was raised to 100° C. and the mixture was heated for 16 h. Following removal of solvent, the residue was purified by ISCO chromatography (0 to 10% methanol:DCM). The resultant material was dissolved in dichloromethane (2 mL) and cooled to 0° C. To this mixture was slowly added TFA (2 mL). The ice bath was removed and the mixture was stirred for 2 h and then concentrated to a light brown residue. The residue was dissolved in DCM (30 mL) and saturated aqueous sodium bicarbonate (5 mL) was added and then the mixture was concentrated. Purification by ISCO chromatography (0 to 20% methanol:DCM) afforded 0.021 g (49%) of the title compound as an off-white solid. $^1$H NMR (400 MHz, CD$_3$OD): δ=9.19 (dd, J=1.4, 4.7 Hz, 1 H), 9.17 (d, J=1.5 Hz, 1 H), 8.46 (s, 1 H), 7.76 (dd, J=4.3, 5.6 Hz, 2 H), 7.43 (s, 1 H), 7.37 (s, 1 H); MS (ESI): 252.17 [M+H]$^+$.

Step B: 2-(imidazo[1,2-a]pyrazin-3-yl)-4-iodofuro[2,3-c]pyridin-7-amine 2-(Imidazo[1,2-a]pyrazin-3-yl)furo[2,3-c]pyridin-7-amine (0.018 g, 0.072 mmol) was dissolved in DMF (1 mL). NIS (0.024 g, 0.11 mmol) was added and the mixture was brought to 40° C. After 4 h, the reaction was cooled to room temperature. Water was added and the resulting solid was filtered off. The solid was dissolved in 2:1 methanol:DCM (~30 mL). To this solution was added aqueous sodium thiosulfate (0.5 mL) and the mixture was then concentrated. Purification by ISCO chromatography (0 to 20% methanol:DCM) afforded 0.018 g (67%) of the title compound as an off-white solid. $^1$H NMR (400 MHz, CD$_3$OD): δ 9.21 (dd, J=1.4, 4.7 Hz, 1 H), 9.17 (d, J=1.5 Hz, 1 H), 8.50 (s, 1 H), 8.14 (d, J=4.8 Hz, 1 H), 7.97 (s, 1 H), 7.27 (s, 1 H); MS (ESI): 378.14 [M+H]$^+$.

Step C: 1-(4-{4-[7-amino-2-(imidazol[1,2-a]pyrazin-3-yl)furo[2,3-d]pyridin-4-yl]-1H-pyrazol-1-yl}piperidin-1-yl)ethanone trifluoroacetic acid salt (Title Compound)

A mixture of 2-(imidazo[1,2-a]pyrazin-3-yl)-4-iodofuro[2,3-c]pyridin-7-amine (0.015 g, 0.040 mmol) and 1-{4-[4-(4,4,5,5-tetramethyl-1,3,2-dioxaborolan-2-yl)-1H-pyrazol-1-yl]piperidin-1-yl}ethanone (0.016 g, 0.052 mmol) in 1,4-dioxane (0.5 mL) and water (0.2 mL) was degassed with nitrogen for 10 min. To this mixture was added potassium carbonate (0.014 g, 0.099 mmol) and 1,1-bis(diphenylphosphino)ferrocenepalladium(11) dichloride dichloromethane adduct (0.0032 g, 0.0040 mmol). The reaction mixture was heated to 95° C. for 10 min. After allowing the mixture to cool to room temperature, solvents were removed by rotary evaporation. Purification by MDP afforded 0.014 g (80%) of the title compound as a yellow gum. $^1$H NMR (400 MHz, CD$_3$OD): δ 9.34 (dd, J=1.3, 4.8 Hz, 1 H), 9.26 (s, 1 H), 8.65 (s, 1 H), 8.34 (s, 1 H), 8.22 (d, J=4.8 Hz, 1 H), 8.06 (s, 1 H), 7.93 (s, 1 H), 7.89 (s, 1 H), 4.72 (d, J=13.6 Hz, 1 H), 4.60 (tt, J=4.2, 11.5 Hz, 1 H), 4.14 (d, J=14.1 Hz, 1 H), 3.43-3.35 (m, 1 H), 2.90 (dt, J=2.9, 12.9 Hz, 1 H), 2.32-2.21 (m, 2 H), 2.20 (s, 3 H), 2.19-2.10 (m, 1 H), 2.06 (qd, J=4.4, 12.8 Hz, 1 H); MS (ESI): 443.32 [M+H]$^+$.

Example 275

1-(4-{4-[7-(methylamino)-2-(thieno[2,3-d]pyridin-3-yl)furo[2,3-d]pyridin-4-yl]-1H-pyrazol-1-yl}piperidin-1-yl)ethanone trifluoroacetic acid salt

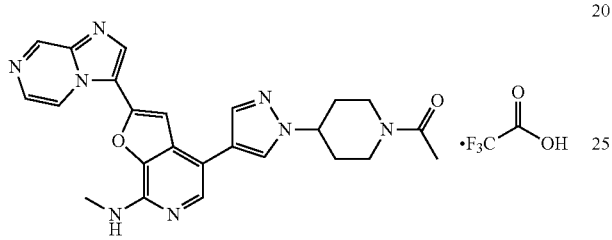

A solution of 1-(4-{4-[2-chloro-7-(methylamino)furo[2,3-c]pyridin-4-yl]-1H-pyrazol-1-yl}piperidin-1-yl)ethanone (22 mg, 0.059 mmol), 3-(4,4,5,5-tetramethyl-1,3,2-dioxaborolan-2-yl)thieno[2,3-c]pyridine (24 mg, 0.071 mmol), and Pd(PPh$_3$)$_4$ (6.8 mg, 0.0059 mmol) in 1,4-dioxane (300 μL) and 1.0 M aqueous sodium carbonate (300 μL) was heated to 120° C. in a microwave for 60 min. The organic phase was separated and concentrated. Purification by MDP afforded 16 mg (46%) of the title compound as a tan solid. $^1$H NMR (400 MHz, CD$_3$OD): δ 9.57 (br. s., 1 H), 9.14 (s, 1 H), 8.90 (d, J=6.3 Hz, 1 H), 8.74 (br. s., 1 H), 8.34 (s, 1 H), 8.05 (s, 1 H), 7.89 (s, 1 H), 7.82 (s, 1 H), 4.77-4.64 (m, 1 H), 4.65-4.46 (m, 1 H), 4.19-4.01 (m, 1 H), 3.42-3.32 (m, 1 H), 3.30 (s, 3 H), 2.95-2.78 (m, 1 H), 2.35-2.15 (m, 5 H), 2.15-1.96 (m, 2 H); MS (ESI): 473.17 [M+H]$^+$; HPLC t$_R$=2.28 min (ZQ3, polar_4 min).

The following Examples were prepared by a procedure analogous to Example 275.

| Ex. # | Structure and NMR Data | Compound Name | MS (ESI) [M + H]$^+$ | HPLC t$_R$ (min) |
|---|---|---|---|---|
| 276 | ![structure] $^1$H NMR (400 MHz, CD$_3$OD): δ 9.63 (br. s., 1H), 9.20 (s, 1H), 8.88-8.56 (m, 2H), 8.34 (s, 1H), 8.05 (s, 1H), 7.88 (s, 1H), 7.81 (s, 1H), 4.77-4.64 (m, 1H), 4.65-4.47 (m, 1H), 4.11 (br. s., 1H), 3.68 (s, 6H), 3.43-3.33 (m, 1H), 2.88 (s, 1H), 2.33-2.15 (m, 5H), 2.15-1.94 (m, 2H) | 1-(4-{4-[7-(dimethylamino)-2-(thieno[2,3-c]pyridin-3-yl)furo[2,3-c]pyridin-4-yl]-1H-pyrazol-1-yl}piperidin-1-yl)ethanone trifluoroacetic acid salt | 487.16 | 2.42 (ZQ3: polar_4 min) |

| Ex. # | Structure and NMR Data | Compound Name | MS (ESI) [M + H]⁺ | HPLC $t_R$ (min) |
|---|---|---|---|---|
| 277 | 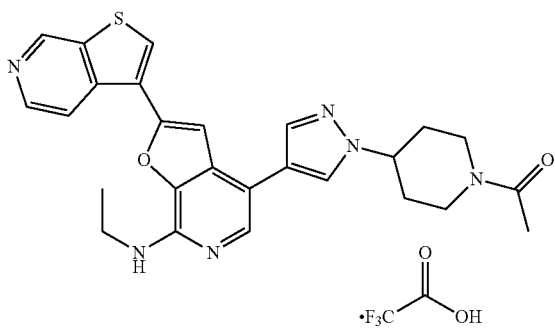<br>¹H NMR (400 MHz, CD₃OD): δ 9.67 (s, 1H), 9.28 (s, 1H), 9.02 (d, J = 6.3 Hz, 1H), 8.77 (d, J = 6.3 Hz, 1H), 8.35 (s, 1H), 8.06 (s, 1H), 7.93 (s, 1H), 7.81 (s, 1H), 4.78-4.65 (m, 1H), 4.65-4.46 (m, 1H), 4.12 (d, J = 11.9 Hz, 1H), 3.70 (q, J = 7.3 Hz, 2H), 3.43-3.33 (m, 1H), 2.96-2.78 (m, 1H), 2.32-2.15 (m, 5H), 2.15-1.95 (m, 2H), 1.49 (t, J = 7.2 Hz, 3H) | 1-(4-{4-[7-(ethylamino)-2-(thieno[2,3-c]pyridin-3-yl)furo[2,3-c]pyridin-4-yl]-1H-pyrazol-1-yl}piperidin-1-yl)ethanone trifluoroacetic acid salt | 487.14 | 2.39 (ZQ3: polar_4 min) |
| 278 | 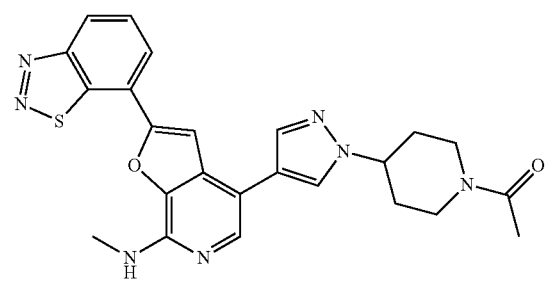<br>¹H NMR (400 MHz, CD₃OD): δ 1.95-2.06 (m, 1H), 2.06-2.15 (m, 1H), 2.19 (s, 3H), 2.19-2.29 (m, 2H), 2.88 (td, J = 12.9, 2.8 Hz, 1H), 3.12 (s, 3H), 3.32-3.41 (m, 1H), 4.06-4.17 (m, 1H), 4.53 (tt, J = 11.5, 4.2 Hz, 1H), 4.67-4.74 (m, 1H), 7.46 (s, 1H), 7.77 (dd, J = 8.1, 7.6 Hz, 1H), 7.84 (s, 1H), 7.85 (s, 1H), 8.05 (s, 1H), 8.29 (s, 2H), 8.31-8.33 (m, 1H), 8.59-8.65 (m, 1H) | 1-(4-{4-[2-(1,2,3-benzothiadiazol-7-yl)-7-(methylamino)furo[2,3-c]pyridin-4-yl]-1H-pyrazol-1-yl}piperidin-1-yl)ethanone | 474.16 | 1.03 (TOF: polar_3 min) |

| Ex. # | Structure and NMR Data | Compound Name | MS (ESI) [M + H]+ | HPLC $t_R$ (min) |
|---|---|---|---|---|
| 279 | 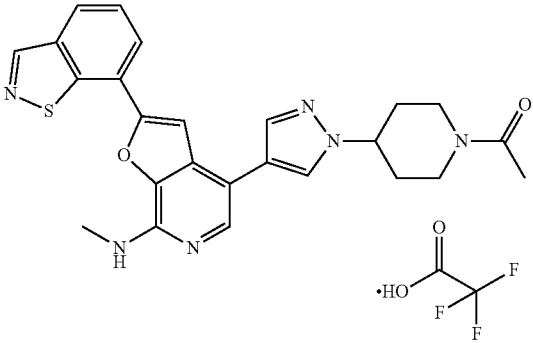<br><br>¹H NMR (400 MHz, CD₃OD): δ 9.15 (s, 1H), 8.43 (d, J = 7.3 Hz, 1H), 8.38 (d, J = 7.8 Hz, 1H), 8.34 (s, 1H), 8.03 (s, 1H), 7.79-7.85 (m, 2H), 7.74 (t, J = 7.7 Hz, 1H), 4.70 (d, J = 13.9 Hz, 1H), 4.54-4.65 (m, 1H), 4.13 (d, J = 13.9 Hz, 1H), 3.37-3.42 (m, 1H), 3.35 (s, 3H), 2.83-2.93 (m, 1H), 2.20-2.30 (m, 2H), 2.18 (s, 3H), 1.97-2.16 (m, 2H) | 1-(4-{4-[2-(1,2-benzothiazol-7-yl)-7-(methylamino)furo[2,3-c]pyridin-4-yl]-1H-pyrazol-1-yl}piperidin-1-yl)ethanone trifluoroacetate | 473.52 | 0.58 (UPLC: Purity_2 min) |
| 280 | 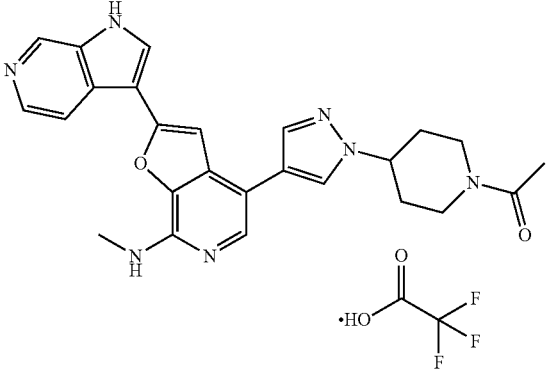<br><br>¹H NMR (400 MHz, DMSO-d₆): δ 13.59 (br. s., 1H), 9.34 (s, 1H), 9.00 (s, 1H), 8.92 (d, J = 6.3 Hz, 1H), 8.53 (d, J = 6.6 Hz, 1H), 8.41 (s, 1H), 8.11 (s, 1H), 7.91 (s, 1H), 7.85 (s, 1H), 4.62-4.44 (m, 2H), 3.98 (d, J = 13.6 Hz, 1H), 3.30-3.22 (m, 1H), 3.17 (br. s., 3H), 2.77 (dt, J = 2.1, 12.8 Hz, 1H), 2.69-2.65 (m, 1H), 2.35-2.31 (m, 1H), 2.18-2.08 (m, 2H), 2.07 (s, 3H), 1.97 (dq, J = 3.9, 12.1 Hz, 1H), 1.86 (dq, J = 4.3, 12.1 Hz, 1H) | 1-(4-{4-[7-(methylamino)-2-(1H-pyrrolo[2,3-c]pyridin-3-yl)furo[2,3-c]pyridin-4-yl]-1H-pyrazol-1-yl}piperidin-1-yl)ethanone trifluoroacetic acid salt | 456.30 | — |

Example 281 trans-4-{4-[7-(methylamino)-2-(thieno[2,3-c]pyridin-3-yl)furo[2,3-c]pyridin-4-yl]-1H-pyrazol-1-yl}cyclohexanol

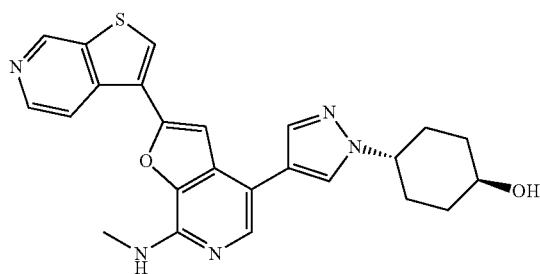 [SMILES: CNc1ncc(-c2cnn([C@H]3CC[C@H](O)CC3)c2)c2cc(-c3csc4cnccc34)oc12]

A mixture of 4-[1-(trans-4-{[tert-butyl(dimethyl)silyl]oxy}cyclohexyl)-1H-pyrazol-4-yl]-2-chloro-N-methylfuro[2,3-c]pyridin-7-amine (44.3 mg, 0.0961 mmol), 3-(4,4,5,5-tetramethyl-1,3,2-dioxaborolan-2-yl)thieno[2,3-c]pyridine (33.9 mg, 0.130 mmol), and Pd(PPh$_3$)$_4$ (12.8 mg, 0.0111 mmol) in 1,4-dioxane (0.5 mL) was charged with 1.0 M aqueous sodium carbonate (0.5 mL) and then irradiated in a microwave at 120° C. for 60 min. The reaction mixture was then charged with 4.0 M hydrochloric acid in 1,4-dioxane (0.6 mL) and stirred at rt for 30 min. The suspension was concentrated in vacuo. The residue was partitioned between a mixture of dichloromethane and aqueous sodium bicarbonate and the layers were separated. The organic layer was washed with brine, dried over anhydrous Na$_2$SO$_4$, filtered, and concentrated in vacuo. Purification by ISCO chromatography (2 to 10% 7 N ammonia/methanol:dichloromethane) afforded 30.1 mg (69%) of the title compound as a yellow solid. $^1$H NMR (400 MHz, DMSO-d$_6$): δ 9.40 (s, 1H), 8.79 (s, 1H), 8.65 (s, 2H), 8.23 (s, 1H), 8.08 (s, 1H), 7.95 (d, J=0.76 Hz, 1H), 7.73 (s, 1H), 6.97 (q, J=4.55 Hz, 1H), 4.70 (d, J=4.55 Hz, 1H), 4.19 (tt, J=3.95, 11.59 Hz, 1H), 3.48-3.59 (m, 1H), 3.02 (d, J=4.80 Hz, 3H), 2.07 (d, J=12.13 Hz, 2H), 1.82-2.01 (m, 4H), 1.31-1.46 (m, 2H); MS (ESI): 446.16 [M+H]$^+$; HPLC t$_R$=2.50 min.

The following Examples were prepared by a procedure analogous to Example 281.

| Ex. # | Structure and NMR Data | Compound Name | MS (ESI) [M + H]$^+$ | HPLC t$_R$ (min) |
|---|---|---|---|---|
| 282 | $^1$H NMR (400 MHz, DMSO-d$_6$): δ 9.22 (s, 1H), 8.38 (dd, J = 0.76, 7.33 Hz, 1H), 8.29 (dd, J = 0.63, 7.96 Hz, 1H), 8.18 (s, 1H), 8.05 (s, 1H), 7.88 (d, J = 0.51 Hz, 1H), 7.82 (s, 1H), 7.68 (t, J = 7.70 Hz, 1H), 6.55 (q, J = 4.72 Hz, 1H), 4.63 (d, J = 4.29 Hz, 1H), 4.14 (tt, J = 3.92, 11.49 Hz, 1H), 3.43-3.51 (m, 1H), 3.00 (d, J = 4.80 Hz, 3H), 2.02 (d, J = 11.62 Hz, 2H), 1.75-1.95 (m, 4H), 1.26-1.40 (m, 2H). | trans-4-{4-[2-(1,2-benzothiazol-7-yl)-7-(methylamino)furo[2,3-c]pyridin-4-yl]-1H-pyrazol-1-yl}cyclohexanol | 446.25 | 2.79 (ZQ3: polar_4 min) |

| Ex. # | Structure and NMR Data | Compound Name | MS (ESI) [M + H]+ | HPLC $t_R$ (min) |
|---|---|---|---|---|
| 283 | 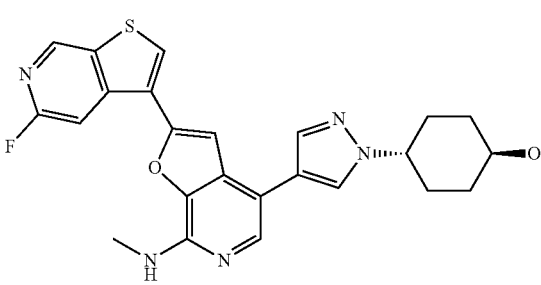<br>¹H NMR (400 MHz, DMSO-d₆): δ 9.09 (s, 1H), 8.92 (s, 1H), 8.37 (s, 1H), 8.23 (d, J = 0.8 Hz, 1H), 8.08 (s, 1H), 7.97 (d, J = 0.4 Hz, 1H), 7.76 (s, 1H), 7.07 (quartet, J = 4.8 Hz, 1H), 4.71 (d, J = 4.0 Hz, 1H), 4.16-4.25 (m, 1H), 3.49-3.59 (m, 1H), 3.03 (d, J = 4.4 Hz, 3 H), 2.04-2.12 (m, 2H), 1.94-2.02 (m, 2H), 1.82-1.94 (m, 2H), 1.33-1.45 (m, 2H) | trans-4-{4-[2-(5-fluorothieno[2,3-c]pyridin-3-yl)-7-(methylamino)furo[2,3-c]pyridin-4-yl]-1H-pyrazol-1-yl}cyclohexanol | 464.32 | 2.74 2.79 (ZQ3: polar_4 min) |
| 284 | 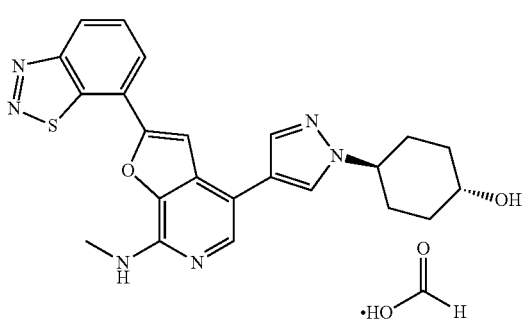<br>¹H NMR (400 MHz, CD₃OD): δ 1.48-1.61 (m, 2H), 1.99 (dtd, J = 13.0, 12.7, 12.7, 3.0 Hz, 2H), 2.12-2.21 (m, 2H), 2.23-2.32 (m, 2H), 3.24 (s, 3H), 3.68-3.80 (m, 1H), 4.26 (tdd, J = 11.8, 11.8, 3.8, 3.7 Hz, 1H), 7.47 (s, 1H), 7.84-7.89 (m, 2H), 7.90 (s, 1H), 7.95 (s, 1H), 8.31 (s, 1H), 8.38 (d, J = 7.3 Hz, 1H), 8.71 (d, J = 8.3 Hz, 1H) | trans-4-{4-{2-[2-(1,2,3-benzothiadiazol-7-yl)-7-(methylamino)furo[2,3-c]pyridin-4-yl]-1H-pyrazol-1-yl}cyclohexanol formate salt | 447.15 | 1.03 (TOF: polar_3 min) |

Example 285 trans-4-{4-[7-amino-2-(1,2-benzothiazol-7-yl)-3-chlorofuro[2,3-c]pyridin-4-yl]-1H-pyrazol-1-yl}cyclohexanol trifluoroacetic Acid Salt

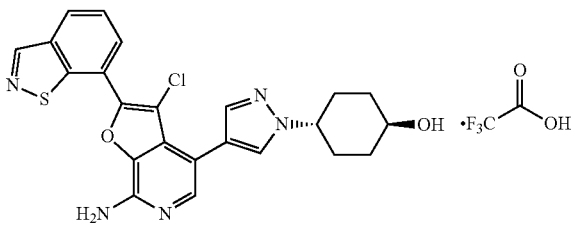

A solution of 4-[1-(trans-4-{[tert-butyl(dimethyl)silyl]oxy}cyclohexyl)-1H-pyrazol-4-yl]-2,3-dichlorofuro[2,3-c]pyridin-7-amine (30 mg, 0.062 mmol), 7-(4,4,5,5-tetramethyl-[1,3,2]dioxaborolan-2-yl)-benzo[d]isothiazole (20 mg, 0.075 mmol), and Pd(PPh$_3$)$_4$ (7.2 mg, 0.0062 mmol) in 1,4-dioxane (0.3 mL) and 1.0 M aqueous sodium carbonate (0.3 mL) was heated to 120° C. in a microwave for 60 min. The organic phase was separated, treated with 12 M aqueous HCl (0.10 mL) at 40° C. for 1 h, and then concentrated. Purification by MDP afforded 14 mg (39%) of the title compound as a yellow solid. $^1$H NMR (400 MHz, CD$_3$OD): δ 9.15 (s, 1 H), 8.55 (d, J=6.8 Hz, 1 H), 8.41 (d, J=8.1 Hz, 1 H), 8.01 (s, 1 H), 7.57-7.83 (m, 3 H), 4.09-4.42 (m, 1 H), 3.60-3.84 (m, 1 H), 2.04-2.32 (m, 4 H), 1.88-2.04 (m, 2 H), 1.36-1.67 (m, 2 H); MS (ESI): 466.25, 468.26 [M+H]$^+$; HPLC t$_R$=2.76 min (ZQ3, polar_4 min).

The following Examples were prepared by a procedure analogous to Example 285.

| Ex. # | Structure and NMR Data | Compound Name | MS (ESI) [M + H]$^+$ | HPLC t$_R$ (min) |
|---|---|---|---|---|
| 286 | $^1$H NMR (400 MHz, DMSO-d$_6$): δ 8.91 (dd, J = 8.3, 0.8 Hz, 1H), 8.67 (dd, J = 7.5, 0.9 Hz, 1H), 8.00 (dd, J = 8.2, 7.5 Hz, 1H), 7.96 (s, 1H), 7.79 (s, 1H), 7.61 (d, J = 0.5 Hz, 1H), 6.63 (s, 2H), 4.67 (br. s., 1H), 4.18 (tt, J = 11.7, 4.2 Hz, 1H), 3.51 (t, J = 10.6 Hz, 1H), 2.07 (m, J = 11.6 Hz, 2H), 1.94 (m, J = 10.1 Hz, 2H), 1.76-1.89 (m, 2H), 1.25-1.49 (m, 2H) | trans-4-{4-[7-amino-2-(1,2,3-benzothiadiazol-7-yl)-3-chlorofuro[2,3-c]pyridin-4-yl]-1H-pyrazol-1-yl}cyclohexanol | 467.26, 469.27 | 2.81 (ZQ3, polar_4 min) |
| 287 | $^1$H NMR (400 MHz, CD$_3$OD): δ 9.29 (s, 1 H), 8.91 (s, 1 H), 8.53-8.64 (m, 2 H), 7.92 (d, J = 0.8 Hz, 1 H), 7.75 (s, 1 H), 7.69 (d, J = 0.8 Hz, 1 H), 4.15-4.38 (m, 1 H), 3.57-3.83 (m, 1 H), 2.07-2.31 (m, 4 H), 1.89-2.04 (m, 2 H), 1.39-1.65 (m, 2 H) | trans-4-{4-[7-amino-3-chloro-2-(thieno[2,3-c]pyridin-3-yl)furo[2,3-c]pyridin-4-yl]-1H-pyrazol-1-yl}cyclohexanol | 466.25, 468.26 | 2.42 (ZQ3, polar_4 min) |

| Ex. # | Structure and NMR Data | Compound Name | MS (ESI) [M + H]+ | HPLC $t_R$ (min) |
|---|---|---|---|---|
| 288 | 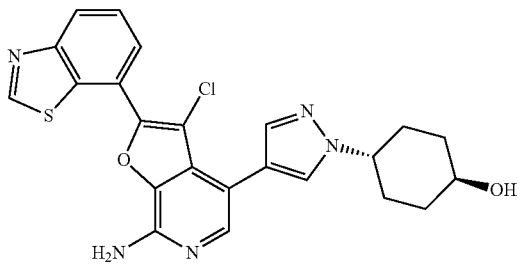 <br> ¹H NMR (400 MHz, CD₃OD): δ 9.36 (s, 1H), 8.30 (d, J = 7.8 Hz, 1H), 8.20 (d, J = 8.1 Hz, 1H), 7.88 (s, 1H), 7.67-7.78 (m, 2H), 7.66 (s, 1H), 4.24 (tt, J = 11.7, 3.9 Hz, 1H), 3.56-3.80 (m, 1H), 2.05-2.28 (m, 4H), 1.86-2.03 (m, 2H), 1.42-1.60 (m, 2H) | trans-4-{4-[7-amino-2-(1,3-benzothiazol-7-yl)-3-chlorofuro[2,3-c]pyridin-4-yl]-1H-pyrazol-1-yl}cyclohexanol | 466.27, 468.26 | 2.62 (ZQ3, polar_4 min) |

30

The following Examples were prepared from 4-iodo-2-thieno[2,3-c]pyridine-3-yl-furo[2,3-c]pyridine-7-ylamine and an appropriate boronic acid or ester by a procedure analogous to Example 68.

| Ex. # | Structure and NMR Data | Compound Name | MS (ESI) [M + H]+ | HPLC $t_R$ (min) |
|---|---|---|---|---|
| 289 | 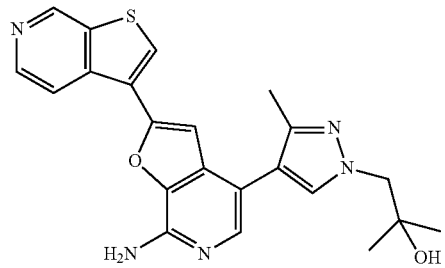 <br> ¹H NMR (400 MHz, CD₃OD): δ 9.57 (s, 1H), 9.15 (s, 1H), 8.87 (d, J = 6.1 Hz, 1H), 8.72 (d, J = 6.1 Hz, 1H), 8.01 (s, 1H), 7.68 (s, 1H), 7.65 (s, 1H), 4.16 (s, 2H), 2.39 (s, 3H), 1.28 (s, 6H) | 1-[4-(7-amino-2-thieno[2,3-c]pyridin-3-yl-furo[2,3-c]pyridin-4-yl)-3-methyl-pyrazol-1-yl]-2-methyl-propan-2-ol | 434.23 | 0.52 (UPLC: Analytical_2 min) |

| Ex. # | Structure and NMR Data | Compound Name | MS (ESI) [M + H]+ | HPLC t$_R$ (min) |
|---|---|---|---|---|
| 290 | 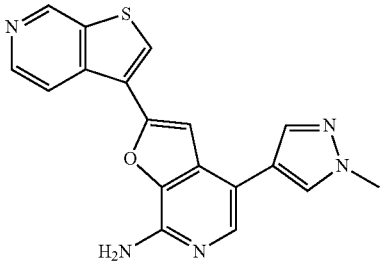 <br> ¹H NMR (400 MHz, CD₃OD): δ 9.50 (s, 1H), 9.08 (s, 1H), 8.84 (d, J = 6.1 Hz, 1H), 8.71 (d, J = 6.1 Hz, 1H), 8.27 (s, 1H), 8.02 (s, 1H), 7.89 (s, 1H), 7.87 (s, 1H), 4.05 (s, 3H) | 4-(1-methyl-1H-pyrazol-4-yl)-2-thieno[2,3-c]pyridin-3-yl-furo[2,3-c]pyridin-7-ylamine | 348.14 | 0.46 (UPLC: Analytical_2 min) |
| 291 | 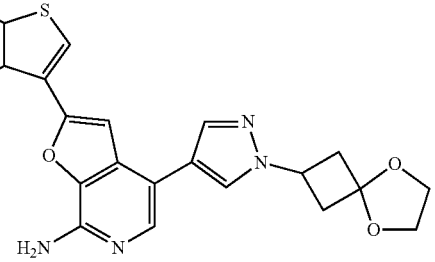 <br> ¹H NMR (400 MHz, CD₃OD): δ 9.51 (s, 1H), 9.10 (s, 1H), 8.85 (d, J = 6.0 Hz, 1H), 8.71 (d, J = 6.3 Hz, 1H), 8.36 (s, 1H), 8.07 (s, 1H), 7.89 (s, 1H), 7.87 (s, 1H), 4.83 (m, 1H), 4.00 (m, 4H), 3.02 (m, 2H), 2.29 (m, 2H) | 4-[1-(5,8-dioxa-spiro[3.4]oct-2-yl)-1H-pyrazol-4-yl]-2-thieno[2,3-c]pyridin-3-yl-furo[2,3-c]pyridin-7-ylamine | 446.19 | 0.57 (UPLC: Analytical_2 min) |
| 292 | 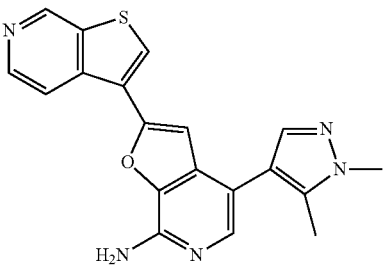 <br> ¹H NMR (400 MHz, CD₃OD): δ 9.53 (s, 1H), 9.11 (s, 1H), 8.84 (d, J = 6.0 Hz, 1H), 8.70 (d, J = 6.3 Hz, 1H), 7.73 (s, 1H), 7.60 (s, 1H), 7.59 (s, 1H), 3.91 (s, 3H), 2.40 (s, 3H) | 4-(1,5-dimethyl-1H-pyrazol-4-yl)-2-thieno[2,3-c]pyridin-3-yl-furo[2,3-c]pyridin-7-ylamine | 362.13 | 0.48 (UPLC: Analytical_2 min) |

| Ex. # | Structure and NMR Data | Compound Name | MS (ESI) [M + H]+ | HPLC $t_R$ (min) |
|---|---|---|---|---|
| 293 | 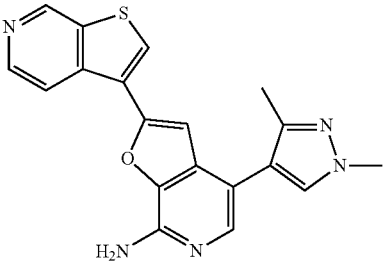<br>¹H NMR (400 MHz, DMSO-d₆): δ 9.39 (s, 1H), 8.79 (s, 1H), 8.62 (s, 2H), 7.92 (s, 1H), 7.73 (s, 1H), 7.44 (s, 1H), 6.49 (s, 2H), 3.85 (s, 3H), 2.25 (s, 3H) | 4-(1,3-dimethyl-1H-pyrazol-4-yl)-2-thieno[2,3-c]pyridin-3-yl-furo[2,3-c]pyridin-7-ylamine | 362.16 | 0.49 (UPLC: Analytical_2 min) |
| 294 | 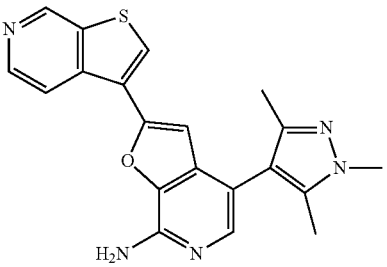<br>¹H NMR (400 MHz, CD₃OD): δ 9.61 (s, 1H), 9.18 (s, 1H), 8.91 (d, J = 6.3 Hz, 1H), 8.71 (d, J = 6.3 Hz, 1H), 7.57 (s, 1H), 7.46 (s, 1H), 3.83 (s, 3H), 2.26 (s, 3H), 2.19 (s, 3H) | 2-thieno[2,3-c]pyridin-3-yl-4-(1,3,5-trimethyl-1H-pyrazol-4-yl)-furo[2,3-c]pyridin-7-ylamine | 376.15 | 0.50 (UPLC: Analytical_2 min) |
| 295 | 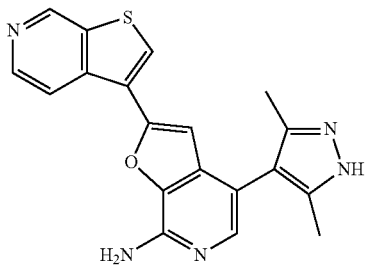<br>¹H NMR (400 MHz, CD₃OD): δ 9.64 (s, 1H), 9.21 (s, 1H), 8.95 (d, J = 6.3 Hz, 1H), 8.73 (d, J = 6.3 Hz, 1H), 7.56 (s, 1H), 7.48 (s, 1H), 3.86 (s, 3H), 2.27 (s, 3H) | 4-(3,5-dimethyl-1H-pyrazol-4-yl)-2-thieno[2,3-c]pyridin-3-yl-furo[2,3-c]pyridin-7-ylamine | 362.13 | 0.43 (UPLC: Analytical_2 min) |

| Ex. # | Structure and NMR Data | Compound Name | MS (ESI) [M + H]+ | HPLC tR (min) |
|---|---|---|---|---|
| 296 | 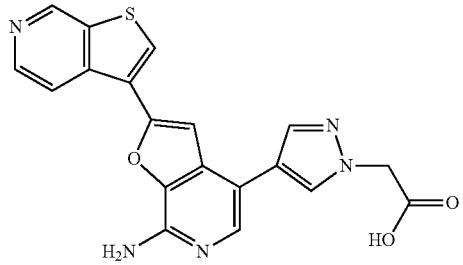<br>¹H NMR (400 MHz, CD₃OD): δ 9.49 (s, 1H), 9.08 (s, 1H), 8.83 (d, J = 6.1 Hz, 1H), 8.69 (d, J = 6.1 Hz, 1H), 8.33 (s, 1H), 8.06 (s, 1H), 7.88 (s, 1H), 7.86 (s, 1H), 5.11 (s, 2H) | [4-(7-amino-2-thieno[2,3-c]pyridin-3-yl-furo[2,3-c]pyridin-4-yl)-pyrazol-1-yl]-acetic acid | 392.18 | 0.39 (UPLC: Analytical_2 min) |
| 297 | 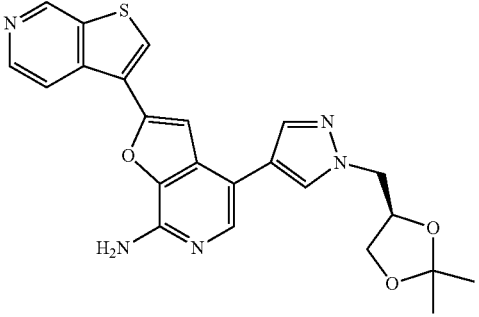<br>¹H NMR (400 MHz, CD₃OD): δ 9.53 (s, 1H), 9.13 (s, 1H), 8.88 (d, J = 6.1 Hz, 1H), 8.70 (d, J = 6.1 Hz, 1H), 8.28 (s, 1H), 8.04 (s, 1H), 7.89 (s, 1H), 7.85 (s, 1H), 4.42 (m, 2H), 4.14 (m, 1H), 3.58 (m, 2H), 1.37 (s, 3H), 1.33 (s, 3H) | 4-[1-((R)-2,2-dimethyl-[1,3]dioxolan-4-ylmethyl)-1H-pyrazol-4-yl]-2-thieno[2,3-c]pyridin-3-yl-furo[2,3-c]pyridin-7-ylamine | 448.24 | 0.61 (UPLC: Analytical_2 min) |
| 298 | 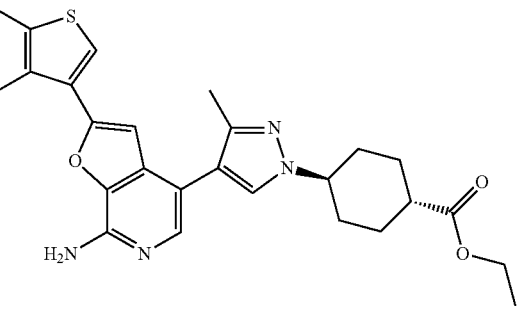<br>¹H NMR (400 MHz, CD₃OD): δ 9.26 (s, 1H), 8.69 (d, J = 13.4 Hz, 1H), 8.60 (dd, J = 6.1 & 2.1 Hz, 1H), 8.52 (dd, J = 6.1 & 2.3 Hz, 1H), 7.93 (s, 1H), 7.86 (s, 1H), 7.69 (s, 1H), 4.19 (m, 1H), 4.15 (q, J = 7.1 Hz, 2H), 3.12 (m, 1H), 2.32 (s, 3H), 2.25 (m, 4H), 1.95 (m, 2H), 1.67 (m, 2H), 1.27 (t, J = 7.1 Hz, 3H) | 4-[4-(7-amino-2-thieno[2,3-c]pyridin-3-yl-furo[2,3-c]pyridin-4-yl)-3-methyl-pyrazol-1-yl]-cyclohexane carboxylic acid ethyl ester | 502.46 | 0.78 (UPLC: Analytical_2 min) |

| Ex. # | Structure and NMR Data | Compound Name | MS (ESI) [M + H]+ | HPLC $t_R$ (min) |
|---|---|---|---|---|
| 299 | 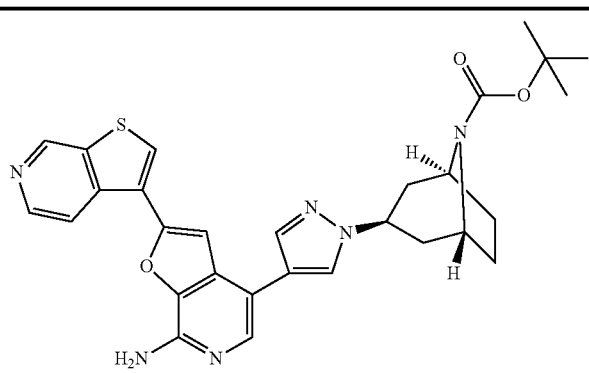<br>¹H NMR (400 MHz, CD₃OD): δ 9.57 (s, 1H), 9.17 (s, 1H), 8.92 (d, J = 6.1 Hz, 1H), 8.73 (d, J = 6.1 Hz, 1H), 8.31 (s, 1H), 8.04 (s, 1H), 7.90 (s, 1H), 7.86 (s, 1H), 4.97 (m, 1H), 4.41 (t, J = 3.3 Hz, 2H), 2.26 (m, 2H), 2.12 (m, 4H), 1.96 (d, J = 7.8 & 1.5 Hz, 2H), 1.54 (s, 9H) | tert-butyl (3-exo)-3-{4-[7-amino-2-(thieno[2,3-c]pyridin-3-yl)furo[2,3-c]pyridin-4-yl]-1H-pyrazol-1-yl}-8-azabicyclo[3.2.1]octane-8-carboxylate | 543.69 | 0.87 (UPLC: Analytical_2 min) |
| 300 | 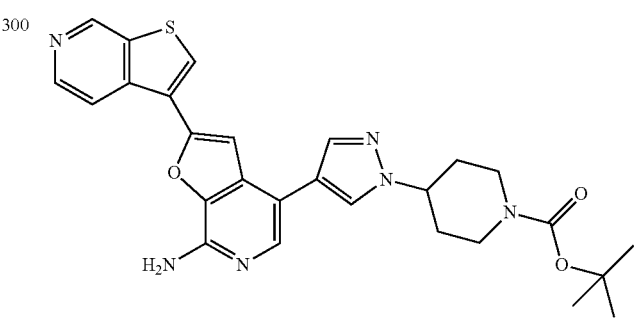 | 4-[4-(7-amino-2-thieno[2,3-c]pyridin-3-yl-furo[2,3-c]pyridin-4-yl)-pyrazol-1-yl] piperidine-1-carboxylic acid tert-butyl ester | | |

The following Examples were prepared from 2-(1,2-benzothiazol-7-yl)-4-iodofuro[2,3-c]pyridin-7-amine by a procedure analogous to Example 68.

| Ex. # | Structure and NMR Data | Compound Name | MS (ESI) [M + H]⁺ | HPLC $t_R$ (min) |
|---|---|---|---|---|
| 301 | 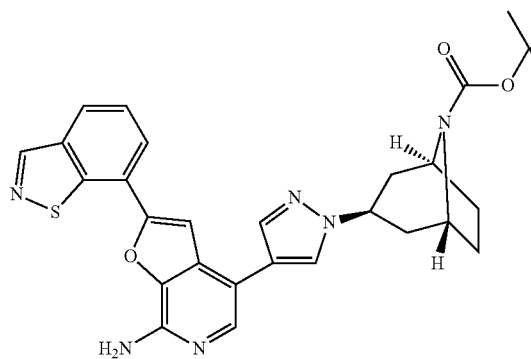<br>¹H NMR (400 MHz, CD₃OD): δ 9.27 (s, 1H), 8.71 (s, 1H), 8.62 (d, J = 5.8 Hz, 1H), 8.57 (d, J = 5.8 Hz, 1H), 8.15 (s, 1H), 7.93 (s, 1H), 7.91 (s, 1H), 7.55 (s, 1H), 4.95 (m, 1H), 4.40 (t, J = 3.3 Hz, 2H), 2.26 (m, 2H), 2.11 (m, 4H), 1.94 (d, J = 7.8 Hz, 2H), 1.52 (s, 9H) | tert-butyl (3-exo)-3-{4-[7-amino-2-(1,2-benzisothiazol-7-yl)furo[2,3-c]pyridin-4-yl]-1H-pyrazol-1-yl}-8-azabicyclo[3.2.1]octane-8-carboxylate | 543.65 | 0.89 (UPLC: Analytical_2 min) |
| 302 | 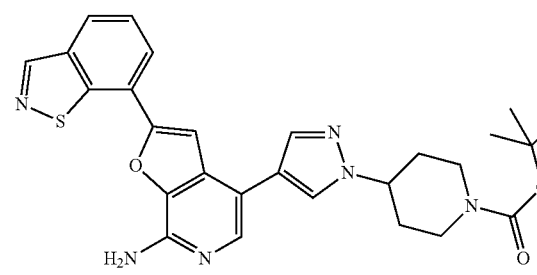<br>¹H NMR (400 MHz, CD₃OD): δ 9.06 (s, 1H), 8.36 (d, J = 7.3 Hz, 1H), 8.30 (d, J = 7.3 Hz, 1H), 8.21 (s, 1H), 7.92 (s, 1H), 7.76 (s, 1H), 7.71 (s, 1H), 7.65 (t, J = 7.6 Hz, 1H), 4.41 (m, 1H), 4.19 (d, J = 13.6 Hz, 2H), 2.98 (br s, 2H), 2.07 (d, J = 13.6 Hz, 2H), 1.95 (m, 2H), 1.40 (s, 9H) | 4-[4-(7-amino-2-benzo[d]isothiazol-7-yl-furo[2,3-c]pyridin-4-yl)-pyrazol-1-yl]-piperidine-1-carboxylic acid tert-butyl ester | 517.62 | 0.81 (UPLC: Analytical_2 min) |

The following Examples were prepared from 4-iodo-2-thieno[2,3-c]pyridine-3-yl-furo[2,3-c]pyridine-7-ylamine and an appropriate boronic acid or ester by a procedure analogous to Example 68 followed by silyl ether deprotection by a procedure analogous to Examples 66 or 229. Examples 307 and 308 were resolved into individual enantiomers by SFC purification on a chiral stationary phase after being prepared as the racemate. Examples 309 and 310 were prepared as a cis/trans mixture and separated by MDP.

| Ex. # | Structure and NMR Data | Compound Name | MS (ESI) [M + H]+ | HPLC $t_R$ (min) |
|---|---|---|---|---|
| 303 | 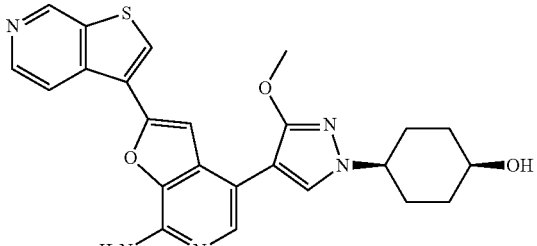<br>¹H NMR (400 MHz, CD₃OD): δ 9.43 (s, 1H), 9.03 (s, 1H), 8.76 (d, J = 6.1 Hz, 1H), 8.68 (d, J = 6.1 Hz, 1H), 8.14 (s, 1H), 7.94 (s, 1H), 7.82 (s, 1H), 4.28 (m, 1H), 4.04 (s, 3H), 4.01 (m, 1H), 2.28 (m, 2H), 1.95 (m, 4H), 1.75 (m, 2H) | 4-[4-(7-amino-2-thieno[2,3-c]pyridin-3-yl-furo[2,3-c]pyridin-4-yl)-3-methoxy-pyrazol-1-yl]-cyclohexanol | 462.26 | 0.62 (UPLC: Analytical_2 min) |
| 304 | 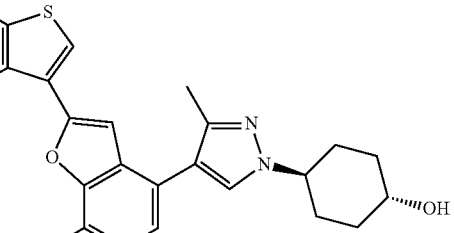<br>¹H NMR (400 MHz, CD₃OD): δ 9.26 (s, 1H), 8.70 (s, 1H), 8.60 (d, J = 6.1 Hz, 1H), 8.52 (d, J = 6.1 Hz, 1H), 7.87 (s, 1H), 7.67 (s, 1H), 7.31 (s, 1H), 4.18 (m, 1H), 3.69 (m, 1H), 2.32 (s, 3H), 2.15 (m, 4H), 1.98 (m, 2H), 1.49 (m, 2H) | 4-[4-(7-amino-2-thieno[2,3-c]pyridin-3-yl-furo[2,3-c]pyridin-4-yl)-3-methyl-pyrazol-1-yl]-cyclohexanol | 446.43 | 0.52 (UPLC: Analytical_2 min) |
| 305 | 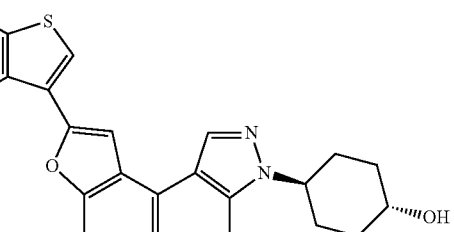<br>¹H NMR (400 MHz, CD₃OD): δ 9.59 (s, 1H), 9.18 (s, 1H), 8.91 (d, J = 6.1, 1H), 8.72 (d, J = 6.1 Hz, 1H), 7.75 (s, 1H), 7.60 (d, J = 2.8 Hz, 2H), 4.28 (m, 1H), 3.71 (m, 1H), 2.41 (s, 3H), 2.10 (m, 6H), 1.55 (m, 2H) | 4-[4-(7-amino-2-thieno[2,3-c]pyridin-3-yl-furo[2,3-c]pyridin-4-yl)-5-methyl-pyrazol-1-yl]-cyclohexanol | 446.58 | 0.52 (UPLC: Analytical_2 min) |

| Ex. # | Structure and NMR Data | Compound Name | MS (ESI) [M + H]+ | HPLC $t_R$ (min) |
|---|---|---|---|---|
| 306 | 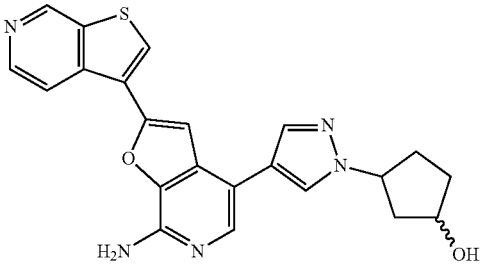<br>¹H NMR (400 MHz, CD₃OD): δ 9.54 (s, 1H), 9.16 (s, 1H), 8.90 (d, J = 6.1 Hz, 1H), 8.74 (d, J = 6.1 Hz, 1H), 8.39 (s, 1H), 8.05 (s, 1H), 7.89 (s, 1H), 7.87 (s, 1H), 4.94 (m, 1H), 4.43 (t, J = 3.3 Hz, 1H), 2.57 (m, 1H), 2.30 (m, 2H), 2.00 (m, 1H), 1.96 (m, 2H) | 3-[4-(7-amino-2-thieno[2,3-c]pyridin-3-yl-furo[2,3-c]pyridin-4-yl)-pyrazol-1-yl]-cyclopentanol | 418.52 | 0.57 (UPLC: Analytical_2 min) |
| 307 | 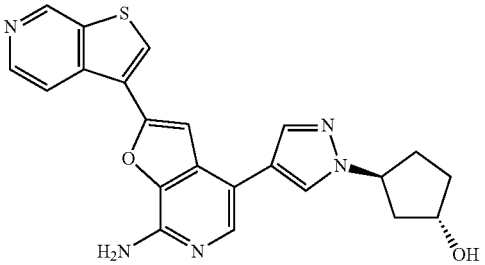<br>¹H NMR (400 MHz, CD₃OD): δ 9.56 (s, 1H), 9.18 (s, 1H), 8.91 (d, J = 6.1 Hz, 1H), 8.74 (d, J = 6.1 Hz, 1H), 8.39 (s, 1H), 8.04 (s, 1H), 7.89 (s, 1H), 7.87 (s, 1H), 4.94 (m, 1H), 4.44 (t, J = 3.3 Hz, 1H), 2.57 (m, 1H), 2.34 (m, 1H), 2.27 (m, 1H), 2.10 (m, 1H), 1.98 (m, 2H) | (1S,3S)-3-[4-(7-amino-2-thieno[2,3-c]pyridin-3-yl-furo[2,3-c]pyridin-4-yl)-pyrazol-1-yl]-cyclopentanol | 418.53 | 0.54 (UPLC: Analytical_2 min) |
| 308 | 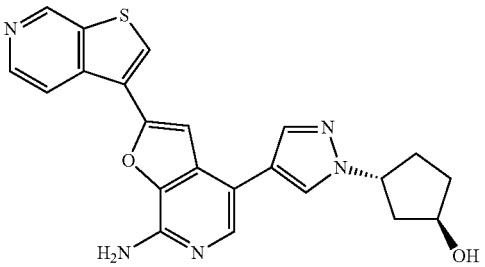<br>¹H NMR (400 MHz, CD₃OD): δ 9.56 (s, 1H), 9.18 (s, 1H), 8.91 (d, J = 6.1 Hz, 1H), 8.74 (d, J = 6.1 Hz, 1H), 8.39 (s, 1H), 8.04 (s, 1H), 7.89 (s, 1H), 7.87 (s, 1H), 4.94 (m, 1H), 4.44 (t, J = 3.3 Hz, 1H), 2.57 (m, 1H), 2.34 (m, 1H), 2.27 (m, 1H), 2.10 (m, 1H), 1.98 (m, 2H) | (1R,3R)-3-[4-(7-amino-2-thieno[2,3-c]pyridin-3-yl-furo[2,3-c]pyridin-4-yl)-pyrazol-1-yl]-cyclopentanol | 418.53 | 0.55 (UPLC: Analytical_2 min) |

| Ex. # | Structure and NMR Data | Compound Name | MS (ESI) [M + H]⁺ | HPLC t_R (min) |
|---|---|---|---|---|
| 309 | 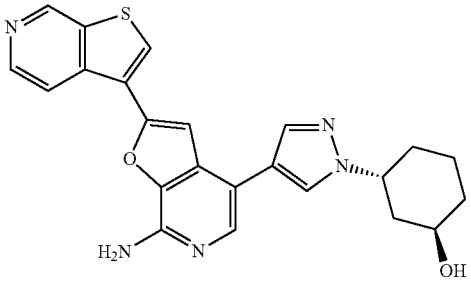 ¹H NMR (400 MHz, CD₃OD): δ 9.35 (s, 1H), 8.79 (s, 1H), 8.69 (d, J = 6.1 Hz, 1H), 8.65 (d, J = 6.1 Hz, 1H), 8.25 (s, 1H), 8.02 (s, 1H), 7.97 (s, 1H), 7.72 (s, 1H), 4.79 (m, 1H), 4.45 (s, 1H), 2.24 (m, 1H), 2.13 (m, 2H), 2.05 (m, 2H), 1.83 (m, 2H), 1.69 (m, 1H) | trans-3-[4-(7-amino-2-thieno[2,3-c]pyridin-3-yl-furo[2,3-c]pyridin-4-yl)-pyrazol-1-yl]-cyclohexanol | 432.54 | 0.59 (UPLC: Analytical_2 min) |
| 310 | 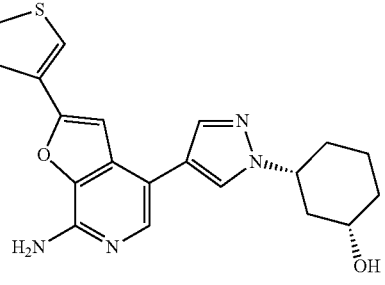 ¹H NMR (400 MHz, CD₃OD): δ 9.27 (s, 1H), 8.74 (s, 1H), 8.60 (d, J = 6.1 Hz, 1H), 8.59 (d, J = 6.1 Hz, 1H), 8.18 (s, 1H), 7.95 (s, 1H), 7.92 (s, 1H), 7.60 (s, 1H), 4.32 (m, 1H), 3.85 (m, 1H), 2.33 (m, 1H), 2.13 (m, 2H), 1.96 (m, 3H), 1.50 (m, 1H), 1.39 (m, 1H) | cis-3-[4-(7-amino-2-thieno[2,3-c]pyridin-3-yl-furo[2,3-c]pyridin-4-yl)-pyrazol-1-yl]-cyclohexanol | 432.55 | 0.56 (UPLC: Analytical_2 min) |
| 311 | 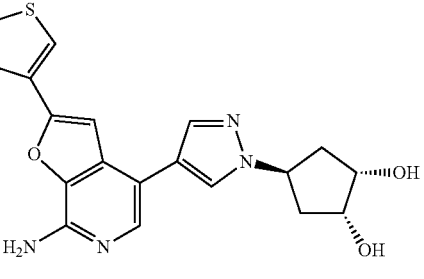 ¹H NMR (400 MHz, CD₃OD): δ 9.51 (s, 1H), 9.12 (s, 1H), 8.88 (d, J = 6.3 Hz, 1H), 8.70 (d, J = 6.3 Hz, 1H), 8.29 (s, 1H), 8.03 (s, 1H), 7.89 (s, 1H), 7.85 (s, 1H), 5.13 (dd, J = 7.6 Hz, 1H), 4.37 (m, 2H), 2.31 (m, 4H) | rel-(1R,2S,4S)-4-[4-(7-amino-2-thieno[2,3-c]pyridin-3-yl-furo[2,3-c]pyridin-4-yl)-pyrazol-1-yl]-cyclopentane-1,2-diol | 434.23 | 0.44 (UPLC: Analytical_2 min) |

| Ex. # | Structure and NMR Data | Compound Name | MS (ESI) [M + H]+ | HPLC $t_R$ (min) |
|---|---|---|---|---|
| 312 | 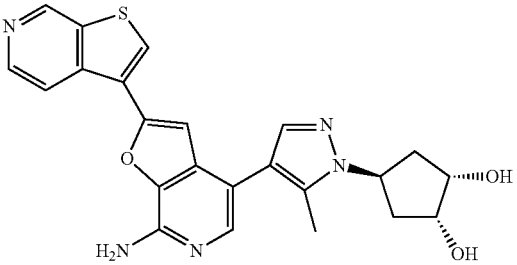<br>$^1$H NMR (400 MHz, CD$_3$OD): δ 9.56 (s, 1H), 9.15 (s, 1H), 8.88 (d, J = 6.1 Hz, 1H), 8.70 (d, J = 6.1 Hz, 1H), 7.77 (s, 1H), 7.60 (s, 1H), 7.59 (s, 1H), 5.13 (dd, J = 7.6 Hz, 1H), 4.39 (m, 2H), 2.39 (s, 3H), 2.28 (m, 4H) | rel-(1R,2S,4S)-4-[4-(7-amino-2-thieno[2,3-c]pyridin-3-yl-furo[2,3-c]pyridin-4-yl)-5-methyl-pyrazol-1-yl]-cyclopentane-1,2-diol | 434.23 | 0.43 (UPLC: Analytical_2 min) |

Example 313 trans-3-[4-(7-amino-2-benzo[d]isothiazol-7-yl-furo[2,3-c]pyridin-4-yl)-pyrazol-1-yl]-cyclohexanol

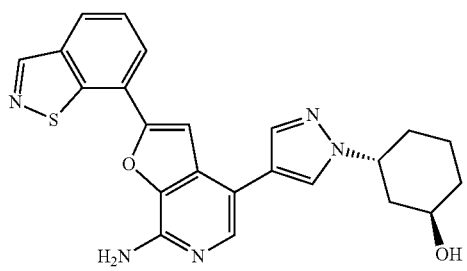 [SMILES: Nc1ncc(-c2cnn([C@@H]3CCC[C@@H](O)C3)c2)c2cc(-c3cccc4cnsc34)oc12]

The title compound was prepared from 2-(1,2-benzothiazol-7-yl)-4-iodofuro[2,3-c]pyridin-7-amine and 2-[3-(tert-butyl-dimethyl-silanyloxy)-cyclohexyl]-4-(4,4,5,5-tetramethyl-[1,3,2]dioxaborolan-2-yl)-1H-pyrazole by a procedure analogous to Example 68 followed by silyl ether deprotection by a procedure analogous to Example 229. $^1$H NMR (400 MHz, CD$_3$OD): δ 9.48 (s, 1H), 9.09 (s, 1H), 8.84 (d, J=5.9 Hz, 1H), 8.71 (d, J=5.9 Hz, 1H), 8.32 (s, 1H), 8.04 (s, 1H), 7.90 (s, 1H), 7.87 (s, 1H), 4.73 (m, 1H), 3.30 (m, 1H), 2.20 (m, 2H), 2.03 (m, 1H), 1.92 (m, 1H), 1.84 (m, 1H), 1.76 (m, 1H), 1.63 (m, 1H), 1.40 (m, 1H); MS (ESI): 432.60 [M+H]$^+$; HPLC $t_R$=0.60 min (HPLC: Analytical_2 min)

Example 314

4-(1-azetidin-3-yl-1H-pyrazol-4-yl)-2-thieno[2,3-c]pyridin-3-yl-furo[2,3-c]pyridin-7-ylamine

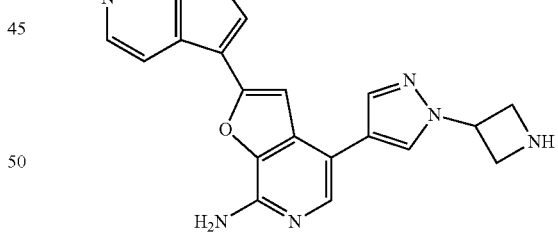

The title compound was prepared from 4-iodo-2-thieno[2,3-c]pyridine-3-yl-furo[2,3-c]pyridine-7-ylamine and tert-butyl 3-[4-(4,4,5,5-tetramethyl-1,3,2-dioxaborolan-2-yl)-1H-pyrazol-1-yl]azetidine-1-carboxylate by a procedure analogous to Example 68 followed by deprotection by a procedure analogous to Example 64, Step B. $^1$H NMR (400 MHz, CD$_3$OD): δ 9.29 (s, 1 H), 8.75 (s, 1 H), 8.63 (d, J=6.1 Hz, 1 H), 8.59 (d, J=6.1 Hz, 1 H), 8.26 (s, 1 H), 8.08 (s, 1H), 7.96 (s, 1H), 7.62 (s, 1H), 5.32 (m, 1H), 4.45 (m, 4H); MS (ESI): 389.18 [M+H]⁺; HPLC $t_R$=0.25 min (HPLC: Analytical_2 min).

Example 315

3-[4-(7-amino-2-thieno[2,3-c]pyridin-3-yl-furo[2,3-c]pyridin-4-yl)-pyrazol-1-yl]-cyclobutanone

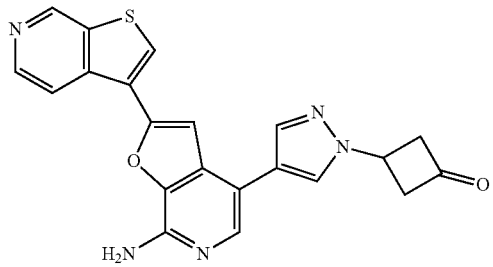 [SMILES: Nc1ncc(-c2cnn(C3CC(=O)C3)c2)c2cc(-c3csc4cnccc34)oc12]

The title compound was prepared from 4-[1-(5,8-dioxaspiro[3.4]oct-2-yl)-1H-pyrazol-4-yl]-2-thieno[2,3-c]pyridin-3-yl-furo[2,3-c]pyridin-7-ylamine by a procedure analogous to Example 66. ¹H NMR (400 MHz, CD₃OD): δ 9.52 (s, 1 H), 9.10 (s, 1 H), 8.86 (d, J=6.0 Hz, 1 H), 8.72 (d, J=6.3 Hz, 1 H), 8.38 (s, 1H), 8.09 (s, 1H), 7.91 (s, 1 H), 7.879 (s, 1 H), 4.85 (m, 1H), 3.15 (m, 4H); MS (ESI): 446.19 [M+H]⁺; HPLC $t_R$=0.50 min (HPLC: Analytical_2 min).

Example 316

1-{3-[4-(7-amino-2-thieno[2,3-c]pyridin-3-yl-furo[2,3-c]pyridin-4-yl)-pyrazol-1-yl]-azetidin-1-yl}-ethanone

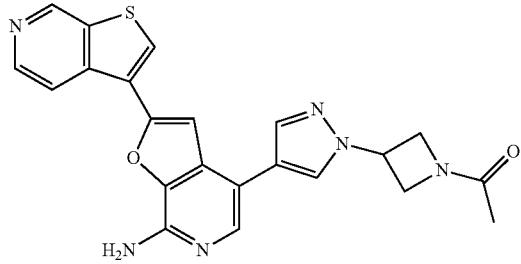 [SMILES: CC(=O)N1CC(n2cc(-c3cnc(N)c4oc(-c5csc6cnccc56)cc34)cn2)C1]

The title compound was prepared from 4-(1-azetidin-3-yl-1H-pyrazol-4-yl)-2-thieno[2,3-c]pyridin-3-yl-furo[2,3-c]pyridin-7-ylamine by a procedure analogous to Example 50. ¹H NMR (400 MHz, CD₃OD): δ 9.51 (s, 1 H), 9.10 (s, 1 H), 8.86 (d, J=6.1 Hz, 1 H), 8.71 (d, J=6.1 Hz, 1 H), 8.40 (s, 1 H), 8.15 (s, 1H), 7.89 (s, 1H), 7.88 (s, 1H), 5.38 (m, 1H), 4.75 (m, 1H), 4.67 (m, 1H), 4.51 (m, 1H), 4.41 (m, 1H), 1.97 (s, 3H); MS (ESI): 431.15 [M+H]⁺; HPLC $t_R$=0.45 min (HPLC: Analytical_2 min).

Example 317

(R)-3-[4-(7-amino-2-thieno[2,3-c]pyridin-3-yl-furo[2,3-c]pyridin-4-yl)-pyrazol-1-yl]-propane-1,2-diol

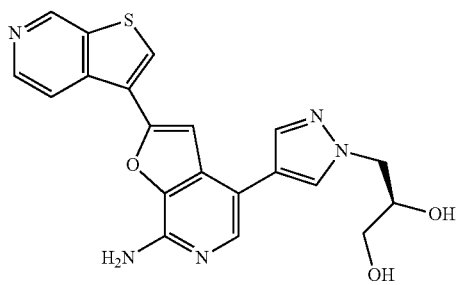 [SMILES: Nc1ncc(-c2cnn(C[C@@H](O)CO)c2)c2cc(-c3csc4cnccc34)oc12]

The title compound was prepared from 4-[1-((R)-2,2-dimethyl-[1,3]dioxolan-4-ylmethyl)-1H-pyrazol-4-yl]-2-thieno[2,3-c]pyridin-3-yl-furo[2,3-c]pyridin-7-ylamine by a procedure analogous to Example 66. ¹H NMR (400 MHz, CD₃OD): δ 9.51 (s, 1H), 9.10 (s, 1 H), 8.85 (d, J=6.1 Hz, 1 H), 8.68 (d, J=6.1 Hz, 1 H), 8.26 (s, 1 H), 8.01 (s, 1 H), 7.86 (s, 1H), 7.83 (s, 1H), 4.39 (m, 2H), 4.07 (m, 1H), 3.52 (m, 2H); MS (ESI): 408.29 [M+H]⁺; HPLC $t_R$=0.38 min (HPLC: Analytical_2 min).

Example 318

(S)-3-[4-(7-amino-2-thieno[2,3-d]pyridin-3-yl-furo[2,3-d]pyridin-4-yl)-3-methyl-pyrazol-1-yl]-propane-1,2-diol

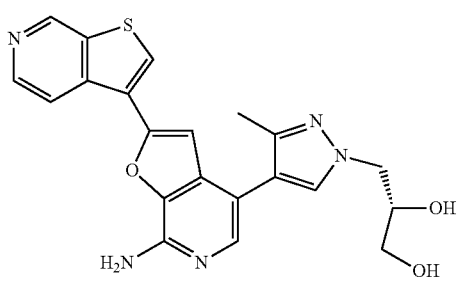 [SMILES: Cc1nn(C[C@H](O)CO)cc1-c1cnc(N)c2oc(-c3csc4cnccc34)cc12]

The title compound was prepared from 4-iodo-2-thieno[2,3-c]pyridine-3-yl-furo[2,3-c]pyridine-7-ylamine by a procedure analogous to Example 69, followed by deprotection by a procedure analogous to Example 66. ¹H NMR (400 MHz, CD₃OD): δ 9.43 (s, 1H), 9.00 (s, 1 H), 8.81 (d, J=6.1 Hz, 1 H), 8.67 (d, J=6.1 Hz, 1 H), 8.01 (s, 1 H), 7.64 (s, 1 H), 7.60 (s, 1H), 4.37 (m, 2H), 4.12 (m, 1H), 3.51 (m, 2H), 2.36 (s, 3H); MS (ESI): 422.14 [M+H]⁺; HPLC t$_R$=0.39 min (HPLC: Analytical_2 min).

Example 319

2-[4-(7-amino-2-thieno[2,3-d]pyridin-3-yl-furo[2,3-d]pyridin-4-yl)-pyrazol-1-yl]-ethanol

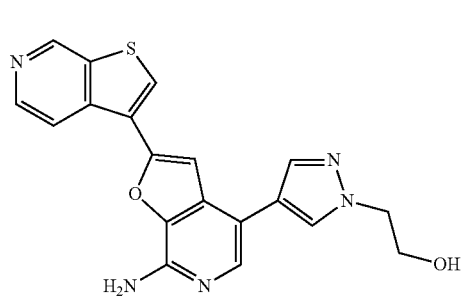 [SMILES: Nc1ncc(-c2cnn(CCO)c2)c2cc(-c3csc4cnccc34)oc12]

To a solution of 4-(7-amino-2-thieno[2,3-c]pyridin-3-yl-furo[2,3-c]pyridin-4-yl)-pyrazol-1-yl]-acetic acid (10.2 mg, 0.025 mmol) in 1,4-dioxane (1 mL) was added 1.0 M diisobutylaluminum hydride in tetrahydrofuran (0.2 mL, 0.2 mmol). The resulting solution stirred at room temperature overnight. The reaction was quenched with methanol (4 mL) and the mixture was dried and then purified by MDP to afford 4.1 mg (43%) of the title compound. ¹H NMR (400 MHz, CD₃OD): δ 9.47 (s, 1H), 9.05 (s, 1 H), 8.81 (d, J=6.1 Hz, 1 H), 8.66 (d, J=6.1 Hz, 1 H), 8.32 (s, 1 H), 8.05 (s, 1 H), 7.89 (s, 1H), 7.85 (s, 1H), 4.44 (t, J=3.6 Hz, 2H), 4.23 (t, J=3.6 Hz, 2H); MS (ESI): 378.14 [M+H]⁺; HPLC t$_R$=0.41 min (HPLC: Analytical_2 min).

Example 320

4-{1-[(3-exo)-8-azabicyclo[3.2.1]oct-3-yl]-1H-pyrazol-4-yl}-2-(thieno[2,3-c]pyridin-3-yl)furo[2,3-c]pyridin-7-amine

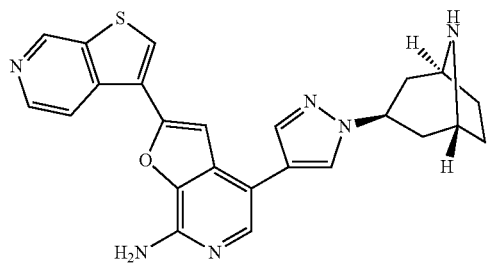 [SMILES: Nc1ncc(-c2cnn([C@@H]3C[C@H]4CC[C@@H](C3)N4)c2)c2cc(-c3csc4cnccc34)oc12]

To a stirred suspension of tert-butyl (3-exo)-3-{4-[7-amino-2-(thieno[2,3-c]pyridin-3-yl)furo[2,3-c]pyridin-4-yl]-1H-pyrazol-1-yl}-8-azabicyclo[3.2.1]-octane-8-carboxylate in methanol (2 mL) was added 4 N hydrochloric acid in 1,4-dioxane (2 mL, 8 mmol). The resulting solution stirred at room temperature for 2 h. The mixture was concentrated and the residue was redissolved in water and freeze dried to afford the title compound. ¹H NMR (400 MHz, CD₃OD): δ 9.59 (s, 1H), 9.20 (s, 1H), 8.98 (d, J=6.1 Hz, 1H), 8.75 (d, J=6.1 Hz, 1H), 8.37 (s, 1H), 8.14 (s, 1H), 7.98 (s, 1H), 7.88 (s, 1H), 4.90 (m, 1H), 4.45 (t, J=3.3 Hz, 2H), 2.28 (m, 2H), 2.14 (m, 4H), 1.99 (d, J=7.8, 1.5 Hz, 2H); MS (ESI): 443.57 [M+H]⁺; HPLC t$_R$=0.43 min (HPLC: Analytical_2 min).

The following Examples were prepared by a procedure analogous to Example 320.

| Ex. # | Structure and NMR Data | Compound Name | MS (ESI) [M + H]⁺ | HPLC t$_R$ (min) |
|---|---|---|---|---|
| 321 | ¹H NMR (400 MHz, CD₃OD): δ 9.28 (s, 1H), 8.74 (s, 1H), 8.60 (d, J = 5.8 Hz, 1H), 8.53 (d, J = 5.8 Hz, 1H), 8.10 (s, 1H), 7.95 (s, 1H), 7.92 (s, 1H), 7.50 (s, 1H), 4.94 (m, 1H), 4.41 (t, J = 3.3 Hz, 2H), 2.30 (m, 2H), 2.18 (m, 4H), 1.93 (d, J = 7.8 Hz, 2H) | 4-{1-[(3-exo)-8-azabicyclo[3.2.1]oct-3-yl]-1H-pyrazol-4-yl}-2-(1,2-benzisothiazol-7-yl)furo[2,3-c]pyridin-7-amine | 443.55 | 0.38 (UPLC: Analytical_2 min) |

| Ex. # | Structure and NMR Data | Compound Name | MS (ESI) [M + H]+ | HPLC $t_R$ (min) |
|---|---|---|---|---|
| 322 | ¹H NMR (400 MHz, CD₃OD): δ 9.53 (s, 1H), 9.11 (s, 1H), 8.90 (d, J = 6.1 Hz, 1H), 8.74 (d, J = 6.1 Hz, 1H), 8.31 (s, 1H), 8.08 (s, 1H), 7.92 (s, 1H), 7.86 (s, 1H), 4.54 (m, 1H), 4.28 (m, 2H), 3.04 (br s, 2H), 2.18 (m, 2H), 2.06 (m, 2H) | 4-(1-piperidin-4-yl-1H-pyrazol-4-yl)-2-thieno[2,3-c]pyridin-3-yl-furo[2,3-c]pyridin-7-ylamine | 417.57 | 0.29 (UPLC: Analytical_2 min) |
| 323 | ¹H NMR (400 MHz, CD₃OD): δ 9.10 (s, 1H), 8.38 (d, J = 7.3 Hz, 1H), 8.33 (d, J = 7.3 Hz, 1H), 8.25 (s, 1H), 7.91 (s, 1H), 7.73 (s, 1H), 7.72 (s, 1H), 7.69 (t, J = 7.6 Hz, 1H), 4.40 (m, 1H), 4.21 (m, 2H), 2.98 (m, 2H), 2.07 (m, 2H), 1.99 (m, 2H) | 2-benzo[d]isothiazol-7-yl-4-(1-piperidin-4-yl-1H-pyrazol-4-yl)-furo[2,3-c]pyridin-7-ylamine | 417.53 | 0.52 (UPLC: Analytical_2 min) |

Example 324

(3-exo)-3-{4-[7-amino-2-(thieno[2,3-c]pyridin-3-yl)furo[2,3-c]pyridin-4-yl]-1H-pyrazol-1-yl}-8-azabicyclo[3.2.1]octane-8-carbaldehyde

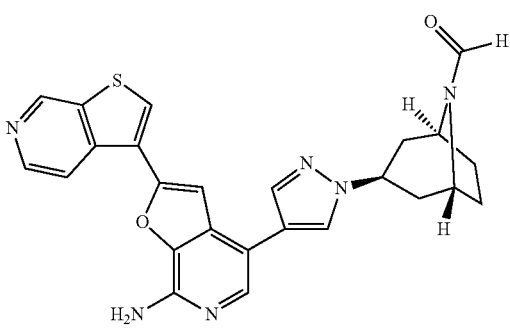 [SMILES: Nc1ncc(-c2cnn([C@@H]3C[C@H]4CC[C@@H](C3)N4C=O)c2)c2cc(-c3csc4cnccc34)oc12]

To a stirred solution of 4-{1-[(3-exo)-8-azabicyclo[3.2.1]oct-3-yl]-1H-pyrazol-4-yl}-2-(thieno[2,3-c]pyridin-3-yl)furo[2,3-c]pyridin-7-amine (18.0 mg, 0.04 mmol) in DMF (0.5 mL) were added diisopropylethylamine (0.05 mL, 6.5 mmol), formic acid (2.8 mg, 0.06 mmol), and N-(3-dimethylaminopropyl)-N'-ethylcarbodimide hydrochloride (11.6 mg, 0.06 mmol). The resulting solution was allowed to stir at room temperature overnight. The mixture was concentrated and then purified by MDP to afford the title compound. ¹H NMR (400 MHz, CD₃OD): δ 9.64 (s, 1H), 9.04 (s, 1H), 8.79 (d, J=6.8 Hz, 1H), 8.70 (d, J=6.8 Hz, 1H), 8.34 (s, 1H), 8.20 (s, 1H), 8.04 (s, 1H), 7.87 (s, 1H), 7.85 (s, 1H), 4.98 (m, 1H), 4.76 (t, J=3.0 Hz, 1H), 4.43 (t, J=3.3 Hz, 1H), 2.30 (m, 2H), 2.21 (m, 4H), 2.05 (m, 2H); MS (ESI): 471.59 [M+H]⁺; HPLC $t_R$=0.54 min (HPLC: Analytical_2 min).

The following Examples were prepared from the appropriate amine and carboxylic acid by a procedure analogous to Example 324.

| Ex. # | Structure and NMR Data | Compound name | MS (ESI) [M + H]+ | HPLC tR (min) |
|---|---|---|---|---|
| 325 | 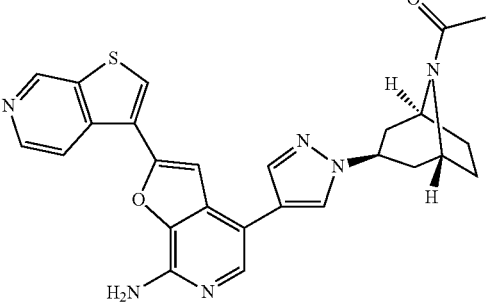 <br> ¹H NMR (400 MHz, CD₃OD): δ 9.56 (s, 1H), 9.16 (s, 1H), 8.90 (d, J = 6.8 Hz, 1H), 8.74 (d, J = 6.8 Hz, 1H), 8.35 (s, 1H), 8.05 (s, 1H), 7.90 (s, 1H), 7.86 (s, 1H), 5.01 (m, 1H), 4.79 (t, J = 3.0 Hz, 1H), 4.50 (t, J = 3.5 Hz, 1H), 2.34 (m, 2H), 2.18 (m, 4H), 2.12 (s, 3H), 1.99 (m, 2H) | 1-[(3-exo)-3-{4-[7-amino-2-(thieno[2,3-c]pyridin-3-yl)furo[2,3-c]pyridin-4-yl]-1H-pyrazol-1-yl}-8-azabicyclo[3.2.1]oct-8-yl]ethanone | 485.60 | 0.58 (UPLC: Analytical_2 min) |
| 326 | 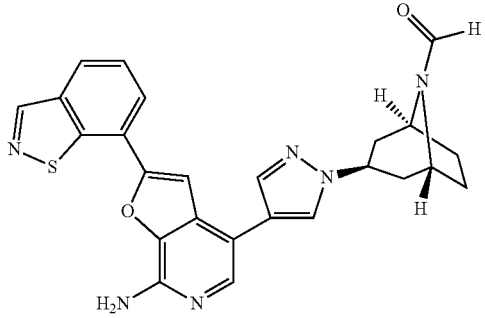 [SMILES: Nc1ncc(-c2cnn([C@@H]3C[C@H]4CC[C@@H](C3)N4C=O)c2)c2cc(-c3cccc4cnsc34)oc12] <br> ¹H NMR (400 MHz, CD₃OD): δ 9.70 (s, 1H), 9.34 (s, 1H), 8.78 (s, 1H), 8.73 (d, J = 6.1 Hz, 1H), 8.68 (d, J = 6.1 Hz, 1H), 8.20 (s, 1H), 7.99 (s, 1H), 7.93 (s, 1H), 7.54 (s, 1H), 4.98 (m, 1H), 4.76 (t, J = 3.0 Hz, 1H), 4.43 (t, J = 3.3 Hz, 1H), 2.30 (m, 2H), 2.21 (m, 4H), 2.05 (m, 2H) | (3-exo)-3-{4-[7-amino-2-(1,2-benzisothiazol-7-yl)furo[2,3-c]pyridin-4-yl]-1H-pyrazol-1-yl}-8-azabicyclo[3.2.1]octane-8-carbaldehyde | 471.59 | 0.54 (UPLC: Analytical_2 min) |
| 327 | 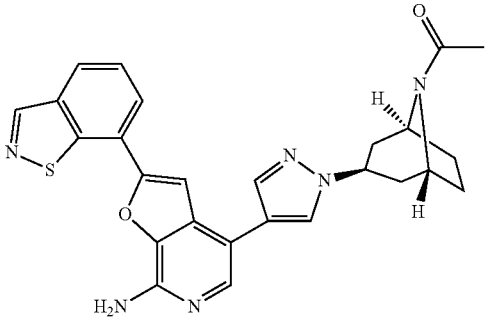 [SMILES: CC(=O)N1[C@@H]2CC[C@H]1C[C@H](n1cc(-c3cnc(N)c4oc(-c5cccc6cnsc56)cc34)cn1)C2] <br> ¹H NMR (400 MHz, CD₃OD): δ 9.35 (s, 1H), 9.16 (s, 1H), 8.90 (d, J = 6.8 Hz, 1H), 8.74 (d, J = 6.8 Hz, 1H), 8.35 (s, 1H), 8.05 (s, 1H), 7.90 (s, 1H), 7.86 (s, 1H), 5.01 (m, 1H), 4.79 (t, J = 3.0 Hz, 1H), 4.50 (t, J = 3.5 Hz, 1H), 2.34 (m, 2H), 2.18 (m, 4H), 2.12 (s, 3H), 1.99 (m, 2H) | 1-[(3-exo)-3-{4-[7-amino-2-(1,2-benzisothiazol-7-yl)furo[2,3-c]pyridin-4-yl]-1H-pyrazol-1-yl}-8-azabicyclo[3.2.1]oct-8-yl]ethanone | 485.60 | 0.58 (UPLC: Analytical_2 min) |

Example 328

4-{1-[(3-exo)-8-methyl-8-azabicyclo[3.2.1]oct-3-yl]-1H-pyrazol-4-yl}-2-(thieno[2,3-c]pyridin-3-yl)furo[2,3-c]pyridin-7-amine

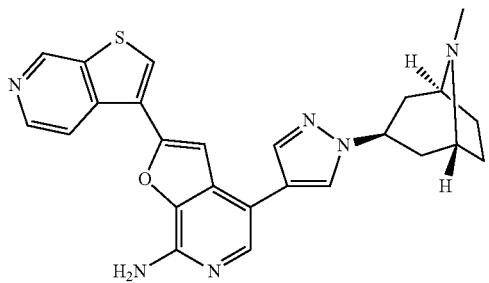 [SMILES: CN1[C@@H]2CC[C@H]1C[C@H](n1cc(-c3cnc(N)c4oc(-c5csc6cnccc56)cc34)cn1)C2]

To a solution of 4-{1-[(3-exo)-8-azabicyclo[3.2.1]oct-3-yl]-1H-pyrazol-4-yl}-2-(thieno[2,3-c]pyridin-3-yl)furo[2,3-c]pyridin-7-amine (18.0 mg, 0.04 mmol) in methanol (0.5 mL) was added two drops of formic acid and 37% formaldehyde solution (0.08 mL, 0.9 mmol). The resulting solution was allowed to stir at room temperature for 6 h when sodium borohydride (150 mg, 4 mmol) was added in two batches. The resulting solution was allowed to stir at room temperature overnight. The mixture was concentrated and purified by MDP to afford the title compound. $^1$H NMR (400 MHz, CD$_3$OD): δ 9.34 (s, 1H), 9.20 (s, 1H), 8.79 (d, J=6.1 Hz, 1H), 8.71 (d, J=6.1 Hz, 1H), 8.34 (s, 1H), 8.10 (s, 1H), 7.90 (s, 1H), 7.81 (s, 1H), 4.92 (m, 1H), 4.25 (s, 2H), 2.89 (s, 3H), 2.20 (m, 2H), 2.10 (m, 4H), 1.90 (d, J=7.8 & 1.5 Hz, 2H); MS (ESI): 457.61 [M+H]$^+$; HPLC $t_R$=0.37 min (HPLC: Analytical_2 min).

The following Examples were prepared from the appropriate amine and aldehyde or ketone by a procedure analogous to Example 328.

| Ex. # | Structure and NMR Data | Compound name | MS (ESI) [M + H]$^+$ | HPLC $t_R$ (min) |
|---|---|---|---|---|
| 329 | $^1$H NMR (400 MHz, CD$_3$OD): δ 9.44 (s, 1H), 9.01 (s, 1H), 8.77 (d, J = 6.1 Hz, 1H), 8.70 (d, J = 6.1 Hz, 1H), 8.38 (s, 1H), 8.09 (s, 1H), 7.88 (s, 1H), 7.85 (s, 1H), 4.96 (m, 1H), 4.28 (s, 2H), 2.83 (m, 1H), 2.56 (m, 1H), 2.40 (m, 4H), 2.26 (m, 3H), 1.49 (d, J = 6.6 Hz, 6H) | 4-{1-[(3-exo)-8-(propan-2-yl)-8-azabicyclo[3.2.1]oct-3-yl]-1H-pyrazol-4-yl}-2-(thieno[2,3-c]pyridin-3-yl)furo[2,3-c]pyridin-7-amine | 485.62 | 0.49 (UPLC: Analytical_2 min) |
| 330 | $^1$H NMR (400 MHz, CD$_3$OD): δ 9.29 (s, 1H), 8.73 (s, 1H), 8.63 (d, J = 5.6 Hz, 1H), 8.58 (d, J = 5.6 Hz, 1H), 8.18 (s, 1H), 7.96 (s, 1H), 7.94 (s, 1H), 7.56 (s, 1H), 4.80 (m, 1H), 3.68 (br s, 2H), 2.63 (s, 3H), 2.44 (t, J = 11.9 Hz, 2H), 2.34 (d, J = 5.0 Hz, 2H), 2.32 (m, 2H), 2.05 (d, J = 8.6 Hz, 2H) | 2-(1,2-benzisothiazol-7-yl)-4-{1-[(3-exo)-8-methyl-8-azabicyclo[3.2.1]oct-3-yl]-1H-pyrazol-4-yl}furo[2,3-c]pyridin-7-amine | 457.59 | 0.42 (UPLC: Analytical_2 min) |

Example 331

1-{4-[4-(7-amino-2-thieno[2,3-c]pyridin-3-yl-furo[2,3-c]pyridin-4-yl)-pyrazol-1-yl]-piperidin-1-yl}-3-phenyl-propan-1-one

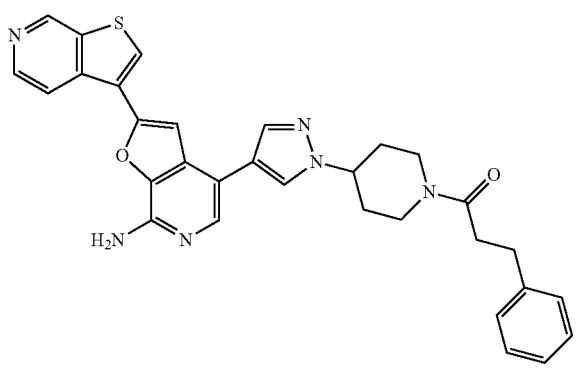 [SMILES: Nc1ncc(-c2cnn(C3CCN(C(=O)CCc4ccccc4)CC3)c2)c2cc(-c3csc4cnccc34)oc12]

To a solution of 4-(1-piperidin-4-yl-1H-pyrazol-4-yl)-2-thieno[2,3-c]pyridin-3-yl-furo[2,3-c]pyridin-7-ylamine (20.8 mg, 0.05 mmol) in DMF (0.5 mL) was added diisopropylethylamine (0.05 mL, 6.5 mmol), dihydrocinnamic acid (0.06 mmol), and N-(3-dimethylaminopropyl)-N'-ethylcarbodiimide hydrochloride (13.5 mg, 0.07 mmol). The resulting solution was allowed to stir at room temperature overnight. The mixture was concentrated and then purified by MDP to afford the title compound. $^1$H NMR (400 MHz, CD$_3$OD): δ 9.50 (s, 1H), 9.10 (s, 1H), 8.59 (d, J=6.1 Hz, 1H), 8.72 (d, J=6.1 Hz, 1H), 8.28 (s, 1H), 8.05 (s, 1H), 7.88 (s, 1H), 7.87 (s, 1H), 7.28 (s, 5H), 4.54 (m, 1H), 4.04 (m, 2H), 3.10 (m, 2H), 2.99 (m, 2H), 2.67 (m, 2H), 2.19 (m, 2H), 1.95 (m, 2H); MS (ESI): 549.64 [M+H]$^+$; HPLC t$_R$=0.86 min (HPLC: Analytical_2 min).

The following Examples were prepared from the appropriate amine and carboxylic acid by a procedure analogous to Example 331.

| Ex. # | Structure and NMR Data | Compound name | MS (ESI) [M + H]$^+$ | HPLC tR (min) (UPLC: Analytical_2 min) |
|---|---|---|---|---|
| 332 | | 1-{4-[4-(7-amino-2-thieno[2,3-c]pyridin-3-yl-furo[2,3-c]pyridin-4-yl)-pyrazol-1-yl]-piperidin-1-yl}-3-piperidin-1-yl-propan-1-one | 556.64 | 0.56 |

$^1$H NMR (400 MHz, CD$_3$OD): δ 9.54 (s, 1H), 9.14 (s, 1H), 8.88 (d, J = 6.1 Hz, 1H), 8.72 (d, J = 6.1 Hz, 1H), 8.35 (s, 1H), 8.08 (s, 1H), 7.91 (s, 1H), 7.88 (s, 1H), 4.11 (m, 1H), 3.61 (m, 2H), 3.44 (t, J = 6.8 Hz, 2H), 3.41 (m, 1H), 3.01 (m, 6H), 2.22 (m, 2H), 2.01 (m, 4H), 1.84 (m, 4H), 1.56 (m, 1H)

| Ex. # | Structure and NMR Data | Compound name | MS (ESI) [M + H]+ | HPLC tR (min) (UPLC: Analytical_2 min) |
|---|---|---|---|---|
| 333 | ¹H NMR (400 MHz, CD₃OD): δ 9.43 (s, 1H), 9.03 (d, J = 1.5 Hz, 1H), 8.80 (d, J = 7.3 Hz, 1H), 8.70 (d, J = 7.3 Hz, 1H), 8.35 (s, 1H), 8.06 (s, 1H), 7.89 (s, 1H), 7.67 (s, 1H), 7.56 (s, 1H), 7.30 (s, 1H), 7.19 (m, 3H), 6.97 (dd, J = 7.0 & 2.0 Hz, 1H), 4.03 (m, 1H), 3.53 (m, 4H), 3.16 (s, 3H), 2.13 (m, 4H) | 1-{4-[4-(7-amino-2-thieno[2,3-c]pyridin-3-yl-furo[2,3-c]pyridin-4-yl)-pyrazol-1-yl]-piperidin-1-yl}-3-(7-methoxy-benzofuran-2-yl)-propenone | 617.79 | 0.90 |
| 334 | ¹H NMR (400 MHz, CD₃OD): δ 9.53 (s, 1H), 9.13 (s, 1H), 8.88 (d, J = 6.1 Hz, 1H), 8.72 (d, J = 6.1 Hz, 1H), 8.34 (s, 1H), 8.07 (s, 1H), 7.91 (s, 1H), 7.88 (s, 1H), 4.72 (d, J = 13.2 Hz, 1H), 4.60 (m, 1H), 4.15 (d, J = 13.2 Hz, 1H), 2.89 (t, J = 2 Hz, 2H), 2.51 (t, J = 8.0 Hz, 2H), 2.12 (m, 2H), 2.06 (m, 2H), 1.78 (m, 6H), 1.56 (m, 2H), 1.32 (mm, 4H), 0.99 (m, 1H) | 1-{4-[4-(7-amino-2-thieno[2,3-c]pyridin-3-yl-furo[2,3-c]pyridin-4-yl)-pyrazol-1-yl]-piperidin-1-yl}-3-cyclohexyl-propan-1-one | 555.75 | 1.04 |
| 335 | ¹H NMR (400 MHz, CD₃OD): δ 9.52 (s, 1H), 9.18 (s, 1H), 8.90 (d, J = 6.1 Hz, 1H), 8.74 (d, J = 6.1 Hz, 1H), 8.31 (s, 1H), 8.05 (s, 1H), 7.93 (s, 1H), 7.84 (s, 1H), 4.70 (d, J = 13.2 Hz, 1H), 4.60 (m, 1H), 4.26 (d, J = 13.2 Hz, 1H), 2.89 (t, J = 2 Hz, 2H), 2.53 (t, J = 8.0 Hz, 2H), 2.10 (m, 2H), 1.83 (m, 6H), 1.64 (m, 2H), 1.32 (mm, 4H), 0.99 (m, 1H) | 1-{4-[4-(7-Amino-2-thieno[2,3-c]pyridin-3-yl-furo[2,3-c]pyridin-4-yl)-pyrazol-1-yl]-piperidin-1-yl}-3-cyclopentyl-propan-1-one | 541.72 | 1.07 |

| Ex. # | Structure and NMR Data | Compound name | MS (ESI) [M + H]+ | HPLC tR (min) (UPLC: Analytical_2 min) |
|---|---|---|---|---|
| 336 | 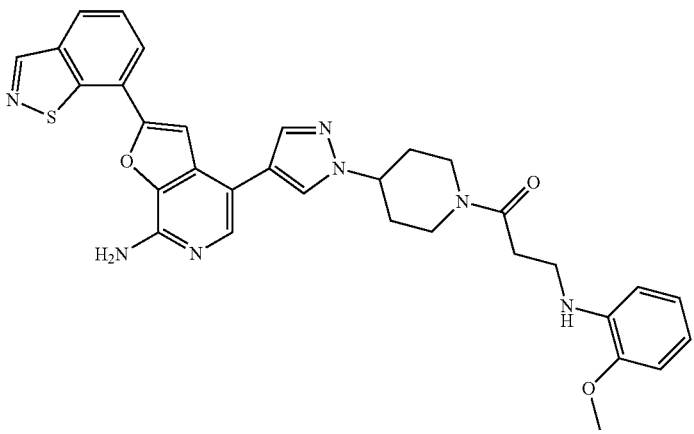 [SMILES: COc1ccccc1NCCC(=O)N1CCC(n2cc(-c3cnc(N)c4oc(-c5cccc6cnsc56)cc34)cn2)CC1]<br><br>¹H NMR (400 MHz, CD₃OD): δ 9.19 (s, 1H), 8.48 (d, J = 7.3 Hz, 1H), 8.42 (d, J = 7.3 Hz, 1H), 8.30 (s, 1H), 8.05 (s, 1H), 7.87 (s, 1H), 7.81 (s, 1H), 7.78 (t, J = 7.8 Hz, 1H), 7.20 (d, J = 7.8 Hz, 1H), 7.13 (d, J = 7.8 Hz, 1H), 7.05 (t, J = 7.8 Hz, 1H), 3.96 (s, 3H), 3.63 (t, J = 5.8 Hz, 2H), 3.36 (m, 1H), 2.95 (m, 1H), 2.88 (m, 2H), 2.67 (s, 2H), 2.24 (d, J = 9.8 Hz, 2H), 2.08 (t, J = 9.8 Hz, 1H), 1.95 (m, 1H), 1.30 (m, 1H) | 1-{4-[4-(7-amino-2-benzo[d]iso-thiazol-7-yl-furo[2,3-c]pyridin-4-yl)-pyrazol-1-yl]-piperidin-1-yl}-3-(2-methoxy-phenyl-amino)-propan-1-one | 594.64 | 0.88 |
| 337 | 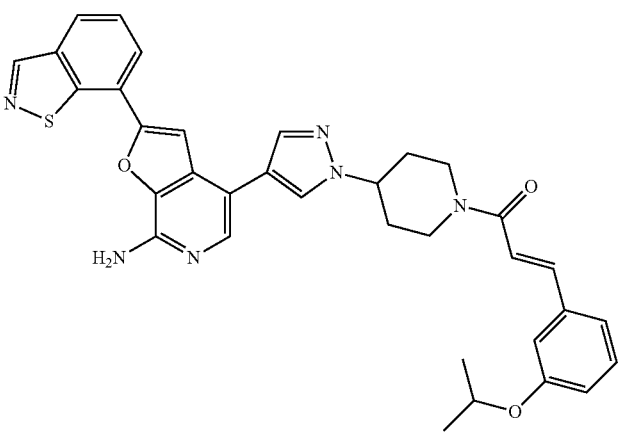 [SMILES: CC(C)Oc1cccc(/C=C/C(=O)N2CCC(n3cc(-c4cnc(N)c5oc(-c6cccc7cnsc67)cc45)cn3)CC2)c1]<br><br>¹H NMR (400 MHz, CD₃OD): δ 9.45 (s, 1H), 9.10 (s, 1H), 8.80 (d, J = 7.3 Hz, 1H), 8.70 (d, J = 7.3 Hz, 1H), 8.38 (d, J = 7.3 Hz, 1H), 8.33 (d, J = 7.3 Hz, 1H), 8.25 (s, 1H), 7.91 (s, 1H), 7.73 (s, 1H), 7.72 (s, 1H), 7.69 (t, J = 7.6 Hz, 1H), 7.30 (s, 1H), 7.19 (m, 1H), 6.97 (dd, J = 14.2 Hz, 1H), 4.40 (m, 1H), 4.21 (m, 2H), 3.91 (m, 1H), 2.98 (m, 2H), 2.07 (m, 2H), 1.99 (m, 2H), 1.78 (d, J = 5.4 Hz, 6H) | (E)-1-{4-[4-(7-amino-2-benzo[d]isothiazol-7-yl-furo[2,3-c]pyridin-4-yl)-pyrazol-1-yl]-piperidin-1-yl}-3-(3-isopropoxy-phenyl)-propenone | 605.73 | 1.11 |

Example 338

4-[4-(7-amino-2-benzo[d]isothiazol-7-yl-furo[2,3-c]pyridin-4-yl)-pyrazol-1-yl]-piperidine-1-carboxylic acid isobutyl-amide

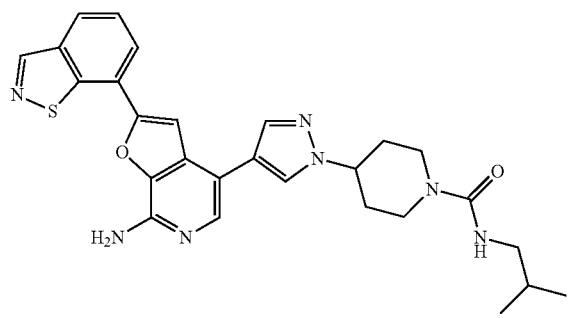 [SMILES: CC(C)CNC(=O)N1CCC(n2cc(-c3cnc(N)c4oc(-c5cccc6cnsc56)cc34)cn2)CC1]

To a solution of 2-benzo[d]isothiazol-7-yl-4-(1-piperidin-4-yl-1H-pyrazol-4-yl)-furo[2,3-c]pyridin-7-ylamine (20.8 mg, 0.05 mmol) in DMF (0.5 mL) was added diisopropylethylamine (0.05 mL, 6.5 mmol) and isobutyl isocyanate (0.06 mmol). The resulting solution stirred at room temperature overnight. The mixture was concentrated and then purified by MDP to afford the title compound as an off-white solid. $^1$H NMR (400 MHz, CD$_3$OD): δ 9.51 (s, 1H), 9.12 (d, J=1.5 Hz, 1H), 8.84 (d, J=7.3 Hz, 1H), 8.72 (d, J=7.3 Hz, 1H), 8.35 (s, 1H), 8.07 (s, 1H), 7.92 (s, 1H), 7.88 (s, 1H), 4.53 (m, 1H), 3.03 (m, 4H), 2.18 (m, 2H), 2.06 (m, 4H), 1.83 (m, 1H), 1.76 (d, J=5.8 Hz, 6H); MS (ESI): MS (ESI): 516.64 [M+H]$^+$; HPLC t$_R$=0.86 min (HPLC: Analytical_2 min).

The following Examples were prepared from 2-benzo[d]isothiazol-7-yl-4-(1-piperidin-4-yl-1H-pyrazol-4-yl)-furo[2,3-c]pyridin-7-ylamine and an appropriate isocyanate by a procedure analogous to Example 338.

| Ex. # | Structure and NMR Data | Compound name | MS (ESI) [M + H]$^+$ | HPLC tR (min) (UPLC: Analytical_2 min) |
|---|---|---|---|---|
| 339 | | 4-[4-(7-amino-2-benzo[d]isothiazol-7-yl-furo[2,3-c]pyridin-4-yl)-pyrazol-1-yl]-piperidine-1-carboxylic acid (3-benzyl-phenyl)-amide | 626.68 | 1.07 |

$^1$H NMR (400 MHz, CD$_3$OD): δ 9.19 (s, 1H), 8.48 (d, J = 7.3 Hz, 1H), 8.42 (d, J = 7.3 Hz, 1H), 8.36 (s, 1H), 8.05 (s, 1H), 7.88 (s, 1H), 7.85 (s, 1H), 7.58 (t, J = 7.8 Hz, 1H), 7.25 (m, 8H), 6.91 (d, J = 7.0 Hz, 1H), 4.60 (m, 1H), 4.35 (d, J = 5.8 Hz, 2H), 3.96 (s, 2H), 3.15 (t, J = 7.8 Hz, 2H), 2.24 (m, 2H), 2.15 (m, 2H)

| Ex. # | Structure and NMR Data | Compound name | MS (ESI) [M + H]+ | HPLC tR (min) (UPLC: Analytical_2 min) |
|---|---|---|---|---|
| 340 | 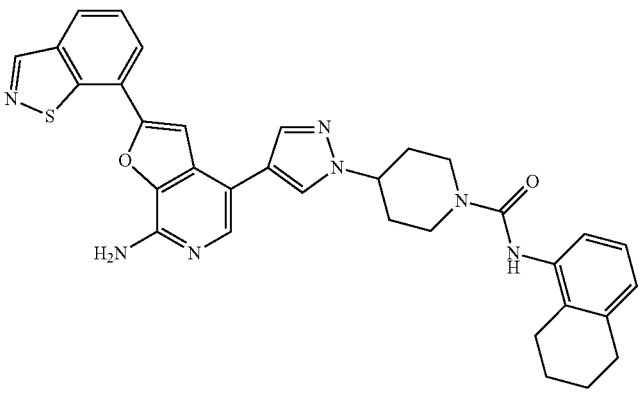 [SMILES: Nc1ncc(-c2cnn(C3CCN(C(=O)Nc4cccc5c4CCCC5)CC3)c2)c2cc(-c3cccc4cnsc34)oc12]<br>¹H NMR (400 MHz, CD₃OD): δ 9.47 (s, 1H), 9.04 (d, J = 1.5 Hz, 1H), 8.80 (d, J = 7.3 Hz, 1H), 8.71 (d, J = 7.3 Hz, 1H), 8.37 (s, 1H), 8.08 (s, 1H), 7.90 (s, 1H), 7.89 (s, 1H), 7.09 (t, J = 7.3 Hz, 1H), 7.03 (d, J = 7.3 Hz, 1H), 6.97 (d, J = 7.3 Hz, 1H), 4.61 (m, 1H), 4.37 (d, J = 13.6 Hz, 2H), 3.17 (t, J = 11.1 Hz, 2H), 2.80 (t, J = 5.3 Hz, 2H), 2.71 (t, J = 5.3 Hz, 2H), 2.23 (m, 4H), 1.82 (m, 4H) | 4-[4-(7-amino-2-benzo[d]isothiazol-7-yl-furo[2,3-c]pyridin-4-yl)-pyrazol-1-yl]-piperidine-1-carboxylic acid (5,6,7,8-tetrahydro-naphthalen-1-yl)-amide | 590.73 | 0.86 |
| 341 | 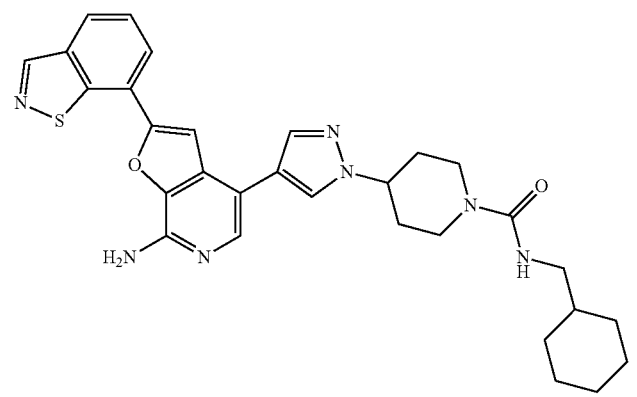 [SMILES: Nc1ncc(-c2cnn(C3CCN(C(=O)NCC4CCCCC4)CC3)c2)c2cc(-c3cccc4cnsc34)oc12]<br>¹H NMR (400 MHz, CD₃OD): δ 9.50 (s, 1H), 9.10 (d, J = 1.5 Hz, 1H), 8.82 (d, J = 7.3 Hz, 1H), 8.70 (d, J = 7.3 Hz, 1H), 8.33 (s, 1H), 8.05 (s, 1H), 7.90 (s, 1H), 7.88 (s, 1H), 4.53 (m, 1H), 4.21 (d, J = 13.1 Hz, 2H), 3.03 (m, 6H), 2.18 (m, 2H), 1.76 (m, 6H), 1.53 (m, 1H), 1.25 (m, 3H), 0.93 (m, 1H) | 4-[4-(7-amino-2-benzo[d]isothiazol-7-yl-furo[2,3-c]pyridin-4-yl)-pyrazol-1-yl]-piperidine-1-carboxylic acid cyclohexylmethyl-amide | 556.74 | 0.84 |

Example 342

4-[1-(3-methoxy-propyl)-1H-pyrazol-4-yl]-2-thieno[2,3-c]pyridin-3-yl-furo[2,3-c]pyridin-7-ylamine

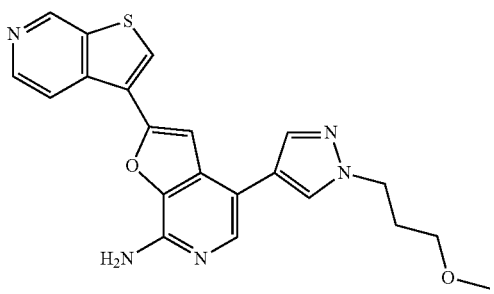 [SMILES: COCCCn1cc(-c2cnc(N)c3oc(-c4csc5cnccc45)cc23)cn1]

Step A: {4-[1-(3-methoxy-propyl)-1H-pyrazol-4-yl]-2-thieno[2,3-c]pyridin-3-yl-furo[2,3-c]pyridin-7-yl}-bis-carbamic acid tert-butyl ester A mixture of (2-thieno[2,3-c]pyridin-3-yl-4-trimethylstannanyl-furo[2,3-c]pyridin-7-yl)-bis-carbamic acid tert-butyl ester (31.5 mg, 0.05 mmol), Pd₂(dba)₃ (~3 mg, 0.003 mmol), and tri-o-tolyphosphine (4 mg, 0.013 mmol) was purged with nitrogen. Anhydrous DMF (1 mL), 4-bromo-1-(2-methoxypropyl)-1H-pyrazole (12 mg, 0.055 mmol) and triethylamine (0.02 mL, 0.15 mmol) was added. The solution was purged with nitrogen again and heated to 70° C. for 5 h. The mixture was concentrated and then purified by solid-phase extraction and MDP to afford 17.7 mg (55%) of the title compound as an off-white solid. ¹H NMR (400 MHz, CD₃OD): δ 9.40 (s, 1H), 8.90 (s, 1H), 8.63 (d, J=6.2 Hz, 1h), 8.57 (d, J=6.2 Hz, 1H), 8.57 (s, 1H), 8.43 (s, 1H), 8.21 (s, 1H), 7.87 (s, 1H), 4.42 (t, J=7.1 Hz, 2H), 3.40 (s, 3H), 3.35 (t, J=10.5 Hz, 2H), 2.28 (tt, J=10.5 & 7.1 Hz, 2H), 1.40 (s, 18H); MS (ESI): 606.65 [M+H]⁺; HPLC tR=1.31 min (HPLC: Analytical_2 min).

Step B: 4-[1-(3-methoxy-propyl)-1H-pyrazol-4-yl]-2-thieno[2,3-c]pyridin-3-yl-furo[2,3-c]pyridin-7-ylamine (Title Compound)

{4-[1-(3-Methoxy-propyl)-1H-pyrazol-4-yl]-2-thieno[2,3-c]pyridin-3-yl-furo[2,3-c]pyridin-7-yl}-bis-carbamic acid tert-butyl ester (12.2 mg, 0.02 mmol) was treated with 4 N hydrochloric acid in 1,4-dioxane (0.5 mL, 2 mmol) for 4 h. The solution was concentrated and the residue was then redissolved in water and lyophilized to afford 7.3 mg (90%) of the title compound as a light brown solid. $^1$H NMR (400 MHz, CD$_3$OD): δ 9.37 (s, 1H), 8.88 (s, 1H), 8.60 (d, J=6.1 Hz, 1h), 8.54 (d, J=6.1 Hz, 1H), 8.50 (s, 1H), 8.41 (s, 1H), 8.19 (s, 1H), 7.84 (s, 1H), 4.39 (t, J=7.1 Hz, 2H), 3.38 (s, 3H), 3.33 (t, J=10.3 Hz, 2H), 2.21 (tt, J=10.3 & 7.1 Hz, 2H); MS (ESI): 406.52 [M+H]$^+$; HPLC t$_R$=0.59 min (HPLC: Analytical_2 min).

The following Examples were prepared from (2-thieno[2,3-c]pyridin-3-yl-4-trimethylstannanyl-furo[2,3-c]pyridin-7-yl)-bis-carbamic acid tert-butyl ester and an appropriate aryl bromide or iodide by procedures analogous to Example 342, Steps A and B.

| Ex. # | Structure and NMR Data | Compound name | MS (ESI) [M + H]$^+$ | HPLC tR (min) (UPLC: Analytical_2 min) |
|---|---|---|---|---|
| 343 | $^1$H NMR (400 MHz, CD$_3$OD): δ 9.43 (s, 1H), 8.99 (s, 1H), 8.76 (d, J = 6.1 Hz, 1H), 8.69 (d, J = 6.1 Hz, 1H), 8.15 (s, 1H), 7.94 (s, 1H), 7.82 (s, 1H), 4.03 (s, 3H), 3.88 (s, 3H) | 4-(3-methoxy-1-methyl-1H-pyrazol-4-yl)-2-thieno[2,3-c]pyridin-3-yl-furo[2,3-c]pyridin-7-ylamine | 378.49 | 0.54 |
| 344 | $^1$H NMR (400 MHz, CD$_3$OD): δ 9.63 (s, 1H), 9.24 (s, 1H), 8.96 (d, J = 6.1 Hz, 1H), 8.74 (d, J = 6.1 Hz, 1H), 7.78 (s, 1H), 7.76 (s, 1H), 7.75 (s, 1H), 3.84 (s, 3H), 3.81 (s, 3H) | 4-(5-methoxy-1-methyl-1H-pyrazol-4-yl)-2-thieno[2,3-c]pyridin-3-yl-furo[2,3-c]pyridin-7-ylamine | 378.48 | 0.50 |
| 345 | $^1$H NMR (400 MHz, CD$_3$OD): δ 9.41 (s, 1H), 8.90 (s, 1H), 8.72 (d, J = 5.8 Hz, 1H), 8.53 (d, J = 5.8 Hz, 1H), 8.45 (s, 1H), 8.34 (s, 1H), 7.69 (s, 1H), 4.04 (s, 3H) | 4-(7-amino-2-thieno[2,3-c]pyridin-3-yl-furo[2,3-c]pyridin-4-yl)-1-methyl-1H-pyrazole-3-carbonitrile | 373.45 | 0.64 |

| Ex. # | Structure and NMR Data | Compound name | MS (ESI) [M + H]+ | HPLC tR (min) (UPLC: Analytical_2 min) |
|---|---|---|---|---|
| 346 | 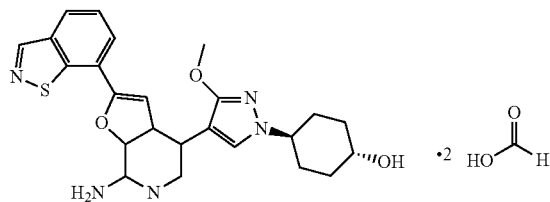 [SMILES: COc1nn([C@H]2CC[C@H](O)CC2)cc1C1CNC(N)C2OC(c3cccc4cnsc34)=CC12 ; O=CO]  ¹H NMR (400 MHz, CD₃OD): δ 9.37 (s, 1H), 8.87 (s, 1H), 8.50 (s, 1H), 8.47 (d, J = 6.1 Hz, 1H), 8.30 (d, J = 6.1 Hz, 1H), 8.18 (s, 1H), 7.98 (s, 1H), 7.64 (s, 1H), 4.58 (t, J = 7.1 Hz, 2H), 3.04 (t, J = 7.1 Hz, 2H), 2.66 (s, 3H), 2.06 (s, 3H) | 3-[4-(7-amino-2-thieno[2,3-c]pyridin-3-yl-furo[2,3-c]pyridin-4-yl)-pyrazol-1-yl]-N,N-dimethyl-propionamide | 457.56 | 0.42 |

Example 347 trans-4-{4-[7-amino-2-(1,2,3-benzothiadiazol-7-yl)furo[2,3-c]pyridin-4-yl]-3-methoxy-1H-pyrazol-1-yl}cyclohexanol diformate salt

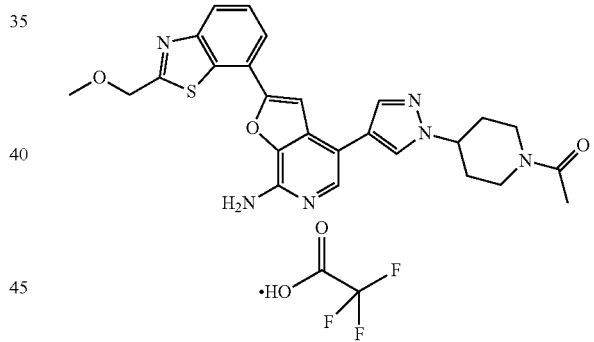

Step A: 4-[1-(trans-4-{[tert-butyl(dimethyl)silyl]oxy}cyclohexyl)-3-methoxy-1H-pyrazol-4-yl]-2-chlorofuro[2,3-c]pyridin-7-amine The title compound was prepared from 2-chloro-4-iodofuro[2,3-c]pyridin-7-amine by a procedure analogous to Intermediate 43. ¹H NMR (400 MHz, CD₃OD): δ 0.10 (s, 6 H), 0.92 (s, 9 H), 1.44-1.58 (m, 2 H), 1.84-1.96 (m, 2 H), 1.97-2.05 (m, 2 H), 2.07-2.16 (m, 2 H), 3.73-3.80 (m, 1 H), 3.95 (s, 3 H), 3.97-4.04 (m, 1 H), 6.92 (s, 1 H), 7.72 (s, 1 H), 7.92 (s, 1 H); MS (ESI): 477.19 [M+H]⁺; HPLC t$_R$=1.68 min (TOF: polar_3 min).

Step B: trans-4-{4-[7-amino-2-(1,2,3-benzothiadiazol-7-yl)furo[2,3-c]pyridin-4-yl]-3-methoxy-1H-pyrazol-1-yl}cyclohexanol diformate salt (Title Compound)

The title compound was prepared from 4-[4-(trans-4-{[tert-butyl(dimethyl)silyl]oxy}cyclohexyl)-3-methoxy-1H-pyrazol-4-yl]-2-chlorofuro[2,3-c]pyridin-7-amine and 7-(4,4,5,5-tetramethyl-1,3,2-dioxaborolan-2-yl)-1,2,3-benzothiadiazole by a procedure analogous to Example 267. ¹H NMR (400 MHz, CD₃OD): δ 1.43-1.57 (m, 2 H), 1.89-2.03 (m, 2 H), 2.06-2.22 (m, 4 H), 3.63-3.74 (m, 1 H), 4.01 (s, 3 H), 4.03-4.11 (m, 1 H), 7.60 (s, 1 H), 7.84-7.92 (m, 2 H), 7.95 (s, 1 H), 8.24 (s, 2 H), 8.47 (d, J=7.6 Hz, 1 H), 8.73 (d, J=8.3 Hz, 1 H); MS (ESI): 463.14 [M+H]⁺; HPLC t$_R$=1.04 min (TOF: polar_3 min).

Example 348

1-[4-(4-{7-amino-2-[2-(methoxymethyl)-1,3-benzothiazol-7-yl]furo[2,3-c]pyridin-4-yl}-1H-pyrazol-1-yl)piperidin-1-yl]ethanone trifluoroacetate

Step A: 2-methoxy-thioacetamide

A three-neck flask equipped with a thermometer, magnetic stirrer, and nitrogen inlet was charged with methoxynitrile (5.3 g, 75 mmol), water (40 mL), 1,4-dioxane (40 mL), sodium hydrogen sulfide hydrate (16.6 g, 225 mmol) and diethylamine hydrochloride (24.6 g, 225 mmol). The solution was heated to 55° C. for 2 h. The reaction mixture was allowed to cool, water was added and the mixture was extracted with ethyl acetate (2×50 mL). The combined organic fractions were dried over sodium sulfate and concentrated to afford 5.2 g (67%) of the title compound. ¹H NMR (300 MHz, CDCl₃): δ 7.8-8.1 (br. s, 2H), 4.25 (s, 2H), 3.4 (s, 3H).

Step B: 2-methoxymethyl-benzothiazole

A mixture of 2-iodoaniline (5 g, 22.8 mmol), 2-methoxy-thioacetamide (2.4 g, 22.8 mmol), calcium oxide (1.28 g, 22.8 mmol), tris(dibenzylideneacetone)dipalladium-chloroform adduct (104 mg, 0.114 mmol), diphenylphosphinoferrocene (253 mg, 0.456 mmol) and DMF (23 mL) was stirred at 60° C. for 2 h under nitrogen. The resulting mixture was purified by column chromatography (10 to 20% ethyl acetate:hexanes) to afford 2.5 g (61%) of the title compound. $^1$H NMR (300 MHz, CDCl$_3$): δ 8.01-7.9 (m, 1H), 7.98-7.89 (m, 1H), 7.50-7.45 (m, 1H), 7.41-7.38 (m, 1H), 4.86 (s, 2H), 3.54 (s, 3H).

Step C: 2-methoxymethyl-6-nitro-benzothiazole

To a cooled (0° C.) solution of 2-methoxymethyl-benzothiazole (2.4 g, 13.4 mmol) in concentrated sulfuric acid (8 mL) was added a mixture of 90% fuming nitric acid (2 mL) and concentrated sulfuric acid (1.3 mL) at a rate to keep the internal temperature below 5° C. After the addition was completed, the reaction mixture was stirred for 15 min at 0° C. and then at RT for 2 h. The mixture was poured into ice cold water. Collection of the precipitated solid by filtration, washing with cold water until the pH of the eluent was neutral, afforded 2.6 g (79%) of the title compound. $^1$H NMR (300 MHz, CDCl$_3$): δ 8.8 (d, J=2.1 Hz, 1H), 8.36 (dd, J=9, 2.1 Hz, 1H), 8.08 (d, J=9 Hz, 1H), 4.90 (s, 2H), 3.59 (s, 3H).

Step D: 2-methoxymethyl-benzothiazol-6-olamine

A mixture of 2-methoxymethyl-6-nitro-benzothiazole (2.5 g, 11.2 mmol) and iron powder (6.1 g, 112 mmol) in ethanol (60 mL) was heated to reflux. A solution of aqueous 0.1 N hydrochloric acid (12 mL) was added and the reaction refluxed until TLC showed no starting material remaining. The reaction mixture was cooled to RT, filtered, and concentrated. The residue was treated with aqueous sodium carbonate solution until it becomes basic. The mixture was filtered through Celite, washing with ethyl acetate. The organic layer was separated, washed with water, dried over sodium sulfate, and concentrated to afford 1.3 g (60%) of the title compound. $^1$H NMR (300 MHz, CDCl$_3$): δ 7.76 (d, J=8.4 Hz, 1H), 7.12 (s, 1H), 6.82 (dd, J=8.4, 2.1 Hz, 1H), 4.78 (s, 2H), 3.50 (s, 3H), 3.82 (br. s, 2H).

Step E: 7-iodo-2-methoxymethyl-benzothiazol-6-ylamine

To a solution of iodine monochloride in water (1.5 mL) and 12 N hydrochloric acid (0.46 mL) was added 2-methoxymethyl-benzothiazol-6-ylamine (0.5 g, 2.57 mmol) in water (3 mL) and 12 N hydrochloric acid (0.23 mL). The reaction mixture stirred at RT for 2 h and was then neutralized with saturated aqueous sodium bicarbonate solution. The reaction mixture was extracted with ethyl acetate, dried over sodium sulfate, filtered and concentrated. Purification of the residue by column chromatography (20 to 30% ethyl acetate:hexanes) afforded 800 mg (91%) of the title compound. $^1$H NMR (300 MHz, CDCl$_3$): δ 7.74 (d, J=8.7 Hz, 1H), 6.86 (d, J=8.7 Hz, 1H), 4.77 (s, 2H), 4.23 (br. s, 2H), 3.53 (s, 3H).

Step F: 7-iodo-2-methoxymethyl-benzothiazole

To a cooled (0° C.) solution of 7-iodo-2-methoxymethyl-benzothiazol-6-ylamine (1.8 g, 5.62 mmol) in THF under nitrogen was added tert-butyl nitrite (3.3 mL, 28.1 mmol) dropwise. The reaction mixture stirred 3 h at 50° C. Water was added and the mixture was extracted with ethyl acetate. The combined organic fractions were washed with water and brine, dried over sodium sulfate, and concentrated. Purification of the residue by column chromatography afforded 1.0 g (60%) of the title compound. $^1$H NMR (300 MHz, CDCl$_3$): δ 7.90 (d, J=8 Hz, 1H), 7.75 (d, J=8 Hz, 1H), 7.19-7.21 (m, 1H), 4.8 (s, 2H), 3.58 (s, 3H).

Step G: 2-(methoxymethyl)-7-(4,4,5,5-tetramethyl-1,3,2-dioxaborolan-2-yl)-1,3-benzothiazole A mixture of 7-iodo-2-(methoxymethyl)-1,3-benzothiazole (100 mg, 0.33 mmol), bis(pinacolato)diboron (416 mg, 1.64 mmol), potassium acetate (225 mg, 2.29 mmol) and 1,1'-bis(diphenylphosphino)ferrocenepalladium(II) dichloride dichloromethane complex (13 mg, 0.016 mmol) in 1,4-dioxane (8 mL) was heated to 100° C. for 8 h. The mixture was diluted with EtOAc and washed with water and brine. The organic fraction was dried over sodium sulfate and purified by ISCO chromatography (0 to 15% EtOAc:heptane) to afford 95 mg (95%) of the title compound as white solid. MS (ESI): 306.52 [M+H]$^+$; HPLC t$_R$=1.46 min (HPLC: Anayltical_2 min).

Step H: 1-[4-(4-{7-amino-2-[2-(methoxymethyl)-1,3-benzothiazol-7-yl]furo[2,3-c]pyridin-4-yl}-1H-pyrazol-1-yl)piperidin-1-yl]ethanone Trifluoroacetate (Title Compound)

The title compound was prepared from 1-{4-[4-(7-amino-2-chlorofuro[2,3-c]pyridin-4-yl)-1H-pyrazol-1-yl]piperidin-1-y}ethanone and 2-(methoxymethyl)-7-(4,4,5,5-tetramethyl-1,3,2-dioxaborolan-2-yl)-1,3-benzothiazole by a procedure analogous to Example 223, Step D. $^1$H NMR (400 MHz, CD$_3$OD): δ 8.29 (s, 1 H), 8.27 (d, J=7.6 Hz, 1 H), 8.14 (d, J=8.1 Hz, 1 H), 8.01 (s, 1 H), 7.83 (s, 1 H), 7.71-7.76 (m, 2 H), 4.94 (s, 2 H), 4.66-4.72 (m, 1 H), 4.59 (tt, J=11.4, 4.1 Hz, 1 H), 4.12 (d, J=14.1 Hz, 1 H), 3.59 (s, 3 H), 3.33-3.41 (m, 1 H), 2.89 (td, J=12.9, 2.5 Hz, 1 H), 2.19-2.29 (m, 2 H), 2.18 (s, 3 H), 1.97-2.15 (m, 2 H); MS (ESI): 503.58 [M+H]$^+$; HPLC t$_R$=0.56 min (HPLC: Purity_2 min).

Example 349 trans-4-(4-{7-amino-2-[2-(methoxymethyl)-1,3-benzothiazol-7-yl]furo[2,3-c]pyridin-4-yl}-1H-pyrazol-1-yl)cyclohexanol Trifluoroacetate (salt)

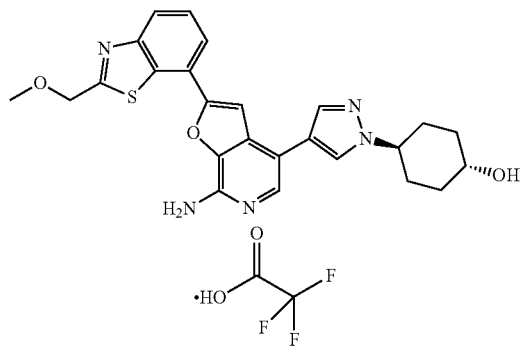

The title compound was prepared from 4-{1-[4-(tert-butyl-dimethyl-silanyloxy)-cyclohexyl]-1H-pyrazol-4-yl}-2-chloro-furo[2,3-c]pyridin-7-ylamine and 2-(methoxymethyl)-7-(4,4,5,5-tetramethyl-1,3,2-dioxaborolan-2-yl)-1,3-benzothiazole by a procedure analogous to Example 229. $^1$H NMR (400 MHz, CD$_3$OD): δ 8.24 (t, J=3.8 Hz, 2 H), 8.10 (d, J=8.1 Hz, 1 H), 7.97 (s, 1H), 7.80 (s, 1 H), 7.66-7.74 (m, 2 H), 4.92 (s, 2 H), 4.31 (tdd, J=11.8, 11.8, 3.8, 3.7 Hz, 1 H), 3.67-3.77 (m, 1 H), 3.58-3.61 (m, 3 H), 2.10-2.26 (m, 4 H), 2.00 (dtd, J=12.9, 12.6, 12.6, 3.0 Hz, 2 H), 1.47-1.60 (m, 2 H); MS (ESI): 476.58 [M+H]⁺; HPLC t$_R$=0.56 min (HPLC: Purity__2 min).

Example 350

1-[4-(4-{7-amino-2-[2-(methylamino)-1,3-benzothiazol-7-yl]furo[2,3-d]pyridin-4-yl}-1H-pyrazol-1-yl)piperidin-1-yl]ethanone trifluoroacetate

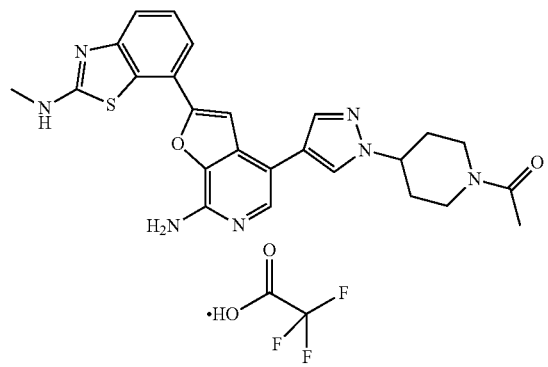

Step A:
7-bromo-N-methyl-1,3-benzothiazol-2-amine

7-Bromo-2-chlorobenzothiazole (85 mg, 0.34 mmol) and methylamine (2 M in THF, 3 mL, 6 mmol) were mixed and heated to 60° C. overnight. The solvent was evaporated. The residue was purified by ISCO chromatography (0 to 30% EtOAc:heptane) to afford 56 mg (67%) of the title compound. MS (ESI): 243.30, 245.26 [M+H]⁺; HPLC t$_R$=1.09 min (HPLC: Anayltical__2 min).

Step B: N-methyl-7-(4,4,5,5-tetramethyl-1,3,2-dioxaborolan-2-yl)-1,3-benzothiazol-2-amine A solution of 7-bromo-N-methyl-1,3-benzothiazol-2-amine (56 mg, 0.23 mmol), bis(pinacolato)diboron (292 mg, 1.15 mmol), potassium acetate (158 mg, 1.61 mmol), and 1,1'-bis(diphenylphosphino)ferrocenepalladium(II) dichloride dichloromethane complex (38 mg, 0.046 mmol) in 1,4-dioxane (6 mL) was heated to 100° C. for 2 h. EtOAc was added to the mixture and the solution was filtered. The organic fraction was washed by water and brine. The crude mixture was purified by ISCO chromatography (0 to 50% EtOAc:heptane) to afford 51 mg (76%) of the title compound as yellow oil. MS (ESI): 291.53 [M+H]⁺; HPLC t$_R$=1.03 min (HPLC: Anayltical__2 min).

Step C: 1-[4-(4-{7-amino-2-[2-(methylamino)-1,3-benzothiazol-7-yl]furo[2,3-c]pyridin-4-yl}-1H-pyrazol-1-yl)piperidin-1-yl]ethanone Trifluoroacetate (Title Compound)

The title compound was prepared from 1-{4-[4-(7-amino-2-chlorofuro[2,3-c]pyridin-4-yl)-1H-pyrazol-1-yl]piperidin-1-yl}ethanone and N-methyl-7-(4,4,5,5-tetramethyl-1,3,2-dioxaborolan-2-yl)-1,3-benzothiazol-2-amine by a procedure analogous to Example 223, Step D. ¹H NMR (400 MHz, CD₃OD): δ 8.28 (s, 1 H), 7.99 (s, 1 H), 7.94 (d, J=7.1 Hz, 1 H), 7.82 (s, 1 H), 7.59-7.64 (m, 2 H), 7.50-7.56 (m, 1 H), 4.66-4.73 (m, 1 H), 4.58 (tdd, J=11.4, 11.4, 4.2, 4.0 Hz, 1H), 4.11 (d, J=14.1 Hz, 1 H), 3.35-3.41 (m, 1 H), 3.15 (s, 3 H), 2.88 (td, J=12.9, 2.5 Hz, 1 H), 2.19-2.29 (m, 2 H), 2.18 (s, 3 H), 1.95-2.17 (m, 2 H); MS (ESI): 488.50 [M+H]⁺; HPLC t$_R$=0.50 min (HPLC: Purity__2 min).

Example 351 trans-4-(4-{7-amino-2-[2-(methylamino)-1,3-benzothiazol-7-yl]furo[2,3-c]pyridin-4-yl}-1H-pyrazol-1-yl)cyclohexanol Trifluoroacetate (Salt)

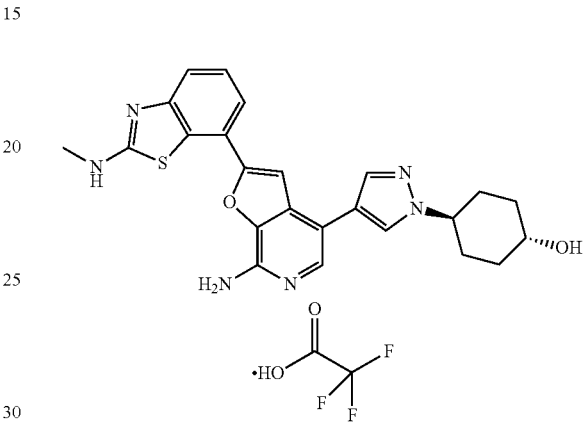

The title compound was prepared from 4-{1-[4-(tert-butyl-dimethyl-silanyloxy)-cyclohexyl]-1H-pyrazol-4-yl}-2-chloro-furo[2,3-c]pyridin-7-ylamine and N-methyl-7-(4,4,5,5-tetramethyl-1,3,2-dioxaborolan-2-yl)-1,3-benzothiazol-2-amine by a procedure analogous to Example 229. ¹H NMR (400 MHz, CD₃OD): δ 8.22 (s, 1 H), 7.94 (s, 1 H), 7.91 (d, J=7.6 Hz, 1 H), 7.79 (s, 1 H), 7.55-7.59 (m, 2 H), 7.46-7.52 (m, 1 H), 4.29 (tt, J=11.7, 3.8 Hz, 1 H), 3.70 (tt, J=10.9, 4.3 Hz, 1 H), 3.13 (s, 3 H), 2.09-2.24 (m, 4 H), 1.94-2.06 (m, 2 H), 1.46-1.59 (m, 2 H); MS (ESI): 461.55 [M+H]⁺; HPLC t$_R$=0.50 min (HPLC: Purity__2 min).

Example 352

1-[4-(4-{7-amino-2-[2-(methylsulfanyl)-1,3-benzothiazol-7-yl]furo[2,3-c]pyridin-4-yl}-1H-pyrazol-1-yl)piperidin-1-yl]ethanone trifluoroacetate

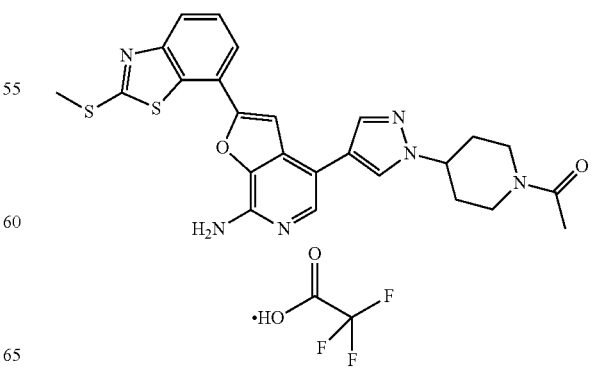

Step A:
7-bromo-2-(methylsulfanyl)-1,3-benzothiazole

Potassium carbonate (67 mg, 0.49 mmol) was added to a solution of 7-bromo-1,3-benzothiazole-2(3H)-thione (100 mg, 0.41 mmol) in DMF (5 mL). The mixture was stirred at room temperature for 30 min. Methyl iodide (25 µL, 0.41 mmol) was added and the resulting mixture was stirred at room temperature for 30 min. EtOAc was added the separated organic fraction was washed with water and brine, dried over sodium sulfate, and concentrated. The title compound thus obtained was used without further purification. MS (ESI): 260.34, 262.32 [M+H]+; HPLC $t_R$=1.54 min (HPLC: Anayltical_2 min).

Step B: 2-(methylsulfanyl)-7(4,4,5,5-tetramethyl-1,3,2-dioxaborolan-2-yl)-1,3-benzothiazole A solution of 7-bromo-2-(methylsulfanyl)-1,3-benzothiazole (91 mg, 0.35 mmol), bis(pinacolato)diboron (455 mg, 1.79 mmol), potassium acetate (246 mg, 2.51 mmol) and 1,1-bis(diphenylphosphino)ferrocenepalladium(II) dichloride dichloromethane complex (59 mg, 0.072 mmol) in 1,4-dioxane (10 mL) was heated to reflux overnight. EtOAc was added to the mixture and the solution was filtered. The organic fraction was washed with water and brine. The crude mixture was purified by ISCO chromatography (0 to 10% EtOAc:heptane) to afford 14 mg (13%) of the title compound. MS (ESI): 308.43 [M+H]+; HPLC $t_R$=1.64 min (HPLC: Anayltical_2 min).

Step C: 1-[4-(4-{7-amino-2-[2-(methylsulfanyl)-1,3-benzothiazol-7-yl]furo[2,3-c]pyridin-4-yl}-1H-pyrazol-1-yl)piperidin-1-yl]ethanone Trifluoroacetate (Title Compound)

The title compound was prepared from 1-{4-[4-(7-amino-2-chlorofuro[2,3-c]pyridin-4-yl)-1H-pyrazol-1-yl]piperidin-1-yl}ethanone and 2-(methylsulfanyl)-7-(4,4,5,5-tetramethyl-1,3,2-dioxaborolan-2-yl)-1,3-benzothiazole by a procedure analogous to Example 223, Step D. 1H NMR (400 MHz, CD3OD+CDCl3): δ 7.89 (t, J=6.9 Hz, 2 H), 7.80 (s, 1 H), 7.75 (s, 1 H), 7.59 (s, 1 H), 7.47-7.52 (m, 1 H), 7.28 (br. s., 1 H), 4.60 (d, J=13.6 Hz, 1 H), 4.32-4.40 (m, 1 H), 4.02 (br. s., 1 H), 3.12-3.20 (m, 1 H), 2.68-2.79 (m, 4 H), 2.09-2.23 (m, 2 H), 2.05 (s, 3 H), 1.86-2.01 (m, 2 H); MS (ESI): 505.52 [M+H]+; HPLC $t_R$=0.64 min (HPLC: Purity_2 min).

Example 353 trans-4-(4-{7-amino-2-[2-(methylsulfanyl)-1,3-benzothiazol-7-yl]furo[2,3-c]pyridin-4-yl}-1H-pyrazol-1-yl)cyclohexanol Trifluoroacetate (Salt)

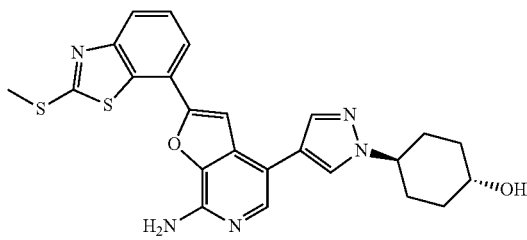

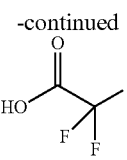

The title compound was prepared from 4-{1-[4-(tert-butyl-dimethyl-silanyloxy)-cyclohexyl]-1H-pyrazol-4-yl}-2-chloro-furo[2,3-c]pyridin-7-ylamine and 2-(methylsulfanyl)-7-(4,4,5,5-tetramethyl-1,3,2-dioxaborolan-2-yl)-1,3-benzothiazole by a procedure analogous to Example 229. 1H NMR (400 MHz, CD3OD+CDCl3): δ 7.87 (d, J=7.83 Hz, 1 H), 7.83 (d, J=8.1 Hz, 1H), 7.74 (s, 1 H), 7.68 (s, 1 H), 7.53 (s, 1 H), 7.45 (t, J=7.8 Hz, 1 H), 7.25 (s, 1 H), 4.03-4.10 (m, 1 H), 3.49-3.59 (m, 1 H), 2.70 (s, 3 H), 2.06 (br. s., 2 H), 1.97 (br. s., 2 H), 1.70-1.85 (m, 2 H), 1.27-1.43 (m, 2 H); MS (ESI): 478.56 [M+H]+; HPLC $t_R$=0.64 min (HPLC: Purity_2 min).

Example 354

1-[4-(4-{7-amino-2-[2-(ethylamino)-1,3-benzothiazol-7-yl]furo[2,3-d]pyridin-4-yl}-1H-pyrazol-1-yl)piperidin-1-yl]ethanone trifluoroacetate

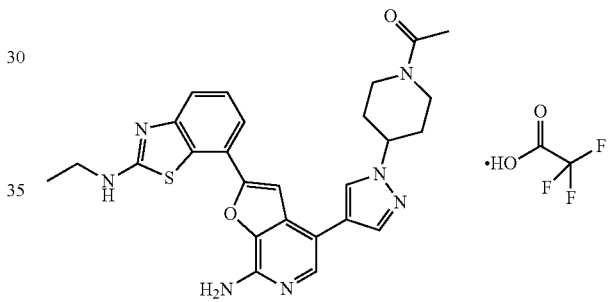

Step A: 7-bromo-N-ethyl-1,3-benzothiazol-2-amine

7-Bromo-2-chlorobenzothiazole (100 mg, 0.40 mmol) was added to ethylamine (2.0 M in THF, 1 mL, 2 mmol) and the solution was heated at 70° C. for 1 h. The crude mixture was purified by ISCO chromatography (100% DCM) to afford 95 mg (92%) of the title compound as white solid. MS (ESI): 257.33, 259.31 [M+H]+; HPLC $t_R$=1.27 min (HPLC: Anayltical_2 min).

Step B: N-ethyl-7-(4,4,5,5-tetramethyl-1,3,2-dioxaborolan-2-yl)-1,3-benzothiazol-2-amine A mixture of bis(pinacolato)diboron (444 mg, 1.75 mmol), 7-bromo-N-ethyl-1,3-benzothiazol-2-amine (90 mg, 0.35 mmol), potassium acetate (240 mg, 2.45 mmol), 1,1'-bis(diphenylphosphino)ferrocenepalladium(II) dichloride dichloromethane complex (57 mg, 0.070 mmol) and 1,4-dioxane (8 mL) was evacuated and charged with nitrogen (3×). The mixture was heated to 105° C. for 2 h. To the crude mixture was added EtOAc. The organic fraction was washed with water and brine, dried over sodium sulfate, and purified by ISCO chromatography (0 to 30% EtOAc:heptane) to afford 93 mg (87%) of the title compound as an oily solid. MS (ESI): 305.48 [M+H]+; HPLC $t_R$=1.22 min (HPLC: Anayltical_2 min).

Step C: 1-[4-(4-{7-amino-2-[2-(ethylamino)-1,3-benzothiazol-7-yl]furo[2,3-c]pyridin-4-yl}-1H-pyrazol-1-yl)piperidin-1-yl]ethanone Trifluoroacetate (Title Compound)

The title compound was prepared from 1-{4-[4-(7-amino-2-chlorofuro[2,3-c]pyridin-4-yl)-1H-pyrazol-1-yl]piperidin-1-yl}ethanone and N-ethyl-7-(4,4,5,5-tetramethyl-1,3,2-dioxaborolan-2-yl)-1,3-benzothiazol-2-amine by a procedure analogous to Example 223, Step D. $^1$H NMR (400 MHz, CD$_3$OD): δ 8.28 (s, 1 H), 8.00 (s, 1 H), 7.94 (dd, J=7.6, 1.0 Hz, 1 H), 7.83 (s, 1 H), 7.59-7.65 (m, 2 H), 7.50-7.55 (m, 1 H), 4.69 (d, J=13.4 Hz, 1 H), 4.58 (tt, J=11.3, 4.1 Hz, 1 H), 4.11 (d, J=14.4 Hz, 1 H), 3.56 (q, J=7.2 Hz, 2 H), 3.34-3.43 (m, 1 H), 2.89 (td, J=13.0, 2.5 Hz, 1 H), 2.09-2.29 (m, 6 H), 1.99-2.07 (m, 1 H), 1.36 (t, J=7.3 Hz, 3 H); MS (ESI): 502.55 [M+H]$^+$; HPLC t$_R$=0.57 min (HPLC: Purity__2 min).

Example 355 trans-4-(4-{7-amino-2-[2-(ethylamino)-1,3-benzothiazol-7-yl]furo[2,3-c]pyridin-4-yl}-1H-pyrazol-1-yl)cyclohexanol Trifluoroacetate (Salt)

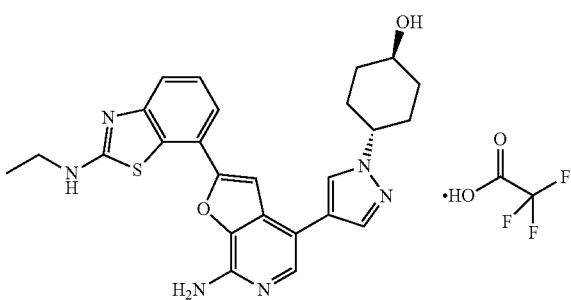

The title compound was prepared from 4-{1-[4-(tert-butyl-dimethyl-silanyloxy)-cyclohexyl]-1H-pyrazol-4-yl}-2-chloro-furo[2,3-c]pyridin-7-ylamine and N-ethyl-7-(4,4,5,5-tetramethyl-1,3,2-dioxaborolan-2-yl)-1,3-benzothiazol-2-amine by a procedure analogous to Example 229. $^1$H NMR (400 MHz, CD$_3$OD): δ 8.24 (s, 1 H), 7.97 (d, J=0.5 Hz, 1 H), 7.94 (dd, J=7.7, 1.1 Hz, 1 H), 7.82 (s, 1 H), 7.59-7.63 (m, 2 H), 7.49-7.55 (m, 1 H), 4.30 (tdd, J=11.8, 11.8, 4.0, 3.9 Hz, 1 H), 3.70 (tt, J=10.9, 4.3 Hz, 1 H), 3.56 (q, J=7.2 Hz, 2 H), 2.07-2.25 (m, 4 H), 2.00 (dtd, J=12.8, 12.6, 12.6, 3.2 Hz, 2 H), 1.47-1.59 (m, 2 H), 1.35 (t, J=7.3 Hz, 3 H); MS (ESI): 475.45 [M+H]$^+$; HPLC t$_R$=0.56 min (HPLC: Purity__2 min).

Example 356 trans-4-(4-{7-amino-2-[6-(3-fluorophenyl)-1,2-benzothiazol-7-yl]furo[2,3-c]pyridin-4-yl}-1H-pyrazol-1-yl)cyclohexanol

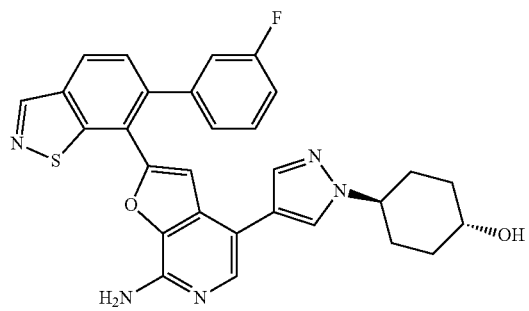 [SMILES: Nc1ncc(-c2cnn([C@H]3CC[C@H](O)CC3)c2)c2cc(-c3c(-c4cccc(F)c4)ccc4cnsc34)oc12]

Step A: 7-bromo-6-(3-fluorophenyl)-1,2-benzothiazole

A suspension of 7-bromo-6-iodo-1,2-benzothiazole (29.6 mg, 0.0871 mmol), 3-fluorobenzeneboronic acid (12.8 mg, 0.0915 mmol), potassium carbonate (39.2 mg, 0.284 mmol), and Pd(PPh$_3$)$_4$ (12.2 mg, 0.0106 mmol) in 4:1 1,4-dioxane: water (1 mL) was heated to 80° C. for 15 h. The reaction mixture was concentrated in vacuo. Purification of the residue by ISCO chromatography (0 to 100% dichloromethane:heptane) to afford 16.2 mg (59%) of the title compound as a white solid. $^1$H NMR (400 MHz, CDCl$_3$): δ 9.08 (s, 1H), 7.73 (d, J=7.58 Hz, 1H), 7.52 (dt, J=5.81, 7.96 Hz, 1H), 7.37 (qd, J=0.88, 7.71 Hz, 1H), 7.33 (d, J=7.58 Hz, 1H), 7.28-7.31 (m, 1H), 7.20 (ddt, J=1.01, 2.59, 8.43 Hz, 1H); MS (ESI): 307.87, 309.86 [M+H]$^+$; HPLC t$_R$=4.33 min (ZQ3: nonpolar__5 min).

Step B: 6-(3-fluorophenyl)-7-(4,4,5,5-tetramethyl-1,3,2-dioxaborolan-2-yl)-1,2-benzothiazole The title compound was prepared in 85% yield from 7-bromo-6-(3-fluorophenyl)-1,2-benzothiazole by a procedure analogous to Example 246, Step A. $^1$H NMR (400 MHz, CDCl$_3$): δ 9.00 (s, 1H), 8.04 (d, J=7.07 Hz, 1H), 7.50 (dt, J=5.81, 7.96 Hz, 1H), 7.43 (d, J=7.07 Hz, 1H), 7.40 (br d, J=7.80 Hz, 1H), 7.32 (td, J=2.02, 9.60 Hz, 1H), 7.18 (ddt, J=0.88, 2.59, 8.37 Hz, 1H), 1.44 (s, 12H); MS (ESI): 354.72, 356.05, 357.05 [M+H]$^+$; HPLC t$_R$=4.56 min (ZQ3: nonpolar__5 min).

Step C: trans-4-(4-{7-amino-2-[6-(3-fluorophenyl)-1,2-benzothiazol-7-yl]furo[2,3-c]pyridin-4-yl}-1H-pyrazol-1-yl)cyclohexanol (Title Compound)

The title compound was prepared from 4-[1-(trans-4-{[tert-butyl(dimethyl)silyl]oxy}cyclohexyl)-1H-pyrazol-4-yl]-2-chlorofuro[2,3-c]pyridin-7-amine and 6-(3-fluorophenyl)-7-(4,4,5,5-tetramethyl-1,3,2-dioxaborolan-2-yl)-1,2-benzothiazole by a procedure analogous to Example 229. $^1$H NMR (400 MHz, DMSO-d$_6$): δ 9.21 (s, 1H), 8.55 (d, J=7.58 Hz, 1H), 8.28 (s, 1H), 8.07 (s, 1H), 7.98 (s, 1H), 7.97 (s, 1H), 7.79 (d, J=7.83 Hz, 1H), 7.59-7.72 (m, 3H), 7.34-7.43 (m, 1H), 6.34 (br s, 2H), 4.70 (d, J=4.29 Hz, 1H), 4.21 (tt, J=3.98, 11.56 Hz, 1H), 3.49-3.60 (m, 1H), 2.09 (br d, J=12.40 Hz, 2H), 1.83-2.02 (m, 4H), 1.33-1.46 (m, 2H); MS (ESI): 526.08 [M+H]$^+$; HPLC $t_R$=2.37 min (ZQ3: nonpolar_4 min).

Example 357 trans-4-{4-[7-amino-2-(1-methyl-1H-indazol-7-yl)furo[2,3-c]pyridin-4-yl]-1H-pyrazol-1-yl}cyclohexanol

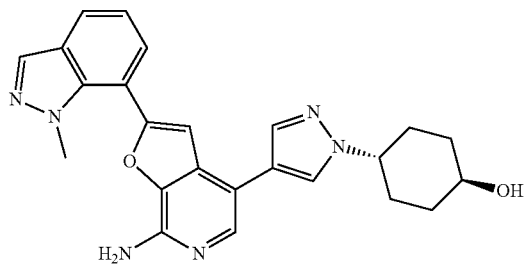 [SMILES: Cn1ncc2cccc(-c3cc4c(-c5cnn([C@H]6CC[C@H](O)CC6)c5)cnc(N)c4o3)c21]

The title compound was prepared in 69% yield from 4-{1-[4-(tert-butyldimethyl-silanyloxy)-cyclohexyl]-1H-pyrazol-4-yl}-2-chlorofuro[2,3-c]pyridin-7-ylamine and 1-methylindazole-7-boronic acid by a procedure analogous to Example 229. The material was further purified by preparative TLC (5% 7 N ammonia/MeOH:ethyl acetate) instead of trituration. $^1$H NMR (400 MHz, DMSO-d$_6$): δ 8.24 (s, 1H), 8.23 (s, 1H), 8.03 (s, 1H), 7.98 (dd, J=0.76, 8.08 Hz, 1H), 7.92 (s, 1H), 7.71 (dd, J=1.01, 7.07 Hz, 1H), 7.56 (s, 1H), 7.29 (dd, J=7.20, 7.96 Hz, 1H), 6.41 (br s, 2H), 4.67 (d, J=4.29 Hz, 1H), 4.15 (tt, J=3.95, 11.59 Hz, 1H), 3.91 (s, 3H), 3.46-3.57 (m, 1H), 2.04 (d, J=12.13 Hz, 2H), 1.79-1.98 (m, 4H), 1.30-1.43 (m, 2H); MS (ESI): 428.94 [M+H]$^+$; HPLC $t_R$=2.63 min (ZQ3: polar_5 min).

Example 358

1-(4-{4-[7-amino-2-(6-fluoro-1,3-benzothiazol-7-yl)furo[2,3-c]pyridin-4-yl]-1H-pyrazol-1-yl}piperidin-1-yl)ethanone bis(trifluoroacetate)

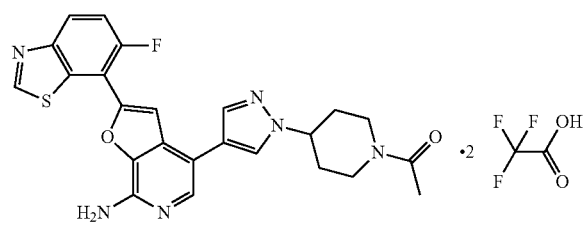 [SMILES: CC(=O)N1CCC(n2cc(-c3cnc(N)c4oc(-c5c(F)ccc6ncsc56)cc34)cn2)CC1 ; O=C(O)C(F)(F)F]

Step A: 2-amino-7-bromo-6-fluorobenzothiazole

To a mixture of 2-amino-6-fluorobenzothiazole (245 mg, 1.46 mmol) and sodium acetate (244 mg, 2.97 mmol) in acetic acid (1.60 mL) was added bromine (1.0 M in AcOH, 1.60 mL, 1.60 mmol) at RT. The mixture was stirred at RT for 1 h. The mixture was then treated with aqueous Na$_2$CO$_3$ until pH=7 and extracted with EtOAc (3×30 mL). The combined organic fractions were washed with water (2×20 mL) and brine (30 mL), dried over MgSO$_4$, filtered, and concentrated. Purification by ISCO chromatography (0 to 30% EtOAc:heptane) afforded 357 mg of the impure title compound as a dark brown solid (357 mg). MS (ESI): 246.92, 248.93 [M+H]$^+$; HPLC $t_R$=1.25 min (TOF: polar_3 min).

Step B: 7-Bromo-6-fluorobenzothiazole

To a solution of impure 2-amino-7-bromo-6-fluorobenzothiazole from Step A in THF (10 mL) was added tert-butyl nitrite (90%, 1.25 mL, 9.46 mmol). The mixture was stirred at 50° C. for 7 h and then purified by ISCO chromatography (0 to 40% EtOAc:heptane) to afford 114 mg (34%) of the title compound as a yellow solid. $^1$H NMR (400 MHz, CDCl$_3$): δ 7.54 (dd, J=2.4, 8.0 Hz, 1H), 7.62 (dd, J=2.4, 8.0 Hz, 1H), 9.03 (s, 1H); $^{19}$F NMR (376 MHz, CDCl$_3$): δ−113.77; MS (ESI): 231.92/233.92 [M+H]$^+$; HPLC $t_R$=1.38 min (TOF: polar_3 min).

Step C: (6-Fluoro-1,3-benzothiazol-7-yl)boronic Acid

A mixture of 7-bromo-6-fluorobenzothiazole (90.7 mg, 0.391 mmol), bis(pinacolato)diboron (149 mg, 0.587 mmol), (1,1'bis-(diphenylphosphino)-ferrocene) palladium dichloride (15.9 mg, 0.0217 mmol), and potassium acetate (76.7 mg, 0.782 mmol) in 1,4-dioxane (1.9 mL) was heated to 85° C. for 24 h. The reaction mixture was concentrated and was then purified by ISCO chromatography (0 to 50% EtOAc:hexane) to give afford 55.3 mg of the title compound as an off-white solid. MS (ESI): 198.02 [M+H]$^+$; HPLC $t_R$=1.18 min (TOF: polar_3 min).

Step D: 1-(4-{4-[7-amino-2-(6-fluoro-1,3-benzothiazol-7-yl)furo[2,3-c]pyridin-4-yl]-1H-pyrazol-1-yl}piperidin-1-yl)ethanone bis(trifluoroacetate) (Title Compound)

The title compound was prepared from 1-{4-[4-(7-amino-2-chlorofuro[2,3-c]pyridin-4-yl)-1H-pyrazol-1-yl]piperidin-1-yl}ethanone (56.7 mg, 0.158 mmol) and (6-fluoro-1,3-benzothiazol-7-yl)boronic acid (44.0 mg, 0.22 mmol) by a procedure analogous to Example 275. The crude material was purified by MDPS to afford 4.6 mg (4%) of the title compound as light-brown oil. $^1$H NMR (400 MHz, CD$_3$OD): δ 9.44 (s, 1H), 8.34 (s, 1H), 8.25 (s, 1H), 8.16 (dd, J=9.8, 2.4 Hz, 1H), 8.03 (dd, J=7.6, 2.4 Hz, 1H), 7.97 (s, 1H), 7.78 (s, 1H), 4.75-4.67 (m, 1H), 4.61 (tt, J=11.4, 4.0 Hz, 1H), 4.17-4.11 (m, 1H), 3.44-3.35 (m, 1H), 2.95-2.87 (m, 1H), 2.68 (s, 3H), 2.31-2.21 (m, 2H), 2.21-2.11 (m, 1H), 2.10-1.96 (m, 1H); MS (ESI): 476.98 [M+H]⁺; HPLC: $t_R$=2.81 min (ZQ3: polar_5 min).

Example 359 trans-4-{4-[7-amino-2-(6-fluoro-1,3-benzothiazol-7-yl)furo[2,3-c]pyridin-4-yl]-1H-pyrazol-1-yl}cyclohexanol

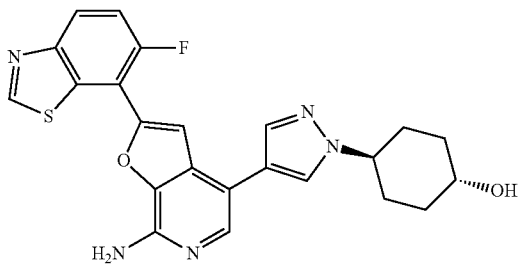 [SMILES: Nc1ncc(-c2cnn([C@H]3CC[C@H](O)CC3)c2)c2cc(-c3c(F)ccc4ncsc34)oc12]

A solution of 4-[1-(trans-4-{[tert-butyl(dimethyl)silyl]oxy}cyclohexyl)-1H-pyrazol-4-yl]-2-chlorofuro[2,3-c]pyridin-7-amine (70.5 mg, 0.158 mmol), (6-fluoro-1,3-benzothiazol-7-yl)boronic acid (44.0 mg, 0.22 mmol), and Pd(PPh₃)₄ (18.2 mg, 0.0158 mmol) in 1,4-dioxane (1.23 mL) and aqueous 1.0 N sodium carbonate solution (0.615 mL, 0.615 mmol) was heated to 120° C. in a microwave for 60 min. Into the reaction mixture was added hydrochloric acid in 1,4-dioxane (4 N in 1,4-dioxane, 0.59 mL, 2.36 mmol), and the reaction mixture was stirred at rt for 30 min, then purified by MDPS to afford 4.4 mg (6%) of the title compound as a brown solid. ¹H NMR (400 MHz, DMSO-d₆): δ 9.63 (s, 1H), 8.23 (s, 1H), 8.21 (s, 1H), 8.18 (s, 1H), 8.16 (s, 1H), 7.91 (s, 1H), 7.81 (s, 1H), 6.52 (brs, 2H), 4.67 (brd, J=3.2 Hz, 1H), 4.21 (tt, J=11.4, 4.0 Hz, 1H), 3.55-3.45 (m, 1H), 2.08-2.02 (m, 2H), 1.97-1.78 (m, 4H), 1.44-1.30 (m, 2H); MS (ESI): 450.03 [M+H]⁺; HPLC: $t_R$=2.85 min (ZQ3: polar_5 min).

Example 360

3-{7-Amino-4-[1-(trans-4-hydroxycyclohexyl)-1H-pyrazol-4-yl]furo[2,3-c]pyridin-2-yl}thieno[2,3-c]pyridin-5-ol

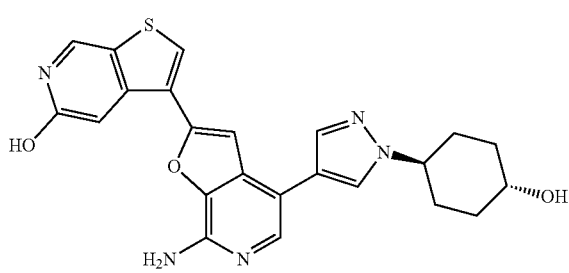 [SMILES: Nc1ncc(-c2cnn([C@H]3CC[C@H](O)CC3)c2)c2cc(-c3csc4cnc(O)cc34)oc12]

A solution of 4-[1-(trans-4-{[tert-butyl(dimethyl)silyl]oxy}cyclohexyl)-1H-pyrazol-4-yl]-2-chlorofuro[2,3-c]pyridin-7-amine (232 mg, 0.520 mmol), 5-fluoro-3-(4,4,5,5-tetramethyl-[1,3,2]dioxaborolan-2-yl)-thieno[2,3-c]pyridine (235 mg, 0.530 mmol), and Pd(PPh₃)₄ (60.1 mg, 0.0520 mmol) in 1,4-dioxane (2.0 mL) and aqueous 1.0 M sodium carbonate solution (2.0 mL, 2.0 mmol) was heated to 120° C. in a microwave reactor for 60 min. Water (10 mL) was added, and the mixture was extracted with EtOAc (3×10 mL). The combined organic extracts were washed with water (2×10 mL) and brine (10 mL), dried over MgSO₄, filtered, and concentrated. The residue was transferred to a sealable vial. To the vial was added sodium methoxide (148 mg, 2.60 mmol) and methanol (5.0 mL, 120 mmol), and the reaction mixture was heated in a microwave at 150° C. for 2 h. Water (10 mL) was added, and the mixture was extracted with EtOAc (3×15 mL). The organic extracts were washed with water (2×10 mL) and brine (10 mL), dried over MgSO₄, filtered, and concentrated. The residue was transferred to a vial, to which was added pyridine hydrochloride (613 mg, 5.20 mmol) and water (10.0 mL), and the mixture was heated at 120° C. for 3 h followed by heating in a microwave at 150° C. for 2 h. Purification of the residue by MDPS afforded 25.6 mg (11%) of the title compound as a yellow solid. ¹H NMR (400 MHz, DMSO-d₆): δ 8.70 (s, 1H), 8.66 (s, 1H), 8.25 (s, 1H), 7.99 (s, 1H), 7.94 (s, 1H), 7.58 (s, 1H), 7.56 (s, 1H), 6.36 (brs, 2H), 4.70 (br s, 1H), 4.19 (tt, J=11.4, 4.0 Hz, 1H), 3.59-3.45 (m, 1H), 2.12-2.04 (m, 2H), 2.02-1.82 (m, 4H), 1.45-1.33 (m, 2H), 1H overlapping with water peak; MS (ESI): 448.31 [M+H]⁺; HPLC: $t_R$=2.37 min (ZQ3: polar_5 min).

Example 361 trans-4-(4-{2-(1,2,3-benzothiadiazol-7-yl)-7-[(²H₃)methylamino]furo[2,3-c]pyridin-4-yl}-1H-pyrazol-1-yl)cyclohexanol

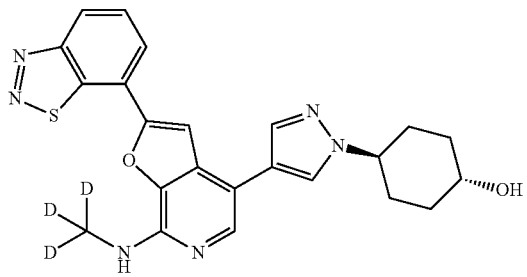 [SMILES: [2H]C([2H])([2H])Nc1ncc(-c2cnn([C@H]3CC[C@H](O)CC3)c2)c2cc(-c3cccc4nnsc34)oc12]

Step A: 2-chloro-4-iodo-N—(²H₃)methylfuro[2,3-c]pyridin-7-amine

The title compound was prepared from 2-chloro-4-iodofuro[2,3-c]pyridin-7-amine and (²H₃)methyl iodide by a procedure analogous to Intermediate 7. ¹H NMR (400 MHz, CD₃OD) δ 7.94 (s, 1 H), 6.60 (s, 1 H); MS (ESI): 311.77, 313.66 [M+H]⁺.

Step B: 4-[1-(trans-4-{[tert-butyl(dimethyl)silyl]oxy}cyclohexyl)-1H-pyrazol-4-yl]-2-chloro-N-²H₃)methylfuro[2,3-c]pyridin-7-amine A mixture of 2-chloro-4-iodo-N—(²H₃)methylfuro[2,3-c]pyridin-7-amine (0.03 g, 0.1 mmol), [1-(trans-4-{[tert-butyl(dimethyl)silyl]oxy}cyclohexyl)-1H-pyrazol-4-yl]boronic acid (0.0375 g, 0.116 mmol), 1,1'-bis(diphenylphosphino)ferrocenepalladium(II) dichloride dichloromethane adduct (0.007 g, 0.0096 mmol) and potassium carbonate (0.0333 g, 0.241 mmol) in 1,4-dioxane (1 mL) and water (0.5 mL) was heated to 70° C. for 15 min. After cooling to RT, the mixture was partitioned between EtOAc and water. Following separation of the layers, the aqueous layer was further extracted with DCM. The combined organic fractions were dried over sodium sulfate, filtered and concentrated. Purification of the residue by ISCO chromatography (0% to 50% EtOAc/heptane) afforded 0.028 g (60%) of the title compound as a yellow solid. $^1$H NMR (400 MHz, CD$_3$OD) δ 7.98 (s, 1 H), 7.91 (s, 1 H), 7.77 (s, 1 H), 7.00 (s, 1 H), 4.21 (tt, J=3.9, 11.5 Hz, 1 H), 3.85-3.72 (m, 1H), 2.18-2.08 (m, 2 H), 2.07-1.88 (m, 4 H), 1.61-1.45 (m, 2 H), 0.92 (s, 9 H), 0.11 (s, 6 H); MS (ESI): 464.00, 466.01 [M+H]$^+$.

Step C: trans-4-(4-{2-(1,2,3-benzothiadiazol-7-yl)-7-[($^2$H$_3$)methylamino]furo[2,3-c]pyridin-4-yl}-1H-pyrazol-1-yl)cyclohexanol (Title Compound)

The title compound was prepared from 4-[1-(trans-4-{[tert-butyl(dimethyl)silyl]oxy}cyclohexyl)-1H-pyrazol-4-yl]-2-chloro-N-($^2$H$_3$)methylfuro[2,3-c]pyridin-7-amine and 7-(4,4,5,5-tetramethyl-1,3,2-dioxaborolan-2-yl)-1,2,3-benzothiadiazole by a procedure analogous to Example 229. $^1$H NMR (400 MHz, CD$_3$OD): δ 8.74-8.68 (m, 1 H), 8.45 (dd, J=0.8, 7.6 Hz, 1 H), 8.09 (s, 1 H), 7.95 (s, 1 H), 7.89-7.84 (m, 2 H), 7.62 (s, 1 H), 4.28 (tt, J=3.9, 11.8 Hz, 1 H), 3.81-3.65 (m, 1 H), 2.26-2.09 (m, 4 H), 2.01 (dq, J=2.7, 12.5 Hz, 2 H), 1.60-1.47 (m, 2 H); MS (ESI): 449.95 [M+H]$^+$.

Example 362 trans-4-{4-[7-amino-2-(1,2,3-benzothiadiazol-7-yl)-3-methylfuro[2,3-c]pyridin-4-yl]-1H-pyrazol-1-yl}cyclohexanol

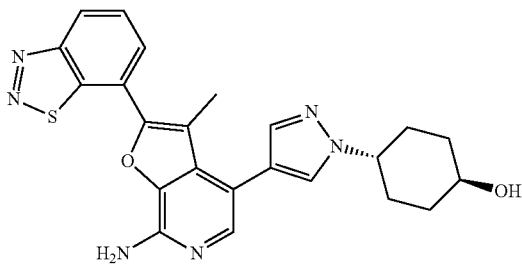 [SMILES: Cc1c(-c2cccc3nnsc23)oc2c(N)ncc(-c3cnn([C@H]4CC[C@H](O)CC4)c3)c12]

A solution of 4-[1-(trans-4-{[tert-butyl(dimethyl)silyl]oxy}cyclohexyl)-1H-pyrazol-4-yl]-2-chloro-3-methylfuro[2,3-c]pyridin-7-amine (20 mg, 0.043 mmol), 7-(4,4,5,5-tetramethyl-1,3,2-dioxaborolan-2-yl)-1,2,3-benzothiadiazole (12.5 mg, 0.0477 mmol), and Pd(PPh$_3$)$_4$ (5.0 mg, 0.0043 mmol) in 1,4-dioxane (0.2 mL) and 1.0 M aqueous sodium carbonate (0.2 mL) was heated to 120° C. in a microwave for 60 min. The organic phase was separated, treated with 12 M aqueous HCl (0.071 mL) at 40° C. for 1 h, and then concentrated. Purification by ISCO chromatography (0 to 15% 7 N NH$_3$/MeOH:DCM) followed by trituration from DCM:hexanes (~5 mL, 1:1) and filtration afforded 5.3 mg (27%) of the title compound as an orange solid. $^1$H NMR (400 MHz, DMSO-d$_6$): δ 8.83 (d, J=7.8 Hz, 1 H), 8.19 (d, J=6.8 Hz, 1 H), 7.90-8.03 (m, 2 H), 7.67 (s, 1 H), 7.58 (d, J=0.5 Hz, 1 H), 6.38 (s, 2 H), 4.67 (d, J=4.3 Hz, 1 H), 4.09-4.27 (m, 1 H), 3.42-3.60 (m, 1 H), 2.27 (s, 3 H), 2.06 (d, J=12.1 Hz, 2 H), 1.90-1.98 (m, 2 H), 1.77-1.90 (m, 2 H), 1.28-1.48 (m, 2 H); MS (ESI): 446.85, 448.96 [M+H]$^+$; HPLC t$_R$=2.51 min (ZQ3: polar_4 min).

Examples 363 and 364

1-(4-{4-[7-amino-2-(1-methyl-1H-pyrazolo[3,4-c]pyridin-3-yl)furo[2,3-c]pyridin-4-yl]-1H-pyrazol-1-yl}piperidin-1-yl)ethanone trifluoroacetic acid salt (769130) and 1-(4-{4-[7-amino-2-(2-methyl-2H-pyrazolo[3,4-d]pyridin-3-yl)furo[2,3-d]pyridin-4-yl]-1H-pyrazol-1-yl}piperidin-1-yl)ethanone trifluoroacetic Acid Salt

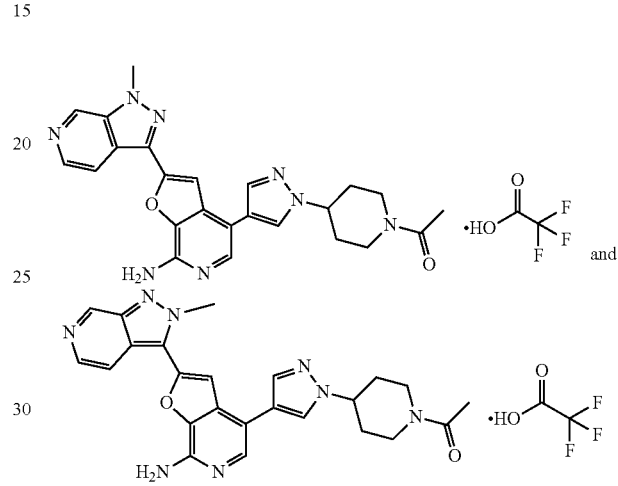

Step A: 3-bromo-1H-pyrazolo[3,4-c]pyridine

To a solution of 1H-pyrazolo[3,4-c]pyridine (0.50 g, 3.5 mmol) in water (10 mL) was added a solution of sodium oxybromide (prepared by dropwise addition of bromine (0.25 mL) to sodium hydroxide solution (0.40 mg in 5 mL) at 0° C. over 5 min). The reaction mixture stirred for 1 h at 10° C. The mixture was then acidified to pH ~5.5 with ammonium chloride, and extracted with ethyl acetate (3×20 mL). The combined organic fractions were dried over sodium sulfate and concentrated to afford 0.43 g (62%) of the title compound. $^1$H NMR (300 MHz, CD$_3$OD): δ 7.79 (dd, J=1.5, 4.2 Hz, 1H), 8.32-8.33 (d, J=5.7 Hz, 1H), 9.07 (s, 1H).

Step B: 3-bromo-1-methyl-1H-pyrazolo[3,4-c]pyridine and 3-bromo-2-methyl-2H-pyrazolo[3,4-c]pyridine To a cooled (0° C.) solution of 3-bromo-1H-pyrazolo[3,4-c]pyridine (0.172 g, 0.89 mmol) in dry DMF (3 mL) was added sodium hydride (0.138 g, 1.5 mmol). The reaction stirred for 30 min and then methyl iodide (0.141 g, 0.97 mmol) was added and the mixture warmed to RT over 30 min. The mixture was diluted with water (10 mL) and extracted with ethyl acetate (5×15 mL). The combined organic fractions were dried over sodium sulfate and concentrated to afford 0.170 g of a 1:2 mixture of the title compounds. $^1$H NMR (300 MHz, CD$_3$OD): δ 4.10 (s, 3H), 7.59 (d, J=5.7, 0.6 Hz, 1H), 8.28 (d, J=5.7 Hz, 1H), 9.07 (s, 1H) and 4.14 (s, 3H), 7.51 (dd, J=6.3, 1.5 Hz, 1H), 8.09 (d, J=6.0 Hz, 1H), 9.04 (s, 1H).

Step C: 2-(1-methyl-1H-pyrazolo[3,4-c]pyridin-3-yl) furo[2,3-c]pyridin-7-amine and 2-(2-methyl-2H-pyrazolo[3,4-c]pyridin-3-yl)furo[2,3-c]pyridin-7-amine A 3:1 mixture of 3-bromo-1-methyl-1H-pyrazolo[3,4-c]pyridine and 3-bromo-2-methyl-2H-pyrazolo[3,4-c]pyridine (80 mg, 0.39 mmol), {7-[bis(tert-butoxycarbonyl)amino] furo[2,3-c]pyridin-2-yl}boronic acid (180 mg, 0.48 mmol), Pd(PPh$_3$)$_4$ (44 mg, 0.038 mmol), potassium carbonate (200 mg, 1.4 mmol) and 4:1 dioxane:water (3 mL) was heated to 70° C. for 3 h. After cooling, concentrated aqueous HCl (0.59 mL, 7.1 mmol) was added and the suspension was stirred at 70° C. for 1 h. After cooling to room temperature, solid sodium bicarbonate was added to the mixture, with stirring, until the bubbling subsided. The reaction mixture was concentrated. Purification of the residue by ISCO chromatography (0 to 20% methanol:DCM) afforded 51 mg (49%) of a 2:1 mixture of the title compounds as an off-white solid.

2-(1-methyl-1H-pyrazolo[3,4-c]pyridin-3-yl)furo[2,3-c] pyridin-7-amine: $^1$H NMR (400 MHz, DMSO-d$_6$): δ 9.29 (d, J=1.0 Hz, 1 H), 8.54-8.47 (m, 1 H), 8.44-8.38 (m, 1H), 7.75 (d, J=5.3 Hz, 1 H), 7.40 (s, 1H), 6.88 (d, J=5.3 Hz, 1 H), 6.54 (s, 2 H), 4.29 (s, 3 H); MS (ESI): 266.20 [M+H]$^+$; HPLC t$_R$=2.11 min.

2-(2-methyl-2H-pyrazolo[3,4-c]pyridin-3-yl)furo[2,3-c] pyridin-7-amine: $^1$H NMR (400 MHz, DMSO-d$_6$): δ 9.25 (s, 1 H), 8.31-8.27 (m, 1 H), 8.25 (d, J=1.0 Hz, 1 H), 7.80 (d, J=5.3 Hz, 1 H), 7.54 (s, 1 H), 6.93 (d, J=2.0 Hz, 1 H), 6.62 (s, 2 H), 4.55 (s, 3 H); MS (ESI): 266.20 [M+H]$^+$; HPLC t$_R$=1.92 min.

Step D: 4-iodo-2-(1-methyl-1H-pyrazolo[3,4-c]pyridin-3-yl)furo[2,3-c]pyridin-7-amine and 4-iodo-2-(2-methyl-2H-pyrazolo[3,4-c]pyridin-3-yl)furo[2,3-c] pyridin-7-amine To a 2:1 mixture of 2-(1-methyl-1H-pyrazolo[3,4-c]pyridin-3-yl)furo[2,3-c]pyridin-7-amine and 2-(2-methyl-2H-pyrazolo[3,4-c]pyridin-3-yl)furo[2,3-c]pyridin-7-amine (0.045 g, 0.17 mmol) in DMF (1.5 mL) was added NIS (0.068 g, 0.30 mmol) and the mixture was stirred overnight at RT. Water was added to the product mixture, and the resulting beige solid was filtered. After washing with water, the solid was dried under vacuum to afford 0.042 g (63%) of a 2:1 mixture of the title compounds.

4-iodo-2-(1-methyl-1H-pyrazolo[3,4-c]pyridin-3-yl)furo [2,3-c]pyridin-7-amine: $^1$H NMR (400 MHz, DMSO-d$_6$): δ 9.30 (s, 1 H), 8.54 (d, J=5.3 Hz, 1 H), 8.43 (d, J=5.6 Hz, 1 H), 7.95 (s, 1 H), 7.11 (s, 1 H), 6.80 (s, 2 H), 4.30 (s, 3 H); MS (ESI): 392.12 [M+H]$^+$; HPLC t$_R$=2.71 min. 4-iodo-2-(2-methyl-2H-pyrazolo[3,4-c]pyridin-3-yl)furo[2,3-c]pyridin-7-amine: $^1$H NMR (400 MHz, DMSO-d$_6$): δ 9.26 (s, 1 H), 8.33-8.30 (m, 1 H), 8.28-8.25 (m, 1 H), 7.99 (s, 1 H), 7.25 (s, 1 H), 6.86 (s, 2 H), 4.57 (s, 3 H); MS (ESI): 392.12 [M+H]$^+$; HPLC t$_R$=2.43 min.

Step E: 1-(4-{4-[7-amino-2-(1-methyl-1H-pyrazolo [3,4-c]pyridin-3-yl)furo[2,3-c]pyridin-4-yl]-1H-pyrazol-1-yl}piperidin-1-yl)ethanone trifluoroacetic acid salt; and 1-(4-{4-[7-amino-2-(2-methyl-2H-pyrazolo[3,4-c]pyridin-3-yl)furo[2,3-c]pyridin-4-yl]-1H-pyrazol-1-yl}piperidin-1-yl)ethanone trifluoroacetic Acid Salt (Title Compounds)

A 2:1 mixture of 4-iodo-2-(1-methyl-1H-pyrazolo[3,4-c] pyridin-3-yl)furo[2,3-c]pyridin-7-amine and 4-iodo-2-(2-methyl-2H-pyrazolo[3,4-c]pyridin-3-yl)furo[2,3-c]pyridin-7-amine (0.042 g, 0.102 mmol) and 1-{4-[4-(4,4,5,5-tetramethyl-1,3,2-dioxaborolan-2-yl)-1H-pyrazol-1-yl] piperidin-1-yl}ethanone (0.041 g, 0.13 mmol) were dissolved in 1,4-dioxane (2 mL) and water (0.8 mL). The mixture was degassed with nitrogen for 10 min. To this mixture was added potassium carbonate (0.0530 g, 0.383 mmol) and 1,1'-bis (diphenylphosphino)ferrocenepalladium(II) dichloride dichloromethane adduct (0.0104 g, 0.0128 mmol), and the mixture was heated to 80° C. for 5 h. Purification of the residue by MDP afforded 0.0143 g (29%) of 1-(4-{4-[7-amino-2-(1-methyl-1H-pyrazolo[3,4-c]pyridin-3-yl)furo[2, 3-c]pyridin-4-yl]-1H-pyrazol-1-yl}piperidin-1-yl)pethanone as a yellow gum (Ex. 363), and 0.0075 g (30%) 1-(4-{4-[7-amino-2-(2-methyl-2H-pyrazolo[3,4-c]pyridin-3-yl) furo[2,3-c]pyridin-4-yl]-1H-pyrazol-1-yl}piperidin-1-yl) ethanone as a yellow gum (Ex. 364). 1-(4-{4-[7-amino-2-(1-methyl-1H-pyrazolo[3,4-c]pyridin-3-yl)furo[2,3-c]pyridin-4-yl]-1H-pyrazol-1-yl}piperidin-1-yl)ethanone: $^1$H NMR (400 MHz, CD$_3$OD): δ 9.77 (s, 1 H), 9.11 (d, J=5.8 Hz, 1 H), 8.60 (d, J=6.3 Hz, 1 H), 8.35 (s, 1 H), 8.03 (d, J=0.5 Hz, 1 H), 7.97 (s, 1 H), 7.89 (s, 1 H), 4.76-4.67 (m, 1 H), 4.61 (tt, J=4.1, 11.4 Hz, 1 H), 4.51 (s, 3 H), 4.18-4.09 (m, 1 H), 3.44-3.35 (m, 1 H), 2.90 (dt, J=2.5, 13.0 Hz, 1 H), 2.33-2.21 (m, 2 H), 2.20 (s, 3 H), 2.18-2.10 (m, 1 H), 2.10-1.98 (m, 1 H); MS (ESI): 457.37 [M+H]$^+$; HPLC t$_R$=2.23 min. 1-(4-{4-[7-amino-2-(2-methyl-2H-pyrazolo[3,4-c]pyridin-3-yl)furo[2,3-c]pyridin-4-yl]-1H-pyrazol-1-yl}piperidin-1-yl)ethanone: $^1$H NMR (400 MHz, CD$_3$OD): δ 9.85 (s, 1 H), 8.90 (d, J=6.6 Hz, 1 H), 8.39 (d, J=6.8 Hz, 1 H), 8.35 (s, 1 H), 8.07 (s, 1 H), 7.97 (s, 1 H), 7.91 (s, 1 H), 4.83 (s, 3 H), 4.73-4.65 (m, 1 H), 4.59 (tt, J=4.2, 11.4 Hz, 1 H), 4.16-4.07 (m, 1 H), 3.41-3.32 (m, 1 H), 2.88 (dt, J=2.5, 12.9 Hz, 1 H), 2.29-2.18 (m, 2 H), 2.17 (s, 3 H), 2.16-2.08 (m, 1 H), 2.08-1.95 (m, 1 H); MS (ESI): 457.37 [M+H]$^+$; HPLC t$_R$=2.14 min.

Example 365 trans-4-{4-[7-amino-2-(imidazo[1,5-a]pyridin-8-yl) furo[2,3-c]pyridin-4-yl]-1H-pyrazol-1-yl}cyclohexanol.diformate

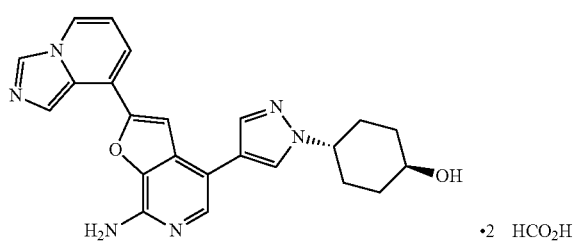

Step A: 1-(3-bromopyridin-2-yl)methanamine hydrochloride

To a cooled (0° C.) solution of 3-bromo-2-cyanopyridine (975.0 mg, 5.328 mmol) in THF (30 mL) was added borane (1.0 M in THF, 27.0 mL, 27.0 mmol) slowly via addition funnel over the course of 15 min. The reaction was stirred at 0° C. for 45 min and then warmed to RT for 17 h. After cooling to 0° C., the reaction was quenched with methanol (35 mL) and concentrated. The residue was dissolved in dichloromethane (6 mL) and charged with hydrochloric acid (4.0 M in 1,4-dioxane, 5 mL, 20 mmol) and then concentrated to afford 1.574 g (>100%) of the title compound as a yellow solid. The crude material thus obtained was used without further purification. MS (ESI): 187.09, 189.12 [M+H]+; HPLC $t_R$=0.67 & 0.97 min (ZQ3: polar_5 min).

Step B: N-1,3-bromopyridin-2-yl)methyl]formamide

To a suspension of 1-(3-bromopyridin-2-yl)methanamine hydrochloride (1.924 g, 4.304 mmol) and N-(3-dimethylaminopropyl)-N'-ethylcarbodiimide hydrochloride (2.116 g, 11.04 mmol) in DMF (25 mL), formic acid (415.0 mg, 9.017 mmol) was added. To this, DIPEA (4.0 mL, 23 mmol) was added and the reaction mixture was stirred at RT for 15 h. The reaction mixture was concentrated. Purification of the residue by ISCO chromatography (2 to 20% 7 N ammonia/MeOH: dichloromethane) afforded 314.9 mg (32%) of the title compound as a dark yellow solid. $^1$H NMR (400 MHz, DMSO-$d_6$): δ 8.49 (dd, J=1.39, 4.67 Hz, 1H), 8.45 (br s, 1H), 8.10 (m, 1H), 8.03 (dd, J=1.52, 8.08 Hz, 1H), 7.25 (dd, J=4.80, 8.08 Hz, 1H), 4.45 (d, J=5.56 Hz, 2H); MS (ESI): 215.09, 217.09 [M+H]+; HPLC $t_R$=2.55 min (ZQ3: polar_5 min).

Step C: 8-bromoimidazo[1,5-a]pyridine

A suspension of N-[(3-bromopyridin-2-yl)methyl]formamide (312.0 mg, 1.451 mmol) in toluene (7.0 mL) was charged with phosphorus oxychloride (0.50 mL, 5.4 mmol) and then refluxed for 1 h. The mixture was concentrated. The residue was cooled to 0° C. and water was added slowly. To the cooled aqueous suspension, aqueous ammonium hydroxide was added until the pH was basic, and the mixture was then extracted with ethyl acetate. The organic fraction was washed with brine, dried over anhydrous $Na_2SO_4$, filtered, and concentrated. Purification of the residue by ISCO chromatography (100% ethyl acetate) afforded 180.5 mg (63%) of the title compound as a yellow solid. $^1$H NMR (400 MHz, DMSO-$d_6$): δ 8.51 (d, J=0.51 Hz, 1H), 8.39 (td, J=0.88, 7.07 Hz, 1H), 7.38 (t, J=0.88 Hz, 1H), 7.12 (d, J=7.07 Hz, 1H), 6.60 (dd, J=6.90, 6.90 Hz, 1H); MS (ESI): 197.05, 198.99 [M+H]+; HPLC $t_R$=2.86 min (ZQ3: polar_5 min).

Step D: 2-(imidazo[1,5-a]pyridin-8-yl)furo[2,3-c]pyridin-7-amine

The title compound was prepared from 8-bromoimidazo[1,5-a]pyridine by a procedure analogous to Example 261, Step B. $^1$H NMR (400 MHz, DMSO-$d_6$): δ 8.54 (s, 1H), 8.47 (d, J=7.07 Hz, 1H), 8.10 (s, 1H), 7.75 (d, J=5.56 Hz, 1H), 7.59 (d, J=6.57 Hz, 1H), 7.56 (s, 1H), 6.86 (d, J=5.31 Hz, 1H), 6.86 (dd, J=7.10, 7.10 Hz, 1H), 6.49 (br s, 2H); MS (ESI): 251.17 [M+H]+; HPLC $t_R$=2.13 min (ZQ3: polar_5 min)

Step E: 2-(imidazo[1,5-a]pyridin-8-yl)-4-iodofuro[2,3-c]pyridin-7-amine

To a cooled (0° C.) solution of 2-(imidazo[1,5-a]pyridin-8-yl)furo[2,3-c]pyridin-7-amine (82.0 mg, 0.328 mmol) in DMF (4 mL) was added NIS (74.0 mg, 0.329 mmol) in portions. After stirring from 0° C. to RT over 1 h, the mixture was adsorbed onto silica gel. Purification by ISCO chromatography (50 to 100% ethyl acetate:heptane and then 15% methanol:dichloromethane), followed by mass-directed purification afforded 11.7 mg (10%) of the title compound as a yellow solid. $^1$H NMR (400 MHz, MeOH-$d_4$): δ 9.37 (s, 1H), 8.65 (br s, 1H), 8.62 (d, J=7.07 Hz, 1H), 8.02 (d, J=7.07 Hz, 1H), 7.98 (s, 1H), 7.64 (s, 1H), 7.23 (t, J=7.10 Hz, 1H); MS (ESI): 376.93 [M+H]+; HPLC $t_R$=2.76 min (ZQ3: polar_5 min).

Step F: trans-4-{4-[7-amino-2-(imidazo[1,5-a]pyridin-8-yl)furo[2,3-c]pyridin-4-yl]-1H-pyrazol-1-yl}cyclohexanol.diformate (Title Compound)

A suspension of 2-(imidazo[1,5-a]pyridin-8-yl)-4-iodofuro[2,3-c]pyridin-7-amine (11.7 mg, 0.0311 mmol), 1-[4-(tert-butyldimethylsilanyloxy)-cyclohexyl]-4-(4,4,5,5-tetramethyl-1,3,2-dioxaborolan-2-yl)-1H-pyrazole (20.5 mg, 0.0504 mmol), Pd(PPh$_3$)$_4$ (6.7 mg, 0.0058 mmol), and potassium carbonate (18.6 mg, 0.134 mmol) in 4:1 1,4-dioxane: water (2.5 mL) was heated to 120° C. in a microwave for 1 h. To the sample, hydrochloric acid (4.0 M in 1,4-dioxane, 0.3 mL, 1.2 mmol) was added and the reaction was stirred at RT for 1 h. Saturated aqueous sodium bicarbonate was added and the mixture was extracted with dichloromethane. The combined organic fractions were washed with brine, dried over anhydrous $Na_2SO_4$, filtered, and concentrated. Purification of the residue by ISCO chromatography (2 to 20% methanol: dichloromethane), followed by preparative HPLC afforded 3.0 mg (19%) of the title compound as a yellow solid. $^1$H NMR (400 MHz, MeOH-$d_4$): δ 8.48 (br s, 1H), 8.36 (d, J=6.57 Hz, 1H), 8.24 (br s, 2H), 8.16 (s, 1H), 8.07 (br s, 1H), 7.92 (s, 1H), 7.87 (br s, 1H), 7.66 (d, J=6.32 Hz, 1H), 7.61 (s, 1H), 6.85 (t, J=6.44 Hz, 1H), 4.28 (br t, J=11.62 Hz, 1H), 3.71 (br t, J=10.61 Hz, 1H), 2.08-2.25 (m, 4H), 2.01 (q, J=12.46 Hz, 2H), 1.53 (q, J=12.29 Hz, 2H); MS (ESI): 415.18 [M+H]+; HPLC $t_R$=0.82 (TOF: polar_3 min).

Example 366 trans-4-{4-[7-amino-2-(phthalazin-5-yl)furo[2,3-c]pyridin-4-yl]-1H-pyrazol-1-yl}cyclohexanol

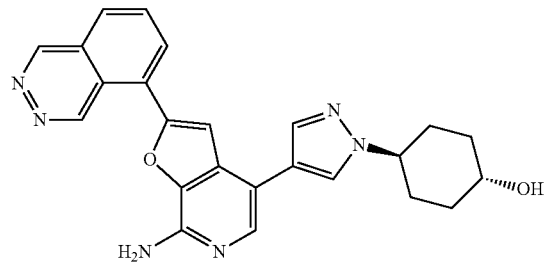 [SMILES: Nc1ncc(-c2cnn([C@H]3CC[C@H](O)CC3)c2)c2cc(-c3cccc4cnncc34)oc12]

Step A: 5-bromophthalazine

The title compound was prepared from phthalazin-5-amine in 19% yield by a procedure analogous to Intermediate 59, Step D, with the exception of heating the reaction to 65° C. for 3 h. $^1$H NMR (400 MHz, DMSO-$d_6$): δ 9.74-9.76 (m, 1H), 9.73 (d, J=1.26 Hz, 1H), 8.36 (dd, J=1.01, 7.58 Hz, 1H), 8.24 (td, J=0.88, 8.08 Hz, 1H), 7.98 (dd, J=8.00, 8.00 Hz, 1H); MS (ESI): 209.00, 210.90 [M+H]+; HPLC $t_R$=2.94 min (ZQ3: polar_5 min).

Step B: 5-(4,4,5,5-tetramethyl-1,3,2-dioxaborolan-2-yl)phthalazine

The title compound was prepared from 5-bromophthalazine by a procedure analogous to Example 246, Step A, with the exception that purification consisted solely of filtration through a plug of Celite. The crude material thus obtained was used without further purification.

Step C: 2-(phthalazin-5-yl)furo[2,3-c]pyridin-7-amine

The title compound was prepared by a procedure analogous to Example 261, Step B. $^1$H NMR (400 MHz, DMSO-$d_6$): δ 10.31 (br s, 1H), 9.79 (d, J=1.52 Hz, 1H), 8.55 (dd, J=1.14, 7.45 Hz, 1H), 8.29 (br d, J=8.10 Hz, 1H), 8.18 (dd, J=7.60, 7.60 Hz, 1H), 7.79 (d, J=5.31 Hz, 1H), 7.63 (s, 1H), 6.93 (d, J=5.31 Hz, 1H), 6.58 (br s, 2H); MS (ESI): 263.18 [M+H]$^+$; HPLC $t_R$=2.19 min (ZQ3: polar_5 min).

Step D: 4-iodo-2-(phthalazin-5-yl)furo[2,3-c]pyridin-7-amine

The title compound was prepared in 85% yield from 2-(phthalazin-5-yl)furo[2,3-c]pyridin-7-amine by a procedure analogous to Example 261, Step C. $^1$H NMR (400 MHz, DMSO-$d_6$): δ 10.32 (s, 1H), 9.79 (d, J=1.52 Hz, 1H), 8.61 (dd, J=1.01, 7.33 Hz, 1H), 8.31 (d, J=8.08 Hz, 1H), 8.17 (dd, J=7.80, 7.80 Hz, 1H), 7.99 (s, 1H), 7.45 (s, 1H), 6.84 (br s, 2H); MS (ESI): 389.12 [M+H]$^+$; HPLC $t_R$=2.97 min (ZQ3: polar_5 min).

Step E: trans-4-{4-[7-amino-2-(phthalazin-5-yl)furo[2,3-c]pyridin-4-yl]-1H-pyrazol-1-yl}cyclohexanol (Title Compound)

The title compound was prepared from 4-iodo-2-(phthalazin-5-yl)furo[2,3-c]pyridin-7-amine and 1-[4-(tert-butyldimethylsilanyloxy)-cyclohexyl]-4-(4,4,5,5-tetramethyl-1,3,2-dioxaborolan-2-yl)-1H-pyrazole by a procedure analogous to Example 365, Step F. $^1$H NMR (400 MHz, DMSO-$d_6$): δ 10.39 (s, 1H), 9.80 (d, J=1.26 Hz, 1H), 8.65 (d, J=7.33 Hz, 1H), 8.25-8.35 (m, 2H), 8.20 (t, J=7.80 Hz, 1H), 8.05 (s, 1H), 7.98 (s, 1H), 7.93 (s, 1H), 6.54 (br s, 2H), 4.68 (d, J=4.29 Hz, 1H), 4.18 (tt, J=3.73, 11.43 Hz, 1H), 3.48-3.59 (m, 1H), 2.07 (br d, J=12.10 Hz, 2H), 1.81-2.01 (m, 4H), 1.31-1.44 (m, 2H); MS (ESI): 427.01 [M+H]$^+$; HPLC $t_R$=2.38 min (ZQ3: polar_5 min).

Example 367

1-(4-{4-[7-amino-2-(phthalazin-5-yl)furo[2,3-c]pyridin-4-yl]-1H-pyrazol-1-yl}piperidin-1-yl)ethanone

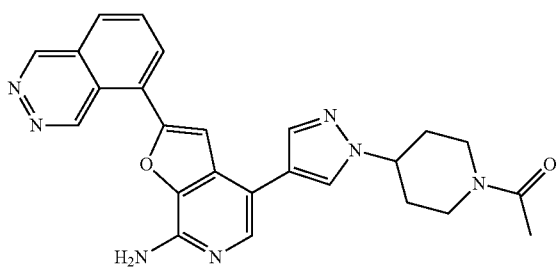 [SMILES: CC(=O)N1CCC(n2cc(-c3cnc(N)c4oc(-c5cccc6cnncc56)cc34)cn2)CC1]

The title compound was prepared in 3% yield from 5-(4,4,5,5-tetramethyl-1,3,2-dioxaborolan-2-yl)phthalazine and 1-{4-[4-(7-amino-2-chlorofuro[2,3-c]pyridin-4-yl)-1H-pyrazol-1-yl]piperidin-1-yl}ethanone, by a procedure analogous to Example 223, Step D. The sample underwent both mass-directed purification and preparative TLC during purification. $^1$H NMR (400 MHz, CD$_3$OD): δ 10.32 (s, 1H), 9.73 (s, 1H), 8.63 (dd, J=0.76, 7.58 Hz, 1H), 8.32 (d, J=8.08 Hz, 1H), 8.18-8.25 (m, 2H), 7.96-8.03 (m, 2H), 7.76 (s, 1H), 4.67-4.76 (m, 1H), 4.55-4.61 (m, 1H), 3.35-3.42 (m, 1H), 2.88 (dt, J=2.65, 12.95 Hz, 1H), 2.21-2.31 (m, 2H), 2.19 (s, 3H), 1.98-2.18 (m, 3H); MS (ESI): 454.19 [M+H]$^+$; HPLC $t_R$=0.85 min (TOF: polar_3 min).

Example 368 trans-4-[4-(7-amino-2-phenylfuro[2,3-c]pyridin-4-yl)-1H-pyrazol-1-yl]cyclohexanol

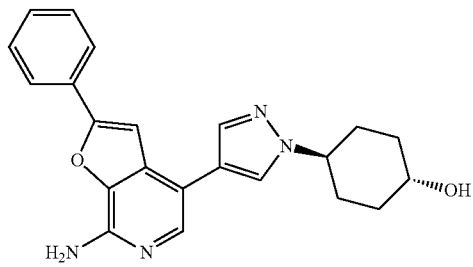 [SMILES: Nc1ncc(-c2cnn([C@H]3CC[C@H](O)CC3)c2)c2cc(-c3ccccc3)oc12]

A mixture of {7-[bis(tert-butoxycarbonyl)amino]-4-[1-(trans-4-{[tert-butyl(dimethyl)silyl]oxy}cyclohexyl)-1H-pyrazol-4-yl]furo[2,3-c]pyridin-2-yl}boronic acid (15.0, 0.0228 mmol), iodobenzene (9.32 mg, 0.0456 mmol), Pd(PPh$_3$)$_4$ (2.64 mg, 0.0023 mmol), potassium carbonate (9.47 mg, 0.0685 mmol) and 4:1 1,4-dioxane:water (1 mL) was heated to 65° C. for 30 min. Concentrated HCl (0.0381 mL, 0.457 mmol) was added, and the solution was heated to 70° C. for 1 h. The solution was concentrated. Purification by ISCO chromatography (2 to 5% 7 N NH$_3$/MeOH:DCM) afforded 2.6 mg (30%) of the title compound as a yellow solid. $^1$H NMR (400 MHz, CD$_3$OD): δ 1.43-1.58 (m, 2 H), 1.91-2.07 (m, 2 H), 2.07-2.24 (m, 4 H), 3.70 (tt, J=10.9, 4.3 Hz, 1 H), 4.21-4.32 (m, 1 H), 7.45-7.57 (m, 3 H), 7.58 (s, 1 H), 7.82 (s, 1 H), 7.92 (s, 1 H), 8.07 (s, 1 H), 8.09 (d, J=1.5 Hz, 1 H), 8.17 (s, 1 H); MS (ESI): 375.16 [M+H]$^+$; HPLC $t_R$=0.75 min (TOF: polar_2 min).

Example 369 trans-4-(4-{7-amino-2-[5-(3-fluorophenyl)-1,2,3-benzothiadiazol-7-yl]furo[2,3-c]pyridin-4-yl}-1H-pyrazol-1-yl)cyclohexanol

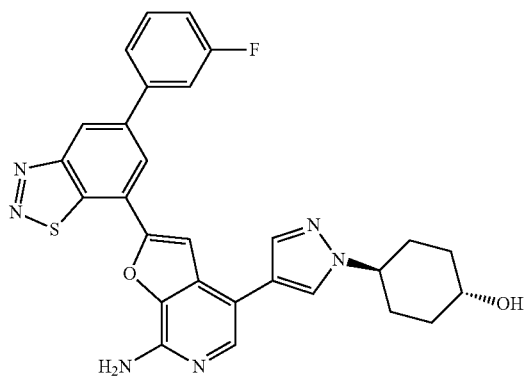 [SMILES: Nc1ncc(-c2cnn([C@H]3CC[C@H](O)CC3)c2)c2cc(-c3cc(-c4cccc(F)c4)cc4nnsc34)oc12]

Step A: 7-bromo-5-(3-fluorophenyl)-1,2,3-benzothiadiazole

A mixture of 7-bromo-5-iodo-1,2,3-benzothiadiazole (20 mg, 0.0586 mmol), 3-fluorophenylboronic acid (9.85 mg, 0.0704 mmol), 1,1'-bis(diphenylphosphino)ferrocenepalladium (II) dichloride dichloromethane complex (2.14 mg, 0.00293 mmol), potassium carbonate (24.3 mg, 0.176 mmol) and 4:1 1,4-dioxane:water (3 mL) was heated to 60° C. for 2 h. The solution was concentrated. Purification by ISCO chromatography (1 to 3% EtOAc:heptane) afforded 15 mg (83%) of the title compound as a white solid. $^1$H NMR (400 MHz, CDCl$_3$): δ 7.13-7.21 (m, 1 H), 7.39 (dt, J=9.7, 2.0 Hz, 1 H), 7.45-7.55 (m, 2 H), 8.04 (d, J=1.5 Hz, 1 H), 8.74 (d, J=1.3 Hz, 1 H).

Step B: trans-4-(4-{7-amino-2-[5-(3-fluorophenyl)-1,2,3-benzothiadiazol-7-yl]furo[2,3-c]pyridin-4-yl}-1H-pyrazol-1-yl)cyclohexanol (Title Compound)

The title compound was prepared from {7-[bis(tert-butoxycarbonyl)amino]-4-[1-(trans-4-{[tert-butyl(dimethyl)silyl]oxy}cyclohexyl)-1H-pyrazol-4-yl]furo[2,3-c]pyridin-2-yl}boronic acid and 7-bromo-5-(3-fluorophenyl)-1,2,3-benzothiadiazole by a procedure analogous to Example 368. $^1$H NMR (400 MHz, CD$_3$OD): δ 1.48-1.57 (m, 2 H), 1.94-2.05 (m, 2 H), 2.11-2.22 (m, 4 H), 3.67-3.75 (m, 1 H), 4.21-4.29 (m, 1 H), 7.19-7.26 (m, 1 H), 7.53-7.63 (m, 2 H), 7.72-7.77 (m, 2 H), 7.89 (s, 2 H), 8.08 (s, 1 H), 8.70 (s, 1 H), 8.90 (s, 1 H); MS (ESI): 527.60 [M+H]$^+$; HPLC t$_R$=1.07 min (TOF: polar__2 min).

Example 370

7-{7-amino-4-[1-(trans-4-hydroxycyclohexyl)-1H-pyrazol-4-yl]furo[2,3-c]pyridin-2-yl}-1,2,3-benzothiadiazole-5-carbonitrile

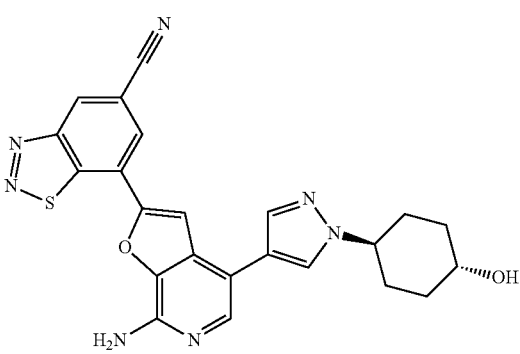 [SMILES: N#Cc1cc(-c2cc3c(-c4cnn([C@H]5CC[C@H](O)CC5)c4)cnc(N)c3o2)c2snnc2c1]

Step A: 7-bromo-1,2,3-benzothiadiazole-5-carbonitrile

A mixture of 7-bromo-5-iodo-1,2,3-benzothiadiazole (22 mg, 0.0645 mmol), zinc cyanide (7.58 mg, 0.0645 mmol), Pd(PPh$_3$)$_4$ (7.46 mg, 0.00645 mmol) and DMF (2 mL) was heated to 60° C. for 4 h. The solution was extracted with EtOAc (50 mL), and the organic fraction was washed with saturated aqueous sodium bicarbonate solution (3×50 mL). The organic fraction was adsorbed onto silica gel and purified by ISCO chromatography (3 to 5% EtOAc:heptane) to afford 14 mg (90%) of the title compound as a white solid. $^1$H NMR (400 MHz, CDCl$_3$): δ 8.03 (d, J=1.0 Hz, 1 H), 8.92 (d, J=1.3 Hz, 1 H).

Step B: 7-{7-amino-4-[1-(trans-4-hydroxycyclohexyl)-1H-pyrazol-4-yl]furo[2,3-c]pyridin-2-yl}-1,2,3-benzothiadiazole-5-carbonitrile (Title Compound)

The title compound was prepared from {7-[bis(tert-butoxycarbonyl)amino]-4-[1-(trans-4-{[tert-butyl(dimethyl)silyl]oxy}cyclohexyl)-1H-pyrazol-4-yl]furo[2,3-c]pyridin-2-yl}boronic acid and 7-bromo-1,2,3-benzothiadiazole-5- carbonitrile by a procedure analogous to Example 368. MS (ESI): 458.14 [M+H]+; HPLC $t_R$=0.79 min (TOF: polar_2 min).

Example 371 trans-4-(4-{7-amino-2-[2-(dimethylamino)-1,3-benzothiazol-7-yl]furo[2,3-c]pyridin-4-yl}-1H-pyrazol-1-yl)cyclohexanol Trifluoroacetate (Salt)

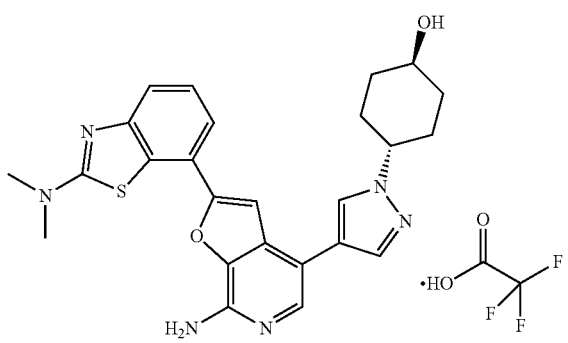

Step A: 7-bromo-N,N-dimethyl-1,3-benzothiazol-2-amine

7-Bromo-2-chlorobenzothiazole (100 mg, 0.40 mmol) was added to dimethylamine (2.0 M in MeOH, 1 mL, 2 mmol) and the solution was heated at 70° C. for 1 h. The crude mixture was purified by ISCO chromatography (100% DCM) to afford 101 mg (98%) of the title compound as white solid. MS (ESI): 257.33, 259.36 [M+H]+; HPLC $t_R$=1.40 min (HPLC: Anayltical_2 min).

Step B: trans-4-(4-{7-amino-2-[2-(dimethylamino)-1,3-benzothiazol-7-yl]furo[2,3-c]pyridin-4-yl}-1H-pyrazol-1-yl)cyclohexanol Trifluoroacetate (Salt) (Title Compound)

The title compound was prepared from {7-[bis(tert-butoxycarbonyl)amino]-4-[1-(trans-4-{[tert-butyl(dimethyl)silyl]oxy}cyclohexyl)-1H-pyrazol-4-yl]furo[2,3-c]pyridin-2-yl}boronic acid and 7-bromo-N,N-dimethyl-1,3-benzothiazol-2-amine by a procedure analogous to Example 368. 1H NMR (400 MHz, CD3OD): δ 8.23 (s, 1 H), 7.96 (s, 1 H), 7.88 (d, J=7.1 Hz, 1 H), 7.80 (s, 1 H), 7.58-7.63 (m, 2 H), 7.46-7.52 (m, 1 H), 4.30 (tdd, J=11.8, 11.8, 3.9, 3.8 Hz, 1 H), 3.65-3.76 (m, 1 H), 3.30 (s, 6 H), 2.08-2.25 (m, 4 H), 1.94-2.07 (m, 2 H), 1.47-1.60 (m, 2 H); MS (ESI): 475.45 [M+H]+; HPLC $t_R$=0.58 min (HPLC: Purity_2 min).

Example 372

7-{7-amino-4-[1-(trans-4-hydroxycyclohexyl)-1H-pyrazol-4-yl]furo[2,3-c]pyridin-2-yl}-1,2-benzothiazole-6-carbonitrile.diformate

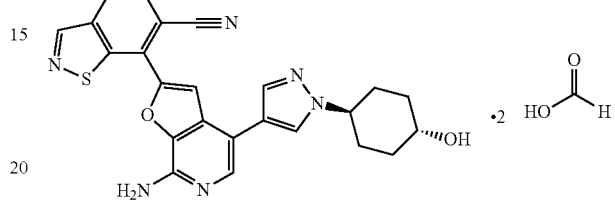

Step A: 7-bromo-1,2-benzothiazole-6-carbonitrile

A suspension of 7-bromo-6-iodo-1,2-benzothiazole (43.2 mg, 0.127 mmol), zinc cyanide (13.6 mg, 0.116 mmol), and Pd(PPh3)4 (15.9 mg, 0.0138 mmol) in DMF (1.6 mL) was heated to 80° C. in a microwave for 15 min. The reaction mixture was concentrated in vacuo. Purification of the residue by ISCO chromatography (20 to 100% dichloromethane:heptane) to afford 16.4 mg (50%) of the title compound as a white solid. 1H NMR (400 MHz, CDCl3): δ 9.25 (s, 1H), 7.77 (d, J=7.58 Hz, 1H), 7.69 (d, J=8.08 Hz, 1H); MS (ESI): 237.15, 239.14 [M−H]+; HPLC $t_R$=0.90 min (HPLC: nonpolar_2 min).

Step B: 7-{7-amino-4-[1-(trans-4-hydroxycyclohexyl)-1H-pyrazol-4-yl]furo[2,3-c]pyridin-2-yl}-1,2-benzothiazole-6-carbonitrile.diformate (Title Compound)

A suspension of {7-[bis(tert-butoxycarbonyl)amino]-4-[1-(trans-4-{[tert-butyl(dimethyl)silyl]oxy}cyclohexyl)-1H-pyrazol-4-yl]furo[2,3-c]pyridin-2-yl}boronic acid (59.0 mg, 0.0898 mmol), 7-bromo-1,2-benzothiazole-6-carbonitrile (15.0 mg, 0.0627 mmol), 1,1'-bis(diphenylphosphino)ferrocenepalladium(II) dichloride dichloromethane complex (5.6 mg, 0.0068 mmol), and potassium carbonate (30.3 mg, 0.219 mmol) in 4:1 1,4-dioxane:water (1.5 mL) was heated to 65° C. for 30 min. Several drops of 12 N HCl were added to the reaction mixture, which was then stirred at 70° C. for 1 h. Saturated aqueous sodium bicarbonate was added and the suspension was concentrated in vacuo to ~25% of the original volume. The salts were filtered off and the filtrate was concentrated in vacuo. Purification of the residue by ISCO chromatography (1 to 15% methanol:dichloromethane), followed by preparative HPLC afforded 9.0 mg (25%) of the title compound as an orange solid. 1H NMR (400 MHz, DMSO-d6): δ 9.39 (s, 1H), 8.61 (d, J=7.58 Hz, 1H), 8.32 (d, J=7.58 Hz, 1H), 8.27 (d, J=5.05 Hz, 3H), 8.18 (s, 1H), 8.08 (s, 1H), 7.97 (s, 1H), 6.42 (s, 2H), 4.19 (tt, J=3.76, 11.53 Hz, 1H), 3.54 (tt, J=3.98, 10.67 Hz, 1H), 2.09 (br d, J=11.60 Hz, 2H), 1.97

(br d, J=10.90 Hz, 2H), 1.82-1.94 (m, 2H), 1.33-1.46 (m, 2H); MS (ESI): 457.12 [M+H]$^+$; HPLC $t_R$=1.10 min (TOF: polar_3 min).

Example 373 trans-4-{4-[7-amino-2-(5-methyl-1,2,3-benzothiadiazol-7-yl)furo[2,3-c]pyridin-4-yl]-1H-pyrazol-1-yl}cyclohexanol

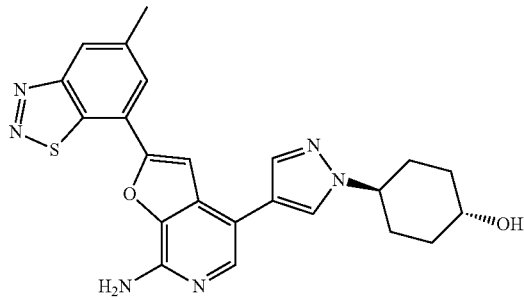 [SMILES: Cc1cc(-c2cc3c(-c4cnn([C@H]5CC[C@H](O)CC5)c4)cnc(N)c3o2)c2snnc2c1]

Step A: 7-bromo-5-methyl-1,2,3-benzothiadiazole

To a solution of 7-bromo-5-iodo-1,2,3-benzothiadiazole (30 mg, 0.088 mmol), Pd(PPh$_3$)$_4$ (10.2 mg, 0.0088 mmol) and 1,4-dioxane (5 mL) was added dimethylzinc (2 M in toluene, 0.1 mL, 0.210 mmol), and the reaction was heated to 50° C. for 3 h. The solution was quenched with MeOH (1 mL), adsorbed onto silica gel, and purified by ISCO chromatography (1 to 3% EtOAc:heptane) to afford 12 mg (60%) of the title compound as a white solid. $^1$H NMR (400 MHz, CDCl$_3$): δ 2.52 (s, 3 H), 7.58 (s, 1 H), 8.27 (s, 1 H).

Step B: trans-4-{4-[7-amino-2-(5-methyl-1,2,3-benzothiadiazol-7-yl)furo[2,3-c]pyridin-4-yl]-1H-pyrazol-1-yl}cyclohexanol (Title Compound)

A mixture of di-tert-butyl {4-[1-(trans-4-{[tert-butyl(dimethyl)silyl]oxy}cyclohexyl)-1H-pyrazol-4-yl]-2-(trimethylstannanyl)furo[2,3-d]pyridin-7-yl}imidodicarbonate (40.6 mg, 0.058 mmol), 7-bromo-5-methyl-1,2,3-benzothiadiazole (12 mg, 0.0524 mmol), Pd(PPh$_3$)$_4$ (3 mg, 0.0026 mmol), cesium fluoride (31.8 mg, 0.210 mmol) and 1,4-dioxane (3 mL) was heated to 100° C. for 16 h. The solution was cooled to 70° C. and concentrated hydrochloric acid (0.087 mL, 1.05 mmol) was added. The reaction stirred for 1 h, then was cooled to RT and neutralized with saturated aqueous potassium carbonate solution. The reaction was concentrated. Purification of the residue by ISCO chromatography (2 to 5% 7 N NH$_3$/MeOH:DCM) afforded 2.4 mg (10%) of the title compound as a yellow solid. $^1$H NMR (400 MHz, CD$_3$OD): δ 1.42-1.56 (m, 2 H), 1.84-1.99 (m, 2 H), 2.08-2.17 (m, 2 H), 2.18-2.28 (m, 2 H), 2.69 (s, 3 H), 3.64-3.73 (m, 1 H), 4.15-4.22 (m, 1 H), 7.36 (s, 1 H), 7.79 (s, 1 H), 7.80 (s, 1 H), 7.93 (br. s, 1 H), 8.15 (s, 1 H), 8.47 (s, 1 H); MS (ESI): 447.14 [M+H]$^+$; HPLC $t_R$=0.81 min (TOF: polar_2 min).

Example 374 trans-4-(4-{7-amino-2-[5-(1H-pyrazol-3-yl)-1,2,3-benzothiadiazol-7-yl]furo[2,3-c]pyridin-4-yl}-1H-pyrazol-1-yl)cyclohexanol

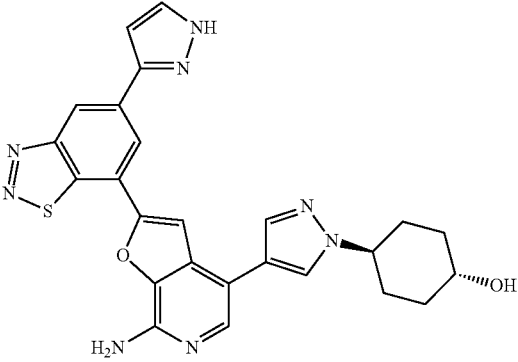 [SMILES: Nc1ncc(-c2cnn([C@H]3CC[C@H](O)CC3)c2)c2cc(-c3cc(-c4cc[nH]n4)cc4nnsc34)oc12]

Step A:
7-bromo-5-(1H-pyrazol-3-yl)-1,2,3-benzothiadiazole

The title compound was prepared from 7-bromo-5-iodo-1,2,3-benzothiadiazole by a procedure analogous to Example 369, Step A. MS (ESI): 280.95 [M+H]$^+$; HPLC $t_R$=0.94 min (TOF: polar_2 min).

Step B: trans-4-(4-{7-amino-2-[5-(1H-pyrazol-3-yl)-1,2,3-benzothiadiazol-7-yl]furo[2,3-c]pyridin-4-yl}-1H-pyrazol-1-yl)cyclohexanol (Title Compound)

The title compound was prepared from di-tert-butyl {4-[1-(trans-4-{[tert-butyl(dimethyl)silyl]oxy}cyclohexyl)-1H-pyrazol-4-yl]-2-(trimethylstannanyl)furo[2,3-c]pyridin-7-yl}imidodicarbonate and 7-bromo-5-(1H-pyrazol-3-yl)-1,2,3-benzothiadiazole by a procedure analogous to Example 373, Step B. $^1$H NMR (400 MHz, CD$_3$OD): δ 1.50-1.61 (m, 2 H), 1.93-2.06 (m, 2 H), 2.13-2.21 (m, 2 H), 2.25-2.33 (m, 2 H), 3.75 (tdd, J=10.9, 10.9, 4.2, 4.0 Hz, 1 H), 4.27 (tdd, J=12.0, 12.0, 4.3, 4.1 Hz, 1 H), 6.97 (d, J=2.3 Hz, 1 H), 7.58 (s, 1 H), 7.78 (d, J=2.3 Hz, 1 H), 7.88 (s, 1 H), 7.93 (s, 1 H), 7.94 (s, 1 H), 8.92 (br. s, 1 H), 9.04 (d, J=1.3 Hz, 1 H).

The following Examples were prepared from 4-iodo-2-thieno[2,3-c]pyridine-3-yl-furo[2,3-c]pyridine-7-ylamine and an appropriate boronic acid or ester by a procedure analogous to Example 68.

| Ex. # | Structure and NMR Data | Compound name | MS (ESI) [M + H]+ | HPLC t_R (min) |
|---|---|---|---|---|
| 375 | 1H NMR (400 MHz, CD3OD): δ 9.43 (s, 1H), 9.04 (s, 1H), 8.74 (d, J = 5.8 Hz, 1H), 8.68 (d, J = 5.8 Hz, 1H), 7.87 (s, 1H), 7.85 (s, 1H), 7.42 (s, 1H), 7.18 (s, 1H), 2.37 (s, 3H) | 4-(4-methyl-thiophen-2-yl)-2-thieno[2,3-c]pyridin-3-yl-furo[2,3-c]pyridin-7-ylamine | 364.06 | 0.74 (UPLC: Analytical_2 min) |
| 376 | 1H NMR (400 MHz, CD3OD): δ 10.84 (br s, 1H), 9.50 (s, 1H), 9.10 (s, 1H), 8.84 (d, J = 6.1 Hz, 1H), 8.69 (d, J = 6.1 Hz, 1H), 7.87 (s, 1H), 7.72 (s, 1H), 7.36 (dd, J = 1.2 & 1.8 hz, 1H), 6.93 (d, J = 1.8 Hz, 1H), 6.58 (d, J = 1.2 Hz, 1H) | 4-(1H-pyrrol-3-yl)-2-thieno[2,3-c]pyridin-3-yl-furo[2,3-c]pyridin-7-ylamine | 333.15 | 0.51 (UPLC: Analytical_2 min) |
| 377 | 1H NMR (400 MHz, CD3OD): δ 9.41 (s, 1H), 9.02 (s, 1H), 8.72 (d, J = 5.8 Hz, 1H), 8.67 (d, J = 5.8 Hz, 1H), 7.85 (s, 1H), 7.44 (s, 1H), 7.19 (s, 1H), 2.91 (s, 3H), 2.37 (s, 3H) | 4-(2,5-dimethyl-thiophen-3-yl)-2-thieno[2,3-c]pyridin-3-yl-furo[2,3-c]pyridin-7-ylamine | 378.12 | 0.83 (UPLC: Analytical_2 min) |
| 378 | 1H NMR (400 MHz, CD3OD): δ 9.51 (s, 1H), 9.12 (s, 1H), 8.85 (d, J = 6.1 Hz, 1H), 8.70 (d, J = 6.1 Hz, 1H), 8.22 (s, 2H), 7.94 (s, 1H), 7.88 (s, 1H), 3.94 (s, 3H) | 4-(7-amino-2-thieno[2,3-c]pyridin-3-yl-furo[2,3-c]pyridin-4-yl)-thiophene-2-carboxylic acid methyl ester | 408.13 | 0.68 (UPLC: Analytical_2 min) |

| Ex. # | Structure and NMR Data | Compound name | MS (ESI) [M + H]+ | HPLC t_R (min) |
|---|---|---|---|---|
| 379 | ¹H NMR (400 MHz, CD₃OD): δ 9.43 (s, 1H), 9.06 (s, 1H), 8.76 (d, J = 6.1 Hz, 1H), 8.68 (d, J = 6.1 Hz, 1H), 8.35 (d, J = 1.3 Hz, 1H), 7.95 (s, 1H), 7.91 (d, J = 1.3 Hz, 1H), 7.87 (s, 1H) | 5-(7-amino-2-thieno[2,3-c]pyridin-3-yl-furo[2,3-c]pyridin-4-yl)-thiophene-3-carboxylic acid | 394.13 | 0.54 (UPLC: Analytical_2 min) |
| 380 | ¹H NMR (400 MHz, CD₃OD): δ 9.47 (s, 1H), 9.10 (s, 1H), 8.79 (d, J = 6.1 Hz, 1H), 8.71 (d, J = 6.1 Hz, 1H), 8.39 (d, J = 1.3 Hz, 1H), 7.95 (s, 1H), 7.92 (d, J = 1.3 Hz, 1H), 7.86 (s, 1H), 3.92 (s, 3H) | 5-(7-amino-2-thieno[2,3-c]pyridin-3-yl-furo[2,3-c]pyridin-4-yl)-thiophene-3-carboxylic acid methyl ester | 408.16 | 0.72 (UPLC: Analytical_2 min) |
| 381 | ¹H NMR (400 MHz, CD₃OD): δ 9.47 (s, 1H), 9.11 (s, 1H), 8.80 (d, J = 6.1 Hz, 1H), 8.69 (d, J = 6.1 Hz, 1H), 8.01 (s, 1H), 7.92 (s, 1H), 7.88 (d, J = 4.1 Hz, 1H), 7.63 (d, J = 4.1 Hz, 1H) | 5-(7-amino-2-thieno[2,3-c]pyridin-3-yl-furo[2,3-c]pyridin-4-yl)-thiophene-2-carboxylic acid | 394.14 | 0.53 (UPLC: Analytical_2 min) |
| 382 | ¹H NMR (400 MHz, CD₃OD): δ 9.47 (s, 1H), 9.10 (s, 1H), 8.79 (d, J = 6.1 Hz, 1H), 8.69 (d, J = 6.1 Hz, 1H), 8.02 (s, 1H), 7.91 (d, J = 4.1 Hz, 1H), 7.90 (s, 1H), 7.63 (d, J = 4.1 Hz, 1H), 3.93 (s, 3H) | 5-(7-amino-2-thieno[2,3-c]pyridin-3-yl-furo[2,3-c]pyridin-4-yl)-thiophene-2-carboxylic acid methyl ester | 408.15 | 0.75 (UPLC: Analytical_2 min) |

| Ex. # | Structure and NMR Data | Compound name | MS (ESI) [M + H]+ | HPLC $t_R$ (min) |
|---|---|---|---|---|
| 383 | ¹H NMR (400 MHz, CD₃OD): δ 9.47 (s, 1H), 9.05 (s, 1H), 8.76 (d, J = 6.1 Hz, 1H), 8.68 (d, J = 6.1 Hz, 1H), 8.06 (s, 1H), 7.84 (d, J = 5.6 Hz, 1H), 7.75 (s, 1H), 7.55 (d, J = 5.6 Hz, 1H) | 2-(7-amino-2-thieno[2,3-c]pyridin-3-yl-furo[2,3-c]pyridin-4-yl)-thiophene-3-carbonitrile | 375.13 | 0.67 (UPLC: Analytical_2 min) |
| 384 | ¹H NMR (400 MHz, CD₃OD): δ 9.46 (s, 1H), 9.03 (s, 1H), 8.76 (d, J = 6.1 Hz, 1H), 8.68 (d, J = 6.1 Hz, 1H), 8.11 (d, J = 5.1 Hz, 1H), 8.02 (s, 1H), 7.70 (s, 1H), 7.61 (d, J = 5.1 Hz, 1H) | 3-(7-amino-2-thieno[2,3-c]pyridin-3-yl-furo[2,3-c]pyridin-4-yl)-thiophene-2-carbonitrile | 375.13 | 0.63 (UPLC: Analytical_2 min) |
| 385 | ¹H NMR (400 MHz, CD₃OD): δ 9.49 (s, 1H), 9.13 (s, 1H), 8.82 (d, J = 6.1 Hz, 1H), 8.70 (d, J = 6.1 Hz, 1H), 7.95 (d, J = 6.1 Hz, 2H), 7.73 (m, 2H), 7.59 (d, J = 3.8 Hz, 1H), 7.54 (d, J = 3.8 Hz, 1H), 7.44 (m, 2H), 7.35 (m, 1H) | 4-(5-phenyl-thiophen-2-yl)-2-thieno[2,3-c]pyridin-3-yl-furo[2,3-c]pyridin-7-ylamine | 426.19 | 1.01 (UPLC: Analytical_2 min) |
| 386 | ¹H NMR (400 MHz, CD₃OD): δ 9.51 (s, 1H), 9.10 (s, 1H), 8.85 (d, J = 6.1 Hz, 1H), 8.68 (d, J = 6.1 Hz, 1H), 8.26 (s, 1H), 8.01 (s, 1H), 7.86 (s, 1H), 7.83 (s, 1H), 2.48 (s, 3H) | 4-(5-methyl-thiophen-2-yl)-2-thieno[2,3-c]pyridin-3-yl-furo[2,3-c]pyridin-7-ylamine | 364.22 | 0.76 (UPLC: Analytical_2 min) |

| Ex. # | Structure and NMR Data | Compound name | MS (ESI) [M + H]+ | HPLC t_R (min) |
|---|---|---|---|---|
| 387 | ¹H NMR (400 MHz, CD₃OD): δ 9.46 (s, 1H), 9.09 (s, 1H), 8.77-8.83 (m, 1H), 8.70 (d, J = 6.1 Hz, 1H), 7.95 (d, J = 5.6 Hz, 2H), 7.02 (d, J = 3.5 Hz, 1H), 6.28 (dd, J = 3.5, 1.0 Hz, 1H), 2.45 (s, 3H) | 4-(5-methylfuran-2-yl)-2-(thieno[2,3-c]pyridin-3-yl)furo[2,3-c]pyridin-7-amine trifluoroacetate | 348.38 | 0.54 (UPLC: Purity_2 min) |
| 388 | ¹H NMR (400 MHz, CD₃OD): δ 9.48 (s, 1H), 9.10 (s, 1H), 8.81 (d, J = 5.8 Hz, 1H), 8.70 (d, J = 6.1 Hz, 1H), 8.07 (s, 1H), 7.92 (s, 1H), 7.84 (s, 1H), 2.81 (s, 3H) | 4-(2-methyl-1,3-thiazol-5-yl)-2-(thieno[2,3-c]pyridin-3-yl)furo[2,3-c]pyridin-7-amine trifluoroacetate | 365.33 | 0.45 (UPLC: Purity_2 min) |
| 389 | ¹H NMR (400 MHz, CD₃OD): δ 9.48 (s, 1H), 9.06 (s, 1H), 8.76-8.80 (m, 1H), 8.68 (d, J = 6.1 Hz, 1H), 7.65 (s, 1H), 7.56 (s, 1H), 6.91-6.96 (m, 1H), 6.40 (dd, J = 3.5, 1.8 Hz, 1H), 6.25 (dd, J = 3.5, 2.8 Hz, 1H), 3.68 (s, 3H) | 4-(1-methyl-1H-pyrrol-3-yl)-2-(thieno[2,3-c]pyridin-3-yl)furo[2,3-c]pyridin-7-amine trifluoroacetate | 347.38 | 0.47 (UPLC: Purity_2 min) |

| Ex. # | Structure and NMR Data | Compound name | MS (ESI) [M + H]+ | HPLC t_R (min) |
|---|---|---|---|---|
| 390 | 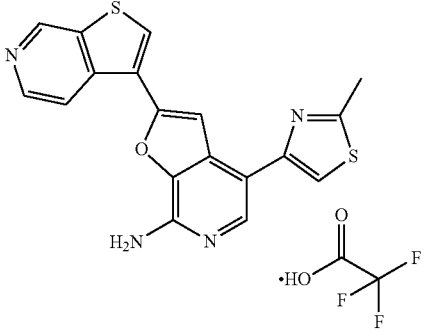<br>¹H NMR (400 MHz, CD₃OD): δ 9.47 (s, 1H), 9.07 (s, 1H), 8.80 (dd, J = 6.1, 0.8 Hz, 1H), 8.70 (d, J = 6.1 Hz, 1H), 8.23 (s, 1H), 8.08 (s, 1H), 7.99 (s, 1H), 2.84 (s, 3H). | 4-(2-methyl-1,3-thiazol-4-yl)-2-(thieno[2,3-c]pyridin-3-yl)furo[2,3-c]pyridin-7-amine trifluoroacetate | 365.33 | 0.47 (UPLC: Purity_2 min) |
| 391 | 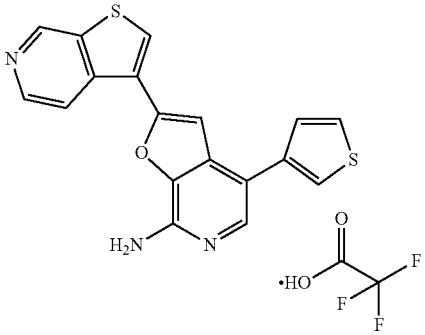<br>¹H NMR (400 MHz, CD₃OD): δ 9.47 (s, 1H), 9.07 (s, 1H), 8.80 (d, J = 5.8 Hz, 1H), 8.69 (d, J = 5.8 Hz, 1H), 7.93 (dd, J = 2.9, 1.4 Hz, 1H), 7.88 (d, J = 8.3 Hz, 2H), 7.69 (dd, J = 5.1, 3.0 Hz, 1H), 7.56 (dd, J = 5.1, 1.3 Hz, 1H) | 2-(thieno[2,3-c]pyridin-3-yl)-4-(thiophen-3-yl)furo[2,3-c]pyridin-7-amine trifluoroacetate | 350.35 | 0.50 (UPLC: Purity_2 min) |
| 392 | 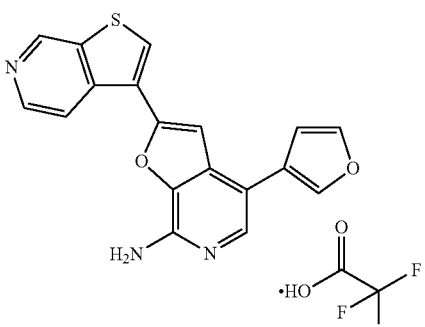<br>¹H NMR (400 MHz, CD₃OD): δ 9.47 (s, 1H), 9.07 (s, 1H), 8.82 (d, J = 6.1 Hz, 1H), 8.69 (d, J = 6.1 Hz, 1H), 8.25 (s, 1H), 7.86 (s, 2H), 7.74 (t, J = 1.6 Hz, 1H), 6.94-7.00 (m, 1H). | 4-(furan-3-yl)-2-(thieno[2,3-c]pyridin-3-yl)furo[2,3-c]pyridin-7-amine trifluoroacetate | 334.33 | 0.45 (UPLC: Purity_2 min) |

Example 393

4-(5-methylthiophen-3-yl)-2-(thieno[2,3-c]pyridin-3-yl)furo[2,3-c]pyridin-7-amine trifluoroacetate

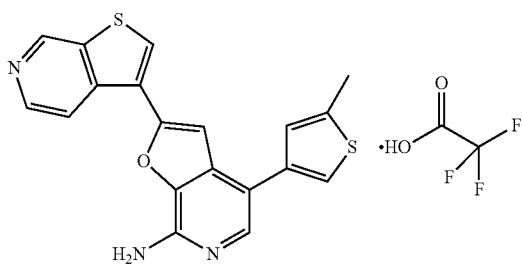

Step A: (5-methylthiophen-3-yl)boronic Acid

4-Bromo-2-methylthiophene (300 mg, 1.69 mmol) and triisopropyl borate (486 μL, 2.12 mmol) were dissolved in THF (1 mL) and the solution was vacuumed and filled with $N_2$ 3 times. The solution was cooled to −70° C. using an acetone/dry ice bath. 2.5 M of n-BuLi in hexane (1.0 mL, 2.54 mmol) was added drop wise and the mixture was stirred for an additional 30 minutes while the temperature was held at −70° C. The reaction mixture was allowed to warm up to −20° C. and 2 mL of 3 N HCl was added. When the mixture was warmed up to room temperature, two layers were separated. The water layer was neutralized to about pH 7, using 5 N NaOH. Both layers were extracted with EtOAc and washed with brine. The organic layer was dried over anhydrous $Na_2SO_4$. The material was not further purified and was used directly in the next step. MS (ESI): 143.05 [M+H]$^+$; HPLC $t_R$=1.30 min (HPLC: Anayltical_2 min).

Step B: 4-(5-methylthiophen-3-yl)-2-(thieno[2,3-c]pyridin-3-yl)furo[2,3-c]pyridin-7-amine trifluoroacetate (Title Compound)

The title compound was prepared from 4-iodo-2-thieno[2,3-c]pyridine-3-yl-furo[2,3-c]pyridine-7-ylamine and (5-methylthiophen-3-yl)boronic acid by a procedure analogous to Example 68. $^1$H NMR (400 MHz, DMSO-d$_6$): δ 9.50 (s, 1 H), 9.06-9.13 (m, 1 H), 8.79 (d, J=5.8 Hz, 1 H), 8.70 (d, J=5.6 Hz, 1 H), 8.61 (br. s., 2 H), 7.99 (s, 1 H), 8.03 (s, 1 H), 7.84 (d, J=1.3 Hz, 1 H), 7.35 (s, 1 H), 2.56 (s, 3 H); MS (ESI): 364.34 [M+H]$^+$; HPLC $t_R$=0.57 min (HPLC: Purity_2 min).

The following Examples were prepared from (2-thieno[2,3-c]pyridin-3-yl-4-trimethylstannanyl-furo[2,3-c]pyridin-7-yl)-bis-carbamic acid tert-butyl ester and an appropriate aryl bromide or iodide by procedures analogous to Example 342, Steps A and B.

| Ex. # | Structure and NMR Data | Compound name | MS (ESI) [M + H]$^+$ | HPLC $t_R$ (min) |
|---|---|---|---|---|
| 394 | $^1$H NMR (400 MHz, CD$_3$OD): δ 9.54 (s, 1H), 9.11 (s, 1H), 8.83 (d, J = 6.0 Hz, 1H), 8.71 (d, J = 6.0 Hz, 1H), 7.80 (s, 1H), 7.59 (s, 1H), 2.78 (s, 3H), 2.42 (s, 3H) | 4-(2,4-dimethyl-thiazol-5-yl)-2-thieno[2,3-c]pyridin-3-yl-furo[2,3-c]pyridin-7-ylamine | 379.12 | 0.56 (UPLC: Analytical_2 min) |
| 395 | $^1$H NMR (400 MHz, CD$_3$OD): δ 9.50 (s, 1H), 9.15 (s, 1H), 9.03 (s, 1H), 8.77 (d, J = 6.1 Hz, 1H), 8.68 (d, J = 6.1 Hz, 1H), 7.96 (s, 1H), 7.88 (d, J = 1.5 Hz, 1H), 7.61 (s, 1H), 3.89 (s, 3H) | 4-(1-methyl-1H-imidazol-4-yl)-2-thieno[2,3-c]pyridin-3-yl-furo[2,3-c]pyridin-7-ylamine | 348.11 | 0.29 (UPLC: Analytical_2 min) |

| Ex. # | Structure and NMR Data | Compound name | MS (ESI) [M + H]+ | HPLC $t_R$ (min) |
|---|---|---|---|---|
| 396 | ¹H NMR (400 MHz, CD₃OD): δ 9.53 (s, 1H), 9.20 (d, J = 1.8 Hz, 1H), 9.14 (s, 1H), 8.88 (d, J = 6.0 Hz, 1H), 8.71 (d, J = 6.0 Hz, 1H), 8.28 (s, 1H), 8.22 (d, J = 1.8 Hz, 1H), 8.13 (s, 1H) | 4-thiazol-4-yl-2-thieno[2,3-c]pyridin-3-yl-furo[2,3-c]pyridin-7-ylamine | 351.10 | 0.54 (UPLC: Analytical_2 min) |
| 397 | ¹H NMR (400 MHz, CD₃OD): δ 9.44 (s, 1H), 8.95 (s, 1H), 8.66 (s, 2H), 7.91 (s, 1H), 7.73 (s, 1H), 7.57 (s, 1H), 3.71 (s, 3H), 2.77 (s, 3H) | 4-(2,3-dimethyl-3H-imidazol-4-yl)-2-thieno[2,3-c]pyridin-3-yl-furo[2,3-c]pyridin-7-ylamine | 362.08 | 0.31 (UPLC: Analytical_2 min) |
| 398 | ¹H NMR (400 MHz, CD₃OD): δ 9.42 (s, 1H), 8.99 (s, 1H), 8.76 (d, J = 6.1 Hz, 1H), 8.68 (d, J = 6.1 Hz, 1H), 7.75 (s, 1H), 7.51 (s, 1H), 7.10 (d, J = 4.0 Hz, 1H), 6.44 (d, J = 4.0 Hz, 1H), 3.89 (s, 3H), 3.86 (s, 3H) | 4-(7-amino-2-thieno[2,3-c]pyridin-3-yl-furo[2,3-c]pyridin-4-yl)-1-methyl-1H-pyrrole-2-carboxylic acid methyl ester | 405.06 | 0.71 (UPLC: Analytical_2 min) |

Example 399

3-chloro-2-(1H-indazol-5-yl)-4-[1-(piperidin-4-yl)-1H-pyrazol-4-yl]furo[2,3-c]pyridin-7-amine hydrochloride

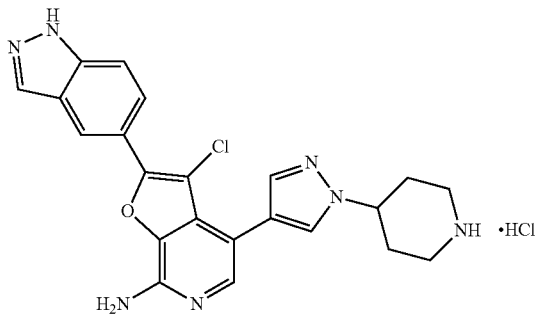 [SMILES: Nc1ncc(-c2cnn(C3CCNCC3)c2)c2c(Cl)c(-c3ccc4[nH]ncc4c3)oc12 ; Cl]

The title compound was prepared by a procedure analogous to Example 12. ¹H NMR (400 MHz, CD₃OD): δ 8.73 (s, 1H), 8.20-8.27 (m, 2H), 8.05 (s, 1H), 7.81 (s, 1H), 7.75 (d, J=8.8 Hz, 1H), 7.61-7.61 (m, 1H), 4.66 (tt, J=10.1, 4.9 Hz, 1H), 3.61 (dt, J=13.1, 2.9 Hz, 2H), 3.18-3.29 (m, 2H), 2.28-2.45 (m, 4H); MS (ESI): 435.90, 436.99 [M+H]⁺; HPLC t$_R$=2.04 min (ZQ3: polar_5 min).

Example 400

3-{4-[7-amino-2-(isoquinolin-5-yl)furo[2,3-c]pyridin-4-yl]-3,5-dimethyl-1H-pyrazol-1-yl}propane-1,2-diol

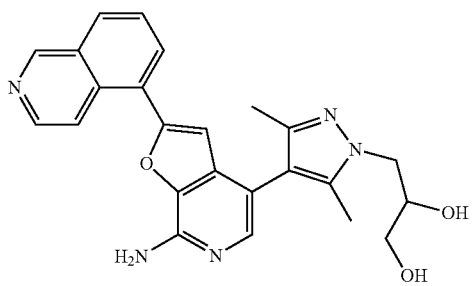 [SMILES: Cc1nn(CC(O)CO)c(C)c1-c1cnc(N)c2oc(-c3cccc4cnccc34)cc12]

The title compound was prepared sequentially by procedures analogous to Examples 68 and 66. ¹H NMR (400 MHz, CD₃OD): δ 9.33 (d, J=0.8 Hz, 1H), 8.56 (d, J=6.1 Hz, 1H), 8.43 (dt, J=6.2, 0.8 Hz, 1H), 8.30 (dd, J=7.3, 1.3 Hz, 1H), 8.18-8.26 (m, 1H), 7.82 (dd, J=8.2, 7.5 Hz, 1H), 7.61 (s, 1H), 7.07 (s, 1H), 3.99-4.33 (m, 3H), 3.50-3.71 (m, 2H), 2.29 (s, 3H), 2.19 (s, 3H); MS (ESI): 430.17 [M+H]⁺; HPLC t$_R$=0.79 min (TOF: polar_3 min).

Example 401 trans-4-(4-{7-amino-2-[3,5-bis(trifluoromethyl)phenyl]furo[2,3-d]pyridin-4-yl}-1H-pyrazol-1-yl)cyclohexanol

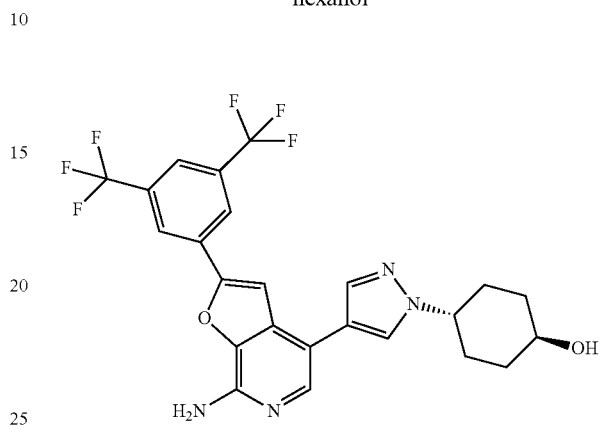

Step A: 2-[3,5-bis(trifluoromethyl)phenyl]-4-[1-(trans-4-{[tert-butyl(dimethyl)silyl]oxy}cyclohexyl)-1H-pyrazol-4-yl]furo[2,3-c]pyridin-7-amine A mixture of 4-[1-(trans-4-{[tert-butyl(dimethyl)silyl]oxy}cyclohexyl)-1H-pyrazol-4-yl]-2-chlorofuro[2,3-c]pyridin-7-amine (83 mg, 0.18 mmol), 3,5-bis(trifluoromethyl)benzeneboronic acid (71 mg, 0.28 mmol), (1,1'-bis-(diphenylphosphino)ferrocene)palladium dichloride (13.5 mg, 0.0186 mmol), and potassium carbonate (77 mg, 0.56 mmol) in 1,4-dioxane (1.0 mL) and water (0.30 mL) was degassed 3× with argon and heated in a microwave reactor at 100° C. for 1 h. The mixture was partitioned between EtOAc and brine and the aqueous phase was extracted with EtOAc. The combined organic fractions were dried over sodium sulfate and concentrated. Purification of the residue by ISCO chromatography (0 to 5% 7 N NH₃/MeOH:DCM) afforded 104 mg (90%) of the title compound as a foam. ¹H NMR (400 MHz, CDCl₃): δ 0.06-0.14 (m, 6H) 0.87-0.98 (m, 9H) 1.49-1.64 (m, 2H) 1.85-2.11 (m, 4H) 2.18-2.33 (m, 2H) 3.69-3.82 (m, 2H), 4.17-4.28 (m, 1H), 5.05 (br. s., 1H) 7.34 (s, 1H) 7.70 (s, 1H) 7.82 (s, 1H) 7.92 (s, 1H) 8.00 (s, 1H) 8.31 (s, 2H); MS (ESI): 624.34 [M+H]⁺; HPLC t$_R$=2.00 min (TOF: nonpolar_3 min).

Step B: trans-4-(4-{7-amino-2-[3,5-bis(trifluoromethyl)phenyl]furo[2,3-c]pyridin-4-yl}-1H-pyrazol-1-yl)cyclohexanol (Title Compound)

A solution of 2-[3,5-bis(trifluoromethyl)phenyl]-4-[1-(4-{[tert-butyl(dimethyl)silyl]oxy}cyclohexyl)-1H-pyrazol-4-yl]furo[2,3-c]pyridin-7-amine (104 mg) in THF (2 mL) was treated with tetra-n-butylammonium fluoride (2.7 M in water, 0.20 mL, 0.56 mmol) and stirred at RT overnight. The solution was diluted with EtOAc and washed with brine. The aqueous phase was extracted with EtOAc and the combined organic fractions were dried over sodium sulfate and concentrated. Purification of the residue by ISCO chromatography (0 to 5% 7 N NH₃/MeOH:EtOAc) afforded 33 mg (35%) of the title compound as a yellow solid. ¹H NMR (400 MHz, CD$_3$OD): δ 1.48-1.60 (m, 2H) 2.01 (qd, J=12.7, 3.2 Hz, 2H) 2.10-2.26 (m, 4H) 3.73 (tt, J=10.9, 4.1 Hz, 1H) 4.26 (tt, J=11.9, 3.9 Hz, 1H) 7.88 (s, 1H) 7.91-7.94 (m, 2H) 8.00-8.03 (m, 1H) 8.12-8.15 (m, 1H) 8.67 (s, 2H); MS (ESI): 510.34 [M+H]$^+$; HPLC t$_R$=1.16 min (TOF: polar_3 min).

Example 402 trans-4-{4-[7-amino-2-(1H-indazol-5-yl)furo[2,3-c]pyridin-4-yl]-1H-pyrazol-1-yl}cyclohexanol

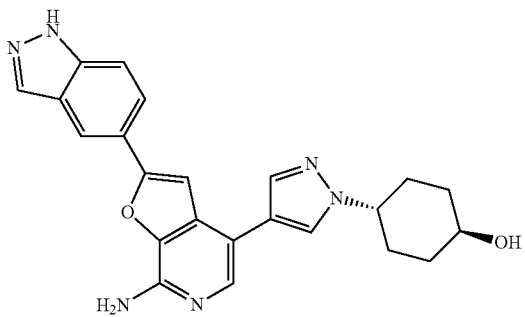 [SMILES: Nc1ncc(-c2cnn([C@H]3CC[C@H](O)CC3)c2)c2cc(-c3ccc4[nH]ncc4c3)oc12]

The title compound was prepared by a procedure analogous to Example 401. MS (ESI): 415.15 [M+H]$^+$; HPLC t$_R$=0.89 min (TOF: polar_3 min).

Example 403

6-{7-amino-4-[1-(trans-4-hydroxycyclohexyl)-1H-pyrazol-4-yl]furo[2,3-c]pyridin-2-yl}-2,3-dihydro-1H-isoindol-1-one

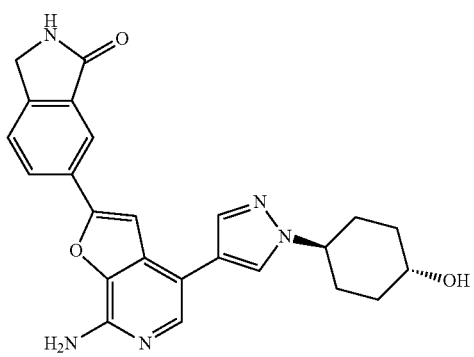 [SMILES: Nc1ncc(-c2cnn([C@H]3CC[C@H](O)CC3)c2)c2cc(-c3ccc4c(c3)C(=O)NC4)oc12]

Step A: 6-{7-amino-4-[1-(trans-4-{[tert-butyl(dimethyl)silyl]oxy}cyclohexyl)-1H-pyrazol-4-yl]furo[2,3-c]pyridin-2-yl}-2,3-dihydro-1H-isoindol-1-one To a solution of 4-{1-[4-(tert-butyl-dimethyl-silanyloxy)-cyclohexyl]-1H-pyrazol-4-yl}-2-chloro-furo[2,3-c]pyridin-7-ylamine (50.0 mg, 0.112 mmol) in DME (0.894 mL) was added 6-(4,4,5,5-tetramethyl-1,3,2-dioxaborolan-2-yl)isoindolin-1-one (43.5 mg, 0.168 mmol), sodium carbonate (2.0 M in water, 0.089 mL, 0.18 mmol), and Pd(PPh$_3$)$_4$ (20 mg, 0.02 mmol) and the reaction mixture was heated at 120° C. for 15 min in a microwave reactor. The reaction mixture was then concentrated. Purification of the residue by ISCO chromatography (0 to 5% 7 N NH3/MeOH:EtOAc) afforded 49 mg (80%) of the title compound.

Step B: 6-{7-amino-4-[1-(trans-4-hydroxycyclohexyl)-1H-pyrazol-4-yl]furo[2,3-c]pyridin-2-yl}-2,3-dihydro-1H-isoindol-1-one (Title Compound)

To a solution of 6-{7-amino-4-[1-(trans-4-{[tert-butyl(dimethyl)silyl]oxy}cyclohexyl)-1H-pyrazol-4-yl]furo[2,3-c]pyridin-2-yl}-2,3-dihydro-1H-isoindol-1-one in THF (2.4 mL) was added tetra-n-butylammonium fluoride (1.0 M in THF, 2.4 mL, 2.4 mmol). After 4 h, the reaction was diluted into EtOAc and washed with sodium bicarbonate and water. The aqueous layer was concentrated. The residual solid was rinsed with MeOH and EtOAc thoroughly, then purified by ISCO chromatography (0 to 10% 7 N NH$_3$/MeOH:EtOAc) to afford 1.5 mg (3%) of the title compound. $^1$H NMR (400 MHz, CD$_3$OD): δ 8.44 (s, 1H), 8.34 (d, J=7.8 Hz, 1H), 8.16 (s, 1H), 7.92 (d, J=5.3 Hz, 2 H), 7.76 (d, J=8.1 Hz, 1H), 7.63 (s, 1H), 4.56-4.58 (m, 2H), 4.23-4.34 (m, 1H), 3.67-3.78 (m, 1H), 2.11-2.25 (m, 4H), 1.97-2.08 (m, 2H), 1.54 (m, 2H); MS (ESI): 430.17 [M+H]$^+$; HPLC t$_R$=0.90 min (TOF: polar_3 min).

The following Examples were prepared from 4-{1-[4-(tert-butyl-dimethyl-silanyloxy)-cyclohexyl]-1H-pyrazol-4-yl}-2-chloro-furo[2,3-c]pyridin-7-ylamine and an appropriate boronic acid or ester by a procedure analogous to Example 403. In Example 407, the silyl ether was removed by treatment with hydrochloric acid in water and ethanol.

| Ex. # | Structure and NMR Data | Compound name | MS (ESI) [M + H]+ | HPLC $t_R$ (min) |
|---|---|---|---|---|
| 404 | | 5-{7-amino-4-[1-(trans-4-hydroxycyclohexyl)-1H-pyrazol-4-yl]furo[2,3-c]pyridin-2-yl}-2,3-dihydro-1H-isoindol-1-one | 430.16 | 0.88 (TOF: polar_3 min) |
| 405 | 1H NMR (400 MHz, CD3OD): δ 8.44 (s, 1H), 8.34 (d, J = 7.8 Hz, 1H), 8.16 (s, 1H), 7.92 (d, J = 5.3 Hz, 2H), 7.76 (d, J = 8.1 Hz, 1H), 7.63 (s, 1H), 4.56-4.58 (m, 2H), 4.23-4.34 (m, 1H), 3.67-3.78 (m, 1H), 2.11-2.25 (m, 4H), 1.97-2.08 (m, 2H), 1.54 (m, 2H) | 5-{7-amino-4-[1-(trans-4-hydroxycyclohexyl)-1H-pyrazol-4-yl]furo[2,3-c]pyridin-2-yl}-1,3-dihydro-2H-indol-2-one | 430.17 | 0.90 (TOF: polar_3 min) |
| 406 | 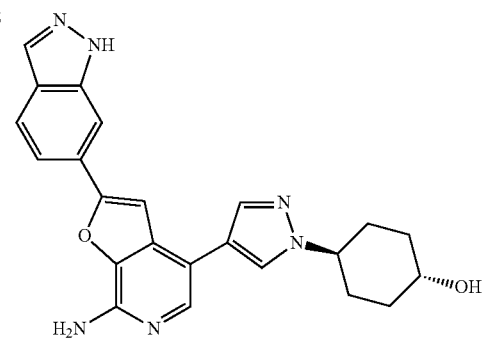 1H NMR (400 MHz, CD3OD): δ 8.21 (s, 1H), 8.10 (m, J = 5.3 Hz, 2H), 7.80-7.92 (m, 4H), 7.53 (s, 1H), 4.13-4.41 (m, 1H), 3.68 (m, J = 10.9 Hz, 1H), 2.06-2.28 (m, 4H), 1.93-2.04 (m, 2H), 1.50 (m, J = 11.9 Hz, 2H) | trans-4-{4-[7-amino-2-(1H-indazol-6-yl)furo[2,3-c]pyridin-4-yl]-1H-pyrazol-1-yl}cyclohexanol | | |

| Ex. # | Structure and NMR Data | Compound name | MS (ESI) [M + H]+ | HPLC $t_R$ (min) |
|---|---|---|---|---|
| 407 | 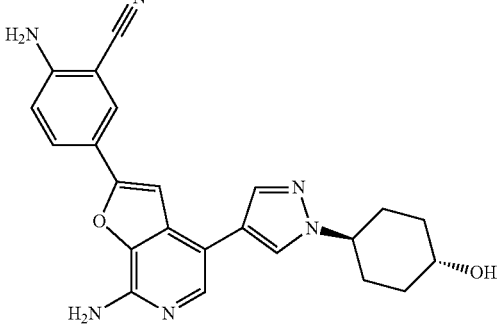<br>¹H NMR (400 MHz, CD₃OD): δ 8.11 (d, J = 2.0 Hz, 1H), 8.10 (s, 1H), 7.99 (dd, J = 8.7, 2.2 Hz, 1H), 7.89 (s, 1H), 7.87 (s, 1H), 7.30 (s, 1H), 6.96 (d, J = 8.8 Hz, 1H), 4.21-4.33 (m, 1H), 3.67-3.77 (m, 1H), 2.10-2.24 (m, 4H), 1.97-2.08 (m, 2H), 1.46-1.59 (m, 2H) | 2-amino-5-{7-amino-4-[1-(trans-4-hydroxycyclohexyl)-1H-pyrazol-4-yl]furo[2,3-c]pyridin-2-yl}benzonitrile | 415.16 | 0.9 (TOF: polar_3 min) |

The following Examples were prepared from 1-{4-[4-(7-amino-2-chlorofuro[2,3-c]pyridin-4-yl)-1H-pyrazol-1-yl]piperidin-1-yl}ethanone and an appropriate boronic acid or ester by a procedure analogous to Example 86. Boronic esters were prepared as needed from the corresponding aryl bromides or iodides by a procedure analogous to Intermediate 59, Step E.

| Ex. # | Structure and NMR Data | Compound name | MS (ESI) [M + H]+ | HPLC $t_R$ (min) |
|---|---|---|---|---|
| 408 | 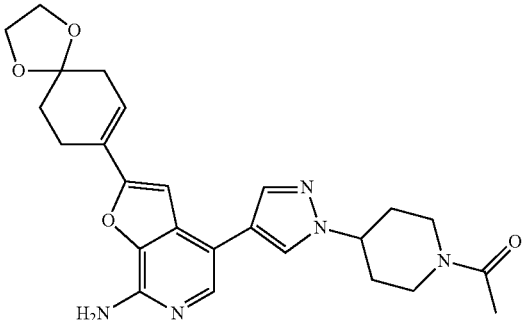 | 1-(4-{4-[7-amino-2-(1,4-dioxaspiro[4.5]dec-7-en-8-yl)furo[2,3-c]pyridin-4-yl]-1H-pyrazol-1-yl}piperidin-1-yl)ethanone | 464.14 | 2.32 |
| 409 | 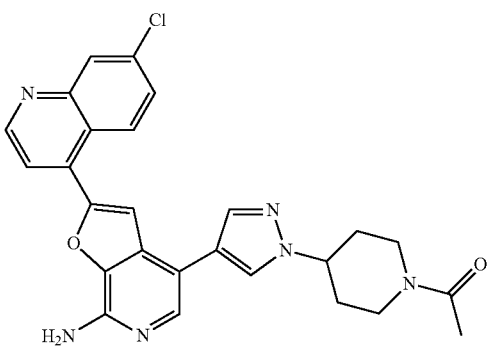 [SMILES: CC(=O)N1CCC(n2cc(-c3cnc(N)c4oc(-c5ccnc6cc(Cl)ccc56)cc34)cn2)CC1]<br>1H NMR (400 MHz, CDCl₃): δ 9.02-9.03 (d, J = 4.4 Hz, 1H), 8.35-8.37 (d, J = 9.2 Hz, 1H), 8.21 (s, 1H), 7.98 (s, 1H), 7.83 (s, 1H), 7.75-7.76 (d, J = 4.4 Hz, 1H), 7.70 (s, 1H), 7.60-7.62 (m, 1H), 7.34 (s, 1H), 5.30-5.37 (s, 2H), 4.76-4.79 (d, J = 12 Hz, 1H), 4.40-4.45 (m, 1H), 3.98-4.01 (d, J = 13.6 Hz, 1H), 3.27 (t, J = 12 Hz, 1H), 2.78 (t, J = 12 Hz, 1H), 2.21-2.32 (m, 2H), 2.15 (s, 3H), 1.97-2.03 (m, 2H) | 1-(4-{4-[7-amino-2-(7-chloroquinolin-4-yl)furo[2,3-c]pyridin-4-yl]-1H-pyrazol-1-yl}piperidin-1-yl)ethanone | 487.08 | 2.51 |

| Ex. # | Structure and NMR Data | Compound name | MS (ESI) [M + H]+ | HPLC t$_R$ (min) |
|---|---|---|---|---|
| 410 | | 1-(4-{4-[7-amino-2-(2-methylphenyl)furo[2,3-c]pyridin-4-yl]-1H-pyrazol-1-yl}piperidin-1-yl)ethanone | 416.13 | 2.44 |
| 411 | | 1-[4-(4-{7-amino-2-[2-(trifluoromethyl)phenyl]furo[2,3-c]pyridin-4-yl}-1H-pyrazol-1-yl)piperidin-1-yl]ethanone | 470.08 | 2.60 |

Biological Properties

In some aspects of the invention, compounds of the invention are inhibitors of one or more kinases, including TAK1. In some aspects of the invention, compounds of the invention are inhibitors of one or more kinases, such as but not limited to RON, MET, Auroras, KDR, PDGFRs, PKCs, HGK/Mink1, JAK2, or PRKD2, or others.

In some aspects of the invention, compounds of the invention are selective inhibitors of TAK1. In some embodiments, the compound is a selective inhibitor of TAK1 over other kinase targets, such as KDR and/or one or more Aurora kinases such as AKB.

In some aspects of the invention, compounds of the invention exhibit selectivity for TAK1 of at least about 5, or 10-fold over KDR and/or one or more Auroras.

The invention includes a compound of Formula I or a pharmaceutically acceptable salt thereof, in any of the above recitations, which exhibits inhibition of TAK1 in a cellular or biochemical assay with an IC$_{50}$ of about 1 µM or less, or about 100 nM or less.

The invention includes a compound of Formula I or a pharmaceutically acceptable salt thereof, which is sufficiently orally bioavailable for effective oral human administration.

The invention includes a compound of Formula I or a pharmaceutically acceptable salt thereof, which has a suitable therapeutic window for effective human administration, oral or otherwise.

Detailed below are ELISA assays for pJNK and p38, and a TAK1 biochemical assay. The pJNK and p38 ELISA data for compounds tested correlated by linear regression with TAK1 biochemical inhibition ($R^2$ values of 0.70 and 0.56, respectively). The p38 and pJNK data also correlated with each other ($R^2$=0.83). Results for compounds described herein are shown in Table 1. Results are shown in Table 1 according to the key: A, IC$_{50}$≦0.1 µM; B, 0.1 µM<IC$_{50}$≦1 µM; C, 1 µM<IC$_{50}$≦10 µM; D, IC$_{50}$>10 µM. In Table 1, Col. A shows mean TAK1 IC$_{50}$; Col. B shows mean HCT-116 pJNK ELISA IC$_{50}$; and Col. C shows mean HCT-116 p-p38 ELISA IC$_{50}$.

Phospho-JNK (Thr183/Tyr185) Meso Scale ELISA Assay

Day 1:
1. Plate HCT-116 cells at 25,000 per well in 100 uL in 96 well clear dishes in normal growth medium.

Day 2:
1. Aspirate medium and replace with 90 µl reduced serum growth medium (1% FCS), incubate for 2 hours at 37° C.
2. Make drugs at 10× in reduced serum medium and add 10 uL per well.
3. Incubate at 37° C. for 4 hrs.
4. Bring capture plates to room temperature.
5. Block with 150 µl Blocking Solution (provided with kit) (600 mg Blocker A into 20 mL 1× Wash Buffer per plate) at room temperature with shaking.
6. Wash plates 4× with 200 µl 1× wash buffer (10× provided with kit) before transferring lysates.
7. Dilute TNFα to 100 ng/µl in reduced serum medium (this makes a 10× working stock).
8. Add 10 µl TNFα to all wells except negative control wells, final concentration is 10 ng/mL.
9. Incubate at 37° C. for 10 minutes.
10. Remove medium by flicking into sink
11. Wash cells with 100 uL ice cold PBS.
12. Remove PBS by flicking into sink and patting on paper towels.
13. Lyse cells in 50 µl ice cold 1× Complete Lysis Buffer plus Phosphatase and Protease inhibitors (all provided with kit) (10 mL Tris Lysis Buffer+200 μl Protease inhibitor solution+100 μl Phosphatase inhibitor I+100 μl Phosphatase inhibitor II).
14. Incubate with shaking at 4° C. for 30 minutes.
15. Transfer 45 μl to capture plate, cover with adhesive cover, and incubate at 4° C. over night with shaking.

Day 3:
1. Wash plates 4× with 200 μl 1× wash buffer (10× provided with kit).
2. Add 25 μl of Anti-Phospho-JNK Ab in antibody dilution buffer (provided with kit) (Antibody Dilution Buffer-1 mL Blocking Solution+2 mL 1× Tris Wash Buffer+150 μl 2% Blocker D-M+30 μl Blocker D-R per plate) (Detection Antibody Solution-2.94 mL Antibody Dilution Buffer+60 μl 50× SULFO-TAG Anti-Phospho-JNK-Antibody (1× final concentration) per plate).
3. Incubate at room temperature with shaking for 1 hour.
4. Wash 4× with 200 μl 1× Wash Buffer.
5. Add 150 μl of 1× Read Buffer (provided with kit) (5 mL 4× Read Buffer T, with surfactant+15 mL deionized water), careful not to make any bubbles in the wells.
6. Read on Sector Imager.

Phospho-p38 Meso Scale ELISA Assay

Day 1:
1. Plate HCT-116 cells at 25,000 per well in 100 uL in 96 well clear dishes in normal growth medium.

zday 2:
1. Aspirate medium and replace with 90 μl reduced serum growth medium (1% FCS), incubate for 2 hours at 37° C.
2. Make drugs at 10× in reduced serum medium and add 10 uL per well.
3. Incubate at 37° C. for 4 hrs.
4. Bring capture plates to room temperature.
5. Block with 150 μl Blocking Solution (provided with kit) (600 mg Blocker A into 20 mL 1× Wash Buffer per plate) at room temperature with shaking.
6. Wash plates 4× with 200 μl 1× wash buffer (10× provided with kit) before transferring lysates.
7. Dilute TNFα to 100 ng/μl in reduced serum medium (this makes a 10× working stock).
8. Add 10 μl TNFα to all wells except negative control wells, final concentration is 10 ng/mL.
9. Incubate at 37° C. for 10 minutes.
10. Remove medium by flicking into sink
11. Wash cells with 100 uL ice cold PBS.
12. Remove PBS by flicking into sink and patting on paper towels.
13. Lyse cells in 50 μl ice cold 1× Complete Lysis Buffer plus phosphatase and protease inhibitors (all provided with kit) (10 mL Tris Lysis Buffer+200 μl Protease inhibitor solution+100 μl Phosphatase inhibitor I+100 μl Phosphatase inhibitor II).
14. Incubate with shaking at 4° C. for 30 minutes.
15. Dilute lysates before transferring to capture plate with 100 μl Complete p38 Lysate Dilution Buffer (provided with kit) (10 mL of Diluent 20±200 μl Protease inhibitor solution+100 μl Phosphatase inhibitor I+100 μl Phosphatase inhibitor II).
16. Transfer 50 μl of diluted lysates to capture plate, cover with adhesive cover, and incubate at 4° C. over night with shaking.

Day 3:
1. Wash plates 4× with 200 μl 1× wash buffer (10× provided with kit).
2. Add 25 μl of Anti-Total-p38 Ab in antibody dilution buffer (provided with kit) (p38 Antibody Dilution Buffer-75 mg Blocker B+15 mL p38 Incomplete Dilution Buffer (Diluent 20) per plate) (Detection Antibody Solution-2.94 mL Antibody Dilution Buffer+60 μl 50× SULFO-TAG Anti-Total-p38-Antibody (1× final concentration) per plate).
3. Incubate at room temperature with shaking for 1 hour.
4. Wash 4× with 200 μl 1× Wash Buffer.
5. Add 150 μl of 1× Read Buffer (provided with kit) (5 mL 4× Read Buffer T, with surfactant+15 mL deionized water), careful not to make any bubbles in the wells!
6. Read on Sector Imager.

TAK1 Biochemical Assay

Compound preparation: Compounds were received in powder form and diluted to 10 mM in 100% DMSO. 10 mM stocks were subsequently diluted to an initial concentration of 0.75 mM, and serially diluted by factors of three in 100% DMSO. 3 μL of each dilution were transferred to 384 well polypropylene plates and diluted with 22 μL H20 to produce working compound plates containing 3× assay concentrations in 12% DMSO. TAK1 activity assays: The inactive mutant of MAP2K7 containing an N-terminal Glutathione-S-Transferase fusion was used as a specific TAK1 substrate (Carna). For activity assays, to each well was added 2.5 μL 3× substrate solution (15 mM Tris, pH7.4, 10 mM MgCl$_2$, 0.01% Tween-20, 0.03% BSA, 2 mM DTT, 186 nM GST-MAP2K$_7$, 300 μM ATP) and 2.5 μL compound from the prepared working plates. Background control wells containing substrate solution lacking ATP were included in all test plates. Reactions were initiated by the addition of 0.088 nM TAK1-TAB1 fusion protein (Carna) in TAK1 assay buffer (15 mM Tris, pH7.4, 10 mM MgCl$_2$, 0.01% Tween-20, 0.03% BSA, 2 mM DTT) and allowed to incubate for 30 minutes at ambient temperature. Detection solution was prepared by diluting both phospho-MKK7 antibody (1:800, Cell Signaling) and AlphaScreen protein A acceptor beads (1:200, Perkin Elmer) into detection buffer (25 mM Tris pH7.5, 200 mM NaCl, 100 mM EDTA, 0.3% BSA, 0.1% Triton X-100) and incubating for 45 minutes with agitation, protected from light. At the end of the enzymatic reaction AlphaScreen glutathione donor beads (1:200, Perkin Elmer) was diluted into the detection solution and reactions were terminated by the addition of 5 uL of complete detection solution. Plates were then incubated for 4 hours at ambient temperature in the dark to allow signal development and read on an EnVision (Perkin-Elmer) plate reader with standard AlphaScreen settings.

TABLE 1

| Structure | Ex. No. | A | B | C |
|---|---|---|---|---|
| (3,5-bis(trifluoromethyl)phenyl furopyridine amine with pyrazole-piperidine) | 1 | | | C |
| (2-phenyl furopyridine amine with pyrazole-piperidine) | 2 | | | C |
| (2-(naphthalen-1-yl) furopyridine amine with pyrazole-piperidine) | 3 | | | C |
| (2-(2,3-dichlorophenyl) furopyridine amine with pyrazole-piperidine) | 4 | | | C |
| (2-(3-fluoro-2-methoxyphenyl) furopyridine amine with pyrazole-piperidine) | 5 | | | C |

TABLE 1-continued

| Structure | Ex. No. | A | B | C |
|---|---|---|---|---|
| 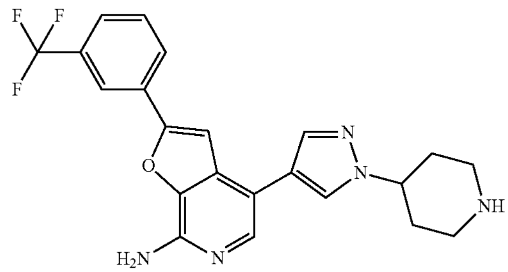 [SMILES: Nc1ncc(-c2cnn(C3CCNCC3)c2)c2cc(-c3cccc(C(F)(F)F)c3)oc12] | 6 | | | C |
| 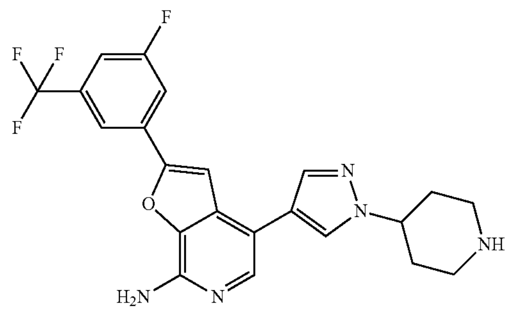 [SMILES: Nc1ncc(-c2cnn(C3CCNCC3)c2)c2cc(-c3cc(F)cc(C(F)(F)F)c3)oc12] | 7 | | | C |
| 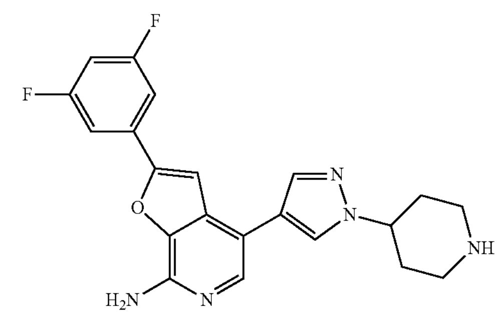 [SMILES: Nc1ncc(-c2cnn(C3CCNCC3)c2)c2cc(-c3cc(F)cc(F)c3)oc12] | 8 | | | C |
| 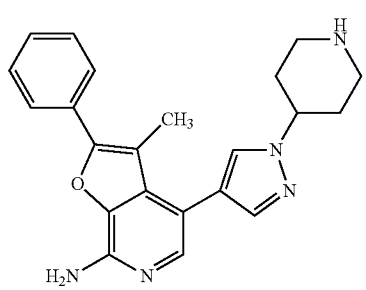 [SMILES: Cc1c(-c2ccccc2)oc2c(N)ncc(-c3cnn(C4CCNCC4)c3)c12] | 9 | | | C |
| 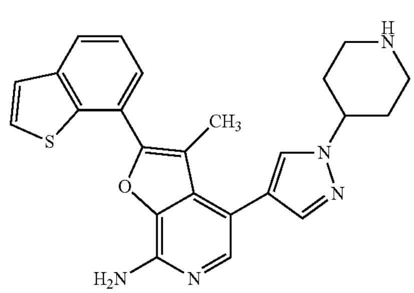 [SMILES: Cc1c(-c2cccc3ccsc23)oc2c(N)ncc(-c3cnn(C4CCNCC4)c3)c12] | 10 | | | C |

TABLE 1-continued

| Structure | Ex. No. | A | B | C |
|---|---|---|---|---|
| 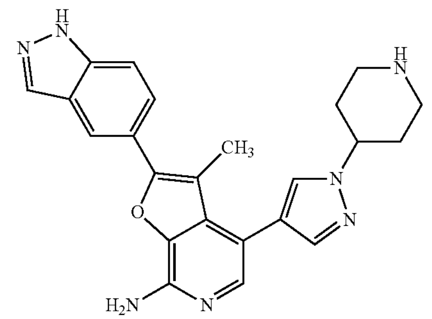 [SMILES: Cc1c(-c2ccc3[nH]ncc3c2)oc2c(N)ncc(-c3cnn(C4CCNCC4)c3)c12] | 11 | | | C |
| 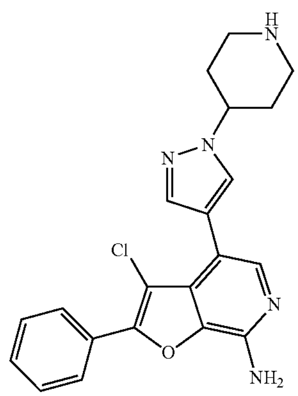 [SMILES: Nc1ncc(-c2cnn(C3CCNCC3)c2)c2c(Cl)c(-c3ccccc3)oc12] | 12 | | B | |
| 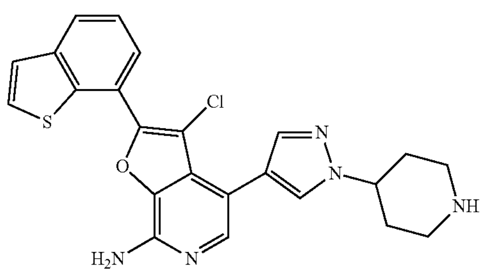 [SMILES: Nc1ncc(-c2cnn(C3CCNCC3)c2)c2c(Cl)c(-c3cccc4ccsc34)oc12] | 13 | A | | |
| 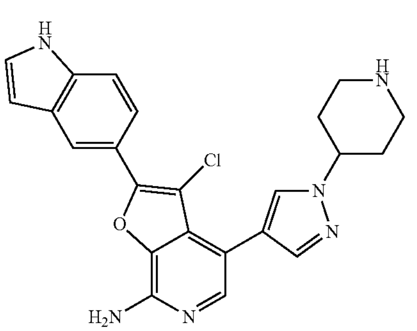 [SMILES: Nc1ncc(-c2cnn(C3CCNCC3)c2)c2c(Cl)c(-c3ccc4[nH]ccc4c3)oc12] | 14 | | | C |

TABLE 1-continued

| Structure | Ex. No. | A | B | C |
|---|---|---|---|---|
| 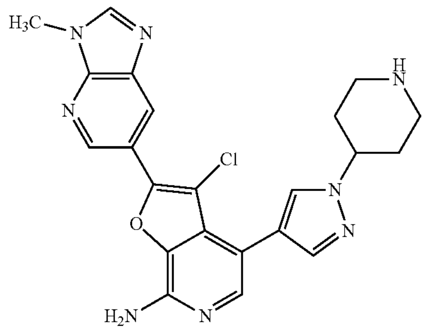 [SMILES: Cn1cnc2cc(-c3oc4c(N)ncc(-c5cnn(C6CCNCC6)c5)c4c3Cl)cnc21] | 15 | | | C |
| 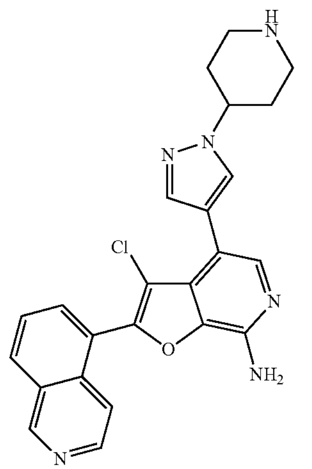 [SMILES: Nc1ncc(-c2cnn(C3CCNCC3)c2)c2c(Cl)c(-c3cccc4cnccc34)oc12] | 16 | | | C |
| 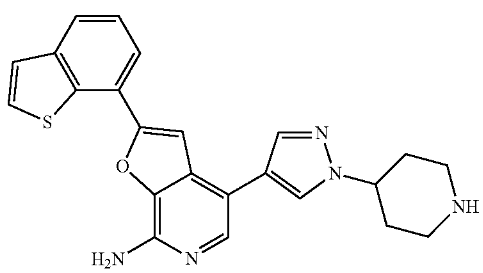 [SMILES: Nc1ncc(-c2cnn(C3CCNCC3)c2)c2cc(-c3cccc4ccsc34)oc12] | 17 | | | C |
| 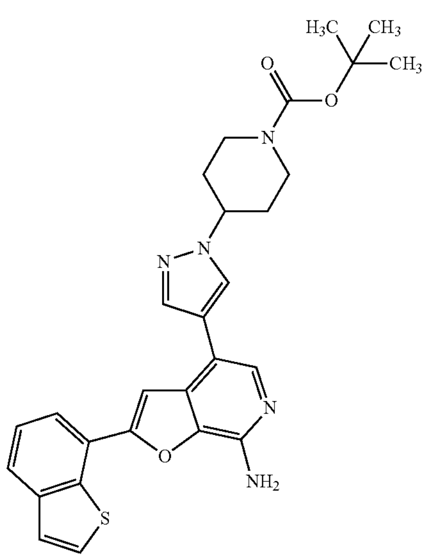 [SMILES: CC(C)(C)OC(=O)N1CCC(n2cc(-c3cnc(N)c4oc(-c5cccc6ccsc56)cc34)cn2)CC1] | 17A | | | D |

TABLE 1-continued
| Structure | Ex. No. | A | B | C |
|---|---|---|---|---|
| 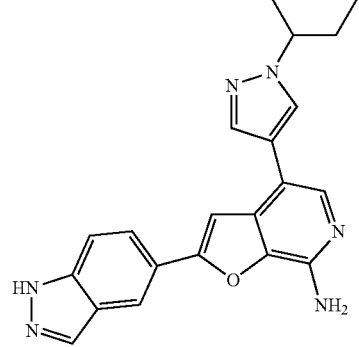 | 18 | A | B | B |
| 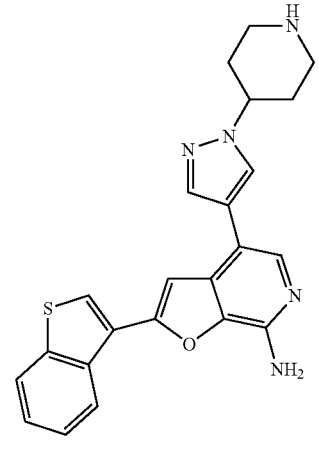 [SMILES: Nc1ncc(-c2cnn(C3CCNCC3)c2)c2cc(-c3csc4ccccc34)oc12] | 19 | | | C |
| 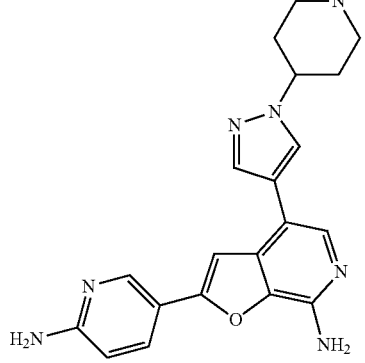 | 20 | | | C |

TABLE 1-continued

| Structure | Ex. No. | A | B | C |
|---|---|---|---|---|
| 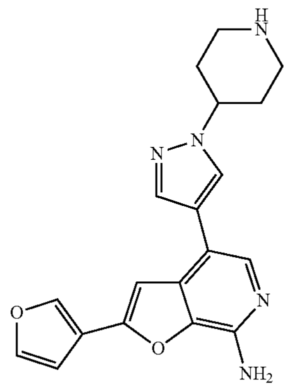 [SMILES: Nc1ncc(-c2cnn(C3CCNCC3)c2)c2cc(-c3ccoc3)oc12] | 21 | | | C |
| | 22 | | | | D |
| 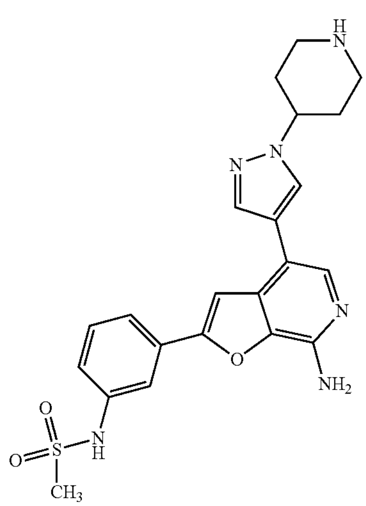 [SMILES: CS(=O)(=O)Nc1cccc(-c2cc3c(-c4cnn(C5CCNCC5)c4)cnc(N)c3o2)c1] | 23 | | | C |

TABLE 1-continued
| Structure | Ex. No. | A | B | C |
|---|---|---|---|---|
| 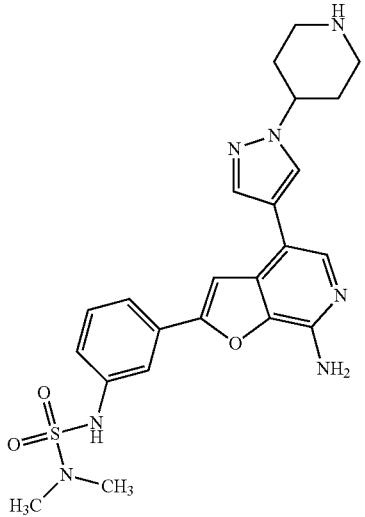 [SMILES: CN(C)S(=O)(=O)Nc1cccc(-c2cc3c(-c4cnn(C5CCNCC5)c4)cnc(N)c3o2)c1] | 24 | | | C |
| 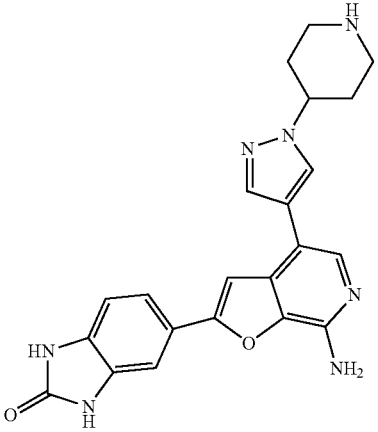 [SMILES: Nc1ncc(-c2cnn(C3CCNCC3)c2)c2cc(-c3ccc4[nH]c(=O)[nH]c4c3)oc12] | 25 | | | C |
| 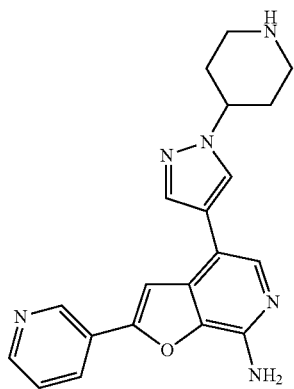 [SMILES: Nc1ncc(-c2cnn(C3CCNCC3)c2)c2cc(-c3cccnc3)oc12] | 26 | | | C |

TABLE 1-continued
| Structure | Ex. No. | A | B | C |
|---|---|---|---|---|
| 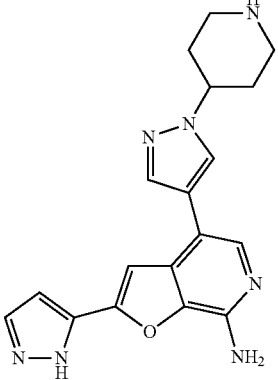 | 27 | | | C |
| 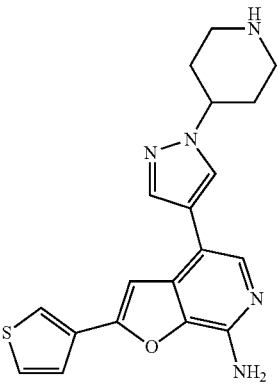 [SMILES: Nc1ncc(-c2cnn(C3CCNCC3)c2)c2cc(-c3ccsc3)oc12] | 28 | | | C |
| 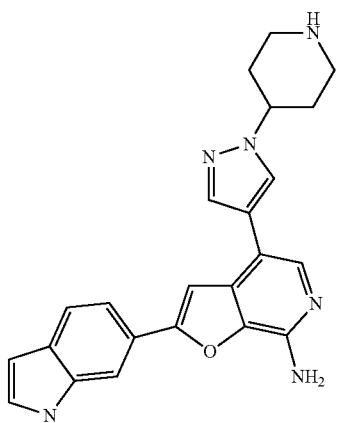 | 29 | | | C |
| 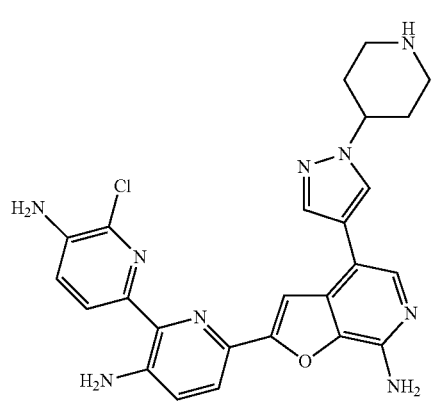 [SMILES: Nc1ccc(-c2nc(-c3cc4c(-c5cnn(C6CCNCC6)c5)cnc(N)c4o3)ccc2N)nc1Cl] | 30 | | B | |

TABLE 1-continued
| Structure | Ex. No. | A | B | C |
|---|---|---|---|---|
| 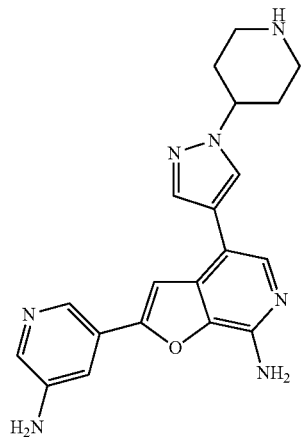 [SMILES: Nc1cncc(-c2cc3c(-c4cnn(C5CCNCC5)c4)cnc(N)c3o2)c1] | 31 | | B | |
| 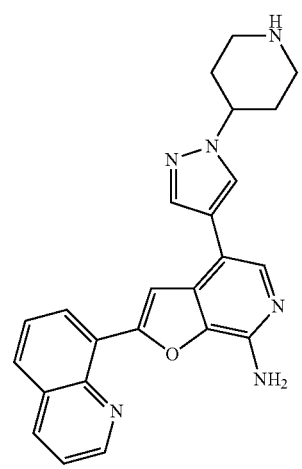 [SMILES: Nc1ncc(-c2cnn(C3CCNCC3)c2)c2cc(-c3cccc4cccnc34)oc12] | 32 | | | C |
| 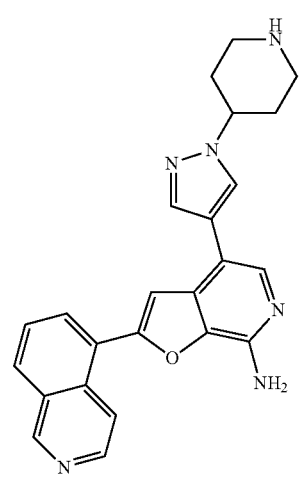 [SMILES: Nc1ncc(-c2cnn(C3CCNCC3)c2)c2cc(-c3cccc4cnccc34)oc12] | 33 | B | B | B |

TABLE 1-continued

| Structure | Ex. No. | A | B | C |
|---|---|---|---|---|
| 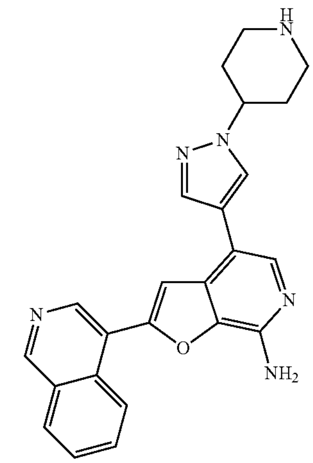 | 34 | | | C |
| 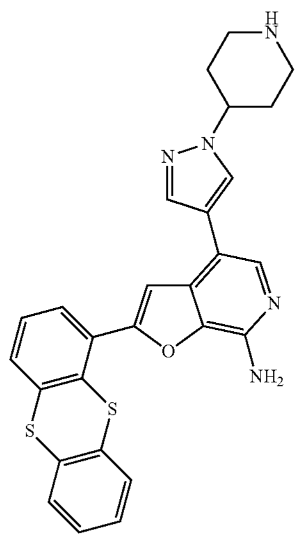 [SMILES: Nc1ncc(-c2cnn(C3CCNCC3)c2)c2cc(-c3cccc4c3Sc3ccccc3S4)oc12] | 35 | | | C |
| 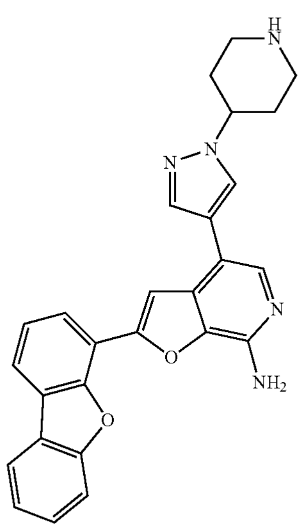 [SMILES: Nc1ncc(-c2cnn(C3CCNCC3)c2)c2cc(-c3cccc4c3oc3ccccc34)oc12] | 36 | | B | |

TABLE 1-continued
| Structure | Ex. No. | A | B | C |
|---|---|---|---|---|
| 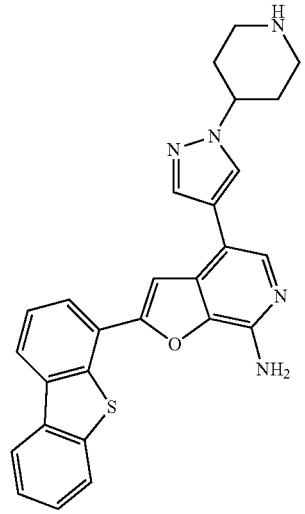 [SMILES: Nc1ncc(-c2cnn(C3CCNCC3)c2)c2cc(-c3cccc4c3sc3ccccc34)oc12] | 37 | B | | |
| 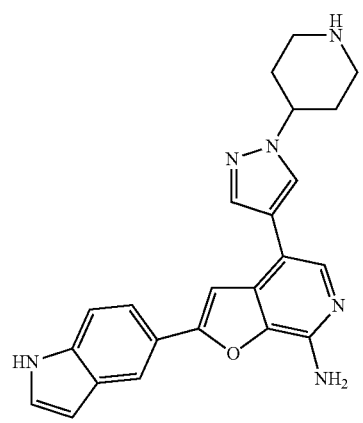 [SMILES: Nc1ncc(-c2cnn(C3CCNCC3)c2)c2cc(-c3ccc4[nH]ccc4c3)oc12] | 38 | B | C | C |
| 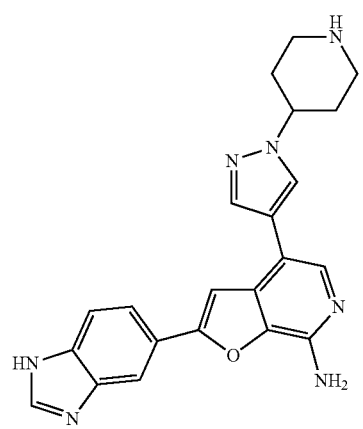 [SMILES: Nc1ncc(-c2cnn(C3CCNCC3)c2)c2cc(-c3ccc4[nH]cnc4c3)oc12] | 39 | B | | |

TABLE 1-continued
| Structure | Ex. No. | A | B | C |
|---|---|---|---|---|
| 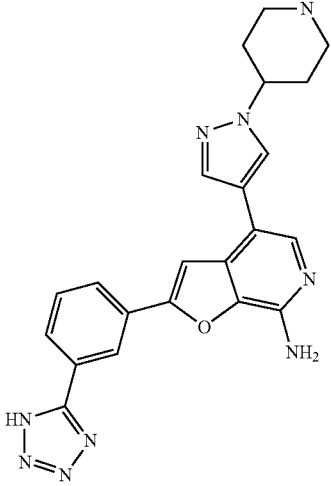 | 40 | | | C |
| 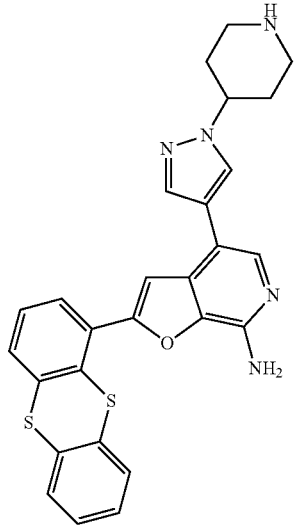 [SMILES: Nc1ncc(-c2cnn(C3CCNCC3)c2)c2cc(-c3cccc4c3Sc3ccccc3S4)oc12] | 41 | | B | |
| 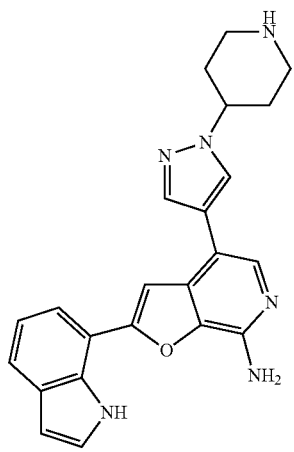 [SMILES: Nc1ncc(-c2cnn(C3CCNCC3)c2)c2cc(-c3cccc4cc[nH]c34)oc12] | 42 | | B | |

TABLE 1-continued

| Structure | Ex. No. | A | B | C |
|---|---|---|---|---|
| 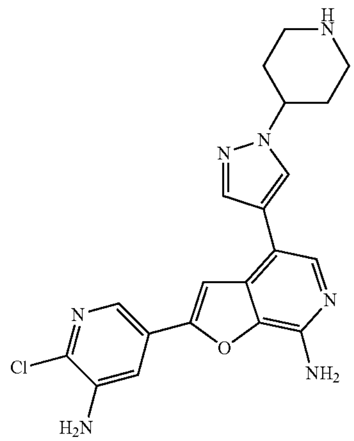 [SMILES: Nc1cc(-c2cc3c(-c4cnn(C5CCNCC5)c4)cnc(N)c3o2)cnc1Cl] | 43 | | B | |
| 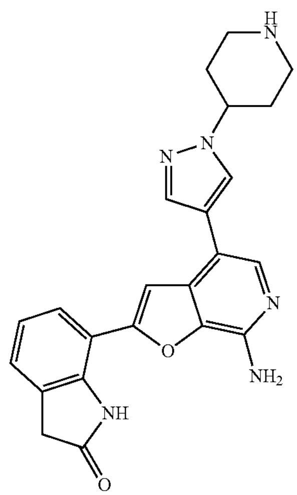 [SMILES: Nc1ncc(-c2cnn(C3CCNCC3)c2)c2cc(-c3cccc4c3NC(=O)C4)oc12] | 44 | | | C |
| 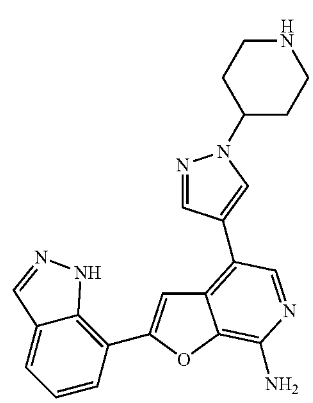 [SMILES: Nc1ncc(-c2cnn(C3CCNCC3)c2)c2cc(-c3cccc4cn[nH]c34)oc12] | 45 | | B | |

TABLE 1-continued

| Structure | Ex. No. | A | B | C |
|---|---|---|---|---|
| 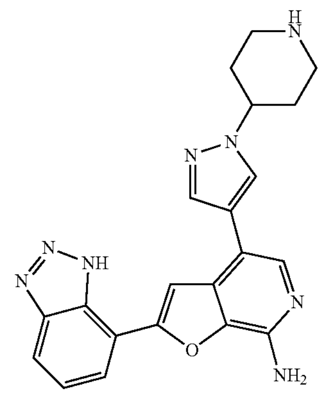 [SMILES: Nc1ncc(-c2cnn(C3CCNCC3)c2)c2cc(-c3cccc4nn[nH]c34)oc12] | 46 | | | C |
| 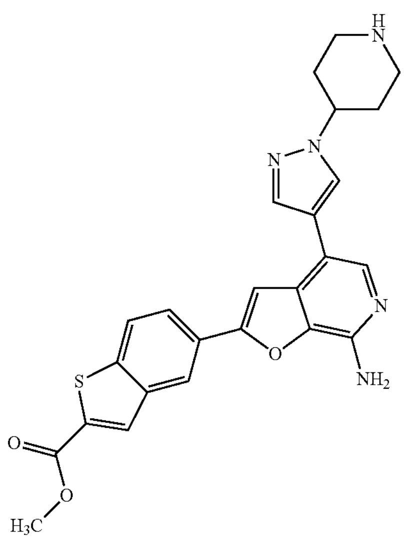 [SMILES: COC(=O)c1cc2cc(-c3cc4c(-c5cnn(C6CCNCC6)c5)cnc(N)c4o3)ccc2s1] | 47 | | | C |
| 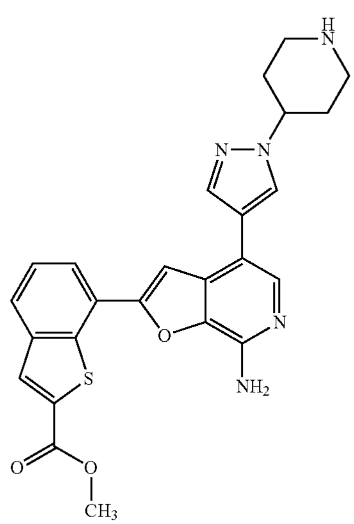 [SMILES: COC(=O)c1cc2cccc(-c3cc4c(-c5cnn(C6CCNCC6)c5)cnc(N)c4o3)c2s1] | 48 | | B | |

TABLE 1-continued
| Structure | Ex. No. | A | B | C |
|---|---|---|---|---|
| 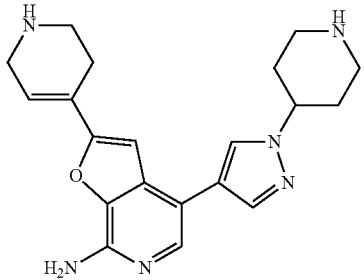 [SMILES: Nc1ncc(-c2cnn(C3CCNCC3)c2)c2cc(C3=CCNCC3)oc12] | 49 | C | | |
| 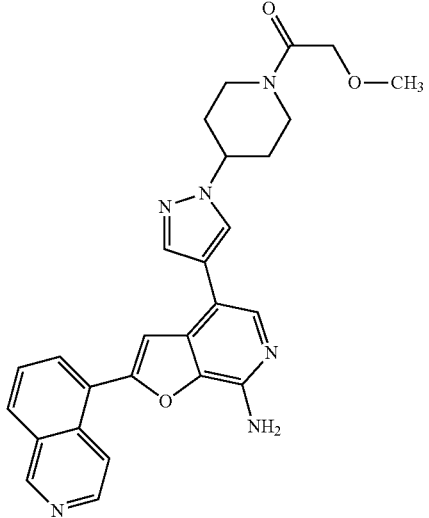 [SMILES: COCC(=O)N1CCC(n2cc(-c3cnc(N)c4oc(-c5cccc6cnccc56)cc34)cn2)CC1] | 50 | B | B | B |
| 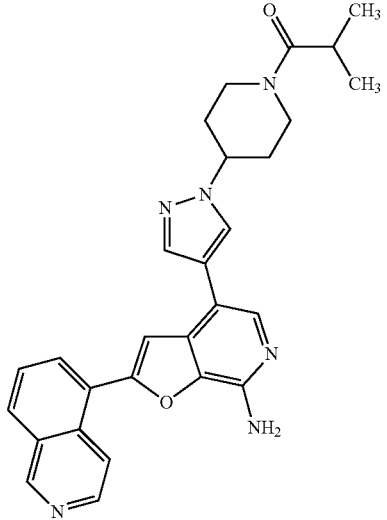 [SMILES: CC(C)C(=O)N1CCC(n2cc(-c3cnc(N)c4oc(-c5cccc6cnccc56)cc34)cn2)CC1] | 51 | B | A | A |

TABLE 1-continued

| Structure | Ex. No. | A | B | C |
|---|---|---|---|---|
| 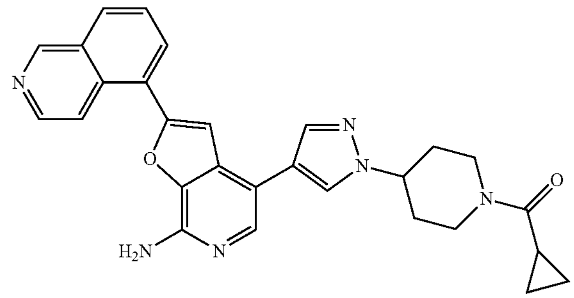 [SMILES: Nc1ncc(-c2cnn(C3CCN(C(=O)C4CC4)CC3)c2)c2cc(-c3cccc4cnccc34)oc12] | 52 | B | B | B |
| 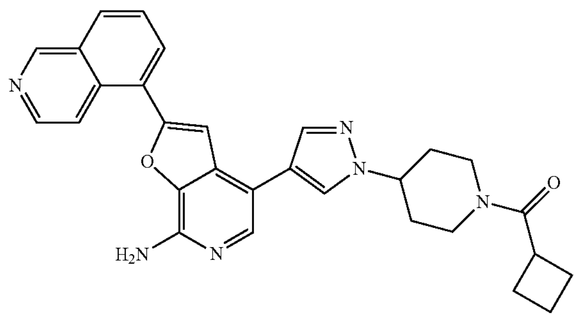 [SMILES: Nc1ncc(-c2cnn(C3CCN(C(=O)C4CCC4)CC3)c2)c2cc(-c3cccc4cnccc34)oc12] | 53 | B | A | B |
| 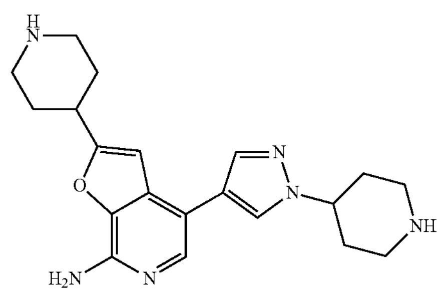 [SMILES: Nc1ncc(-c2cnn(C3CCNCC3)c2)c2cc(C3CCNCC3)oc12] | 54 | D | | |
| 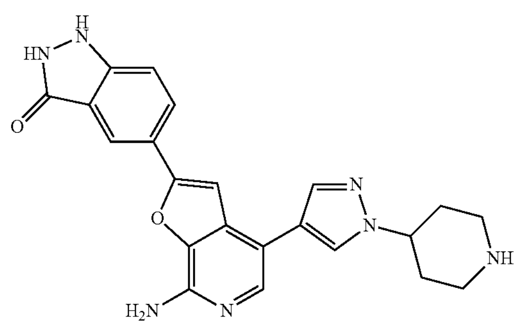 [SMILES: Nc1ncc(-c2cnn(C3CCNCC3)c2)c2cc(-c3ccc4[nH][nH]c(=O)c4c3)oc12] | 55 | A | D | D |
| 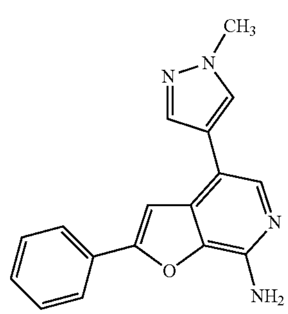 [SMILES: Cn1cc(-c2cnc(N)c3oc(-c4ccccc4)cc23)cn1] | 56 | D | | |

TABLE 1-continued
| Structure | Ex. No. | A | B | C |
|---|---|---|---|---|
| 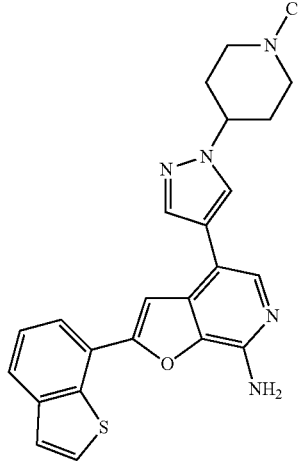 | 57 | | | C |
| 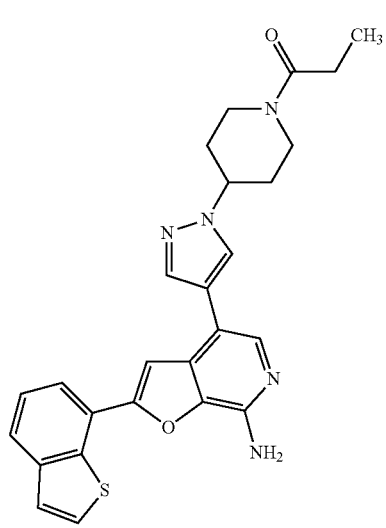 [SMILES: CCC(=O)N1CCC(n2cc(-c3cnc(N)c4oc(-c5cccc6ccsc56)cc34)cn2)CC1] | 58 | | | C |
| 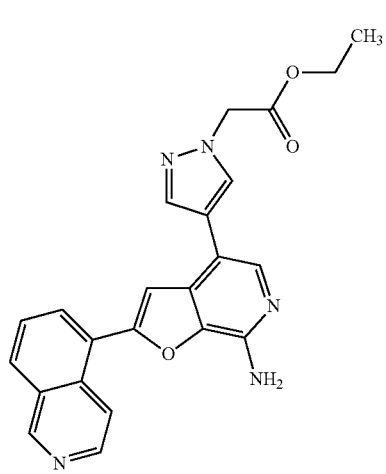 [SMILES: CCOC(=O)Cn1cc(-c2cnc(N)c3oc(-c4cccc5cnccc45)cc23)cn1] | 59 | | | C |

TABLE 1-continued
| Structure | Ex. No. | A | B | C |
|---|---|---|---|---|
| 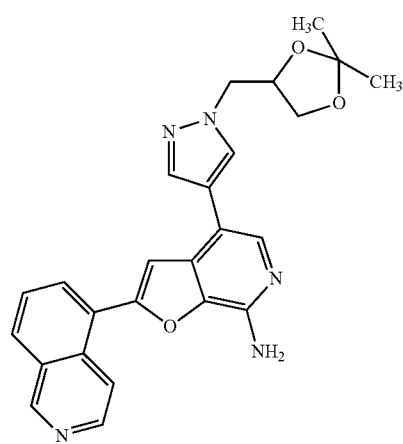 [SMILES: CC1(C)OCC(Cn2cc(-c3cnc(N)c4oc(-c5cccc6cnccc56)cc34)cn2)O1] | 60 | B | B | B |
| 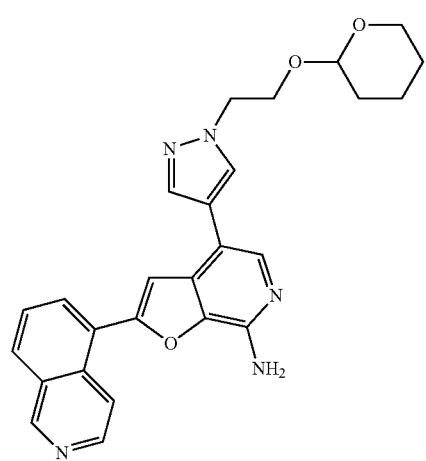 | 61 | | | C |
| 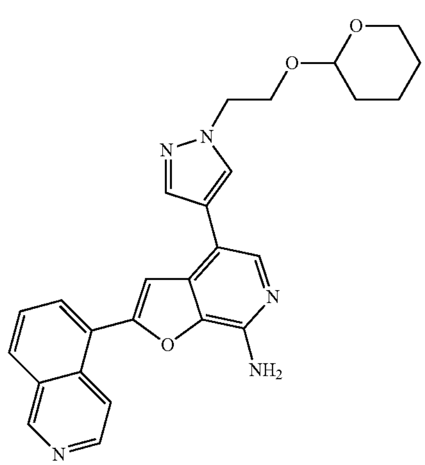 [SMILES: Nc1ncc(-c2cnn(CCOC3CCCCO3)c2)c2cc(-c3cccc4cnccc34)oc12] | 62 | | | |

TABLE 1-continued

| Structure | Ex. No. | A | B | C |
|---|---|---|---|---|
| (structure) | 63 | D | | |
| (structure) | 64 | B | | |
| (structure) | 65 | B | A | B |

TABLE 1-continued
| Structure | Ex. No. | A | B | C |
|---|---|---|---|---|
| 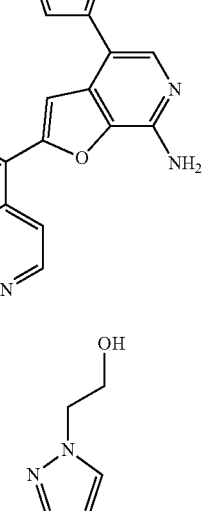 | 66 | | | C |
| 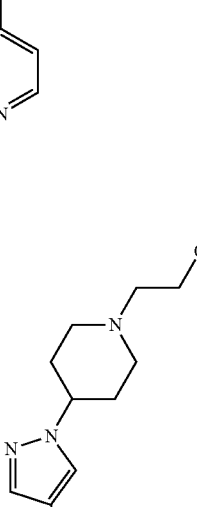 | 67 | | | C |
| 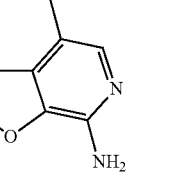 | 68 | B | B | B |

TABLE 1-continued

| Structure | Ex. No. | A | B | C |
|---|---|---|---|---|
| (structure) | 69 | C | B | B |
| (structure) | 70 | C | B | B |
| (structure) | 71 | C | | |
| (structure) | 72 | B | | |

TABLE 1-continued

| Structure | Ex. No. | A | B | C |
|---|---|---|---|---|
| 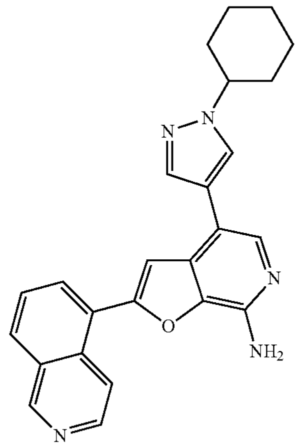 [SMILES: Nc1ncc(-c2cnn(C3CCCCC3)c2)c2cc(-c3cccc4cnccc34)oc12] | 73 | | | C |
| 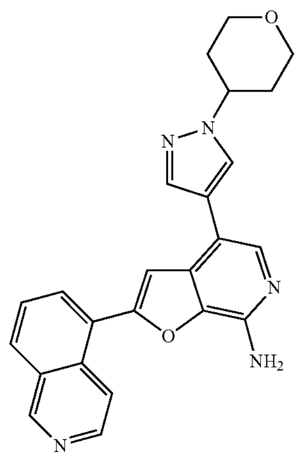 [SMILES: Nc1ncc(-c2cnn(C3CCOCC3)c2)c2cc(-c3cccc4cnccc34)oc12] | 74 | B | B | C |
| 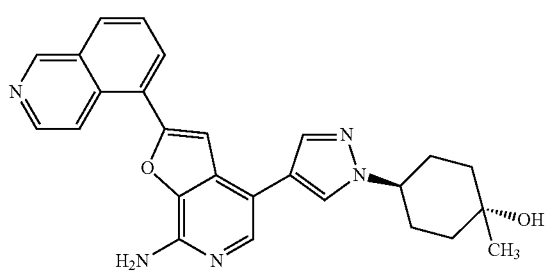 [SMILES: C[C@]1(O)CC[C@H](n2cc(-c3cnc(N)c4oc(-c5cccc6cnccc56)cc34)cn2)CC1] | 75 | B | | |
| 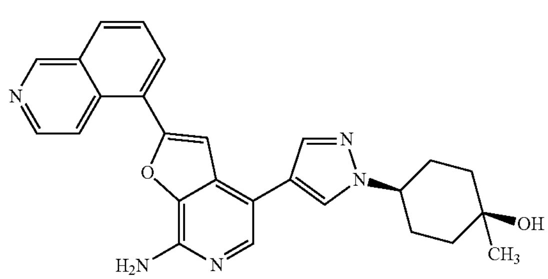 [SMILES: C[C@]1(O)CC[C@@H](n2cc(-c3cnc(N)c4oc(-c5cccc6cnccc56)cc34)cn2)CC1] | 76 | B | B | B |

TABLE 1-continued

| Structure | Ex. No. | A | B | C |
|---|---|---|---|---|
| (structure) | 77 | B | A | B |
| (structure) | 78 | B | B | B |
| (structure) | 79 | B | B | B |

TABLE 1-continued

| Structure | Ex. No. | A | B | C |
|---|---|---|---|---|
| 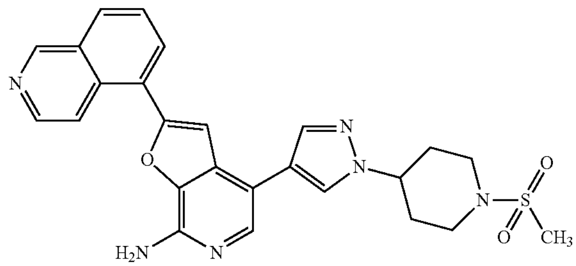 [SMILES: CS(=O)(=O)N1CCC(n2cc(-c3cnc(N)c4oc(-c5cccc6cnccc56)cc34)cn2)CC1] | 80 | B | A | B |
| 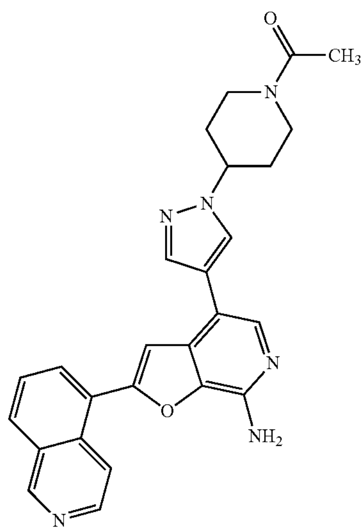 [SMILES: CC(=O)N1CCC(n2cc(-c3cnc(N)c4oc(-c5cccc6cnccc56)cc34)cn2)CC1] | 81 | B | B | B |
| 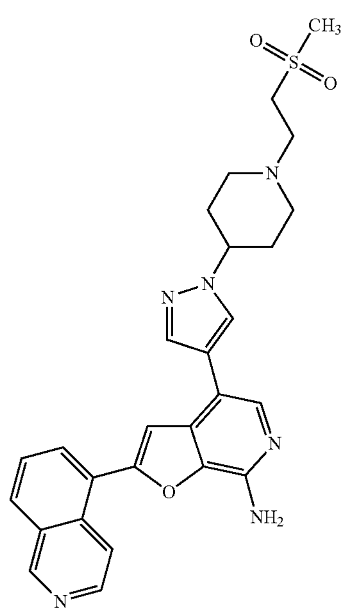 [SMILES: CS(=O)(=O)CCN1CCC(n2cc(-c3cnc(N)c4oc(-c5cccc6cnccc56)cc34)cn2)CC1] | 82 | B | B | B |

TABLE 1-continued

| Structure | Ex. No. | A | B | C |
|---|---|---|---|---|
| (structure) | 83 | B | A | B |
| (structure) | 84 | C | B | B |
| (structure) | 85 | B | B | B |

TABLE 1-continued
| Structure | Ex. No. | A | B | C |
|---|---|---|---|---|
| 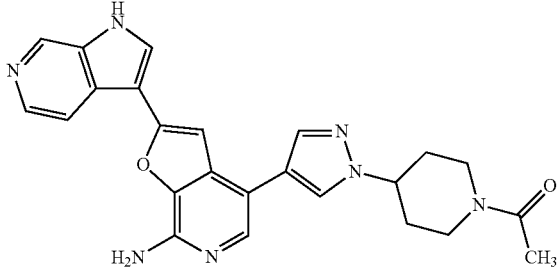 [SMILES: CC(=O)N1CCC(n2cc(-c3cnc(N)c4oc(-c5c[nH]c6cnccc56)cc34)cn2)CC1] | 86 | A | C | C |
| 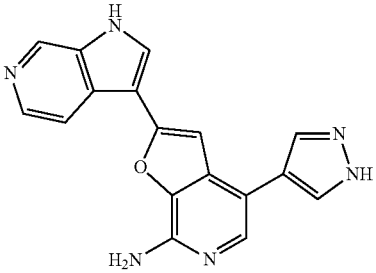 [SMILES: Nc1ncc(-c2cn[nH]c2)c2cc(-c3c[nH]c4cnccc34)oc12] | 87 | A | B | C |
| 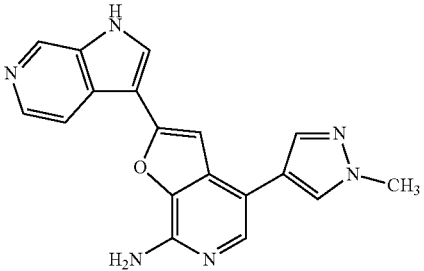 [SMILES: Cn1cc(-c2cnc(N)c3oc(-c4c[nH]c5cnccc45)cc23)cn1] | 88 | A | B | B |
| 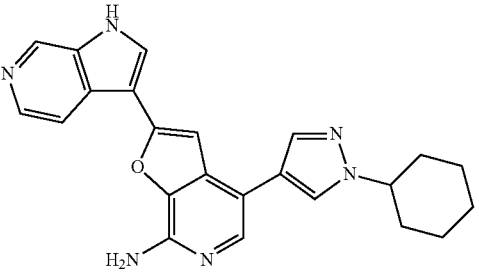 [SMILES: Nc1ncc(-c2cnn(C3CCCCC3)c2)c2cc(-c3c[nH]c4cnccc34)oc12] | 89 | A | B | B |
| 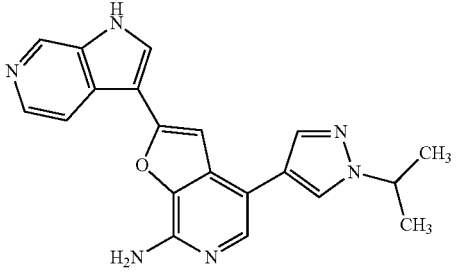 [SMILES: CC(C)n1cc(-c2cnc(N)c3oc(-c4c[nH]c5cnccc45)cc23)cn1] | 90 | A | B | A |

TABLE 1-continued
| Structure | Ex. No. | A | B | C |
|---|---|---|---|---|
| 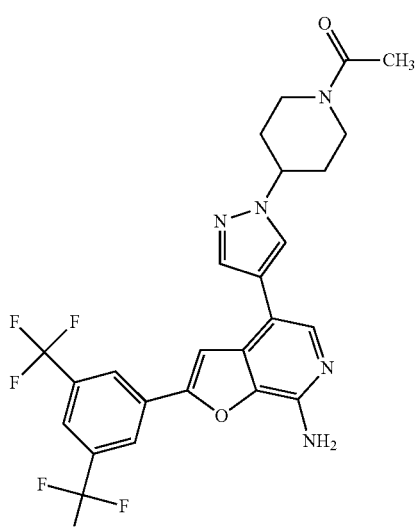 | 91 | D | C | C |
| 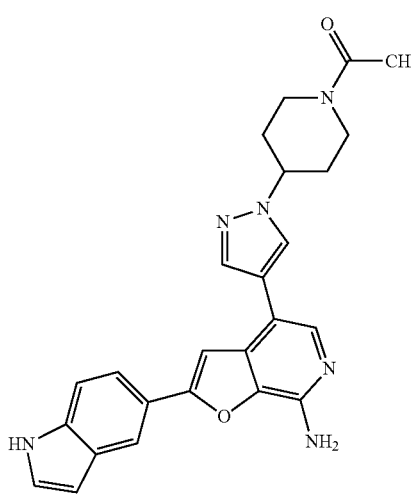 | 92 | C | B | B |
| 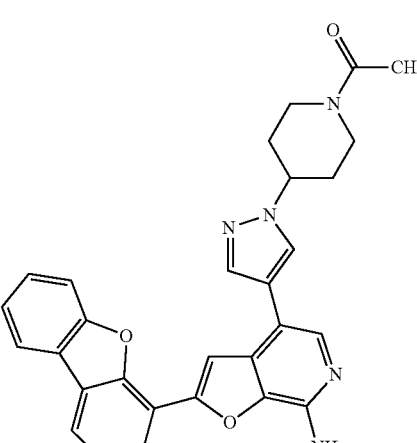 | 93 | D | C | C |

TABLE 1-continued

| Structure | Ex. No. | A | B | C |
|---|---|---|---|---|
| 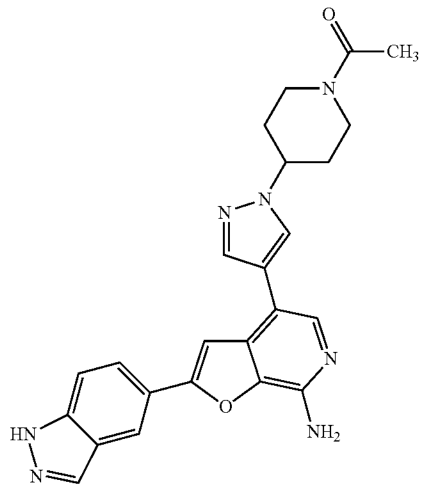 [SMILES: CC(=O)N1CCC(n2cc(-c3cnc(N)c4oc(-c5ccc6[nH]ncc6c5)cc34)cn2)CC1] | 94 | B | B | C |
| 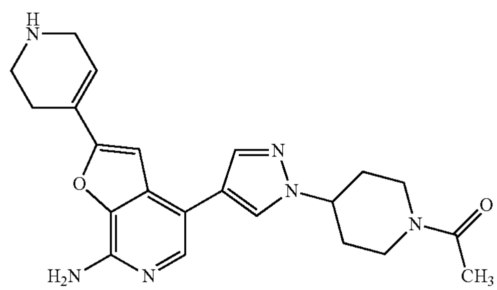 [SMILES: CC(=O)N1CCC(n2cc(-c3cnc(N)c4oc(C5=CCNCC5)cc34)cn2)CC1] | 95 | B | | |
| 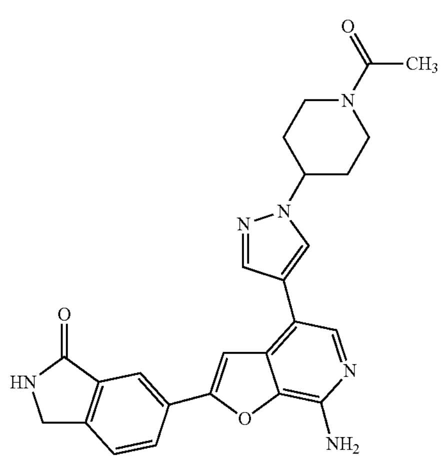 [SMILES: CC(=O)N1CCC(n2cc(-c3cnc(N)c4oc(-c5ccc6c(c5)C(=O)NC6)cc34)cn2)CC1] | 96 | B | C | D |

TABLE 1-continued
| Structure | Ex. No. | A | B | C |
|---|---|---|---|---|
| 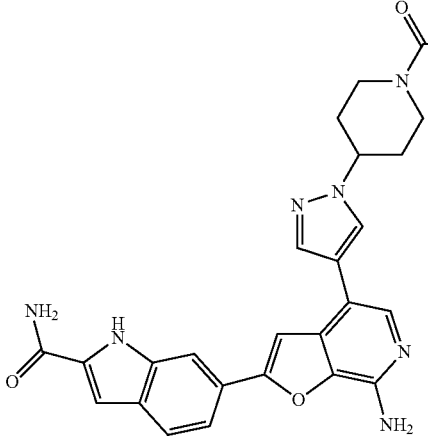 | 97 | | B | |
| 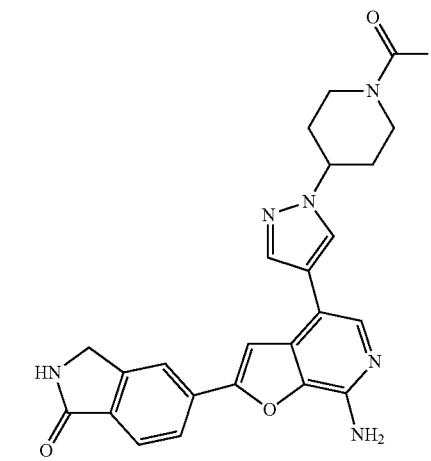 | 98 | D | D | D |
| 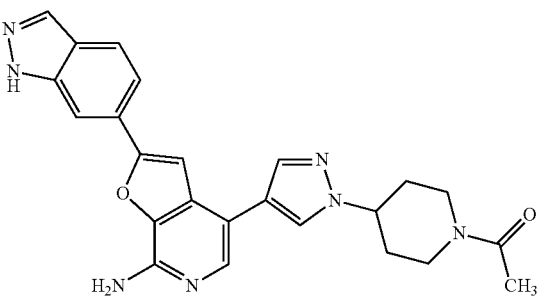 [SMILES: CC(=O)N1CCC(n2cc(-c3cnc(N)c4oc(-c5ccc6cn[nH]c6c5)cc34)cn2)CC1] | 99 | | B | |

TABLE 1-continued

| Structure | Ex. No. | A | B | C |
|---|---|---|---|---|
| 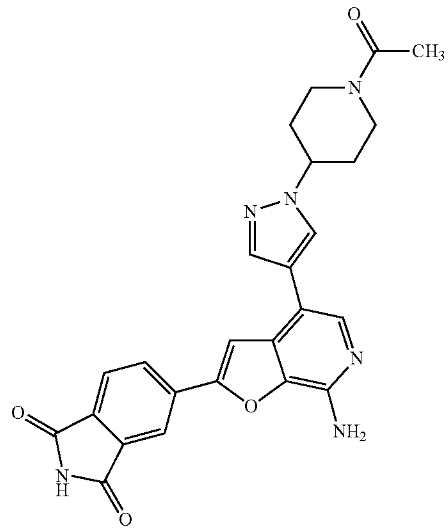 [SMILES: CC(=O)N1CCC(n2cc(-c3cnc(N)c4oc(-c5ccc6c(c5)C(=O)NC6=O)cc34)cn2)CC1] | 100 | | | C |
| 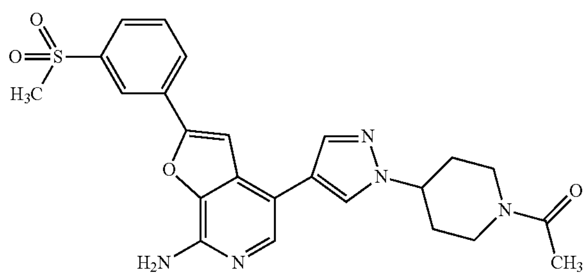 [SMILES: CC(=O)N1CCC(n2cc(-c3cnc(N)c4oc(-c5cccc(S(C)(=O)=O)c5)cc34)cn2)CC1] | 101 | C | C | C |
| 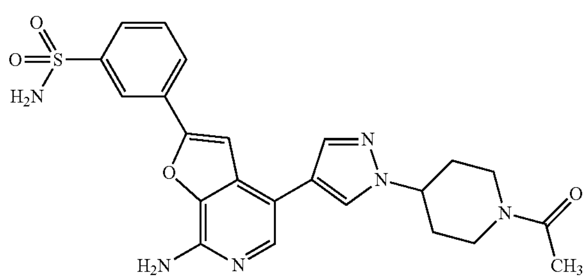 [SMILES: CC(=O)N1CCC(n2cc(-c3cnc(N)c4oc(-c5cccc(S(N)(=O)=O)c5)cc34)cn2)CC1] | 102 | | | C |
| 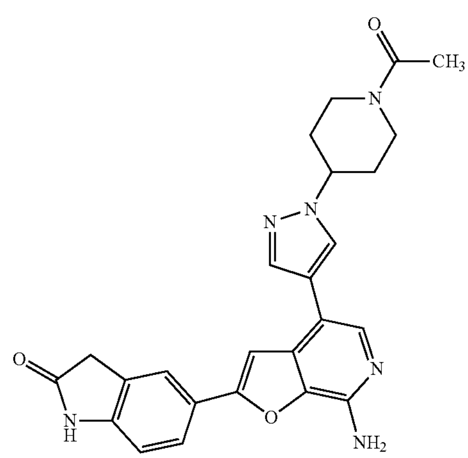 [SMILES: CC(=O)N1CCC(n2cc(-c3cnc(N)c4oc(-c5ccc6c(c5)CC(=O)N6)cc34)cn2)CC1] | 103 | | | C |

TABLE 1-continued

| Structure | Ex. No. | A | B | C |
|---|---|---|---|---|
| (structure) | 104 | | | C |
| (structure) | 105 | B | C | C |
| (structure) | 106 | B | B | B |
| (structure) | 107 | B | B | B |

TABLE 1-continued

| Structure | Ex. No. | A | B | C |
|---|---|---|---|---|
| (structure) | 108 | B | B | A |
| (structure) | 109 | B | B | C |
| (structure) | 110 | C | | |
| (structure) | 111 | B | C | D |
| (structure) | 112 | A | B | B |

TABLE 1-continued

| Structure | Ex. No. | A | B | C |
|---|---|---|---|---|
| (structure) | 113 | D | C | C |
| (structure) | 114 | C | B | B |
| (structure) | 115 | B | C | D |
| (structure) | 116 | C | | |
| (structure) | 117 | C | C | C |

TABLE 1-continued

| Structure | Ex. No. | A | B | C |
|---|---|---|---|---|
| 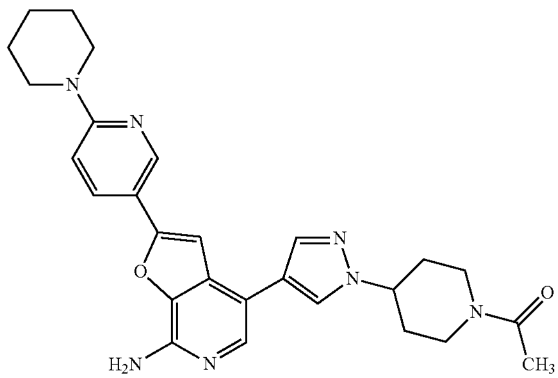 [SMILES: CC(=O)N1CCC(n2cc(-c3cnc(N)c4oc(-c5ccc(N6CCCCC6)nc5)cc34)cn2)CC1] | 118 | D | | |
| 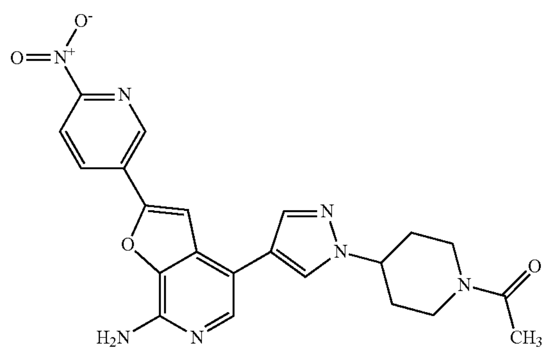 [SMILES: CC(=O)N1CCC(n2cc(-c3cnc(N)c4oc(-c5ccc([N+](=O)[O-])nc5)cc34)cn2)CC1] | 119 | C | | |
| 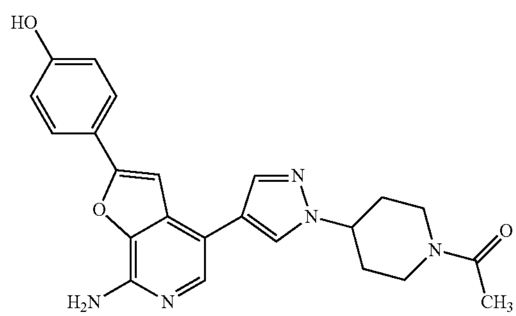 [SMILES: CC(=O)N1CCC(n2cc(-c3cnc(N)c4oc(-c5ccc(O)cc5)cc34)cn2)CC1] | 120 | B | B | B |
| 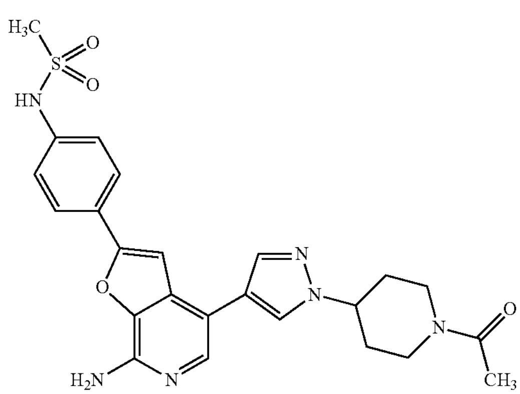 [SMILES: CC(=O)N1CCC(n2cc(-c3cnc(N)c4oc(-c5ccc(NS(C)(=O)=O)cc5)cc34)cn2)CC1] | 121 | C | | |

TABLE 1-continued

| Structure | Ex. No. | A | B | C |
|---|---|---|---|---|
| (structure) | 122 | B | | |
| (structure) | 123 | B | C | C |
| (structure) | 124 | C | B | C |
| (structure) | 125 | D | | |
| (structure) | 126 | C | | |

TABLE 1-continued

| Structure | Ex. No. | A | B | C |
|---|---|---|---|---|
| 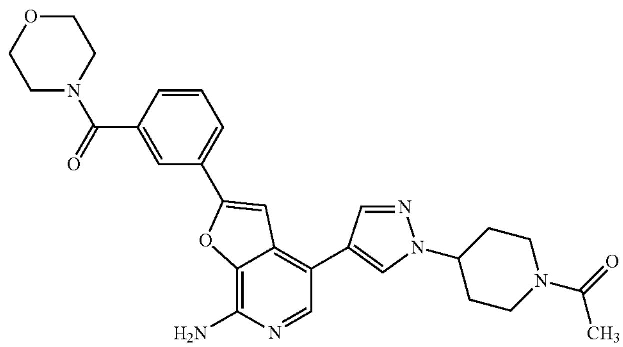 [SMILES: CC(=O)N1CCC(n2cc(-c3cnc(N)c4oc(-c5cccc(C(=O)N6CCOCC6)c5)cc34)cn2)CC1] | 127 | | | C |
| 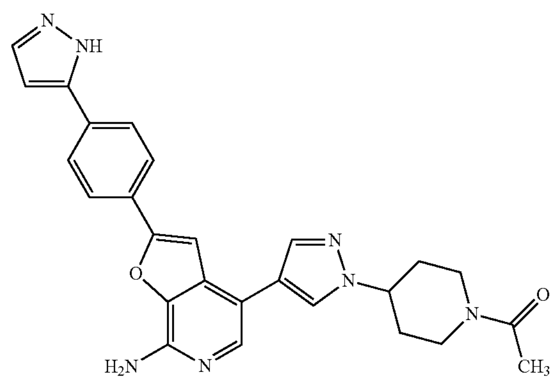 [SMILES: CC(=O)N1CCC(n2cc(-c3cnc(N)c4oc(-c5ccc(-c6ccn[nH]6)cc5)cc34)cn2)CC1] | 128 | | | C |
| 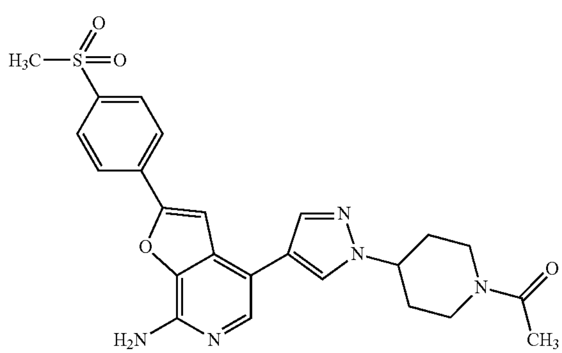 [SMILES: CC(=O)N1CCC(n2cc(-c3cnc(N)c4oc(-c5ccc(S(C)(=O)=O)cc5)cc34)cn2)CC1] | 129 | D | D | D |
| 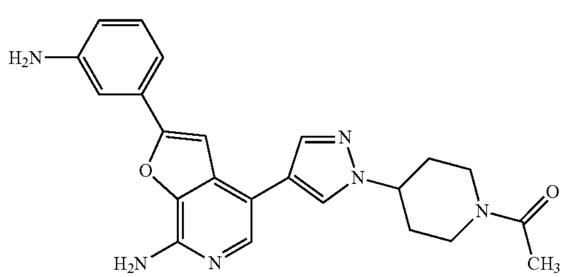 [SMILES: CC(=O)N1CCC(n2cc(-c3cnc(N)c4oc(-c5cccc(N)c5)cc34)cn2)CC1] | 130 | | B | |

TABLE 1-continued

| Structure | Ex. No. | A | B | C |
|---|---|---|---|---|
| (structure 131) | 131 | B | B | C |
| (structure 132) | 132 | A | B | B |
| (structure 133) | 133 | C | C | C |
| (structure 134) | 134 | C | | |
| (structure 135) | 135 | B | B | B |

TABLE 1-continued
| Structure | Ex. No. | A | B | C |
|---|---|---|---|---|
| 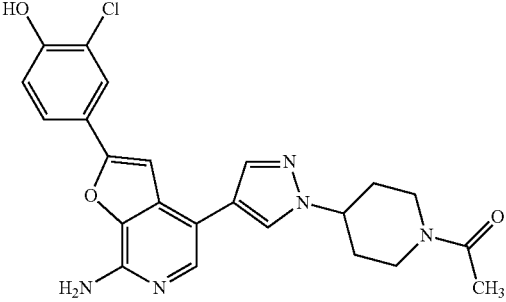 [SMILES: CC(=O)N1CCC(n2cc(-c3cnc(N)c4oc(-c5ccc(O)c(Cl)c5)cc34)cn2)CC1] | 136 | B | B | C |
| 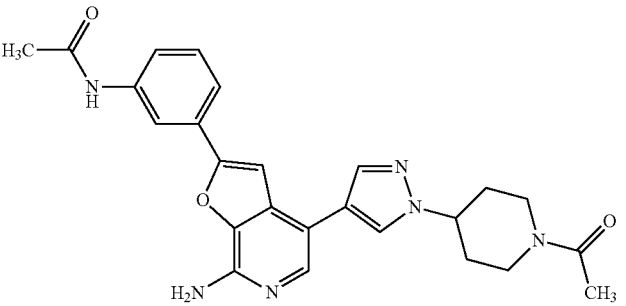 [SMILES: CC(=O)Nc1cccc(-c2cc3c(-c4cnn(C5CCN(C(C)=O)CC5)c4)cnc(N)c3o2)c1] | 137 | C | | |
| 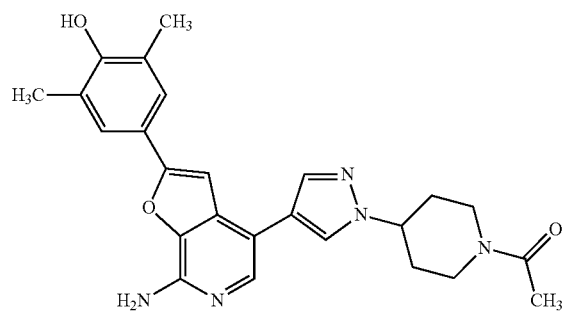 [SMILES: CC(=O)N1CCC(n2cc(-c3cnc(N)c4oc(-c5cc(C)c(O)c(C)c5)cc34)cn2)CC1] | 138 | C | B | C |
| 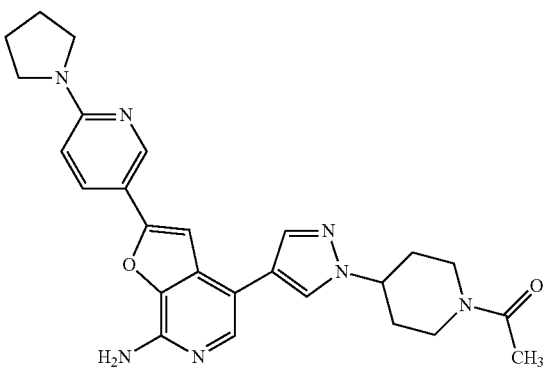 [SMILES: CC(=O)N1CCC(n2cc(-c3cnc(N)c4oc(-c5ccc(N6CCCC6)nc5)cc34)cn2)CC1] | 139 | D | | |

TABLE 1-continued

| Structure | Ex. No. | A | B | C |
|---|---|---|---|---|
| (structure) | 140 | | | C |
| (structure) | 141 | | | D |
| (structure) | 142 | B | B | C |
| (structure) | 143 | B | B | B |
| (structure) | 144 | | | C |

TABLE 1-continued

| Structure | Ex. No. | A | B | C |
|---|---|---|---|---|
| 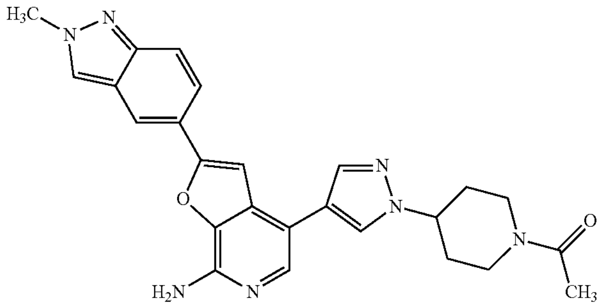 [SMILES: CC(=O)N1CCC(n2cc(-c3cnc(N)c4oc(-c5ccc6nn(C)cc6c5)cc34)cn2)CC1] | 145 | D | C | C |
| 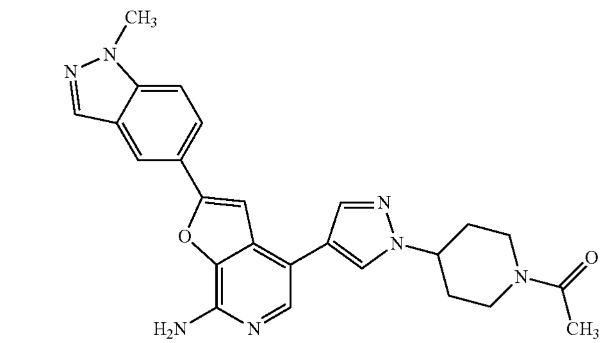 [SMILES: CC(=O)N1CCC(n2cc(-c3cnc(N)c4oc(-c5ccc6c(cnn6C)c5)cc34)cn2)CC1] | 146 | C | B | C |
| 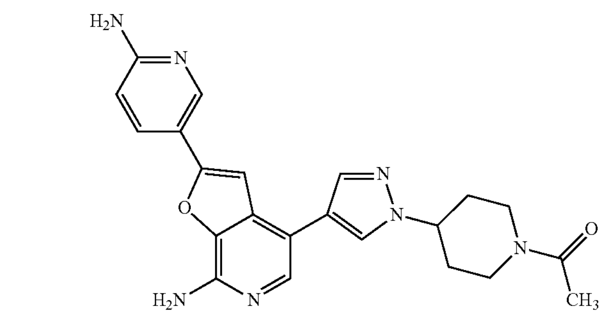 [SMILES: CC(=O)N1CCC(n2cc(-c3cnc(N)c4oc(-c5ccc(N)nc5)cc34)cn2)CC1] | 147 | B | | |
| 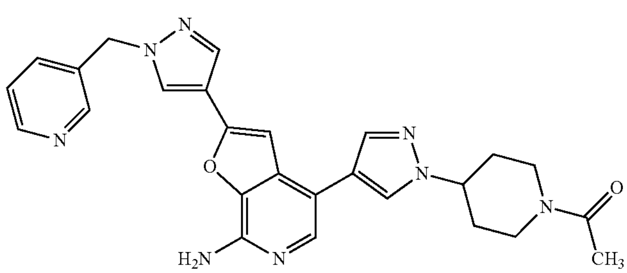 [SMILES: CC(=O)N1CCC(n2cc(-c3cnc(N)c4oc(-c5cnn(Cc6cccnc6)c5)cc34)cn2)CC1] | 148 | C | D | D |
| 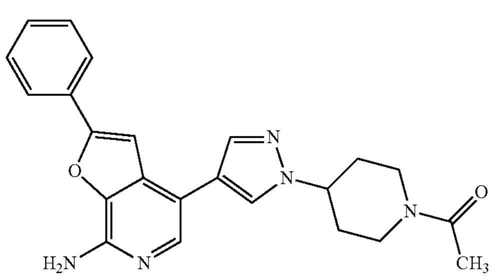 [SMILES: CC(=O)N1CCC(n2cc(-c3cnc(N)c4oc(-c5ccccc5)cc34)cn2)CC1] | 149 | C | B | C |

TABLE 1-continued

| Structure | Ex. No. | A | B | C |
|---|---|---|---|---|
| 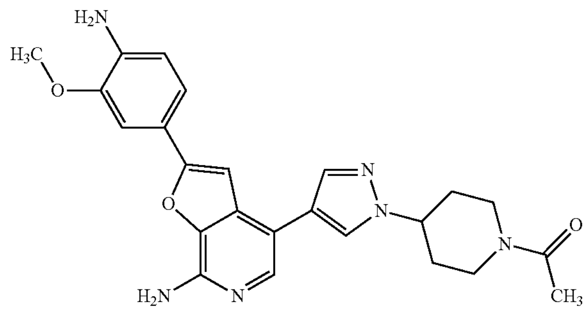 | 150 | C | | |
| 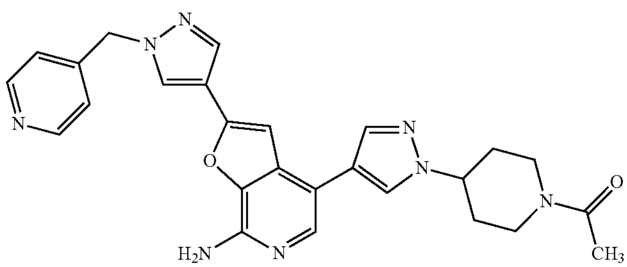 [SMILES: CC(=O)N1CCC(n2cc(-c3cnc(N)c4oc(-c5cnn(Cc6ccncc6)c5)cc34)cn2)CC1] | 151 | C | | |
| 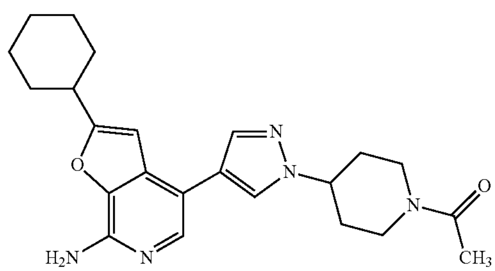 | 152 | B | | |
| 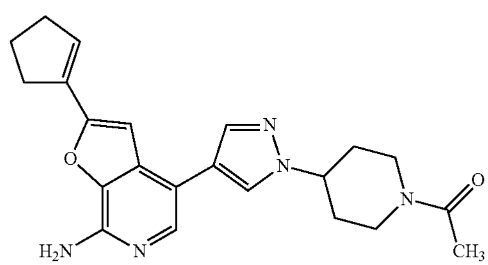 [SMILES: CC(=O)N1CCC(n2cc(-c3cnc(N)c4oc(C5=CCCC5)cc34)cn2)CC1] | 153 | C | | |
| 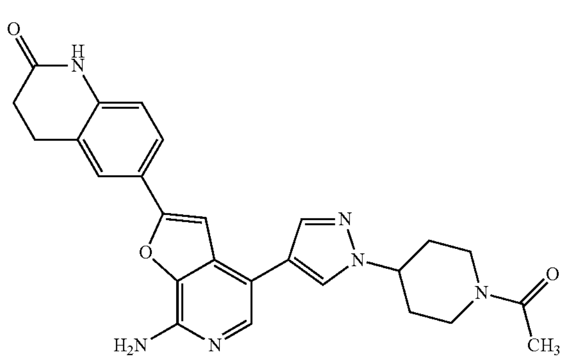 [SMILES: CC(=O)N1CCC(n2cc(-c3cnc(N)c4oc(-c5ccc6c(c5)CCC(=O)N6)cc34)cn2)CC1] | 154 | B | C | C |

TABLE 1-continued

| Structure | Ex. No. | A | B | C |
|---|---|---|---|---|
| 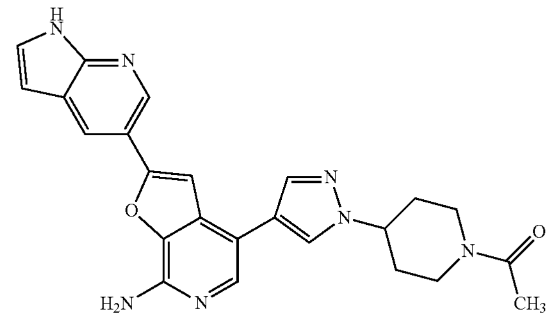 [SMILES: CC(=O)N1CCC(n2cc(-c3cnc(N)c4oc(-c5cnc6[nH]ccc6c5)cc34)cn2)CC1] | 155 | B | B | C |
| 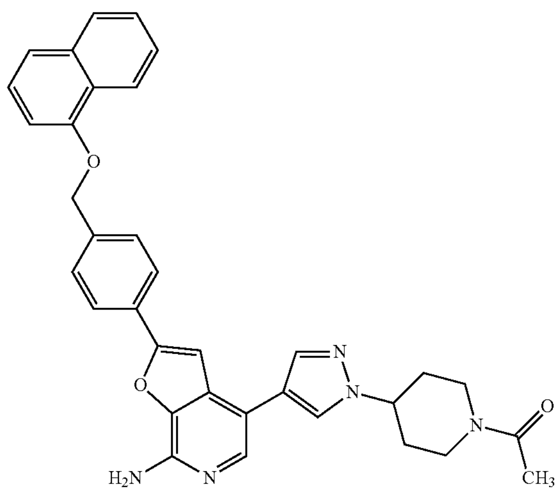 [SMILES: CC(=O)N1CCC(n2cc(-c3cnc(N)c4oc(-c5ccc(COc6cccc7ccccc67)cc5)cc34)cn2)CC1] | 156 | D | | |
| 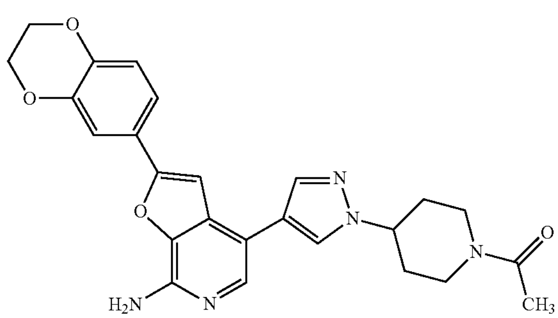 [SMILES: CC(=O)N1CCC(n2cc(-c3cnc(N)c4oc(-c5ccc6c(c5)OCCO6)cc34)cn2)CC1] | 157 | B | | |
| 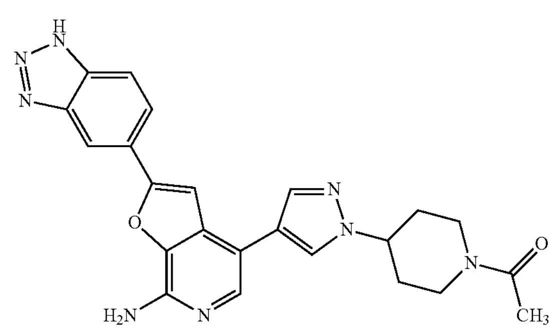 [SMILES: CC(=O)N1CCC(n2cc(-c3cnc(N)c4oc(-c5ccc6[nH]nnc6c5)cc34)cn2)CC1] | 158 | A | D | D |

TABLE 1-continued
| Structure | Ex. No. | A | B | C |
|---|---|---|---|---|
| 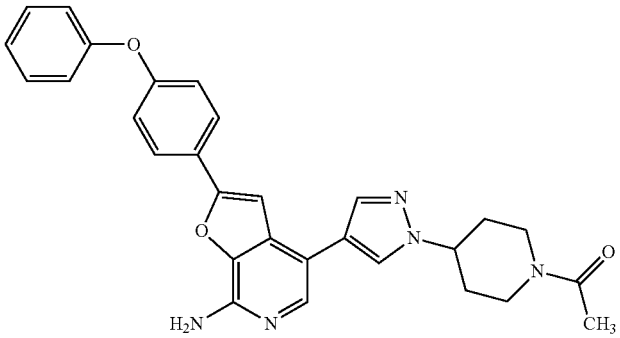 [SMILES: CC(=O)N1CCC(n2cc(-c3cnc(N)c4oc(-c5ccc(Oc6ccccc6)cc5)cc34)cn2)CC1] | 159 | D | | |
| 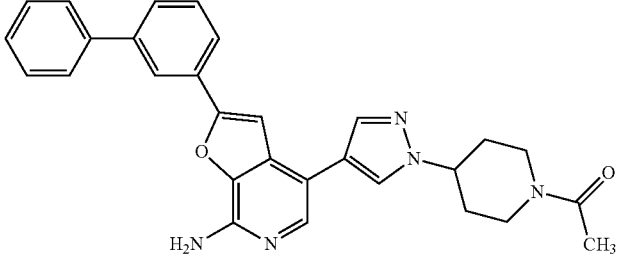 [SMILES: CC(=O)N1CCC(n2cc(-c3cnc(N)c4oc(-c5cccc(-c6ccccc6)c5)cc34)cn2)CC1] | 160 | C | | |
| 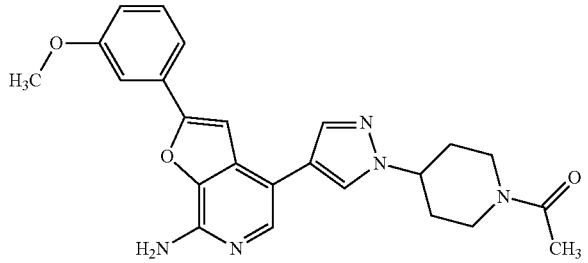 [SMILES: COc1cccc(-c2cc3c(-c4cnn(C5CCN(C(C)=O)CC5)c4)cnc(N)c3o2)c1] | 161 | C | | |
| 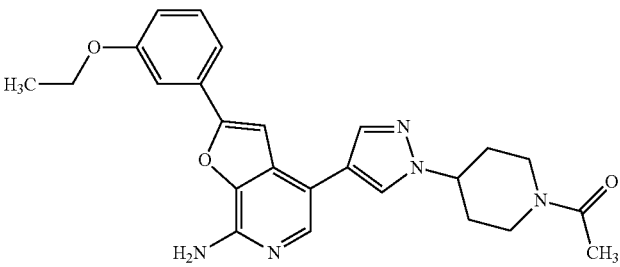 [SMILES: CCOc1cccc(-c2cc3c(-c4cnn(C5CCN(C(C)=O)CC5)c4)cnc(N)c3o2)c1] | 162 | C | | |
| 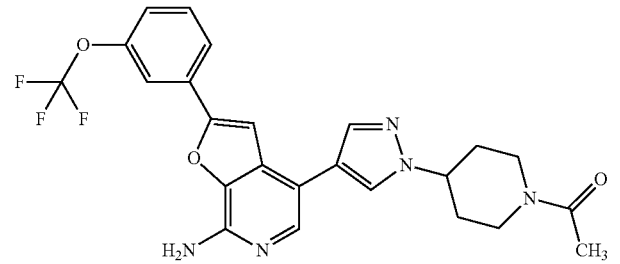 [SMILES: CC(=O)N1CCC(n2cc(-c3cnc(N)c4oc(-c5cccc(OC(F)(F)F)c5)cc34)cn2)CC1] | 163 | C | | |

TABLE 1-continued
| Structure | Ex. No. | A | B | C |
|---|---|---|---|---|
| 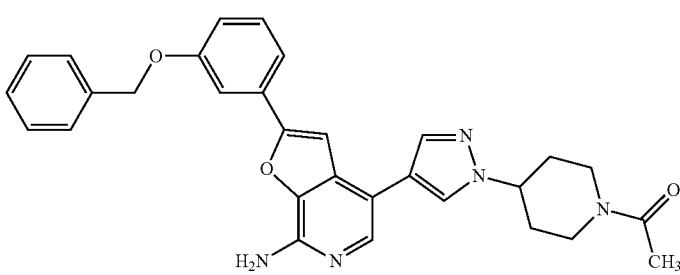 [SMILES: CC(=O)N1CCC(n2cc(-c3cnc(N)c4oc(-c5cccc(OCc6ccccc6)c5)cc34)cn2)CC1] | 164 | | | D |
| 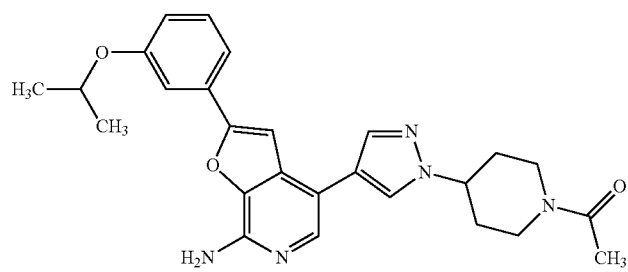 [SMILES: CC(=O)N1CCC(n2cc(-c3cnc(N)c4oc(-c5cccc(OC(C)C)c5)cc34)cn2)CC1] | 165 | | | C |
| 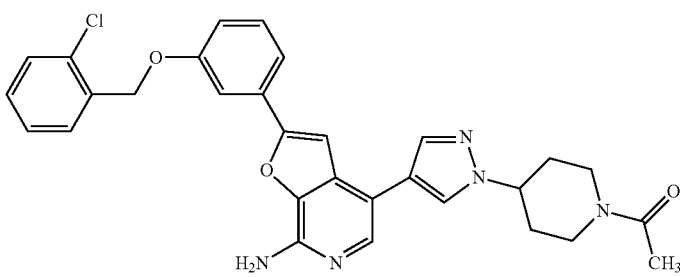 [SMILES: CC(=O)N1CCC(n2cc(-c3cnc(N)c4oc(-c5cccc(OCc6ccccc6Cl)c5)cc34)cn2)CC1] | 166 | | | D |
| 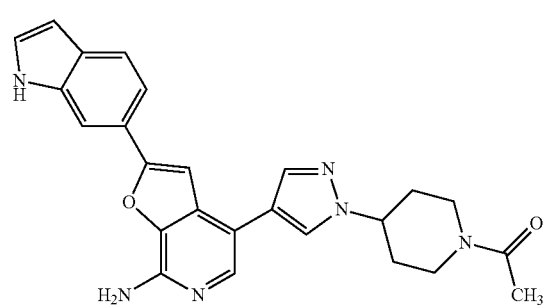 [SMILES: CC(=O)N1CCC(n2cc(-c3cnc(N)c4oc(-c5ccc6cc[nH]c6c5)cc34)cn2)CC1] | 167 | | | C |
| 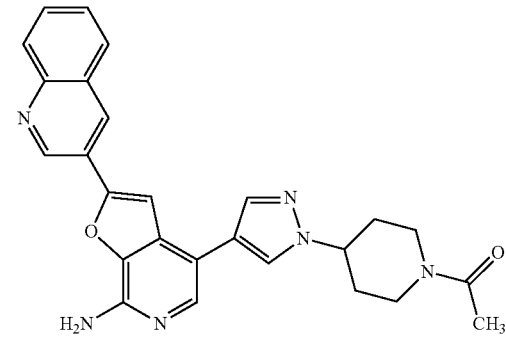 [SMILES: CC(=O)N1CCC(n2cc(-c3cnc(N)c4oc(-c5cnc6ccccc6c5)cc34)cn2)CC1] | 168 | | | C |

TABLE 1-continued
| Structure | Ex. No. | A | B | C |
|---|---|---|---|---|
| 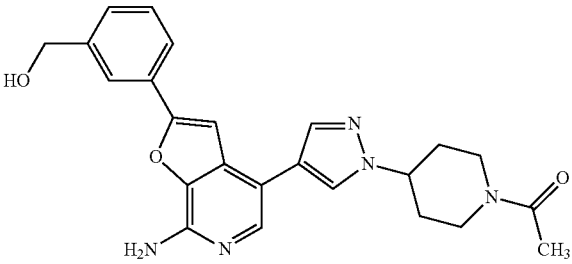 [SMILES: CC(=O)N1CCC(n2cc(-c3cnc(N)c4oc(-c5cccc(CO)c5)cc34)cn2)CC1] | 169 | B | B | C |
| 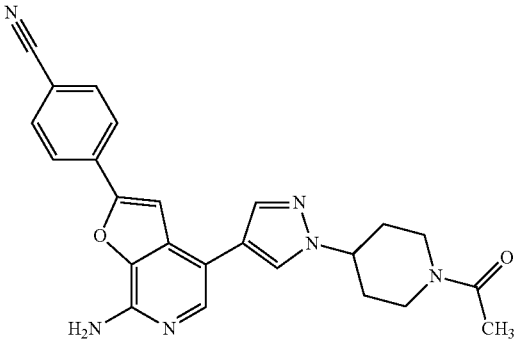 [SMILES: CC(=O)N1CCC(n2cc(-c3cnc(N)c4oc(-c5ccc(C#N)cc5)cc34)cn2)CC1] | 170 | C | | |
| 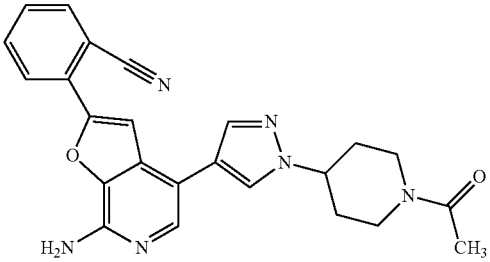 [SMILES: CC(=O)N1CCC(n2cc(-c3cnc(N)c4oc(-c5ccccc5C#N)cc34)cn2)CC1] | 171 | B | C | C |
| 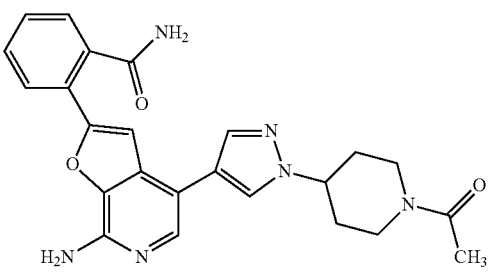 [SMILES: CC(=O)N1CCC(n2cc(-c3cnc(N)c4oc(-c5ccccc5C(N)=O)cc34)cn2)CC1] | 172 | C | | |
| 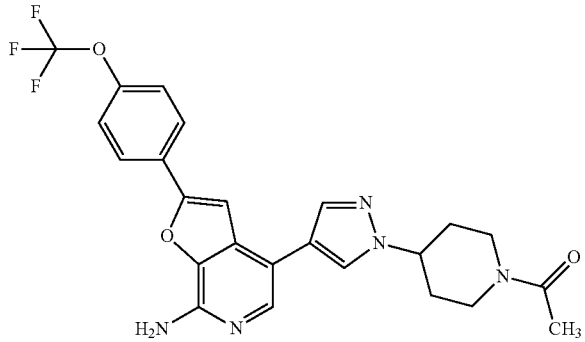 [SMILES: CC(=O)N1CCC(n2cc(-c3cnc(N)c4oc(-c5ccc(OC(F)(F)F)cc5)cc34)cn2)CC1] | 173 | D | | |

TABLE 1-continued

| Structure | Ex. No. | A | B | C |
|---|---|---|---|---|
| 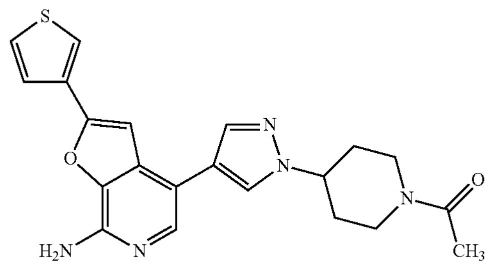 [SMILES: CC(=O)N1CCC(n2cc(-c3cnc(N)c4oc(-c5ccsc5)cc34)cn2)CC1] | 174 | B | C | C |
| 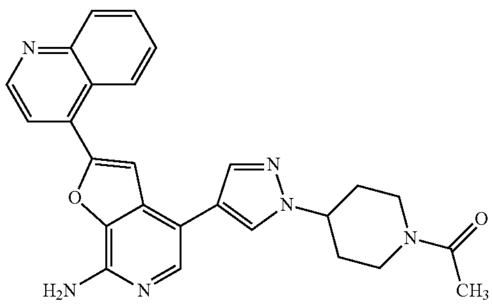 | 175 | B | | |
| 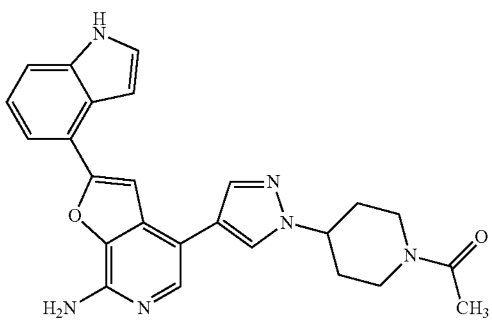 [SMILES: CC(=O)N1CCC(n2cc(-c3cnc(N)c4oc(-c5cccc6[nH]ccc56)cc34)cn2)CC1] | 176 | A | B | B |
| 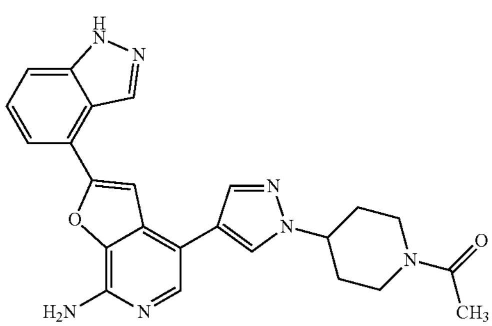 [SMILES: CC(=O)N1CCC(n2cc(-c3cnc(N)c4oc(-c5cccc6[nH]ncc56)cc34)cn2)CC1] | 177 | A | B | B |
| 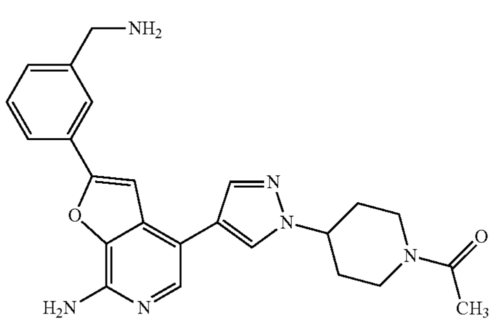 [SMILES: CC(=O)N1CCC(n2cc(-c3cnc(N)c4oc(-c5cccc(CN)c5)cc34)cn2)CC1] | 178 | B | | |

TABLE 1-continued

| Structure | Ex. No. | A | B | C |
|---|---|---|---|---|
| (structure) | 179 | C | | |
| (structure) | 180 | B | C | C |
| (structure) | 181 | D | | |
| (structure) | 182 | C | | |

TABLE 1-continued

| Structure | Ex. No. | A | B | C |
|---|---|---|---|---|
| 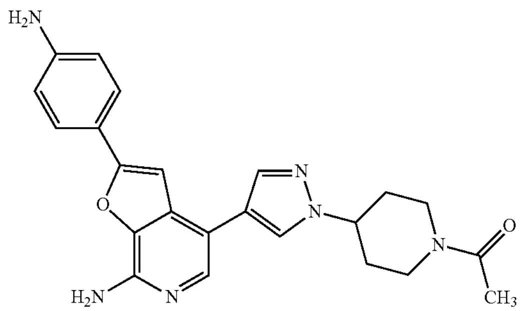 [SMILES: CC(=O)N1CCC(n2cc(-c3cnc(N)c4oc(-c5ccc(N)cc5)cc34)cn2)CC1] | 183 | | | C |
| 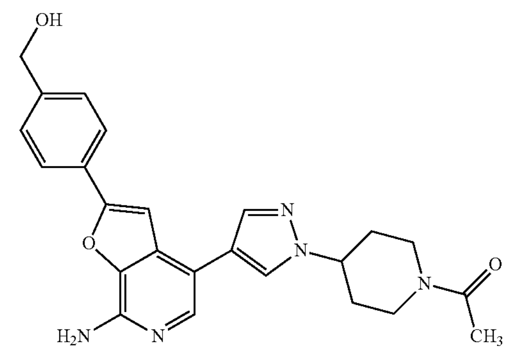 [SMILES: CC(=O)N1CCC(n2cc(-c3cnc(N)c4oc(-c5ccc(CO)cc5)cc34)cn2)CC1] | 184 | | | C |
| 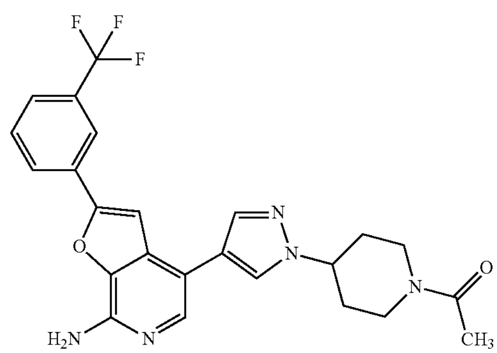 [SMILES: CC(=O)N1CCC(n2cc(-c3cnc(N)c4oc(-c5cccc(C(F)(F)F)c5)cc34)cn2)CC1] | 185 | | | C |
| 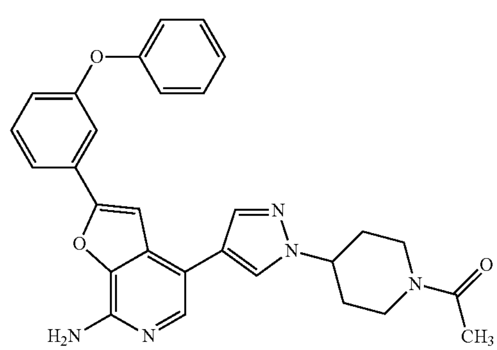 [SMILES: CC(=O)N1CCC(n2cc(-c3cnc(N)c4oc(-c5cccc(Oc6ccccc6)c5)cc34)cn2)CC1] | 186 | | | D |

TABLE 1-continued
| Structure | Ex. No. | A | B | C |
|---|---|---|---|---|
| 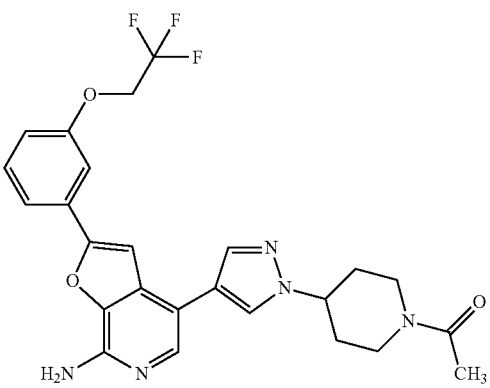 [SMILES: CC(=O)N1CCC(n2cc(-c3cnc(N)c4oc(-c5cccc(OCC(F)(F)F)c5)cc34)cn2)CC1] | 187 | C | | |
| 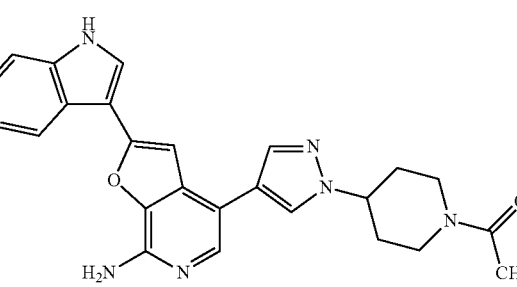 | 188 | D | | |
| 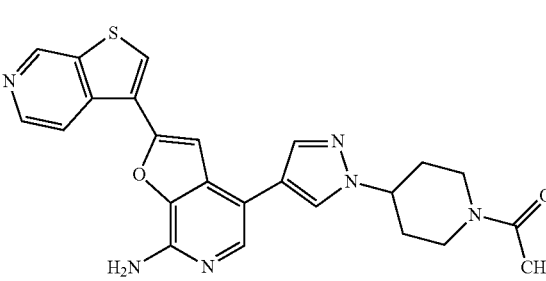 | 189 | A | A | B |
| 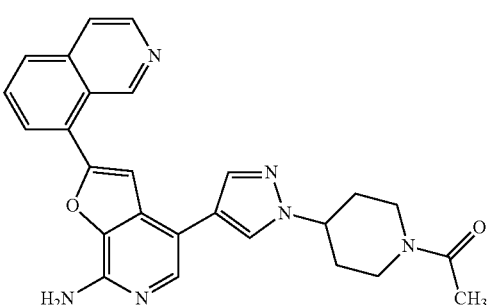 | 190 | C | | |
| 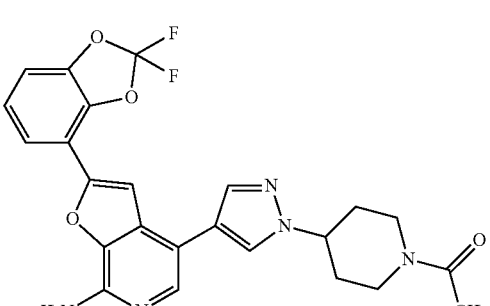 | 191 | B | B | B |

TABLE 1-continued

| Structure | Ex. No. | A | B | C |
|---|---|---|---|---|
| 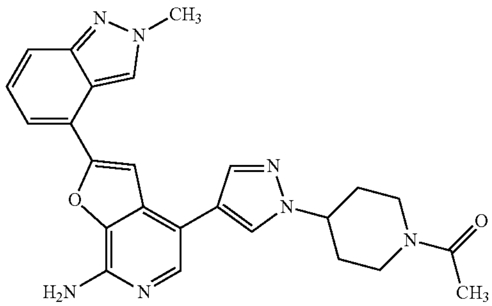 [SMILES: CC(=O)N1CCC(n2cc(-c3cnc(N)c4oc(-c5cccc6nn(C)cc56)cc34)cn2)CC1] | 192 | C | C | C |
| 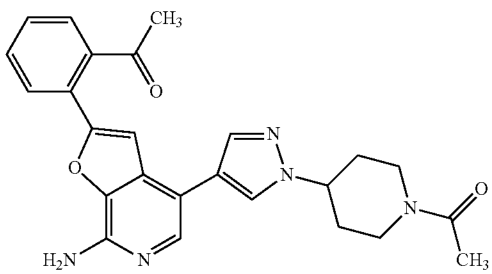 [SMILES: CC(=O)c1ccccc1-c1cc2c(-c3cnn(C4CCN(C(C)=O)CC4)c3)cnc(N)c2o1] | 193 | C | | |
| 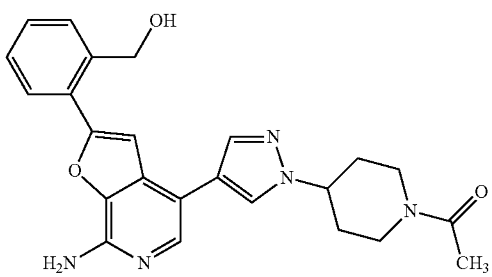 [SMILES: CC(=O)N1CCC(n2cc(-c3cnc(N)c4oc(-c5ccccc5CO)cc34)cn2)CC1] | 194 | B | | |
| 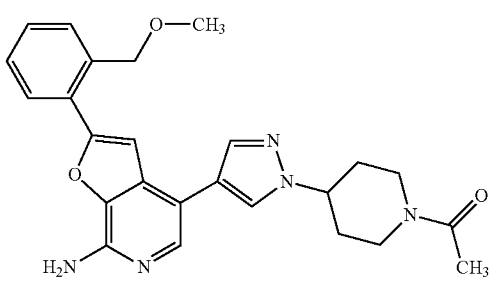 [SMILES: COCc1ccccc1-c1cc2c(-c3cnn(C4CCN(C(C)=O)CC4)c3)cnc(N)c2o1] | 195 | C | | |
| 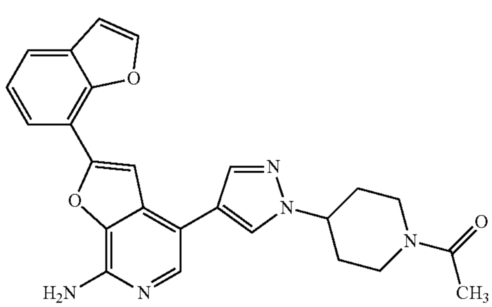 [SMILES: CC(=O)N1CCC(n2cc(-c3cnc(N)c4oc(-c5cccc6ccoc56)cc34)cn2)CC1] | 196 | D | | |

TABLE 1-continued
| Structure | Ex. No. | A | B | C |
|---|---|---|---|---|
| 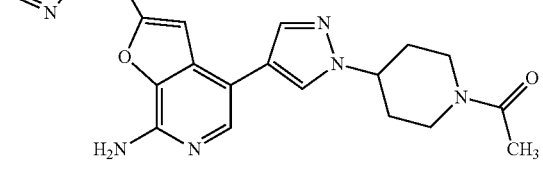 | 197 | B | B | B |
| 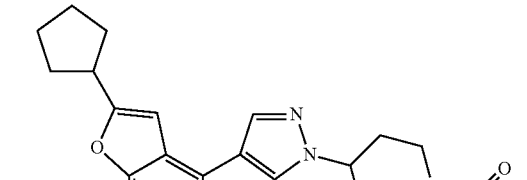 | 198 | C | | |
| 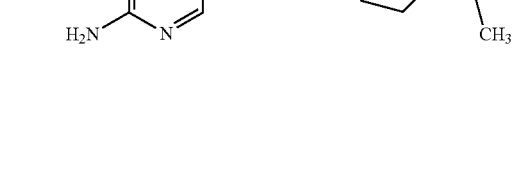 | 199 | C | | |
| 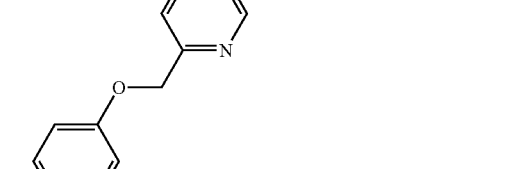 | 200 | C | | |

TABLE 1-continued

| Structure | Ex. No. | A | B | C |
|---|---|---|---|---|
| 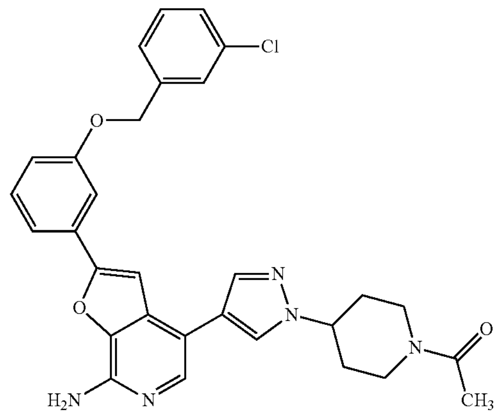 [SMILES: CC(=O)N1CCC(n2cc(-c3cnc(N)c4oc(-c5cccc(OCc6cccc(Cl)c6)c5)cc34)cn2)CC1] | 201 | D | | |
| 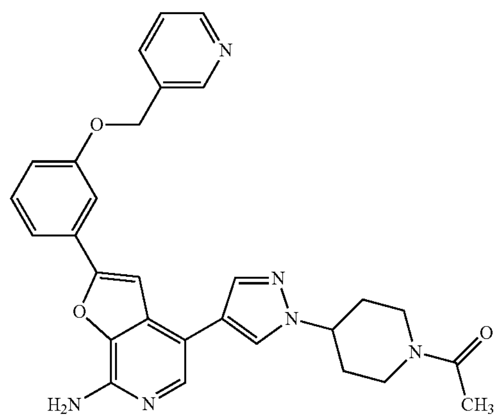 [SMILES: CC(=O)N1CCC(n2cc(-c3cnc(N)c4oc(-c5cccc(OCc6cccnc6)c5)cc34)cn2)CC1] | 202 | | | C |
| 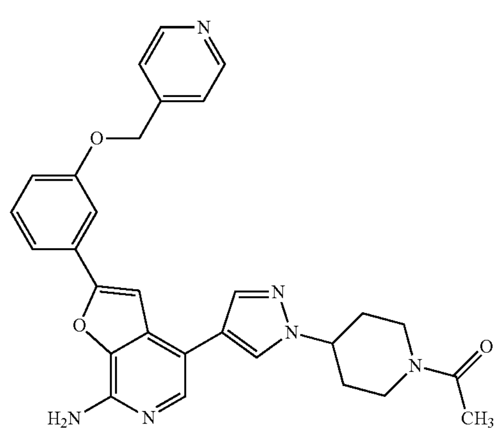 [SMILES: CC(=O)N1CCC(n2cc(-c3cnc(N)c4oc(-c5cccc(OCc6ccncc6)c5)cc34)cn2)CC1] | 203 | | B | |

TABLE 1-continued

| Structure | Ex. No. | A | B | C |
|---|---|---|---|---|
| 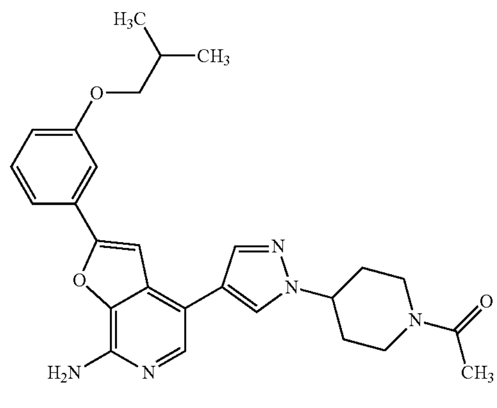 [SMILES: CC(=O)N1CCC(n2cc(-c3cnc(N)c4oc(-c5cccc(OCC(C)C)c5)cc34)cn2)CC1] | 204 | D | | |
| 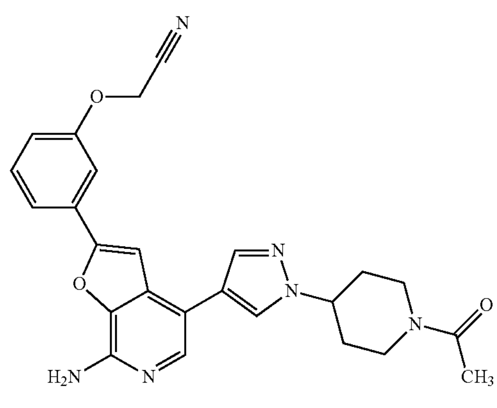 [SMILES: CC(=O)N1CCC(n2cc(-c3cnc(N)c4oc(-c5cccc(OCC#N)c5)cc34)cn2)CC1] | 205 | B | B | B |
| 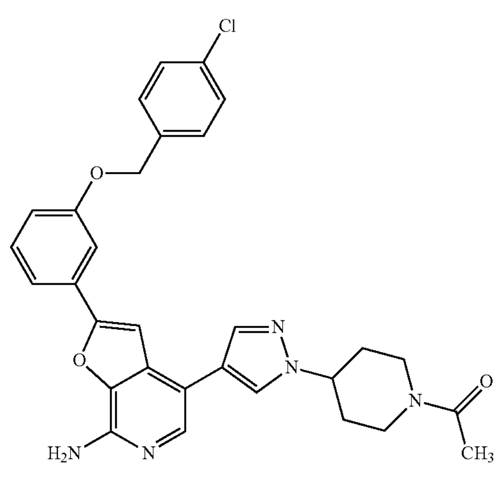 [SMILES: CC(=O)N1CCC(n2cc(-c3cnc(N)c4oc(-c5cccc(OCc6ccc(Cl)cc6)c5)cc34)cn2)CC1] | 206 | D | | |

TABLE 1-continued

| Structure | Ex. No. | A | B | C |
|---|---|---|---|---|
| (structure) | 207 | D | | |
| (structure) | 208 | D | | |
| (structure) | 209 | D | | |
| (structure) | 210 | D | | |

TABLE 1-continued

| Structure | Ex. No. | A | B | C |
|---|---|---|---|---|
| 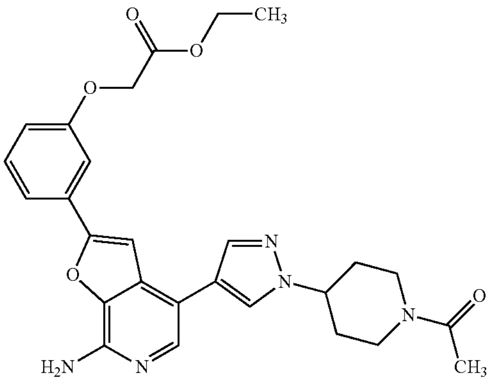 [SMILES: CCOC(=O)COc1cccc(-c2cc3c(-c4cnn(C5CCN(C(C)=O)CC5)c4)cnc(N)c3o2)c1] | 211 | D | | |
| 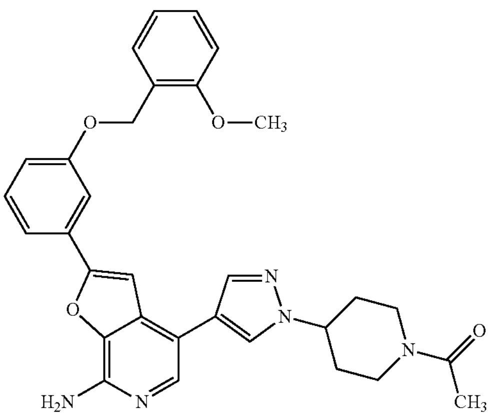 [SMILES: COc1ccccc1COc1cccc(-c2cc3c(-c4cnn(C5CCN(C(C)=O)CC5)c4)cnc(N)c3o2)c1] | 212 | D | | |
| 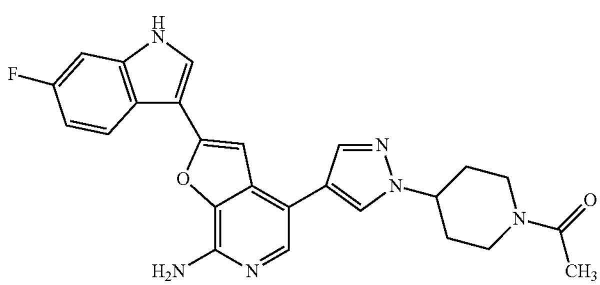 [SMILES: CC(=O)N1CCC(n2cc(-c3cnc(N)c4oc(-c5c[nH]c6cc(F)ccc56)cc34)cn2)CC1] | 213 | B | B | B |
| 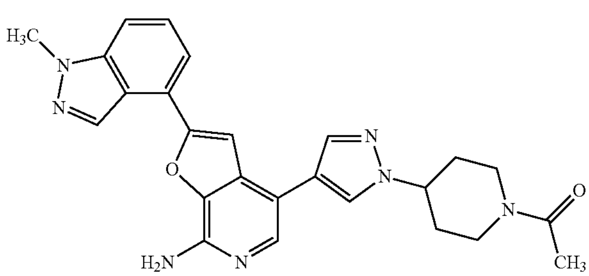 [SMILES: CC(=O)N1CCC(n2cc(-c3cnc(N)c4oc(-c5cccc6c5cnn6C)cc34)cn2)CC1] | 214 | B | | |

TABLE 1-continued
| Structure | Ex. No. | A | B | C |
|---|---|---|---|---|
| 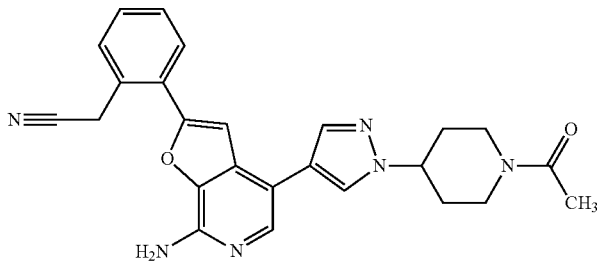 [SMILES: CC(=O)N1CCC(n2cc(-c3cnc(N)c4oc(-c5ccccc5CC#N)cc34)cn2)CC1] | 215 | B | B | B |
| 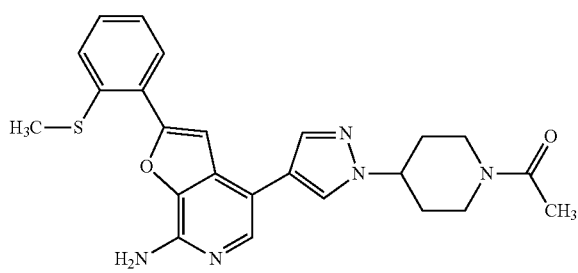 [SMILES: CSc1ccccc1-c1cc2c(-c3cnn(C4CCN(C(C)=O)CC4)c3)cnc(N)c2o1] | 216 | B | B | B |
| 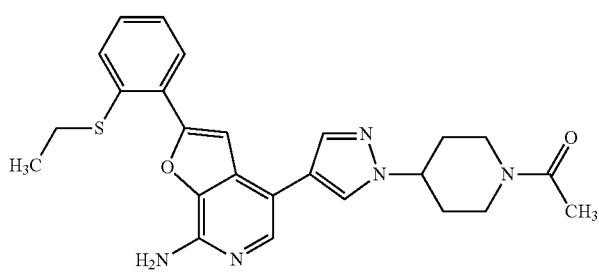 [SMILES: CCSc1ccccc1-c1cc2c(-c3cnn(C4CCN(C(C)=O)CC4)c3)cnc(N)c2o1] | 217 | B | B | B |
| 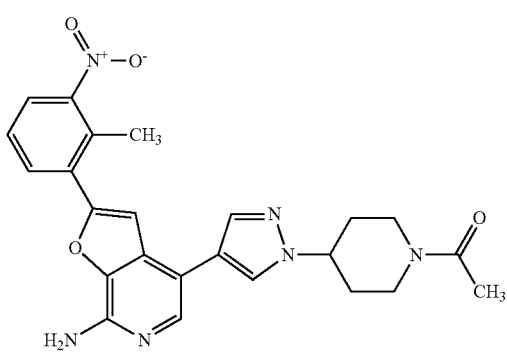 [SMILES: CC(=O)N1CCC(n2cc(-c3cnc(N)c4oc(-c5cccc([N+](=O)[O-])c5C)cc34)cn2)CC1] | 218 | A | B | B |
| 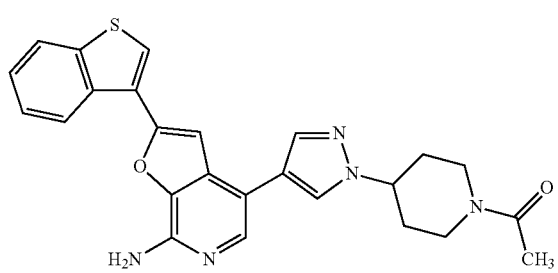 [SMILES: CC(=O)N1CCC(n2cc(-c3cnc(N)c4oc(-c5csc6ccccc56)cc34)cn2)CC1] | 219 | B | B | B |

TABLE 1-continued

| Structure | Ex. No. | A | B | C |
|---|---|---|---|---|
| 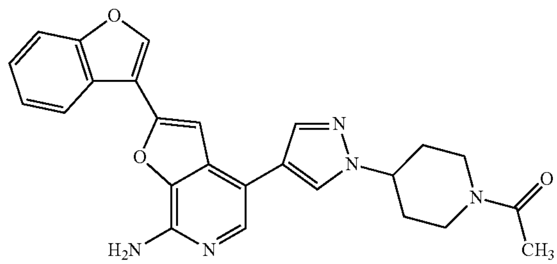 [SMILES: CC(=O)N1CCC(n2cc(-c3cnc(N)c4oc(-c5coc6ccccc56)cc34)cn2)CC1] | 220 | C | | |
| 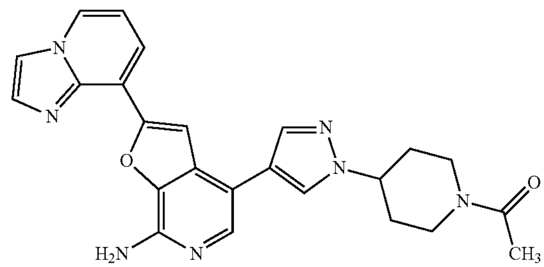 [SMILES: CC(=O)N1CCC(n2cc(-c3cnc(N)c4oc(-c5cccn6ccnc56)cc34)cn2)CC1] | 221 | B | B | B |
| 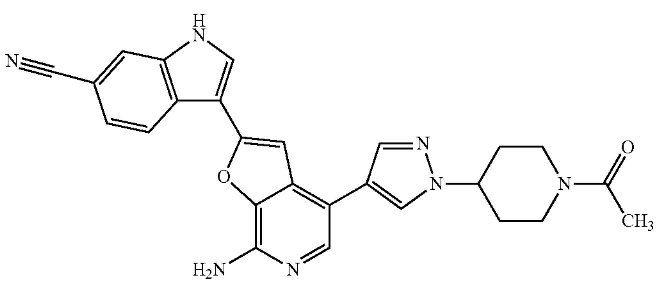 [SMILES: CC(=O)N1CCC(n2cc(-c3cnc(N)c4oc(-c5c[nH]c6cc(C#N)ccc56)cc34)cn2)CC1] | 222 | B | B | B |
| 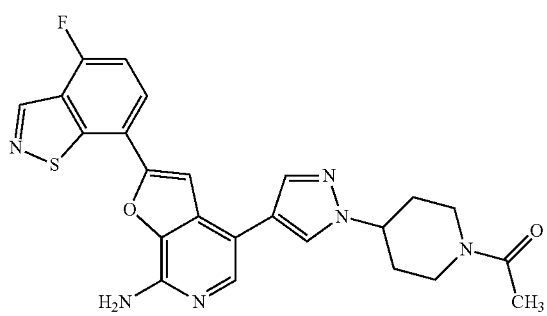 [SMILES: CC(=O)N1CCC(n2cc(-c3cnc(N)c4oc(-c5ccc(F)c6cnsc56)cc34)cn2)CC1] | 223 | B | B | |
| 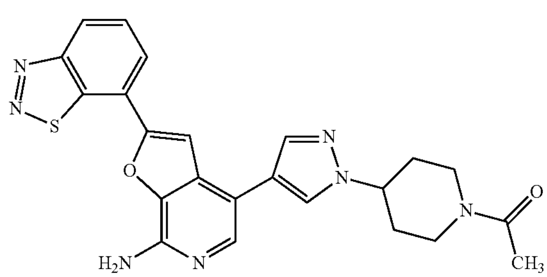 [SMILES: CC(=O)N1CCC(n2cc(-c3cnc(N)c4oc(-c5cccc6nnsc56)cc34)cn2)CC1] | 224 | A | A | A |

TABLE 1-continued

| Structure | Ex. No. | A | B | C |
|---|---|---|---|---|
| 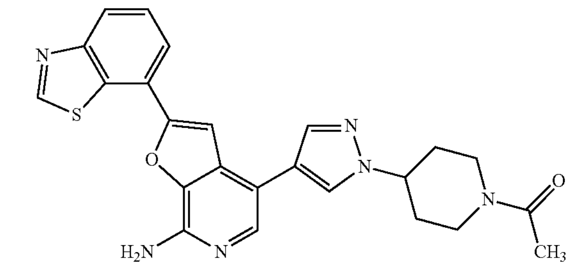 [SMILES: CC(=O)N1CCC(n2cc(-c3cnc(N)c4oc(-c5cccc6ncsc56)cc34)cn2)CC1] | 225 | A | A | |
| 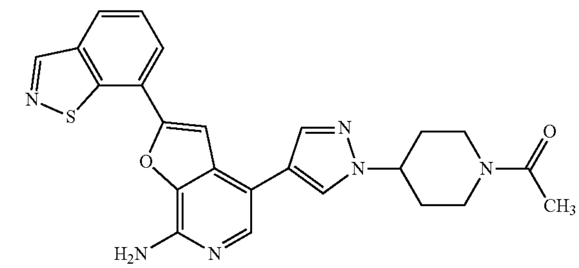 [SMILES: CC(=O)N1CCC(n2cc(-c3cnc(N)c4oc(-c5cccc6cnsc56)cc34)cn2)CC1] | 226 | A | A | A |
| 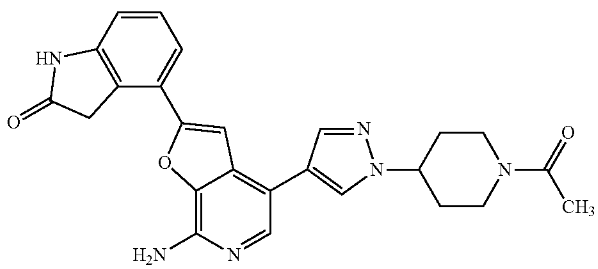 [SMILES: CC(=O)N1CCC(n2cc(-c3cnc(N)c4oc(-c5cccc6c5CC(=O)N6)cc34)cn2)CC1] | 227 | B | C | C |
| 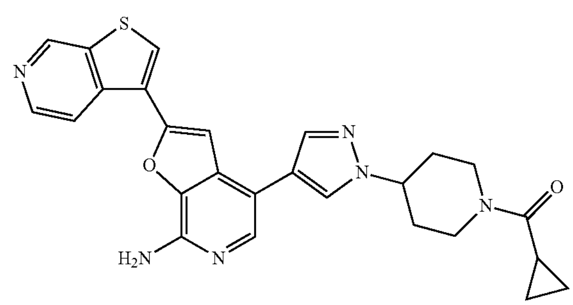 [SMILES: Nc1ncc(-c2cnn(C3CCN(C(=O)C4CC4)CC3)c2)c2cc(-c3csc4cnccc34)oc12] | 228 | A | A | |
| 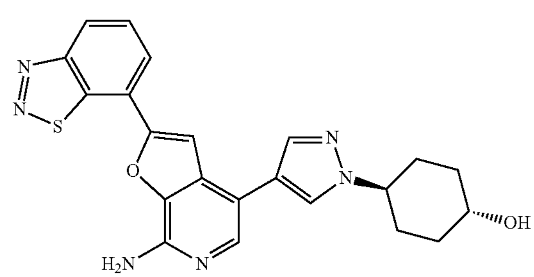 [SMILES: Nc1ncc(-c2cnn([C@H]3CC[C@H](O)CC3)c2)c2cc(-c3cccc4nnsc34)oc12] | 229 | A | A | A |

TABLE 1-continued

| Structure | Ex. No. | A | B | C |
|---|---|---|---|---|
| 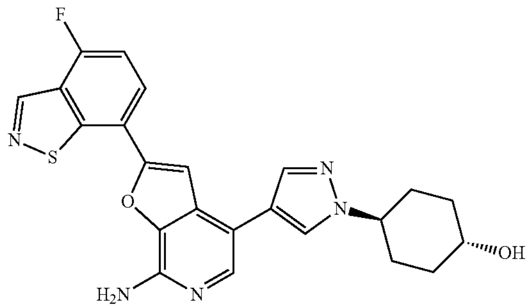 [SMILES: Nc1ncc(-c2cnn([C@H]3CC[C@H](O)CC3)c2)c2cc(-c3ccc(F)c4cnsc34)oc12] | 230 | B | B | B |
| 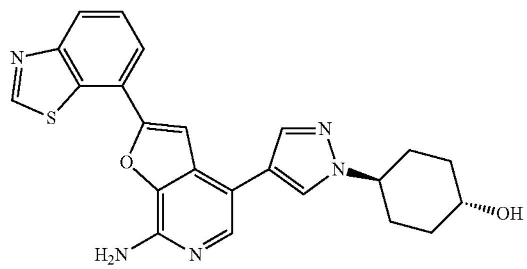 [SMILES: Nc1ncc(-c2cnn([C@H]3CC[C@H](O)CC3)c2)c2cc(-c3cccc4ncsc34)oc12] | 231 | A | A | |
| 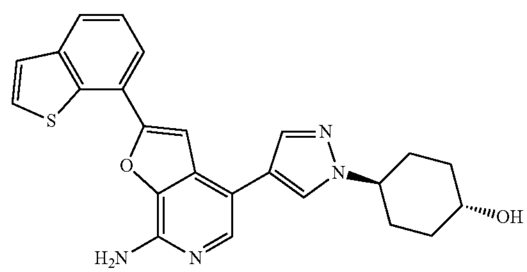 [SMILES: Nc1ncc(-c2cnn([C@H]3CC[C@H](O)CC3)c2)c2cc(-c3cccc4ccsc34)oc12] | 232 | B | | |
| 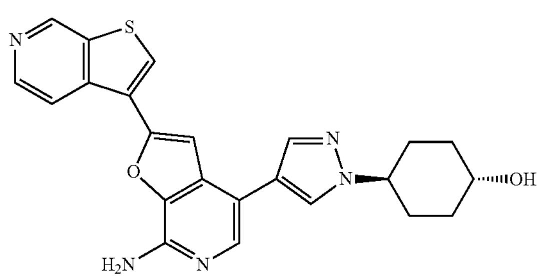 [SMILES: Nc1ncc(-c2cnn([C@H]3CC[C@H](O)CC3)c2)c2cc(-c3csc4cnccc34)oc12] | 233 | A | A | A |
| 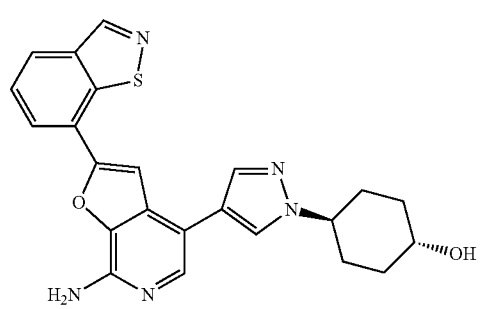 [SMILES: Nc1ncc(-c2cnn([C@H]3CC[C@H](O)CC3)c2)c2cc(-c3cccc4cnsc34)oc12] | 234 | A | A | B |

TABLE 1-continued

| Structure | Ex. No. | A | B | C |
|---|---|---|---|---|
| 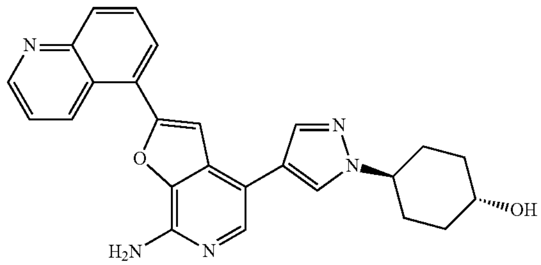 [SMILES: Nc1ncc(-c2cnn([C@H]3CC[C@H](O)CC3)c2)c2cc(-c3cccc4ncccc34)oc12] | 235 | C | | |
| 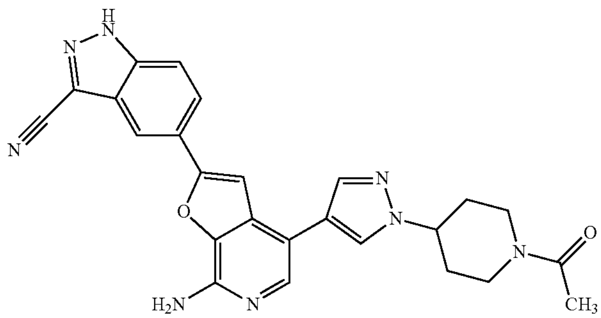 [SMILES: CC(=O)N1CCC(n2cc(-c3cnc(N)c4oc(-c5ccc6[nH]nc(C#N)c6c5)cc34)cn2)CC1] | 236 | B | C | D |
| 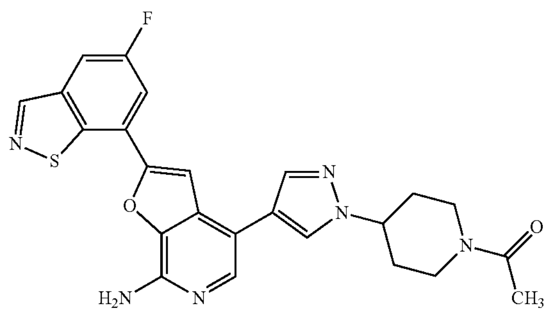 [SMILES: CC(=O)N1CCC(n2cc(-c3cnc(N)c4oc(-c5cc(F)cc6cnsc56)cc34)cn2)CC1] | 237 | A | A | |
| 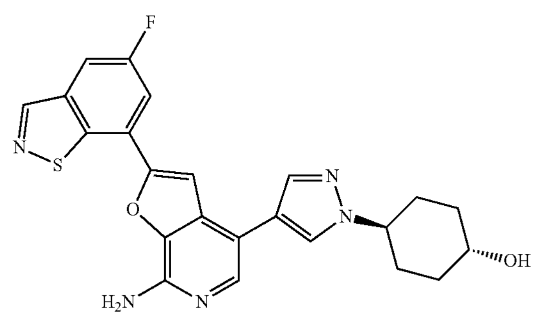 [SMILES: Nc1ncc(-c2cnn([C@H]3CC[C@H](O)CC3)c2)c2cc(-c3cc(F)cc4cnsc34)oc12] | 238 | B | A | B |
| 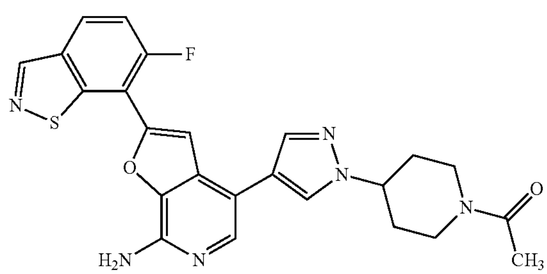 | 239 | B | B | |

TABLE 1-continued

| Structure | Ex. No. | A | B | C |
|---|---|---|---|---|
| 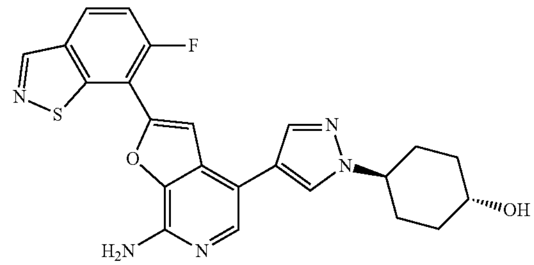 [SMILES: Nc1ncc(-c2cnn([C@H]3CC[C@H](O)CC3)c2)c2cc(-c3c(F)ccc4cnsc34)oc12] | 240 | B | A | B |
| 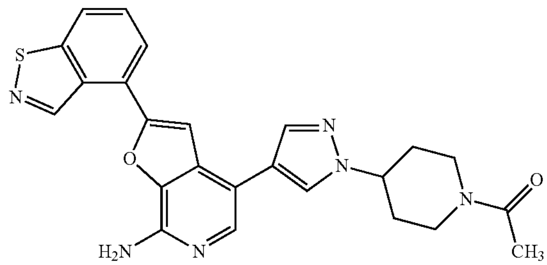 | 241 | A | A | |
| 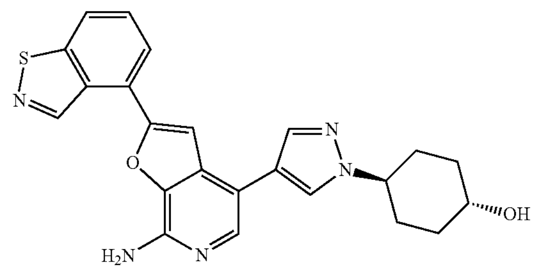 [SMILES: Nc1ncc(-c2cnn([C@H]3CC[C@H](O)CC3)c2)c2cc(-c3cccc4sncc34)oc12] | 242 | A | A | |
| 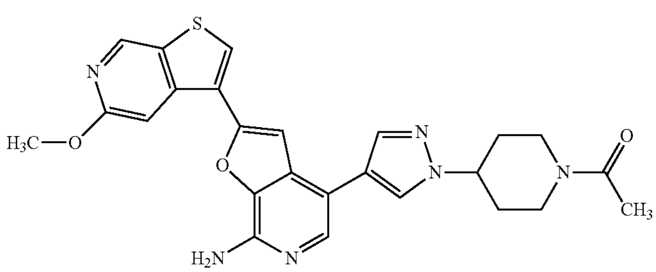 [SMILES: COc1cc2c(-c3cc4c(-c5cnn(C6CCN(C(C)=O)CC6)c5)cnc(N)c4o3)csc2cn1] | 243 | C | B | C |
| 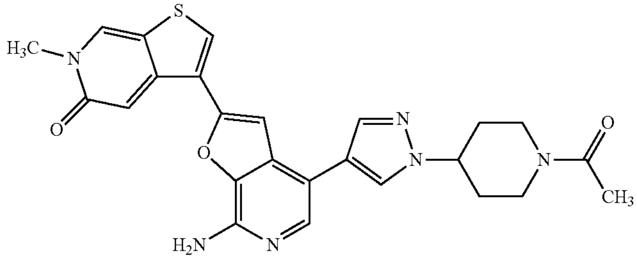 [SMILES: CC(=O)N1CCC(n2cc(-c3cnc(N)c4oc(-c5csc6cn(C)c(=O)cc56)cc34)cn2)CC1] | 244 | C | | |

TABLE 1-continued
| Structure | Ex. No. | A | B | C |
|---|---|---|---|---|
| 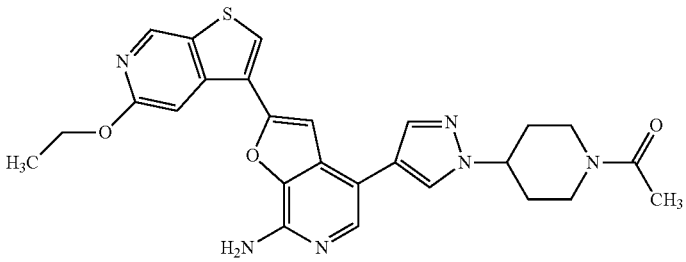 [SMILES: CCOc1cc2c(-c3cc4c(-c5cnn(C6CCN(C(C)=O)CC6)c5)cnc(N)c4o3)csc2cn1] | 245 | B | | |
| 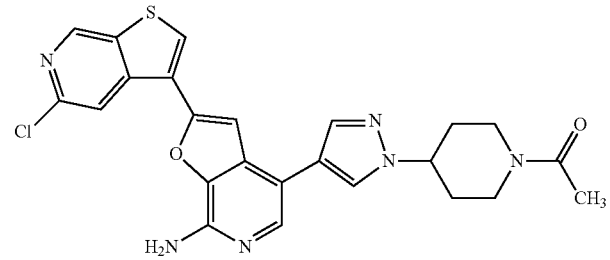 [SMILES: CC(=O)N1CCC(n2cc(-c3cnc(N)c4oc(-c5csc6cnc(Cl)cc56)cc34)cn2)CC1] | 246 | B | B | |
| 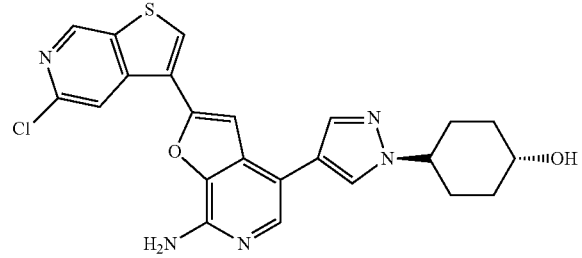 | 247 | B | B | |
| 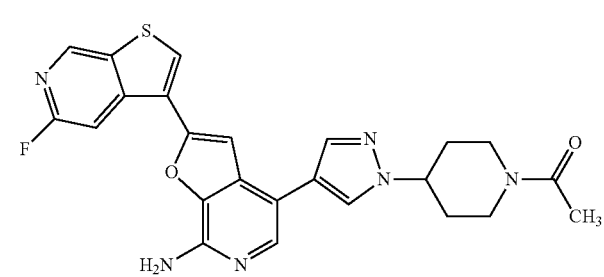 [SMILES: CC(=O)N1CCC(n2cc(-c3cnc(N)c4oc(-c5csc6cnc(F)cc56)cc34)cn2)CC1] | 248 | A | A | |
| 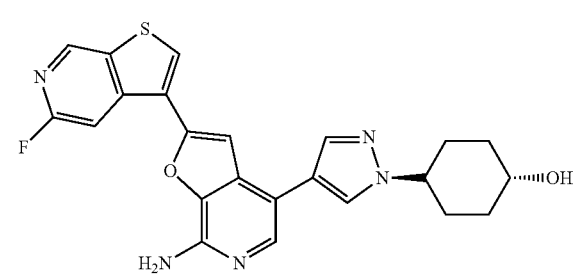 | 249 | A | A | A |

TABLE 1-continued

| Structure | Ex. No. | A | B | C |
|---|---|---|---|---|
| (structure 250) | 250 | | | C |
| (structure 251) | 251 | | B | C |
| (structure 252) | 252 | | B | B |
| (structure 253) | 253 | A | B | C |
| (structure 254) | 254 | A | B | B |

TABLE 1-continued
| Structure | Ex. No. | A | B | C |
|---|---|---|---|---|
| 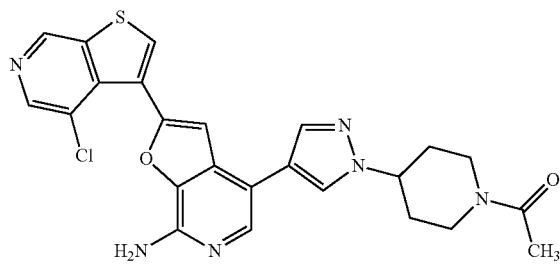 [SMILES: CC(=O)N1CCC(n2cc(-c3cnc(N)c4oc(-c5csc6cncc(Cl)c56)cc34)cn2)CC1] | 255 | | | C |
| 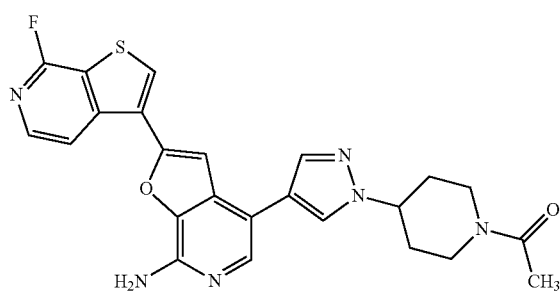 [SMILES: CC(=O)N1CCC(n2cc(-c3cnc(N)c4oc(-c5csc6c(F)nccc56)cc34)cn2)CC1] | 256 | | B | B |
| 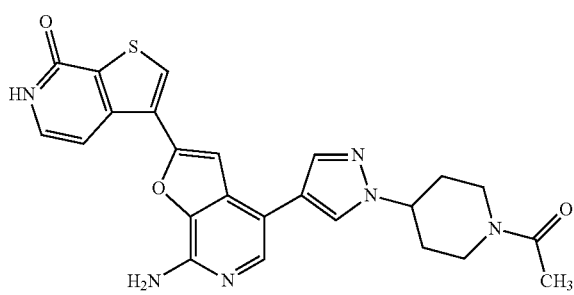 | 257 | | | C |
| 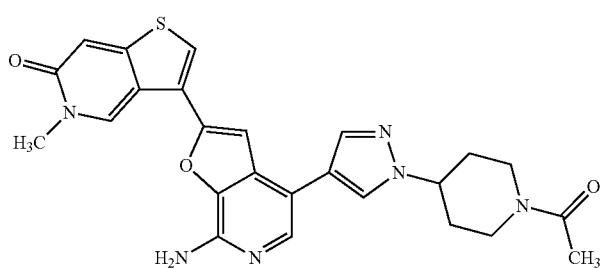 [SMILES: CC(=O)N1CCC(n2cc(-c3cnc(N)c4oc(-c5csc6cc(=O)n(C)cc56)cc34)cn2)CC1] | 258 | | | C |
| 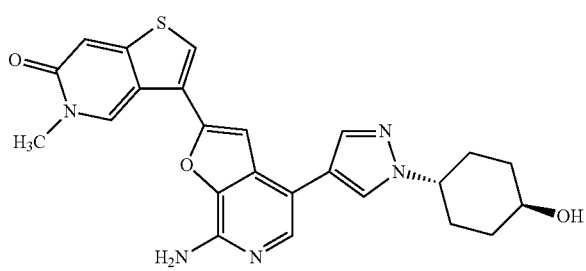 [SMILES: Cn1cc2c(-c3cc4c(-c5cnn([C@H]6CC[C@H](O)CC6)c5)cnc(N)c4o3)csc2cc1=O] | 259 | | | D |

TABLE 1-continued

| Structure | Ex. No. | A | B | C |
|---|---|---|---|---|
| 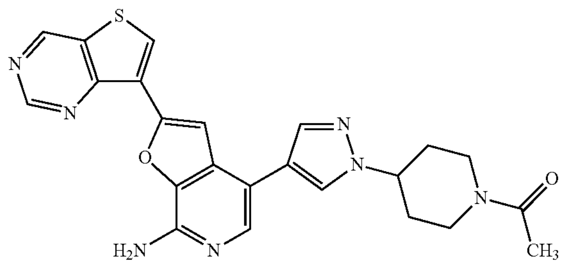 [SMILES: CC(=O)N1CCC(n2cc(-c3cnc(N)c4oc(-c5csc6cncnc56)cc34)cn2)CC1] | 260 | B | C | C |
| 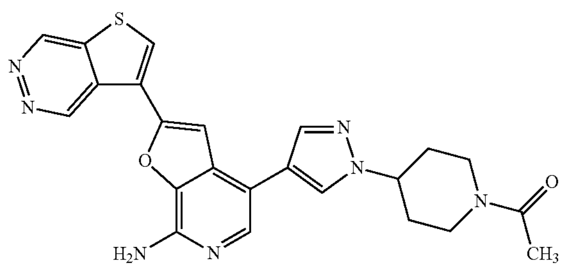 [SMILES: CC(=O)N1CCC(n2cc(-c3cnc(N)c4oc(-c5csc6cnncc56)cc34)cn2)CC1] | 261 | A | B | |
| 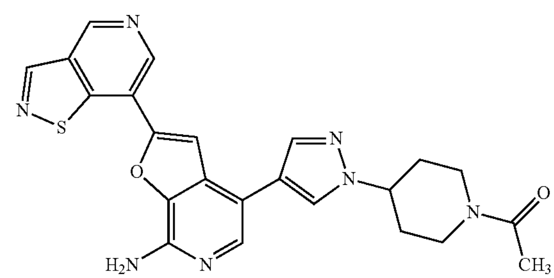 [SMILES: CC(=O)N1CCC(n2cc(-c3cnc(N)c4oc(-c5cncc6cnsc56)cc34)cn2)CC1] | 262 | B | B | B |
| 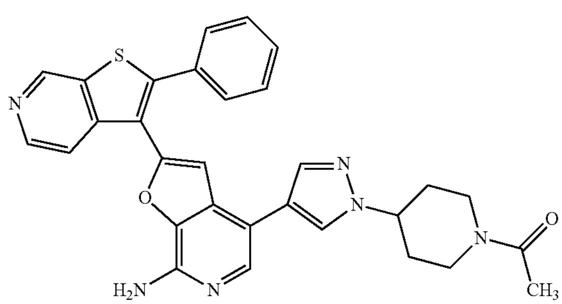 [SMILES: CC(=O)N1CCC(n2cc(-c3cnc(N)c4oc(-c5c(-c6ccccc6)sc6cnccc56)cc34)cn2)CC1] | 263 | B | | |
| 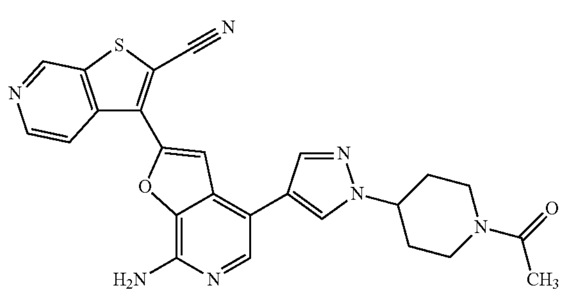 [SMILES: CC(=O)N1CCC(n2cc(-c3cnc(N)c4oc(-c5c(C#N)sc6cnccc56)cc34)cn2)CC1] | 264 | B | A | |

TABLE 1-continued

| Structure | Ex. No. | A | B | C |
|---|---|---|---|---|
| (structure) | 265 | B | | |
| (structure) | 266 | A | B | |
| (structure) | 267 | B | A | B |
| (structure) | 268 | A | A | |
| (structure) | 269 | C | | |

TABLE 1-continued

| Structure | Ex. No. | A | B | C |
|---|---|---|---|---|
| 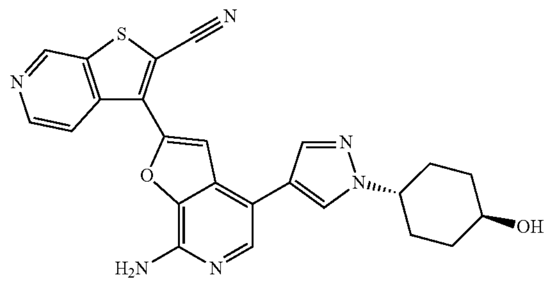 [SMILES: N#Cc1sc2cnccc2c1-c1cc2c(-c3cnn([C@H]4CC[C@H](O)CC4)c3)cnc(N)c2o1] | 270 | | B | A |
| 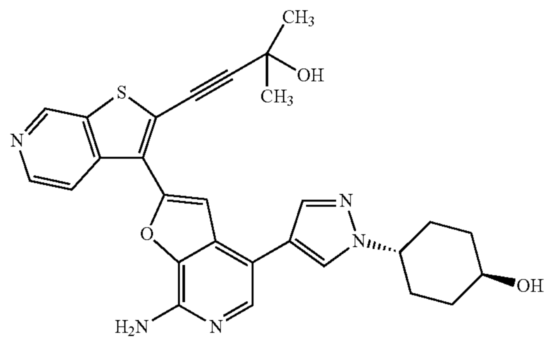 [SMILES: CC(C)(O)C#Cc1sc2cnccc2c1-c1cc2c(-c3cnn([C@H]4CC[C@H](O)CC4)c3)cnc(N)c2o1] | 271 | | B | C |
| 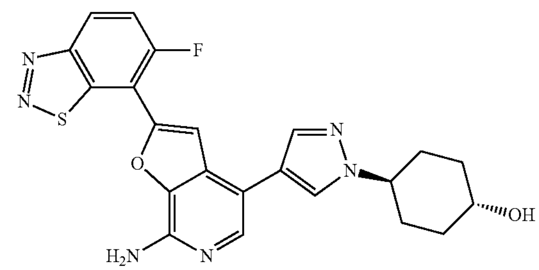 [SMILES: Nc1ncc(-c2cnn([C@H]3CC[C@H](O)CC3)c2)c2cc(-c3c(F)ccc4nnsc34)oc12] | 272 | | A | A |
| 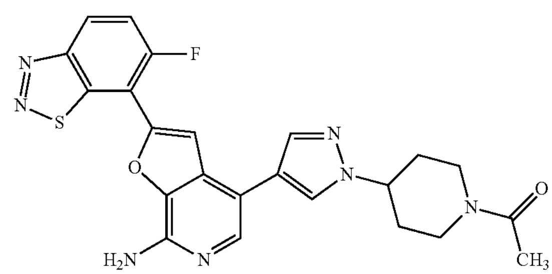 [SMILES: CC(=O)N1CCC(n2cc(-c3cnc(N)c4oc(-c5c(F)ccc6nnsc56)cc34)cn2)CC1] | 273 | | A | B |
| | 274 | | | C | |

TABLE 1-continued

| Structure | Ex. No. | A | B | C |
|---|---|---|---|---|
| 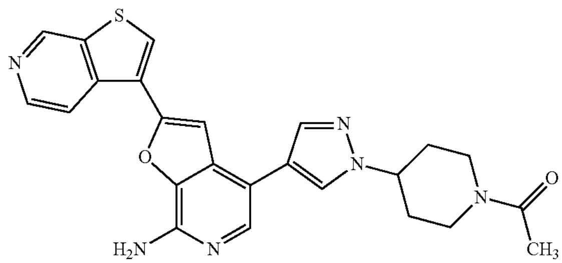 [SMILES: CC(=O)N1CCC(n2cc(-c3cnc(N)c4oc(-c5csc6cnccc56)cc34)cn2)CC1] | 275 | A | A | A |
| 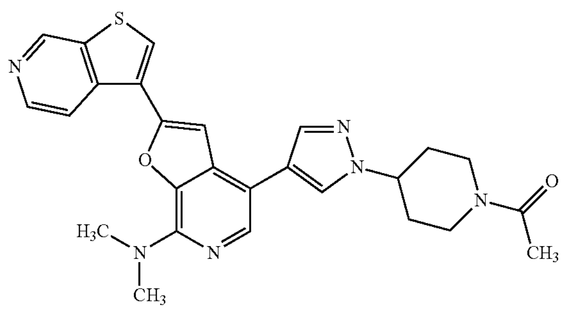 [SMILES: CC(=O)N1CCC(n2cc(-c3cnc(N(C)C)c4oc(-c5csc6cnccc56)cc34)cn2)CC1] | 276 | C | | |
| 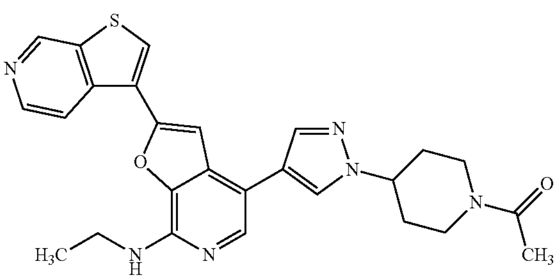 [SMILES: CCNc1ncc(-c2cnn(C3CCN(C(C)=O)CC3)c2)c2cc(-c3csc4cnccc34)oc12] | 277 | C | | |
| 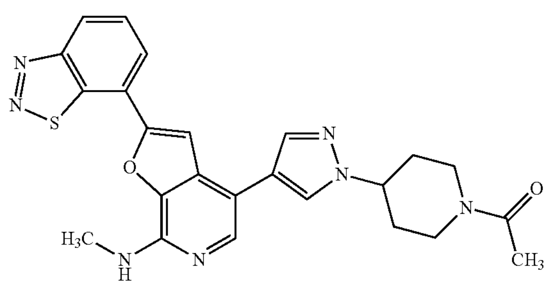 [SMILES: CNc1ncc(-c2cnn(C3CCN(C(C)=O)CC3)c2)c2cc(-c3cccc4nnsc34)oc12] | 278 | A | A | |
| 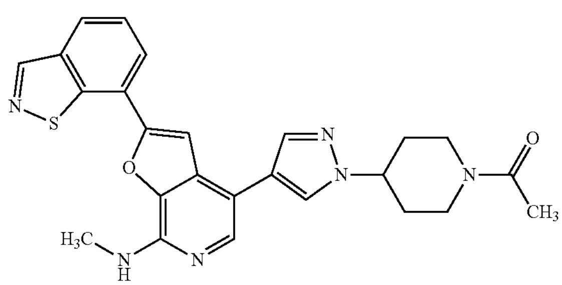 [SMILES: CNc1ncc(-c2cnn(C3CCN(C(C)=O)CC3)c2)c2cc(-c3cccc4cnsc34)oc12] | 279 | B | | |

TABLE 1-continued

| Structure | Ex. No. | A | B | C |
|---|---|---|---|---|
| 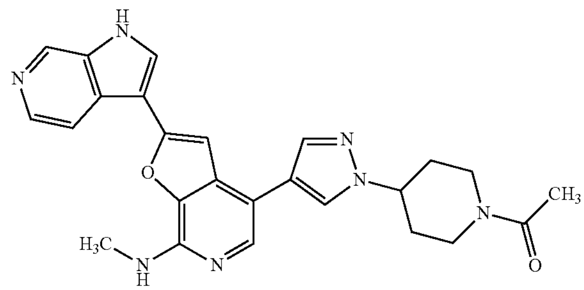 [SMILES: CNc1ncc(-c2cnn(C3CCN(C(C)=O)CC3)c2)c2cc(-c3c[nH]c4cnccc34)oc12] | 280 | A | C | B |
| 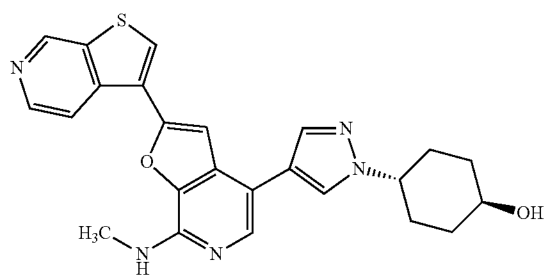 [SMILES: CNc1ncc(-c2cnn([C@H]3CC[C@H](O)CC3)c2)c2cc(-c3csc4cnccc34)oc12] | 281 | A | A | A |
| 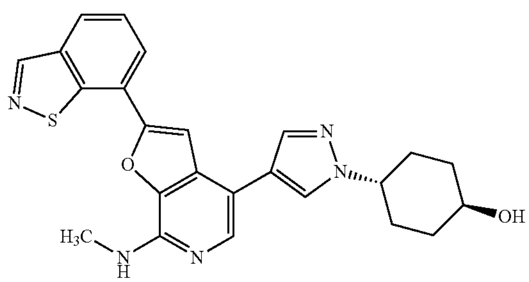 [SMILES: CNc1ncc(-c2cnn([C@H]3CC[C@H](O)CC3)c2)c2cc(-c3cccc4cnsc34)oc12] | 282 | B | B | |
| 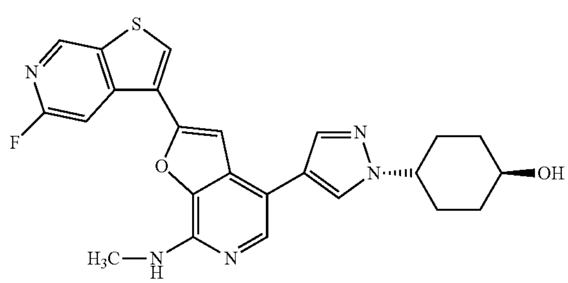 | 283 | A | A | |
| 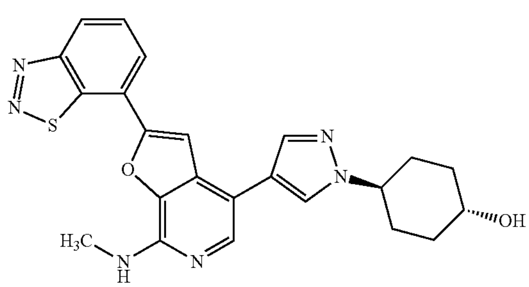 [SMILES: CNc1ncc(-c2cnn([C@H]3CC[C@H](O)CC3)c2)c2cc(-c3cccc4nnsc34)oc12] | 284 | A | A | |

TABLE 1-continued

| Structure | Ex. No. | A | B | C |
|---|---|---|---|---|
| 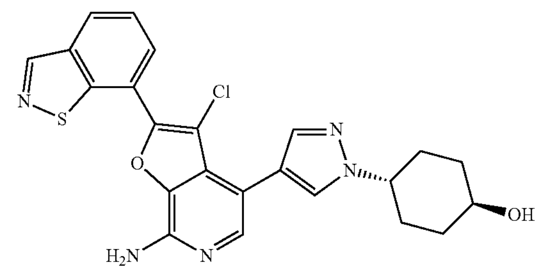 [SMILES: Nc1ncc(-c2cnn([C@H]3CC[C@H](O)CC3)c2)c2c(Cl)c(-c3cccc4cnsc34)oc12] | 285 | B | B | |
| 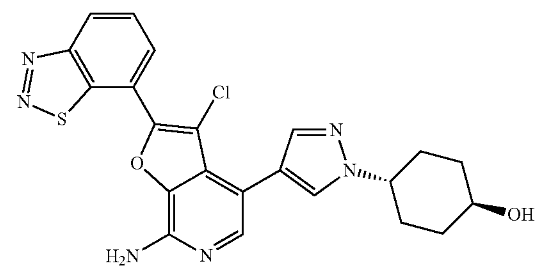 [SMILES: Nc1ncc(-c2cnn([C@H]3CC[C@H](O)CC3)c2)c2c(Cl)c(-c3cccc4nnsc34)oc12] | 286 | A | A | |
| 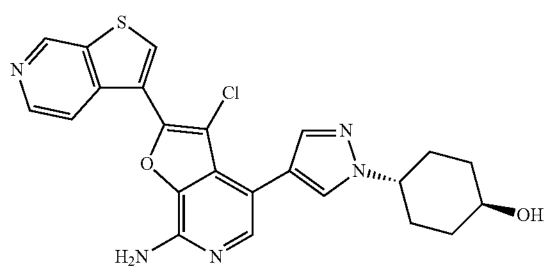 [SMILES: Nc1ncc(-c2cnn([C@H]3CC[C@H](O)CC3)c2)c2c(Cl)c(-c3csc4cnccc34)oc12] | 287 | B | A | |
| 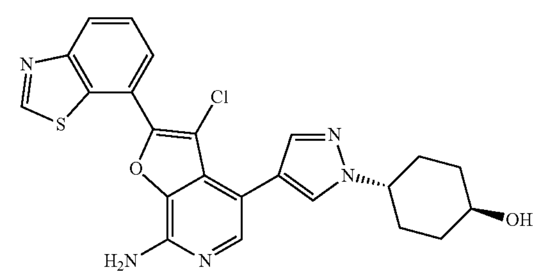 [SMILES: Nc1ncc(-c2cnn([C@H]3CC[C@H](O)CC3)c2)c2c(Cl)c(-c3cccc4ncsc34)oc12] | 288 | A | A | |
| 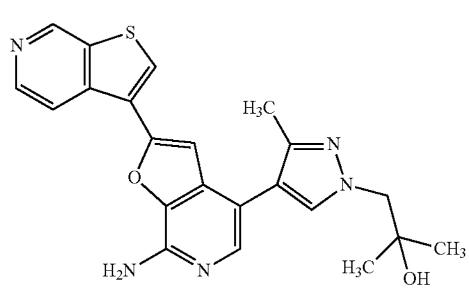 [SMILES: Cc1nn(CC(C)(C)O)cc1-c1cnc(N)c2oc(-c3csc4cnccc34)cc12] | 289 | C | B | C |

TABLE 1-continued
| Structure | Ex. No. | A | B | C |
|---|---|---|---|---|
| 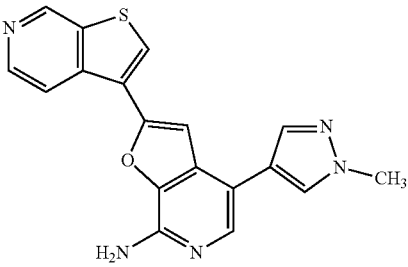 [SMILES: Cn1cc(-c2cnc(N)c3oc(-c4csc5cnccc45)cc23)cn1] | 290 | B | B | B |
| 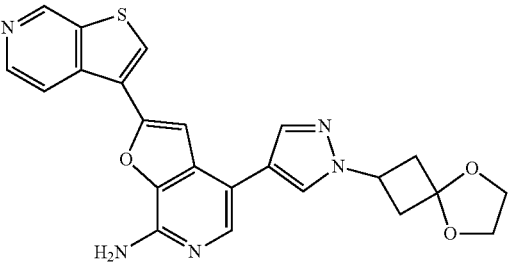 [SMILES: Nc1ncc(-c2cnn(C3CC4(C3)OCCO4)c2)c2cc(-c3csc4cnccc34)oc12] | 291 | A | B | B |
| 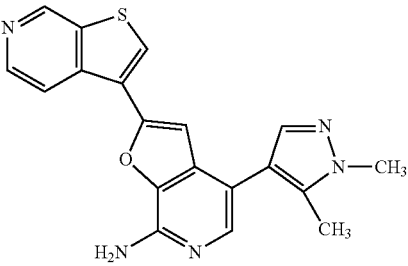 [SMILES: Cc1c(-c2cnc(N)c3oc(-c4csc5cnccc45)cc23)cnn1C] | 292 | C | | |
| 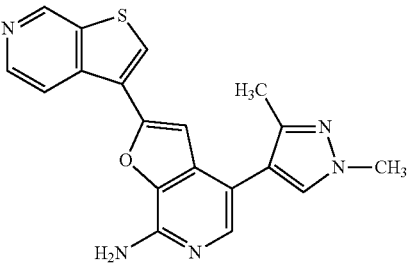 [SMILES: Cc1nn(C)cc1-c1cnc(N)c2oc(-c3csc4cnccc34)cc12] | 293 | C | B | C |
| 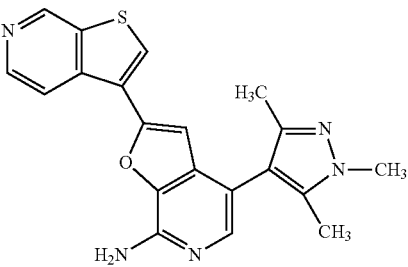 [SMILES: Cc1nn(C)c(C)c1-c1cnc(N)c2oc(-c3csc4cnccc34)cc12] | 294 | D | | |

TABLE 1-continued
| Structure | Ex. No. | A | B | C |
|---|---|---|---|---|
| 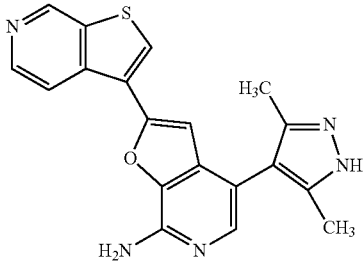 [SMILES: Cc1n[nH]c(C)c1-c1cnc(N)c2oc(-c3csc4cnccc34)cc12] | 295 | C | | |
| 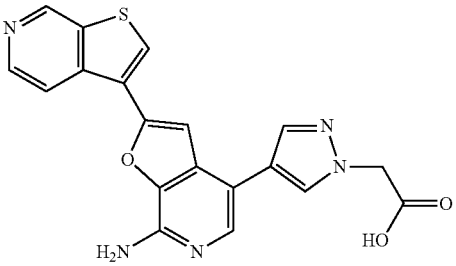 [SMILES: Nc1ncc(-c2cnn(CC(=O)O)c2)c2cc(-c3csc4cnccc34)oc12] | 296 | B | | |
| 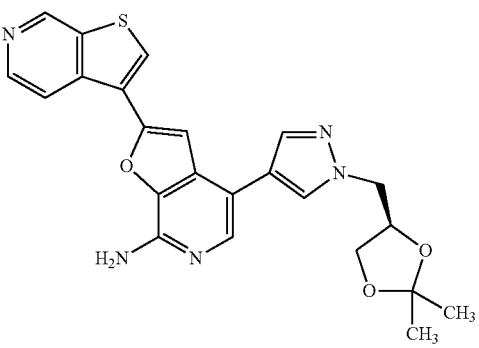 [SMILES: CC1(C)OC[C@@H](Cn2cc(-c3cnc(N)c4oc(-c5csc6cnccc56)cc34)cn2)O1] | 297 | B | B | C |
| 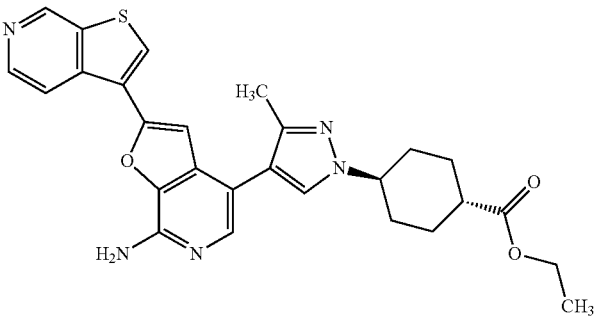 [SMILES: CCOC(=O)[C@H]1CC[C@H](n2cc(-c3cnc(N)c4oc(-c5csc6cnccc56)cc34)c(C)n2)CC1] | 298 | D | | |
| 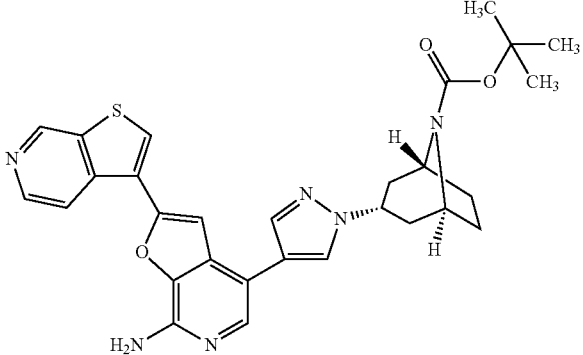 [SMILES: CC(C)(C)OC(=O)N1[C@@H]2CC[C@H]1C[C@H](n1cc(-c3cnc(N)c4oc(-c5csc6cnccc56)cc34)cn1)C2] | 299 | B | B | |

TABLE 1-continued

| Structure | Ex. No. | A | B | C |
|---|---|---|---|---|
| 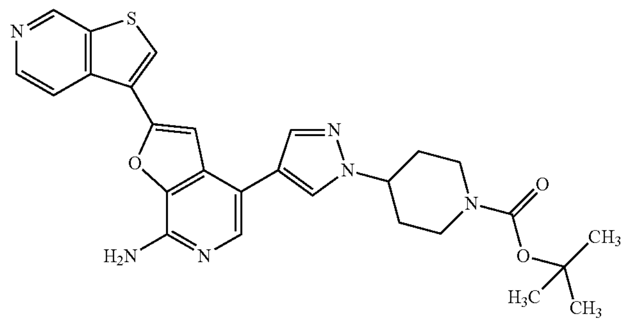 [SMILES: CC(C)(C)OC(=O)N1CCC(n2cc(-c3cnc(N)c4oc(-c5csc6cnccc56)cc34)cn2)CC1] | 300 | B | B | B |
| 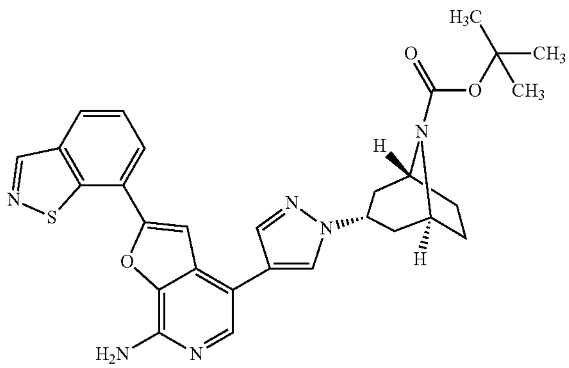 [SMILES: CC(C)(C)OC(=O)N1[C@@H]2CC[C@H]1C[C@H](n1cc(-c3cnc(N)c4oc(-c5cccc6cnsc56)cc34)cn1)C2] | 301 | B | B | |
| 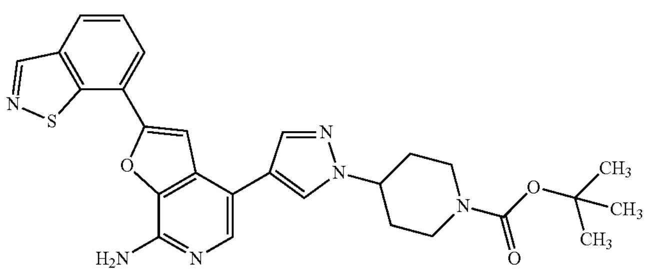 [SMILES: CC(C)(C)OC(=O)N1CCC(n2cc(-c3cnc(N)c4oc(-c5cccc6cnsc56)cc34)cn2)CC1] | 302 | B | B | C |
| 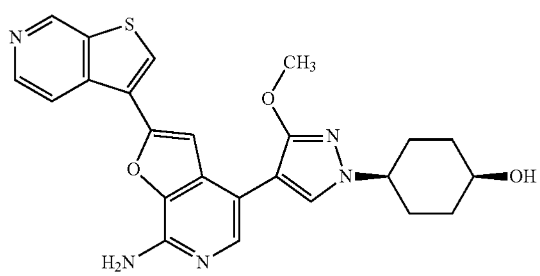 [SMILES: COc1nn([C@H]2CC[C@@H](O)CC2)cc1-c1cnc(N)c2oc(-c3csc4cnccc34)cc12] | 303 | B | B | C |
| 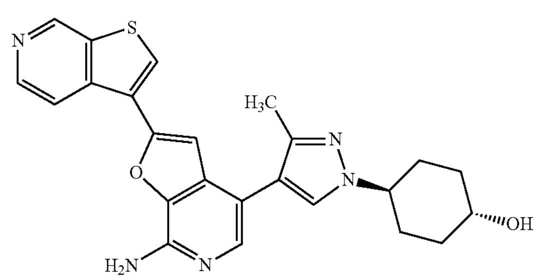 [SMILES: Cc1nn([C@H]2CC[C@H](O)CC2)cc1-c1cnc(N)c2oc(-c3csc4cnccc34)cc12] | 304 | C | | |

TABLE 1-continued

| Structure | Ex. No. | A | B | C |
|---|---|---|---|---|
| (structure) | 305 | | | C |
| (structure) | 306 | A | B | |
| (structure) | 307 | A | B | |
| (structure) | 308 | A | B | |
| (structure) | 309 | A | A | |

TABLE 1-continued
| Structure | Ex. No. | A | B | C |
|---|---|---|---|---|
| 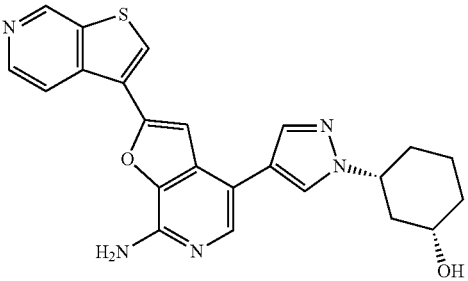 [SMILES: Nc1ncc(-c2cnn([C@@H]3CCC[C@H](O)C3)c2)c2cc(-c3csc4cnccc34)oc12] | 310 | A | A | |
| 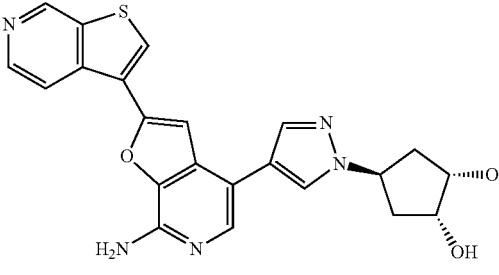 | 311 | A | B | B |
| 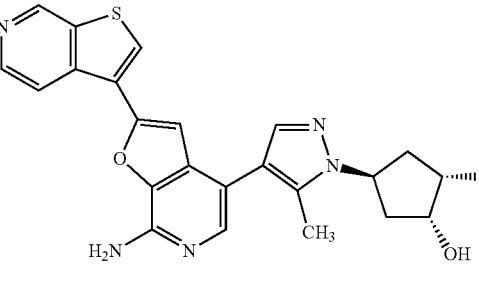 | 312 | C | | |
| 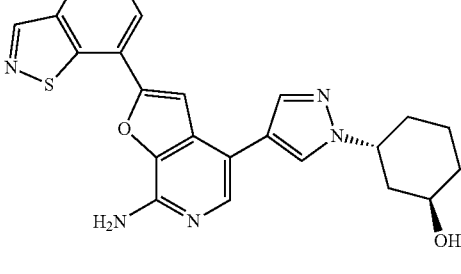 | 313 | A | B | |
| 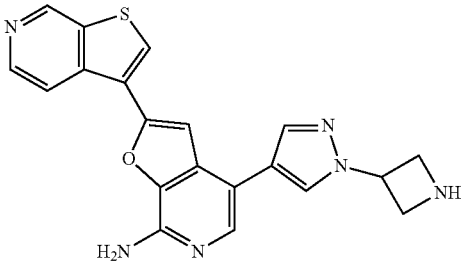 [SMILES: Nc1ncc(-c2cnn(C3CNC3)c2)c2cc(-c3csc4cnccc34)oc12] | 314 | A | C | B |

TABLE 1-continued
| Structure | Ex. No. | A | B | C |
|---|---|---|---|---|
| 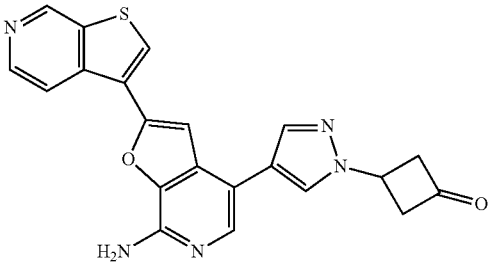 [SMILES: Nc1ncc(-c2cnn(C3CC(=O)C3)c2)c2cc(-c3csc4cnccc34)oc12] | 315 | B | B | B |
| 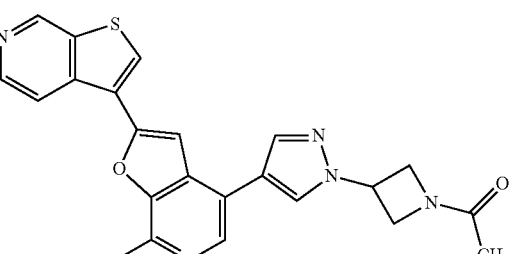 | 316 | A | B | B |
| 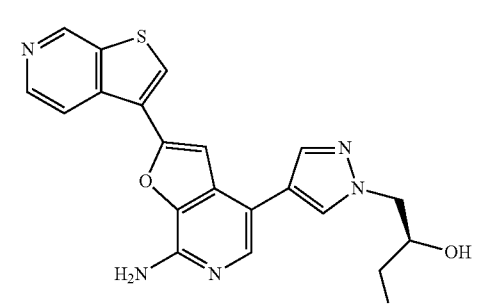 | 317 | A | C | C |
| 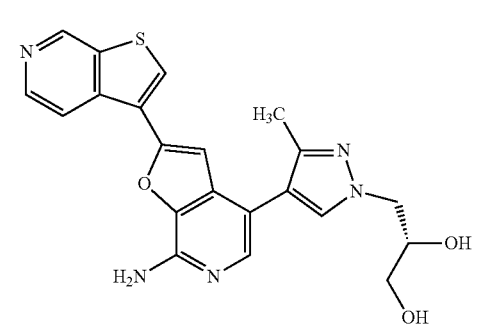 [SMILES: Cc1nn(C[C@H](O)CO)cc1-c1cnc(N)c2oc(-c3csc4cnccc34)cc12] | 318 | C | | |
| 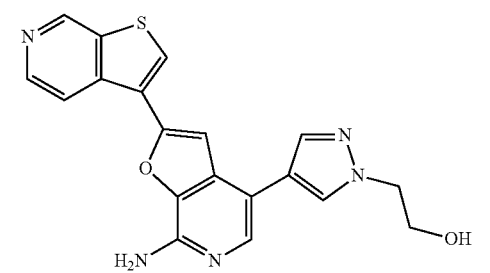 [SMILES: Nc1ncc(-c2cnn(CCO)c2)c2cc(-c3csc4cnccc34)oc12] | 319 | B | | |

TABLE 1-continued

| Structure | Ex. No. | A | B | C |
|---|---|---|---|---|
| 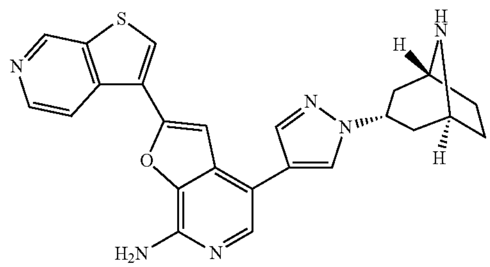 [SMILES: Nc1ncc(-c2cnn([C@@H]3C[C@H]4CC[C@@H](C3)N4)c2)c2cc(-c3csc4cnccc34)oc12] | 320 | A | B | |
| 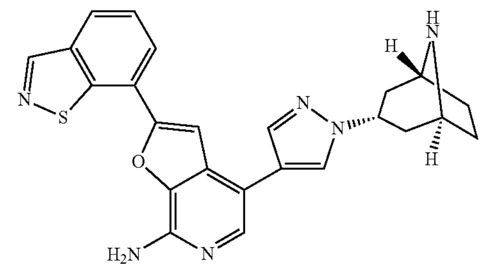 [SMILES: Nc1ncc(-c2cnn([C@@H]3C[C@H]4CC[C@@H](C3)N4)c2)c2cc(-c3cccc4cnsc34)oc12] | 321 | A | B | |
| 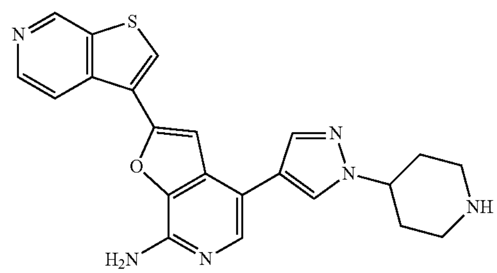 [SMILES: Nc1ncc(-c2cnn(C3CCNCC3)c2)c2cc(-c3csc4cnccc34)oc12] | 322 | A | B | B |
| 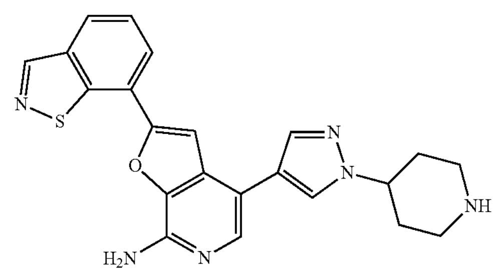 [SMILES: Nc1ncc(-c2cnn(C3CCNCC3)c2)c2cc(-c3cccc4cnsc34)oc12] | 323 | A | C | B |
| 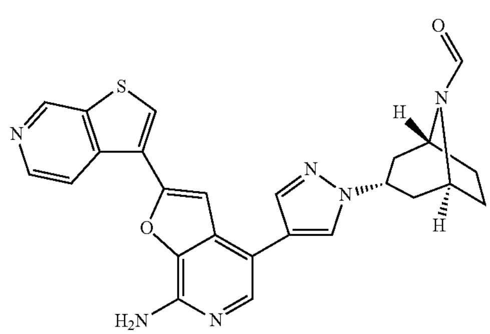 [SMILES: Nc1ncc(-c2cnn([C@@H]3C[C@H]4CC[C@@H](C3)N4C=O)c2)c2cc(-c3csc4cnccc34)oc12] | 324 | A | A | |

TABLE 1-continued

| Structure | Ex. No. | A | B | C |
|---|---|---|---|---|
| 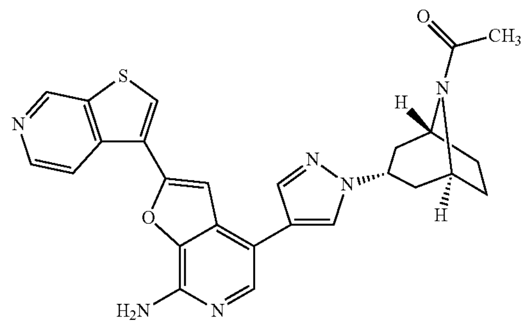 [SMILES: CC(=O)N1[C@@H]2CC[C@H]1C[C@H](n1cc(-c3cnc(N)c4oc(-c5csc6cnccc56)cc34)cn1)C2] | 325 | A | A | |
| 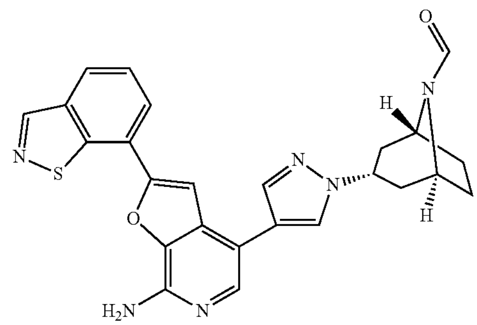 [SMILES: Nc1ncc(-c2cnn([C@@H]3C[C@H]4CC[C@@H](C3)N4C=O)c2)c2cc(-c3cccc4cnsc34)oc12] | 326 | A | A | |
| 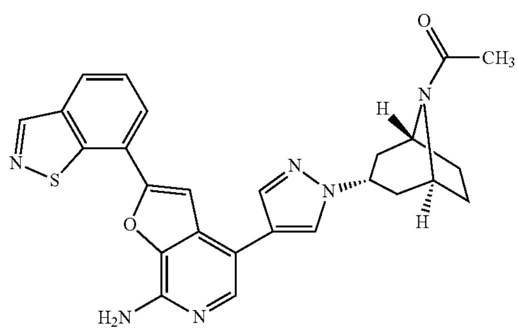 [SMILES: CC(=O)N1[C@@H]2CC[C@H]1C[C@H](n1cc(-c3cnc(N)c4oc(-c5cccc6cnsc56)cc34)cn1)C2] | 327 | A | A | |
| 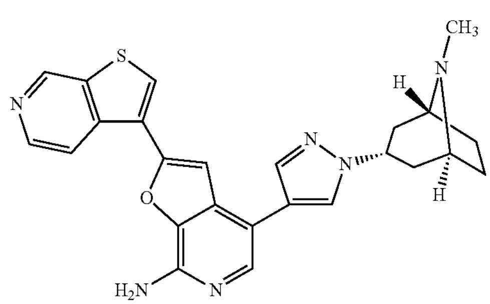 [SMILES: CN1[C@@H]2CC[C@H]1C[C@H](n1cc(-c3cnc(N)c4oc(-c5csc6cnccc56)cc34)cn1)C2] | 328 | A | B | |
| 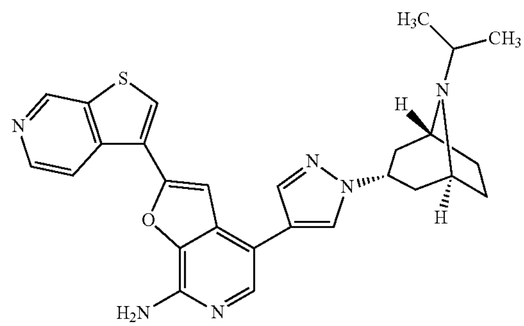 [SMILES: CC(C)N1[C@@H]2CC[C@H]1C[C@H](n1cc(-c3cnc(N)c4oc(-c5csc6cnccc56)cc34)cn1)C2] | 329 | A | B | |

TABLE 1-continued

| Structure | Ex. No. | A | B | C |
|---|---|---|---|---|
| (structure) | 330 | A | B | |
| (structure) | 331 | B | B | |
| (structure) | 332 | A | B | |
| (structure) | 333 | B | | |

TABLE 1-continued
| Structure | Ex. No. | A | B | C |
|---|---|---|---|---|
| 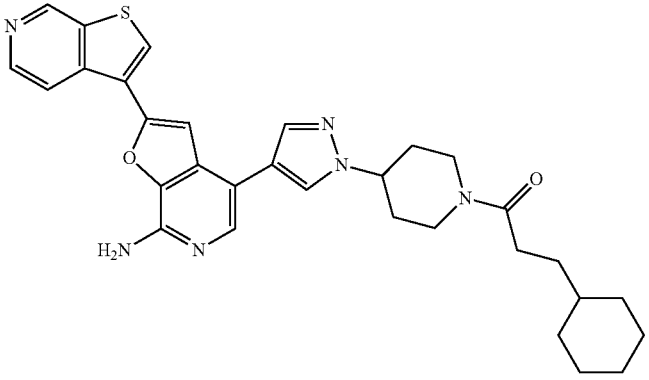 [SMILES: Nc1ncc(-c2cnn(C3CCN(C(=O)CCC4CCCCC4)CC3)c2)c2cc(-c3csc4cnccc34)oc12] | 334 | | | C |
| 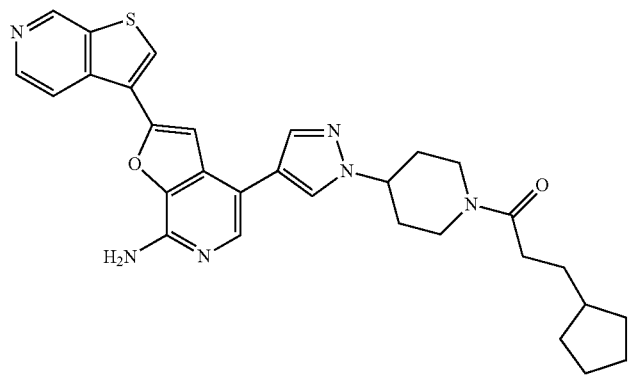 [SMILES: Nc1ncc(-c2cnn(C3CCN(C(=O)CCC4CCCC4)CC3)c2)c2cc(-c3csc4cnccc34)oc12] | 335 | | | C |
| 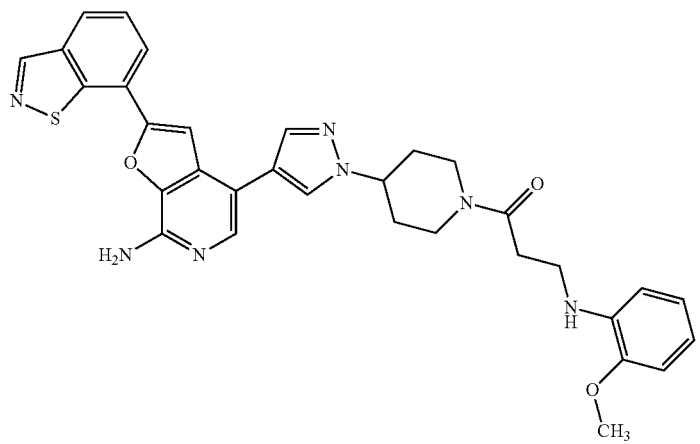 [SMILES: COc1ccccc1NCCC(=O)N1CCC(n2cc(-c3cnc(N)c4oc(-c5cccc6cnsc56)cc34)cn2)CC1] | 336 | | B | |

TABLE 1-continued
| Structure | Ex. No. | A | B | C |
|---|---|---|---|---|
| 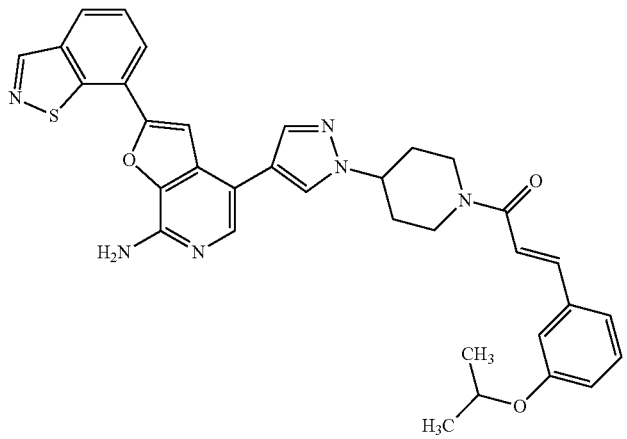 [SMILES: CC(C)Oc1cccc(/C=C/C(=O)N2CCC(n3cc(-c4cnc(N)c5oc(-c6cccc7cnsc67)cc45)cn3)CC2)c1] | 337 | | | C |
| 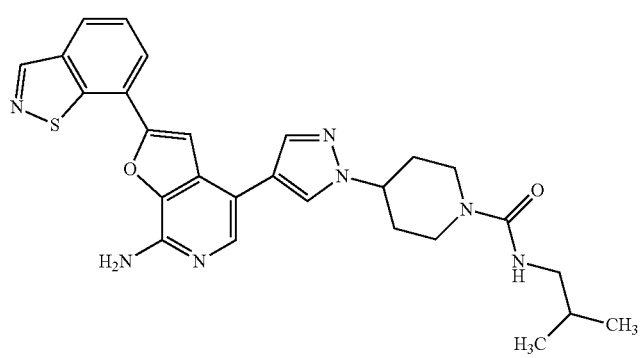 [SMILES: CC(C)CNC(=O)N1CCC(n2cc(-c3cnc(N)c4oc(-c5cccc6cnsc56)cc34)cn2)CC1] | 338 | | B | B |
| 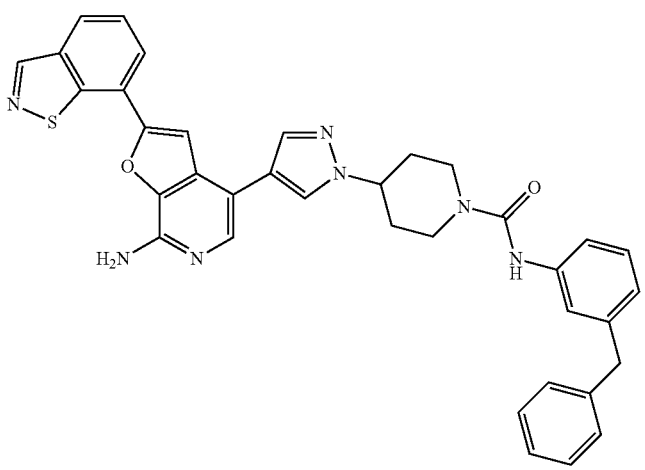 [SMILES: Nc1ncc(-c2cnn(C3CCN(C(=O)Nc4cccc(Cc5ccccc5)c4)CC3)c2)c2cc(-c3cccc4cnsc34)oc12] | 339 | | | C |

TABLE 1-continued

| Structure | Ex. No. | A | B | C |
|---|---|---|---|---|
| 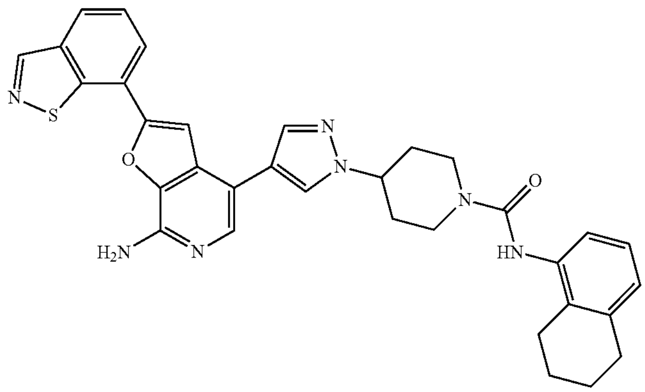 [SMILES: Nc1ncc(-c2cnn(C3CCN(C(=O)Nc4cccc5c4CCCC5)CC3)c2)c2cc(-c3cccc4cnsc34)oc12] | 340 | | B | B |
| 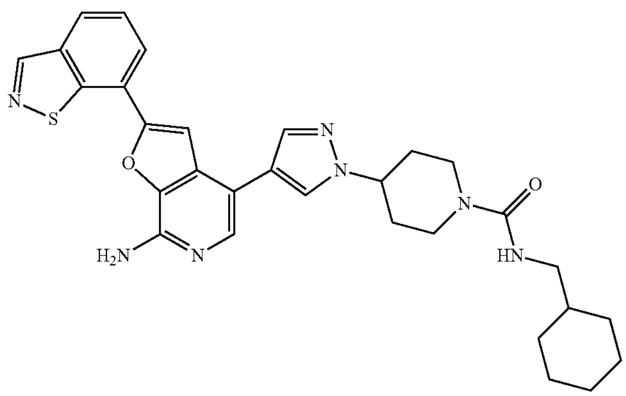 [SMILES: Nc1ncc(-c2cnn(C3CCN(C(=O)NCC4CCCCC4)CC3)c2)c2cc(-c3cccc4cnsc34)oc12] | 341 | | B | A |
| 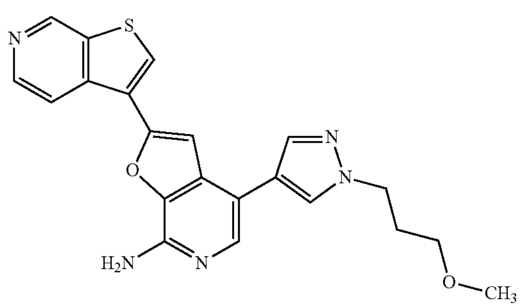 [SMILES: COCCCn1cc(-c2cnc(N)c3oc(-c4csc5cnccc45)cc23)cn1] | 342 | | B | B |
| 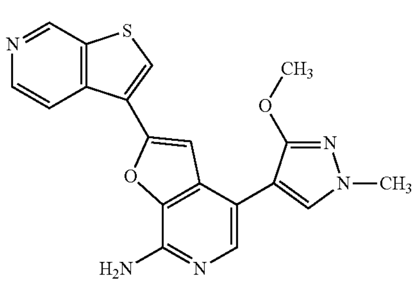 [SMILES: COc1nn(C)cc1-c1cnc(N)c2oc(-c3csc4cnccc34)cc12] | 343 | | B | |

TABLE 1-continued

| Structure | Ex. No. | A | B | C |
|---|---|---|---|---|
| 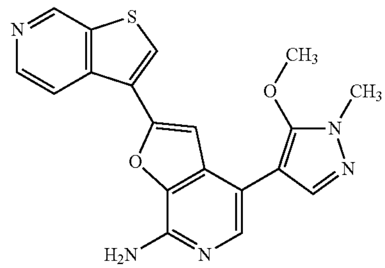 [SMILES: COc1c(-c2cnc(N)c3oc(-c4csc5cnccc45)cc23)cnn1C] | 344 | B | | |
| 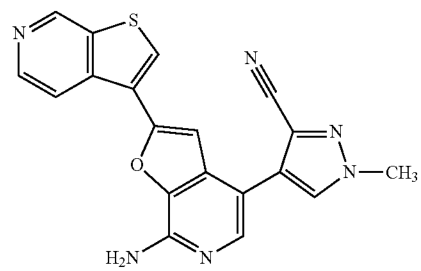 [SMILES: Cn1cc(-c2cnc(N)c3oc(-c4csc5cnccc45)cc23)c(C#N)n1] | 345 | D | | |
| 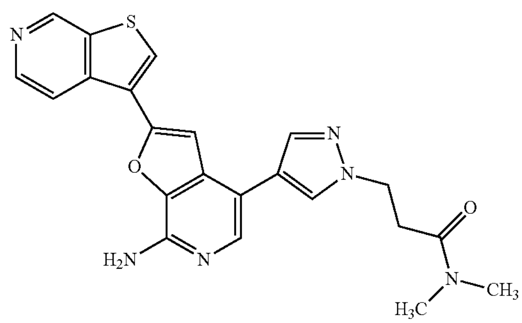 [SMILES: CN(C)C(=O)CCn1cc(-c2cnc(N)c3oc(-c4csc5cnccc45)cc23)cn1] | 346 | B | C | |
| 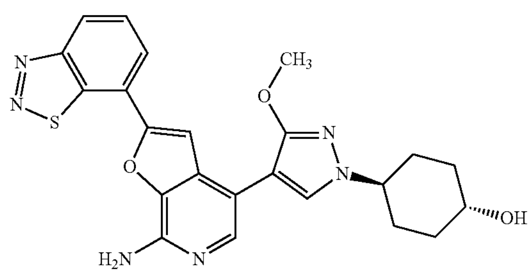 [SMILES: COc1nn([C@H]2CC[C@H](O)CC2)cc1-c1cnc(N)c2oc(-c3cccc4nnsc34)cc12] | 347 | A | A | |
| 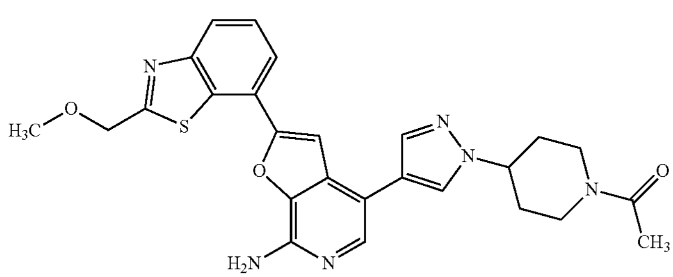 [SMILES: COCc1nc2cccc(-c3cc4c(-c5cnn(C6CCN(C(C)=O)CC6)c5)cnc(N)c4o3)c2s1] | 348 | A | A | |

TABLE 1-continued

| Structure | Ex. No. | A | B | C |
|---|---|---|---|---|
| 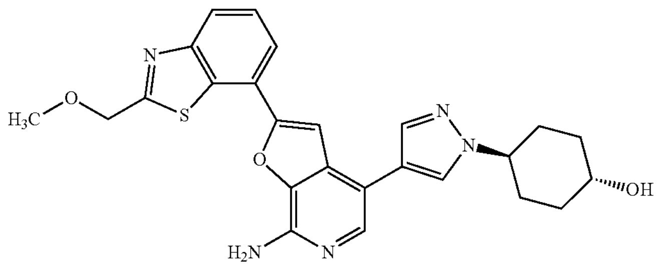 [SMILES: COCc1nc2cccc(-c3cc4c(-c5cnn([C@H]6CC[C@H](O)CC6)c5)cnc(N)c4o3)c2s1] | 349 | A | A | |
| 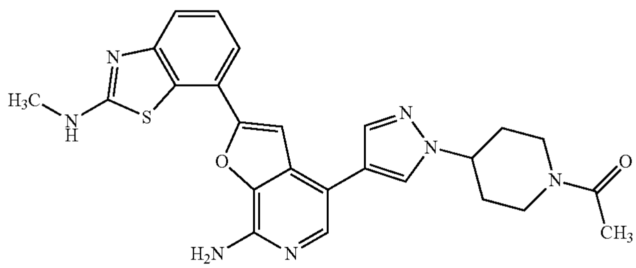 [SMILES: CNc1nc2cccc(-c3cc4c(-c5cnn(C6CCN(C(C)=O)CC6)c5)cnc(N)c4o3)c2s1] | 350 | A | A | |
| 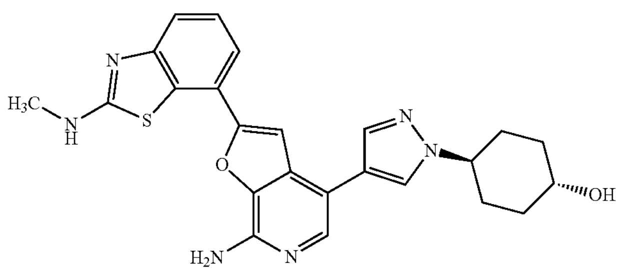 [SMILES: CNc1nc2cccc(-c3cc4c(-c5cnn([C@H]6CC[C@H](O)CC6)c5)cnc(N)c4o3)c2s1] | 351 | A | A | |
| 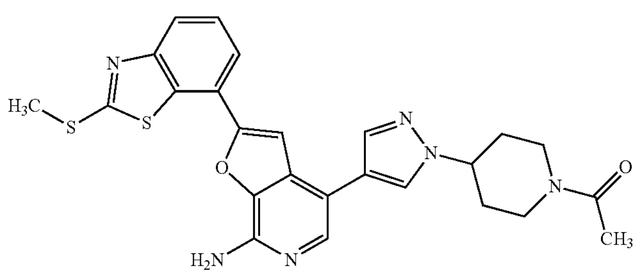 [SMILES: CSc1nc2cccc(-c3cc4c(-c5cnn(C6CCN(C(C)=O)CC6)c5)cnc(N)c4o3)c2s1] | 352 | | | C |
| 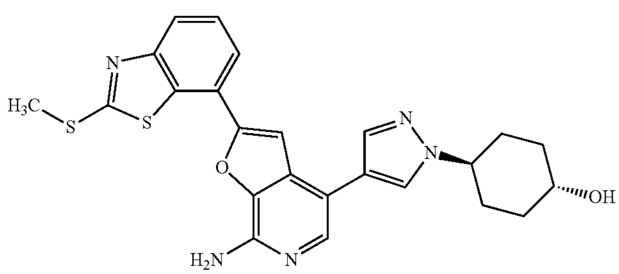 [SMILES: CSc1nc2cccc(-c3cc4c(-c5cnn([C@H]6CC[C@H](O)CC6)c5)cnc(N)c4o3)c2s1] | 353 | | | C |

TABLE 1-continued
| Structure | Ex. No. | A | B | C |
|---|---|---|---|---|
| 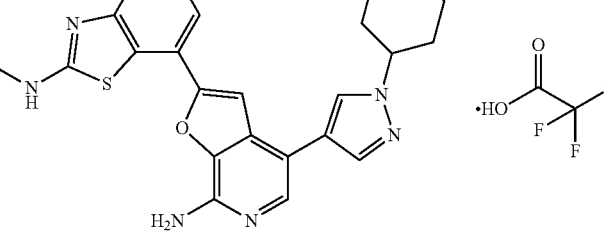 | 354 | A | A | |
| 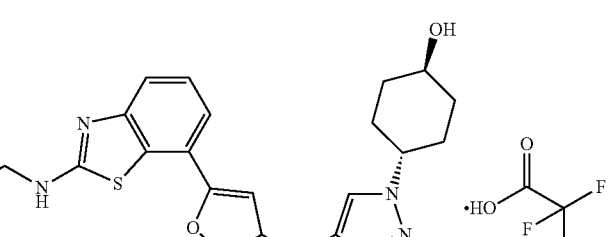 | 355 | A | A | |
| 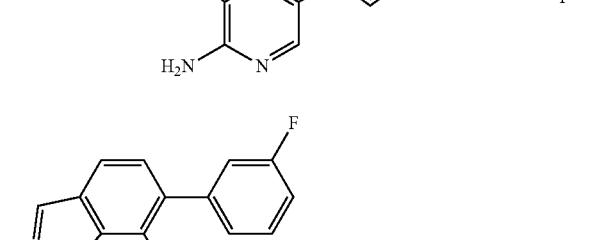 | 356 | D | | |
| 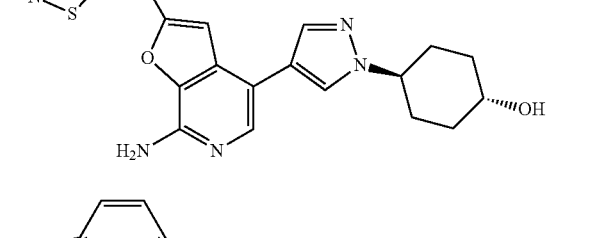 | 357 | C | | |
| 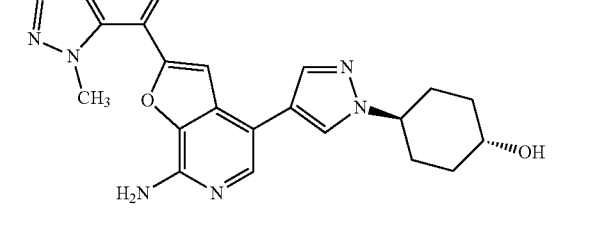 | 358 | B | | |

TABLE 1-continued

| Structure | Ex. No. | A | B | C |
|---|---|---|---|---|
| 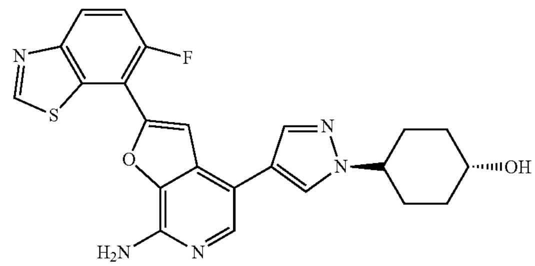 | 359 | | | C |
| 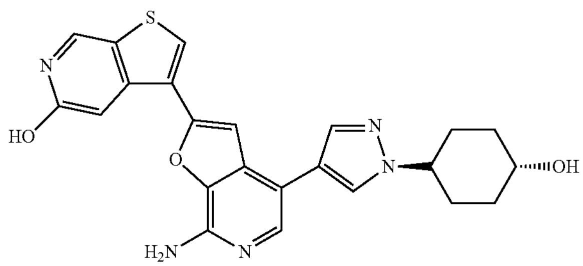 | 360 | | B | C |
| 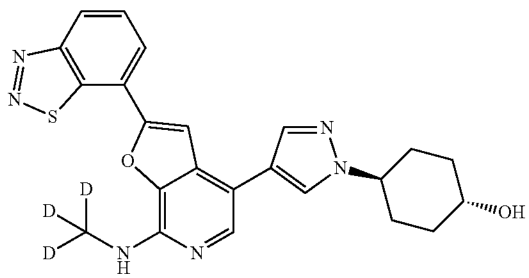 [SMILES: [2H]C([2H])([2H])Nc1ncc(-c2cnn([C@H]3CC[C@H](O)CC3)c2)c2cc(-c3cccc4nnsc34)oc12] | 361 | A | A | |
| 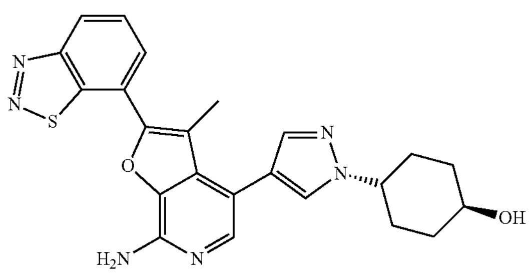 | 362 | A | A | |
| 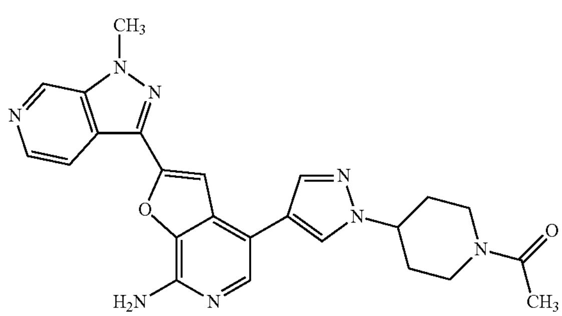 [SMILES: CC(=O)N1CCC(n2cc(-c3cnc(N)c4oc(-c5nn(C)c6cnccc56)cc34)cn2)CC1] | 363 | A | B | |

TABLE 1-continued

| Structure | Ex. No. | A | B | C |
|---|---|---|---|---|
| 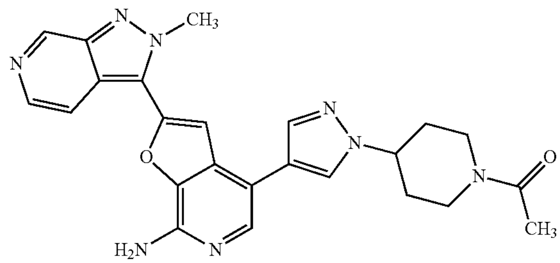 [SMILES: CC(=O)N1CCC(n2cc(-c3cnc(N)c4oc(-c5c6ccncc6nn5C)cc34)cn2)CC1] | 364 |  | B | C |
| 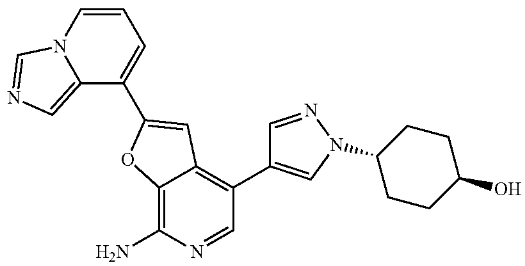 [SMILES: Nc1ncc(-c2cnn([C@H]3CC[C@H](O)CC3)c2)c2cc(-c3cccn4cncc34)oc12] | 365 |  | A | A |
| 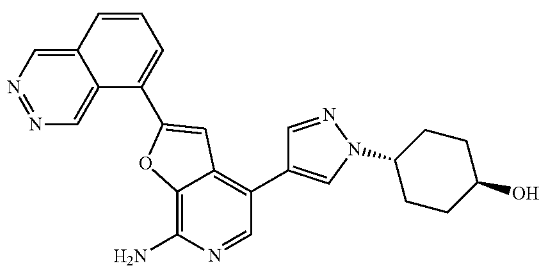 [SMILES: Nc1ncc(-c2cnn([C@H]3CC[C@H](O)CC3)c2)c2cc(-c3cccc4cnncc34)oc12] | 366 |  | A | A |
| 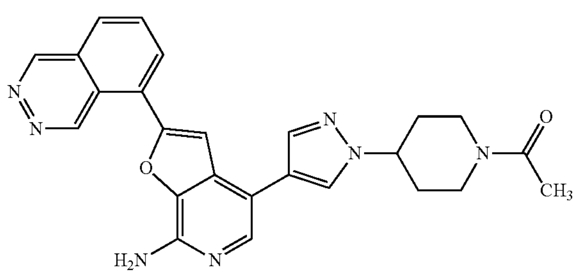 [SMILES: CC(=O)N1CCC(n2cc(-c3cnc(N)c4oc(-c5cccc6cnncc56)cc34)cn2)CC1] | 367 |  | B | B |
| 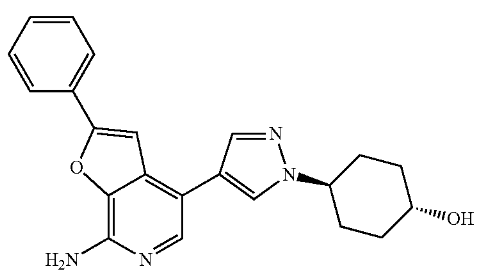 [SMILES: Nc1ncc(-c2cnn([C@H]3CC[C@H](O)CC3)c2)c2cc(-c3ccccc3)oc12] | 368 |  | B | B |

TABLE 1-continued

| Structure | Ex. No. | A | B | C |
|---|---|---|---|---|
| 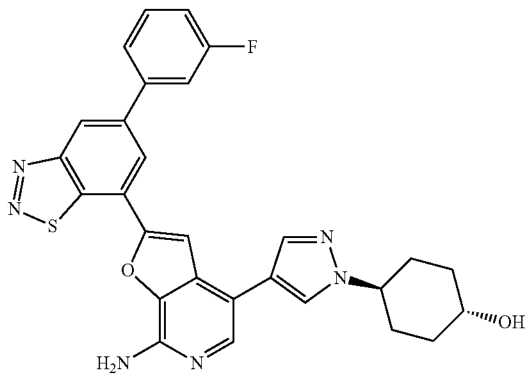 [SMILES: Nc1ncc(-c2cnn([C@H]3CC[C@H](O)CC3)c2)c2cc(-c3cc(-c4cccc(F)c4)cc4nnsc34)oc12] | 369 | | | C |
| 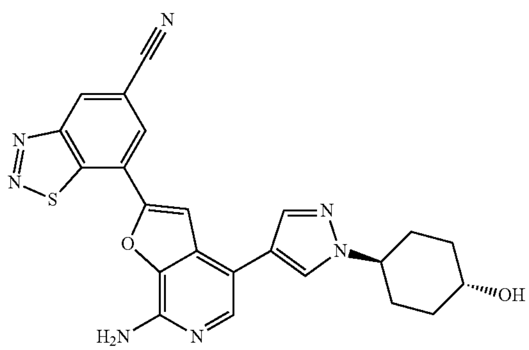 [SMILES: N#Cc1cc(-c2cc3c(-c4cnn([C@H]5CC[C@H](O)CC5)c4)cnc(N)c3o2)c2snnc2c1] | 370 | | B | A |
| 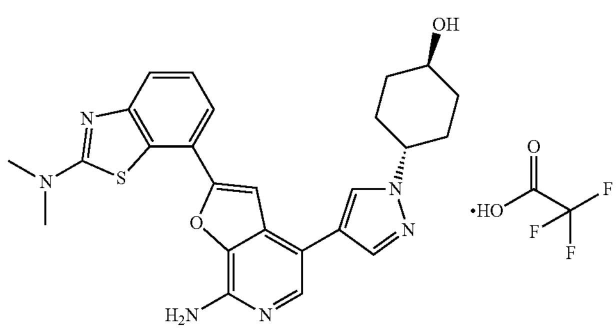 | 371 | | | C |
| | 372 | | | C | B |

TABLE 1-continued

| Structure | Ex. No. | A | B | C |
|---|---|---|---|---|
| 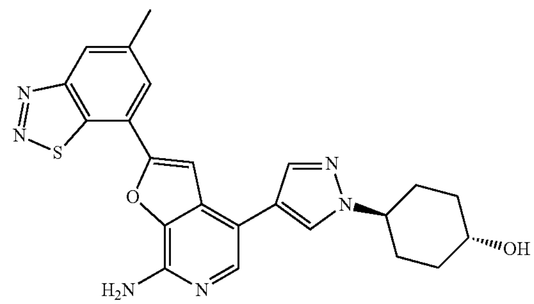 [SMILES: Cc1cc(-c2cc3c(-c4cnn([C@H]5CC[C@H](O)CC5)c4)cnc(N)c3o2)c2snnc2c1] | 373 | A | A | |
| 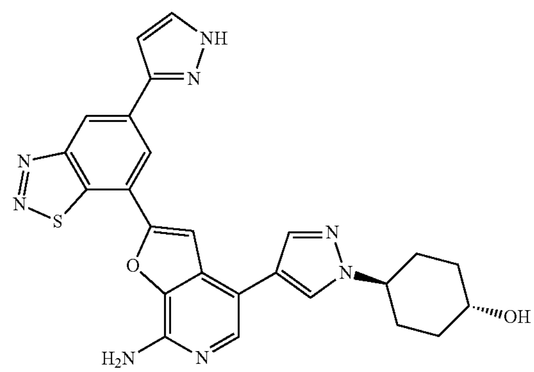 [SMILES: Nc1ncc(-c2cnn([C@H]3CC[C@H](O)CC3)c2)c2cc(-c3cc(-c4cc[nH]n4)cc4nnsc34)oc12] | 374 | B | | |
| 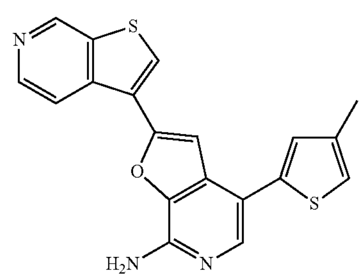 [SMILES: Cc1csc(-c2cnc(N)c3oc(-c4csc5cnccc45)cc23)c1] | 375 | | | C |
| 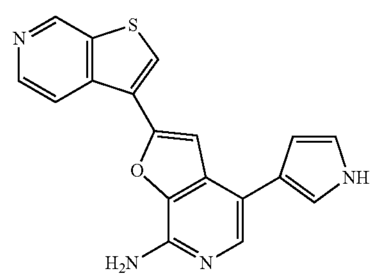 [SMILES: Nc1ncc(-c2cc[nH]c2)c2cc(-c3csc4cnccc34)oc12] | 376 | C | B | C |
| 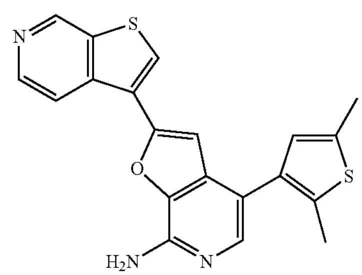 [SMILES: Cc1cc(-c2cnc(N)c3oc(-c4csc5cnccc45)cc23)c(C)s1] | 377 | | | C |

TABLE 1-continued
| Structure | Ex. No. | A | B | C |
|---|---|---|---|---|
| 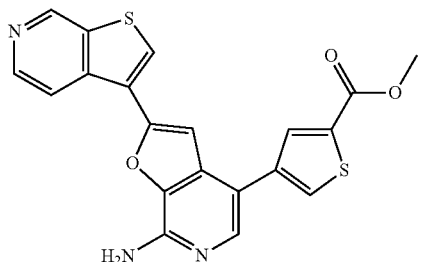 | 378 | | | D |
| 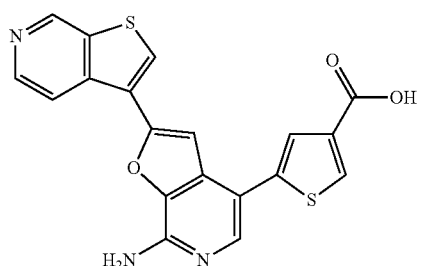 | 379 | | | C |
| 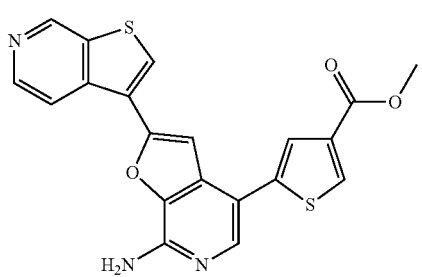 [SMILES: COC(=O)c1csc(-c2cnc(N)c3oc(-c4csc5cnccc45)cc23)c1] | 380 | | | C |
| 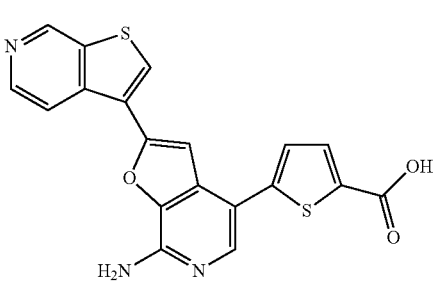 [SMILES: Nc1ncc(-c2ccc(C(=O)O)s2)c2cc(-c3csc4cnccc34)oc12] | 381 | | | C |
| 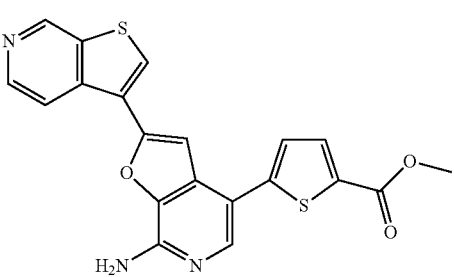 [SMILES: COC(=O)c1ccc(-c2cnc(N)c3oc(-c4csc5cnccc45)cc23)s1] | 382 | | | D |

TABLE 1-continued

| Structure | Ex. No. | A | B | C |
|---|---|---|---|---|
| 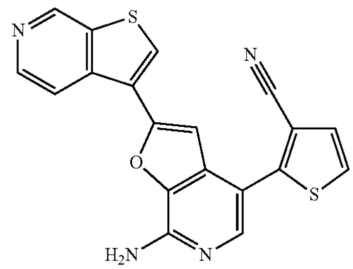 [SMILES: N#Cc1ccsc1-c1cnc(N)c2oc(-c3csc4cnccc34)cc12] | 383 | | | D |
| 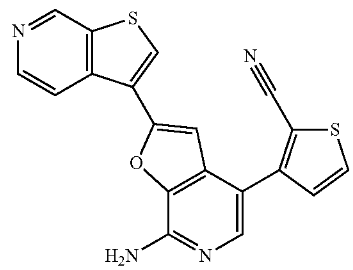 [SMILES: N#Cc1sccc1-c1cnc(N)c2oc(-c3csc4cnccc34)cc12] | 384 | | | D |
| 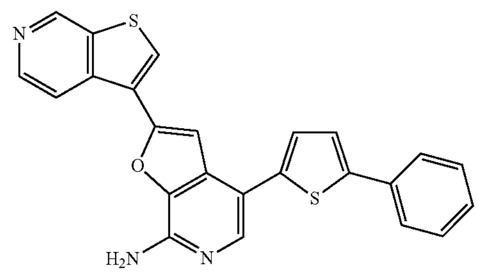 [SMILES: Nc1ncc(-c2ccc(-c3ccccc3)s2)c2cc(-c3csc4cnccc34)oc12] | 385 | | | D |
| 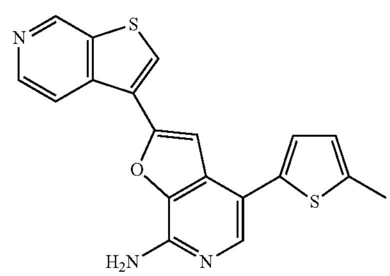 [SMILES: Cc1ccc(-c2cnc(N)c3oc(-c4csc5cnccc45)cc23)s1] | 386 | | | C |
| 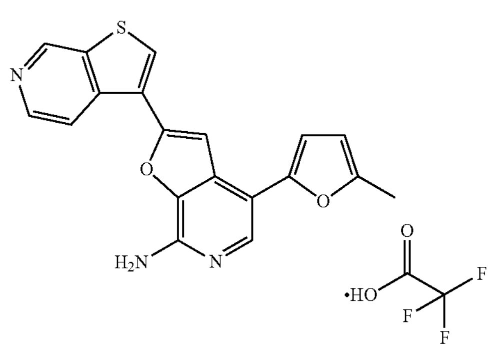 | 387 | | | C |

TABLE 1-continued

| Structure | Ex. No. | A | B | C |
|---|---|---|---|---|
| (structure) | 388 | | B | B |
| (structure) | 389 | | | C |
| (structure) | 390 | | | C |
| (structure) | 391 | | | C |

TABLE 1-continued

| Structure | Ex. No. | A | B | C |
|---|---|---|---|---|
| 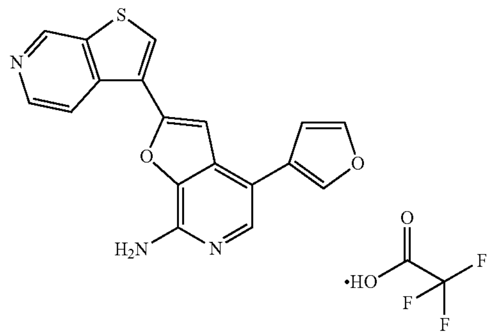 | 392 | | B | C |
| 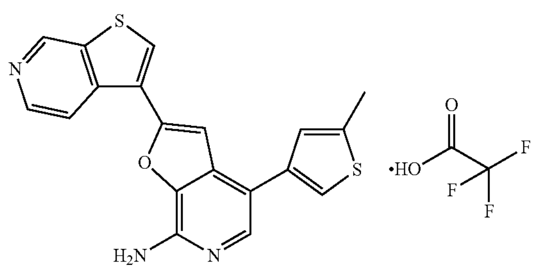 | 393 | | | C |
| 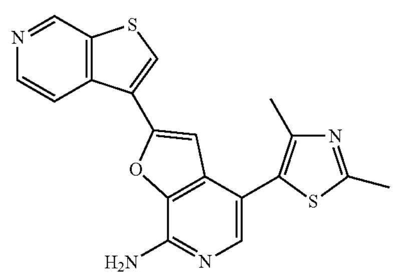 [SMILES: Cc1nc(C)c(-c2cnc(N)c3oc(-c4csc5cnccc45)cc23)s1] | 394 | | | C |
| 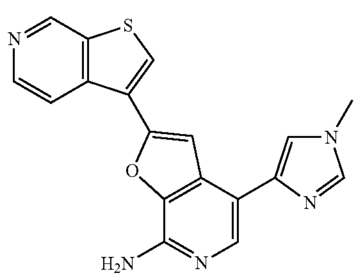 [SMILES: Cn1cnc(-c2cnc(N)c3oc(-c4csc5cnccc45)cc23)c1] | 395 | | | D |
| 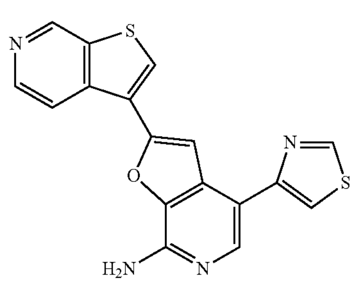 [SMILES: Nc1ncc(-c2cscn2)c2cc(-c3csc4cnccc34)oc12] | 396 | | | C |

TABLE 1-continued
| Structure | Ex. No. | A | B | C |
|---|---|---|---|---|
| 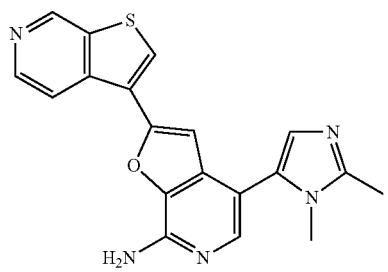 [SMILES: Cc1ncc(-c2cnc(N)c3oc(-c4csc5cnccc45)cc23)n1C] | 397 | | | C |
| 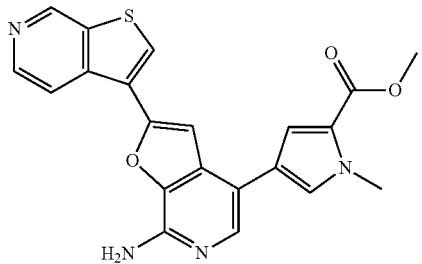 [SMILES: COC(=O)c1cc(-c2cnc(N)c3oc(-c4csc5cnccc45)cc23)cn1C] | 398 | | | C |
| 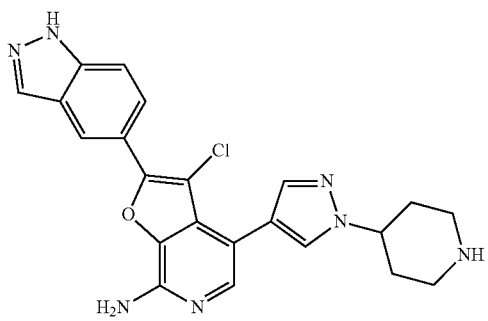 [SMILES: Nc1ncc(-c2cnn(C3CCNCC3)c2)c2c(Cl)c(-c3ccc4[nH]ncc4c3)oc12] | 399 | | | C |
| 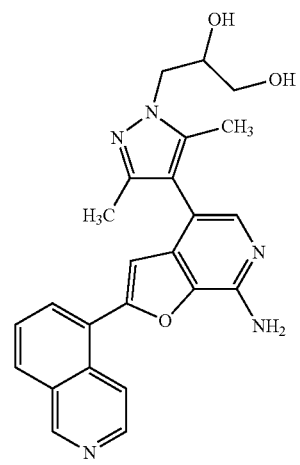 [SMILES: Cc1nn(CC(O)CO)c(C)c1-c1cnc(N)c2oc(-c3cccc4cnccc34)cc12] | 400 | D | C | C |

TABLE 1-continued

| Structure | Ex. No. | A | B | C |
|---|---|---|---|---|
| (structure) | 401 | D | | |
| (structure) | 402 | B | B | C |
| (structure) | 403 | B | | |
| (structure) | 404 | C | | |

TABLE 1-continued

| Structure | Ex. No. | A | B | C |
|---|---|---|---|---|
| (structure) | 405 | | | C |
| (structure) | 406 | | B | |
| (structure) | 407 | | B | |
| (structure) | 408 | | | D |

TABLE 1-continued

| Structure | Ex. No. | A | B | C |
|---|---|---|---|---|
| (structure) | 409 | | | C |
| (structure) | 410 | B | B | C |
| (structure) | 411 | D | | |
| (structure) | | | | B |

Compositions

The invention includes pharmaceutical compositions comprising a compound or pharmaceutically acceptable salt thereof of the invention, which is formulated for a desired mode of administration with or without one or more pharmaceutically acceptable and useful carriers. The compounds can also be included in pharmaceutical compositions in combination with one or more other therapeutically active compounds.

The pharmaceutical compositions of the present invention comprise a compound of the invention (or a pharmaceutically acceptable salt thereof) as an active ingredient, optional pharmaceutically acceptable carrier(s) and optionally other therapeutic ingredients or adjuvants. The compositions include compositions suitable for oral, rectal, topical, and parenteral (including subcutaneous, intramuscular, and intravenous) administration, although the most suitable route in any given case will depend on the particular host, and nature and severity of the conditions for which the active ingredient is being administered. The pharmaceutical compositions may be conveniently presented in unit dosage form and prepared by any of the methods well known in the art of pharmacy.

Compounds of the invention can be combined as the active ingredient in intimate admixture with a pharmaceutical carrier according to conventional pharmaceutical compounding techniques. The carrier may take a wide variety of forms depending on the form of preparation desired for administration, e.g., oral or parenteral (including intravenous). Thus, the pharmaceutical compositions of the present invention can be presented as discrete units suitable for oral administration such as capsules, cachets or tablets each containing a predetermined amount of the active ingredient. Further, the compositions can be presented as a powder, as granules, as a solution, as a suspension in an aqueous liquid, as a non-aqueous liquid, as an oil-in-water emulsion, or as a water-in-oil liquid emulsion. In addition to the common dosage forms set out above, the compound represented by Formula I, or a pharmaceutically acceptable salt thereof, may also be administered by controlled release means and/or delivery devices. The compositions may be prepared by any of the methods of pharmacy. In general, such methods include a step of bringing into association the active ingredient with the carrier that constitutes one or more necessary ingredients. In general, the compositions are prepared by uniformly and intimately admixing the active ingredient with liquid carriers or finely divided solid carriers or both. The product can then be conveniently shaped into the desired presentation.

The pharmaceutical carrier employed can be, for example, a solid, liquid, or gas. Examples of solid carriers include lactose, terra alba, sucrose, talc, gelatin, agar, pectin, acacia, magnesium stearate, and stearic acid. Examples of liquid carriers are sugar syrup, peanut oil, olive oil, and water. Examples of gaseous carriers include carbon dioxide and nitrogen.

A tablet containing the composition of this invention may be prepared by compression or molding, optionally with one or more accessory ingredients or adjuvants. Compressed tablets may be prepared by compressing, in a suitable machine, the active ingredient in a free-flowing form such as powder or granules, optionally mixed with a binder, lubricant, inert diluent, surface active or dispersing agent. Molded tablets may be made by molding in a suitable machine, a mixture of the powdered compound moistened with an inert liquid diluent. Each tablet preferably contains from about 0.05 mg to about 5 g of the active ingredient and each cachet or capsule preferably containing from about 0.05 mg to about 5 g of the active ingredient.

A formulation intended for the oral administration to humans may contain from about 0.5 mg to about 5 g of active agent, compounded with an appropriate and convenient amount of carrier material which may vary from about 5 to about 95 percent of the total composition. Unit dosage forms will generally contain between from about 1 mg to about 2 g of the active ingredient, typically 25 mg, 50 mg, 100 mg, 200 mg, 300 mg, 400 mg, 500 mg, 600 mg, 800 mg, or 1000 mg.

Compounds of the invention can be provided for formulation at high purity, for example at least about 90%, 95%, or 98% pure by weight. Pharmaceutical compositions of the present invention suitable for parenteral administration may be prepared as solutions or suspensions of the active compounds in water. A suitable surfactant can be included such as, for example, hydroxypropylcellulose. Dispersions can also be prepared in glycerol, liquid polyethylene glycols, and mixtures thereof in oils. Further, a preservative can be included to prevent the detrimental growth of microorganisms.

Pharmaceutical compositions of the present invention suitable for injectable use include sterile aqueous solutions or dispersions. Furthermore, the compositions can be in the form of sterile powders for the extemporaneous preparation of such sterile injectable solutions or dispersions. In all cases, the final injectable form must be sterile and must be effectively fluid for easy syringability. The pharmaceutical compositions must be stable under the conditions of manufacture and storage; thus, preferably should be preserved against the contaminating action of microorganisms such as bacteria and fungi. The carrier can be a solvent or dispersion medium containing, for example, water, ethanol, polyol (e.g., glycerol, propylene glycol and liquid polyethylene glycol), vegetable oils, and suitable mixtures thereof.

Pharmaceutical compositions of the present invention can be in a form suitable for topical use such as, for example, an aerosol, cream, ointment, lotion, dusting powder, or the like. Further, the compositions can be in a form suitable for use in transdermal devices. These formulations may be prepared, utilizing a compound represented by Formula I of this invention, or a pharmaceutically acceptable salt thereof, via conventional processing methods. As an example, a cream or ointment is prepared by admixing hydrophilic material and water, together with about 5wt % to about 10wt % of the compound, to produce a cream or ointment having a desired consistency.

Pharmaceutical compositions of this invention can be in a form suitable for rectal administration wherein the carrier is a solid. It is preferable that the mixture forms unit dose suppositories. Suitable carriers include cocoa butter and other materials commonly used in the art. The suppositories may be conveniently formed by first admixing the composition with the softened or melted carrier(s) followed by chilling and shaping in molds.

In addition to the aforementioned carrier ingredients, the pharmaceutical formulations described above may include, as appropriate, one or more additional carrier ingredients such as diluents, buffers, flavoring agents, binders, surface-active agents, thickeners, lubricants, preservatives (including anti-oxidants) and the like. Furthermore, other adjuvants can be included to render the formulation isotonic with the blood of the intended recipient. Compositions containing a compound described by Formula I, or pharmaceutically acceptable salts thereof, may also be prepared in powder or liquid concentrate form.

Uses

In some aspects of the invention, compounds of the invention are inhibitors of one or more kinases, including TAK1. In some aspects of the invention, compounds of the invention are inhibitors of one or more kinases, such as but not limited to RON, MET, Auroras, KDR, PDGFRs, PKCs, HGK/Mink1, JAK2, or PRKD2. The compounds can be used in any settings in which their biological activity is relevant, including but not limited to the above-listed targets.

Compounds of the invention inhibit the activity of tyrosine kinase enzymes in animals, including humans, and are useful in the treatment and/or prevention of various diseases and conditions such as hyperproliferative disorders such as cancer. In particular, compounds disclosed herein are inhibitors of TAK1.

Thus, in some aspects, the invention includes a method of inhibiting TAK1 comprising contacting a cell that expresses TAK1 with an effective amount of a compound of the invention.

In some aspects, the invention includes a method of treating or preventing cancer comprising administering to a mammal in need thereof a therapeutically effective amount of a compound or salt of the invention.

In some aspects, the invention includes methods of treating or preventing cancer, which is mediated at least in part by TAK1 comprising administering to a mammal in need thereof a therapeutically effective amount of a compound or salt of the invention.

In some aspects, the invention includes methods of treating or preventing, without limitation, allergic or inflammatory disorders, including disorders mediated at least in part by TAK1 comprising administering to a mammal in need thereof a therapeutically effective amount of a compound or salt of the invention.

The compounds of Formula I of the present invention are useful in the treatment of a variety of cancers, including, but not limited to, solid tumor and other cancers, sarcoma, fibrosarcoma, osteoma, melanoma, retinoblastoma, rhabdomyosarcoma, glioblastoma, neuroblastoma, teratocarcinoma, hematopoietic malignancy, and malignant ascites. More specifically, the cancers include, but not limited to, lung cancer, bladder cancer, pancreatic cancer, kidney cancer, gastric cancer, breast cancer, colon cancer, prostate cancer (including bone metastases), hepatocellular carcinoma, ovarian cancer, esophageal squamous cell carcinoma, melanoma, an anaplastic large cell lymphoma, an inflammatory myofibroblastic tumor, and a glioblastoma.

In some aspects, the above methods are used to treat one or more of bladder, colorectal, nonsmall cell lung, breast, or pancreatic cancer. In some aspects, the above methods are used to treat one or more of ovarian, gastric, head and neck, prostate, hepatocellular, renal, glioma, blood cancers, or sarcoma cancer.

In some aspects, the invention includes a method, including the above methods, wherein the compound is used to inhibit EMT.

In some aspects, the invention includes a compound, salt, medicament or pharmaceutical composition manufactured for any of the purposes or uses herein. In some aspects, the invention includes the use of a compound of the invention in the manufacture of a medicament for any of the purposes herein.

Generally, dosage levels on the order of from about 0.01 mg/kg to about 150 mg/kg of body weight per day are useful in the treatment of the above-indicated conditions, or alternatively about 0.5 mg to about 7 g per patient per day. For example, inflammation, cancer, psoriasis, allergy/asthma, disease and conditions of the immune system, disease and conditions of the central nervous system (CNS), may be effectively treated by the administration of from about 0.01 to 50 mg of the compound per kilogram of body weight per day, or alternatively about 0.5 mg to about 3.5 g per patient per day.

It is understood, however, that the specific dose level for any particular patient will depend upon a variety of factors including the age, body weight, general health, sex, diet, time of administration, route of administration, rate of excretion, drug combination and the severity of the particular disease undergoing therapy.

In some aspects, the invention includes a method of treating cancer comprising administering to a mammal in need thereof a therapeutically effective amount of a compound or salt of the invention, wherein at least one additional active anti-cancer agent is used as part of the method.

General Definitions and Abbreviations

Except where otherwise indicated, the following general conventions and definitions apply. Unless otherwise indicated herein, language and terms are to be given their broadest reasonable interpretation as understood by the skilled artisan. Any examples given are nonlimiting.

Any section headings or subheadings herein are for the reader's convenience and/or formal compliance and are non-limiting.

A recitation of a compound herein is open to and embraces any material or composition containing the recited compound (e.g., a composition containing a racemic mixture, tautomers, epimers, stereoisomers, impure mixtures, etc.). In that a salt, solvate, or hydrate, polymorph, or other complex of a compound includes the compound itself, a recitation of a compound embraces materials containing such forms. Isotopically labeled compounds are also encompassed except where specifically excluded. For example, hydrogen is not limited to hydrogen containing zero neutrons.

The term "active agent" of the invention means a compound of the invention in any salt, polymorph, crystal, solvate, or hydrated form.

The term "pharmaceutically acceptable salt(s)" is known in the art and includes salts of acidic or basic groups which can be present in the compounds and prepared or resulting from pharmaceutically acceptable bases or acids.

The term "substituted" and substitutions contained in formulas herein refer to the replacement of one or more hydrogen radicals in a given structure with a specified radical, or, if not specified, to the replacement with any chemically feasible radical. When more than one position in a given structure can be substituted with more than one substituent selected from specified groups, the substituents can be either the same or different at every position (independently selected) unless otherwise indicated. In some cases, two positions in a given structure can be substituted with one shared substituent. It is understood that chemically impossible or highly unstable configurations are not desired or intended, as the skilled artisan would appreciate.

In descriptions and claims where subject matter (e.g., substitution at a given molecular position) is recited as being selected from a group of possibilities, the recitation is specifically intended to include any subset of the recited group. In the case of multiple variable positions or substituents, any combination of group or variable subsets is also contemplated.

Unless indicated otherwise, a substituent, diradical or other group referred to herein can be bonded through any suitable position to a referenced subject molecule. For example, the term "indolyl" includes 1-indolyl, 2-indolyl, 3-indolyl, etc.

The convention for describing the carbon content of certain moieties is "$(C_{a-b})$" or "$C_a$-$C_b$," meaning that the moiety can contain any number of from "a" to "b" carbon atoms. $C_0$alkyl means a single covalent chemical bond when it is a connecting moiety, and a hydrogen when it is a terminal moiety. Similarly, "x-y" can indicate a moiety containing from x to y atoms, e.g., $_{5-6}$heterocycloalkyl means a heterocycloalkyl having either five or six ring members. "$C_{x-y}$" may be used to define number of carbons in a group. For example, "$C_{0-12}$alkyl" means alkyl having 0-12 carbons, wherein $C_o$alkyl means a single covalent chemical bond when a linking group and means hydrogen when a terminal group. $_{x-y}$cyclic means a ring system have from x to y ring member atoms.

The term "absent," as used herein to describe a structural variable (e.g., "—R— is absent") means that diradical R has no atoms, and merely represents a bond between other adjoining atoms, unless otherwise indicated.

Unless otherwise indicated (such as by a connecting "—"), the connections of compound name moieties are at the rightmost recited moiety. That is, the substituent name starts with a terminal moiety, continues with any bridging moieties, and ends with the connecting moiety. For example, "heteroarylthio$C_{1-4}$alkyl is a heteroaryl group connected through a thio sulfur to a $C_{1-4}$ alkyl, which alkyl connects to the chemical species bearing the substituent.

The term "aliphatic" means any hydrocarbon moiety, and can contain linear, branched, and cyclic parts, and can be saturated or unsaturated.

The term "alkyl" means any saturated hydrocarbon group that is straight-chain or branched. Examples of alkyl groups include methyl, ethyl, propyl, 2-propyl, n-butyl, iso-butyl, tert-butyl, pentyl, and the like.

The term "alkenyl" means any ethylenically unsaturated straight-chain or branched hydrocarbon group. Representative examples include, but are not limited to, ethenyl, 1-propenyl, 2-propenyl, 1-, 2-, or 3-butenyl, and the like.

The term "alkynyl" means any acetylenically unsaturated straight-chain or branched hydrocarbon group. Representative examples include, but are not limited to, ethynyl, 1-propynyl, 2-propynyl, 1-, 2-, or 3-butynyl, and the like. The term "alkoxy" means —O-alkyl, —O-alkenyl, or —O-alkynyl. "Haloalkoxy" means an—O-(haloalkyl) group. Representative examples include, but are not limited to, trifluoromethoxy, tribromomethoxy, and the like.

"Haloalkyl" means an alkyl, preferably lower alkyl, that is substituted with one or more same or different halo atoms.

"Hydroxyalkyl" means an alkyl, preferably lower alkyl, that is substituted with one, two, or three hydroxy groups; e.g., hydroxymethyl, 1 or 2-hydroxyethyl, 1,2-, 1,3-, or 2,3-dihydroxypropyl, and the like.

The term "alkanoyl" means —C(O)-alkyl, —C(O)-alkenyl, or —C(O)-alkynyl.

"Alkylthio" means an—S-(alkyl) or an—S-(unsubstituted cycloalkyl) group. Representative examples include, but are not limited to, methylthio, ethylthio, propylthio, butylthio, cyclopropylthio, cyclobutylthio, cyclopentylthio, cyclohexylthio, and the like.

The term "cyclic" means any ring system with or without heteroatoms (N, O, or $S(O)_{0-2}$), and which can be saturated or unsaturated. Ring systems can be bridged and can include fused rings. The size of ring systems may be described using terminology such as "$_{x-y}$cyclic," which means a cyclic ring system that can have from x to y ring atoms. For example, the term "9-iocarbocyclic" means a 5,6 or 6,6 fused bicyclic carbocyclic ring system which can be satd., unsatd. or aromatic. It also means a phenyl fused to one 5 or 6 membered satd. or unsatd. carbocyclic group. Nonlimiting examples of such groups include naphthyl, 1,2,3,4 tetrahydronaphthyl, indenyl, indanyl, and the like. In a structural drawing of a ring, a dashed or broken line means an optional bond. For example, a solid line adjacent to a dashed line means that there can be a single or a double bond.

The term "carbocyclic" means a cyclic ring moiety containing only carbon atoms in the ring(s) without regard to aromaticity. A 3-10 membered carbocyclic means chemically feasible monocyclic and fused bicyclic carbocyclics having from 3 to 10 ring atoms. Similarly, a 4-6 membered carbocyclic means monocyclic carbocyclic ring moieties having 4 to 6 ring carbons, and a 9-10 membered carbocyclic means fused bicyclic carbocyclic ring moieties having 9 to 10 ring carbons.

The term "cycloalkyl" means a non-aromatic 3-12 carbon mono-cyclic, bicyclic, or polycyclic aliphatic ring moiety. Cycloalkyl can be bicycloalkyl, polycycloalkyl, bridged, or spiroalkyl. One or more of the rings may contain one or more double bonds but none of the rings has a completely conjugated pi-electron system. Examples, without limitation, of cycloalkyl groups are cyclopropane, cyclobutane, cyclopentane, cyclopentene, cyclohexane, cyclohexadiene, adamantane, cycloheptane, cycloheptatriene, and the like.

The term "unsaturated carbocyclic" means any cycloalkyl containing at least one double or triple bond. The term "cycloalkenyl" means a cycloalkyl having at least one double bond in the ring moiety.

The terms "bicycloalkyl" and "polycycloalkyl" mean a structure consisting of two or more cycloalkyl moieties that have two or more atoms in common. If the cycloalkyl moieties have exactly two atoms in common they are said to be "fused". Examples include, but are not limited to, bicyclo[3.1.0]hexyl, perhydronaphthyl, and the like. If the cycloalkyl moieties have more than two atoms in common they are said to be "bridged". Examples include, but are not limited to, bicyclo[2.2.1]heptyl ("norbornyl"), bicyclo[2.2.2]octyl, and the like.

The term "spiroalkyl" means a structure consisting of two cycloalkyl moieties that have exactly one atom in common. Examples include, but are not limited to, spiro[4.5]decyl, spiro[2.3]hexyl, and the like.

The term "aromatic" means a planar ring moieties containing 4n+2 pi electrons, wherein n is an integer.

The term "aryl" means an aromatic moieties containing only carbon atoms in its ring system. Non-limiting examples include phenyl, naphthyl, and anthracenyl. The terms "arylalkyl" or "arylalkyl" or "aralkyl" refer to any alkyl that forms a bridging portion with a terminal aryl.

"Aralkyl" means alkyl, preferably lower alkyl, that is substituted with an aryl group as defined above; e.g., —CH$_2$ phenyl, —(CH$_2$)$_2$-phenyl, —(CH$_2$)$_3$ phenyl, CH$_3$CH(CH$_3$) CH$_2$-phenyl, and the like and derivatives thereof.

The term "heterocyclic" means a cyclic ring moiety containing at least one heteroatom (N, O, or $S(O)_{0-2}$), including heteroaryl, heterocycloalkyl, including unsaturated heterocyclic rings.

The term "heterocycloalkyl" means a non-aromatic monocyclic, bicyclic, or polycyclic heterocyclic ring moiety of 3 to 12 ring atoms containing at least one ring having one or more heteroatoms. The rings may also have one or more double bonds. However, the rings do not have a completely conjugated pi-electron system. Examples of heterocycloalkyl rings include azetidine, oxetane, tetrahydrofuran, tetrahydropyran, oxepane, oxocane, thietane, thiazolidine, oxazolidine, oxazetidine, pyrazolidine, isoxazolidine, isothiazolidine, tetrahydrothiophene, tetrahydrothiopyran, thiepane, thiocane, azetidine, pyrrolidine, piperidine, N-methylpiperidine, azepane, 1,4-diazapane, azocane, [1,3]dioxane, oxazolidine, piperazine, homopiperazine, morpholine, thiomorpholine, 1,2,3,6-tetrahydropyridine and the like. Other examples of heterocycloalkyl rings include the oxidized forms of the sulfur-containing rings. Thus, tetrahydrothiophene-1-oxide, tetrahydrothiophene-1,1-dioxide, thiomorpholine-1-oxide, thiomorpholine-1,1-dioxide, tetrahydrothiopyran-1-oxide, tetrahydrothiopyran-1,1-dioxide, thiazolidine-1-oxide, and thiazolidine-1,1-dioxide are also considered to be heterocycloalkyl rings. The term "heterocycloalkyl" also includes fused ring systems and can include a carbocyclic ring that is partially or fully unsaturated, such as a benzene ring, to form benzofused heterocycloalkyl rings. For example, 3,4-dihydro-1,4-benzodioxine, tetrahydroquinoline, tetrahydroisoquinoline and the like. The term "heterocycloalkyl" also includes heterobicycloalkyl, heteropolycycloalkyl, or heterospiroalkyl, which are bicycloalkyl, polycycloalkyl, or spiroalkyl, in which one or more carbon atom(s) are replaced by one or more heteroatoms selected from O, N, and S. For example, 2-oxa-spiro[3.3]heptane, 2,7-diaza-spiro[4.5]decane, 6-oxa-2-thia-spiro[3.4]octane, octahydropyrrolo[1,2-a]pyrazine, 7-aza-bicyclo[2.2.1]heptane, 2-oxa-bicyclo[2.2.2]octane, and the like, are such heterocycloalkyls.

Examples of saturated heterocyclic groups include, but are not limited to oxiranyl, thiaranyl, aziridinyl, oxetanyl, thiatanyl, azetidinyl, tetrahydrofuranyl, tetrahydrothiophenyl, pyrrolidinyl, tetrahydropyranyl, tetrahydrothiopyranyl, piperidinyl, 1,4-dioxanyl, 1,4-oxathianyl, morpholinyl, 1,4-dithianyl, piperazinyl, 1,4-azathianyl, oxepanyl, thiepanyl, azepanyl, 1,4-dioxepanyl, 1,4-oxathiepanyl, 1,4-oxaazepanyl, 1,4-dithiepanyl, 1,4-thieazepanyl, 1,4-diazepanyl Non-aryl heterocyclic groups include satd. and unsatd. systems and can include groups having only 4 atoms in their ring system. The heterocyclic groups include benzo-fused ring systems and ring systems substituted with one or more oxo moieties. Recitation of ring sulfur is understood to include the sulfide, sulfoxide or sulfone where feasible. The heterocyclic groups also include partially unsatd. or fully satd. 4-10 membered ring systems, e.g., single rings of 4 to 8 atoms in size and bicyclic ring systems, including aromatic 6-membered aryl or heteroaryl rings fused to a non-aromatic ring. Also included are 4-6 membered ring systems ("4-6 membered heterocyclic"), which include 5-6 membered heteroaryls, and include groups such as azetidinyl and piperidinyl. Heterocyclics can be heteroatom-attached where such is possible. For instance, a group derived from pyrrole can be pyrrol-1-yl (N-attached) or pyrrol-3-yl (C-attached). Other heterocyclics include imidazo[4,5-b]pyridin-3-yl and benzoimidazol-1-yl.

Examples of heterocyclic groups include pyrrolidinyl, tetrahydrofuranyl, tetrahydrothienyl, tetrahydropyranyl, tetrahydrothiopyranyl, piperidino, morpholino, thiomorpholino, thioxanyl, piperazinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, 2-pyrrolinyl, 3-pyrrolinyl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, quinolizinyl, and the like.

The term "unsaturated heterocyclic" means a heterocycloalkyl containing at least one unsaturated bond. The term "heterobicycloalkyl" means a bicycloalkyl structure in which at least one carbon atom is replaced with a heteroatom. The term "heterospiroalkyl" means a spiroalkyl structure in which at least one carbon atom is replaced with a heteroatom.

Examples of partially unsaturated heteroalicyclic groups include, but are not limited to: 3,4-dihydro-2H-pyranyl, 5,6-dihydro-2H-pyranyl, 2H-pyranyl, 1,2,3,4-tetrahydropyridinyl, and 1,2,5,6-tetrahydropyridinyl.

The terms "heteroaryl" or "hetaryl" mean a monocyclic, bicyclic, or polycyclic aromatic heterocyclic ring moiety containing 5-12 atoms. Examples of such heteroaryl rings include, but are not limited to, furyl, thienyl, pyrrolyl, pyrazolyl, imidazolyl, oxazolyl, isoxazolyl, thiazolyl, isothiazolyl, triazolyl, oxadiazolyl, thiadiazolyl, tetrazolyl, pyridyl, pyridazinyl, pyrimidinyl, pyrazinyl, and triazinyl. The terms "heteroaryl" also include heteroaryl rings with fused carbocyclic ring systems that are partially or fully unsaturated, such as a benzene ring, to form a benzofused heteroaryl. For example, benzimidazole, benzoxazole, benzothiazole, benzofuran, quinoline, isoquinoline, quinoxaline, and the like. Furthermore, the terms "heteroaryl" include fused 5-6, 5-5, 6-6 ring systems, optionally possessing one nitrogen atom at a ring junction. Examples of such hetaryl rings include, but are not limited to, pyrrolopyrimidinyl, imidazo[1,2-a]pyridinyl, imidazo[2,1-b]thiazolyl, imidazo[4,5-b]pyridine, pyrrolo[2,1-f][1,2,4]triazinyl, and the like. Heteroaryl groups may be attached to other groups through their carbon atoms or the heteroatom(s), if applicable. For example, pyrrole may be connected at the nitrogen atom or at any of the carbon atoms.

Heteroaryls include, e.g., 5 and 6 membered monocyclics such as pyrazinyl and pyridinyl, and 9 and 10 membered fused bicyclic ring moieties, such as quinolinyl. Other examples of heteroaryl include quinolin-4-yl, 7-methoxyquinolin-4-yl, pyridin-4-yl, pyridin-3-yl, and pyridin-2-yl. Other examples of heteroaryl include pyridinyl, imidazolyl, pyrimidinyl, pyrazolyl, triazolyl, pyrazinyl, tetrazolyl, furanyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, furopyridinyl, and the like. Examples of 5-6 membered heteroaryls include, thiophenyl, isoxazolyl, 1,2,3-triazolyl, 1,2,3-oxadiazolyl, 1,2,3-thiadiazolyl, 1,2,4-triazolyl, 1,3,4-oxadiazolyl, 1,3,4-thiadiazolyl, 1,2,5-oxadiazolyl, 1,2,5-thiadiazolyl, pyridyl, pyridazinyl, pyrimidinyl, pyrazinyl, 1,2,4 oxadiazolyl, 1,2,5-triazinyl, 1,3,5-triazinyl, and the like.

"Heteroaralkyl" group means alkyl, preferably lower alkyl, that is substituted with a heteroaryl group; e.g., —$CH_2$ pyridinyl, —$(CH_2)_2$pyrimidinyl, —$(CH_2)_3$imidazolyl, and the like, and derivatives thereof.

A pharmaceutically acceptable heteroaryl is one that is sufficiently stable to be attached to a compound of the invention, formulated into a pharmaceutical composition and subsequently administered to a patient in need thereof.

Examples of monocyclic heteroaryl groups include, but are not limited to: pyrrolyl, furanyl, thiophenyl, pyrazolyl, imidazolyl, isoxazolyl, oxazolyl, isothiazolyl, thiazolyl, 1,2,3-triazolyl, 1,3,4-triazolyl, 1-oxa-2,3-diazolyl, 1-oxa-2,4-diazolyl, 1-oxa-2,5-diazolyl, 1-oxa-3,4-diazolyl, 1-thia-2,3-diazolyl, 1-thia-2,4-diazolyl, 1-thia-2,5-diazolyl, 1-thia-3,4-diazolyl, tetrazolyl, pyridinyl, pyridazinyl, pyrimidinyl, pyrazinyl.

Examples of fused ring heteroaryl groups include, but are not limited to: benzoduranyl, benzothiophenyl, indolyl, benzimidazolyl, indazolyl, benzotriazolyl, pyrrolo[2,3-b]pyridinyl, pyrrolo[2,3-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-b]pyridinyl, isoindolyl, indazolyl, purinyl, indolinyl, imidazo[1,2-a]pyridinyl, imidazo[1,5-a]pyridinyl, pyrazolo[1,5-a]pyridinyl, pyrrolo[1,2-b]pyridazinyl, imidazo[1,2-c]pyrimidinyl, quinolinyl, isoquinolinyl, cinnolinyl, azaquinazoline, quinoxalinyl, phthalazinyl, 1,6-naphthyridinyl, 1,7-naphthyridinyl, 1,8-naphthyridinyl, 1,5-naphthyridinyl, 2,6-naphthyridinyl, 2,7-naphthyridinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrimido[2,3-b]pyrazinyl, pyrimido[4,5-d]pyrimidinyl.

"Arylthio" means an —S-aryl or an —S-heteroaryl group, as defined herein. Representative examples include, but are not limited to, phenylthio, pyridinylthio, furanylthio, thienylthio, pyrimidinylthio, and the like and derivatives thereof.

The terms "9-10 membered heterocyclic" and "$_{9\text{-}10}$heterocyclic" mean a fused 5, 6 or 6,6 bicyclic heterocyclic ring moiety, which can be satd., unsatd. or aromatic. The term "9-10 membered fused bicyclic heterocyclic" also means a phenyl fused to one 5 or 6 membered heterocyclic group. Examples include benzofuranyl, benzothiophenyl, indolyl, benzoxazolyl, 3H-imidazo[4,5-c]pyridin-yl, dihydrophthazinyl, 1H-imidazo[4,5-c]pyridin-1-yl, imidazo[4,5-b]pyridyl, 1,3benzo[1,3]dioxolyl, 2H-chromanyl, isochromanyl, 5-oxo-2,3dihydro-5H-[1,3]thiazolo[3,2-a]pyrimidyl, 1,3-benzothiazolyl, 1,4,5,6tetrahydropyridazyl, 1,2,3,4,7,8hexahydropteridinyl, 2-thioxo-2,3,6,9-tetrahydro-1H-purin-8-yl, 3,7-dihydro-1H-purin-8-yl, 3,4-dihydropyrimidin-1-yl, 2,3-dihydro-1,4-benzodioxinyl, benzo[1,3]dioxolyl, 2H-chromenyl, chromanyl, 3,4-dihydrophthalazinyl, 2,3-dihydro-1H-indolyl, 1,3-dihydro-2H-isoindol-2-yl, 2,4,7-trioxo-1,2,3,4,7,8-hexahydropteridin-yl, thieno[3,2-d]pyrimidinyl, 4-oxo-4,7-dihydro-3H-pyrrolo[2,3-d]pyrimidi n-yl, 1,3-dimethyl-6-oxo-2-thioxo-2,3,6,9-tetrahydro-1H-purinyl, 1,2-dihydroisoquinolinyl, 2-oxo-1,3-benzoxazolyl, 2,3-dihydro-5H-1,3-thiazolo-[3,2-a]pyrimidinyl, 5,6,7,8-tetrahydro-quinazolinyl, 4-oxochromanyl, 1,3-benzothiazolyl, benzimidazolyl, benzotriazolyl, purinyl, furylpyridyl, thiophenylpyrimidyl, thiophenylpyridyl, pyrrolylpiridyl, oxazolylpyridyl, thiazolylpiridyl, 3,4-dihydropyrimidin-1-yl imidazolylpyridyl, quinoliyl, isoquinolinyl, quinazolinyl, quinoxalinyl, naphthyridinyl, pyrazolyl[3,4]pyridine, 1,2-dihydroisoquinolinyl, cinnolinyl, 2,3-dihydro-benzo[1,4]dioxin-4-yl, 4,5,6,7-tetrahydro-benzo[b]-thiophenyl-2-yl, 1,8-naphthyridinyl, 1,5-napthyridinyl, 1,6-naphthyridinyl, 1,7-napthyridinyl, 3,4-dihydro-2H-1,4-benzothiazine, 4,8-dihydroxy-quinolinyl, 1-oxo-1,2-dihydro-isoquinolinyl, 4-phenyl-[1,2,3]thiadiazolyl, and the like.

"Aryloxy" means an —O-aryl or an —O-heteroaryl group, as defined herein. Representative examples include, but are not limited to, phenoxy, pyridinyloxy, furanyloxy, thienyloxy, pyrimidinyloxy, pyrazinyloxy, and the like, and derivatives thereof.

One in the art understands that an "oxo" requires a second bond from the atom to which the oxo is attached. Accordingly, it is understood that oxo cannot be subststituted onto an aryl or heteroaryl ring.

The term "halo" means fluoro, chloro, bromo, or iodo.

"Acyl" means a —C(O)R group, where R can be selected from the nonlimiting group of hydrogen or optionally substituted lower alkyl, trihalomethyl, unsubstituted cycloalkyl, aryl.

"Thioacyl" or "thiocarbonyl" means a —C(S)R" group, with R as defined above.

The term "protecting group" means a suitable chemical group that can be attached to a functional group and removed at a later stage to reveal the intact functional group. Examples of suitable protecting groups for various functional groups are described in T. W. Greene and P. G. M. Wuts, Protective Groups in Organic Synthesis, 2d Ed., John Wiley and Sons (1991 and later editions); L. Fieser and M. Fieser, Fieser and Fieser's Reagents for Organic Synthesis, John Wiley and Sons (1994); and L. Paquette, ed. Encyclopedia of Reagents for Organic Synthesis, John Wiley and Sons (1995). The term "hydroxy protecting group", as used herein, unless otherwise indicated, includes Ac, CBZ, and various hydroxy protecting groups familiar to those skilled in the art including the groups referred to in Greene.

As used herein, the term "pharmaceutically acceptable salt" means those salts which retain the biological effectiveness and properties of the parent compound and do not present insurmountable safety or toxicity issues.

The term "pharmaceutical composition" means an active compound in any form suitable for effective administration to a subject, e.g., a mixture of the compound and at least one pharmaceutically acceptable carrier.

As used herein, a "physiologically/pharmaceutically acceptable carrier" means a carrier or diluent that does not cause significant irritation to an organism and does not abrogate the biological activity and properties of the administered compound.

A "pharmaceutically acceptable excipient" means an inert substance added to a pharmaceutical composition to further facilitate administration of a compound. Examples, without limitation, of excipients include calcium carbonate, calcium phosphate, various sugars and types of starch, cellulose derivatives, gelatin, vegetable oils and polyethylene glycols.

The terms "treat," "treatment," and "treating" means reversing, alleviating, inhibiting the progress of, or partially or completely preventing the disorder or condition to which such term applies, or one or more symptoms of such disorder or condition. "Preventing" means treating before an infection occurs.

"Therapeutically effective amount" means that amount of the compound being administered which will relieve to some extent one or more of the symptoms of the disorder being treated, or result in inhibition of the progress or at least partial reversal of the condition.

The following abbreviations are used:
min. minute(s)
h hour(s)
d day(s)
RT or rt room temperature
$t_R$ retention time
L liter
mL milliliter
mmol millimole
μmol micromole
equiv. or eq. equivalents
NMR nuclear magnetic resonance
MDP(S) mass-directed HPLC purification (system)
LC/MS liquid chromatography mass spectrometry
HPLC high performance liquid chromatography
TLC thin layer chromatography
$CDCl_3$ deuterated chloroform
$CD_3OD$ or MeOD deuterated methanol
DMSO-$d_6$ deuterated dimethylsulfoxide
LDA lithium diisopropylamide
DCM dichloromethane
THF tetrahydrofuran
EtOAc ethyl acetate
MeCN acetonitrile
MeOH methanol
EtOH ethanol
DMSO dimethylsulfoxide
Boc tert-butyloxycarbonyl
DME 1,2-dimethoxyethane
DMF N,N-dimethylformamide
DIPEA diisopropylethylamine
PS-DIEA polymer-supported diisopropylethylamine
PS—$PPh_3$-Pd polymer-supported $Pd(PPh_3)_4$
EDC 1-(3-dimethylaminopropyl)-3-ethylcarbodiimide
HOBt 1-hydroxybenzotriazole
DMAP 4-dimethylaminopyridine
TBTU O-(benzotriazol-1-yl)-N,N,N',N'-tetramethyluronium tetrafluoroborate
TEMPO 2,2,6,6-tetramethylpiperidine-1-oxyl
TFA trifluoroacetic acid
$MgSO_4$ magnesium sulfate
$Na_2SO_4$ sodium sulfate
$NaHCO_3$ sodium bicarbonate
$Cs_2CO_3$ cesium carbonate
$K_2CO_3$ potassium carbonate
$Pd(PPh_3)_4$ tetrakis(triphenylphoshino)palladium (0)
$PdCl_2$dppf or $Pd(dppf)Cl_2$: 1,1'-Bis(diphenylphosphino)ferrocene-palladium(II) dichloride
$Pd(PPh_3)_2Cl_2$ or $PdCl_2(PPh_3)_2$: 1,1'-Bis(diphenylphosphino)ferrocene-palladium(II) dichloride
$NH_4Cl$ ammonium chloride
DMAP N,N-dimethylaminopyridine
$Na_2S_2O_3$ sodium thiosulfate
NIS N-iodosuccinimide

The invention claimed is:
1. A compound, or pharmaceutically acceptable salt thereof, of Formula 1:

[Structure 1: furopyridine with substituents $R^1$, $R^3$, $R^{30}$, and A-$R^2$]

wherein:
A is optionally substituted 5-membered heterocyclic;
$R^1$ is optionally substituted $_{5-6}$cyclic that is optionally substituted by $R^4$ or fused to $R^4$ at two atoms;
$R^2$ is an optional substituent;
$R^3$ is H, $C_{1-6}$aliphatic, CN, or halogen;
$R^4$ is optionally substituted $_{5-10}$cyclic; and
$R^{30}$ is —$NR^{31}R^{32}$, wherein $R^{31}$ and $R^{32}$ are independently H or $C_{1-3}$aliphatic.

2. The compound or salt of claim 1, having the Formula 2:

[Structure 2: furopyridine fused with pyrazole bearing $R^1$, $R^3$, $R^{30}$, $R^{40}$, $R^{41}$, $R^2$]

wherein:
$R^2$ is H or an optional substituent; and
each $R^{40}$ and $R^{41}$ is independently H, —CN, $C_{1-3}$aliphatic, —$OC_{1-3}$aliphatic, or —C(O)O—($C_{1-3}$aliphatic).

3. The compound or salt of claim 2, wherein:
$R^2$ is $_{4-9}$cyclic or substituted $_{4-9}$cyclic.

4. The compound or salt of claim 3, wherein:
$R^1$ is optionally substituted $_{5-6}$heteroaryl or phenyl and $R^1$ is fused to $R^4$ at two atoms; and
$R^4$ is optionally substituted $_{5-6}$heterocyclic.

5. The compound or salt of claim 4, wherein:
each $R^{40}$ and $R^{41}$ is independently H, methyl, or methoxy.

6. The compound or salt of claim 5, wherein:
$R^{31}$ and $R^{32}$ are independently H or $C_{1-2}$aliphatic.

7. The compound or salt of claim 6, wherein:
$R^3$ is H, —$CH_3$, or Cl.

8. The compound or salt of claim 7, wherein:
$R^1$ and $R^4$ are independently unsubstituted or substituted by one or more G1 groups;
each G1 is independently selected from —$PR^{12}R^{13}$, —$P(OR^{12})(OR^{13})$, —$PR^{12}(OR^{13})$, —$P(O)R^{12}R^{13}$, —$P(O)(OR^{12})(OR^{13})$, —$P(O)R^{12}(OR^{13})$, —$BR^{12}R^{13}$, —$B(OR^{12})(OR^{13})$, —$SF_5$, —NHS(O)($R^{12}$)=$NR^{13}$, or —$C_{1-6}$aliphatic-S(O)($R^{12}$)=$NR^{13}$;
or selected from halo, —CN, —$CF_3$, —$OCF_3$, —$NO_2$, $C_{1-12}$aliphatic, $_{3-12}$heterocyclic$C_{0-12}$aliphatic, $C_{4-12}$carbocyclic$C_{0-12}$aliphatic;
or selected from —$OR^{12}$, —$S(O)_mR^{12}$, —$NR^{12}R^{13}$, —$SO_2NR^{12}R^{13}$, —$C(O)R^b$, —$C(O)NR^{12}R^{13}$, —$C(O)C(O)NR^{12}R^{13}$, —$C(O)OR^{12}$, —$C(O)C(O)OR^{12}$, —$OC(O)R^b$, —$NR^{12}C(O)R^b$, —$NR^{12}S(O)_2R^{13}$, —$(CR^{14}R^{15})_nC(O)R^b$, —$(CR^{14}R^{15})_nC(O)OR^{12}$, —$(CR^{14}R^{15})_nC(O)NR^{12}R^{13}$, —$(CR^{14}R^{15})_nS(O)_2NR^{12}R^{13}$, —$(CR^{14}R^{15})_nNR^{12}R^{13}$, —$(CR^{14}R^{15})_nOR^{12}$, —$(CR^{14}R^{15})_nS(O)_mR^{12}$, —$NR^{16}C(O)NR^{12}R^{13}$, —$NR^{16}S(O)_2NR^{12}R^{13}$ or —$NR^{16}S(O)NR^{12}R^{13}$;
each G1 is optionally substituted with 1 or 2 independent E1 substituents;
each E1 is independently selected from halo, —CN, —OH, —$NH_2$, —$NO_2$, oxo, —$CF_3$, —$OCF_3$, —$CO_2H$, —S(O)$_m$H, —$OC_{1-12}$aliphatic, $C_{1-12}$aliphatic, $_{3-12}$heterocyclic$C_{0-12}$aliphatic, $C_{4-12}$carbocyclic$C_{0-12}$aliphatic;
or selected from aryol$C_{3-12}$cycloalkyl, heteroaryl$C_{3-12}$cycloalkyl, $C_{3-12}$heterocycloalkyl $C_{3-12}$cycloalkyl, $C_{3-12}$cycloalkyl$C_{3-12}$cycloalkyl, $C_{1-12}$aliphatic $C_{3-12}$heterocycloalkyl, $C_{3-12}$heterocycloalkyl$C_{3-12}$heterocycloalkyl, aryl$C_{3-12}$heterocycloalkyl or heteroaryl$C_{3-12}$heterocycloalkyl, any of which is optionally substituted with one or more independent halo, —CN, —OH, —$NH_2$, $C_{1-10}$aliphatic which may be partially or fully halogenated, or —$OC_{1-10}$aliphatic which may be partially or fully halogenated;
each $R^{12}$, $R^{13}$, $R^{14}$, $R^{15}$, $R^{16}$, and $R^b$ is independently selected from H, $C_{1-12}$aliphatic, $_{3-12}$heterocyclic$C_{0-12}$aliphatic, $C_{4-12}$carbocyclic$C_{0-12}$aliphatic, aryl$C_{3-12}$cycloalkyl, heteroaryl $C_{3-12}$cycloalkyl, $C_{3-12}$heterocycloalkyl$C_{3-12}$cycloalkyl, $C_{3-12}$cycloalkyl$C_{3-12}$cycloalkyl, $C_{1-12}$alkyl$C_{3-12}$heterocycloalkyl, $C_{3-12}$heterocycloalkyl$C_{3-12}$heterocycloalkyl, aryl $C_{3-12}$heterocycloalkyl, or heteroaryl$C_{3-12}$heterocycloalkyl substituents;
each $R^{12}$ and $R^{13}$ pair, or $R^{14}$ and $R^{15}$ pair, respectively, is optionally taken together with the nitrogen atom to which they are attached to form a 3-12 membered saturated or unsaturated ring which optionally includes one or more heteroatoms selected from O, N, or $S(O)_m$;
wherein any H atom of $R^1$ or $R^4$ can be deuterium;
each m is independently 0-2; and
each n is independently 0-6.

9. The compound or salt of claim 8, wherein;
each G1 is independently selected from oxo, $C_{1-3}$aliphatic, amino, carboxyl, amido, $_{5-6}$cyclic, or hydroxy, any of which is optionally substituted, or selected from nitro or halogen.

10. The compound or salt of claim 8, wherein: $R^1$ is $_{9-10}$heteroaryl.

11. The compound or salt of claim 8, wherein:
$R^2$ is $_{4-6}$cyclic that is optionally substituted by one or more Q1 groups;
each Q1 is independently selected from —$PR^{17}R^{18}$, —$P(OR^{17})(OR^{18})$, —$PR^{17}(OR^{18})$, —$P(O)R^{17}R^{18}$, —$P(O)(OR^{17})(OR^{18})$, —$P(O)R^{17}(OR^{18})$, —$BR^{17}R^{18}$, —$B(OR^{17})(OR^{18})$, —$SF_5$, —NHS(O)($R^{17}$)=$NR^{18}$, or —$C_{1-6}$aliphatic-S(O($R^{17}$)=$NR^{18}$;
or selected from halogen, —CN, —$CF_3$, —$OCF_3$, —$NO_2$, $C_{1-12}$aliphatic, $_{3-12}$heterocyclic$C_{0-12}$aliphatic, $C_{4-12}$carbocyclic$C_{0-12}$aliphatic;
or selected from —$OR^{17}$, —$S(O)_mR^{17}$, —$NR^{17}R^{18}$, —$SO_2NR^{17}R^{18}$, —$C(O)R^c$, —$C(O)NR^{17}R^{18}$, —$C(O)C(O)NR^{17}R^{18}$, —$C(O)OR^{17}$, —$C(O)C(O)OR^{17}$, —$OC(O)R^c$, —$NR^{17}C(O)R^c$, —$NR^{17}S(O)_2R^{18}$, —$(CR^{19}R^{20})_nC(O)R^c$, —$(CR^{19}R^{20})_nC(O)OR^{17}$, —$(CR^{19}R^{20})_nC(O)NR^{17}R^{18}$, —$(CR^{19}R^{20})_nS(O)_2NR^{17}R^{18}$, —$(CR^{19}R^{20})_nNR^{17}R^{18}$, —$(CR^{19}R^{20})_nOR^{17}$, $(CR^{19}R^{20})_nS(O)_mR^{17}$, —$NR^{21}C(O)NR^{17}R^{18}$, —$NR^{21}S(O)_2NR^{17}R^{18}$ or —$NR^{21}S(O)NR^{17}R^{18}$;
wherein each Q1 is optionally substituted with 1-2 independent F1 substituents;

each F1 is independently selected from halogen, —CN, —OH, —NH$_2$, —NO$_2$, oxo, —CF$_3$, —OCF$_3$, —CO$_2$H, —S(O)$_m$H, —OC$_{1-12}$aliphatic, C$_{1-12}$aliphatic, $_{3-12}$heterocyclicC$_{0-12}$aliphatic, C$_{4-12}$carbocyclicC$_{0-12}$aliphatic;

or from arylC$_{3-12}$cycloalkyl, heteroarylC$_{3-12}$cycloalkyl, C$_{3-12}$heterocycloalkylC$_{3-12}$cycloalkyl, C$_{3-12}$cycloalkylC$_{3-12}$cycloalkyl, C$_{1-12}$aliphaticC$_{3-12}$heterocycloalkyl, C$_{3-12}$heterocycloalkylC$_{3-12}$heterocycloalkyl, arylC$_{3-12}$heterocycloalkyl or heteroarylC$_{3-12}$heterocycloalkyl, any of which is optionally substituted with one or more independent halo, —CN, —OH, —NH$_2$, C$_{1-10}$aliphatic which may be partially or fully halogenated, or —OC$_{1-10}$aliphatic which may be partially or fully halogenated;

each R$^{17}$—R$^{21}$ and R$^c$ is independently selected from H, C$_{1-12}$aliphatic, $_{3-12}$heterocyclicC$_{0-12}$aliphatic, C$_{4-12}$carbocyclicC$_{0-12}$aliphatic, arylC$_{3-12}$cycloalkyl, heteroarylC$_{3-12}$cycloalkyl, C$_{3-12}$heterocycloalkylC$_{3-12}$cycloalkyl, C$_{3-12}$cycloalkylC$_{3-12}$cycloalkyl, C$_{1-12}$alkyl C$_{3-12}$heterocycloalkyl, C$_{3-12}$heterocycloalkylC$_{3-12}$heterocycloalkyl, arylC$_{3-12}$heterocycloalkyl, or heteroarylC$_{3-12}$heterocycloalkyl substituents;

each R$^{17}$ and R$^{18}$ pair, or R$^{19}$ and R$^{20}$ pair, respectively, is optionally taken together with the nitrogen atom to which they are attached to form a 3-12 membered saturated or unsaturated ring, wherein said ring optionally includes one or more heteroatoms selected from O, N, or S(O)$_m$;

wherein any H atom of R$^2$ can be deuterium;

each m is independently 0-2; and each n is independently 0-6.

12. The compound or salt of claim 10, wherein:

R$^2$ is $_{5-6}$heterocyclic that is optionally substituted by 1-2 Q1 groups;

each Q1 is independently selected from halo, —CN, —NO$_2$, oxo, —CF$_3$, —OCF$_3$, C$_{1-12}$aliphatic, —(CR$^{19}$R$^{20}$)$_n$C(O)R$^c$, —(CR$^{19}$R$^{20}$)$_n$C(O)OR$^{17}$, —(CR$^{19}$R$^{20}$)$_n$C(O)NR$^{17}$R$^{18}$, —C(O)C(O)NR$^{17}$R$^{18}$, —(CR$^{19}$R$^{20}$)$_n$S(O)$_2$NR$^{17}$R$^{18}$, —(CR$^{19}$R$^{20}$)$_n$NR$^{17}$R$^{18}$, —(CR$^{19}$R$^{20}$)$_n$OR$^{17}$, —(CR$^{19}$R$^{20}$)$_n$S(O)$_m$R$^{17}$, —NR$^{21}$C(O)NR$^{17}$R$^{18}$, —NR$^{21}$S(O)$_2$NR$^{17}$R$^{18}$ or —NR$^{21}$S(O)NR$^{17}$R$^{18}$;

each R$^{17}$—R$^{21}$ and R$^c$ is independently selected from H, C$_{1-12}$aliphatic, arylC$_{0-12}$aliphatic, heteroarylC$_{0-12}$aliphatic, C$_{3-12}$cycloalkylC$_{0-12}$aliphatic, C$_{3-12}$heterocycloalkylC$_{0-12}$aliphatic, arylC$_{3-12}$cycloalkyl, heteroarylC$_{3-12}$cycloalkyl, C$_{3-12}$heterocycloalkyl C$_{3-12}$cycloalkyl, C$_{3-12}$cycloalkylC$_{3-12}$cycloalkyl, C$_{1-12}$alkylC$_{3-12}$heterocycloalkyl, C$_{3-12}$heterocycloalkylC$_{3-12}$heterocycloalkyl, arylC$_{3-12}$heterocycloalkyl, or heteroarylC$_{3-12}$heterocycloalkyl substituents;

each m is independently 0-2; and each n is independently 0-6.

13. The compound or salt of claim 12, wherein:

R$^2$ is a six membered saturated or partially unsaturated ring containing 0-2 heteroatoms and substituted by 1-2 Q1 groups.

14. The compound or salt of claim, having the formula:

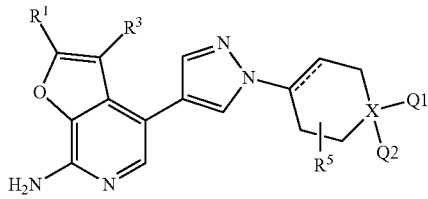

wherein the dashed line indicates a single or double bond;

R$^3$ is H or Cl;

R$^5$ can be at any open position and is selected from C$_{0-6}$aliphatic optionally substituted by —N(C$_{0-6}$aliphatic)(C$_{0-6}$ aliphatic), —S(O)$_{0-2}$-C$_{0-6}$aliphatic, or —OC$_{0-6}$aliphatic;

X is >O and Q1 and Q2 are absent, or

X is >C, Q1 is H or C$_{1-6}$aliphatic optionally substituted by one or more halogen atoms, and Q2 is OH or —OC$_{1-6}$aliphatic optionally substituted by one or more halogen atoms;

X is >N, Q1 is absent, and Q2 is selected from H, C$_{1-6}$aliphatic, R$^8$O—C$_{2-6}$aliphatic, R$^8$R$^9$N—C$_{2-6}$aliphatic, R$^8$S(O)$_{0-2}$—C$_{2-6}$aliphatic, —C(O)R$^a$, R$^8$O—C$_{0-6}$aliphaticC(O)—, R$^8$R$^9$N—C$_{0-6}$aliphaticC(O)—, R$^8$S(O)$_{0-2}$C$_{0-6}$aliphaticC(O)—, —CO$_2$R$^8$, —C(O)NR$^8$R$^9$, —S(O)$_{0-2}$R$^8$, —SO$_2$NR$^8$R$^9$, —C(S)OR$^8$, C$_{3-6}$cycloalkylC$_{0-6}$aliphatic, C$_{3-6}$cycloalkenylC$_{1-6}$aliphatic, C$_{3-6}$heterocycloalkylC$_{0-6}$aliphatic, arylC$_{0-6}$aliphatic, heteroarylC$_{0-6}$aliphatic, C$_{1-6}$aliphaticC$_{3-6}$cycloalkyl, C$_{3-6}$cycloalkylC$_{3-6}$cycloalkyl, C$_{3-6}$cycloalkenylC$_{3-6}$cycloalkyl, C$_{3-6}$heterocycloalkylC$_{3-6}$cycloalkyl, arylC$_{3-6}$cycloalkyl, heteroarylC$_{3-6}$cycloalkyl, C$_{1-6}$aliphaticC$_{3-6}$heterocycloalkyl, C$_{3-6}$cycloalkylC$_{3-6}$heterocycloalkyl, C$_{3-6}$cycloalkenylC$_{3-6}$heterocycloalkyl, C$_{3-6}$heterocycloalkylC$_{3-6}$heterocycloalkyl, aryl C$_{3-6}$heterocycloalkyl, or heteroarylC$_{3-6}$heterocycloalkyl, any of which is optionally substituted by one or more halogen atoms; and each R$^a$, R$^8$, and R$^9$ is independently selected from H or C$_{1-6}$aliphatic optionally substituted by one or more C$_{0-3}$alkoxy or halogen.

15. The compound or salt of claim 14, wherein:

X is >N;

Q1 is selected from H, —(CR$^8$R$^9$)$_n$C(O)R$^a$—OR$^{10}$, —(CR$^8$R$^9$)$_n$C(O)R$^{10}$, —(CR$^8$R$^9$)$_n$C(O)OR$^{10}$, —(CR$^8$R$^9$)$_n$C(O)NR$^{10}$R$^{11}$, —(CR$^8$R$^9$)$_n$S(O)$_{0-2}$NR$^{10}$R$^{11}$, —(CR$^8$R$^9$)$_n$NR$^{10}$R$^{11}$, —(CR$^8$R$^9$)$_n$OR$^{10}$, —(CR$^8$R$^9$)$_n$S(O)$_{0-2}$R$^{10}$, C$_{1-6}$aliphatic, or C$_{1-6}$aliphatic-OC$_{0-6}$aliphatic, wherein any of the foregoing can be singly or multiply halogen substituted;

each R$^a$ and R$^8$-R$^{11}$ is independently selected from H or C$_{1-6}$aliphatic optionally substituted by one or more C$_{0-3}$alkoxy or halogen;

each n is independently 0-6; and each R$^8$ and R$^9$ pair is optionally taken together to form a 3-6 membered saturated or unsaturated ring, wherein said ring optionally includes one or more heteroatoms selected from O, N, or S(O)$_{0-2}$.

16. The compound or salt of claim 15, wherein:

Q1 is H, C$_{1-6}$aliphatic, —C(O)R$^a$, wherein any of the foregoing can be singly or multiply halogen substituted.

17. The compound or salt of claim 14, wherein:

X is >C,

Q1 is H or C$_{1-3}$aliphatic; and

Q2 is OH.

18. The compound or salt of claim 14, having the formula:

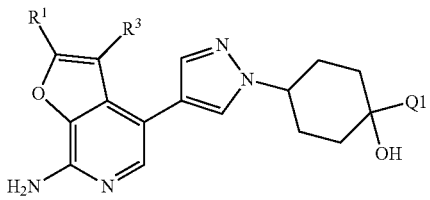

wherein Q1 is H or $C_{1-3}$aliphatic.

19. The compound or salt of claim 1, having the formula:

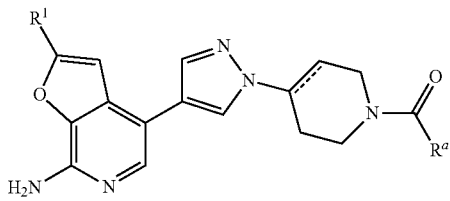

wherein:
$R^1$ is optionally substituted $_{9-10}$unsaturated heterocyclic; and $R^a$ is H or $C_{1-6}$aliphatic optionally substituted by one or more $C_{0-3}$alkoxy or halogen.

20. The compound or salt of claim 1, wherein:
$R^1$ is phenyl optionally substituted by 1-2 independent —$NO_2$, —OH, or —CN.

21. The compound or salt of claim 13, wherein:
$R^1$ is selected from azaindolyl, quinolinyl, isoquinolinyl, isoindolinonyl, indazolyl, benzothiophenyl, thienopyridinyl, benzothiazoyl, benzoisothiazoyl, benzothiadiazoyl, or indolyl.

22. The compound or salt of claim 1, which exhibits inhibition of TAK1 in a biochemical assay with an $IC_{50}$ of about 100 nM or less.

23. The compound or pharmaceutically acceptable salt thereof of claim 1, which is selected from any one of Examples 1-411 herein.

24. A pharmaceutical composition comprising a compound of claim 1, formulated with or without one or more pharmaceutically acceptable carriers.

* * * * *